US011994523B2

(12) United States Patent
Van Eyk et al.

(10) Patent No.: US 11,994,523 B2
(45) Date of Patent: May 28, 2024

(54) BIOMARKERS AND METHODS FOR DIAGNOSING AND EVALUATING TRAUMATIC BRAIN INJURY

(71) Applicants: Abbott Laboratories, Abbott Park, IL (US); Cedars-Sinai Medical Center, Los Angeles, CA (US)

(72) Inventors: Jennifer Van Eyk, Los Angeles, CA (US); Beth McQuiston, Abbott Park, IL (US); Saul Datwyler, Abbott Park, IL (US); Raj Chandran, Abbott Park, IL (US); Vidya Venkatraman, Los Angeles, CA (US); Shenyan Zhang, Los Angeles, CA (US)

(73) Assignees: ABBOTT LABORATORIES, Abbott Park, IL (US); CEDARS-SINAI MEDICAL CENTER, Los Angeles, CA (US)

(*) Notice: Subject to any disclaimer, the term of this patent is extended or adjusted under 35 U.S.C. 154(b) by 329 days.

(21) Appl. No.: 17/224,685

(22) Filed: Apr. 7, 2021

(65) Prior Publication Data
US 2021/0302441 A1    Sep. 30, 2021

Related U.S. Application Data

(62) Division of application No. 16/233,895, filed on Dec. 27, 2018, now abandoned.

(60) Provisional application No. 62/630,704, filed on Feb. 14, 2018, provisional application No. 62/611,778, filed on Dec. 29, 2017.

(51) Int. Cl.
*G01N 33/68*    (2006.01)

(52) U.S. Cl.
CPC ..... *G01N 33/6896* (2013.01); *G01N 2560/00* (2013.01); *G01N 2800/28* (2013.01); *G01N 2800/50* (2013.01); *G01N 2800/52* (2013.01); *G01N 2800/60* (2013.01)

(58) Field of Classification Search
CPC .......... G01N 33/6896; G01N 2560/00; G01N 2800/28; G01N 2800/50; G01N 2800/52; G01N 2800/60
See application file for complete search history.

(56) References Cited

U.S. PATENT DOCUMENTS

| | | |
|---|---|---|
| 7,456,027 B2 | 11/2008 | Wang et al. |
| 8,492,107 B2 | 7/2013 | Wang et al. |
| 9,265,441 B2 | 2/2016 | Pereira et al. |
| 2003/0199000 A1 | 10/2003 | Valkirs et al. |
| 2010/0261286 A1 | 10/2010 | Kim et al. |
| 2011/0143375 A1 | 6/2011 | Wang et al. |
| 2012/0202231 A1 | 8/2012 | Wang et al. |
| 2012/0244555 A1 | 9/2012 | Blyth et al. |
| 2012/0322682 A1 | 12/2012 | McDevitt et al. |
| 2013/0029859 A1 | 1/2013 | Svetlov et al. |
| 2014/0004087 A1 | 1/2014 | Ichim et al. |
| 2014/0273035 A1 | 9/2014 | Dowell et al. |
| 2014/0303041 A1 | 10/2014 | Hayes et al. |
| 2014/0342381 A1 | 11/2014 | Hayes et al. |
| 2014/0370531 A1 | 12/2014 | Blyth et al. |
| 2015/0057193 A1 | 2/2015 | Dave et al. |
| 2015/0224499 A1 | 8/2015 | Wang et al. |
| 2015/0268252 A1 | 9/2015 | Svetlov et al. |
| 2017/0023591 A1 | 1/2017 | Bowser et al. |
| 2017/0089926 A1 | 3/2017 | Travis et al. |
| 2017/0146555 A1 | 5/2017 | Wang et al. |
| 2017/0176460 A1 | 6/2017 | Larner |
| 2017/0227538 A1 | 8/2017 | Noji |
| 2017/0254822 A1 | 9/2017 | Sabbadini |
| 2018/0106800 A1 | 4/2018 | Datwyler et al. |
| 2018/0106818 A1 | 4/2018 | Jewell et al. |
| 2018/0313837 A1 | 11/2018 | McQuiston et al. |
| 2019/0064187 A1 | 2/2019 | Svetlov et al. |
| 2019/0091687 A1 | 3/2019 | Alhasnani |
| 2019/0302127 A1 | 10/2019 | Lukaszewska |

FOREIGN PATENT DOCUMENTS

| | | |
|---|---|---|
| CN | 105085629 A | 11/2015 |
| EP | 105085629 A1 | 3/2005 |
| EP | 1838442 B1 | 9/2013 |
| EP | 3916387 A1 | 12/2021 |
| JP | 2012500388 A | 1/2012 |
| JP | 2017125853 A | 7/2017 |
| WO | WO 2005/029088 | 3/2005 |

(Continued)

OTHER PUBLICATIONS

Agoston, Denes V. et al., "Biofluid Biomarkers of Traumatic Brain Injury" *Brain Injury*, 31(9):1195-1203 (Jul. 29, 2017).
Anderson, GD et al., "Effect of Traumatic Brain Injury, Erythropoietin, and Anakinra on Hepatic Metabolizing Enzymes and Transporters in an Experimental Rat Model." *The AAPS Journal*. Sep. 1, 2015;17(5):1255-67.

(Continued)

*Primary Examiner* — Olga N Chernyshev
(74) *Attorney, Agent, or Firm* — Casimir Jones SC; Lisa Mueller

(57) ABSTRACT

The present disclosure relates to methods for diagnosing and evaluating a subject that has sustained or may have sustained an injury to the head, such as a traumatic brain injury (TBI). In particular, the present disclosure identifies various biomarkers, the detection and/or differential expression of which can be used to assess the presence or absence of a TBI in a subject, and can be used as a basis for diagnosing a subject as having a specific type of TBI (e.g., severe TBI or subclasses of mild TBI). The various TBI biomarkers can be detected individually or in combination and can be used as an important diagnostic, prognostic, and/or TBI risk stratification tool as part of assessing a subject's TBI status.

7 Claims, 7 Drawing Sheets
Specification includes a Sequence Listing.

(56) References Cited

FOREIGN PATENT DOCUMENTS

| | | |
|---|---|---|
| WO | WO 2005/106038 | 10/2005 |
| WO | WO 2005/113798 | 12/2005 |
| WO | WO 2009/100131 | 8/2009 |
| WO | 2010019553 A2 | 2/2010 |
| WO | WO 2010/019553 A2 | 2/2010 |
| WO | 2010102279 A1 | 9/2010 |
| WO | 2010148391 A2 | 12/2010 |
| WO | WO 2010/148391 | 12/2010 |
| WO | WO 2011/011334 A2 | 1/2011 |
| WO | WO 2011/032155 | 3/2011 |
| WO | WO 2011/160096 A2 | 12/2011 |
| WO | WO 2012/051519 | 4/2012 |
| WO | 2014124174 A2 | 8/2014 |
| WO | WO 2014/183110 | 11/2014 |
| WO | WO 2014/194329 | 12/2014 |
| WO | WO 2015/009907 | 1/2015 |
| WO | WO 2015/066211 | 5/2015 |
| WO | WO 2015/157300 | 10/2015 |
| WO | WO 2016/055148 A2 | 4/2016 |
| WO | WO 2016/166419 A1 | 10/2016 |
| WO | WO 2016/179426 | 11/2016 |
| WO | WO 2016/196522 A1 | 12/2016 |
| WO | WO 2016/205730 | 12/2016 |
| WO | WO 2017/008894 | 1/2017 |
| WO | WO 2017/087500 | 5/2017 |
| WO | WO 2018/067468 A1 | 4/2018 |
| WO | WO 2018/067474 | 4/2018 |
| WO | WO 2018/081649 A1 | 5/2018 |
| WO | WO 2018/136825 A1 | 7/2018 |
| WO | WO 2018/175942 | 9/2018 |
| WO | WO 2018/191531 | 10/2018 |
| WO | 2018217792 A1 | 11/2018 |
| WO | WO 2018/200823 | 11/2018 |
| WO | WO 2018/218169 | 11/2018 |
| WO | WO 2018/222783 | 12/2018 |
| WO | WO 2018/222784 | 12/2018 |
| WO | WO 2019/112860 | 6/2019 |
| WO | WO 2019/113525 | 6/2019 |
| WO | WO 2019/133717 | 7/2019 |
| WO | 2019199869 A1 | 10/2019 |
| WO | 2021026261 A1 | 2/2021 |

OTHER PUBLICATIONS

Bansal, V et al., "The hormone ghrelin prevents traumatic brain injury induced intestinal dysfunction." *Journal of Neurotrauma.* Dec. 1, 2010;27(12):2255-60.

Banyan BTI Brain Trauma Indicator, Publicly available Feb. 2018.

Bazarian et al., "Serum GFAP and UCH-L1 for prediction of absence of intracranial injuries on head CT (ALERT-TBI): a multicentre observational study" The Lancelot, Neurology, vol. 17, Issue 9, p. 782-789, Sep. 1, 2018.

Benninger et al., "Glial fibrillary acidic protein as a marker of astrocytic activation in the cerebrospinal fluid of patients with amyotrophic lateral sclerosis." *Journal of Clinical Neuroscience*, 26:75-78 (Nov. 2015).

Berger, et al., "Serum Concentrations of Ubiquitin C-Terminal Hydrolase-L1 and all-Spectrin Breakdown Product 145 kDa Correlate with Outcome after Pediatric TBI." Journal of Neurotrauma, Jan. 1, 2012; 29:162-167.

Blyth, Brian J. et al., "Elevated Serum Ubiquitin Carboxy-Terminal Hydrolase L1 is Associated with Abnormal Blood-Brain Barrier Function after Traumatic Brain Injury", *Journal of Neurotrauma.*, 28(12): 2453-2462 (Dec. 1, 2011).

Bogoslovsky T. et al., "Fluid Biomarkers of Traumatic Brain Injury and Intended Context of Use." Diagnostics (Basel). Oct. 18, 2016; 6(4). pii: E37.

Brophy, M. et al., "Biokinetic analysis of ubiquitin C-terminal hydrolase-L1 (UCH-L1) in severe traumatic brain injury patient biofluids." J Neurotrauma. Jun. 2011; 28(6):861-70.

Cai et al.,"The role of cardiac troponin I in prognostication of patients with isolated severe traumatic brain injury." *J. Trauma Acute Care Surg.*, 80(3):477-483 (Mar. 2016).

Dash et al.; "Biomarkers for Diagnosis, Prognosis, and Evaluation of Treatment Efficacy for Traumatic Brain Injury." Neurotherapeutics, Jan. 2010, 7(1): 100-114.

Diaz-Arrastia, et al., "Acute biomarkers of traumatic brain injury: relationship between plasma levels of ubiquitin C-terminal hydrolase-L1 and glial fibrillary acidic protein.", *Journal of Neurotrauma*, 31:19-25 (Jan. 1, 2014).

Haerter, "Microarrays and expression Profiling in Microglia Research and in Inflammatory Brain Disorders." Journal of Neuroscience Research 81:327-341.

Hamdi, et al., "Predictive Value of Cardiac Troponin I in Traumatic Brain Injury.", *Egypt J. Neurol. Psychiat. Neurosurg*, 49(4):365-373 (Oct. 2012).

Haskins, "Rapid Discovery of Putative Protein Biomarkers of Traumatic Brain Injury by SDS-PAGE-Capillary Liquid Chromatography-Tandem Mass Spectrometry." Journal of Neurotrauma, 2005, 22(6): 629-644.

Kaya et al., "Expression of nestin after traumatic brain injury in rat brain." Brain Res. Sep. 4, 1999; 840(1-2):153-7.

Kiiski, H. et al., "Increased plasma UCH-L1 after aneurysmal subarachnoid hemorrhage is associated with unfavorable neurological outcome." J Neurol Sci. Feb. 15, 2016; 361:144-9.

Kiviniemi et al., "Serum levels of GFAP and EGFR in primary and recurrent high-grade gliomas: correlation to tumor volume, molecular markers, and progression-free survival." *Journal of Neuro-Oncology*, 124(2):237-245 (Jun. 2015).

Kobeissy, Firas H. et al., "Novel Differential Neuroproteomics Analysis of Traumatic Brain Injury in Rats" *Molecular & Cellular Proteomics*, 5(10):1887-1898 (Oct. 1, 2006).

Kochanek et al., "Multi-Center Pre-clinical Consortia to Enhance Translation of Therapies and Biomarkers for Traumatic Brain Injury: Operation Brain Trauma Therapy and Beyond." Frontiers in Neurology Aug. 2018, vol. 9, 13 pages.

Korley et al., "Performance Evaluation of a Multiplex Assay for Simultaneous Detection of Four Clinically Relevant Traumatic Brain Injury Biomarkers." Journal of Neurotrauma, 2015, 35:1-6.

Kou et al., "Combining Biochemical and Imaging Markers to Improve Diagnosis and Characterization of Mild Traumatic Brain Injury in the Acute Setting: Results from a Pilot Study." PLOS ONE Nov. 2013, 8(11): e80296, 14 pages.

Lecky, "Should plasma GFAP guide the management of patients with traumatic brain injury and a negative CT scan?" Lancet Neurol 2019, 2 pages.

Lee et al., "A Role of Serum-Based Neuronal and Glial Markers as Potential Predictors for Distinguishing Severity and Related Outcomes in Traumatic Brain Injury", *J. Korean Neurosurgical Society*, 58(2):93-100 (Aug. 2015).

Lippi et al., "The concentration of highly-sensitive troponin I is increased in patients with brain injury after mild head trauma." *International Journal of Cardiology*, 168(2):1617-1618 (Sep. 2013).

Liu et al., "Ubiquitin C-terminal hydrolase-L1 as a biomarker for ischemic and traumatic brain injury in rats", *Eur. J. Neurosci.*, 31(4): 722-732 (Feb. 2010).

Luger et al., "Glial Fibrillary Acidic Protein Serum Levels Distinguish between Intracerebral Hemorrhage and Cerebral Ischemia in the Early Phase of Stroke", *Clinical Chemistry*, 63(1):377-385 (Nov. 23, 2016).

McMahon et al., "Measurement of the glial fibrillary acidic protein and its breakdown products GFAP-BDP biomarker for the detection of traumatic brain injury compared to computed tomography and magnetic resonance imaging." J Neurotrauma. Apr. 15, 2015; 32(8):527-33.

Metting et al., "GFAP and S100B in the acute phase of mild tramautic brain injury." Neurology, 78: 1428-1433 (2012).

Missler et al., "Measurement of Glial Fibrillary Acidic Protein in Human Blood: Analytical Method and Preliminary Clinical Results." Clinical Chemistry, 45(1):138-141 (1999).

Mondello et al., "Clinical utility of serum levels of ubiquitin cterminal hydrolase as a biomarker for severe traumatic brain injury" Neurosurgery. Mar. 2012; 70(3): 666-675.

(56) References Cited

OTHER PUBLICATIONS

Mondello et al., "Neuronal and glial markers are differently associated with computed tomography findings and outcome in patients with severe traumatic brain injury: a case control study." Care 2011, 15:R156, 10 pages.

Mondello et al., "Serum Concentrations of Ubiquitin C-Terminal Hydrolase-L1 and Glial Fibrillary Acidic Protein after Pediatric Traumatic Brain Injury." *Scientific Reports*, 6(28203):1-6 (Jun. 2016).

Nylen et al., "Increased serum-GFAP in patients with severe traumatic brain injury is related to outcome" J. of Neurological Sciences, 240: 85-91 (2006).

Okonkwo et al., "GFAP-BDP as an acute diagnostic marker in traumatic brain injury: results from the prospective transforming research and clinical knowledge in traumatic brain injury study." J Neurotrauma. Sep. 1, 2013; 30(17):1490-7.

Ottens, AK et al., "Neuroproteomics: a biochemical means to discriminate the extent and modality of brain injury.", *Journal of Neurotrauma*, 27(10), pp. 1837-1852. (Oct. 2010).

Papa et al., "Elevated levels of serum glial fibrillary acidic protein breakdown products in mild and moderate traumatic brain injury are associated with intracranial lesions and neurosurgical intervention." Ann Emerg Med. Jun. 2012;59(6):471-83.

Papa et al., "Serum levels of Ubiquitin C-terminal Hydrolase (UCH-L1) distinguish mild traumatic brain injury (TBI) from trauma controls and are elevated in mild and moderate TBI patients with intracranial lesions and neurosurgical intervention", *J. Trauma Acute Care Surg.*, 72(5):1335-1344 (May 2012).

Papa et al., "Time Course and Diagnostic Accuracy of Glial and Neuronal Blood Biomarkers GFAP and UCH-L1 in a Large Cohort of Trauma Patients With and Without Mild Traumatic Brain Injury." *JAMA*, 73(5) 551-560 (Mar. 28, 2016).

Papa et al., "Ubiquitin C-terminal hydrolase is a novel biomarker in humans for severe traumatic brain injury*", *Crit. Care Med.*, 38(1):138-144 (Jan. 2010).

Pelinka et al., "Glial fibrillary acidic protein in serum after traumatic brain injury and multiple trauma." J Trauma. Nov. 2004; 57(5):1006-12.

Posti et al., "Glial Fibrillary Acidic Protein and Ubiquitin C-Terminal Hydrolase-L1 are not Specific Biomarkers for Mild CT-Negative Traumatic Brain Injury" Journal of Neurotrauma, 34(7):1427-1438 (Apr. 1, 2017).

Prieto et al., "Proteomic analysis of traumatic brain injury: the search for biomarkers." Expert Rev Proteomics. Apr. 2008; 5(2):283-91.

Pun et al., "Low level primary blast injury in rodent brain." Front Neurol. Apr. 4, 2011;2:19.

Puvenna et al., "Significance of ubiquitin carboxy-terminal hydrolase L1 elevations in athletes after sub-concussive head hits.", *PLOS ONE*, 9(5):e96296 (May 2014).

Rhine et al., "Are UCH-L1 and GFAP promising biomarkers for children with mild traumatic brain injury?" Brain Injury 2016, Early Online: 1-8.

Salim et al., "Significance of Troponin Elevation After Severe Traumatic Brain Injury." The Journal of TRAUMA Injury, Infection, and Critical Care 2008, 64 (1): 46-52.

Shahjouei et al., "The diagnostic values of UCH-L1 in traumatic brain injury: A meta analysis" Brain Injury (2017)—From email on Jun. 5 at 4:14.

Shen et al., "High plasma adiponectin levels in patients with severe traumatic brain injury." Clin Chim Acta. Jan. 1, 2014; 427:37-41.

Song et al., "Development of Digital Elisas for Ultrasensitive Measurement of Serum Glial Fibrillary Acid Protein and Ubiquitin C-Terminal Hydrolase With Clinical Utilities in Human Traumatic Brain Injury." Alzheimer's & Dementia, 13(7):P3-240 (Jul. 2017).

Stephen et al., "The Role of Cardiac Troponin I in Prognostication of Patients with Isolated Severe Traumatic Brain Injury." J Trauma Acute Care Surg. Mar. 2016 ; 80(3):477-483.

Strathmann et al., "Blood-based biomarkers for traumatic brain injury: evaluation of research approaches, available methods and potential utility from the clinician and clinical laboratory perspectives." Clin Biochem. Jul. 2014; 47(10-11):876-88.

Streeter et al., "Diagnostic Protein Biomarkers for Severe, Moderate, and Mild Traumatic Brain Injury", Sensing Technologies for Global Health, Military Medicine, Disaster Response, and Environmental Monitoring; and Biometric Technology for Human Identification VIII, 8029(1):1-16 (May 13, 2011).

Takala et al., "Glial Fibrillary Acidic Protein and Ubiquitin C-Terminal Hydrolase-L1 as Outcome Predictors in Traumatic Brain Injury." World Neurosurg. Mar. 2016; 87:8-20.

Tate et al., "Fibronectin and laminin increase in the mouse brain after controlled cortical impact injury." *Journal of Neurotrauma*. Jan. 1, 2007;24(1):226-30.

Thelin et al., "Serial Sampling of Serum Protein Biomarkers for Monitoring Human Traumatic Brain injury Dynamics: A Systematic Review." Frontiers in Neurology Jul. 2017, vol. 8, Article 300, 23 pages.

Thermo Scientific, "Thermo Scientific Pierce Assay Development Handbook." 2006, 76 pages.

Vos et al., "Glial and neuronal proteins in serum predict outcome after severe traumatic brain injury." Neurology. Apr. 27, 2004; 62(8):1303-10.

Wang et al., "An update on diagnostic and prognostic biomarkers for traumatic brain injury." Expert Review of Molecular Diagnostics, 18(2):165-180 (Jan. 2018).

Wang et al., "Proteomic identification of biomarkers of traumatic brain injury" Expert Review of Proteomics, 2(4):603-614 (Aug. 2005).

Welch et al., "Ability of Serum Glial Fibrillary Acidic Protein, Ubiquitin C-Terminal Hydrolase-L1, and S100B to Differentiate Normal and Abnormal Head Computed Tomography Findings in Patients with Suspected Mild or Moderate Traumatic Brain Injury." *Journal of Neurotrauma*, 33:203-214 (Jan. 15, 2016).

White et al., "Gene expression patterns following unilateral traumatic brain injury reveals a local pro-inflammatory and remote anti-inflammatory response" *BMC Genomics*. Apr. 25, 2013;14(1):282.

Yamauchi et al., "Ubiquitin-mediated stress response in the spinal cord after transient ischemia." Stroke. Jun. 2008; 39(6):1883-9.

Yue et al., "Association between plasma GFAP concentrations and MRI abnormalities in patients with CT-negative traumatic brain injury in the TRACK-TBI cohort: a prospective multicentre study." Lancet Neurol 2019, 9 pages.

Zhang et al., "Biomarkers of Traumatic Brain Injury and Their Relationship to Pathology", Laskowitz D, Grant G, editors. Translational Research in Traumatic Brain Injury, Chapter 12, Taylor and Francis Group, 2016, 12 pages.

Zhou, H. et al., "Moderate traumatic brain injury triggers rapid necrotic death of immature neurons in the hippocampus." *Journal of Neuropathology and Experimental Neurology*. Apr. 1, 2012;71(4):348-59.

Zoltewicz et al., "Characterization of Antibodies that Detect Human GFAP after Traumatic Brain Injury." Biomarker Insights 2012; 7:71-79.

UCH-L1 Antibody (C-4): sc-271639. Datasheet [online]. Santa Cruz Biotechnology Inc., 2007, Retrieved from the Internet: <URL:https://www.scbt.com/p/uch-11-antibody-c-4>.

UCH-L1 Antibody Goat Anti Human Protein Gene Product 9.5 (N-Terminal) [online]. Genwaybio, 1998, Retrieved from the Internet: <URL:https://www.genwaybio.com/protein-gene-product-9-1037>.

International Search Report & Written Opinion mailed Dec. 7, 2017 for International Application No. PCT/US2017/054787, 15 pages.

International Search Report & Written Opinion mailed Sep. 17, 2018 for International Application No. PCT/US2018/040612, 15 pages.

International Search Report & Written Opinion mailed Sep. 10, 2018 for International Application No. PCT/US2018/024112, 19 pages.

International Search Report & Written Opinion mailed Sep. 10, 2018 for International Application No. PCT/US2018/034694, 15 pages.

International Search Report & Written Opinion mailed Aug. 2, 2018 for International Application No. PCT/US2018/027353, 21 pages.

(56) References Cited

OTHER PUBLICATIONS

International Search Report & Written Opinion mailed Dec. 1, 2017 for International Application No. PCT/US2017/054775, 14 pages.
International Search Report & Written Opinion mailed Dec. 1, 2017 for International Application No. PCT/US2018/035232, 15 pages.
International Search Report & Written Opinion mailed Aug. 2, 2018 for International Application No. PCT/US2018/029585, 23 pages.
International Search Report & Written Opinion mailed Sep. 3, 2018 for PCT/US2018/035231, 14 pages.
International Search Report & Written Opinion mailed Apr. 2, 2019 for International Application No. PCT/US2018/062888, 18 pages.
International Search Report & Written Opinion mailed Jun. 4, 2019 for International Application No. PCT/US2018/064587, 26 pages.
International Search Report & Written Opinion mailed May 31, 2019 for International Application No. PCT/US2018/067683, 21 pages.
International Preliminary Report on Patentability issued Apr. 9, 2019 for International Application No. PCT/US2017/054787, 7 pages.
International Preliminary Report on Patentability issued Apr. 9, 2019 for International Application No. PCT/US2017/054775, 7 pages.
International Preliminary Report on Patentability mailed Jan. 16, 2020 for International Application No. PCT/US2018/040612, 7 pages.
International Preliminary Report on Patentability mailed Oct. 3, 2019 for International Application No. PCT/US2018/024112, 11 pages.
International Preliminary Report on Patentability mailed Oct. 3, 2019 for International Application No. PCT/US2018/027353, 13 pages.
International Preliminary Report on Patentability mailed Nov. 7, 2019 for International Application No. PCT/US2018/029585, 14 pages.
International Preliminary Report on Patentability mailed Dec. 5, 2019 for International Application No. PCT/US2018/034694, 14 pages.
International Preliminary Report on Patentability mailed Dec. 12, 2019 for International Application No. PCT/US2018/035232, 8 pages.
International Preliminary Report on Patentability mailed Dec. 12, 2019 for International Application No. PCT/US2018/035231, 8 pages.
International Searching Authority, International Search Report and Written Opinion for International Application No. PCT/US2022/077128, mailed Jan. 3, 2023.
Lawrence M. Lewis et al., Utility of Serum Biomarkers in the Diagnosis and Stratification of Mild Traumatic Brain Injury, Academic Emergency Medicine, Jun. 1, 2017, vol. 24, No. 6, pp. 710-720.
International Searching Authority, International Search Report and Written Opinion for International Application No. PCT/US2022/075638, mailed Dec. 16, 2022.
Andrew K. Ottens et al., "Neuroproteomics: A Biochemical Means to Discriminate the Extent and Modality of Brain Injury", Journal of Neurotrauma, Mary Ann Liebert, Inc., publishers., Oct. 1, 2010, 27(10), 1837-1852.
Papa Linda et al: "Evaluating glial and neuronal blood biomarkers GFAP and UCH-L1 as gradients of brain injury in concussive, subconcussive and non-concussive trauma: a prospective cohort study", BMJ Paediatrics Open, vol. 3, No. 1, Aug. 1, 2019 (Aug. 1, 2019), p. e000473, XP055951121, DOI: 10.1136/bmjpo-2019-000473 Retrieved from the Internet: URL:https://bmjpaedsopen.bmj.com/content/b mjpo/3/1/e000473.full.pdf>.
Rhine Tara et al: "2443 : Investigating markers of early traumatic brain injury (iMet): An interim analysis", Journal of Clinical and Translational Science, vol. 1, No. S1, Sep. 1, 2017 (Sep. 1, 2017), pp. 78-78, XP055951100, DOI: 10.1017/cts.2017.276.

International Searching Authority, International Search Report and Written Opinion for PCT Application No. PCT/US2022/029798, mailed Aug. 31, 2022.
Metzger Ryan R. et al: "Temporal response profiles of serum ubiquitin C-terminal hydrolase-L1 and the 145-kDa alpha II-spectrin breakdown product after severe traumatic brain injury in children", Journal of Neurosurgery. Pediatrics, vol. 22, No. 4, Oct. 1, 2018 (Oct. 1, 2018), pp. 369-374, XP055951102, us, ISSN: 1933-0707, DOI: 10.3171/2018.4.PEDS17593.
Rhine Tara et al.: "Investigating Markers of Early Traumatic Brain Injury (iMet)", Pediatrics, Aug. 1, 2019 (Aug. 1, 2019), pp. 1-4, XP055951099, Retrieved from the Internet: URL:https://publications.aap.org/pediatric s/article/144/2_MeetingAbstract/429/3499/I nvestigating-Markers-of-Early-Traumatic-Brain.
Lynne Babcock et al: "Are UCH-L1 and GFAP promising biomarkers for children with mild traumatic brain injury?", Brain Injury, vol. 30, No. 10, Aug. 23, 2016 (Aug. 23, 2016), pp. 1231-1238, XP055951118, GB, ISSN: 0269-9052, DOI: 10. 1080/02699052.2016.1178396 Retrieved from the Internet: URL:https://www.ncbi.nlm.nih.gov/pmc/articles/PMC5818714/pdf/nihms831590.pdf>.
International Searching Authority, International Search Report and Written Opinion for International Application No. PCT/US2022/033337, mailed Nov. 14, 2022.
Salim, A., et al., "Significance of Troponin Elevation After Severe Traumatic Brain Injury," The Journal of Trauma Injury, Infection, and Critical Care, Jan. 1, 2008.
Lippi, G., et al., "The concentration of highly-sensitive troponin I is increased with patients with brain injury after mild head trauma," Letter to the Editor, vol. 168, Issue 2, p. 1617-1618, Sep. 30, 2013, International Journal of Cardiology.
Giuseppe Lippi, et al., The concentration of highly-sensitive troponin I is increased in patients with brain injury after mild head trauma, International Journal of Cardiology, Jan. 1, 2013, vol. 168, No. 2, pp. 1617-1618.
Stephen S. Cai, et al., The Role of Cardiac Troponin I in Prognostication of Patients with Isolated Severe Traumatic Brain Injury, J Trauma Acute Care Surg., Jan. 1, 2016, vol. 80, No. 3, pp. 477-483.
Japan Patent Office, First Office Action for Japanese Patent Application No. 2019-565417, Mailing Date: Nov. 2, 2021.
Japan Patent Office, First Office Action for Japanese Patent Application No. 2019-565410 Mailing Date: Nov. 2, 2021.
Japan Patent Office, Office Action for Japanese Patent Application No. 2019-556261, Mailing Date: Oct. 26, 2021.
European Patent Office, Office Action for European Application No. 18731687 mailed Jun. 14, 2021.
Yuh Esther L. et al: "Magnetic resonance imaging improves 3-month outcome prediction in mild traumatic brain injury : MRI in MTBI", Annals of Neurology, vol. 73, No. 2, Dec. 7, 2012 (Dec. 7, 2012), pp. 224-235, XP055811737, Boston, US, ISSN: 0364-5134, DOI: 10.1002/ana.23783.
Japan Patent Office, First Office Action for Japanese Patent Application No. 2019-555751. Mailing Date: Mar. 8, 2022.
China National Intellectual Property Administration, First Office Action for Chinese Patent Application No. 201780061647.7 mailed Dec. 14, 2021.
Canadian Intellectual Property Office, Office Action for Canadian Application No. 3,036,717, mailed Jul. 9, 2021.
IP Australia, Examination report No. 1 for standard patent application for Australian Application No. 2017339858, mailed Feb. 5, 2021.
IP Australia, Examination report No. 2 for standard patent application for Australian Application No. 2017339858, mailed Jun. 3, 2021.
Japan Patent Office, First Office Action for Japanese Patent Application No. 2019-517951. Mailing Date: Aug. 3, 2021.
Japan Patent Office, First Office Action for Japanese Patent Application No. 2019-552078. Mailing Date: Mar. 8, 2022.
International Searching Authority, International Search Report and Written Opinion for International Application No. PCT/US2022/080578, mailed Mar. 24, 2023.

(56) References Cited

OTHER PUBLICATIONS

Korley, F. K., et al., "Comparison of GFAP and UCH-L1 Measurements from Two Prototype Assays: The Abbott i-STAT and ARCHITECT Assays," Neurotrauma Reports, vol. 2, No. 1, Apr. 7, 2021, pp. 193-199.
International Searching Authority, International Search Report and Written Opinion for International Application No. PCT/US2022/082449, mailed Mar. 24, 2023.
International Searching Authority, International Search Report and Written Opinion for International Application No. PCT/US2023/061894, mailed May 11, 2023.
Natarajan Satheesh et al: "A novel time-resolved fluorescent lateral flow immunoassay for quantitative detection of the trauma brain injury biomarker-glial fibrillary acidic protein", Sensors & Diagnostics, vol. 1, No. 1, Jan. 20, 2022 (Jan. 20, 2022), pp. 193-197.
Evgeni Eltzov et al: "Lateral Flow Immunoassays—from Paper Strip to Smartphone Technology", Electroanalysis, VHC Publishers, Inc, US, vol. 27, No. 9, Aug. 24, 2015 (Aug. 24, 2015), pp. 2116-2130.
De Puig Helena et al: "Challenges of the Nano-Bio Interface in Lateral Flow and Dipstick Immunoassays", Trends in Biotechnology, vol. 35, No. 12, Dec. 2017 (Dec. 2017), pp. 1169-1180.
International Searching Authority, International Search Report and Written Opinion for International Application No. PCT/US2022/081763, mailed May 19, 2023.
Hauser Janosch, et al., "An Autonomous Microfluidic Device for Generating Volume-Defined Dried Plasma Spots," Analytical Chemistry, vol. 91, No. 11, May 7, 2019, pp. 7125-7130.
Hart et al., "Anger Self-Management in Chronic Traumatic Brain Injury: Protocol for a Psycho-educational Treatment With a Structurally Equivalent Control and an Evaluation of Treatment Enactment," Contemp. Clin. Trials., 40:180-192 (2015).
Gomez-de-Regil, et al., "Psychological Intervention in Traumatic Brain Injury Patients," Behavioural Neurology, pp. 1-8 (2019).
Zhang Z, et al. Human traumatic brain injury induces autoantibody response against glial fibrillary acidic protein and its breakdown products. PLoS One. Mar. 25, 2014;9(3):e92698. doi: 10.1371/journal.pone.0092698. Erratum in: PLoS One. 2014;9(6):e101712.
Kim, et al. Large-scale femtoliter droplet array for digital counting of single biomolecules, Lab Chip, 2012,12, 4986-4991.
Haacke EM, et al. Imaging iron stores in the brain using magnetic resonance imaging. Magn Reson Imaging. Jan. 2005;23(1):1-25.
Ward MD, Weber A, et al., Predictive Performance of Traumatic Brain Injury Biomarkers in High-Risk Elderly Patients. J Appl Lab Med. May 1, 2020;5(3):608.
Johns Hopkins Medicine, Rehabilitation After Traumatic Brain Injury, Available at: https://www.hopkinsmedicine.org/health/treatment-tests-and-therapies/rehabilitation-after-traumatic-brain-injury Published online: Nov. 19, 2019.
European Patent Office, Partial Search Report for EP Application No. 20806307.3 mailed Jun. 26, 2023.
Bazarian Jeffrey J. et al: "Persistent, Long-term Cerebral White Matter Changes after Sports-Related Repetitive Head Impacts", PLOS ONE, vol. 9, No. 4, Apr. 16, 2014 (Apr. 16, 2014), pp. 1-12, XP93054623.
Koerte Inga K. et al: "A Review of Neuroimaging Findings in Repetitive Brain Trauma: Neuroimaging Findings in Repetitive Brain Trauma", Brain Pathology. vol. 25, No. 3, Apr. 23, 2015 (Apr. 23, 2015), pp. 318-349, XP055792317.
Sengupta Mohor B et al: "Increased expression of ApoAI after neuronal injury may be beneficial for healing", Molecular and Cellular Biochemistry, Springer US, New York, vol. 424, No. 1, Oct. 13, 2016 (Oct. 13, 2016), pp. 45-55, XP036127824.
E. Mark Haacke, "Common Data Elements in Radiologic Imaging of Traumatic Brain Injury," Journal of Magnetic Resonance Imaging 32, Apr. 28, 2010, pp. 516-543.
Jennifer Middleton, "UCH-L1 and GFAP Testing {i-STAT TBI Plasma) for the Detection of Intracranial Injury Following Mild Traumatic Brain Injury," Am Fam Physician, Mar. 1, 2022;105(3):313-314.
Wheeler, S., et al. "Effectiveness of Interventions to Improve Occupational Performance for People with Psychosocial, Behavioral, and Emotional Impairments After Brain Injury: A Systematic Review," The American Journal of Occupational Therapy, 70(3):1-9 (May/Jun. 2016).
Ustinova, K.I., et al. entitled "Physical therapy for correcting postural and coordination deficits in patients with mild-to-moderate traumatic brain injury," Physiotherapy Theory and Practice, 31(1):1-7 (2015).
Neselius Sanna et al: "CSF-Biomarkers in Olympic Boxing: Diagnosis and Effects of Repetitive Head Trauma", Plos One, vol. 7, No. 4, Apr. 4, 2012 (Apr. 4, 2012), p. e33606, XP093111333.
Biberthaler Peter et al: "Evaluation of Acute Glial Fibrillary Acidic Protein and Ubiquitin C-Terminal Hydrolase-L1 Plasma Levels in Traumatic Brain Injury Patients with and without Intracranial Lesions", Neurotrauma Reports, vol. 2, No. 1, Dec. 1, 2021 (Dec. 1, 2021), pp. 617-625, XP093043101.
Czeiter Endre et al: "Brain Injury Biomarkers May Improve the Predictive Power of the Impact Outcome Calculator", Journal of Neurotrauma., vol. 29, No. 9, Jun. 10, 2012 (Jun. 10, 2012), pp. 1770-1778, XP093111467.
International Searching Authority, International Search Report and Written Opinion for International Application No. PCT/2023/074185 mailed Jan. 5, 2024.
European Patent Office, Communication Pursuant to Article 94(3) EPC for European Application No. 18731687.2 mailed Feb. 2, 2024.
European Patent Office, Communication Pursuant to Article 94(3) EPC for European Application No. 18830037 mailed Dec. 12, 2023.
European Patent Office, Extended European Search Report for European Application No. 20806307.3 mailed Dec. 15, 2023.

FIG. 4A
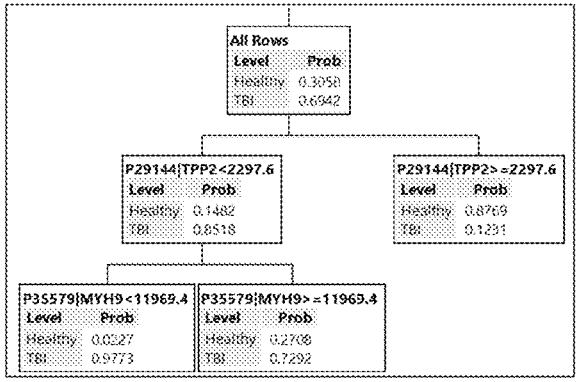
FIG. 4B
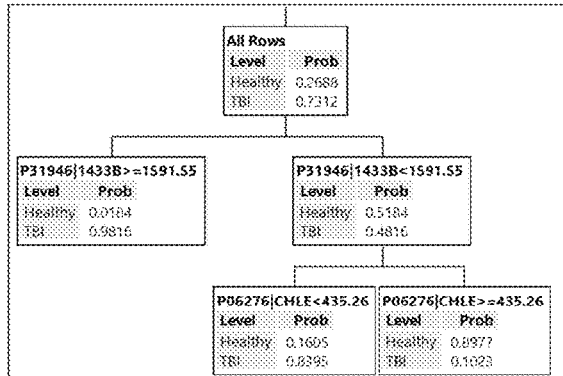
FIG. 4C
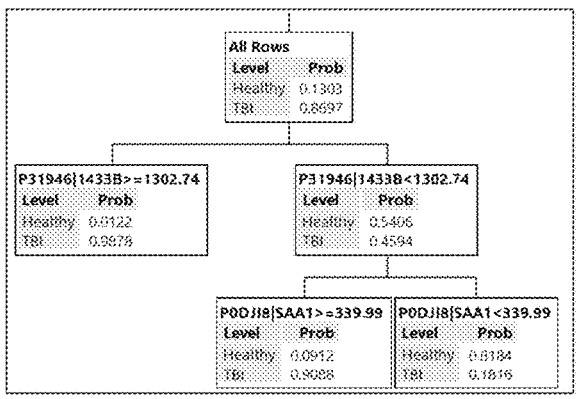
FIG. 4D
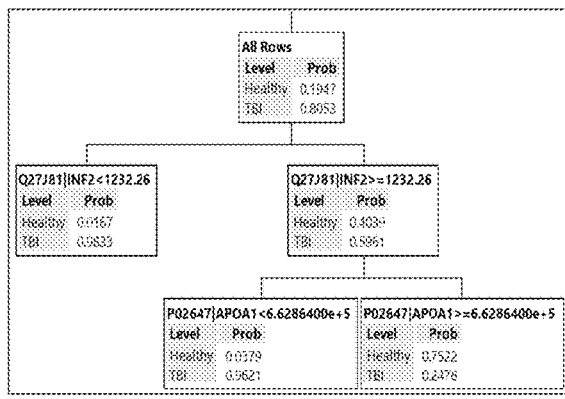
FIG. 4E
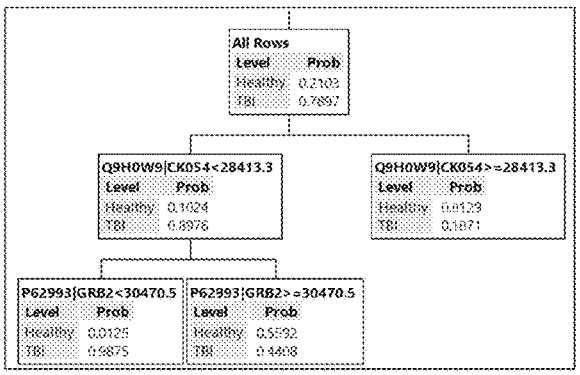
FIGS. 4A-4E

Bootstrap Forest Analysis of TBI Samples and Healthy Controls

| UniProtID | Protein name | # Splits | G^2 | | Portion |
|---|---|---|---|
| P02743 | SAMP | 1 | 2.80906154 | | 0.1212 |
| P31946 | 1433B | 2 | 2.36996202 | | 0.1022 |
| P02675 | FIBB | 1 | 2.23489869 | | 0.0964 |
| P62857 | RS28 | 1 | 2.04682092 | | 0.0883 |
| P02787 | TRFE | 1 | 1.51582032 | | 0.0654 |
| P29144 | TPP2 | 1 | 1.48716867 | | 0.0642 |
| P22352 | GPX3 | 1 | 1.23957932 | | 0.0535 |
| O75636 | FCN3 | 1 | 1.22877508 | | 0.0530 |
| P06276 | CHLE | 1 | 1.22031991 | | 0.0526 |
| Q9H0W9 | CK054 | 1 | 1.13548511 | | 0.0490 |
| P02647 | APOA1 | 1 | 1.08939039 | | 0.0470 |
| P62993 | GRB2 | 1 | 0.93895874 | | 0.0405 |
| Q27J81 | INF2 | 1 | 0.91560601 | | 0.0395 |
| P01023 | A2MG | 1 | 0.83757742 | | 0.0361 |
| P0DJI8 | SAA1 | 1 | 0.67301167 | | 0.0290 |
| P07814 | SYEP | 1 | 0.57416285 | | 0.0248 |
| P35579 | MYH9 | 1 | 0.43339278 | | 0.0187 |
| P01714 | LV301 | 1 | 0.43168406 | | 0.0186 |

FIG. 5

BIOMARKERS AND METHODS FOR DIAGNOSING AND EVALUATING TRAUMATIC BRAIN INJURY

CROSS REFERENCE TO RELATED APPLICATIONS

This application is a divisional of U.S. application Ser. No. 16/233,895, filed Dec. 27, 2018, which claims priority to U.S. Provisional Application No. 62/611,778, filed Dec. 29, 2017, and U.S. Provisional Application No. 62/630,704, filed Feb. 14, 2018, all of which are incorporated herein by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 334,546 Byte ASCII (Text) file named "2021-06-09_36107-404_SQL_ST25," created on Jun. 9, 2021.

FIELD

The present disclosure relates to methods for diagnosing and evaluating a subject that has sustained or may have sustained an injury to the head, such as a traumatic brain injury (TBI). In particular, the present disclosure identifies various biomarkers, the detection and/or differential expression of which can be used to assess the presence or absence of a TBI in a subject, and can be used as a basis for diagnosing a subject as having a specific type of TBI (e.g., severe TBI or subclasses of mild TBI). The various TBI biomarkers can be detected individually or in combination and can be used as an important diagnostic, prognostic, and/or TBI risk stratification tool as part of assessing a subject's TBI status.

BACKGROUND

More than 5 million mild traumatic brain injuries (mTBIs) occur each year in the United States alone. Currently, there is no simple, objective, accurate measurement available to help in patient assessment. In fact, much of TBI evaluation and diagnosis is based on subjective data. Unfortunately, objective measurements such as head CT and Glasgow Coma Score (GCS) are not very comprehensive or sensitive in evaluating mild TBI. Moreover, head CT is unrevealing for the vast majority of the time for mTBI, is expensive, and exposes the patient to unnecessary radiation. Additionally, a negative head CT does not mean the patient has been cleared from having a concussion; rather, it may simply indicate that certain interventions, such as surgery, are not warranted. Clinicians and patients need objective, reliable information to accurately evaluate this condition to promote appropriate triage and recovery. To date, limited data have been available for the use of biomarkers to aid in patient diagnosis, evaluation, and management.

The majority of TBI's are mild; however, the ability to diagnose and treat mTBI is insufficient, in large part because the ability to characterize accurately the different TBI disease states or "disease signatures" is lacking. This insufficiency generally stems from challenges associated with interpreting ambiguous clinically presented symptoms and ineffective imaging techniques. Thus, researchers have begun to explore cellular and molecular based approaches to improve both diagnosis and prognosis. This has been met with a variety of challenges, including difficulty in relating biological markers to current clinical symptoms, and overcoming our lack of fundamental understanding of the pathophysiology of mTBI. However, recent adoption of techniques such as high-throughput technologies and computational biology have provided the means for more accurately determining and characterizing TBI disease states.

Because the underlying pathophysiology of TBI remains undetermined, effective and efficient diagnostic, prognostic, risk stratification, and/or therapeutic tools are not yet currently available, especially in a clinical setting. Researchers have begun to investigate TBI at the cellular and molecular level, as shortcomings in current brain imaging techniques and flawed clinical diagnostic approaches have increased the appeal of utilizing the peripheral blood to identify immune and damage related signaling between the brain and the periphery. The ultimate goal of this approach is to uncover single TBI biomarkers or panels of biomarkers to aid in early detection and diagnosis, to effectively distinguish between various TBI disease states (e.g., mTBI vs. severe TBI or sTBI), and to help predict patient outcomes. Furthermore, these approaches may help elucidate underlying biological mechanisms and provide greater insight into therapeutic strategies.

SUMMARY

Embodiments of the present disclosure include a method of measuring or detecting at least one biomarker. In accordance with these embodiments, the method includes obtaining a sample from a subject after an actual or suspected head injury; and measuring or detecting at least one biomarker or fragment thereof selected from the group consisting of AL9A1, ATPG, C1RL, CAND1, EPIPL, GLO2, IGHA2, PZP, SYTC, SYYC, or any combinations thereof in the sample; and/or measuring or detecting at least one biomarker of fragment thereof selected from the group consisting of ABHEB, AL9A1, DNM1L, FCN2, INF2, K22E, M3K5, NCOR1, SBSN, SYEP, TPP2, or any combinations thereof in the sample. In some embodiments, the measurement or detection of the at least one biomarker indicates that the subject has sustained or may have sustained a traumatic brain injury (TBI).

Embodiments of the present disclosure also include a method of measuring or detecting at least one biomarker that includes obtaining a sample from a subject after an actual or suspected head injury; and measuring or detecting at least one biomarker or fragment thereof selected from the group consisting of 1433G, ACK1, ACY1, AKA12, ARGI1, CADH5, CLH1, COPG2, DPOD2, DSG2, HV307, IQGA2, K1C14, K1C19, KV105, LAMC1, MDHM, NQO2, PERM, PLST, PNCB, PTPRC, SEPT7, SYRC, TRXR2, TXNL1, UGGG1, WDR1 or any combinations thereof in the sample. In some embodiments, the measurement or detection of the at least one biomarker indicates that the subject has sustained or may have sustained a mild traumatic brain injury (mTBI).

Embodiments of the present disclosure also include a biomarker panel for determining traumatic brain injury (TBI) status of a subject. In accordance with these embodiments, the panel includes at least one of the following biomarkers: TPP2, CAND1, NCOR1, K22E, AL9A1, ABHEB, DNM1L, INF2, or any combinations thereof; wherein measurement or detection of the at least one biomarker indicates that the subject has sustained or may have sustained a mild TBI of subclass 4.

Embodiments of the present disclosure also include a biomarker panel for determining traumatic brain injury (TBI) status of a subject that includes at least one of the following biomarkers: TPP2, NCOR1, HV103, INF2, IGHD, CK054, M3K5, ABHEB, AL9A1, DNM1L, or any combinations thereof; wherein measurement or detection of the at least one biomarker indicates that the subject has sustained or may have sustained a mild TBI of subclass 3.

Embodiments of the present disclosure also include a biomarker panel for determining traumatic brain injury (TBI) status of a subject that includes at least one of the following biomarkers: NCOR1, TPP2, K22E, ABHEB, INF2, SBSN, AL9A1, MA2B2, or any combinations thereof; wherein measurement or detection of the at least one biomarker indicates that the subject has sustained or may have sustained a mild TBI of subclass 2.

Embodiments of the present disclosure also include a biomarker panel for determining traumatic brain injury (TBI) status of a subject that includes at least one of the following biomarkers: K22E, DNM1L, DIAP1, ABHEB, PLOD1, SYEP, KV133, AL9A1, EPHB4, or any combinations thereof; wherein measurement or detection of the at least one biomarker indicates that the subject has sustained or may have sustained a mild TBI of subclass 1.

Embodiments of the present disclosure also include a biomarker panel for determining traumatic brain injury (TBI) status of a subject that includes at least one of the following biomarkers: CAND1, NCOR1, K22E, ABHEB, DNM1L, SBSN, GLO2, SYEP, or any combinations thereof; wherein measurement or detection of higher levels of the at least one biomarker in the subject as compared to levels of the at least one biomarkers in a healthy subject indicates that the subject has sustained or may have sustained a mild TBI of subclass 4.

Embodiments of the present disclosure also include a biomarker panel for determining traumatic brain injury (TBI) status of a subject that includes at least one of the following biomarkers: NCOR1, HV103, IGHD, ABHEB, DNM1L, ALBU, THIM, IGHA2, KV139, and, or any combinations thereof; wherein measurement or detection of higher levels of the at least one biomarker in the subject as compared to levels of the at least one biomarkers in a healthy subject indicates that the subject has sustained or may have sustained a mild TBI of subclass 3.

Embodiments of the present disclosure also include a biomarker panel for determining traumatic brain injury (TBI) status of a subject that includes at least one of the following biomarkers: NCOR1, K22E, ABHEB, SBSN, DNM1L, DIAP1, DYL1, PSA, EPHB4, or any combinations thereof; wherein measurement or detection of higher levels of the at least one biomarker in the subject as compared to levels of the at least one biomarkers in a healthy subject indicates that the subject has sustained or may have sustained a mild TBI of subclass 2.

Embodiments of the present disclosure also include a biomarker panel for determining traumatic brain injury (TBI) status of a subject that includes at least one of the following biomarkers: K22E, DNM1L, DIAP1, ABHEB, PLOD1, SYEP, EPHB4, FBLN3, or any combinations thereof; wherein measurement or detection of higher levels of the at least one biomarker in the subject as compared to levels of the at least one biomarkers in a healthy subject indicates that the subject has sustained or may have sustained a mild TBI of subclass 1.

Embodiments of the present disclosure also include a biomarker panel for determining that a subject has not sustained a traumatic brain injury (TBI) that includes at least one of the following biomarkers: ACTBL, ALDH2, ANXA5, CAMP, CPNE3, CRAC1, CYTC, DNPEP, EIF3I, GSHB, ICAM1, HV323, HNRPD, KVD33, FA9, FHR4, FRPD1, HS90B, MA2A1, PCYOX, PNPH, PROC, RL3, SH3L3, SRRM2, TBB1, TENA, TRAP1 or any combinations thereof; wherein measurement or detection of the at least one biomarker in the subject indicates that the subject has not sustained a TBI.

BRIEF DESCRIPTION OF THE DRAWINGS

FIG. 1A is a representative phylogenic plot resulting from unsupervised clustering analysis of whole proteome profile data showing two major clusters (control cluster) and TBI clusters (TBI subclass 1=TBI-1; TBI subclass 2=TBI-2; TBI subclass 3=TBI-3; and TBI subclass 4=Complex TBI), along with associated patient and sample characteristics that were extracted post-hoc including Age; Gender; Normalized GFAP MS peak area (using targeted mass spectrometry-based GFAP assay based on quantification of individual proteotypic peptides); CT scan (positive/negative; gray indicates no data); and ELISA-based GFAP biomarker scores (positive/negative; gray indicates no data). Predominant pathological clusters of mild TBI subclasses include subclass 1 (TBI-1), subclass 2 (TBI-2), subclass 3 (TBI-3), and subclass 4 (Complex TBI), which is also referred to herein as "complicated mild TBI. " FIG. 1B includes results from principal component analysis of the whole proteome profile. FIG. 1C includes representative phylogenic clustering depicted as a constellation plot.

FIG. 2A is a representative Venn diagram that includes shared and/or unique proteins between the five identified subgroup clusters. FIG. 3B includes a numeric count of total proteins and/or unique proteins quantified in each subgroup cluster. FIG. 3C includes Uniprot ID and short name designations for the unique proteins quantified in each subgroup cluster.

FIGS. 3A-3B include a representative Venn plot of proteins that are shared or unique between healthy (left circle) and TBI patient samples (including the pooled severe sample; right circle). Only proteins detected in all the samples in each group were included in this analysis (FIG. 3A). FIG. 3B includes a list of 8 proteins uniquely expressed in all TBI samples, including their Uniprot ID and protein name. AL9A1 and SYTC are expressed in brain while FA5 is related to coagulation (both designations are based on annotated information from UniProt (uniprot.org)).

FIG. 4A-4E include representative schematics of Bootstrap Forest Analysis as an alternative approach to traditional supervised analysis of quantitative independent acquisition-mass spectrometry (DIA-MS) data. Contributions of individual proteins were analyzed and summarized in the five separate decision trees that met the criteria of the prediction model (FIGS. 4A-4E). This analysis ascribed a quantitative cutoff for the ability of a given protein to serve as a biomarker capable of distinguishing patients with TBI from their healthy counterparts, along with an associated diagnostic probability. In the case where a single protein was insufficiently capable of making this distinction, a combination of multiple proteins is identified and defined.

FIG. 5 is a table of a Bootstrap Forest Analysis that was performed as an alternative approach to traditional supervised analysis of quantitative DIA-MS data. This analysis ranks proteins according to their contributing portion of a whole.

DETAILED DESCRIPTION

Figures 1A, 1B, 1C:
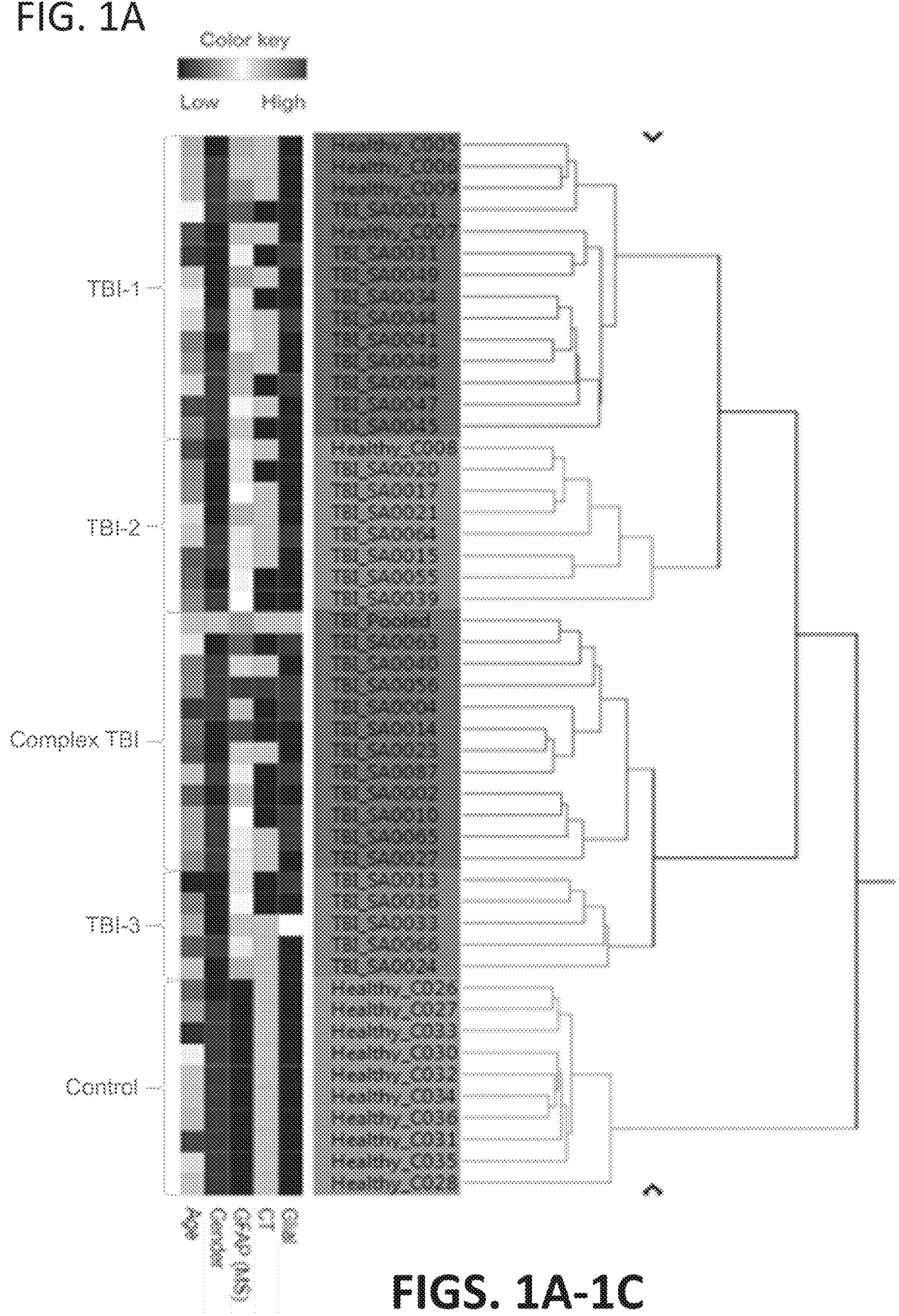
FIGS. 1A-1C include representative graphs obtained from unsupervised clustering analysis of quantitative mass spectrometry discovery proteomic data from plasma samples obtained from subjects classified as healthy or as having mild TBI based on clinical physiological information, as well as pooled plasma from severe (i.e. CT positive) subjects. All data points are labeled according to their cluster locations in FIG. 1A.

The present disclosure relates to methods for diagnosing and evaluating a subject that has sustained or may have sustained an injury to the head, such as a traumatic brain injury (TBI). In particular, the present disclosure identifies various biomarkers, the detection and/or differential expression of which can be used to assess the presence or absence of a TBI in a subject, and can be used as a basis for diagnosing a subject as having a specific type of TBI (e.g., severe TBI or subclasses of mTBI). The various TBI biomarkers can be detected individually or in combination and can be used as an important diagnostic and therapeutic tool for assessing a subject's TBI status.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

An "absolute amount" as used herein refers to the absolute value of a change or difference between at least two assay results taken or sampled at different time points and, which similar to a reference level, has been linked or is associated herein with various clinical parameters (e.g., presence of disease, stage of disease, severity of disease, progression, non-progression, or improvement of disease, etc.). "Absolute value" as used herein refers to the magnitude of a real number (such as, for example, the difference between two compared levels (such as levels taken at a first time point and levels taken at a second time point)) without regard to its sign, i.e. regardless of whether it is positive or negative.

This disclosure provides exemplary reference levels and absolute amounts (e.g., calculated by comparing reference levels at different time points). However, it is well-known that reference levels and absolute amounts may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels and absolute amounts for those other immunoassays based on the description provided by this disclosure. Whereas the precise value of the reference level and absolute amount may vary between assays, the findings as described herein should be generally applicable and capable of being extrapolated to other assays.

"Affinity matured antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994); Schier et al., *Gene*, 169: 147-155 (1995); Yelton et al., *J. Immunol.*, 155: 1994-2004 (1995); Jackson et al., *J. Immunol.*, 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11): 1290-1297 (2007) and PCT International Application WO 2001/058956, the contents of each of which are herein incorporated by reference), or domain antibodies (dAbs) (e.g., such as described in Holt et al. (2014) Trends in Biotechnology 21:484-490), and including single domain antibodies sdAbs that are naturally occurring, e.g., as in cartilaginous fishes and camelid, or which are synthetic, e.g., nanobodies, VHH, or other domain structure), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2).

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$. (or $FeO \cdot Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., *Nature*, 305(5934): 537-540 (1983)), by chemical conjugation of two different monoclonal antibodies (see, Staerz et al., *Nature*, 314(6012): 628-631 (1985)), or by knob-into-hole or similar approaches, which introduce mutations in the Fc region (see Holliger et al., *Proc. Natl. Acad. Sci. USA*, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, *J. Mol. Biol.*, 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, *FASEB J.*, 9: 133-139 (1995), and MacCallum, *J. Mol. Biol.*, 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Coefficient of variation" (CV), also known as "relative variability," is equal to the standard deviation of a distribution divided by its mean.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"Controls" as used herein generally refers to a reagent whose purpose is to evaluate the performance of a measurement system in order to assure that it continues to produce results within permissible boundaries (e.g., boundaries ranging from measures appropriate for a research use assay on one end to analytic boundaries established by quality specifications for a commercial assay on the other end). To accomplish this, a control should be indicative of patient results and optionally should somehow assess the impact of error on the measurement (e.g., error due to reagent stability, calibrator variability, instrument variability, and the like). As used herein, a "control subject" relates to a subject or subjects that have not sustained a traumatic brain injury (TBI). An "ortho control" as used herein relates to (e.g., is based on) samples or information from a subject or subjects that have sustained an orthopedic injury but have not sustained an apparent TBI. As used herein, an "ortho control subject" relates to a subject or subjects that have sustained an orthopedic injury but have not sustained an apparent TBI. In some cases, "ortho control subjects" are adult orthopedic patients who have an Abbreviated Injury Score of ≤4 (not life threatening) for their extremity and/or pelvis injury and/or rib fracture. A "healthy control" as used herein relates to (e.g., is based on) samples or information from a subject or subjects that are considered healthy and have sustained no apparent TBI or orthopedic injury. As used herein, a "healthy control subject" relates to a subject or subjects that are considered to be healthy and have sustained no apparent TBI or orthopedic injury. As used herein, "TBI control" as used herein relates to (e.g., is based on) samples or information from a subject or subjects that have sustained a head injury but have not sustained an apparent TBI. As used herein, a "TBI control subject" relates to a subject or subjects that have sustained a head injury but have not sustained an apparent TBI.

"Correlated to" as used herein refers to compared to.

"CT scan" as used herein refers to a computerized tomography (CT) scan. A CT scan combines a series of X-ray images taken from different angles and uses computer processing to create cross-sectional images, or slices, of the bones, blood vessels and soft tissues inside your body. The CT scan may use X-ray CT, positron emission tomography (PET), single-photon emission computed tomography (SPECT), computed axial tomography (CAT scan), or computer aided tomography. The CT scan may be a conventional CT scan or a spiral/helical CT scan. In a conventional CT scan, the scan is taken slice by slice and after each slice the scan stops and moves down to the next slice, e.g., from the top of the abdomen down to the pelvis. The conventional CT scan requires patients to hold their breath to avoid movement artefact. The spiral/helical CT scan is a continuous scan which is taken in a spiral fashion and is a much quicker process where the scanned images are contiguous.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"DIA-MS" or "data-independent acquisition mass spectrometry" is used herein to refer to a method of molecular structure determination in which all ions within a selected m/z range are fragmented and analyzed in a second stage of tandem mass spectrometry. Typically, a complex protein mixture (e.g., plasma samples) is digested into peptides and the peptides are analyzed in a mass spectrometer. Tandem mass spectra are generally acquired on each peptide either by fragmenting all ions that enter the mass spectrometer at a given time (i.e. DIA-MS) or by sequentially isolating and fragmenting ranges of m/z (i.e. data-dependent acquisition-MS or DDA-MS). DIA-MS is an alternative to DDA-MS where a fixed number of precursor ions are selected and analyzed by tandem mass spectrometry, but most often can provide the same protein information. Proteotypic peptides (a peptide that is unique to a specific protein identification) are used for quantification of each protein. (See: Holewinski, R. J., et al. Methods Mol Biol. 2016; 1410:165-279; Kirk, J. A., et al. Sci Transl Med. 2015 Dec. 23; 7(319): 319ra; and Parker, S. J., et al. Proteomics. 2016 August; 16(15-16): 2221-2237.)

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e. capable of binding one antigen (or one specific epitope), or multispecific, i.e. capable of binding two or more antigens (i.e. two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e. two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

"Dynamic range" as used herein refers to range over which an assay readout is proportional to the amount of target molecule or analyte in the sample being analyzed. The dynamic range can be the range of linearity of the standard curve.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fragment," "biomarker fragment," or "biomarker peptide" as used herein includes any identifying fragment of any of the TBI biomarkers identified and described herein. "Fragment(s)" include peptides, prototypic peptides, proteolytic peptides, isoforms, including SNPs or post-translationally modified forms, and any endogenously or exogenously induced forms, of any TBI biomarker identified and described herein. Biomarker peptides can be used to represent the quantity of their representative protein in DIA-MS, DDA-MS, multiple reaction monitoring (MRM, also known as selective reaction monitoring or SRM) mass spectrometry assays, or parrell reaction monitoring (PRM) mass spectrometry assays. Proteolytic peptide(s) can be targeted for MS quantification individual or along with internal standards. (See: Fu, Q., et al. J Proteome Res. 2017 November (doi: 10.1021/acs.jproteome.7b00623); Fu, Q., et al. Methods Mol Biol. 2016; 1410: 249-264; and Liu, X., et al. Methods. 2013 Jun. 15; 61(3): 304-312.)

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMunoGeneTics® (IMGT®) information system (hypertext transfer protocol://imgt.cines.fr/texts/IMGTrepertoire/LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"GFAP" is used herein to describe glial fibrillary acidic protein. GFAP is a protein that is encoded by the GFAP gene in humans, and which can be produced (e.g., by recombinant means, in other species). "GFAP status" can mean either the level or amount of GFAP that is circulating at a point in time (such as with a single measure of GFAP), the level or amount of GFAP associated with monitoring (such as with a repeat test on a subject to identify an increase or decrease in GFAP amount), the level or amount of GFAP associated with treatment for traumatic brain injury (whether a primary brain injury and/or a secondary brain injury) or combinations thereof. GFAP was measured by ELISA and by targeted mass spectrometry to specific peptides that were unique to GFAP.

"Glasgow Coma Scale" or "GCS" as used herein refers to a 15 point scale for estimating and categorizing the outcomes of brain injury on the basis of overall social capability or dependence on others. The test measures the motor response, verbal response and eye opening response with these values: I. Motor Response (6—Obeys commands fully; 5—Localizes to noxious stimuli; 4—Withdraws from noxious stimuli; 3—Abnormal flexion, i.e. decorticate posturing; 2—Extensor response, i.e. decerebrate posturing; and 1—No response); II. Verbal Response (5—Alert and Oriented; 4—Confused, yet coherent, speech; 3—Inappropriate words and jumbled phrases consisting of words; 2—Incomprehensible sounds; and 1—No sounds); and III. Eye Opening (4—Spontaneous eye opening; 3—Eyes open to speech; 2—Eyes open to pain; and 1—No eye opening). The final score is determined by adding the values of I+II+III. The final score can be categorized into four possible levels for survival, with a lower number indicating a more severe injury and a poorer prognosis: Mild (13-15); Moderate Disability (9-12) (Loss of consciousness greater than 30 minutes; Physical or cognitive impairments which may or may resolve: and Benefit from Rehabilitation); Severe Disability (3-8) (Coma: unconscious state. No meaningful response, no voluntary activities); and Vegetative State (Less Than 3) (Sleep wake cycles; Arousal, but no interaction with environment; No localized response to pain). Moderate brain injury is defined as a brain injury resulting in a loss of consciousness from 20 minutes to 6 hours and a Glasgow Coma Scale of 9 to 12. Severe brain injury is defined as a brain injury resulting in a loss of consciousness of greater than 6 hours and a Glasgow Coma Scale of 3 to 8.

"Glasgow Outcome Scale" as used herein refers to a global scale for functional outcome that rates patient status into one of five categories: Dead, Vegetative State, Severe Disability, Moderate Disability or Good Recovery.

"Extended Glasgow Outcome Scale" or "GOSE" as used interchangeably herein provides more detailed categorization into eight categories by subdividing the categories of severe disability, moderate disability and good recovery into a lower and upper category as shown in Table 1.

TABLE 1

| 1 | Death | D | |
|---|---|---|---|
| 2 | Vegetative state | VX | |
| 3 | Lower severe disability | SD− | Condition of unawareness with only reflex responses but with periods of spontaneous eye opening |
| 4 | Upper severe disability | SD+ | |
| 5 | Lower moderate disability | MD− | Patient who is dependent for daily support for mental or physical disability, usually a combination of both. If the patient can be left alone for more than 8 hours at home it is upper level of SD, if not then it is low level of SD. |
| 6 | Upper moderate disability | MD+ | |

TABLE 1-continued

| 7 | Lower good recovery | GR− | Patients have some disability such as aphasia, hemiparesis or epilepsy and/or deficits of memory or personality but are able to look after themselves. They are independent at home but dependent outside. If they are able to return to work even with special arrangement it is upper level of MD, if not then it is lowlevel of MD. |
|---|---|---|---|
| 8 | Upper good recovery | GR+ | |

"Humanized antibody" is used herein to describe an antibody that comprises heavy and light chain variable region sequences from a non-human species (e.g., a mouse) but in which at least a portion of the VH and/or VL sequence has been altered to be more "human-like," i.e. more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e. donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)." In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the amino acid or nucleotide sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Imaging procedure" as used herein refers to a medical test that allows the inside of a body to be seen in order to diagnose, treat, and monitor health conditions. An imaging procedure can be a non-invasive procedure that allows diagnosis of diseases and injuries without being intrusive. Examples of imaging procedures include MRI, CT scan, X-rays, positron emission tomography (PET) scan, single-photon emission computed tomography (SPECT), and diffusion tensor imaging (DTI) scan.

"Injury to the head" or "head injury" as used interchangeably herein, refers to any trauma to the scalp, skull, or brain. Such injuries may include only a minor bump on the skull or may be a serious brain injury. Such injuries include primary injuries to the brain and/or secondary injuries to the brain. Primary brain injuries occur during the initial insult and result from displacement of the physical structures of the brain. More specifically, a primary brain injury is the physical damage to parenchyma (tissue, vessels) that occurs during the traumatic event, resulting in shearing and compression of the surrounding brain tissue. Secondary brain injuries occur subsequent to the primary injury and may involve an array of cellular processes. More specifically, a secondary brain injury refers to the changes that evolve over a period of time (from hours to days) after the primary brain injury. It includes an entire cascade of cellular, chemical, tissue, or blood vessel changes in the brain that contribute to further destruction of brain tissue.

An injury to the head can be either closed or open (penetrating). A closed head injury refers to a trauma to the scalp, skull or brain where there is no penetration of the skull by a striking object. An open head injury refers a trauma to the scalp, skull or brain where there is penetration of the skull by a striking object. An injury to the head may be caused by physical shaking of a person, by blunt impact by an external mechanical or other force that results in a closed or open head trauma (e.g., vehicle accident such as with an automobile, plane, train, etc.; blow to the head such as with a baseball bat, or from a firearm), a cerebral vascular accident (e.g., stroke), one or more falls (e.g., as in sports or other activities), explosions or blasts (collectively, "blast injuries") and by other types of blunt force trauma. Alternatively, an injury to the head may be caused by the ingestion and/or exposure to a chemical, toxin or a combination of a chemical and toxin. Examples of such chemicals and/or toxins include fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. Alternatively, an injury to the head may be caused as a result of a subject suffering from an autoimmune disease, a metabolic disorder, a brain tumor, one or more viruses, meningitis, hydrocephalus, hypoxia or any combinations thereof. In some cases, it is not possible to be certain whether any such event or injury has occurred or taken place. For example, there may be no history on a patient or subject, the subject may be unable to speak, the subject may not be aware of or have full information on what events they were exposed to, etc. Such circumstances are described herein as the subject "may have sustained an injury to the head." In certain embodiments herein, the closed head injury does not include and specifically excludes a cerebral vascular accident, such as stroke.

"Intracranial lesion" as used herein refers to an area of injury within the brain. An intracranial lesion can be an abnormality seen on a imaging procedure or brain-imaging test, such as MRI or CT scan. On CT or MRI scans, brain lesions can appear as dark or light spots that do not look like normal brain tissue.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oregon. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. *Med. Chem. Lett.* 16: 1324-1328 (2006); Adamczyk et al., *Bioorg. Med. Chem. Lett.* 4: 2313-2317 (2004); Adamczyk et al., *Biorg. Med. Chem. Lett.* 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamczyk et al., *J. Org. Chem.* 63: 5636-5639 (1998); Adamczyk et al., *Tetrahedron* 55: 10899-10914 (1999); Adamczyk et al., *Org. Lett.* 1: 779-781 (1999); Adamczyk et al., *Bioconjugate Chem.* 11: 714-724 (2000); Mattingly et al., *In Luminescence Biotechnology: Instruments and Applications*; Dyke, K. V. Ed.; CRC Press: Boca Raton, pp. 77-105 (2002); Adamczyk et al., *Org. Lett.* 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, MI). Methods for preparing acridinium 9-carboxylate aryl esters are described in McCapra et al., *Photochem. Photobiol.* 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e. in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Limit of Blank (LoB)" as used herein refers to the highest apparent analyte concentration expected to be found when replicates of a blank sample containing no analyte are tested.

"Limit of Detection (LoD)" as used herein refers to the lowest concentration of the measurand (i.e. a quantity intended to be measured) that can be detected at a specified level of confidence. The level of confidence is typically 95%, with a 5% likelihood of a false negative measurement. LoD is the lowest analyte concentration likely to be reliably distinguished from the LoB and at which detection is feasible. LoD can be determined by utilizing both the measured LoB and test replicates of a sample known to contain a low concentration of analyte. The LoD term used herein is based on the definition from Clinical and Laboratory Standards Institute (CLSI) protocol EP17-A2 ("Protocols for Determination of Limits of Detection and Limits of Quantitation; Approved Guideline—Second Edition," EP17A2E, by James F. Pierson-Perry et al., Clinical and Laboratory Standards Institute, Jun. 1, 2012).

"Limit of Quantitation (LoQ)" as used herein refers to the lowest concentration at which the analyte can not only be reliably detected but at which some predefined goals for bias and imprecision are met. The LoQ may be equivalent to the LoD or it could be at a much higher concentration.

"Linearity" refers to how well the method or assay's actual performance across a specified operating range approximates a straight line. Linearity can be measured in terms of a deviation, or non-linearity, from an ideal straight line. "Deviations from linearity" can be expressed in terms of percent of full scale. In some of the methods disclosed herein, less than 10% deviation from linearity (DL) is achieved over the dynamic range of the assay. "Linear" means that there is less than or equal to about 20%, about 19%, about 18%, about 17%, about 16%, about 15%, about 14%, about 13%, about 12%, about 11%, about 10%, about 9%, or about 8% variation for or over an exemplary range or value recited.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6×His tag, which has an amino acid sequence of HHHHHH (SEQ ID NO: 1), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO: 2) and derivatives thereof (e.g., ADDDDK (SEQ ID NO: 3), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Magnetic resonance imaging" or "MRI" as used interchangeably herein refers to a medical imaging technique used in radiology to form pictures of the anatomy and the physiological processes of the body in both health and disease. MRI is a form of medical imaging that measures the response of the atomic nuclei of body tissues to high-frequency radio waves when placed in a strong magnetic field, and that produces images of the internal organs. MRI scanners, which is based on the science of nuclear magnetic resonance (NMR), use strong magnetic fields, radio waves, and field gradients to generate images of the inside of the body.

"Monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long term care and/or hospice facility). Examples of point-of-care devices include those produced by Abbott Laboratories (Abbott Park, IL) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a reference level or control level (e.g., "low", "medium", or "high" levels), can be used. Multiple calibrators (i.e. more than one calibrator or a varying amount of calibrator(s)) can be used in conjunction to comprise a "sensitivity panel."

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e. the bifunctional antibodies have a dual specificity.

"Reference level" as used herein refers to an assay cutoff value that is used to assess diagnostic, prognostic, or therapeutic efficacy and that has been linked or is associated herein with various clinical parameters (e.g., presence of disease, stage of disease, severity of disease, progression, non-progression, or improvement of disease, etc.) This disclosure provides exemplary reference levels. However, it is well-known that reference levels may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels for those other immunoassays based on the description provided by this disclosure. Whereas the precise value of the reference level may vary between assays, the findings as described herein should be generally applicable and capable of being extrapolated to other assays.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "specimen," "sample from a subject," and "patient sample" as used herein may be used interchangeably and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

A variety of cell types, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, red blood cells, platelets, interstitial fluid, cerebral spinal fluid, etc. Cell types and tissues may also include lymph fluid, cerebrospinal fluid, a fluid collected by A tissue or cell type may be provided by removing a sample of cells from a human and a non-human animal, but can also be accomplished by using previously isolated cells (e.g., isolated by another person, at another time, and/or for another purpose). As well as IPSC or IPSC-derived cell types (e.g., motor neurons) from individuals. Archival tissues, such as those having treatment or outcome history, may also be used. Protein or nucleotide isolation and/or purification may not be necessary.

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, aptamers (e.g., RNA and DNA aptamers), and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Subject" and "patient" as used herein interchangeably refers to any vertebrate, including, but not limited to, a mammal and a human. In some embodiments, the subject may be a human or a non-human. The subject or patient may be undergoing other forms of treatment. In some embodiments, when the subject is a human, the subject does not include any humans who have suffered a cerebrovascular accident (e.g., a stroke). In some embodiments, the subject is suspected to have sustained an injury to the head. In some embodiments, the subject is known to have sustained an injury to the head. In some embodiments, the subject is suspected to be suffering from mild, moderate or severe TBI. In some embodiments, the subject is suspected to be suffering from mild TBI. In some embodiments, the subject is suspected to be suffering from moderate TBI. In some embodiments, the subject is suspected to be suffering from severe TBI.

"Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

As used herein the term "single molecule detection" refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

"Traumatic Brain Injury" or "TBI" as used interchangeably herein refers to a complex injury with a broad spectrum of symptoms and disabilities. TBI is most often an acute event similar to other injuries. TBI can be classified as "mild," "moderate," or "severe." When referred to herein merely as "TBI," generally this means any category of TBI (e.g., mild, moderate, or severe). The causes of TBI are diverse and include, for example, physical shaking by a person, a car accident, injuries from firearms, cerebral vascular accidents (e.g., strokes), falls, explosions or blasts and other types of blunt force trauma. Other causes of TBI include the ingestion and/or exposure to one or more chemicals or toxins (such as fires, molds, asbestos, pesticides and insecticides, organic solvents, paints, glues, gases (such as carbon monoxide, hydrogen sulfide, and cyanide), organic metals (such as methyl mercury, tetraethyl lead and organic tin), one or more drugs of abuse or combinations thereof). Alternatively, TBI can occur in subjects suffering from an autoimmune disease, a metabolic disorder, a brain tumor, hypoxia, one or more viruses, meningitis, hydrocephalus or combinations thereof. Young adults and the elderly are the age groups at highest risk for TBI. In certain embodiments herein, traumatic brain injury or TBI does not include and specifically excludes cerebral vascular accidents such as strokes.

"Mild TBI" as used herein refers to a brain injury where loss of consciousness is brief and usually a few seconds or minutes and/or confusion and disorientation is shorter than 1 hour. Mild TBI is also referred to as a concussion, minor head trauma, minor TBI, minor brain injury, and minor head injury. While MRI and CT scans are often normal, the individual with mild TBI may have cognitive problems such as headache, difficulty thinking, memory problems, attention deficits, mood swings and frustration.

Mild TBI is the most prevalent TBI and is often missed at time of initial injury. Typically, a subject has a Glasgow Coma scale number of between 13-15 (such as 13-15 or 14-15). Fifteen percent (15%) of people with mild TBI have symptoms that last 3 months or more. Mild TBI is defined as the result of the forceful motion of the head or impact causing a brief change in mental status (confusion, disorientation or loss of memory) or loss of consciousness for less than 30 minutes. Common symptoms of mild TBI include fatigue, headaches, visual disturbances, memory loss, poor attention/concentration, sleep disturbances, dizziness/loss of balance, irritability-emotional disturbances, feelings of depression, and seizures. Other symptoms associated with mild TBI include nausea, loss of smell, sensitivity to light and sounds, mood changes, getting lost or confused, and/or slowness in thinking.

"Mild TBI subclass 1" (TBI-1) refers to subjects who are classified as having mild TBI and also exhibit a plasma proteome signature that is different from controls (e.g., healthy controls, or controls that have not sustained a TBI), different from subjects with moderate to severe TBI, and different from subjects with a mild TBI of each of subclasses 2, 3, or 4.

"Mild TBI subclass 2" (TBI-2) refers to subjects who are classified to having mild TBI and also exhibit a plasma proteome signature that is different from controls (e.g., healthy controls, or controls that have not sustained a TBI), different from subjects with moderate to severe TBI, and different from subjects with a mild TBI of each of subclasses 1, 3, or 4.

"Mild TBI subclass 3" (TBI-3) refers to subjects who are classified to having mild TBI and also exhibit a plasma proteome signature that is different from controls (e.g., healthy controls, or controls that have not sustained a TBI), different from subjects with moderate to severe TBI, and different from subjects with a mild TBI of each of subclasses 1, 2, or 4.

"Mild TBI subclass 4" (Complex TBI), also referred to herein as "complicated mild TBI," refers to subjects who are classified to having mild TBI, and also exhibit plasma proteome signature that is different from controls (e.g., healthy controls, or controls that have not sustained a TBI), different from subjects with moderate to severe TBI, and different from subjects with a mild TBI of each of subclasses 1, 2, or 3. Additionally, subjects with mild TBI subclass 4 exhibit a proteome signature that resembles the proteome signature obtained from pooled samples of subjects having severe TBI. In data disclosed herein, the mild TBI subclass 4 cluster contained the highest number of subjects having elevated GFAP levels (based on ELISA-based GFAP assay and GFAP mass spectrometry), and the only subject having a positive CT scan.

"Severe TBI" as used herein refers to a brain injury where loss of consciousness and/or confusion and disorientation is between 1 and 24 hours and the subject has a Glasgow Coma scale number of between 9-12. The individual with moderate TBI have abnormal brain imaging results. "Severe TBI" as used herein refers to a brain injury where loss of consciousness is more than 24 hours and memory loss after the injury or penetrating skull injury longer than 24 hours and the subject has a Glasgow Coma scale number between 3-8. The deficits range from impairment of higher level cognitive functions to comatose states. Survivors may have limited function of arms or legs, abnormal speech or language, loss of thinking ability or emotional problems. Individuals with severe injuries can be left in long-term unresponsive states. For many people with severe TBI, long-term rehabilitation is often necessary to maximize function and independence.

Common symptoms of moderate to severe TBI include cognitive deficits including difficulties with attention, concentration, distractibility, memory, speed of processing, confusion, perseveration, impulsiveness, language processing, and/or "executive functions", not understanding the spoken word (receptive aphasia), difficulty speaking and being understood (expressive aphasia), slurred speech, speaking very fast or very slow, problems reading, problems writing, difficulties with interpretation of touch, temperature, movement, limb position and fine discrimination, the integration or patterning of sensory impressions into psychologically meaningful data, partial or total loss of vision, weakness of eye muscles and double vision (diplopia), blurred vision, problems judging distance, involuntary eye movements (nystagmus), intolerance of light (photophobia), hearing, such as decrease or loss of hearing, ringing in the ears (tinnitus), increased sensitivity to sounds, loss or diminished sense of smell (anosmia), loss or diminished sense of taste, the convulsions associated with epilepsy that can be several types and can involve disruption in consciousness, sensory perception, or motor movements, control of bowel and bladder, sleep disorders, loss of stamina, appetite changes, regulation of body temperature, menstrual difficulties, dependent behaviors, emotional ability, lack of motivation, irritability, aggression, depression, disinhibition, or denial/lack of awareness.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e. replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Diagnosing and Evaluating Whether a Subject has Sustained a Traumatic Brain Injury The present disclosure relates to methods of aiding in the diagnosis, prognosis, risk stratification, and evaluation of whether a subject has sustained or may have sustained an injury to the head, including whether the subject sustained a TBI or types of mild TBI. These methods can aid in determining the extent and/or severity of TBI in a human subject with a suspected injury to the head, including for example, determining whether the subject has sustained a mild TBI, and if so, the subclass of mild TBI sustained, whether the subject has sustained a moderate to severe TBI, or whether the subject has not sustained a TBI. More specifically, the biomarkers of the present disclosure can be used in diagnostic tests to determine, qualify, and/or assess brain injury status, for example, to diagnose TBI, in an individual, subject or patient. In some embodiments, TBI status can include determining a patient's subclinical brain injury status or SCI status, for example, to diagnose SCI, in an individual, subject or patient. Detection or measuring the biomarkers of the present disclosure can aid in diagnosing TBI, and can aid in generating a TBI signature, for example, for subclasses of mild TBI.

Determining whether a subject has mild TBI (or a subclass of mTBI) or moderate to severe TBI can include measuring or detecting one or more TBI biomarkers and integrating that information with other information (e.g., clinical assessment data), to determine that the subject is more likely than not to have sustained a TBI, and if so, what type of TBI was sustained. The method can include performing an assay on a sample obtained from the human subject within about 24 hours, such as within about 2 hours, after a suspected injury to the head to measure or detect a level of one or more TBI biomarkers in the sample and determining whether the subject has sustained a mild or a moderate to severe traumatic brain injury (sTBI). In some embodiments, the subject is determined as having a TBI and/or a subclass of mild TBI when the level of one or more TBI biomarkers in a sample is altered (e.g., higher or lower expression level), as compared to a reference level of one or more TBI biomarkers (e.g., level of the TBI biomarker in a control sample). In other embodiments, the subject is determined as having a TBI and/or a subclass of mild TBI when the level of one or more TBI biomarkers in a sample is detected, without the need to for ascertaining biomarker levels or comparing to a reference or control sample.

The sample can be a biological sample. "Sample," as used herein may be used interchangeably (e.g., sample, test sample, or biological sample) and may be a sample of blood, such as whole blood, tissue, urine, serum, plasma, amniotic fluid, cerebrospinal fluid, placental cells or tissue, endothelial cells, leukocytes, or monocytes. In some embodiments, the method can include obtaining a sample from a subject within about 48 hours of a suspected injury to the subject and contacting the sample with an antibody for a TBI biomarker to allow formation of a complex of the antibody and the TBI biomarker. The method also includes detecting the resulting antibody-TBI biomarker complex.

In some embodiments, the subject may have received a Glasgow Coma Scale score before or after the level of a TBI biomarker is determined at one or more time points. In certain embodiments, the subject may be suspected of having a mild TBI based on the Glasgow Coma Scale score. In certain embodiments, the subject may be suspected of having a mild TBI based on an abnormal head CT. In some embodiments, the subject has received a CT scan before or after the assay is performed. In some embodiments, the subject has a normal head CT. In some embodiments, the reference level of a TBI biomarker is correlated with subjects having a TBI. In some embodiments, the reference level of a TBI biomarker is correlated with a Glasgow Coma Scale score.

Generally, a reference level of a TBI biomarker can also be employed as a benchmark against which to assess results obtained upon assaying a test sample for a TBI biomarker. Generally, in making such a comparison, the reference level of a TBI biomarker is obtained by running a particular assay a sufficient number of times and under appropriate conditions such that a linkage or association of analyte presence, amount or concentration with a particular stage or endpoint of TBI or with particular indicia can be made. Typically, the reference level of a TBI biomarker is obtained with assays of reference subjects (or populations of subjects). The TBI biomarker measured can include fragments thereof, degradation products thereof, and/or enzymatic cleavage products thereof. In certain embodiments, the reference level may be correlated with control subjects that have not sustained a head injury.

The nature of the assay employed in the methods described herein is not critical and the test can be any assay known in the art such as, for example, immunoassays, protein immunoprecipitation, immunoelectrophoresis, Western blot, or protein immunostaining, or spectrometry methods, such as high-performance liquid chromatography (HPLC), liquid chromatography-mass spectrometry (LC/MS), DIA-MS, DDA-MS, PRM-MS or SRM/MRM-MS mass spectrometry assays directly or with enrichment (e.g., enrichment can be via an antibody to the target protein(s)). Capture reagents used to selectively enrich samples for candidate biomarker proteins prior to mass spectroscopic analysis include but are not limited to aptamers, antibodies, nucleic acid probes, chimeras, small molecules, an F(ab')2 fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g., diabodies etc.) imprinted polymers, avimers, peptidomimetics, peptoids, peptide nucleic acids, threose nucleic acid, a hormone receptor, a cytokine receptor, and synthetic receptors, and modifications and fragments of these. With enrichment, matrix assisted laser desorption/ionization time-of-flight (MALDI-TOF MS or MALDI-TOF) can also be used. Also, the assay can be employed in clinical chemistry format such as would be known by one skilled in the art.

3. TBI Biomarker Panels

Biomarkers of the present disclosure can be used in diagnostic tests to assess, determine, and/or qualify (used interchangeably herein) brain injury status in a patient, such as TBI status. The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time), the effectiveness or response to treatment of brain injury (e.g., clinical follow up and surveillance of brain injury after treatment), and type of brain injury, such as TBI or a subclass of TBI. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

Analysis of the data described in the present disclosure, as well as clinical data from a cohort of TBI and control patients, resulted in the generation of various TBI biomarkers that can be used individually, or in various combinations with each other and with other biomarkers in the form of a panel, to diagnose and/or evaluate a brain injury in a subject. TBI biomarker panels may include any one of the TBI biomarkers disclosed herein, and may include more than one and up to 20 different biomarkers corresponding to distinct proteins. TBI biomarker panels can also include non-TBI biomarkers (e.g., assay control biomarkers), and biomarkers previously identified to be associated with TBI (e.g., GFAP and/or UCH-L1 and/or NSE). In some embodiments, the biomarker panels of the present disclosure may show a statistical difference in different TBI statuses. Diagnostic tests that use these biomarkers may show an ROC of at least 0.6, at least about 0.7, at least about 0.8, or at least about 0.9.

TBI biomarkers can be differentially present/expressed depending on the type or subclass of TBI (e.g., a TBI signature) and, therefore, panels of more than one TBI biomarker can be useful in aiding in the determination of brain injury status. In some embodiments, biomarkers are measured in a patient sample using the methods described herein and compared, for example, to predefined biomarker levels and correlated to TBI status. In some embodiments, the measurement(s) may then be compared with a relevant diagnostic amount(s), cut-off(s), or multivariate model scores that distinguish a positive TBI status from a negative TBI status. The diagnostic amount(s) represents a measured amount of a biomarker(s) above which or below which a patient is classified as having a particular TBI status. For example, if the biomarker(s) is/are up-regulated compared to a control subject (e.g., a subject that has not sustained a TBI) during brain injury, then a measured amount(s) above the diagnostic cutoff(s) can provide a diagnosis of TBI. Additionally, if the biomarker(s) is/are present during brain injury and not detectable in controls, then any detectably measured amount(s) can provide a diagnosis of brain injury. Alternatively, if the biomarker(s) is/are down-regulated during brain injury, then a measured amount(s) at or below the diagnostic cutoff(s) can provide a diagnosis of non-brain injury. Additionally, if the biomarker(s) is/are not present during brain injury and are detectable in controls, then any detectably measured amount(s) can provide a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

4. Assessment of TBI Characteristics Using Biomarkers

In some embodiments, the present disclosure provides methods for characterizing and/or categorizing TBI based on the detection, non-detection, and/or detection levels of one or more TBI biomarkers, such as characterizing the severity of TBI different types of TBI. Each class or subclass of TBI likely has a characteristic level of a biomarker or relative levels of a set of biomarkers (a signature). In one embodiment, the present disclosure provides methods for evaluating the progress of TBI status in a patient over time, including progression (worsening) and regression (improvement). Over time, the amount or relative amount (e.g., the pattern or signature) of the TBI biomarkers may change. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a patient at least two different time points (e.g., a first time and a second time, and comparing the change, if any).

In some embodiments, a class or subclass of TBI can be characterized by measuring the relevant biomarkers and then either submitting them to a classification algorithm or comparing them with a reference amount (e.g., a predefined level or pattern of biomarkers that is associated with the particular class or subclass).

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

5. Treatment and Monitoring of Subjects Suffering from TBI

The subject identified or assessed as having TBI may be treated or monitored based on the assessment, which can include detecting or measuring various TBI biomarkers. In some embodiments, the method further includes treating the human subject assessed as having TBI with a treatment, which can take a variety of forms depending on the severity of the injury to the head. For example, for subjects suffering from mild TBI, the treatment may include one or more of rest, abstaining from physical activities, such as sports, avoiding light or wearing sunglasses when out in the light, medication for relief of a headache or migraine, anti-nausea medication, etc. Treatment for patients suffering from severe TBI might include administration of one or more appropriate medications (such as, for example, diuretics, anti-convulsant medications, medications to sedate and put an individual in a drug-induced coma, or other pharmaceutical or biopharmaceutical medications (either known or developed in the future for treatment of TBI), one or more surgical procedures (such as, for example, removal of a hematoma, repairing a skull fracture, decompressive craniectomy, etc.) and one or more therapies (such as, for example one or more rehabilitation, cognitive behavioral therapy, anger management, counseling psychology, etc.). In some embodiments, the method further includes monitoring the human subject assessed as having traumatic brain injury (e.g., mild or moderate to severe traumatic). In some embodiments, a subject identified as having traumatic brain injury, such as mild traumatic brain injury or severe traumatic brain injury, may be monitored with CT scan or MRI.

In one embodiment, the present disclosure provides methods for determining the risk of developing TBI in a patient. TBI biomarker percentages, amounts or patterns are characteristic of various risk states (e.g., high, medium or low). The risk of developing a TBI can be determined by measuring the relevant biomarkers and then either submitting them to a classification algorithm or comparing them with a reference amount (e.g., a predefined level or signature of biomarkers that is associated with the particular risk level).

In some embodiments, treating a subject that has sustained a TBI can include managing patient treatment based on TBI status as established using one or more TBI biomarkers. Such management can include the actions of the physician or clinician subsequent to determining TBI status. For example, if a physician makes a diagnosis of mild TBI, then a certain regime of monitoring would follow. An assessment of the course of TBI using the methods of the present disclosure may then require a certain TBI therapy regimen. Alternatively, a diagnosis of non-TBI might be followed with further testing to determine a specific disease that the patient might be suffering from. Also, further tests may be called for if the diagnostic test gives an inconclusive result on TBI status.

In another embodiment, the present disclosure provides methods for determining the therapeutic efficacy of a pharmaceutical drug in the context of TBI treatment. These methods can be useful in performing clinical trials of a drug, as well as monitoring the progress of a patient on a drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or signature) of one or more of the TBI biomarkers of the present invention may change toward a non-brain injury profile. Therefore, one can follow the course of one or more TBI biomarkers in the patient during the course of treatment.

Accordingly, this method may involve measuring one or more TBI biomarkers in a patient receiving drug therapy, and correlating the biomarker levels with the TBI status of the patient (e.g., by comparison to predefined levels of the biomarkers that correspond to different brain injury statuses). One embodiment of this method can involve determining the levels of one or more TBI biomarkers at least two different time points during a course of drug therapy (e.g., a first time and a second time, and comparing the change in levels of the biomarkers, if any). For example, the levels of one or more TBI biomarkers can be measured before and after drug administration or at two different time points during drug administration. The effect of therapy is determined based on these comparisons. If a treatment is effective, then the one or more TBI biomarkers will trend toward normal, while if treatment is ineffective, the one or more TBI biomarkers will trend toward brain injury indications.

6. Biomarkers of TBI

The methods described herein may be used to identify one or more TBI biomarkers or candidate TBI biomarkers that can aid in the diagnosis and evaluation of in a subject that may have sustained a TBI. Exemplary TBI biomarkers are described below.

a. Rule-In TBI Biomarkers

As described below, the following TBI biomarkers were identified as being capable of distinguishing a healthy subject from a subject that has sustained a TBI when detected alone or in combination:

Ezrin (EZR).

EZR is also known as cytovillin or villin-2, and encodes a protein that in humans is encoded by the EZR gene. The N-terminus of Ezrin contains a FERM domain which is further subdivided into three subdomains. The C-terminus contains a ERM domain. Ezrin is thought to be involved in connections of major cytoskeletal structures to the plasma membrane. In epithelial cells, required for the formation of microvilli and membrane ruffles on the apical pole. Along with PLEKHG6, required for normal micropinocytosis. (UniProt Primary accession number: P15311.)

4-trimethylaminobutyraldehyde dehydrogenase (ALDH9A1 or AL9A1).

AL9A1 is also known as 4-trimethylaminobutyraldehyde dehydrogenase, TMABADH, Aldehyde dehydrogenase E3 isozyme, Aldehyde dehydrogenase family 9 member A1, Gamma-aminobutyraldehyde dehydrogenase, R-aminobutyraldehyde dehydrogenase. The protein converts gamma-trimethylaminobutyraldehyde into gamma-butyrobetaine, and catalyzes the irreversible oxidation of a broad range of aldehydes to the corresponding acids in an NAD-dependent reaction. The protein is highly expressed in adult liver, skeletal muscle, and kidney, expressed in low levels in heart, pancreas, lung and brain, and is expressed in all regions of the brain. Expression levels are variable in the different brain areas, with the highest levels in the spinal cord and the lowest in the occipital pole. (UniProt Primary accession number: P49189.)

ATP Synthase Subunit Gamma, Mitochondrial (ATPG).

Mitochondrial membrane ATP synthase ($F_1F_0$ ATP synthase or Complex V) produces ATP from ADP in the presence of a proton gradient across the membrane which is generated by electron transport complexes of the respiratory chain. F-type ATPases consist of two structural domains, $F_1$-containing the extramembraneous catalytic core, and $F_0$-containing the membrane proton channel, linked together by a central stalk and a peripheral stalk. During catalysis, ATP synthesis in the catalytic domain of $F_1$ is coupled via a rotary mechanism of the central stalk subunits to proton translocation. Part of the complex $F_1$ domain and the central stalk which is part of the complex rotary element. The gamma subunit protrudes into the catalytic domain formed of $alpha_3beta_3$. Rotation of the central stalk against the surrounding $alpha_3beta_3$ subunits leads to hydrolysis of ATP in three separate catalytic sites on the beta subunits. (UniProt Primary accession number: P36542.)

Complement C1r subcomponent-like protein (C1RL).

C1RL mediates the proteolytic cleavage of HP/haptoglobin in the endoplasmic reticulum. Diseases associated with C1RL include Ovary Adenocarcinoma. (UniProt Primary accession number: Q9NZP8.)

Cullin-associated NEDD8-dissociated protein 1 (CAND1).

CAND1 is a key assembly factor of SCF (SKP1-CUL1-F-box protein) E3 ubiquitin ligase complexes that promotes the exchange of the substrate-recognition F-box subunit in SCF complexes, thereby playing a key role in the cellular repertoire of SCF complexes. Acts as a F-box protein exchange factor. The exchange activity of CAND1 is coupled with cycles of neddylation conjugation: in the deneddylated state, cullin-binding CAND1 binds CUL1-RBX1, increasing dissociation of the SCF complex and promoting exchange of the F-box protein. Probably plays a similar role in other cullin-RING E3 ubiquitin ligase complexes. (UniProt Primary accession number: Q86VP6.)

Epiplakin (EPIPL or EPPK1).

EPIPL is a cytoskeletal linker protein that connects to intermediate filaments and controls their reorganization in response to stress. In response to mechanical stress like wound healing, is associated with the machinery for cellular motility by slowing down keratinocyte migration and proliferation and accelerating keratin bundling in proliferating keratinocytes thus contributing to tissue architecture. However in wound healing in corneal epithelium it also positively regulates cell differentiation and proliferation and negatively regulates migration thereby controlling corneal epithelium morphogenesis and integrity. In response to cellular stress, plays a role in keratin filament reorganization, probably by protecting keratin filaments against disruption. During liver and pancreas injuries, the protein plays a protective role by chaperoning disease-induced intermediate filament reorganization (By similarity). (UniProt Primary accession number: P58107.)

Hydroxyacylglutathione hydrolase, mitochondrial (GLO2 or HAGH).

GLO2 is a thiolesterase that catalyzes the hydrolysis of S-D-lactoyl-glutathione to form glutathione and D-lactic acid. (UniProt Primary accession number: Q16775.)

Immunoglobulin heavy constant alpha 2 (IGHA2).

IGHA2 is a constant region of immunoglobulin heavy chains. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. Ig alpha is the major immunoglobulin class in body secretions. (UniProt Primary accession number: P01877.)

Pregnancy zone protein (PZP).

PZP is able to inhibit all four classes of proteinases by a unique "trapping" mechanism. This protein has a peptide stretch, called the 'bait region' which contains specific cleavage sites for different proteinases. When a proteinase cleaves the bait region, a conformational change is induced in the protein which traps the proteinase. The entrapped enzyme remains active against low molecular weight substrates (activity against high molecular weight substrates is greatly reduced). Following cleavage in the bait region a thioester bond is hydrolyzed and mediates the covalent binding of the protein to the proteinase. (UniProt Primary accession number: P20742.)

Threonine-tRNA ligase, cytoplasmic (SYTC or TARS).

SYTC catalyzes the reaction: ATP+L-threonine+tRNA (Thr)=AMP+diphosphate+L-threonyl-tRNA (Thr). It is inhibited by borrelidin (BN, IC 50 is 7 nM), which binds to 4 distinct subsites in the protein, preventing binding of all 3 substrates. (UniProt Primary accession number: P26639.)

Tyrosine-tRNA ligase, cytoplasmic (SYYC or YARS).

SYYC catalyzes the attachment of tyrosine to tRNA(Tyr) in a two-step reaction: tyrosine is first activated by ATP to form Tyr-AMP and then transferred to the acceptor end of tRNA(Tyr). (UniProt Primary accession number: P54577.)

Protein ABHD14B (ABHEB of ABHD14B).

ABHEB exhibits hydrolase activity towards p-nitrophenyl butyrate (in vitro) and may activate transcription. (UniProt Primary accession number: Q96IU4.)

Dynamin-1-like protein (DNM1L).

DNM1L functions in mitochondrial and peroxisomal division. The protein mediates membrane fission through oligomerization into membrane-associated tubular structures that wrap around the scission site to constrict and sever the mitochondrial membrane through a GTP hydrolysis-dependent mechanism. Through its function in mitochondrial division, it ensures the survival of at least some types of postmitotic neurons, including Purkinje cells, by suppressing oxidative damage. It is required for normal brain development, including that of cerebellum. It facilitates developmentally regulated apoptosis during neural tube formation. It is required for a normal rate of cytochrome c release and caspase activation during apoptosis; this requirement may depend upon the cell type and the physiological apoptotic cues. It plays an important role in mitochondrial fission during mitosis. It is required for formation of endocytic vesicles. It is proposed to regulate synaptic vesicle membrane dynamics through association with BCL2L1 isoform Bcl-X(L) which stimulates its GTPase activity in synaptic vesicles; the function may require its recruitment by MFF to clathrin-containing vesicles. And it is required for programmed necrosis execution. (UniProt Primary accession number: O00429.)

Ficolin-2 (FCN2).

FCN2 may function in innate immunity through activation of the lectin complement pathway. It exhibits calcium-dependent and GlcNAc-binding to lectin. It enhances phagocytosis of *S. typhimurium* by neutrophils, suggesting an opsonic effect via the collagen region. (UniProt Primary accession number: Q15485.)

Inverted formin-2 (IFN2).

IFN2 is involved in the severing of actin filaments and accelerates their polymerization and depolymerization. (UniProt Primary accession number: Q27J81.)

Keratin, type II cytoskeletal 2 epidermal (K22E or KRT2).

K22E is an intermediate protein and is thought to contribute to terminal cornification. The protein is associated with keratinocyte activation, proliferation and keratinization. (UniProt Primary accession number: P35908.)

Mitogen-activated protein kinase kinase kinase 5 (M3K5 or MAP3K5).

M3K5 is a serine/threonine kinase which acts as an essential component of the MAP kinase signal transduction pathway. It plays an important role in the cascades of cellular responses evoked by changes in the environment. It mediates signaling for determination of cell fate such as differentiation and survival. It plays a crucial role in the apoptosis signal transduction pathway through mitochondria-dependent caspase activation. MAP3K5/ASK1 is required for the innate immune response, which is essential for host defense against a wide range of pathogens. It mediates signal transduction of various stressors like oxidative stress as well as by receptor-mediated inflammatory signals, such as the tumor necrosis factor (TNF) or lipopolysaccharide (LPS). Once activated, it acts as an upstream activator of the MKK/JNK signal transduction cascade and the p38 MAPK signal transduction cascade through the phosphorylation and activation of several MAP kinase kinases like MAP2K4/SEK1, MAP2K3/MKK3, MAP2K6/MKK6 and MAP2K7/MKK7. These MAP2Ks in turn activate p38 MAPKs and c-jun N-terminal kinases (JNKs). Both p38 MAPK and JNKs control the transcription factors activator protein-1 (AP-1). (UniProt Primary accession number: Q99683.)

Nuclear receptor corepressor 1 (NCOR1).

NCOR1 mediates transcriptional repression by certain nuclear receptors. It is part of a complex which promotes histone deacetylation and the formation of repressive chromatin structures which may impede the access of basal transcription factors. It participates in the transcriptional repressor activity produced by BCL6. (UniProt Primary accession number: O75376.)

Suprabasin (SBSN).

SBSN is a novel gene expressed in mouse and human differentiating keratinocytes. It is thought to be secreted from the spinous layer of the stratified epithelia and may form a novel gene complex on chromosome 2 with dermokine-alpha/-beta and Kdap. (UniProt Primary accession number: Q6UWP8.)

Bifunctional glutamate/proline-tRNA ligase (SYEP or EPRS).

SYEP catalyzes the attachment of the cognate amino acid to the corresponding tRNA in a two-step reaction: the amino acid is first activated by ATP to form a covalent intermediate with AMP and is then transferred to the acceptor end of the cognate tRNA. It is a component of the GAIT (gamma interferon-activated inhibitor of translation) complex which mediates interferon-gamma-induced transcript-selective translation inhibition in inflammation processes. Upon interferon-gamma activation and subsequent phosphorylation, it dissociates from the multisynthetase complex and assembles into the GAIT complex which binds to stem loop-containing GAIT elements in the 3'-UTR of diverse inflammatory mRNAs (such as ceruplasmin) and suppresses their translation. (UniProt Primary accession number: P07814.)

Tripeptidyl-peptidase 2 (TPP2).

TPP2 is a component of the proteolytic cascade acting downstream of the 26S proteasome in the ubiquitin-proteasome pathway. It may be able to complement the 26S proteasome function to some extent under conditions in which the latter is inhibited. It stimulates adipogenesis (By similarity). (UniProt Primary accession number: P29144.)

Annexin A6 (ANXA6).

ANXA6 may associate with CD21, and may regulate the release of $Ca^{2+}$ from intracellular stores. It can be secreted. (UniProt Primary accession number: P08133.)

Endoplasmic reticulum aminopeptidase 1 (ERAP1).

ERAP1 is an aminopeptidase that plays a central role in peptide trimming, a step required for the generation of most HLA class I-binding peptides. Peptide trimming is essential to customize longer precursor peptides to fit them to the correct length required for presentation on MHC class I molecules. Strongly prefers substrates 9-16 residues long. Rapidly degrades 13-mer to a 9-mer and then stops. It preferentially hydrolyzes the residue Leu and peptides with a hydrophobic C-terminus, while it has weak activity toward peptides with charged C-terminus. May play a role in the inactivation of peptide hormones. It may be involved in the regulation of blood pressure through the inactivation of angiotensin II and/or the generation of bradykinin in the kidney. (UniProt Primary accession number: Q9NZ08.)

Coagulation factor V (FA5 or F5).

FA5 is a central regulator of hemostasis. It serves as a critical cofactor for the prothrombinase activity of factor Xa that results in the activation of prothrombin to thrombin. (UniProt Primary accession number: P12259.)

Glucose-6-phosphate isomerase (G6PI or GPI).

G6PI is a glycolytic enzyme, and mammalian G6PI can function as a tumor-secreted cytokine and an angiogenic factor (AMF) that stimulates endothelial cell motility. In the cytoplasm, the gene product functions as a glycolytic enzyme (glucose-6-phosphate isomerase) that interconverts glucose-6-phosphate (G6P) and fructose-6-phosphate (F6P). Extracellularly, the encoded protein (also referred to as neuroleukin) functions as a neurotrophic factor that promotes survival of skeletal motor neurons and sensory neurons, and as a lymphokine that induces immunoglobulin secretion. The encoded protein is also referred to as autocrine motility factor (AMF) based on an additional function as a tumor-secreted cytokine and angiogenic factor. Defects in this gene are the cause of nonspherocytic hemolytic anemia, and a severe enzyme deficiency can be associated with hydrops fetalis, immediate neonatal death and neurological impairment. Alternative splicing results in multiple transcript variants. (UniProt Primary accession number: P06744.)

Myosin light chain kinase, smooth muscle (MYLK).

MYLK is a calcium/calmodulin-dependent myosin light chain kinase implicated in smooth muscle contraction via phosphorylation of myosin light chains (MLC). It also regulates actin-myosin interaction through a non-kinase activity. It phosphorylates PTK2B/PYK2 and myosin light-chains. Involved in the inflammatory response (e.g. apoptosis, vascular permeability, leukocyte diapedesis), cell motility and morphology, airway hyperreactivity and other activities relevant to asthma. It is required for tonic airway smooth muscle contraction that is necessary for physiological and asthmatic airway resistance. It is necessary for gastrointestinal motility. It is implicated in the regulation of endothelial as well as vascular permeability, probably via the regulation of cytoskeletal rearrangements. In the nervous system it has been shown to control the growth initiation of astrocytic processes in culture and to participate in transmitter release at synapses formed between cultured sympathetic ganglion cells. It is critical participant in signaling sequences that result in fibroblast apoptosis. It plays a role in the regulation of epithelial cell survival. Required for epithelial wound healing, especially during actomyosin ring contraction during purse-string wound closure. It mediates RhoA-dependent membrane blebbing. It triggers TRPC5 channel activity in a calcium-dependent signaling, by inducing its subcellular localization at the plasma membrane. It promotes cell migration (including tumor cells) and tumor metastasis. PTK2B/PYK2 activation by phosphorylation mediates ITGB2 activation and is thus essential to trigger neutrophil transmigration during acute lung injury (ALI). It may regulate optic nerve head astrocyte migration. It is probably involved in mitotic cytoskeletal regulation. Regulates tight junction probably by modulating ZO-1 exchange in the perijunctional actomyosin ring. It mediates burn-induced microvascular barrier injury; triggers endothelial contraction in the development of microvascular hyperpermeability by phosphorylating MLC. It is essential for intestinal barrier dysfunction. It me=ediates Giardia spp.-mediated reduced epithelial barrier function during giardiasis intestinal infection via reorganization of cytoskeletal F-actin and tight junctional ZO-1. It is necessary for hypotonicity-induced $Ca^{2+}$ entry and subsequent activation of volume-sensitive organic osmolyte/anion channels (VSOAC) in cervical cancer cells. It is responsible for high proliferative ability of breast cancer cells through anti-apoptosis. (UniProt Primary accession number: Q15746.)

Serum amyloid P-component (SAMP or APCS).

SAMP can interact with DNA and histones and may scavenge nuclear material released from damaged circulating cells. It may also function as a calcium-dependent lectin. (UniProt Primary accession number: P02743.)

In some embodiments, one or more of the TBI biomarkers listed above can be used to determine that a subject has sustained a TBI based on detection of one or more of these TBI biomarkers in a sample from the subject, and a lack of detection of the one or more TBI biomarkers in a control subject (e.g., a subject that has not sustained a TBI). These TBI biomarkers can include one or more of AL9A1, ATPG, C1RL, EPIPL, IGHA2, PZP, SYTC, SYYC, ABHEB, DNM1L, FCN2, INF2, K22E, M3K5, NCOR1, SBSN, SYEP, TPP2, ANXA6, ERAP1, EZRI, FA5, G6PI, MYLK, SAMP, or any combinations thereof. The measurement or detection of one or more of these TBI biomarkers in a subject can be sufficient to indicate that the subject has sustained a TBI, independent of the need to detect, measure, compare, and/or quantify the amount, concentration, and/or expression level of the one or more TBI biomarkers in a control subject. Although one or more of these TBI biomarkers may be present in a control subject, or in a subject that has not sustained a TBI, it is generally present in an amount that is not able to be detected though conventional means, as described herein. Thus, in some cases, detection of one or more of these TBI biomarkers in a subject indicates that a subject has sustained a TBI.

In some embodiments, one or more of the TBI biomarkers listed above can be used to determine that a subject has sustained a severe TBI based on detection of one or more of these TBI biomarkers in a sample from the subject, and a lack of detection of the one or more TBI biomarkers in a control subject (e.g., a subject that has not sustained a TBI) or a lack of detection in a subject that has sustained a mild TBI. These TBI biomarkers can include one or more of ATPG, C1RL, SYYC, or any combinations thereof. The measurement or detection of one or more of these TBI biomarkers in a subject can be sufficient to indicate that the subject has sustained a severe TBI, independent of the need to detect, measure, compare, or quantify the amount, concentration, or expression level of the one or more TBI biomarkers in a control subject or a subject that has sustained a mild TBI.

In some embodiments, one or more of the TBI biomarkers listed above can be used to determine that a subject has sustained a TBI based on detection of one or more of these TBI biomarkers in a sample from the subject at an amount, concentration, and/or expression level that is higher than an amount, concentration and/or expression level of the corresponding TBI biomarker in a control subject. These TBI biomarkers can include one or more of CAND1 and GLO2, or any combinations thereof. The measurement or detection of an increased level of one or more of these TBI biomarkers in a subject as compared to a control subject (e.g., a subject that has not sustained a TBI) can be sufficient to indicate that the subject has sustained a TBI, and in some cases, can be sufficient to indicate that the subject has sustained a severe TBI.

In some embodiments, one or more of the TBI biomarkers listed above can be used to determine that a subject has sustained a TBI based on detection of one or more of these TBI biomarkers in a sample from the subject at an amount, concentration, and/or expression level that is higher or lower than an amount, concentration and/or expression level of the corresponding TBI biomarker in a control subject. These TBI biomarkers can include one or more of ABHEB, AL9A1, DNM1L, or any combinations thereof. The measurement or detection of an increased or decreased level of one or more of these TBI biomarkers in a subject as compared to a control subject (e.g., a subject that has not sustained a TBI) can be sufficient to indicate that the subject has sustained a TBI, and in some cases, can be sufficient to indicate that the subject has sustained a severe TBI. For example, detection or measurement of a higher level of ABHED, and/or a lower level of AL9A1 and/or DNM1L in a subject that may have sustained a TBI as compared to levels from a control subject can indicate that the subject has indeed sustained a TBI. Levels of these TBI biomarkers can be detected or measured alone or in combination as part of a TBI panel or signature.

In some embodiments, one or more of the TBI biomarkers listed above can be used to determine that a subject has sustained a mild TBI based on detection of one or more of these TBI biomarkers in a sample from the subject at an amount, concentration, and/or expression level that is higher or lower than an amount, concentration and/or expression level of the corresponding TBI biomarker in a control subject. These TBI biomarkers can include one or more of M3K5, SBSN, SYEP, or any combinations thereof. The measurement or detection of an increased or decreased level of one or more of these TBI biomarkers in a subject as compared to a control subject (e.g., a subject that has not sustained a TBI) can be sufficient to indicate that the subject has sustained a TBI, and in some cases, can be sufficient to indicate that the subject has sustained a mild TBI. For example, detection or measurement of a higher level of SBSN and/or SYEP, and/or a lower level of M3K5 in a subject that may have sustained a TBI as compared to levels from a control subject can indicate that the subject has indeed sustained a mild TBI. Levels of these TBI biomarkers can be detected or measured alone or in combination as part of a TBI panel or signature.

In some embodiments, one or more of the TBI biomarkers listed above can be included with other biomarkers that may or may not have been identified as TBI biomarkers. For example, one or more of the TBI biomarkers listed above can be included in a panel of biomarkers that may include one or more of ANXA6, ERAP1, EZRI, FA5, G6PI, MYLK, SAMP, or combinations thereof. In some cases, a panel of TBI biomarkers, in conjunction with other TBI biomarkers and non-TBI biomarkers can aid in the diagnosis of TBI to a greater extent than individual biomarkers alone.

b. Rule-In Mild TBI Biomarkers

As described below, the following TBI biomarkers were identified as being capable of distinguishing a healthy subject from a subject that has sustained a mild TBI when detected alone or in combination:

Poly(rC)-binding protein 2 (Alpha-CP2) (PCBP2).

Poly(rC)-binding protein 2 is a protein that in humans is encoded by the PCBP2 gene. The protein encoded by this gene appears to be multifunctional. It along with PCBP-1 and hnRNPK corresponds to the major cellular poly(rC)-binding proteins. It contains three K-homologous (KH) domains which may be involved in RNA binding. This encoded protein together with PCBP-1 also functions as translational coactivators of poliovirus RNA via a sequence-specific interaction with stem-loop IV of the IRES and promote poliovirus RNA replication by binding to its 5'-terminal cloverleaf structure. It has also been implicated in translational control of the 15-lipoxygenase mRNA, human Papillomavirus type 16 L2 mRNA, and hepatitis A virus RNA. The encoded protein is also suggested to play a part in formation of a sequence-specific alpha-globin mRNP complex which is associated with alpha-globin mRNA stability. This multiexon structural mRNA is thought to be retrotransposed to generate PCBP-1 intronless gene which has similar functions. This gene and PCBP-1 has paralogues PCBP3 and PCBP4 which is thought to arose as a result of duplication events of entire genes. It also has two processed pseudogenes PCBP2P1 and PCBP2P2. There are presently two alternatively spliced transcript variants described for this gene. In humans, the PCBP2 gene overlaps with TUC338, a transcribed ultra-conserved element implicated in Hepatocellular carcinoma. (UniProt Primary accession number: Q15366.)

Thioredoxin reductase 2, mitochondrial (TRXR2).

Thioredoxin reductases (TR, TrxR) (EC 1.8.1.9) are the only known enzymes to reduce thioredoxin (Trx). Two classes of thioredoxin reductase have been identified: one class in bacteria and some eukaryotes and one in animals. Both classes are flavoproteins which function as homodimers. Each monomer contains a FAD prosthetic group, a NADPH binding domain, and an active site containing a redox-active disulfide bond. Thioredoxin reductase is the only enzyme known to catalyze the reduction of thioredoxin and hence is a central component in the thioredoxin system. Together with thioredoxin (Trx) and NADPH this system's most general description is as a method of forming reduced disulfide bonds in cells. Electrons are taken from NADPH via TrxR and are transferred to the active site of Trx, which goes on to reduce protein disulfides or other substrates. The Trx system exists in all living cells and has an evolutionary history tied to DNA as a genetic material, defense against oxidative damage due to oxygen metabolism, and redox signaling using molecules like hydrogen peroxide and nitric oxide. (UniProt Primary accession number: Q9NNW7.)

14-3-3 protein gamma (1433G or YWHAG).

1433G is an adapter protein implicated in the regulation of a large spectrum of both general and specialized signaling pathways. Binds to a large number of partners, usually by recognition of a phosphoserine or phosphothreonine motif. Binding generally results in the modulation of the activity of the binding partner. (UniProt Primary accession number: P61981.)

Activated CDC42 kinase 1 (ACK1 or TKN2).

ACK1 is a non-receptor tyrosine-protein and serine/threonine-protein kinase that is implicated in cell spreading and migration, cell survival, cell growth and proliferation. Transduces extracellular signals to cytosolic and nuclear effectors. It phosphorylates AKT1, AR, MCF2, WASL and WWOX. Implicated in trafficking and clathrin-mediated endocytosis through binding to epidermal growth factor receptor (EGFR) and clathrin. It binds to both poly- and mono-ubiquitin and regulates ligand-induced degradation of EGFR, thereby contributing to the accumulation of EGFR at the limiting membrane of early endosomes. It is a downstream effector of CDC42 which mediates CDC42-dependent cell migration via phosphorylation of BCAR1. It may be involved both in adult synaptic function and plasticity and in brain development. Activates AKT1 by phosphorylating it on "Tyr-176." Phosphorylates AR on "Tyr-267" and "Tyr-363" thereby promoting its recruitment to androgen-responsive enhancers (AREs). It phosphorylates WWOX on "Tyr-287." It phosphorylates MCF2, thereby enhancing its activity as a guanine nucleotide exchange factor (GEF) toward Rho family proteins. It contributes to the control of AXL receptor levels. It confers metastatic properties on cancer cells and promotes tumor growth by negatively regulating tumor suppressor such as WWOX and positively regulating pro-survival factors such as AKT1 and AR. It phosphorylates WASP. (UniProt Primary accession number: Q07912.)

Aminoacylase-1 (ACY1).

ACY1 is involved in the hydrolysis of N-acylated or N-acetylated amino acids (except L-aspartate). (UniProt Primary accession number: Q03154.)

A-kinase anchor protein 12 (AKAl2 or AKAP12).

AKA12 is an anchoring protein that mediates the subcellular compartmentation of protein kinase A (PKA) and protein kinase C (PKC). (UniProt Primary accession number: Q02952.)

Arginase-1 (ARGl1 or ARG1).

ARGI1 is key element of the urea cycle converting L-arginine to urea and L-ornithine, which is further metabolized into metabolites proline and polyamides that drive collagen synthesis and bioenergetic pathways critical for cell proliferation, respectively; the urea cycle takes place primarily in the liver and, to a lesser extent, in the kidneys. It functions in L-arginine homeostasis in nonhepatic tissues characterized by the competition between nitric oxide synthase (NOS) and arginase for the available intracellular substrate arginine. Arginine metabolism is a critical regulator of innate and adaptive immune responses. It is involved in an antimicrobial effector pathway in polymorphonuclear granulocytes (PMN). Upon PMN cell death, it is liberated from the phagolysosome and depletes arginine in the microenvironment leading to suppressed T cell and natural killer (NK) cell proliferation and cytokine secretion. In group 2 innate lymphoid cells (ILC2s), it promotes acute type 2 inflammation in the lung and is involved in optimal ILC2 proliferation but not survival (By similarity). (UniProt Primary accession number: P05089.)

Cadherin-5 (CADH5 or CDH5).

CADH5 is a cadherin; cadherins are calcium-dependent cell adhesion proteins. They preferentially interact with themselves in a homophilic manner in connecting cells; cadherins may thus contribute to the sorting of heterogeneous cell types. This cadherin may play a important role in endothelial cell biology through control of the cohesion and organization of the intercellular junctions. It associates with alpha-catenin forming a link to the cytoskeleton. It acts in concert with KRIT1 to establish and maintain correct endothelial cell polarity and vascular lumen. These effects are mediated by recruitment and activation of the Par polarity complex and RAP1B. It is required for activation of PRKCZ and for the localization of phosphorylated PRKCZ, PARD3, TIAM1 and RAP1B to the cell junction. (UniProt Primary accession number: P33151.)

Clathrin heavy chain 1 (CLH1 of CLTC).

CLH1 is the major protein of the polyhedral coat of coated pits and vesicles. Two different adapter protein complexes link the clathrin lattice either to the plasma membrane or to the trans-Golgi network. It acts as component of the TACC3/ch-TOG/clathrin complex proposed to contribute to stabilization of kinetochore fibers of the mitotic spindle by acting as inter-microtubule bridge. The TACC3/ch-TOG/clathrin complex is required for the maintenance of kinetochore fiber tension. It plays a role in early autophagosome formation. (UniProt Primary accession number: Q00610.)

Coatomer subunit gamma-2 (COPG2).

COPG2 is a cytosolic protein complex that binds to dilysine motifs and reversibly associates with Golgi non-clathrin-coated vesicles, which further mediate biosynthetic protein transport from the ER, via the Golgi up to the trans Golgi network. A coatomer complex is required for budding from Golgi membranes, and is essential for the retrograde Golgi-to-ER transport of dilysine-tagged proteins. In mammals, the coatomer can only be recruited by membranes associated to ADP-ribosylation factors (ARFs), which are small GTP-binding proteins; the complex also influences the Golgi structural integrity, as well as the processing, activity, and endocytic recycling of LDL receptors (By similarity). (UniProt Primary accession number: Q9UBF2.)

DNA polymerase delta subunit 2 (DPOD2 or POLD2).

As a component of the trimeric and tetrameric DNA polymerase delta complexes (Pol-delta3 and Pol-delta4, respectively), DPOD2 plays a role in high fidelity genome replication, including in lagging strand synthesis, and repair. Pol-delta3 and Pol-delta4 are characterized by the absence or the presence of POLD4. They exhibit differences in catalytic activity. Most notably, Pol-delta3 shows higher proofreading activity than Pol-delta4. Although both Pol-delta3 and Pol-delta4 process Okazaki fragments in vitro, Pol-delta3 may also be better suited to fulfill this task, exhibiting near-absence of strand displacement activity compared to Pol-delta4 and stalling on encounter with the 5'-blocking oligonucleotides. Pol-delta3 idling process may avoid the formation of a gap, while maintaining a nick that can be readily ligated. Along with DNA polymerase kappa, DNA polymerase delta carries out approximately half of nucleotide excision repair (NER) synthesis following UV irradiation. Under conditions of DNA replication stress, required for the repair of broken replication forks through break-induced replication (BIR). Involved in the translesion synthesis (TLS) of templates carrying O6-methylguanine or abasic sites performed by Pol-delta4, independently of DNA polymerase zeta (REV3L) or eta (POLH). Facilitates abasic site bypass by DNA polymerase delta by promoting extension from the nucleotide inserted opposite the lesion. Also involved in TLS as a component of the POLZ complex. Along with POLD3, dramatically increases the efficiency and processivity of DNA synthesis of the minimal DNA polymerase zeta complex, consisting of only REV3L and REV7. (UniProt Primary accession number: P49005.)

Desmoglein-2 (DSG2).

DSG2 is a component of intercellular desmosome junctions. It is involved in the interaction of plaque proteins and intermediate filaments mediating cell-cell adhesion. (UniProt Primary accession number: Q14126.)

Immunoglobulin heavy variable 3-7 (HV307 or IGHV3-7).

HV307 is the V region of the variable domain of immunoglobulin heavy chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01780.)

Ras GTPase-activating-like protein IQGAP2 (IQGA2 or IQGAP2).

IQGA2 binds to activated CDC42 and RAC1 but does not seem to stimulate their GTPase activity. It is associates with calmodulin. (UniProt Primary accession number: Q13576.)

Keratin, type I cytoskeletal 14 (K1C14 or KRT14).

K1C14 is an intermediate filament protein and the non-helical tail domain is involved in promoting KRT5-KRT14 filaments to self-organize into large bundles and enhances the mechanical properties involved in resilience of keratin intermediate filaments in vitro. (UniProt Primary accession number: P02533.)

Keratin, type I cytoskeletal 19 (K1C19 or KRT19).

K1C19 is involved in the organization of myofibers. Together with KRT8, it helps to link the contractile apparatus to dystrophin at the costameres of striated muscle. (UniProt Primary accession number: P08727.)

Immunoglobulin kappa variable 1-5 (KV105 of IGKV1-5).

KV105 is the V region of the variable domain of immunoglobulin light chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01602.)

Laminin subunit gamma-1 (LAMC1).

Binding to cells via a high affinity receptor, LAMC1 is thought to mediate the attachment, migration and organization of cells into tissues during embryonic development by interacting with other extracellular matrix components. (UniProt Primary accession number: P11047.)

Malate dehydrogenase, mitochondrial (MDHM or MDH2).

MDHM catalyzes the reversible oxidation of malate to oxaloacetate, utilizing the NAD/NADH cofactor system in the citric acid cycle. The protein encoded by this gene is localized to the mitochondria and may play pivotal roles in the malate-aspartate shuttle that operates in the metabolic coordination between cytosol and mitochondria. Several transcript variants encoding different isoforms have been found for this gene. (UniProt Primary accession number: P40926.)

Ribosyldihydronicotinamide dehydrogenase [quinone] (NQO2).

NQO2 serves as a quinone reductase in connection with conjugation reactions of hydroquinones involved in detoxification pathways as well as in biosynthetic processes such as the vitamin K-dependent gamma-carboxylation of glutamate residues in prothrombin synthesis. (UniProt Primary accession number: P16083.)

Myeloperoxidase (PERM or MPO).

PERM is part of the host defense system of polymorphonuclear leukocytes. It is responsible for microbicidal activity against a wide range of organisms. In the stimulated PMN, MPO catalyzes the production of hypohalous acids, primarily hypochlorous acid in physiologic situations, and other toxic intermediates that greatly enhance PMN microbicidal activity. (UniProt Primary accession number: P05164.)

Plastin-3 (PLST or PLS3).

PLST is an actin-bundling protein found in intestinal microvilli, hair cell stereocilia, and fibroblast filopodia. It may play a role in the regulation of bone development. (UniProt Primary accession number: P13797.)

Nicotinate phosphoribosyltransferase (PNCB or NAPRT).

PNCB catalyzes the conversion of nicotinic acid (NA) to NA mononucleotide (NaMN). It is essential for NA to increase cellular NAD levels and prevent oxidative stress of the cells. It catalyzes the synthesis of beta-nicotinate D-ribonucleotide from nicotinate and 5-phospho-D-ribose 1-phosphate at the expense of ATP. (UniProt Primary accession number: Q6XQN6.)

Receptor-type tyrosine-protein phosphatase C (PTPRC).

PTPRC is a protein tyrosine-protein phosphatase required for T-cell activation through the antigen receptor. It acts as a positive regulator of T-cell coactivation upon binding to DPP4. The first PTPase domain has enzymatic activity, while the second one seems to affect the substrate specificity of the first one. Upon T-cell activation, it recruits and dephosphorylates SKAP1 and FYN. It dephosphorylates LYN, and thereby modulates LYN activity (By similarity). (UniProt Primary accession number: P08575.)

Septin-7 (SEPT7).

SEPT7 is a filament-forming cytoskeletal GTPase. It is required for normal organization of the actin cytoskeleton. It is required for normal progress through mitosis. It is involved in cytokinesis. It is required for normal association of CENPE with the kinetochore. It plays a role in ciliogenesis and collective cell movements. It forms a filamentous structure with SEPT12, SEPT6, SEPT2 and probably SEPT4 at the sperm annulus which is required for the structural integrity and motility of the sperm tail during postmeiotic differentiation. (UniProt Primary accession number: Q16181.)

Arginine-tRNA ligase, cytoplasmic (STRC or RARS).

SYRC forms part of a macromolecular complex that catalyzes the attachment of specific amino acids to cognate tRNAs during protein synthesis. It modulates the secretion of AIMP1 and may be involved in generation of the inflammatory cytokine EMAP2 from AIMP1. (UniProt Primary accession number: P54136.)

Thioredoxin-like protein 1 (TXNL1).

TXNL1 is an active thioredoxin with a redox potential of about −250 mV. (UniProt Primary accession number: O43396.)

UDP-glucose:glycoprotein glucosyltransferase 1 (UGGG1 or UGGT1).

UGGG1 recognizes glycoproteins with minor folding defects. It reglucosylates single N-glycans near the misfolded part of the protein, thus providing quality control for protein folding in the endoplasmic reticulum. Reglucosylated proteins are recognized by calreticulin for recycling to the endoplasmic reticulum and refolding or degradation. (UniProt Primary accession number: Q9NYU2.)

WD repeat-containing protein 1 (WDR1).

WDR1 induces disassembly of actin filaments in conjunction with ADF/cofilin family proteins. It enhances cofilin-mediated actin severing (By similarity). It is involved in cytokinesis. It is involved in chemotactic cell migration by restricting lamellipodial membrane protrusions. It is involved in myocardium sarcomere organization. It is required for cardiomyocyte growth and maintenance (By similarity). It is involved in megakaryocyte maturation and platelet shedding. It is required for the establishment of planar cell polarity (PCP) during follicular epithelium development and for cell shape changes during PCP; the function seems to implicate cooperation with CFL1 and/or DSTN/ADF. It is involved in the generation/maintenance of cortical tension (By similarity). It is involved in assembly and maintenance of epithelial apical cell junctions and plays a role in the organization of the perijunctional actomyosin belt. (UniProt Primary accession number: O75083.)

Neuroblast differentiation-associated protein AHNAK (AHNK of AHNAK).

AHNK is thought to be required for neuronal cell differentiation. (UniProt Primary accession number: Q09666.)

Retinal dehydrogenase 1 (AL1A1 of ALDH1A1).

AL1A1 converts/oxidizes retinaldehyde to retinoic acid. It binds free retinal and cellular retinol-binding protein-bound retinal (By similarity). It may have a broader specificity and oxidize other aldehydes in vivo. (UniProt Primary accession number: P00352.)

Aminopeptidase N (AMPN or ANPEP).

AMPN is a broad specificity aminopeptidase which plays a role in the final digestion of peptides generated from hydrolysis of proteins by gastric and pancreatic proteases. It is also involved in the processing of various peptides including peptide hormones, such as angiotensin III and IV, neuropeptides, and chemokines. It may also be involved the cleavage of peptides bound to major histocompatibility complex class II molecules of antigen presenting cells. It may have a role in angiogenesis and promote cholesterol crystallization. IT acts as a receptor for human coronavirus 229E/HCoV-229E. In case of human coronavirus 229E (HCoV-229E) infection, serves as receptor for HCoV-229E spike glycoprotein. It mediates as well human cytomegalovirus (HCMV) infection. (UniProt Primary accession number: P15144.)

F-actin-capping protein subunit beta (CAPZB).

CAPZB is an F-actin-capping protein that bind in a $Ca^{2+}$-independent manner to the fast growing ends of actin filaments (barbed end) thereby blocking the exchange of subunits at these ends. Unlike other capping proteins (such as gelsolin and severin), these proteins do not sever actin filaments. It plays a role in the regulation of cell morphology and cytoskeletal organization. (UniProt Primary accession number: P47756.)

Cathepsin D (CATD of CTSD).

CATD is an acid protease active in intracellular protein breakdown. It plays a role in APP processing following cleavage and activation by ADAM30 which leads to APP degradation. It is involved in the pathogenesis of several diseases such as breast cancer and possibly Alzheimer disease. (UniProt Primary accession number: P07339.)

CAP-Gly domain-containing linker protein 2 (CLIP2).

CLIP2 links microtubules to dendritic lamellar body (DLB), a membranous organelle predominantly present in bulbous dendritic appendages of neurons linked by dendro-dendritic gap junctions. It may operate in the control of brain-specific organelle translocations (By similarity). (UniProt Primary accession number: Q9UDT6.)

Chromogranin-A (CMGA or CHGA).

Pancreastatin: Strongly inhibits glucose induced insulin release from the pancreas.

Catestatin: Inhibits catecholamine release from chromaffin cells and noradrenergic neurons by acting as a non-competitive nicotinic cholinergic antagonist. Displays antibacterial activity against Gram-positive bacteria S. aureus and M. luteus, and Gram-negative bacteria E. coli and P. aeruginosa. Can induce mast cell migration, degranulation and production of cytokines and chemokines. Acts as a potent scavenger of free radicals in vitro. May play a role in the regulation of cardiac function and blood pressure. Serpinin: Regulates granule biogenesis in endocrine cells by up-regulating the transcription of protease nexin 1 (SERPINE2) via a cAMP-PKA-SP1 pathway. This leads to inhibition of granule protein degradation in the Golgi complex which in turn promotes granule formation. (UniProt Primary accession number: P10645.)

Fascin (FSCN1).

FSCN1 organizes filamentous actin into bundles with a minimum of 4.1:1 actin/fascin ratio. It plays a role in the organization of actin filament bundles and the formation of microspikes, membrane ruffles, and stress fibers. It is important for the formation of a diverse set of cell protrusions, such as filopodia, and for cell motility and migration. (UniProt Primary accession number: Q16658.)

GMP reductase 2 (GMPR2).

GMPR2 catalyzes the irreversible NADPH-dependent deamination of GMP to IMP. It functions in the conversion of nucleobase, nucleoside and nucleotide derivatives of G to A nucleotides, and in maintaining the intracellular balance of A and G nucleotides. It plays a role in modulating cellular differentiation. (UniProt Primary accession number: Q9P2T1.)

78 kDa glucose-regulated protein (GRP78 or HSPA5).

GRP78 plays a role in facilitating the assembly of multimeric protein complexes inside the endoplasmic reticulum. It is involved in the correct folding of proteins and degradation of misfolded proteins via its interaction with DNAJC10, probably to facilitate the release of DNAJC10 from its substrate (By similarity). It is thought to be a secreted protein. (UniProt Primary accession number: P11021.)

Glutamate-cysteine ligase catalytic subunit (GSH1 or GCLC).

GSH1, also known as gamma-glutamylcysteine synthetase, is the first rate-limiting enzyme of glutathione synthesis. The enzyme consists of two subunits: a heavy catalytic subunit and a light regulatory subunit. This locus encodes the catalytic subunit, while the regulatory subunit is derived from a different gene located on chromosome 1p22-p21. Mutations at this locus have been associated with hemolytic anemia due to deficiency of gamma-glutamylcysteine synthetase and susceptibility to myocardial infarction. (UniProt Primary accession number: P48506.)

Isocitrate dehydrogenase [NADP] cytoplasmic (IDHC of IDH1).

IDHC is an enzyme that in humans is encoded by the IDH1 gene on chromosome 2. Isocitrate dehydrogenases catalyze the oxidative decarboxylation of isocitrate to 2-oxoglutarate. These enzymes belong to two distinct subclasses, one of which uses $NAD^+$ as the electron acceptor and the other $NADP^+$. Five isocitrate dehydrogenases have been reported: three $NAD^+$-dependent isocitrate dehydrogenases, which localize to the mitochondrial matrix, and two $NADP^+$-dependent isocitrate dehydrogenases, one of which is mitochondrial and the other predominantly cytosolic. Each $NADP^+$-dependent isozyme is a homodimer. The protein encoded by this gene is the $NADP^+$-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production. Alternatively spliced transcript variants encoding the same protein have been found for this gene. (UniProt Primary accession number: 075874.)

Keratin, type I cytoskeletal 20 (K1C20 or KRT20).

K1C20 plays a significant role in maintaining keratin filament organization in intestinal epithelia. When phosphorylated, it plays a role in the secretion of mucin in the small intestine (By similarity). (UniProt Primary accession number: P35900.)

KRR1 small subunit processome component homolog (KRR1).

KRR1 is required for 40S ribosome biogenesis. It is involved in nucleolar processing of pre-18S ribosomal RNA and ribosome assembly (By similarity). (UniProt Primary accession number: Q13601.)

Mannose-binding protein C (MBL2).

MBL2 is a calcium-dependent lectin involved in innate immune defense. It binds mannose, fucose and N-acetylglucosamine on different microorganisms and activates the lectin complement pathway. It binds to late apoptotic cells, as well as to apoptotic blebs and to necrotic cells, but not to early apoptotic cells, facilitating their uptake by macrophages. It may bind DNA. (UniProt Primary accession number: P11226.)

Nuclear transport factor 2 (NTF2 or NUTF2).

NTF2 mediates the import of GDP-bound RAN from the cytoplasm into the nucleus which is essential for the function of RAN in cargo receptor-mediated nucleocytoplasmic transport. Thereby, it plays indirectly a more general role in cargo receptor-mediated nucleocytoplasmic transport. It interacts with GDP-bound RAN in the cytosol, recruits it to the nuclear pore complex via its interaction with nucleoporins and promotes its nuclear import. (UniProt Primary accession number: P61970.)

Phosphoglycerate kinase 1 (PGK1).

In addition to its role as a glycolytic enzyme, PGK-1 acts as a polymerase alpha cofactor protein (primer recognition protein). It may play a role in sperm motility. (UniProt Primary accession number: P00558.)

Serum amyloid A-1 protein (SAA1).

SAA1 is a protein that in humans is encoded by the SAM gene. SAA1 is a major acute-phase protein mainly produced by hepatocytes in response to infection, tissue injury and malignancy. When released into blood circulation, SAA1 is present as an apolipoprotein associated with high-density lipoprotein (HDL). SAA1 is a major precursor of amyloid A (AA), the deposit of which leads to inflammatory amyloidosis. (UniProt Primary accession number: PODJI8.)

Transferrin receptor protein 1 (TFR1 or TFRC).

Cellular uptake of iron occurs via receptor-mediated endocytosis of ligand-occupied transferrin receptor into specialized endosomes. Endosomal acidification leads to iron release. The apotransferrin-receptor complex is then recycled to the cell surface with a return to neutral pH and the concomitant loss of affinity of apotransferrin for its receptor. Transferrin receptor is necessary for development of erythrocytes and the nervous system (By similarity). A second ligand, the hereditary hemochromatosis protein HFE, competes for binding with transferrin for an overlapping C-terminal binding site. Positively regulates T and B cell proliferation through iron uptake. (UniProt Primary accession number: P02786.)

In some embodiments, one or more of the TBI biomarkers listed above can be used to determine that a subject has sustained a TBI based on detection of one or more of these TBI biomarkers in a sample from the subject, and a lack of detection of the one or more TBI biomarkers in a control subject (e.g., a subject that has not sustained a TBI), or in some cases, lack of detection in a subject that has sustained a severe TBI. These TBI biomarkers can include one or more of 1433G, ACK1, ACY1, AKAl2, ARGIL CADH5, CLH1, COPG2, DPOD2, DSG2, HV307, IQGA2, K1C14, K1C19, KV105, LAMC1, MDHM, NQO2, PERM, PLST, PNCB, PTPRC, SEPT7, SYRC, TRXR2, TXNL1, UGGG1, WDR1, AHNK, AL1A1, AMPN, CAPZB, CATD, CLIP2, CMGA, FSCN1, GMPR2, GRP78, GSH1, IDHC, K1C20, KRR1, MBL2, NTF2, PCBP2, PGK1, SAA1, TFR1, or any combinations thereof. The measurement or detection of one or more of these TBI biomarkers in a subject can be sufficient to indicate that the subject has sustained a mild TBI, independent of the need to detect, measure, compare, and/or quantify the amount, concentration, and/or expression level of the one or more TBI biomarkers in a control subject, or a subject that has sustained a severe TBI. Although one or more of these TBI biomarkers may be present in a control subject, or in a subject that has not sustained a TBI, it is generally present in an amount that is not able to be detected though conventional means, as described herein. Thus, in some cases, detection of one or more of these TBI biomarkers in a subject indicates that a subject has sustained a mild TBI.

In some embodiments, one or more of the TBI biomarkers listed above can be used to determine that a subject has sustained a mild TBI of a particular subclassification. Without being bound to a particular theory, underlying etiology, or disease mechanism, one or more of these TBI biomarkers can be used to classify a subject that has a sustained a mild TBI into one of four subclasses (e.g., subclass 1, subclass 2, subclass 3, or subclass 4). For example, detection or measurement of one or more of ACK1, ACY1, PLST, PNCB, PTPRC, UGGG1, or any combinations thereof in a subject that may have sustained a TBI can indicate that the subject has indeed sustained a mild TBI of subclass 1. Detection or measurement of one or more of AKAl2, HV307, PERM, KV105, NQO2, SEPT7, SYRC, TRXR2, or any combinations thereof in a subject that may have sustained a TBI can indicate that the subject has indeed sustained a mild TBI of subclass 2. And detection or measurement of one or more of 1433B, ARGI1, CADH5, CLH1, COPG2, DPOD2, DSG2, IQGA2, K1C14, LAMC1, MDHM, TXNL1, or any combinations thereof in a subject that may have sustained a TBI can indicate that the subject has indeed sustained a mild TBI of subclass 3. Levels of these TBI biomarkers can be detected or measured alone or in combination as part of a mild TBI panel or signature.

In some embodiments, one or more of the TBI biomarkers listed above can be included with other biomarkers that may or may not have been identified as TBI biomarkers. For example, one or more of the TBI biomarkers listed above can be included in a panel of biomarkers that may include one or more of AHNK, AL1A1, AMPN, CAPZB, CATD, CLIP2, CMGA, FSCN1, GMPR2, GRP78, GSH1, IDHC, K1C20, KRR1, MBL2, NTF2, PCBP2, PGK1, SAA1, TFR1, or combinations thereof. In some cases, a panel of TBI biomarkers, in conjunction with other TBI biomarkers and non-TBI biomarkers can aid in the diagnosis of TBI to a greater extent than individual biomarkers alone.

c. Mild TBI Signatures

As described below, the following mild TBI biomarkers were identified as being capable of distinguishing a healthy subject from a subject that has sustained a mild TBI and/or a mild TBI of a specific subclass when detected alone or in combination:

Ephrin type-B receptor 4 (EPHB4).

Ephrin type-B receptor 4 is a protein that in humans is encoded by the EPHB4 gene. Ephrin receptors and their ligands, the ephrins, mediate numerous developmental processes, particularly in the nervous system. Based on their structures and sequence relationships, ephrins are divided into the ephrin-A (EFNA) class, which are anchored to the membrane by a glycosylphosphatidylinositol linkage, and the ephrin-B (EFNB) class, which are transmembrane proteins. The Eph family of receptors are divided into 2 groups based on the similarity of their extracellular domain sequences and their affinities for binding ephrin-A and ephrin-B ligands. Ephrin receptors make up the largest subgroup of the receptor tyrosine kinase (RTK) family. The protein encoded by this gene binds to ephrin-B2 and plays an essential role in vascular development. (UniProt Primary accession number: P54760.)

Immunoglobulin heavy variable 1-3 (HV103 or IGHV1-3).

HV103 is the V region of the variable domain of immunoglobulin heavy chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: A0A0C4DH29.)

Immunoglobulin heavy constant delta (IGHD).

IGHD is a constant region of immunoglobulin heavy chains. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. IgD is the major antigen receptor isotype on the surface of most peripheral B-cells, where it is coexpressed with IgM. The membrane-bound IgD (mIgD) induces the phosphorylation of CD79A and CD79B by the Src family of protein tyrosine kinases. Soluble IgD (sIgD) concentration in serum below those of IgG, IgA, and IgM but much higher than that of IgE. IgM and IgD molecules present on B cells have identical V regions and antigen-binding sites. After the antigen binds to the B-cell receptor, the secreted form sIgD is shut off. IgD is a potent inducer of TNF, IL1B, and IL1RN. IgD also induces release of IL6, IL10, and LIF from peripheral blood mononuclear cells. Monocytes seem to be the main producers of cytokines in vitro in the presence of IgD. (UniProt Primary accession number: P01880.)

Ester hydrolase C11orf54 (CK054 of C11orf54).

CK054 is a protein that in humans is encoded by the C11orf54 gene. The human gene, C11orf54, is also known as PTD012 and PTOD12. C11orf54 exhibits hydrolase activity on p-nitrophenyl acetate and acts on ester bonds, though the overall function is still not fully understood by the scientific community. The protein is highly conserved with the most distant homolog found is in bacteria (UniProt Primary accession number: Q9HOW9.)

Epididymis-specific alpha-mannosidase (MA2B2 or MAN2B2).

MA2B2 catalyzes the hydrolysis of terminal, non-reducing alpha-D-mannose residues in alpha-D-mannosides. (UniProt Primary accession number: Q9Y2E5.)

Protein diaphanous homolog 1 (DIAP1 or DIAPH1).

DIAP1 acts in a Rho-dependent manner to recruit PFY1 to the membrane. It is required for the assembly of F-actin structures, such as actin cables and stress fibers. Nucleates actin filaments. It binds to the barbed end of the actin filament and slows down actin polymerization and depolymerization. It is required for cytokinesis, and transcriptional activation of the serum response factor. DFR proteins couple Rho and Src tyrosine kinase during signaling and the regulation of actin dynamics. It functions as a scaffold protein for MAPRE1 and APC to stabilize microtubules and promote cell migration (By similarity). It has neurite outgrowth promoting activity (By similarity). In hear cells, it may play a role in the regulation of actin polymerization in hair cells. The MEMO1-RHOA-DIAPH1 signaling pathway plays an important role in ERBB2-dependent stabilization of microtubules at the cell cortex. It controls the localization of APC and CLASP2 to the cell membrane, via the regulation of GSK3B activity. In turn, membrane-bound APC allows the localization of the MACF1 to the cell membrane, which is required for microtubule capture and stabilization. It plays a role in the regulation of cell morphology and cytoskeletal organization. It is required in the control of cell shape. It plays a role in brain development. (UniProt Primary accession number: O60610.)

Procollagen-lysine, 2-oxoglutarate 5-dioxygenase 1 (PLOD1).

PLOD1 is part of a complex composed of PLOD1, P3H3 and P3H4 that catalyzes hydroxylation of lysine residues in collagen alpha chains and is required for normal assembly and cross-linking of collagen fibrils (By similarity). It forms hydroxylysine residues in -Xaa-Lys-Gly- sequences in collagens. These hydroxylysines serve as sites of attachment for carbohydrate units and are essential for the stability of the intermolecular collagen cross-links (Probable). (UniProt Primary accession number: Q02809.)

Immunoglobulin kappa variable 1-33 (KV133 or IGKV1-33).

KV133 is the V region of the variable domain of immunoglobulin light chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01594.)

As disclosed herein, the following biomarkers were also identified as being capable of distinguishing a healthy subject from a subject that has sustained a mild TBI and/or a mild TBI of a specific subclass when detected alone or in combination with each other and with the other biomarkers in this section: TPP2, CAND1, NCOR1, K22E, AL9A1, ABHEB, DNM1L, INF2, M3K5, SBSN, SYEP, MYLK, and SAMP. Descriptions of these biomarkers were provided above and are not replicated here.

In some embodiments, one or more of the TBI biomarkers listed above can be used to determine that a subject has sustained a mild TBI of a particular subclassification. Without being bound to a particular theory, underlying etiology, or disease mechanism, one or more of these TBI biomarkers can be used to classify a subject that has a sustained a mild TBI into one of four subclasses (e.g., subclass 1, subclass 2, subclass 3, or subclass 4). In some embodiments, one or more of the TBI biomarkers listed above can be used to determine that a subject has sustained a mild TBI based on detection of one or more of these TBI biomarkers in a sample from the subject at an amount, concentration, and/or expression level that is higher or lower than an amount, concentration and/or expression level of the corresponding TBI biomarker in a control subject. The measurement or detection of an increased or decreased level of one or more of these TBI biomarkers in a subject as compared to a control subject (e.g., a subject that has not sustained a TBI) can be sufficient to indicate that the subject has sustained a mild TBI, and in some cases, can be sufficient to indicate that the subject has sustained a mild TBI of a particular subclass.

For example, detection or measurement of one or more of TPP2, CAND1, NCOR1, K22E, AL9A1, ABHEB, DNM1L, INF2, or any combinations thereof in a subject that may have sustained a TBI can indicate that the subject has indeed sustained a mild TBI of subclass 4. In some cases, detection or measurement of a higher level of CAND1, NCOR1, K22E, ABHEB, DNM1L, or any combination thereof and/or a lower level of TPP2, AL9A1, INF2, or any combination thereof in a subject that may have sustained a TBI as compared to levels from a control subject can indicate that the subject has indeed sustained a mild TBI of subclass 4.

In some embodiments, detection or measurement of one or more of TPP2, NCOR1, HV103, INF2, IGHD, CK054, M3K5, ABHEB, AL9A1, DNM1L, or any combinations thereof in a subject that may have sustained a TBI can indicate that the subject has indeed sustained a mild TBI of subclass 3. In some cases, detection or measurement of a higher level of NCOR1, HV103, IGHD, ABHEB, DNM1L, or any combination thereof and/or a lower level of TPP2, IGHD, CK054, M3K5, AL9A1, or any combination thereof in a subject that may have sustained a TBI as compared to levels from a control subject can indicate that the subject has indeed sustained a mild TBI of subclass 3.

In some embodiments, detection or measurement of one or more of NCOR1, TPP2, K22E, ABHEB, INF2, SBSN, AL9A1, MA2B2, or any combinations thereof in a subject that may have sustained a TBI can indicate that the subject has indeed sustained a mild TBI of subclass 2. In some cases, detection or measurement of a higher level of NCOR1, K22E, ABHEB, SBSN, or any combination thereof and/or a lower level of TPP2, INF2, AL9A1, MA2B2, or any combination thereof in a subject that may have sustained a TBI as compared to levels from a control subject can indicate that the subject has indeed sustained a mild TBI of subclass 2.

In other embodiments, detection or measurement of one or more of K22E, DNM1L, DIAP1, ABHEB, PLOD1, SYEP, KV133, AL9A1, EPHB4, or any combinations thereof in a subject that may have sustained a TBI can indicate that the subject has indeed sustained a mild TBI of subclass 1. In some cases, detection or measurement of a higher level of K22E, DNM1L, DIAP1, ABHEB, PLOD1, SYEP, EPHB4, or any combination thereof and/or a lower level of KV133 and AL9A1, or any combination thereof in a subject that may have sustained a TBI as compared to levels from a control subject can indicate that the subject has indeed sustained a mild TBI of subclass 1.

Levels of these TBI biomarkers can be detected or measured alone or in combination as part of a mild TBI panel or signature.

In some embodiments, one or more of the TBI biomarkers listed above can be included with other biomarkers that may or may not have been identified as TBI biomarkers. For example, one or more of the TBI biomarkers listed above can be included in a panel of biomarkers that may include one or more of MYLK, SAMP or combinations thereof. In some cases, a panel of TBI biomarkers, in conjunction with other TBI biomarkers and non-TBI biomarkers can aid in the diagnosis of TBI to a greater extent than individual biomarkers alone.

As described below, the following mild TBI biomarkers were identified as being capable of distinguishing a healthy subject from a subject that has sustained a mild TBI and/or a mild TBI of a specific subclass when detected alone or in combination:

Dynein light chain 1, cytoplasmic (DYL1 or DYNLL1).

DYL1 acts as one of several non-catalytic accessory components of the cytoplasmic dynein 1 complex that are thought to be involved in linking dynein to cargos and to adapter proteins that regulate dynein function. Cytoplasmic dynein 1 acts as a motor for the intracellular retrograde motility of vesicles and organelles along microtubules. It may play a role in changing or maintaining the spatial distribution of cytoskeletal structures. It binds and inhibits the catalytic activity of neuronal nitric oxide synthase. It promotes transactivation functions of ESR1 and plays a role in the nuclear localization of ESR1. It regulates apoptotic activities of BCL2L11 by sequestering it to microtubules. Upon apoptotic stimuli the BCL2L11-DYNLL1 complex dissociates from cytoplasmic dynein and translocates to mitochondria and sequesters BCL2 thus neutralizing its antiapoptotic activity. (UniProt Primary accession number: P63167.) Puromycin-sensitive aminopeptidase (PSA or NPEPPS).

PSA is an aminopeptidase with broad substrate specificity for several peptides. It is involved in proteolytic events essential for cell growth and viability. It may act as regulator of neuropeptide activity. It plays a role in the antigen-processing pathway for MHC class I molecules. It is involved in the N-terminal trimming of cytotoxic T-cell epitope precursors. It digests the poly-Q peptides found in many cellular proteins. It digests tau from normal brain more efficiently than tau from Alzheimer disease brain. (UniProt Primary accession number: P55786.)

EGF-containing fibulin-like extracellular matrix protein 1 (FBLN3 or EFEMP1).

FBLN3 binds EGFR, the EGF receptor, inducing EGFR autophosphorylation and the activation of downstream signaling pathways. It may play a role in cell adhesion and migration. It may function as a negative regulator of chondrocyte differentiation. In the olfactory epithelium, it may regulate glial cell migration, differentiation and the ability of glial cells to support neuronal neurite outgrowth. (UniProt Primary accession number: Q12805.)

Serum albumin (ALBU or ALB).

ALBU is the main protein of plasma, has a good binding capacity for water, $Ca^{2+}$, $Na^+$, $K^+$, fatty acids, hormones, bilirubin and drugs. Its main function is the regulation of the colloidal osmotic pressure of blood. It is a major zinc transporter in plasma, typically binds about 80% of all plasma zinc. (UniProt Primary accession number: P02768.)

3-ketoacyl-CoA thiolase, mitochondrial (THIM or ACAA2).

THIM is involved in abolishing BNIP3-mediated apoptosis and mitochondrial damage. (UniProt Primary accession number: P42765.)

Immunoglobulin kappa variable 1-39 (KV139 or IGKV1-39).

KV139 is the V region of the variable domain of immunoglobulin light chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01597.)

Mannan-binding lectin serine protease 2 (MASP2).

MASP2 is a serum protease that plays an important role in the activation of the complement system via mannose-binding lectin. After activation by auto-catalytic cleavage it cleaves C2 and C4, leading to their activation and to the formation of C3 convertase. (UniProt Primary accession number: O00187.)

As disclosed herein, the following mild TBI biomarkers were identified as being capable of distinguishing a healthy subject from a subject that has sustained a mild TBI and/or a mild TBI of a specific subclass when detected alone or in combination with each other and with the other biomarkers in this section: ANXA6, CAND1, NCOR1, K22E, ABHEB, DIAP1, DNM1L, EPHB4, GLO2, HV103, IGHA2, IGHD, PLOD1, SBSN, SYEP, MYLK, and SAMP. Descriptions of these biomarkers were provided above and are not replicated here.

In some embodiments, one or more of the TBI biomarkers listed above can be used to determine that a subject has sustained a mild TBI of a particular subclassification. Without being bound to a particular theory, underlying etiology, or disease mechanism, one or more of these TBI biomarkers can be used to classify a subject that has a sustained a mild TBI into one of four subclasses (e.g., subclass 1, subclass 2, subclass 3, or subclass 4). In some embodiments, one or more of the TBI biomarkers listed above can be used to determine that a subject has sustained a mild TBI based on detection of one or more of these TBI biomarkers in a sample from the subject at an amount, concentration, and/or expression level that is higher or lower than an amount, concentration and/or expression level of the corresponding TBI biomarker in a control subject. The measurement or detection of an increased or decreased level of one or more of these TBI biomarkers in a subject as compared to a control subject (e.g., a subject that has not sustained a TBI) can be sufficient to indicate that the subject has sustained a mild TBI, and in some cases, can be sufficient to indicate that the subject has sustained a mild TBI of a particular subclass.

For example, detection or measurement of one or more of CAND1, NCOR1, K22E, ABHEB, DNM1L, SBSN, GLO2, SYEP, or any combinations thereof in a subject that may have sustained a TBI can indicate that the subject has indeed sustained a mild TBI of subclass 4. In some cases, detection or measurement of a higher level of CAND1, NCOR1, K22E, ABHEB, DNM1L, SBSN, GLO2, SYEP, or any combinations thereof in a subject that may have sustained a TBI as compared to levels from a control subject can indicate that the subject has indeed sustained a mild TBI of subclass 4.

In some embodiments, detection or measurement of one or more of NCOR1, HV103, IGHD, ABHEB, DNM1L, ALBU, THIM, IGHA2, KV139, or any combinations thereof in a subject that may have sustained a TBI can indicate that the subject has indeed sustained a mild TBI of subclass 3. In some cases, detection or measurement of a higher level of NCOR1, HV103, IGHD, ABHEB, DNM1L, ALBU, THIM, IGHA2, KV139, or any combinations thereof in a subject that may have sustained a TBI as compared to levels from a control subject can indicate that the subject has indeed sustained a mild TBI of subclass 3.

In some embodiments, detection or measurement of one or more of NCOR1, K22E, ABHEB, SBSN, DNM1L, DIAP1, DYL1, PSA, EPHB4, or any combinations thereof in a subject that may have sustained a TBI can indicate that the subject has indeed sustained a mild TBI of subclass 2. In some cases, detection or measurement of a higher level of NCOR1, K22E, ABHEB, SBSN, DNM1L, DIAP1, DYL1, PSA, EPHB4, or any combinations thereof in a subject that may have sustained a TBI as compared to levels from a control subject can indicate that the subject has indeed sustained a mild TBI of subclass 2.

In other embodiments, detection or measurement of one or more of K22E, DNM1L, DIAP1, ABHEB, PLOD1, SYEP, EPHB4, FBLN3, or any combinations thereof in a subject that may have sustained a TBI can indicate that the subject has indeed sustained a mild TBI of subclass 1. In some cases, detection or measurement of a higher level of K22E, DNM1L, DIAP1, ABHEB, PLOD1, SYEP, EPHB4, FBLN3, or any combinations thereof in a subject that may have sustained a TBI as compared to levels from a control subject can indicate that the subject has indeed sustained a mild TBI of subclass 1.

Levels of these TBI biomarkers can be detected or measured alone or in combination as part of a mild TBI panel or signature.

In some embodiments, one or more of the TBI biomarkers listed above can be included with other biomarkers that may or may not have been identified as TBI biomarkers. For example, one or more of the TBI biomarkers listed above can be included in a panel of biomarkers that may include one or more of ANXA6, MASP2, MYLK, SAMP, or combinations thereof. In some cases, a panel of TBI biomarkers, in conjunction with other TBI biomarkers and non-TBI biomarkers can aid in the diagnosis of TBI to a greater extent than individual biomarkers alone.

d. Rule-Out TBI Biomarkers

As described below, the following TBI biomarkers were identified as being capable of distinguishing a healthy subject from a subject that has sustained a TBI when detected alone or in combination:

SH3 domain-binding glutamic acid-rich-like protein (SH3BGRL).

SH3 domain-binding glutamic acid-rich-like protein 3 is a protein that in humans is encoded by the SH3BGRL3 gene. The 10.5 kDa protein SH3 binding glutamic acid-rich protein-like 3 has an isoelectric point of 5.0. SH3 binding glutamic acid-rich (SH3BGR) gene is located to human chromosome 21. Two homologous genes, SH3BGRL and SH3BGRL3 are located to chromosome Xq13.3 and 1p34.3-35, respectively and code for small proteins similar to the N-terminal region of the SH3BGR protein. SH3BGRL3 protein shows a significant similarity to glutaredoxin 1 of *E. coli*, and all the three proteins are predicted to belong to thioredoxin-like protein family. Glutaredoxins (GRXs) are ubiquitous oxidoreductases, which catalyze the reduction of many intra-cellular protein disulfides and play an important role in many redox pathways. However, the SH3BGRL3 protein lacks the enzymatic function of glutaredoxins and may have a role as a regulator of redox activity. (UniProt Primary accession number: O75368.)

Beta-actin-like protein 2 (ACTBL or ACTBL2).

ACTBL is a member of the actin family. Actins are highly conserved proteins that are involved in various types of cell motility and are ubiquitously expressed in all eukaryotic cells. (UniProt Primary accession number: Q562R1.)

Aldehyde dehydrogenase, mitochondrial (ALDH2).

ALDH2 catalyzes the oxidation of aldehydes. Despite the name "dehydrogenase", their mode of oxidation is by addition of oxygen rather than by removal of hydrogen—that is, they convert aldehydes (R—C(=O)—H) to carboxylic acids (R—C(=O)-O—H). To date, nineteen ALDH genes have been identified within the human genome. These genes participate in a wide variety of biological processes including the detoxification of exogenously and endogenously generated aldehydes. (UniProt Primary accession number: P05091.)

Annexin A5 (ANXA5).

ANXA5 is an anticoagulant protein that acts as an indirect inhibitor of the thromboplastin-specific complex, which is involved in the blood coagulation cascade. (UniProt Primary accession number: P08758.)

Cathelicidin antimicrobial peptide (CAMP).

CAMP binds to bacterial lipopolysaccharides (LPS), and exhibits antibacterial activity. (UniProt Primary accession number: P49913.)

Copine-3 (CPNE3).

CPNE3 is a calcium-dependent phospholipid-binding protein that plays a role in ERBB2-mediated tumor cell migration in response to growth factor heregulin stimulation. (UniProt Primary accession number: O75131.)

Cartilage acidic protein 1 (CRAC1 or CRTAC1).

CRAC1 encodes a glycosylated extracellular matrix protein that is found in the interterritorial matrix of articular deep zone cartilage. This protein is used as a marker to distinguish chondrocytes from osteoblasts and mesenchymal stem cells in culture. The presence of FG-GAP motifs and an RGD integrin-binding motif suggests that this protein may be involved in cell-cell or cell-matrix interactions. Copy number alterations in this gene have been observed in neurofibromatosis type 1-associated glomus tumors. Alternative splicing results in multiple transcript variants. (UniProt Primary accession number: Q9NQ79.)

Cystatin-C (CYTC or CST3).

As an inhibitor of cysteine proteinases, CYTC is thought to serve an important physiological role as a local regulator of this enzyme activity. (UniProt Primary accession number: P01034.)

Aspartyl aminopeptidase (DNPEP).

DNPEP is an aminopeptidase with specificity towards an acidic amino acid at the N-terminus. It is likely to play an important role in intracellular protein and peptide metabolism. (UniProt Primary accession number: Q9ULA0.)

Eukaryotic translation initiation factor 3 subunit I (EIF3I).

EIF3I is a component of the eukaryotic translation initiation factor 3 (eIF-3) complex, which is required for several steps in the initiation of protein synthesis. The eIF-3 complex associates with the 40S ribosome and facilitates the recruitment of eIF-1, eIF-1A, eIF-2:GTP:methionyl-tRNAi and eIF-5 to form the 43S pre-initiation complex (43S PIC). The eIF-3 complex stimulates mRNA recruitment to the 43S PIC and scanning of the mRNA for AUG recognition. The eIF-3 complex is also required for disassembly and recycling of post-termination ribosomal complexes and subsequently prevents premature joining of the 40S and 60S ribosomal subunits prior to initiation. The eIF-3 complex specifically targets and initiates translation of a subset of mRNAs involved in cell proliferation, including cell cycling, differentiation and apoptosis, and uses different modes of RNA stem-loop binding to exert either translational activation or repression. (UniProt Primary accession number: Q13347.)

Glutathione synthetase (GSHB of GSS).

GSHB is the second enzyme in the glutathione (GSH) biosynthesis pathway. It catalyses the condensation of gamma-glutamylcysteine and glycine, to form glutathione. Glutathione synthetase is also a potent antioxidant. It is found in a large number of species including bacteria, yeast, mammals, and plants. In humans, defects in GSS are inherited in an autosomal recessive way and are the cause of severe metabolic acidosis, 5-oxoprolinuria, increased rate of haemolysis, and defective function of the central nervous system. Deficiencies in GSS can cause a spectrum of deleterious symptoms in plants and human beings alike. In eukaryotes, this is a homodimeric enzyme. The substrate-binding domain has a 3-layer alpha/beta/alpha structure. This enzyme utilizes and stabilizes an acylphosphate intermediate to later perform a favorable nucleophilic attack of glycine. (UniProt Primary accession number: P48637.)

Intercellular adhesion molecule 1 (ICAM1).

ICAM1 proteins are ligands for the leukocyte adhesion protein LFA-1 (integrin alpha-L/beta-2). During leukocyte trans-endothelial migration, ICAM1 engagement promotes the assembly of endothelial apical cups through ARHGEF26/SGEF and RHOG activation. It acts as a receptor for major receptor group rhinovirus A-B capsid proteins. Acts as a receptor for Coxsackievirus A2I capsid proteins. Upon Kaposi's sarcoma-associated herpesvirus/HHV-8 infection, it is degraded by viral E3 ubiquitin ligase MIR2, presumably to prevent lysis of infected cells by cytotoxic T-lymphocytes and NK cell. (UniProt Primary accession number: P05362.) (HV323 or IGHV3-23).

HV323 is V region of the variable domain of immunoglobulin heavy chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01764.)

Heterogeneous nuclear ribonucleoprotein D0 (HNRPD or HNRNPD).

HNRPD binds with high affinity to RNA molecules that contain AU-rich elements (AREs) found within the 3'-UTR of many proto-oncogenes and cytokine mRNAs. It also binds to double- and single-stranded DNA sequences in a specific manner and functions a transcription factor. Each of the RNA-binding domains specifically can bind solely to a single-stranded non-monotonous 5'-UUAG-3' sequence and also weaker to the single-stranded 5'-TTAGGG-3' telomeric DNA repeat. It binds RNA oligonucleotides with 5'-UUAGGG-3' repeats more tightly than the telomeric single-stranded DNA 5'-TTAGGG-3' repeats. Binding of RRM1 to DNA inhibits the formation of DNA quadruplex structure which may play a role in telomere elongation. It may be involved in translationally coupled mRNA turnover. It is implicated with other RNA-binding proteins in the cytoplasmic deadenylation/translational and decay interplay of the FOS mRNA mediated by the major coding-region determinant of instability (mCRD) domain. It may play a role in the regulation of the rhythmic expression of circadian clock core genes. It directly binds to the 3'UTR of CRY1 mRNA and induces CRY1 rhythmic translation. It may also be involved in the regulation of PER2 translation. (UniProt Primary accession number: Q14103.)

Immunoglobulin kappa variable 1D-33 (KVD33 or IGKV1D-33).

KVD33 is the V region of the variable domain of immunoglobulin light chains that participates in the antigen recognition. Immunoglobulins, also known as antibodies, are membrane-bound or secreted glycoproteins produced by B lymphocytes. In the recognition phase of humoral immunity, the membrane-bound immunoglobulins serve as receptors which, upon binding of a specific antigen, trigger the clonal expansion and differentiation of B lymphocytes into immunoglobulins-secreting plasma cells. Secreted immunoglobulins mediate the effector phase of humoral immunity, which results in the elimination of bound antigens. The antigen binding site is formed by the variable domain of one heavy chain, together with that of its associated light chain. Thus, each immunoglobulin has two antigen binding sites with remarkable affinity for a particular antigen. The variable domains are assembled by a process called V-(D)-J rearrangement and can then be subjected to somatic hypermutations which, after exposure to antigen and selection, allow affinity maturation for a particular antigen. (UniProt Primary accession number: P01593.)

Coagulation factor IX (FA9 or F9).

FA9 is a factor IX is a vitamin K-dependent plasma protein that participates in the intrinsic pathway of blood coagulation by converting factor X to its active form in the presence of $Ca^{2+}$ ions, phospholipids, and factor VIIIa. (UniProt Primary accession number: P00740.)

Complement factor H-related protein 4 (FHR4 or CFHR4).

FHR4 is involved in complement regulation. It can associate with lipoproteins and may play a role in lipid metabolism. (UniProt Primary accession number: Q92496.)

PERM and PDZ domain-containing protein 1 (FRPD1 or FRMPD1).

FRPD1 acts to stabilize membrane-bound GPSM1, and thereby promotes its interaction with GNAI1. (UniProt Primary accession number: Q5SYB0.)

Heat shock protein HSP 90-beta (HS90B or HSP90AB1).

HS90B is a molecular chaperone that promotes the maturation, structural maintenance and proper regulation of specific target proteins involved for instance in cell cycle control and signal transduction. It undergoes a functional cycle that is linked to its ATPase activity. This cycle probably induces conformational changes in the client proteins, thereby causing their activation. It interacts dynamically with various co-chaperones that modulate its substrate recognition, ATPase cycle and chaperone function. It engages with a range of client protein classes via its interaction with various co-chaperone proteins or complexes, which act as adapters, simultaneously able to interact with the specific client and the central chaperone itself. Recruitment of ATP and co-chaperone followed by client protein forms a functional chaperone. After the completion of the chaperoning process, properly folded client protein and co-chaperone leave HSP90 in an ADP-bound partially open conformation and finally, ADP is released from HSP90 which acquires an open conformation for the next cycle. Apart from its chaperone activity, it also plays a role in the regulation of the transcription machinery. HSP90 and its co-chaperones modulate transcription at least at three different levels. In the first place, they alter the steady-state levels of certain transcription factors in response to various physiological cues. Second, they modulate the activity of certain epigenetic modifiers, such as histone deacetylases or DNA methyl transferases, and thereby respond to the change in the environment. Third, they participate in the eviction of histones from the promoter region of certain genes and thereby turn on gene expression. It antagonizes STUB1-mediated inhibition of TGF-beta signaling via inhibition of STUB1-mediated SMAD3 ubiquitination and degradation. It promotes cell differentiation by chaperoning BIRC2 and thereby protecting from auto-ubiquitination and degradation by the proteasomal machinery. It is the main chaperone that is involved in the phosphorylation/activation of the STAT1 by chaperoning both JAK2 and PRKCE under heat shock and in turn, activates its own transcription. (UniProt Primary accession number: P08238.)

Alpha-mannosidase 2 (MA2A1 or MAN2A1).

MA2A1 catalyzes the first committed step in the biosynthesis of complex N-glycans. It controls conversion of high mannose to complex N-glycans; the final hydrolytic step in the N-glycan maturation pathway. (UniProt Primary accession number: Q16706.)

Prenylcysteine oxidase 1 (PCYOX or PCYOX1).

PCYOX is involved in the degradation of prenylated proteins. It cleaves the thioether bond of prenyl-L-cysteines, such as farnesylcysteine and geranylgeranylcysteine. (UniProt Primary accession number: Q9UHG3.)

Purine nucleoside phosphorylase (PNPH of PNP).

PNPH is a purine nucleoside phosphorylase that catalyzes the phosphorolytic breakdown of the N-glycosidic bond in the beta-(deoxy)ribonucleoside molecules, with the formation of the corresponding free purine bases and pentose-1-phosphate. (UniProt Primary accession number: P00491.)

Vitamin K-dependent protein C (PROC).

PROC is a vitamin K-dependent serine protease that regulates blood coagulation by inactivating factors Va and VIIIa in the presence of calcium ions and phospholipids. It exerts a protective effect on the endothelial cell barrier function. (UniProt Primary accession number: P04070.)

60S ribosomal protein L3 (RL3 or RPL3).

RL3 is a component of the large subunit of cytoplasmic ribosomes. (UniProt Primary accession number: P39023.)

Serine/arginine repetitive matrix protein 2 (SRRM2).

SRRM2 is involved in pre-mRNA splicing. It may function at or prior to the first catalytic step of splicing at the catalytic center of the spliceosome. It may do so by stabilizing the catalytic center or the position of the RNA substrate (By similarity). It binds to RNA. (UniProt Primary accession number: Q9UQ35.)

Tubulin beta-1 chain (TBB1 or TUBB1).

TBBI is a subunit of tubulin, which is the major constituent of microtubules. It binds two moles of GTP, one at an exchangeable site on the beta chain and one at a non-exchangeable site on the alpha chain (By similarity). (UniProt Primary accession number: Q9H4B7.)

Tenascin (TENA or TNC).

TENA is an extracellular matrix protein implicated in guidance of migrating neurons as well as axons during development, synaptic plasticity as well as neuronal regeneration. It promotes neurite outgrowth from cortical neurons grown on a monolayer of astrocytes. It is a ligand for integrins alpha-8/beta-1, alpha-9/beta-1, alpha-V/beta-3 and alpha-V/beta-6. In tumors, it stimulates angiogenesis by elongation, migration and sprouting of endothelial cells. (UniProt Primary accession number: P24821.)

Heat shock protein 75 kDa, mitochondrial (TRAP1).

TRAP1 is a chaperone that expresses an ATPase activity. It is involved in maintaining mitochondrial function and polarization, downstream of PINK I and mitochondrial complex I. It is a negative regulator of mitochondrial respiration able to modulate the balance between oxidative phosphorylation and aerobic glycolysis. The impact of TRAP1 on mitochondrial respiration is probably mediated by modulation of mitochondrial SRC and inhibition of SDHA. (UniProt Primary accession number: Q12931.)

In some embodiments, one or more of the TBI biomarkers listed above can be used to determine that a subject has not sustained a TBI based on detection of one or more of these TBI biomarkers in a sample from the subject (rule-out TBI). These TBI biomarkers can include one or more of ACTBL, ALDH2, ANXA5, CAMP, CPNE3, CRAC1, CYTC, DNPEP, EIF3I, GSHB, ICAM1, HV323, HNRPD, KVD33, FA9, FHR4, FRPD1, HS90B, MA2A1, PCYOX, PNPH, PROC, RL3, SH3L3, SRRM2, TBB1, TENA, TRAP1, or any combinations thereof. The measurement or detection of one or more of these TBI biomarkers in a subject can be sufficient to indicate that the subject has not sustained a TBI, independent of the need to detect, measure, compare, and/or quantify the amount, concentration, and/or expression level of the one or more TBI biomarkers in a control subject. Although one or more of these TBI biomarkers may be present in a subject that has sustained a TBI, it is generally present in an amount that is not able to be detected though conventional means, as described herein. Thus, in some cases, detection of one or more of these TBI biomarkers in a subject indicates that a subject has not sustained a TBI. Levels of these TBI biomarkers can be detected or measured alone or in combination as part of a mild TBI panel or signature.

7. Methods for Measuring the Level of a TBI Biomarker

In the methods described above, TBI biomarker levels can be measured by any means, such as antibody dependent methods, such as immunoassays, protein immunoprecipitation, immunoelectrophoresis, chemical analysis, SDS-PAGE and Western blot analysis, protein immunostaining, electrophoresis analysis, a protein assay, a competitive binding assay, a functional protein assay, or chromatography or spectrometry methods, such as high-performance liquid chromatography (HPLC), mass spectrometry, or liquid chromatography-mass spectrometry (LC/MS) or capillary electrophoresis (CE)-MS, or direct infusion, or any separating front end coupled with MS. Also, the assay can be employed in clinical chemistry format such as would be known by one skilled in the art.

In some embodiments, measuring the level of a TBI biomarker includes contacting the sample with a first specific binding member and second specific binding member. In some embodiments the first specific binding member is a capture antibody and the second specific binding member is a detection antibody. In some embodiments, measuring the level of a TBI biomarker includes contacting the sample, either simultaneously or sequentially, in any order: (1) a capture antibody (e.g., a TBI biomarker-capture antibody), which binds to an epitope on a TBI biomarker or a TBI biomarker fragment to form a capture antibody-TBI biomarker antigen complex (e.g., TBI biomarker-capture antibody-TBI biomarker antigen complex), and (2) a detection antibody (e.g., TBI biomarker-detection antibody), which includes a detectable label and binds to an epitope on a TBI biomarker that is not bound by the capture antibody, to form a TBI biomarker antigen-detection antibody complex (e.g., TBI biomarker antigen-TBI biomarker-detection antibody complex), such that a capture antibody-TBI biomarker antigen-detection antibody complex (e.g., TBI biomarker-capture antibody-TBI biomarker antigen-TBI biomarker-detection antibody complex) is formed, and measuring the amount or concentration of a TBI biomarker in the sample based on the signal generated by the detectable label in the capture antibody-TBI biomarker antigen-detection antibody complex.

In some embodiments, the first specific binding member is immobilized on a solid support. In some embodiments, the second specific binding member is immobilized on a solid support. In some embodiments, the first specific binding member is a TBI biomarker antibody as described below.

In some embodiments, the sample is diluted or undiluted. The sample can be from about 1 to about 25 microliters, about 1 to about 24 microliters, about 1 to about 23 microliters, about 1 to about 22 microliters, about 1 to about 21 microliters, about 1 to about 20 microliters, about 1 to about 18 microliters, about 1 to about 17 microliters, about 1 to about 16 microliters, about 15 microliters or about 1 microliter, about 2 microliters, about 3 microliters, about 4 microliters, about 5 microliters, about 6 microliters, about 7 microliters, about 8 microliters, about 9 microliters, about 10 microliters, about 11 microliters, about 12 microliters, about 13 microliters, about 14 microliters, about 15 microliters, about 16 microliters, about 17 microliters, about 18 microliters, about 19 microliters, about 20 microliters, about 21 microliters, about 22 microliters, about 23 microliters, about 24 microliters or about 25 microliters. In some embodiments, the sample is from about 1 to about 150 microliters or less or from about 1 to about 25 microliters or less.

Some instruments (such as, for example the Abbott Laboratories instruments ARCHITECT®, Abbott Alinity instruments, and other core laboratory instruments) other than a point-of-care device may be capable of measuring levels of a TBI biomarker in a sample at about 0.032 μg/L at 10% CV or lower. Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

a. Detection by Mass Spectrometry

As used herein, "MS data" generally refers to raw MS data obtained from a mass spectrometer and/or processed MS data in which peptides and their fragments (e.g., transitions and MS peaks) are already identified, analyzed and/or quantified. In some embodiments of the present disclosure, methods based on MRM-MS or SRM-MS and/or PRM-MS allow for the detection and accurate quantification of specific peptides in complex mixtures. SRM/MRM-MS is a technology with the potential for reliable and comprehensive quantification of substances of low abundance in complex samples. SRM/MRM-MS is performed on triple quadrupole-like instruments, in which increased selectivity is obtained through collision-induced dissociation. It is a non-scanning mass spectrometry technique, where two mass analyzers (Q1 and Q3) are used as static mass filters, to monitor a particular fragment of a selected precursor. On triple quadrapole instruments, various ionization methods can be used, including without limitation, electrospray ionization, chemical ionization, electron ionization, atmospheric pressure chemical ionization, and matrix-assisted laser desorption ionization. Both the first mass analyzer and the collision cell are continuously exposed to ions from the source in a time dependent manner. Once the ions move into the third mass analyzer time dependence becomes a factor. On triple quadrupole instruments, the first quadrupole mass filter, Q1, is the primary m/z selector after the sample leaves the ionization source. Any ions with mass-to-charge ratios other than the one selected for will not be allowed to infiltrate Q1. The collision cell, denoted as "q2", located between the first quadrapole mass filter Q1 and second quadrapole mass filter Q3, is where fragmentation of the sample occurs in the presence of an inert gas like argon, helium, or nitrogen. Upon exiting the collision cell, the fragmented ions then travel onto the second quadrapole mass filter Q3, where m/z selection can occur again.

The specific pair of mass-over-charge (m/z) values associated to the precursor and fragment ions selected is referred to as a "transition." The detector acts as a counting device for the ions matching the selected transition thereby returning an intensity distribution over time. MRM-MS is when multiple SRM-MS transitions are measured within the same experiment on the chromatographic time scale by rapidly switching between the different precursor/fragment pairs. Typically, the triple quadrupole instrument cycles through a series of transitions and records the signal of each transition as a function of the elution time. The method allows for additional selectivity by monitoring the chromatographic co-elution of multiple transitions for a given analyte.

For general references on mass spectrometry and proteomics, see e.g., Salvatore Sechi, *Quantitative Proteomics by Mass Spectrometry* (Methods in Molecular Biology) 2nd ed. 2016 Edition, Humana Press (New York, NY, 2009); Daniel Martins-de-Souza, Shotgun *Proteomics: Methods and Protocols* 2014 edition, Humana Press (New York, NY, 2014); Jörg Reinders and Albert Sickmann, *Proteomics: Methods and Protocols* (Methods in Molecular Biology) 2009 edition, Humana Press (New York, NY, 2009); and Jörg Reinders, *Proteomics in Systems Biology: Methods and Protocols* (Methods in Molecular Biology) $1^{st}$ ed. 2016 edition, Humana Press (New York, NY, 2009).

In addition to PRM-MS is also an application of SRM with parallel detection of all transitions in a single analysis using a high resolution mass spectrometer. PRM-MS provides high selectivity, high sensitivity and high-throughput to quantify selected peptide (Q1), hence quantify proteins (MS1). Again, multiple peptides can be specifically selected for each protein. PRM-MS methodology uses the quadrupole of a mass spectrometer to isolate a target precursor ion, fragments the targeted precursor ion in the collision cell, and then detects the resulting product ions in the Orbitrap mass analyzer. Quantification is carried out after data acquisition by extracting one or more fragment ions with 5-10 ppm mass windows. PRM-MS uses a quadrupole time-of-flight (QTOF) or hybrid quadrupole-orbitrap (QOrbitrap) mass spectrometer to carry out the peptides/proteins quantitation. Examples of QTOF include but are not limited to: TripleTOF 6600 or 5600 System (Sciex); X500R QTOF System (Sciex); 6500 Series Accurate-Mass Quadrupole Time-of-Flight (Q-TOF) (Agilent); or Xevo G2-XS QTof Quadrupole Time-of-Flight Mass Spectrometry (Waters). Examples of QObitrap include but are not limited to: Q Exactive Hybrid Quadrupole-Orbitrap Mass Spectrometer (Thermo Scientific); or Orbitrap Fusion Tribrid (Thermo Scientific).

In some embodiments, the developed methods herein can be applied to the quantification of polypeptides(s) or protein(s) in biological sample(s). Any kind of biological samples comprising polypeptides or proteins can be the starting point and be analyzed by the methods disclosed herein. Indeed, any protein/peptide containing sample can be used for and analyzed by the methods produced here (e.g., tissues, cells). The methods herein can also be used with peptide mixtures obtained by digestion. Digestion of a polypeptide or protein includes any kind of cleavage strategies, such as, enzymatic, chemical, physical or combinations thereof. According to some embodiments, the following parameters of the methods provided herein are determined: trypsin (or other protease) digestion and peptide clean up, best responding polypeptides, best responding proteins, best responding peptides, best responding fragments, fragment intensity ratios (increased high and reproducible peak intensities), optimal collision energies, and all the optimal parameters to maximize sensitivity and/or specificity of the methods.

In other embodiments, quantification of the polypeptides and/or of the corresponding proteins or activity/regulation of the corresponding proteins is desired. A selected peptide is labeled with a stable-isotope and used as an internal standard (SIL) to achieve absolute quantification of a protein of interest. The addition of a quantified stable-labeled peptide analogue of the tag to the peptide sample in known amount; and subsequently the tag and the peptide of interest is quantified by mass spectrometry and absolute quantification of the endogenous levels of the proteins is obtained.

In some embodiments, biomarkers of the present disclosure can be detected by mass spectrometry, a method that employs a mass spectrometer to detect gas phase ions, as described above. Examples of mass spectrometers are time-of-flight, magnetic sector, quadrupole filter, ion trap, ion cyclotron resonance, electrostatic sector analyzer, hybrids or combinations of the foregoing, and the like. In one embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein or with enrichment. In another embodiment, the mass spectrometric technique is multiple reaction monitoring (MRM) or quantitative MRM.

In some embodiments, the mass spectrometry method involves first enrichment by capturing one or more biomarkers on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In one embodiment, one could fractionate on an anion exchange resin and detect by MALDI directly. In another embodiment, one could capture the biomarkers on an immuno-chromatographic resin that comprises antibodies that bind the biomarkers, wash the resin to remove unbound material, elute the biomarkers from the resin and detect the eluted biomarkers by MALDI or on to another MS instrument (using any method for quantification).

The biomarkers of the present disclosure can also be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry) or by mass spectrometry using any MS instrument and any MS method.

8. TBI Biomarker-Recognizing Antibodies

The methods described herein may use an isolated antibody that specifically binds to a TBI biomarker or fragments thereof, referred to as "TBI biomarker antibody." TBI biomarker antibodies can be used to assess the status of a TBI biomarker as a measure of traumatic brain injury, detect the presence of a TBI biomarker in a biological sample, quantify the amount of a TBI biomarker present in a biological sample, or detect the presence of and quantify the amount of a TBI biomarker in a biological sample.

TBI biomarker antibodies include any antibody that binds to a TBI biomarker, a fragment thereof, an epitope of a TBI biomarker, or a variant thereof. The antibody may be a fragment of the anti-TBI biomarker antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab') 2, Fv or scFv fragments. The antibody derivatives can be produced by peptidomimetics. Further, techniques described for the production of single chain antibodies can be adapted to produce single chain antibodies.

The anti-TBI biomarker antibodies may be a chimeric anti-TBI biomarker antibody or a humanized anti-TBI biomarker antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., *BMC Biotechnology*, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-TBI biomarker antibodies. For example, libraries of naïve human single chain variable fragments (scFv) may be used to select human anti-TBI biomarker I antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

The antibody may immunospecifically bind to the peptide of a TBI biomarker, a fragment thereof, or a variant thereof. The antibody may immunospecifically recognize and bind at least three amino acids, at least four amino acids, at least five amino acids, at least six amino acids, at least seven amino acids, at least eight amino acids, at least nine amino acids, or at least ten amino acids within an epitope region. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of an epitope region.

9. Antibody Preparation/Production

Antibodies may be prepared by any of a variety of techniques, including those well known to those skilled in the art. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies include Chinese Hamster Ovary (CHO cells) (including dhfr-CHO cells, described in Urlaub and Chasin, *Proc. Natl. Acad. Sci. USA,* 77: 4216-4220 (1980)), used with a DHFR selectable marker, e.g., as described in Kaufman and Sharp, *J. Mol. Biol.,* 159: 601-621 (1982), NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure may be performed. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies. In addition, bifunctional antibodies may be produced in which one heavy and one light chain are an antibody (i.e. binds human troponin I) and the other heavy and light chain are specific for an antigen other than a human TBI biomarker by crosslinking an antibody to a second antibody by standard chemical crosslinking methods.

In a preferred system for recombinant expression of an antibody, or antigen-binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the method of synthesizing a recombinant antibody may be by culturing a host cell in a suitable culture medium until a recombinant antibody is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with a TBI biomarker or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes electrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161) that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994)).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914,128 B1.

Antibody variants can also be prepared using delivering a polynucleotide encoding an antibody to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al., (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

Antibody production via the use of hybridoma technology, the selected lymphocyte antibody method (SLAM), transgenic animals, and recombinant antibody libraries is described in more detail below.

10. TBI Biomarker-Recognizing Aptamers

The methods of the present disclosure include the use of aptamers to detect or identify one or more TBI biomarkers. Aptamers are suitable for use in developing probes having high affinity and selectivity for target molecules, such as TBI peptide biomarkers. Aptamers include single-stranded DNA (ssDNA), RNA, or modified nucleic acids, which have the ability to bind specifically to their targets, which range from small organic molecules to proteins and peptides. The basis for target recognition is the tertiary structures formed by the single-stranded oligonucleotides, as known in the art. In some embodiments, aptamers used to detect or identify one or more TBI biomarkers can be obtained through an in vitro selection process known as SELEX, in which aptamers are selected from a library of random sequences of synthetic DNA or RNA by repetitive binding of the oligonucleotides to target molecules.

In some embodiments, nucleic acids that constitute an aptamer library mixture used for screening for candidate TBI biomarker capture agents can be single-stranded DNA or RNA with or without chemical modifications. The introduction of additional chemical entities into DNA during the selection process can include, for example, the use of a 5-alkyne modified nucleobase, (e.g., thymine). Additionally, 5-C8-alkyne modified nucleotide-triphosphates, for example deoxythymidines, are commercially available or can be synthesized. Such 5-C8-alkyne modified nucleobases can be introduced into DNA by PCR. Such modifications can be further derivatized with so called bio-orthogonal chemistry, for example, using the Cu(I) catalyzed 1,3-dipolar cycloaddition of respective azides with the alkyne. Beside the Cu(I) catalysed azide-alkyne cycloaddition (CuAAC), copper-free strain-promoted azide-alkyne cycloaddition (SPAAC) reactions also are useful. In some embodiments involving cellular or living systems, the strain-promoted azide-alkyne cycloaddition can overcome toxicity issues associated with the use of Cu(I). Any number of desirable chemical modifications can be added to the oligonucleotide library used for screening purposes. Examples of such modifications include without limitation aliphatic- aromatic-, charged-, basic-, acidic, heteroaromatic-, sugar-kind of-, metal-containing or peptide-residues.

In some embodiments, a nucleobase that is to be modified to contain an azide-alkyne chemical group can include an ethynyl-, propynyl- or butynyl- dU, dA, dC or dG nucleotide. In other embodiments, a nucleobase that is to be modified to contain an azide-alkyne chemical group may be an ethynyl-dU nucleotide, or an ethynyl-dA nucleotide, an ethynyl-dC nucleotide or an ethynyl-dG nucleotide. Nucleotide aptamer libraries with these example modifications can be used in various SELEX-based selection methods, in order to enhance the chemical diversity of DNA aptamer libraries. The starting, or candidate, mixture of nucleic acids can be modified such that at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, at least 99%, or 100% of the members of the mixture are modified to comprise the functionalization introduced by click chemistry, for example. Less than 100% modification may allow for enhanced diversity by allowing certain positions in an oligonucleotide to be modified but not others, whereas 100% modification ensures consistency during the selection process. In some embodiments, different modifications are made at different positions in the oligonucleotide to further enhance diversity.

TBI biomarker-recognizing aptamers can be used in various methods to detect a presence or level of one or more TBI biomarker in a biological sample (e.g., biological entities of interest such as proteins, nucleic acids, or microvesicles). The aptamer can function as a binding agent or capture agent to assess presence or level of the cognate TBI biomarker. In various embodiments of the present disclosure directed to diagnostics and/or prognostics, one or more aptamers can be configured in a ligand-target based assay, where one or more aptamer can be contacted with a selected biological sample to allow the or more aptamer to associate with or binds to its target TBI biomarker molecule. Aptamers can also be used to identify a profile of multiple TBI biomarkers (a "biomarker" profile or signature) based on the biological samples assessed and biomarkers detected. A biomarker profile of a biological sample may comprise a presence, level or other characteristic of one or more biomarker of interest that can be assessed, including without limitation a presence, level, sequence, mutation, rearrangement, translocation, deletion, epigenetic modification, methylation, post-translational modification, allele, activity, complex partners, stability, half -life, and the like.

Biomarker profiles or signatures can be used to evaluate diagnostic and/or prognostic criteria such as presence of disease, disease staging, disease monitoring, disease stratification, or surveillance for detection, metastasis or recurrence or progression of disease. For example, methods of the present disclosure can include methods for correlating a TBI biomarker profile to a selected condition or disease, such as severe TBI, mild TBI, or a subclass of mild TBI. A biomarker profile can also be used clinically in making decisions concerning treatment modalities including therapeutic intervention. A biomarker profile based on aptamer detection, identification, and/or quantification can further be used clinically to make treatment decisions, including whether to perform an imaging procedure (e.g., MRI).

11. Variations on Methods

The disclosed methods of determining the presence or amount of analyte of interest (e.g., TBI biomarker) present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc.

a. Immunoassay

The analyte of interest, and/or peptides of fragments thereof (e.g., TBI biomarker and/or peptides or fragments thereof), may be analyzed using TBI biomarker antibodies in an immunoassay. The presence or amount of analyte (e.g., TBI biomarker) can be determined using antibodies and detecting specific binding to the analyte. For example, the antibody, or antibody fragment thereof, may specifically bind to the analyte. If desired, one or more of the antibodies can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

The presence or amount of analyte (e.g., TBI biomarker) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, MN)). An example of a point-of-care device that can be used is i-STAT® (Abbott, Laboratories, Abbott Park, IL). Other methods that can be used include a chemiluminescent microparticle immunoassay, in particular one employing the ARCHITECT® automated analyzer (Abbott Laboratories, Abbott Park, IL), as an example. Other methods include, for example, mass spectrometry, and immunohistochemistry (e.g., with sections from tissue biopsies), using anti-analyte (e.g., anti-TBI biomarker) antibodies (monoclonal, polyclonal, chimeric, humanized, human, etc.) or antibody fragments thereof against analyte (e.g., TBI biomarker). Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the analyte can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., TBI biomarker) and a specific binding partner. The order in which the test sample and the specific binding partner are added to form the mixture is not critical. The test sample is simultaneously contacted with the specific binding partner. In some embodiments, the specific binding partner and any TBI biomarker contained in the test sample may form a specific binding partner-analyte (e.g., TBI biomarker)-antigen complex. The specific binding partner may be an anti-analyte antibody (e.g., anti-TBI biomarker antibody that binds to an epitope having an amino acid sequence comprising at least three contiguous (3) amino acids of the TBI biomarker. Moreover, the specific binding partner may be labeled with or contains a detectable label as described above.

A heterogeneous format may be used. For example, after the test sample is obtained from a subject, a first mixture is prepared. The mixture contains the test sample being assessed for analyte (e.g., TBI biomarker) and a first specific binding partner, wherein the first specific binding partner and any TBI biomarker contained in the test sample form a first specific binding partner-analyte (e.g., TBI biomarker)-antigen complex. The first specific binding partner may be an anti-analyte antibody (e.g., anti-TBI biomarker antibody that binds to an epitope having an amino acid sequence comprising at least three contiguous (3) amino acids of the TBI biomarker. The order in which the test sample and the first specific binding partner are added to form the mixture is not critical.

The first specific binding partner may be immobilized on a solid phase. The solid phase used in the immunoassay (for the specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., TBI biomarker) antigen complex is formed, any unbound analyte (e.g., TBI biomarker) is removed from the complex using any technique known in the art. For example, the unbound analyte can be removed by washing. Desirably, however, the first specific binding partner is present in excess of any analyte present in the test sample, such that all analyte that is present in the test sample is bound by the first specific binding partner.

After any unbound analyte (e.g., TBI biomarker) is removed, a second specific binding partner is added to the mixture to form a first specific binding partner-analyte of interest (e.g., TBI biomarker)-second specific binding partner complex. The second specific binding partner may be an anti-analyte antibody (e.g., TBI biomarker antibody that binds to an epitope having an amino acid sequence comprising at least three contiguous (3) amino acids of the TBI biomarker. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

(1) Sandwich immunoassay

A sandwich immunoassay measures the amount of antigen between two layers of antibodies (i.e. at least one capture antibody) and a detection antibody (i.e. at least one detection antibody). The capture antibody and the detection antibody bind to different epitopes on the antigen, e.g., analyte of interest such as a TBI biomarker). Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., TBI biomarker) in a test sample. More specifically, the at least two antibodies bind to certain epitopes of analyte forming an immune complex which is referred to as a "sandwich." One or more antibodies can be used to capture the analyte in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte do not bind to all or part of an epitope recognized by the second or subsequent antibodies, thereby interfering with the ability of the one or more second detection antibodies to bind to the analyte.

The antibodies may be used as a first antibody in said immunoassay. The antibody immunospecifically binds to epitopes on analyte (e.g., TBI biomarker). In addition to the antibodies of the present disclosure, said immunoassay may comprise a second antibody that immunospecifically binds to epitopes that are not recognized or bound by the first antibody.

A test sample suspected of containing analyte (e.g., TBI biomarker) can be contacted with at least one first capture antibody (or antibodies) and at least one second detection antibodies either simultaneously or sequentially. In the sandwich assay format, a test sample suspected of containing analyte is first brought into contact with the at least one first capture antibody that specifically binds to a particular epitope under conditions which allow the formation of a first antibody-analyte antigen complex. If more than one capture antibody is used, a first multiple capture antibody-TBI biomarker antigen complex is formed. In a sandwich assay, the antibodies, preferably, the at least one capture antibody, are used in molar excess amounts of the maximum amount of analyte expected in the test sample. For example, from about 5 μg/mL to about 1 mg/mL of antibody per ml of microparticle coating buffer may be used.

i. Anti-TBI biomarker Capture Antibody

Optionally, prior to contacting the test sample with the at least one first capture antibody, the at least one first capture antibody can be bound to a solid support which facilitates the separation the first antibody-analyte (e.g., TBI biomarker) complex from the test sample. Any solid support known in the art can be used, including but not limited to, solid supports made out of polymeric materials in the forms of wells, tubes, or beads (such as a microparticle). The antibody (or antibodies) can be bound to the solid support by adsorption, by covalent bonding using a chemical coupling agent or by other means known in the art, provided that such binding does not interfere with the ability of the antibody to bind analyte. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing analyte (e.g., TBI biomarker) is incubated in order to allow for the formation of a first capture antibody (or multiple antibody)-analyte complex. The incubation can be carried out at a pH of from about 4.5 to about 10.0, at a temperature of from about 2° C. to about 45° C., and for a period from at least about one (1) minute to about eighteen (18) hours, from about 2-6 minutes, from about 7-12 minutes, from about 5-15 minutes, or from about 3-4 minutes.

ii. Detection Antibody

After formation of the first/multiple capture antibody-analyte (e.g., TBI biomarker) complex, the complex is then contacted with at least one second detection antibody (under conditions that allow for the formation of a first/multiple antibody-analyte antigen-second antibody complex). In some embodiments, the test sample is contacted with the detection antibody simultaneously with the capture antibody. If the first antibody-analyte complex is contacted with more than one detection antibody, then a first/multiple capture antibody-analyte-multiple antibody detection complex is formed. As with first antibody, when the at least second (and subsequent) antibody is brought into contact with the first antibody-analyte complex, a period of incubation under conditions similar to those described above is required for the formation of the first/multiple antibody-analyte-second/multiple antibody complex. Preferably, at least one second antibody contains a detectable label. The detectable label can be bound to the at least one second antibody prior to, simultaneously with or after the formation of the first/multiple antibody-analyte-second/multiple antibody complex. Any detectable label known in the art can be used.

Chemiluminescent assays can be performed in accordance with the methods described in Adamczyk et al., *Anal. Chim. Acta* 579(1): 61-67 (2006). While any suitable assay format can be used, a microplate chemiluminometer (Mithras LB-940, Berthold Technologies U.S.A., LLC, Oak Ridge, TN) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-antigen (e.g., TBI biomarker) complexes form. Alternatively, if a second specific binding partner is used and the second specific binding partner is detectably labeled with an acridinium compound, detectably labeled first specific binding partner-analyte-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of analyte (e.g., TBI biomarker) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. Other labels other than chemiluminescent labels can be employed. For instance, enzymatic labels (including but not limited to alkaline phosphatase) can be employed.

The chemiluminescent signal, or other signal, that is generated can be detected using routine techniques known to those skilled in the art. Based on the intensity of the signal generated, the amount of analyte of interest (e.g., TBI biomarker) in the sample can be quantified. Specifically, the amount of analyte in the sample is proportional to the intensity of the signal generated. The amount of analyte present can be quantified by comparing the amount of light generated to a standard curve for analyte or by comparison to a reference standard. The standard curve can be generated using serial dilutions or solutions of known concentrations of analyte by mass spectroscopy, gravimetric methods, and other techniques known in the art.

(2) Forward Competitive Inhibition Assay

In a forward competitive format, an aliquot of labeled analyte of interest (e.g., TBI biomarker) having a fluorescent label, a tag attached with a cleavable linker, etc.) of a known concentration is used to compete with analyte of interest in a test sample for binding to analyte of interest antibody (e.g., a TBI biomarker antibody).

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an antispecies antibody, that has been immobilized on a solid support, such as a microparticle or planar substrate.

The labeled analyte of interest, the test sample and the antibody are incubated under conditions similar to those described above in connection with the sandwich assay format. Two different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

(3) Reverse Competitive Inhibition Assay

In a reverse competition assay, an immobilized analyte of interest (e.g., TBI biomarker) can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

(4) One-Step Immunoassay or "Capture on the Fly" Assay

In a capture on the fly immunoassay, a solid substrate is pre-coated with an immobilization agent. The capture agent, the analyte (e.g., TBI biomarker) and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody. This method can also be coupled with MS detection and quantification.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest (e.g., TBI biomarker). The second specific binding member comprises a detectable label and binds to an analyte of interest. The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected, or their amounts, levels or concentrations, measured, determined or assessed, including using mass spectrometry.

The use of a capture on the fly assay can be done in a variety of formats as described herein, and known in the art. For example the format can be a sandwich assay such as described above, but alternately can be a competition assay, can employ a single specific binding member, or use other variations such as are known. This method can also be coupled with MS detection and quantification.

12. Other Factors

The methods of diagnosing, prognosticating, risk stratifying, and/or assessing, as described above, can further include using other factors for the diagnosis, prognostication, and assessment. In some embodiments, traumatic brain injury may be diagnosed using the Glasgow Coma Scale or the Extended Glasgow Outcome Scale (GOSE). Other tests, scales or indices can also be used either alone or in combination with the Glasgow Coma Scale. An example is the Ranchos Los Amigos Scale. The Ranchos Los Amigos Scale measures the levels of awareness, cognition, behavior and interaction with the environment. The Ranchos Los Amigos Scale includes: Level I: No Response; Level II: Generalized Response; Level III: Localized Response; Level IV: Confused-agitated; Level V: Confused-inappropriate; Level VI: Confused-appropriate; Level VII: Automatic-appropriate; and Level VIII: Purposeful-appropriate.

13. Samples

In some embodiments, the sample is obtained after the human subject sustained an injury to the head caused by physical shaking, blunt impact by an external mechanical or other force that results in a closed or open head trauma, one or more falls, explosions or blasts or other types of blunt force trauma. In some embodiments, the sample is obtained after the human subject has ingested or been exposed to a chemical, toxin or combination of a chemical and toxin. Examples of such chemicals and/or toxins include, fires, molds, asbestos, pesticides and insecticides, organic solvents, paints, glues, gases (such as carbon monoxide, hydrogen sulfide, and cyanide), organic metals (such as methyl mercury, tetraethyl lead and organic tin) and/or one or more drugs of abuse. In some embodiments, the sample is obtained from a human subject that suffers from an autoimmune disease, a metabolic disorder, a brain tumor, hypoxia, one or more viruses, meningitis, hydrocephalus or combinations thereof.

In yet another embodiment, the methods described herein use samples that also can be used to determine whether or not a subject has or is at risk of developing mild traumatic brain injury by determining the levels of a TBI biomarker in a subject using the anti-TBI biomarker antibodies described below, or antibody fragments thereof. Thus, in particular embodiments, the disclosure also provides a method for determining whether a subject having, or at risk for, traumatic brain injuries, discussed herein and known in the art, is a candidate for therapy or treatment. Generally, the subject is at least one who: (i) has experienced an injury to the head; (ii) ingested and/or been exposed to one or more chemicals and/or toxins; (iii) suffers from an autoimmune disease, a metabolic disorder, a brain tumor, hypoxia, one or more viruses, meningitis, hydrocephalus or suffers from any combinations thereof; or (iv) any combinations of (i)-(iii); or, who has actually been diagnosed as having, or being at risk for TBI (such as, for example, subjects suffering from an autoimmune disease, a metabolic disorder, a brain tumor, hypoxia, one or more viruses, meningitis, hydrocephalus or combinations thereof), and/or who demonstrates an unfavorable (i.e. clinically undesirable) concentration or amount of a TBI biomarker or a TBI biomarker fragment, as described herein.

a. Test or Biological Sample

As used herein, "sample", "test sample", "biological sample" refer to fluid sample containing or suspected of containing a TBI biomarker. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing a TBI biomarker may be assayed directly. In a particular example, the source containing a TBI biomarker is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source containing a TBI biomarker is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing a TBI biomarker is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

b. Controls

It may be desirable to include a control. The control may be analyzed concurrently with the sample from the subject as described above. The results obtained from the subject sample can be compared to the results obtained from the control sample. Standard curves may be provided, with which assay results for the sample may be compared. Such standard curves present levels of marker as a function of assay units, i.e. fluorescent signal intensity, if a fluorescent label is used. Using samples taken from multiple donors, standard curves can be provided for reference levels of a TBI biomarker in normal healthy tissue, as well as for "at-risk" levels of the TBI biomarker in tissue taken from donors, who may have one or more of the characteristics set forth above.

Thus, in view of the above, a method for determining the presence, amount, or concentration of a TBI biomarker in a test sample is provided. The method comprises assaying the test sample for a TBI biomarker by an immunoassay, for example, employing at least one capture antibody that binds to an epitope on a TBI biomarker and at least one detection antibody that binds to an epitope on a TBI biomarker which is different from the epitope for the capture antibody and optionally includes a detectable label, and comprising comparing a signal generated by the detectable label as a direct or indirect indication of the presence, amount or concentration of a TBI biomarker in the test sample to a signal generated as a direct or indirect indication of the presence, amount or concentration of a TBI biomarker in a calibrator. The calibrator is optionally, and is preferably, part of a series of calibrators in which each of the calibrators differs from the other calibrators in the series by the concentration of the TBI biomarker.

14. Kit

Provided herein is a kit, which may be used for assaying or assessing a test sample for one or more TBI biomarkers and/or fragments thereof. The kit comprises at least one component for assaying the test sample for a TBI biomarker and instructions for assaying the test sample for a TBI biomarker. For example, the kit can comprise instructions for assaying the test sample for a TBI biomarker by immunoassay (e.g., chemiluminescent microparticle immunoassay) or by mass spectrometry assay (e.g., PRM-MS or MRM/SRM-MS). Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to a TBI biomarker. The antibody may be a TBI biomarker detection antibody and/or capture antibody.

Alternatively or additionally, the kit can comprise a calibrator or control (e.g., purified, and optionally lyophilized, TBI biomarker) and/or at least one container (e.g., tube, microtiter plates or strips, which can be already coated with an anti-TBI biomarker antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e. reagents, standards, buffers, diluents, etc., which are necessary to perform the assay. The instructions also can include instructions for generating a standard curve.

The kit may further comprise reference standards for quantifying a TBI biomarker. The reference standards may be employed to establish standard curves for interpolation and/or extrapolation of TBI biomarker concentrations. Standards cans include proteins or peptide fragments composed of amino acids residues or N15 stable isotopic labeled proteins or peptide fragments for various analytes, as well as standards for sample processing, including standards involving spikes in proteins and quantitative peptides. In some embodiments, the reference standards for a TBI biomarker can correspond to the 99th percentile derived from a healthy reference population. Such reference standards can be determined using routine techniques known in the art.

Any antibodies, which are provided in the kit, such as recombinant antibodies specific for a TBI biomarker, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes (e.g., TBI biomarker) or reagents for detecting the analyte (e.g., TBI biomarker). The antibodies, standard peptides or peptide fragments, calibrators, and/or controls can be provided in separate containers or pre-dispensed into an appropriate assay format, for example, into microtiter plates, Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, whole blood, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of traumatic brain injury or disorder.

a. Adaptation of Kit and Method

The kit (or components thereof), as well as the method for assessing or determining the concentration of a TBI biomarker in a test sample by an immunoassay as described herein, can be adapted for use in a variety of automated and semi-automated systems (including those wherein the solid phase comprises a microparticle), as described, e.g., U.S. Pat. No. 5,063,081, U.S. Patent Application Publication Nos. 2003/0170881, 2004/0018577, 2005/0054078, and 2006/0160164 and as commercially marketed e.g., by Abbott Laboratories (Abbott Park, IL) as Abbott Point of Care (i-STAT® or i-STAT Alinity, Abbott Laboratories) as well as those described in U.S. Pat. Nos. 5,089,424 and 5,006,309, and as commercially marketed, e.g., by Abbott Laboratories (Abbott Park, IL) as ARCHITECT® or the series of Abbott Alinity devices.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT®, Alinity, and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT®, Alinity, and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits, and kit components can be employed in other formats, for example, on electrochemical or other hand-held or point-of-care assay systems. As mentioned previously, the present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent App. Publication Nos. 2003/0170881, 2004/0018577, 2005/0054078, and 2006/0160164, which are incorporated in their entireties by reference for their teachings regarding same.

In particular, with regard to the adaptation of an assay to the i-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an i-STAT® cartridge with a fluidics format suitable for immunoassay. On a portion of the silicon chip, there is a specific binding partner for a TBI biomarker, such as one or more TBI biomarker antibodies one or more monoclonal/polyclonal antibody or a fragment thereof, a variant thereof, or a fragment of a variant thereof that can bind a TBI biomarker) or one or more anti-TBI biomarker DVD-Igs (or a fragment thereof, a variant thereof, or a fragment of a variant thereof that can bind a TBI biomarker), any of which can be detectably labeled. Within the fluid pouch of the cartridge is an aqueous reagent that includes p-aminophenol phosphate.

In operation, a sample from a subject suspected of suffering from TBI is added to the holding chamber of the test cartridge, and the cartridge is inserted into the i-STAT® reader. A pump element within the cartridge pushes the sample into a conduit containing the chip. The sample is brought into contact with the sensors allowing the enzyme conjugate to dissolve into the sample. The sample is oscillated across the sensors to promote formation of the sandwich of approximately 2-12 minutes. In the penultimate step of the assay, the sample is pushed into a waste chamber and wash fluid, containing a substrate for the alkaline phosphatase enzyme, is used to wash excess enzyme conjugate and sample off the sensor chip. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of a TBI biomarker in the sample by means of an embedded algorithm and factory-determined calibration curve.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, IL) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, IL), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an i-STAT® cartridge format, using a nucleic acid sequence linked to the signal antibody as a signal amplifier. Adaptation of a cartridge for multiplex use, such as used for i-Stat, has been described in the patent literature, such as for example, U.S. Pat. No. 6,438,498, the contents of which are herein incorporated by reference.

The methods and kits as described herein may also involve single molecule counting. In certain embodiments, a method for analyte analysis may involve assessing an analyte present in a sample. In certain embodiments, the assessing may be used for determining presence of and/or concentration of an analyte in a sample. In certain embodiments, the method may also be used for determining presence of and/or concentration of a plurality of different analytes present in a sample.

Any device known in the art that allows for the detection of a single molecule of one or more analytes of interest can be used in the systems described herein. For example, the device can be a microfluidics device, digital microfluidics device (DMF), a surface acoustic wave based microfluidic device (SAW), an integrated DMF and analyte detection device, an integrated SAW and analyte detection device, or robotics based assay processing unit. Examples of other devices that can be used include the Quanterix SIMOA™ (Lexington, MA), Singulex's single molecule counting (SMC™) technology (Alameda, CA, see for example, U.S. Pat. No. 9,239,284, the contents of which are herein incorporated by reference), etc.

Other methods of detection include the use of or can be adapted for use on a nanopore device or nanowell device. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

The methods and kits as described herein can involve mass spectrometry using DIA-MS, DDA-MS or SRM/MRM-MS or PRM-MS. In certain embodiments, methods for analyte analysis can involve assessing a sample for the presence of an analyte. In certain embodiments, assessing a sample for the presence of an analyte can be used for determining presence of and/or concentration of an analyte or a fragment in a sample. In certain embodiments, a method can also be used for determining presence of and/or concentration of a plurality of different analytes or analyte fragments present in a sample. Quantification can be performed using internal control proteins or peptide fragments.

While certain embodiments herein are advantageous when employed to assess disease, such as traumatic brain injury, the assays and kits also optionally can be employed to assess various biomarkers in other diseases, disorders, and conditions as appropriate.

The method of assay also can be used to identify a compound that ameliorates diseases, such as traumatic brain injury. For example, a cell that expresses any of the various biomarkers described herein can be contacted with a candidate compound. The level of expression of one or more of these biomarkers in the cell contacted with the compound can be compared to that in a control cell using the methods and assays described herein.

The present disclosure has multiple aspects, illustrated by the following non-limiting examples.

15. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Development of a Multi-Modality Classification Scheme for Traumatic Brain Injury This study was directed at developing a classification scheme for brain injury that indicates the nature (type) and severity of injury. Trauma patients were divided into three groups for analysis: only brain injured, only non-brain injured, and combined injury. Brain injured and non-brain injured trauma groups were compared to each other and to the combination of brain/nonbrain trauma. These trauma groups were compared to non-trauma controls. CSF from trauma patients was compared to CSF from non-trauma patients. A secondary goal was to determine whether any of the measures, alone or in combination, had utility as a predictor of clinical outcome after TBI.

An objective multi-modality classification scheme and outcome measure for traumatic brain injury was developed based on several measures: 1) blood-based biomarkers; 2) physiologic measures and evaluation; and 3) radiographic measures (CT and 3Tesla (also known as 3T) MRI). Blood-based biomarkers can indicate which cell types are damaged (e.g., glial vs. neuronal) and radiography can detect structural changes.

Study Site: Trauma patient were recruited at Hennepin County Medical Center (HCMC) in the state of Minnesota. Participants included trauma patients of all ages presenting to the HCMC Emergency Department (ED), trauma bay, or as direct transfer to neurosurgery. Trauma patients were excluded if they had a major psychiatric or neurologic disorder, were developmentally abnormal, or were prisoners. Subjects were identified by searching medical records for all trauma admissions and cross-checking with the American College of Surgeons trauma registry utilized in the hospital.

All trauma patients were recruited for screening at the time of presentation and underwent: 1) a standardized (templated) history and physical examination; 2) analysis of serum biomarkers if blood was drawn for other indications; 3) radiographic study as clinically indicated; 4) follow-up as clinically indicated with 1)-3); 5) pathologic specimen analysis in patients going to the operating room only; 6) CSF analysis in patients receiving ventriculostomy catheters only; 7) brain tissue oxygenation analysis in patients receiving Licox only; and 8) outcome assessment in the TBI center as clinically indicated. At the time of admission, the potential participants underwent a 24 hour screening process (Table 2) before providing informed consent.

TABLE 2

| Screening Assessments | | |
|---|---|---|
| | Adult | Pediatric |
| All | | Surgery-Trauma History and Physical |
| | | Selections from Neurosurgery-Trauma History and Physical |
| Awake | SCAT3: SAC, SSS-C | Child SCAT3: SAC-C, SSS-C |
| OR | | Pathogenic Specimen |
| VC | | CSF Analysis |
| Licox | | Brain Tissue Oxygenation |

OR: Patients going to the operating room;
VC: Patients receiving ventriculostomy catheters;
Licox: Patients receiving Licox Patients who consented and controls (age and gender matched) who had undergone the above were subject to the following additional studies: 1) genomic, serum, and CSF screening; and 2) 3T MRI in select circumstances (serum markers in the test group; normal markers in the control group). Trauma patients included the full spectrum ranging from non-brain injured, CT-negative to structurally brain injured, requiring surgery. Patients and controls were recruited over approximately 15 months. Surviving trauma subjects were followed until they were discharged from HCMC services. Subjects evaluated in the ER and released were invited for research follow-up.

The screening process included a standardized and templated medical history and physical examination. The template was the current "Surgery-Trauma History and Physical" template in EPIC with one additional question that asks if the patient suffered a head trauma. If the patient did, three sections automatically dropped down for additional information. The first was information from the Neurosurgery trauma history and physical template, including subarachnoid grade, hemorrhage grade, intracerebral hemorrhage, and social history (level of education, employment, living arrangements, and ethnicity). The final two were standardized brain injury assessment tools: the Standardized Assessment of Concussion (SAC) and the Symptom Severity Score (SSS). Pediatric versions of these assessments were available and used when indicated. Additionally, the loss of consciousness question already included in the "Surgery Trauma History and Physical" template was copied into this drop down section with a subset of questions that provided a more clear understanding of the loss of consciousness event and the patient's current orientation. The most clinically accurate assessment taken during the first 24 hours of admission was used for future data analysis.

Non-TBI subjects were also included based on the following criteria: be between 15 and 50 years of age at the time of enrollment; have similar characteristics as the TBI population in terms of gender, age, handedness, educational level, and scanner criteria; and be capable of sufficiently clear communication and language fluency to allow the subject to provide written informed consent, or assent with parental or guardian consent for minors, and to complete study assessments for participation in all parts of the study. Non-TBI subjects were excluded if they have: been diagnosed of mild TBI within the past 6 months; a prior moderate to severe TBI (GCS <13) within past 10 years; epilepsy with recurring seizures in the past 10 years; drug abuse (except marijuana) in the past 10 years based on DAST-10 screening; alcohol abuse based on AUDIT-C screening; current primary Axis I or II psychiatric disorders, except for disorders classified as minor and not expected to impact study conduct or integrity; a history of brain mass, neurosurgery, stroke, white matter disease, and/or dementia;

a known cognitive dysfunction or structural brain disease/ malformation; a structural brain injury on prior neuroimaging findings; been prescribed antipsychotic/antiepileptic medications; been unable (such as due to urgent medical care needs) or unwilling to complete study procedures accurately or have any conflict of interest that could affect study results, in the opinion of the investigator; or contraindications to MRI scanning, including: a. current or suspected pregnancy per site practice; b. other conditions that may constitute a hazard to the subject during study participation, per investigator; and c. inability to comply with any part of the site's MR safety policy.

Specimen Collection and Handling. Up to 40 mL (approximately 3 tablespoons) of blood were obtained at each specimen collection. 2 tubes of serum and 2 tubes of plasma were drawn at Encounters 1, 2 4, and 5. At Encounter 3, 2 tubes of serum, 1 tube of plasma and 1 or 2 tubes of whole blood were drawn. These study specimens were processed, aliquoted, frozen, and shipped to Abbott Laboratories for biomarker testing and storage. Sample aliquots were sent to testing sites for additional TBI biomarker testing. A specimen was considered unevaluable for the study if: it contained insufficient volume to perform necessary measurements, it was grossly hemolyzed, lipemic, or icteric; it was not collected in the proper type of collection tube; it was not properly labeled; or it was not properly stored by the collection site or at Abbott Laboratories.

Serum/plasma specimens were obtained via blood draw. If a blood draw was obtained at the time of admission for clinical purposes, additional specimen was obtained and retained for research purposes. If blood was not drawn for clinical purposes, trained research personnel drawn the blood required for research. The blood was drawn through venipuncture unless a central venous access was required by the standard of care, in which case the blood was withdrawn via that access. The first blood draw was taken upon admission, the second 3-6 hours after the first, and the third was taken at 24 hours after the trauma. Discovery efforts were also ongoing to find genetic markers of susceptibility to TBI or predictive markers of TBI. At each time point, 40 mL (less than 3 tablespoons) of blood was collected: 20 mL of serum (2 tubes) and 20 mL of plasma (2 tubes). During Encounter 1, only 2 tubes of serum and 1 tube of plasma were collected for blood biomarker analysis. This whole blood collection was 6.0 mL in a whole blood tube. If a patient was enrolled at Encounter 2 instead of Encounter 1, they had 2 tubes of serum and 1 tube of plasma collected for blood biomarker analysis. This whole blood collection was 6.0 mL in a whole blood tube.

The amount of blood drawn was limited according to the NINOS standardized table (Table 3). The number of attempts to draw blood was limited for children under the age of seven to two attempts. In the case that the NINOS standardized table did not allow enough blood to be drawn for the study or there were two failed attempts to draw blood in a child patient, access to leftover blood samples drawn under the clinical standard of care was requested for complete biomarker analysis in this study. This blood draw allowed for the analysis of up to 390 blood-based biomarkers related to traumatic brain injuries.

TABLE 3

Maximum Allowable Total Blood Draw Volumes

| Body Wt (Kg) | Body Wt (lbs) | Total blood volume (mL) | Maximum allowable volume (mL) in one blood draw (=2.5% of total blood volume) | Maximum volume (clinical + research) (mL) in a 30-day period | Minimum Hgb required at time of blood draw | Minimum Hgb required at time of blood draw if subject has respiratory/CV compromise |
|---|---|---|---|---|---|---|
| 1 | 2.2 | 100 | 2.5 | 5 | 7.0 | 9.0-10.0 |
| 2 | 4.4 | 200 | 5 | 10 | 7.0 | 9.0-10.0 |
| 3 | 6.3 | 240 | 6 | 12 | 7.0 | 9.0-10.0 |
| 4 | 8.8 | 320 | 8 | 16 | 7.0 | 9.0-10.0 |
| 5 | 11 | 400 | 10 | 20 | 7.0 | 9.0-10.0 |
| 6 | 13.2 | 480 | 12 | 24 | 7.0 | 9.0-10.0 |
| 7 | 15.4 | 560 | 14 | 28 | 7.0 | 9.0-10.0 |
| 8 | 17.6 | 640 | 16 | 32 | 7.0 | 9.0-10.0 |
| 9 | 19.8 | 720 | 18 | 36 | 7.0 | 9.0-10.0 |
| 10 | 22 | 800 | 20 | 40 | 7.0 | 9.0-10.0 |
| 11-15 | 24-33 | 880-1200 | 22-30 | 44-60 | 7.0 | 9.0-10.0 |
| 16-20 | 35-44 | 1280-1600 | 32-40 | 64-80 | 7.0 | 9.0-10.0 |
| 21-25 | 46-55 | 1680-2000 | 42-50 | 64-100 | 7.0 | 9.0-10.0 |
| 26-30 | 57-66 | 2080-2400 | 52-60 | 104-120 | 7.0 | 9.0-10.0 |
| 31-35 | 68-77 | 2480-2800 | 62-70 | 124-140 | 7.0 | 9.0-10.0 |
| 36-40 | 79-88 | 2880-3200 | 72-80 | 144-160 | 7.0 | 9.0-10.0 |
| 41-45 | 90-99 | 3280-3600 | 82-90 | 164-180 | 7.0 | 9.0-10.0 |
| 46-50 | 101-110 | 3680-4000 | 92-100 | 184-200 | 7.0 | 9.0-10.0 |
| 51-55 | 112-121 | 4080-4400 | 102-110 | 204-220 | 7.0 | 9.0-10.0 |
| 56-60 | 123-132 | 4480-4800 | 112-120 | 224-240 | 7.0 | 9.0-10.0 |
| 61-65 | 134-143 | 4880-5200 | 122-130 | 244-260 | 7.0 | 9.0-10.0 |
| 68-70 | 145-154 | 5280-5600 | 132-140 | 264-280 | 7.0 | 9.0-10.0 |
| 71-75 | 156-185 | 5680-6000 | 142-150 | 284-300 | 7.0 | 9.0-10.0 |
| 76-80 | 167-176 | 6080-6400 | 152-160 | 304-360 | 7.0 | 9.0-10.0 |
| 81-85 | 178-187 | 6480-6800 | 162-170 | 324-340 | 7.0 | 9.0-10.0 |
| 86-90 | 189-198 | 6880-7200 | 172-180 | 344-360 | 7.0 | 9.0-10.0 |
| 91-95 | 200-209 | 7280-7600 | 182-190 | 364-380 | 7.0 | 9.0-10.0 |
| 96-100 | 211-220 | 7680-8000 | 192-200 | 384-400 | 7.0 | 9.0-10.0 |

In addition to the initial physical exam, those patients that were sent to the operating room undergone pathologic specimen analysis, those patients that received Licox had brain tissue oxygenation information recorded, and those patients that received ventriculostomy catheters had CSF collected for analysis. In order to analyze the CSF, 5.0 mL was collected at the same intervals that blood was drawn. Radiographic studies were performed in accordance with the standard of care. None of the assessments performed during the screening processes were analyzed with the rest of the data until informed consent was obtained. If the patient did not ultimately consent to research, the specimens, and initial assessments were discarded.

After the participants were discharged, the patients' medical records were accessed for information about the clinical course, including time spent in the ED, any surgeries or other neuromonitoring methods used, and the acute care outcome evaluation. If the patient spent time in the ICU, information was extracted from that time period as well, including data from Moberg monitors and daily therapeutic intensity level.

Trauma patients were divided into three groups for analysis: only brain injured, only non-brain injured, and combined injury. Two age- and gender-matched control groups were included in this study and recruited from the ED: non-trauma and CSF controls. Non-trauma controls were those who did not experience any trauma, and this group composed largely of family and friends of the patients admitted for brain injury. Both control groups were consented to undergo a single intensive assessment that included a blood draw and cognitive, neurological, and quality of life assessments (SAC, NOS-TBI, QoLABI). Patients receiving elective ventriculostomy or lumbar drain catheters were (pre-operatively) consented to be a part of the CSF control group. 5 mL of CSF was collected from the ventriculostomy catheter of patients in this control group for comparison with the CSF collected from the portion of the study group that received a ventriculostomy catheter as a part of their standard of care. The CSF control group was also offered the chance to participate in the same intensive assessment as the other two controls groups that included a blood draw and a 3T MRI scan.

Follow-Up: All patients that consented to participate in the follow-up portion of the study were asked to return to the hospital. Patients who returned were seen in the TBI Outpatient Clinic at 2 weeks, 4 weeks, months, 6 months, and 1 year. If they did not have a scheduled appointment at the TBI Outpatient Clinic, they were scheduled a time to come into the Brain Injury Research Lab (PL.610) at those time points. Table 4 provides a timeline for each of the assessments. Blood draws for biomarker analysis were done at each of the five follow-up time points in the same method, as described above. The outcome assessment battery listed in Tables 10 and 11 were completed at 3 months, 6 months, and one year. Radiographic scans that were a part of the standard of care were accessed through the participant's medical records, but select consented participants and controls also underwent 3T MRI scans at 2 weeks and 6 months after their brain injury. Each MRI examination took approximately one hour and included the following pulse sequences: (1) Sagittal short TR localizer, (2) Axial Fse, (3) Axial FLAIR, (4) Axial SWI, (5) Axial T2* imaging. In the case that patients were not able to come into the hospital for follow-up, they were contacted via phone at three months and one year after their injury to complete the BT ACT, which was a 15-20 minute cognitive assessment designed to be administered over the phone.

TABLE 4

Outcome Timeline

|  | Blood Draw | 3 T MRI | CSF Collection | CT Scan | Assessments | Total Time (minutes) |
|---|---|---|---|---|---|---|
| ADM | X |  | X (if indicated) |  |  | 10 |
| 2 weeks | X | X |  |  |  | 70 |
| 4 weeks | X |  |  |  |  | 10 |
| 3 months | X |  |  |  | X | 70 |
| 6 months | X | X |  |  |  | 70 |
| 1 year | X | X |  | X* | X | 160 (130 without CT) |

TABLE 5

Outcome Assessments - Not Finalized

|  |  | Adult | Pediatric |
|---|---|---|---|
| Outcome | All |  |  |
|  | Awake | GOS and GOSE | Pediatric GOSE |
|  |  | SCAT3: SSS and SAC | Child SCAT3: Child & Parent Report; SAC-C |
|  |  | GOAT | COAT |
|  |  | Duration of Amnesia | Duration of Amnesia |
|  |  | NOS-TBI | NOS-TBI |
|  |  | Quality of Life: | Quality of Life: |
|  |  | MPAI-4 | Neuropsychiatric Rating Schedule |
|  |  |  | Pediatric Quality of Life Inventory |
|  |  |  | (For Child and for Proxy) |
|  | Not Awake | CRS-R (Just Brain Stem Reflex Grid') |  |

TABLE 6

Possible Infant Assessments

| Name | Age | Time | Description |
|---|---|---|---|
| Bayley III, BSID* | 0-3.5 | 30-90 | Cognitive, language (receptive and expressive) and motor development. Most commonly used in test for this age range |
| BITSEA* | 1-3 | 7-12 | Parent perception of Social and Emotional behavior 17 items of 42 are for autism, so may be able to be made shorter |
| CBCL | 1.5-5 | 25-30 | Parent perception of performance on Activities, Social, and School performance |
| MSEL* | 1 3 5 | 15 25-35 40-60 | Cognitive and Motor Ability (Gross Motor, Visual Reception, Fine Motor, Language Mostly for readiness for school |
| Shape School* | 3-6 | 45-75 | Inhibition and Switching Processes: Emerging Executive Functions |
| Trails-Preschool* | 2-6 | 5-10 | Neuropsychological Function: Psychomotor speed, Complex Attention, Executive Function Advanced Trail Making Test |

*Requested Access

Statistical Analysis Plan. Biomarker data was analyzed by examining maximum concentration draw for each biomarker per patient, or by time from incident buckets, or both. To address the primary objective of determining associations between biomarker concentrations in blood and clinical neurological and magnetic resonance imaging data, multiple analyses was employed. Principal components analysis was used to examine which biomarkers may be explaining the same variance, or if a biomarker was contributing very little variance. The biomarkers were used in a logistic regression analysis, and some biomarkers were excluded based on the results from the principal components analysis, and clinical input. A significance level of 0.05 was used for the logistic regression analysis. ROC analysis was also used to examine the predictive ability of each biomarker in determining MRI status or neurological testing outcomes, for this set of data.

Example 2

DIA-MS Analysis

Discovery based mass spectrometry using data independent acquisition (DIA-MS) was carried out on 49 plasmas from individuals with mild TBI and controls. Fifteen (15) of these samples were derived from healthy patients who had no known traumatic brain injury. Of the remaining 34 samples, 33 samples were derived from patients who were physician-diagnosed as having endured mild traumatic brain injury (mTBI), with the remaining sample being a pool of plasma from patients who were physician-diagnosed as having endured a severe traumatic brain injury (sTBI). GCS scores for each of the patients in the cohort were also obtained, and all where within normal range (with the exception of the pooled severe TBI samples). CT scans were performed on a subset of subjects, and samples from a CT-positive subject was included (see FIG. 1A). Plasma samples were digested with trypsin to generate peptides which were analyzed using DIA-MS (peptide identities are included below). All quantifiable peptides and proteins were included. GFAP detection based on 2 unique peptides was also selectively pulled out of the data and included in FIG. 1, and GFAP levels assessed independently using an immunoassay (ELISA-based GFAP assay) were also included in FIG. 1.

The methods described above were used to identify TBI biomarkers for the various classes and subclasses of TBI. Table 7 shows candidate TBI biomarkers associated with severe TBI (clustered with the pooled sTBI sample with detectable levels of GFAP). SAMP was downregulated in the sTBI group (and upregulated in the healthy control group), and CAND1 and GLO2 were upregulated in the sTBI group (downregulated in the healthy control group). ERAP1, SYYC, C1RL, and ATPG were only detected in the sTBI group and not the healthy controls (i.e. unique expression).

TABLE 7

Candidate Biomarkers for Severe TBI

| UniProtID|Protein | log2FC (severe/healthy) |
|---|---|
| Q86VP6|CAND1 | 2.67 |
| P02743|SAMP | −1.6 |
| Q16775|GLO2 | 1.38 |
| Q9NZ08 ERAP1 | Only in severe |
| P54577 SYYC | Only in severe |
| Q9NZP8 C1RL | Only in severe |
| P36542 ATPG | Only in severe |

Figures 1A, 1B, 1C:
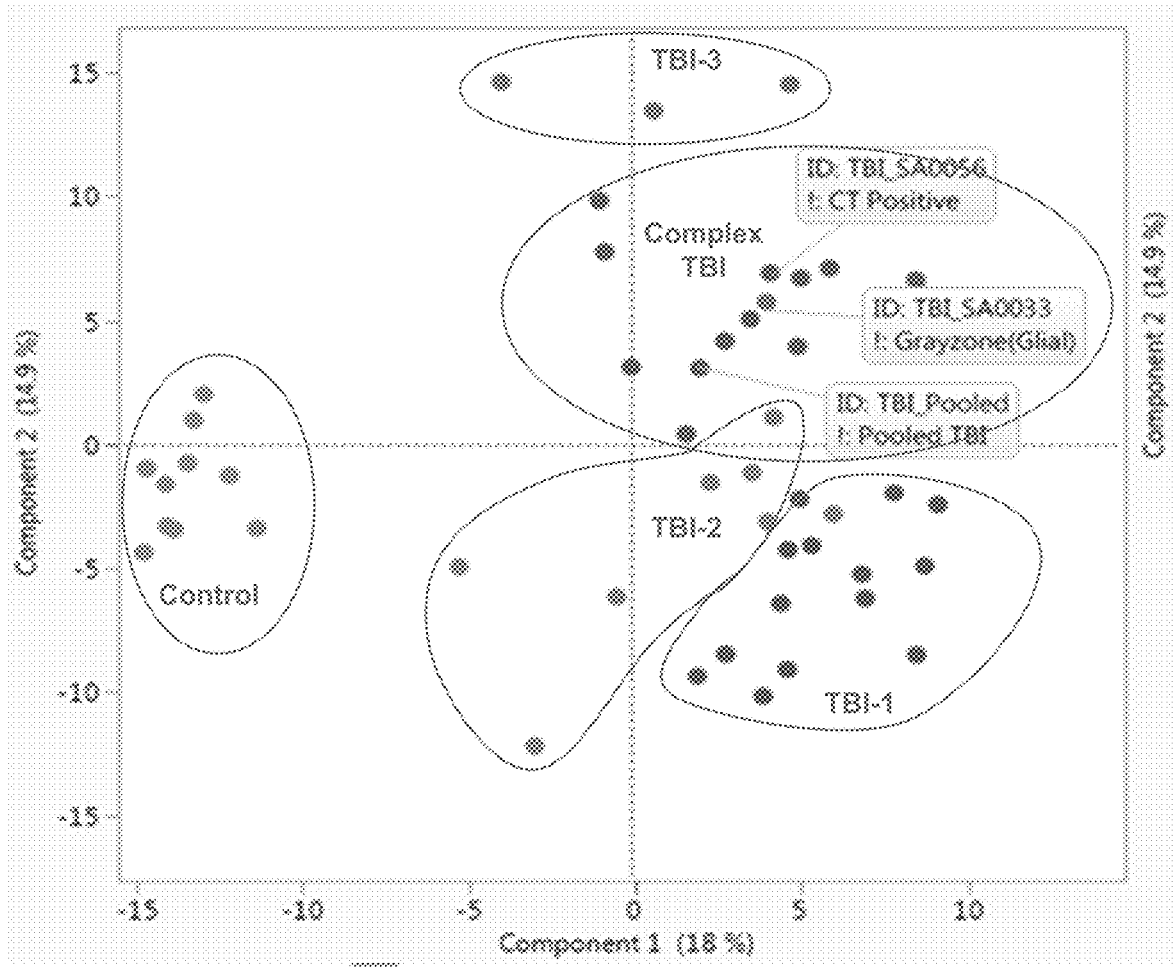
Figures 1A, 1B, 1C:
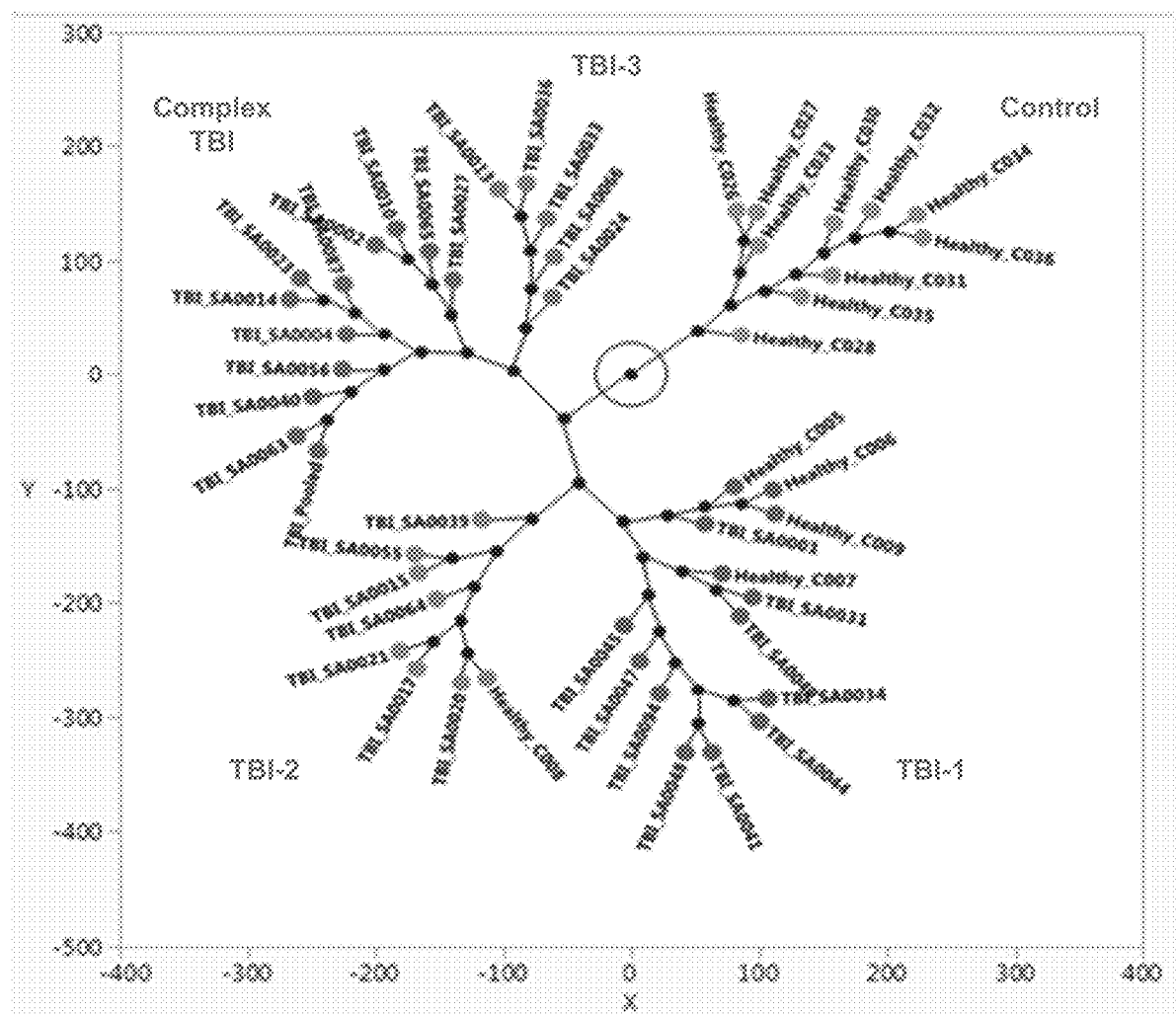

Unsupervised Analysis. Unsupervised clustering analysis was applied to the proteomic data obtained by DIA-MS to determine how the patient cohort samples clustered according to their molecular proteomic profiles, unbiased by any clinical grouping. The null hypothesis in this analysis is that the proteomic data is randomly scattered across all samples, without any clustering pattern that relates to the presence or severity of a TBI. As shown in FIG. 1A, the Control branch of the clustering analysis (bottom most grouping of the five groupings) successfully discerned 10 of 15 healthy samples from TBI samples. Ultimately, four additional sub-clusters emerged, and correspond to subclasses of mild TBI. These data are summarized and outlined below.

Unsupervised cluster analysis yielded 5 clusters (FIGS. 1A-1C). This includes a cluster of "healthy" subjects (i.e. Control grouping) that consists of the original ten samples designated as healthy individuals. Additionally, these data and the accompanying analysis demonstrated the presence of four distinct subclasses of mild TBI. For the purposes of clarity and differentiation, each of these clusters was assigned a number: the TBI-1 cluster=mild TBI subclass 1; the TBI-2 cluster=mild TBI subclass 2; the TBI-3 cluster=mild TBI subclass 3; and the Complex TBI cluster=mild TBI subclass 4 (also referred to as "complicated mild" TBI).

"Mild TBI subclass 1" (TBI-1) refers to subjects who are classified as having mild TBI and also exhibit a plasma proteome signature that is different from controls (e.g., healthy controls, or controls that have not sustained a TBI), different from subjects with moderate to severe TBI, and different from subjects with a mild TBI of each of subclasses 2, 3, or 4. "Mild TBI subclass 2" (TBI-2) refers to subjects who are classified to having mild TBI and also exhibit a plasma proteome signature that is different from controls (e.g., healthy controls, or controls that have not sustained a TBI), different from subjects with moderate to severe TBI, and different from subjects with a mild TBI of each of subclasses 1, 3, or 4. "Mild TBI subclass 3" (TBI-3) refers to subjects who are classified to having mild TBI and also exhibit a plasma proteome signature that is different from controls (e.g., healthy controls, or controls that have not sustained a TBI), different from subjects with moderate to severe TBI, and different from subjects with a mild TBI of each of subclasses 1, 2, or 4. "Mild TBI subclass 4" (Complex TBI) refers to subjects who are classified as having mild TBI, and also exhibit plasma proteome signature that is different from controls (e.g., healthy controls, or controls that have not sustained a TBI), different from subjects with moderate to severe TBI, and different from subjects with a mild TBI of each of subclasses 1, 2, or 3. Additionally, subjects with mild TBI subclass 4 exhibit a proteome signature that resembles the proteome signature obtained from pooled samples of subjects having severe TBI; thus, this subclass is referred to herein as "complicated mild TBI." In data disclosed herein, the mild TBI subclass 4 cluster ("Complex TBI") contained the highest number of subjects having elevated GFAP levels (based on ELISA-based GFAP assay and GFAP mass spectrometry), and the only subject having a positive CT scan.

Sample origins were de-identified upon completion of unsupervised clustering, and four key parameters were separately included and shown in FIG. 1A. These parameters included a Glial biomarker score (positive (gray) (ELISA-based GFAP assay), negative (lack), border zone (white), inconclusive, or lacking information (light grey)); a CT scan score (positive (gray), negative (black), or not performed (light grey)); a GFAP protein expression level obtained using MS (numerical continuum between lowest (black) to highest (gray)); Gender (male (gray) or female (black)); and Age (numeric continuum between 20 (black) and 59 (gray) years).

Based on this analysis, it was concluded that TBI as a disease indication includes a spectrum of injury states that can be described and categorized based on TBI biomarker signatures. Four different clusters were identified as corresponding to four different subclasses of mild TBI (FIGS. 1B-1C). The Complex TBI cluster represents the most severe of the mild TBI subclasses, as this cluster contains the severe TBI pooled sample, the only individual with a positive CT scan, the most number of GFAP biomarker positive samples (detected by immunoassay), and the most number of GFAP positive samples (based on MS data).

The control cluster represents healthy individuals, as it is negative for all clinical and biochemical markers and exclusively contains samples from patients without known TBI. This group was used as the healthy control set for all subsequent analysis.

The TBI-1 cluster represents the least severe subclass of mild TBI. This cluster contains some designated control samples and samples with low but detectable levels of GFAP by MS. Additionally, as shown in FIGS. 1B-1C, unsupervised clustering analysis led to the identification of two additional mild TBI subclasses, the TBI-2 cluster and the TBI-3 cluster. Both the TBI-2 and TBI-3 groupings represent discrete clusters that were shown to be distinct from both the TBI-1 cluster (least severe) and the Complex TBI cluster (most severe).

Thus, these data and the accompanying analysis demonstrate the presence of four distinct subclasses of mild TBI.

Next, these four "non-healthy" sub-clusters were compared against the "healthy" cluster (controls), and this comparison was expressed as log 2[fold change] values. Tables 8A and 8B include the identities of the ten most differentially regulated proteins and the ten most upregulated proteins, respectively, according to their log 2[fold change] values.

TABLE 8A

Differentially Regulated TBI Biomarkers Among Control and mTBI Subclasses
Table 8A. Top 10 proteins in each subclass with the largest changes

| Subclass 4/Healthy | | Subclass 2/Healthy | | Subclass 1/Healthy | | Subclass 3/Healthy | |
| --- | --- | --- | --- | --- | --- | --- | --- |
| UniProtID \| Protein name | log2FC NML1 | UniProtID \| Protein name | log2FC | UniProtID \| Protein name | log2FC | UniProtID Protein name | log2FC |
| P29144 \| TPP2 | −3.07 | O75376 \| NCOR1 | 2.93 | Q15746 \| MYLK | 2.26 | P29144 \| TPP2 | −3.42 |
| Q86VP6 \| CAND1 | 2.67 | P29144 \| TPP2 | −2.35 | P35908 \| K22E | 2.09 | O75376 \| NCOR1 | 2.72 |
| O75376 \| NCOR1 | 2.64 | P35908 \| K22E | 2.03 | P00429 \| DNM1L | 1.67 | P23083 \| HV103 | 2.07 |
| P35908 \| K22E | 2.04 | Q15746 \| MYLK | 1.99 | O60610 \| DIAP1 | 1.66 | Q27J81 \| INF2 | −2.01 |
| Q15746 \| MYLK | 1.84 | Q961U4 \| ABHEB | 1.98 | Q96IU4 \| ABHEB | 1.59 | P01880 \| 1GHD | 1.98 |
| P49189 \| AL9A1 | −1.79 | P02743 \| SAMP | −1.82 | Q02809 \| PLOD1 | 1.49 | Q9HOW9 \| CK054 | −1.94 |
| Q96IU4 \| ABHEB | 1.72 | Q27J81 \| INF2 | −1.75 | P07814 \| SYEP | 1.42 | A99683 \| M3K5 | −1.75 |
| O00429 \| DNM1L | 1.68 | Q6UWP8 \| SBSN | 1.71 | P01594 \| KV102 | −1.41 | Q96IU4 \| ABHEB | 1.75 |
| Q27J81 \| INF2 | −1.67 | P49189 \| AL9A1 | −1.69 | P49189 \| AL9A1 | −1.40 | P49189 \| AL9A1 | −1.65 |
| P02743 \| SAMP | −1.60 | Q9Y2E5 \| MA2B2 | −1.53 | P54760 \| EPHB4 | 1.38 | O00429 \| DNM1L | 1.48 |

TABLE 8B

Upregulated TBI Biomarkers Among Control and mTBI Subclasses

| Subclass 4/Healthy | | Subclass 2/Healthy | | Subclass 1/Healthy | | Subclass 3/Healthy | |
| --- | --- | --- | --- | --- | --- | --- | --- |
| UniProtID \| Protein name | log2FC | UniProtID \| Protein name | log2FC | UniProtID \| Protein name | log2FC | UniProtID \| Protein name | log2FC |
| Q86VP6 \| CAND1 | 2.67 | O75376 \| NCOR1 | 2.93 | Q15746 \| MYLK | 2.26 | O75376 \| NCOR1 | 2.72 |
| O75376 \| NCOR1 | 2.64 | P35908 \| K22E | 2.03 | P35908 \| K22E | 2.09 | P23083 \| HV103 | 2.07 |
| P35908 \| K22E | 2.04 | Q15746 \| MYLK | 1.99 | O00429 \| DNM1L | 1.67 | P01880 \| IGHD | 1.98 |
| Q15746 \| MYLK | 1.84 | Q96IU4 \| ABHEB | 1.98 | O60610 \| DIAP1 | 1.66 | Q96IU4 \| ABHEB | 1.75 |
| P96IU4 \| ABHEB | 1.72 | Q6UWP8 \| SBSN | 1.71 | Q96IU4 \| ABHEB | 1.59 | O00429 \| DNM1L | 1.48 |
| O00429 \| DNM1L | 1.68 | O00429 \| DNM1L | 1.40 | Q02809 \| PLOD1 | 1.49 | P02768 \| ALBU | 1.21 |
| Q6UWP8 \| SBSN | 1.54 | O60610 \| DIAP1 | 1.33 | P07814 \| SYEP | 1.42 | P42765 \| THIM | 1.19 |
| P08133 \| ANXA6 | 1.49 | P63167 \| DYL1 | 1.30 | P54760 \| EPHB4 | 1.38 | P01597 \| IGHA2 | 1.13 |
| Q16775 \| GLO2 | 1.38 | P55786 \| PSA | 1.28 | P08133 \| ANXA6 | 1.32 | P01597 \| HV105 | 1.11 |
| P07814 \| SYEP | 1.30 | P54760 \| EPHB4 | 1.26 | Q12805 \| FBLN3 | 1.31 | O00187 \| MASP2 | 1.09 |

Additionally, to differentiate between each of the disease clusters, preliminary stratification analysis was carried out based on putative classes or severities of the mild TBI subclasses. Relative pairwise comparisons were performed between each combination of "unhealthy" clusters in the absence of the "healthy" control cluster. These data are summarized below in Table 9 as ten proteins in each group with the largest magnitude log 2[fold change] values, along with their UniProt ID's.

Figures 2A, 2B, 2C:
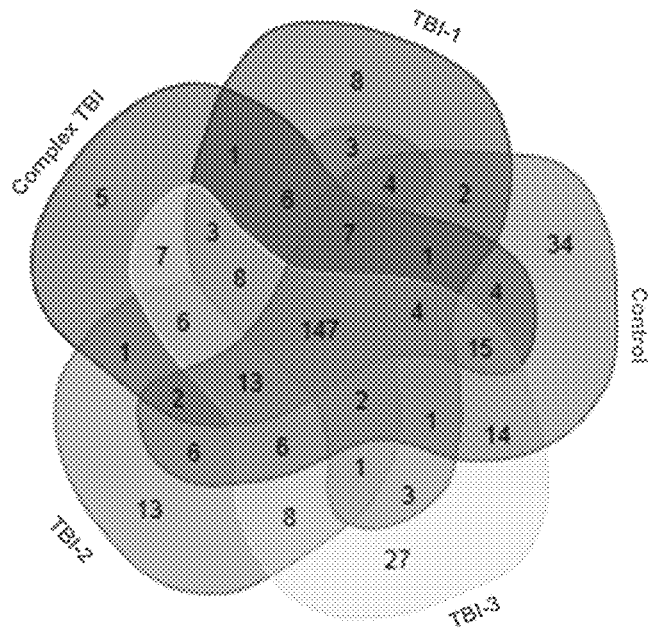
FIGS. 2A-2C include representative clustering of proteins that are shared and/or unique between sample clusters based on unsupervised analysis. Predominant pathological clusters of mild TBI subclasses include subclass 1 (TBI-1), subclass 2 (TBI-2), subclass 3 (TBI-3), and subclass 4, or complicated mild TBI (Complex TBI); a healthy control cluster is also shown (Control). Each of five main sample sub-clusters derived from unsupervised clustering analysis has a minimum of five uniquely expressed proteins.

The data was then assessed in an effort to identify proteins that were unique to each cluster, as these could potentially be included as exclusive candidate TBI biomarkers for a given subclass of TBI (FIGS. 2A-2C). Each of five main sample sub-clusters derived from unsupervised clustering analysis contained a minimum of five uniquely expressed proteins. These proteins can be included with the proteins which are uniquely increased in each subclass (Tables 8 and 9). FIGS. 2A-2C include proteins that are shared and unique

| Subclass 4/Subclass 2 | | Subclass 4/Subclass 1 | | Subclass 3/Subclass 4 | | Subclass 3/Subclass 1 | |
| --- | --- | --- | --- | --- | --- | --- | --- |
| UniProtID\| Protein name | log2FC | UniProtID\| Protein name | log2FC | UniProtID\| Protein name | log2FC | UniProtID\| Protein name | log2FC |
| P08519 \| APOA | 1.31 | P80748 \| ILV302 | −1.54 | P23083 \| HV103 | 1.53 | P23083 \| HV103 | 2.31 |
| B9A064 \| IGLL5 | −1.17 | P01594 \| KV102 | 1.35 | P01880 \| IGHD | 1.13 | P01594 \| KV102 | 1.73 |
| Q9Y2H5 \| PKHA6 | 1.01 | P01860 \| IGHG3 | 0.92 | P01871 \| IGHM | −0.98 | P48681 \| NEST | −1.54 |
| P04220 \| MUCB | 0.98 | P23083 \| HV103 | 0.78 | P04220 \| MUCB | −0.90 | P12931 \| SRC | −1.35 |
| Q13790 \| APOF | 0.97 | P21291 \| CSRP1 | −0.76 | P12931 \| SRC | −0.84 | O43583 \| DENR | −1.29 |
| P13727 \| PRG2 | 0.89 | P08582 \| TRFM | 0.68 | P02751 \| FINC | −0.78 | P01880 \| IGHD | 1.28 |
| P02745 \| C1QA | 0.82 | P07195 \| LDHB | 0.65 | O43583 \| DENR | −0.76 | P23526 \| SAHH | −1.27 |
| P04207 \| KV308 | 0.80 | P15311 \| EZRI | 0.63 | P23526 \| SAHH | −0.75 | P01860 \| IGHG3 | 1.10 |
| Q15848 \| ADIPO | 0.76 | O43396 \| TXNL1 | −0.62 | O43866 \| CD5L | −0.71 | O75368 \| SH3L1 | −1.06 |
| P29144 \| TPP2 | −0.72 | P18065 \| IBP2 | −0.61 | Q15848 \| ADIPO | −0.68 | P19652 \| A1AG2 | 0.97 |

| Subclass 3/Subclass 2 | | Subclass 2/Subclass 1 | |
| --- | --- | --- | --- |
| UniProtID \| Protein name | log2FC | UniProtID \| Protein name | log2FC |
| P01880 \| GHD | 1.71 | P01594 \| KV102 | 1.58 |
| P12931 \| SRC | −1.49 | Q9Y2H5 \| PKHA6 | −1.26 |
| P08519 \| APOA | 1.42 | P01860 \| IGHG3 | 1.16 |
| P23083 \| HV103 | 1.21 | P23083 \| HV103 | 1.10 |
| O43583 \| DENR | −1.18 | P13727 \| PRG2 | −1.08 |
| O75368 \| SH3L1 | −1.09 | P21291 \| CSRP1 | −0.92 |
| P29144 \| TPP2 | −1.07 | P02775 \| CXCL7 | −0.86 |
| P01019 \| ANGT | 1.04 | B9A064 \| IGLL5 | 0.86 |
| B9A064 \| IGLL5 | −1.02 | P02745 \| C1QA | −0.80 |
| Q13790 \| APOF | 1.01 | P00338 \| LDHA | −0.80 | between sample clusters based on unsupervised analysis. Each of five main sample sub-clusters derived from unsupervised clustering analysis has a minimum of five uniquely expressed proteins. FIG. 2A includes a Venn diagram with shared and unique proteins between the five identified subgroup clusters; and FIG. 2B includes a numeric count of total proteins and unique proteins quantified in each subgroup cluster. FIG. 2C includes the UniProt ID and short name for the unique proteins quantified in each subgroup cluster.

Supervised Analysis. Once the blinded unsupervised analyses were complete, the samples were de-identified in terms of the TBI status of the patients from which they were derived. This additional information enabled several iterations of supervised analyses to be performed.

In the first iteration of this supervised analysis, all proteins quantities obtained from the TBI-derived samples were compared with those form the non-TBI samples (based on patient characterizations), and the proteins were ranked according to the magnitude of their differential expression. This was done according to two separate criteria: 1) ranking the proteins according to the magnitude of their differential expression irrespective of the directionality of the change (upregulated and downregulated); and 2) because upregulated proteins lend themselves more favorably to detection as a biomarker, ranking the proteins according to the magnitude of their differentially upregulated expression. These are high probability TBI biomarker candidates useful for distinguishing mild TBI from a control. These data are summarized in Table 10 and FIGS. 2A-2C.

TABLE 10

Supervised Analysis Between TBI Samples and Healthy Controls
Table 10: Top TBI changes compared to all
healthy individuals based on supervised analysis

| Top differential Protein (UniProtID \| Protein Name) | log$_2$FC | Top upregulated protein (UniProtID \| Protein Name) | log$_2$FC |
| --- | --- | --- | --- |
| O75376 \| NCOR1 | 3.42 | O75376 \| NCOR1 | 3.42 |
| P29144 \| TPP2 | -2.78 | Q96IU4 \| ABHEB | 1.13 |
| P02743 \| SAMP | -1.25 | P08133 \| ANXA6 | 0.98 |
| Q27J81 \| INF2 | -1.15 | O00429 \| DNM1L | 0.98 |
| Q99683 \| MEK5 | -1.13 | Q15485 \| FCN2 | 0.98 |
| Q96IU4 \| ABHEB | 1.13 | P69905 \| HBA | 0.97 |
| P49189 \| AL9A1 | -1.01 | Q15746 \| MYLK | 0.95 |
| P08133 \| ANXA6 | 0.98 | Q6UWP8 \| SBSN | 0.94 |
| O00429 \| DNMIL | 0.98 | Q09666 \| AHNK | 0.93 |
| Q15485 \| FCN2 | 0.98 | P35908 \| K22E | 0.91 |

Figures 3A, 3B:
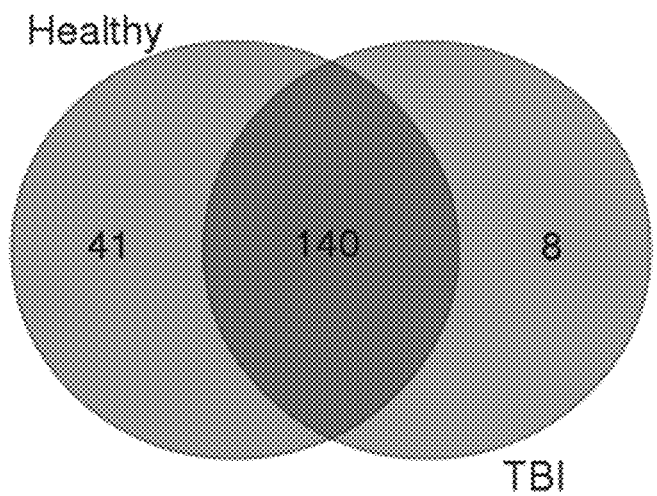

FIGS. 3A-3B include a representative Venn plot of proteins that are shared or unique between healthy and TBI patient samples. Only proteins detected in all the samples in each group were included in this analysis (FIG. 3A). FIG. 3B includes a list of 8 proteins uniquely expressed in all TBI samples, including their UniProt ID and protein name. AL9A1 and SYTC are expressed in brain while FA5 is related to coagulation (both designations are based on annotated information from UniProt (uniprot.org)). These proteins show increased or unique expression in all of the 34 TBI samples, encompassing all subclasses 1-3 (TBI-1, TBI-2, TBI-3) and the more severe mild TBI subclass 4 (Complex TBI), compared to the 15-healthy control sample cohort (see FIGS. 1 and 2). FIGS. 3A-3B represent a high probability grouping, and some of these proteins were found as part of the protein panels from the supervised and unsupervised models.

Additionally, Table 11 below provides more of a holistic approach for determining a subject's TBI, such as severe TBI, mild TBI, or absence of TBI. Table 11 includes proteins found across all classes of TBI using difference models.

TABLE 11

Commonly Found TBI Biomarkers
Table 11. Proteins found in TBI (all classes)
and commonly found by difference models P29144 | TPP2
Q99683 | M3K5
O75376 | NCOR1
P35908 | K22E
Q15746 | MYLK
P49189 | AL9A1
Q96IU4 | ABHEB
O00429 | DNM1L
Q27J81 | INF2
P02743 | SAMP
Q6UWP8 | SBSN
P08133 | ANXA6
Q15485 | FCN2
P07814 | SYEP Bootstrap Forest Analysis. In another iteration of supervised analysis, Bootstrap Forest Analysis was performed as an alternative approach to traditional supervised analysis of quantitative DIA-MS data. This analysis ranks proteins according to their contributing portion of a whole, and is summarized in FIG. 5.

In addition to summarizing the overall dataset through Bootstrap Forest Analysis, the contribution of individual proteins was assessed. This approach is summarized as a total of five separate decision trees that met the criteria of the prediction model, as shown in FIGS. 4A-4E. This analysis ascribed a quantitative cutoff for the ability of a given protein to serve as a biomarker capable of distinguishing patients with TBI from their healthy counterparts, along with an associated diagnostic probability. In the case where a single protein was insufficiently capable of making this distinction, a combination of multiple proteins is identified and defined.

Example 3

TBI Biomarker Proteins and Peptide Fragments

Mass spectrometry techniques typically involve the detection of ions that have undergone physical change(s) in a mass spectrometer. Frequently, the physical change involves fragmenting a selected precursor ion and recording the mass spectrum of the resultant fragment ions. The information in the fragment ion mass spectrum is often a useful aid in elucidating the structure of the precursor ion. The general approach used to obtain a mass spectrometry/mass spectrometry (MS/MS or MS$^2$) spectrum is to isolate a selected precursor ion with a suitable m/z analyzer, to subject the precursor ion to energetic collisions with a neutral gas in order to induce dissociation, and finally to mass analyze the fragment ions in order to generate a mass spectrum.

As would be recognized by one of ordinary skill in the art based on the present disclosure, such peptide fragments used in DIA-MS (or DDA-MS) can be used to identify proteins/biomarkers. More specifically, the following tables include the UniProt ID Nos. and short names of the various TBI biomarkers identified and described herein, listed alongside their corresponding peptide fragment sequences.

In addition to DIA-MS, DDA-MS and SRM/MRM-MS can be used for reliable and comprehensive quantification of various peptide analytes. SRM/MRM-MS is generally performed on triple quadrupole-like instruments, in which increased selectivity is obtained through collision-induced dissociation. It is a non-scanning mass spectrometry technique, where two mass analyzers (Q1 and Q3) are used as static mass filters, to monitor a particular fragment of a selected precursor. On triple quadrupole instruments, various ionization methods can be used including without limitation electrospray ionization, chemical ionization, electron ionization, atmospheric pressure chemical ionization, and matrix-assisted laser desorption ionization. The specific pair of mass-over-charge (m/z) values associated to the precursor and fragment ions selected is referred to as a "transition". The detector acts as a counting device for the ions matching the selected transition thereby returning an intensity distribution over time. MRM-MS is when multiple SRM-MS transitions are measured within the same experiment on the chromatographic time scale by rapidly switching between the different precursor/fragment pairs. Typically, the triple quadrupole instrument cycles through a series of transitions and records the signal of each transition as a function of the elution time. The method allows for additional selectivity by monitoring the chromatographic co-elution of multiple transitions for a given analyte. Potential peptides are listed in Tables 13-21 for the different classifications outlined in the present disclosure.

In addition, PRM-MS can be used in which there is parallel detection of all transitions in a single analysis using a high resolution mass spectrometer. PRM-MS provides high selectivity, high sensitivity and high-throughput to quantify selected peptide (Q1), hence quantify proteins. Again, multiple peptides can be specifically selected for each protein. PRM-MS methodology uses the quadrupole of a mass spectrometer to isolate a target precursor ion, fragments the targeted precursor ion in the collision cell, and then detects the resulting product ions in the Orbitrap mass analyzer. PRM-MS uses a quadrupole time-of-flight (QTOF) or hybrid quadrupole-orbitrap (QOrbitrap) mass spectrometer to carry out the peptides/proteins quantitation. Potential peptides are listed in Tables 13-21 for the different classifications outlined in the present disclosure.

In some embodiments, the methods described herein can be applied to the quantification of polypeptides(s) or protein(s) in biological sample(s). Any kind of biological samples comprising polypeptides or proteins can be the starting point and be analyzed by the methods herein. Indeed, any protein/peptide containing sample can be used for and analyzed by the methods produced here (e.g., tissues, cells). The methods herein can also be used with peptide mixtures obtained by digestion. Digestion of a polypeptide or protein includes any kind of cleavage strategies, such as, enzymatic, chemical, physical or combinations thereof. According to some embodiments, the following parameters of the methods provided herein are determined: trypsin (or other protease) digestion and peptide clean up, best responding polypeptides, best responding proteins, best responding peptides, best responding fragments, fragment intensity ratios (increased high and reproducible peak intensities), optimal collision energies, and all the optimal parameters to maximize sensitivity and/or specificity of the methods.

In other embodiments, quantification of the polypeptides and/or of the corresponding proteins or activity/regulation of the corresponding proteins is desired. A selected peptide is labeled with a stable-isotope and used as an internal standard (SIL) to achieve absolute quantification of a protein of interest. The addition of a quantified stable-labeled peptide analogue of the tag to the peptide sample in known amount; and subsequently the tag and the peptide of interest is quantified by mass spectrometry and absolute quantification of the endogenous levels of the proteins is obtained.

TABLE 13

Rule-In TBI Biomarkers - Unique

| Unique Protein | Abbreviated Name | Descriptor | UniProt Primary Accession Number | SEQ ID NO: |
|---|---|---|---|---|
| | PZP | PZP_HUMAN | P20742 | |
| | EPIPL | EPIPL_HUMAN | P58107 | |
| | IGHA2 | IGHA2_HUMAN | P01877 | |
| | AL9A1 | AL9A1_HUMAN | P49189 | |
| | G6PI | G6PI_HUMAN | P06744 | |
| | SYTC | SYTC_HUMAN | P26639 | |
| | EZRI | EZRI_HUMAN | P15311 | |
| | FA5 | FAS_HUMAN | P12259 | |

| Protein | Peptide Sequence | |
|---|---|---|
| P06744 | DPQFQK | 4 |
| P06744 | LQQWYR | 5 |
| P06744 | SELNLR | 6 |
| P06744 | FNHFSLTLNTNHGHILVDYSK | 7 |
| P06744 | INYTEGR | 8 |
| P06744 | AVLHVALR | 9 |
| P06744 | SNTPILVDGK | 10 |
| P06744 | VWYVSNIDGTHIAK | 11 |
| P06744 | TLAQLNPESSLFIIASK | 12 |
| P06744 | TFTTQETITNAETAK | 13 |
| P06744 | EWFLQAAK | 14 |
| P06744 | DPSAVAK | 15 |
| P06744 | HFVALSTNTTK | 16 |
| P06744 | ELQAAGK | 17 |
| P06744 | VFEGNRPTNSIVFTK | 18 |
| P06744 | IFVQGIIWDINSFDQWGVELGK | 19 |
| P12259 | LWVLVVLGTSWVGWGSQGTEAAQLR | 20 |
| P12259 | EYEPYFK | 21 |

TABLE 13-continued

| | | |
|---|---|---|
| P12259 | EKPQSTISGLLGPTLYAEVGDIIK | 22 |
| P12259 | ADKPLSIHPQGIR | 23 |
| P12259 | LSEGASYLDHTFPAEK | 24 |
| P12259 | GTLTEGGTQK | 25 |
| P12259 | QIVLLFAVFDESK | 26 |
| P12259 | WIISSLTPK | 27 |
| P12259 | SQHLDNFSNQIGK | 28 |
| P12259 | EDGILGPIIR | 29 |
| P12259 | AVQPGETYTYK | 30 |
| P12259 | AADIEQQAVFAVFDENK | 31 |
| P12259 | SWYLEDNINK | 32 |
| P12259 | LEPEDEESDADYDYQNR | 33 |
| P12259 | LAAALGIR | 34 |
| P12259 | FTVNNLAEPQK | 35 |
| P12259 | APSHQQATTAGSPLR | 36 |
| P12259 | LLSLGAGEFK | 37 |
| P12259 | SQEHAK | 38 |
| P12259 | DPPSDLLLLK | 39 |
| P12259 | QSNSSK | 40 |
| P12259 | WHLASEK | 41 |
| P12259 | AWGESTPLANKPGK | 42 |
| P12259 | QSGHPK | 43 |
| P12259 | SQFLIK | 44 |
| P12259 | HTHHAPLSPR | 45 |
| P12259 | TFHPLR | 46 |
| P12259 | SEAYNTFSER | 47 |
| P12259 | HSLVLHK | 48 |
| P12259 | EFNPLVIVGLSK | 49 |
| P12259 | DGTDYIEIIPK | 50 |
| P12259 | EEVQSSEDDYAEIDYVPYDDPYK | 51 |
| P12259 | TNINSSR | 52 |
| P12259 | DPDNIAAWYLR | 53 |
| P12259 | SNNGNR | 54 |
| P12259 | NYYIAAEEISWDYSEFVQR | 55 |
| P12259 | ETDIEDSDDIPEDTTYK | 56 |
| P12259 | YLDSTFTK | 57 |
| P12259 | GEYEEHLGILGPIIR | 58 |
| P12259 | AEVDDVIQVR | 59 |
| P12259 | NLASRPYSLHAHGLSYEK | 60 |
| P12259 | TYEDDSPEWFK | 61 |
| P12259 | EDNAVQPNSSYTYVWHATER | 62 |
| P12259 | AWAYYSAVNPEK | 63 |
| P12259 | SWYYEK | 64 |
| P12259 | QHQLGVWPLLPGSFK | 65 |
| P12259 | ASKPGWWLLNTEVGENQR | 66 |
| P12259 | ASEFLGYWEPR | 67 |
| P12259 | LNNGGSYNAWSVEK | 68 |
| P12259 | EVIITGIQTOGAK | 69 |
| P12259 | ENQFDPPIVAR | 70 |
| P12259 | AYNRPTLR | 71 |
| P12259 | QITASSFK | 72 |
| P12259 | SWWGDYWEPFR | 73 |
| P12259 | VNAWQAK | 74 |
| P12259 | QWLEIDLLK | 75 |
| P12259 | SYTIHYSEQGVEWKPYR | 76 |
| P12259 | IFEGNTNTK | 77 |
| P12259 | NFFNPPIISR | 78 |
| P12259 | TWNQSIALR | 79 |
| P15311 | EVWYFGLHYVDNK | 80 |
| P15311 | GFPTWLK | 81 |
| P15311 | VSAQEVR | 82 |
| P15311 | FYPEDVAEELIQDITQK | 83 |
| P15311 | FGDYNK | 84 |
| P15311 | SGYLSSER | 85 |
| P15311 | DQWEDR | 86 |
| P15311 | IQVWHAEHR | 87 |
| P15311 | GTDLWLGVDALGLNIYEK | 88 |
| P15311 | QQLETEK | 89 |
| P15311 | LQDYEEK | 90 |
| P15311 | ELSEQIQR | 91 |
| P15311 | ALQLEEER | 92 |
| P15311 | QAVDQIK | 93 |
| P15311 | SQEQLAAELAEYTAK | 94 |
| P15311 | IALLEEAR | 95 |
| P15311 | EDEVEEWQHR | 96 |
| P15311 | EAQDDLVK | 97 |
| P15311 | QLLTLSSELSQAR | 98 |
| P15311 | IDEFEAL | 99 |
| P20742 | VVSVDENFRPR | 100 |
| P20742 | NELIPLIYLENPR | 101 |

TABLE 13-continued

| | | |
|---|---|---|
| P20742 | IAQWQSLK | 102 |
| P20742 | LEAGINQLSFPLSSEPIQGSYR | 103 |
| P20742 | VVVQTESGGR | 104 |
| P20742 | IQHPFTVEEFVLPK | 105 |
| P20742 | EEGTDLEVTANR | 106 |
| P20742 | ISEITNIVSK | 107 |
| P20742 | QGIPFFAQVLLVDGK | 108 |
| P20742 | GSFALSFPVESDVAPIAR | 109 |
| P20742 | VFTNSK | 110 |
| P20742 | GEVFTLK | 111 |
| P20742 | LPSNVVK | 112 |
| P20742 | AVGYLITGYQR | 113 |
| P20742 | HQDGSYSTFGER | 114 |
| P20742 | EGTHGSHVYTK | 115 |
| P20742 | ALLAYAFSLLGK | 116 |
| P20742 | EILNSLDK | 117 |
| P20742 | EDNLVHWERPQRPK | 118 |
| P20742 | QQNAQGGFSSTQDTVVALHALSR | 119 |
| P20742 | EDSPFALK | 120 |
| P20742 | SLFTDLVAEK | 121 |
| P20742 | ISASSEVAFLSIQIK | 122 |
| P20742 | GPTQDFR | 123 |
| P20742 | VSVQLK | 124 |
| P20742 | ASPAFLASQNTK | 125 |
| P20742 | QTLSWTVTPK | 126 |
| P20742 | TLLVEAEGIEQEK | 127 |
| P26639 | ASSPSGK | 128 |
| P26639 | EGSGDGGR | 129 |
| P26639 | AELNPWPEYIYTR | 130 |
| P26639 | AEHDSILAEK | 131 |
| P26639 | DSKPIK | 132 |
| P26639 | VTLPDGK | 133 |
| P26639 | QVDAESWK | 134 |
| P26639 | VNTPTTTVYR | 135 |
| P26639 | NSSTYWEGK | 136 |
| P26639 | IYGISFPDPK | 137 |
| P26639 | GAYIYNALIEFIR | 138 |
| P26639 | GFQEVVTPNIFNSR | 139 |
| P26639 | LADFGVLHR | 140 |
| P26639 | NELSGALTGLTR | 141 |
| P26639 | TVYSVFGFSFK | 142 |
| P26639 | LNLSTRPEK | 143 |
| P26639 | FLGDIEVWDQAEK | 144 |
| P26639 | QLENSLNEFGEK | 145 |
| P26639 | WELNSGDGAFYGPK | 146 |
| P26639 | IDIQIK | 147 |
| P26639 | FNLTYVSHDGDDK | 148 |
| P26639 | RPVIVHR | 149 |
| P26639 | QQFHDAK | 150 |
| P26639 | ISGTVNIR | 151 |
| P26639 | TISETIER | 152 |
| P49189 | ILLEAAR | 153 |
| P49189 | SIFEAR | 154 |
| P49189 | GIKPVTLELGGK | 155 |
| P49189 | FTEEVVK | 156 |
| P49189 | IGDPLLEDTR | 157 |
| P49189 | VLGFVK | 158 |
| P49189 | ANDTTFGLAAGVFTR | 159 |
| P49189 | VTIEYYSQLK | 160 |
| P49189 | VEPADASGTEK | 161 |
| P49189 | AFEPATGR | 162 |
| P49189 | EVNLAVQNAK | 163 |
| P58107 | GQLLPVSK | 164 |
| P58107 | ALQQGLVGLELK | 165 |
| P58107 | ATTGYPDPYGGEK | 166 |
| P58107 | LALFQAIGK | 167 |
| P58107 | LSELEPGTGDLR | 168 |
| P58107 | FLNPNTLER | 169 |
| P58107 | LTYHQLLER | 170 |
| P58107 | APGSGLALLPLK | 171 |
| P58107 | LAAVDVSAR | 172 |
| P58107 | YLEGTGSVAGVVLLPEGHK | 173 |
| P58107 | LWVDEAVR | 174 |
| P58107 | GLVDRPLALR | 175 |
| P58107 | LPLEAALR | 176 |
| P58107 | QLSQAGSFSDGTHGGLR | 177 |
| P58107 | GGEPQGPPFIK | 178 |
| P58107 | QALSTATATVSVGK | 179 |
| P58107 | GRPVSLWELLFSEAISSEQR | 180 |
| P58107 | LAAELSATLEQAAATAR | 181 |

TABLE 13-continued

| | | |
|---|---|---|
| P58107 | VTFSGLR | 182 |
| P58107 | DTVTPGELLK | 183 |
| P58107 | AEIIDQDLYER | 184 |
| P58107 | LEHGQATAK | 185 |
| P58107 | DVGSLASAQR | 186 |
| P58107 | LSIYEAR | 187 |
| P58107 | GLLRPGTALILLEAQAATGFIIDPK | 188 |
| P58107 | GHSVEEALR | 189 |
| P58107 | AAVIGPDVFAK | 190 |
| P58107 | VSAWELINSEYFSEGR | 191 |
| P58107 | EVTLGQVAK | 192 |
| P58107 | LLEAETQR | 193 |
| P58107 | GVVGPELYGR | 194 |
| P58107 | AEGAIAGFR | 195 |
| P58107 | GLIPWEQAAR | 196 |
| P58107 | SLQAVPGAK | 197 |
| P58107 | GLLEDVQEGR | 198 |
| P58107 | TTVPQLLASVQR | 199 |
| P58107 | ASIAQAVR | 200 |
| P58107 | DGLLPTGLGQR | 201 |
| P58107 | LLEAQVASGFLVDPLNNQR | 202 |
| P58107 | LSVEDAVK | 203 |
| P58107 | VGLVGR | 204 |
| P58107 | ELSEQLGQAER | 205 |
| P58107 | AAAGYPDPYSR | 206 |
| P58107 | LGLLDTQTSQVLTAVDK | 207 |
| P58107 | FFFDPSAR | 208 |
| P58107 | DQVTYQQLR | 209 |
| P58107 | VPVSTGR | 210 |
| P58107 | QVVSAVTALVEAAER | 211 |
| P58107 | QPLQATFR | 212 |
| P58107 | TLDELSQGTTTVK | 213 |
| P58107 | SLEGGNFIAGVLIQGTQER | 214 |
| P58107 | LTVEEAFK | 215 |
| P58107 | ILADPSDDTK | 216 |
| P58107 | GENYVYINEATR | 217 |
| P58107 | FADQVVSFWDLLSSPYFTEDR | 218 |
| P58107 | ELIQEYGAQSGGLEK | 219 |
| P58107 | LLEIITTTIEETETQNQGIK | 220 |
| P58107 | GEVTAADLFNSR | 221 |
| P58107 | TLHTLR | 222 |
| P58107 | LSVDEAVDVGLVNEELR | 223 |
| P58107 | AATGYR | 224 |
| P58107 | LLEVOVATGGVIDPQHHHR | 225 |
| P58107 | LPLETAYR | 226 |
| P58107 | DIYALISDQK | 227 |
| P58107 | FVDPNTQEK | 228 |
| P58107 | DSEHIDDETR | 229 |
| P58107 | ALEAEQVEITVGR | 230 |
| P58107 | GQKPTLWALLNSEYVTEEK | 231 |
| P58107 | ALQTVAQLILELIEK | 232 |
| P58107 | QETSNK | 233 |
| P58107 | HLWFQGIR | 234 |
| P58107 | LSVEEPVPAGVVGSEIQEK | 235 |
| P58107 | GFFDPNTHENLTYVQLLR | 236 |
| P58107 | GSAVHQLSEELR | 237 |
| P58107 | VTPGSGALQGQSVSVWELLFYR | 238 |
| P58107 | EVSEDR | 239 |
| P58107 | AGTLTVEELGATLTSLLAQAQAQAR | 240 |
| P58107 | AEAEAGSPRPDPR | 241 |
| P58107 | AVPVWDVLASGYVSR | 242 |
| P58107 | EELLAEFGSGTLDLPALTR | 243 |
| P58107 | LTAIIEEAEEAPGARPQLQDAR | 244 |
| P58107 | EPGPAGR | 245 |
| P58107 | GDGDSGR | 246 |
| P58107 | EGQGEGETQEAAAAAAAAR | 247 |
| P58107 | QEQTLR | 248 |
| P58107 | GQFQGRPVSVWDVLFSSYLSEAR | 249 |
| P58107 | DELLAQHAAGALGLPDLVAVLTR | 250 |
| P58107 | VIEETEER | 251 |
| P58107 | QVSASELHTSGILGPETLR | 252 |
| P58107 | DLAQGTK | 253 |
| P58107 | LSVEEAVAAGVVGGEIQEK | 254 |
| P58107 | AVPVWDVLASGYVSGAAR | 255 |
| P58107 | LTAIIEEAEEAPGARPQLQDAWR | 256 |
| P58107 | ASTLTVEELGATLTSLLAQAQAQAR | 257 |
| P58107 | EGQGEGETQEAAAATAAAR | 258 |
| P58107 | GFFDPNTHENLTYLQLLQR | 259 |
| P58107 | ATLDPETGLLFLSLSLQ | 260 |

TABLE 14

Rule-In TBI Biomarkers - Supervised Analysis

| Unique Protein | Abbreviated Name | Descriptor | UniProt Primary Accession Number | SEQ ID NO: |
|---|---|---|---|---|
| | NCOR1 | NCOR1_HUMAN | O75376 | |
| | ABHEB | ABHEB_HUMAN | Q96IU4 | |
| | ANXA6 | ANXA6_HUMAN | P08133 | |
| | DNM1L | DNM1L_HUMAN | O00429 | |
| | FCN2 | FCN2_HUMAN | Q15485 | |
| | HBA | HBA_HUMAN | P69905 | |
| | MYLK | MYLK_HUMAN | Q15746 | |
| | SBSN | SBSN_HUMAN | Q6UWP8 | |
| | AHNK | AHNK_HUMAN | Q09666 | |
| | K22E | K22E_HUMAN | P35908 | |

| Protein | Peptide Sequence | | | |
|---|---|---|---|---|
| O00429 | SSVLESLVGR | | | 261 |
| O00429 | GTGIVTR | | | 262 |
| O00429 | RPLILQLVHVSQEDK | | | 263 |
| O00429 | TTGEENGVEAEEWGK | | | 264 |
| O00429 | LYTDFDEIR | | | 265 |
| O00429 | QEIENETER | | | 266 |
| O00429 | ISGNNK | | | 267 |
| O00429 | GVSPEPIHLK | | | 268 |
| O00429 | VPVGDQPK | | | 269 |
| O00429 | DIELQIR | | | 270 |
| O00429 | EVDPDGR | | | 271 |
| O00429 | TLAVITK | | | 272 |
| O00429 | LGIIGVVNR | | | 273 |
| O00429 | SQLDINNK | | | 274 |
| O00429 | SVTDSIR | | | 275 |
| O00429 | DEYAFLQK | | | 276 |
| O00429 | YPSLANR | | | 277 |
| O00429 | INVLAAQYQSLLNSYGEPVDDK | | | 278 |
| O00429 | SATLLQLITK | | | 279 |
| O00429 | TLESVDPLGGLNTIDILTAIR | | | 280 |
| O00429 | NATGPRPALFVPEVSFELLVK | | | 281 |
| O00429 | LEEPSLR | | | 282 |
| O00429 | ELPSAVSR | | | 283 |
| O00429 | VPSALAPASQEPSPAASAEADGK | | | 284 |
| O00429 | LIQDSR | | | 285 |
| O00429 | NVASGGGGVGDGVQEPTTGNWR | | | 286 |
| O00429 | AEELLAEEK | | | 287 |
| O00429 | GHAVNLLDVPVPVAR | | | 288 |
| O00429 | SYFLIVR | | | 289 |
| O00429 | NIQDSVPK | | | 290 |
| O00429 | DTLQSELVGQLYK | | | 291 |
| O00429 | ALQGASQIIAEIR | | | 292 |
| O75376 | YPPHSVQYTFPNTR | | | 293 |
| O75376 | HQQEFAVPDYR | | | 294 |
| O75376 | SSHLEVSQASQLLQQQQQQQLR | | | 295 |
| O75376 | RPSLLSEFHPGSDRPQER | | | 296 |
| O75376 | TSYEPFHPGPSPVDHDSLESK | | | 297 |
| O75376 | LEQVSDSHFQR | | | 298 |
| O75376 | VSAAVLPLVHPLPEGLR | | | 299 |
| O75376 | ASADAK | | | 300 |
| O75376 | SIVQIIYDENR | | | 301 |
| O75376 | IFEGLGPK | | | 302 |
| O75376 | VELPLYNQPSDTK | | | 303 |
| O75376 | VYHENIK | | | 304 |
| O75376 | LILFFK | | | 305 |
| O75376 | GAGLSATIAR | | | 306 |
| O75376 | SEHEISEIIDGLSEQENNEK | | | 307 |
| O75376 | FIQHPK | | | 308 |
| O75376 | NFGLIASYLER | | | 309 |
| O75376 | NQQIARPSQEEK | | | 310 |
| O75376 | IDGTAEETEER | | | 311 |
| O75376 | EQATPR | | | 312 |
| O75376 | GLVEHGR | | | 313 |
| O75376 | NWAAIAK | | | 314 |
| O75376 | HNLDNLLQQHK | | | 315 |
| O75376 | ADSVDVEVR | | | 316 |
| O75376 | VPENHASK | | | 317 |
| O75376 | VEGDNTK | | | 318 |
| O75376 | EWEVLQPAPHQVITNLPEGVR | | | 319 |
| O75376 | LPTTRPTRPPPPLIPSSK | | | 320 |

TABLE 14-continued

| | | |
|---|---|---|
| O75376 | QQESAK | 321 |
| O75376 | SATLPYIK | 322 |
| O75376 | QEEFSPR | 323 |
| O75376 | SQNSQPEGLLVR | 324 |
| O75376 | AQHEGVVR | 325 |
| O75376 | GTAGAIQEGSITR | 326 |
| O75376 | ISVESIPSLR | 327 |
| O75376 | GSITQGTPALPQTGIPTEALVK | 328 |
| O75376 | SGHILSYDNIK | 329 |
| O75376 | TAHEISLK | 330 |
| O75376 | SYESVEGNIK | 331 |
| O75376 | GSPHSDLK | 332 |
| O75376 | ATTESFEDGLK | 333 |
| O75376 | ESPPIR | 334 |
| O75376 | AFEGAITK | 335 |
| O75376 | GKPYDGITTIK | 336 |
| O75376 | QDILTQESR | 337 |
| O75376 | TPEVVQSTRPIIEGSISQGTPIK | 338 |
| O75376 | FDNNSGQSAIK | 339 |
| O75376 | SLITGPSK | 340 |
| O75376 | AGETVR | 341 |
| O75376 | HTSVVSSGPSVLR | 342 |
| O75376 | STLHEAPK | 343 |
| O75376 | AQLSPGIYDDTSAR | 344 |
| O75376 | TSDVTISSNK | 345 |
| O75376 | STNHER | 346 |
| O75376 | STLTPTQR | 347 |
| O75376 | ESIPAK | 348 |
| O75376 | SPVPGVDPVVSHSPFDPHHR | 349 |
| O75376 | GSTAGEVYR | 350 |
| O75376 | ALDPAAAAYLFQR | 351 |
| O75376 | EQPLGLPYPATR | 352 |
| O75376 | YETPSDAIEVISPASSPAPPQEK | 353 |
| O75376 | LQTYQPEVVK | 354 |
| O75376 | ANQAENDPTR | 355 |
| O75376 | YSPESQAQSVHHQRPGSR | 356 |
| O75376 | VSPENLVDK | 357 |
| O75376 | SHVSSEPYEPISPPQVPVVHEK | 358 |
| O75376 | QDSLLLLSQR | 359 |
| O75376 | GAEPAEQR | 360 |
| O75376 | SPGSISYLPSFFTK | 361 |
| O75376 | GHSFADPASNLGLEDIIR | 362 |
| O75376 | EPAPLLSAQYETLSDSDD | 363 |
| O75376 | SAAVSEQQQLEQK | 364 |
| O75376 | TLEVEK | 365 |
| O75376 | TTITAANFIDVIITR | 366 |
| O75376 | QIASDK | 367 |
| O75376 | GSQSSDSSSSLSSHR | 368 |
| P08133 | GFGSDK | 369 |
| P08133 | EAILDIITSR | 370 |
| P08133 | DLIADLK | 371 |
| P08133 | YELTGK | 372 |
| P08133 | DAISGIGTDEK | 373 |
| P08133 | DLEADIIGDTSGHFQK | 374 |
| P08133 | EEDDVVSEDLVQQDVQDLYEAGELK | 375 |
| P08133 | WGTDEAQFIYILGNR | 376 |
| P08133 | LVFDEYLK | 377 |
| P08133 | TTGKPIEASIR | 378 |
| P08133 | GELSGDFEK | 379 |
| P08133 | STPEYFAER | 380 |
| P08133 | NDTSGEYK | 381 |
| P08133 | GTVRPANDFNPDADAK | 382 |
| P08133 | GLGTDEDTIIDIITHR | 383 |
| P08133 | SEISGDLAR | 384 |
| P08133 | ALIEILATR | 385 |
| P08133 | TNAEIR | 386 |
| P08133 | AINEAYK | 387 |
| P08133 | SLEDALSSDTSGHFR | 388 |
| P08133 | ILISLATGHR | 389 |
| P08133 | EEGGENLDQAR | 390 |
| P08133 | EDAQVAAEILEIADTPSGDK | 391 |
| P08133 | SYPHLR | 392 |
| P08133 | VFQEFIK | 393 |
| P08133 | DAFVAIVQSVK | 394 |
| P08133 | NKPLFFADK | 395 |
| P08133 | GAGTDEK | 396 |
| P08133 | SEIDLLNIR | 397 |
| P08133 | SLHQAIEGDTSGDFLK | 398 |
| P35908 | GFSSGSAVVSGGSR | 399 |
| P35908 | HGGGGGGFGGGGFGSR | 400 |

TABLE 14-continued

| | | |
|---|---|---|
| P35908 | SLVGLGGTK | 401 |
| P35908 | SISISVAGGGGGFGAAGGFGGR | 402 |
| P35908 | VDPEIQNVK | 403 |
| P35908 | YLDGLTAER | 404 |
| P35908 | TAAENDFVTLK | 405 |
| P35908 | VELQSK | 406 |
| P35908 | VDLLNQEIEFLK | 407 |
| P35908 | EEAEALYHSK | 408 |
| P35908 | YEELQVTVGR | 409 |
| P35908 | LQGEIAHVK | 410 |
| P35908 | NVQDAIADAEQR | 411 |
| P35908 | GEHALK | 412 |
| P35908 | LNDLEEALQQAK | 413 |
| P35908 | AAFGGSGGR | 414 |
| P35908 | GSSSGGGYSSGSSSYGSGGR | 415 |
| P35908 | GGSGGGGSISGGGYGSGGGSGGR | 416 |
| P35908 | YGSGGGSK | 417 |
| P35908 | GGSISGGGYGSGGGK | 418 |
| P35908 | HSSGGGSR | 419 |
| P35908 | GGSSSGGGYGSGGGGSSSVK | 420 |
| P35908 | GSSGEAFGSSVTFSFR | 421 |
| P69905 | VGAHAGEYGAEALER | 422 |
| P69905 | TYFPHFDLSHGSAQVK | 423 |
| P69905 | FLASVSTVLTSK | 424 |
| Q09666 | ELLLPNWQGSGSHGLTIAQR | 425 |
| Q09666 | DDGVFVQEVTQNSPAAR | 426 |
| Q09666 | SPEPGQTWTR | 427 |
| Q09666 | SEDGVEGDLGETQSR | 428 |
| Q09666 | TITVTR | 429 |
| Q09666 | VTAYTVDVTGR | 430 |
| Q09666 | DIDISSPEFK | 431 |
| Q09666 | HELTEISNVDVETQSGK | 432 |
| Q09666 | LPSGSGAASPTGSAVDIR | 433 |
| Q09666 | AGAISASGPELQGAGHSK | 434 |
| Q09666 | VGGSGVNVAK | 435 |
| Q09666 | GLDLGGR | 436 |
| Q09666 | GGVQVPAVDISSSLGGR | 437 |
| Q09666 | AVEVOGPSLESGDHGK | 438 |
| Q09666 | FGVSTGR | 439 |
| Q09666 | EGQTPK | 440 |
| Q09666 | VSAPEVSVGHK | 441 |
| Q09666 | GPQITGPSLEGDLGLK | 442 |
| Q09666 | FSVSGAK | 443 |
| Q09666 | VSAPGVQGDVK | 444 |
| Q09666 | GPQVALK | 445 |
| Q09666 | VDIETPNLEGTLTGPR | 446 |
| Q09666 | LGSPSGK | 447 |
| Q09666 | GGVDVTLPR | 448 |
| Q09666 | VPEVDVR | 449 |
| Q09666 | VDVSAPDVEAHGPEWNLK | 450 |
| Q09666 | GDISISGPK | 451 |
| Q09666 | VNVEAPDVNLEGLGGK | 452 |
| Q09666 | GEYDVTVPK | 453 |
| Q09666 | VDIDAPDVDVHGPDWHLK | 454 |
| Q09666 | FSVPGFK | 455 |
| Q09666 | AEGPEVDVNLPK | 456 |
| Q09666 | ADVDISGPK | 457 |
| Q09666 | IDVTAPDVSIEEPEGK | 458 |
| Q09666 | VPDVELK | 459 |
| Q09666 | VGVEVPDVNIEGPEGK | 460 |
| Q09666 | GEGPEFDVNLSK | 461 |
| Q09666 | ANVDISAPK | 462 |
| Q09666 | VDTNAPDLSLEGPEGK | 463 |
| Q09666 | GNVDISAPK | 464 |
| Q09666 | APDVEGQGLDWSLK | 465 |
| Q09666 | GEGPEVDVNLPK | 466 |
| Q09666 | ADVVVSGPK | 467 |
| Q09666 | VDIEAPDVSLEGPEGK | 468 |
| Q09666 | GDVDVSVPK | 469 |
| Q09666 | VPDVEIK | 470 |
| Q09666 | EVDVNLPK | 471 |
| Q09666 | ADIDVSGPK | 472 |
| Q09666 | VDVEVPDVSLEGPEGK | 473 |
| Q09666 | VDISAPDVDVHGPDWHLK | 474 |
| Q09666 | GEGPEVDVK | 475 |
| Q09666 | ADVDVSGPK | 476 |
| Q09666 | ISIPDVGLHLK | 477 |
| Q09666 | GDYDVTVPK | 478 |
| Q09666 | VEGEIK | 479 |
| Q09666 | APDVDIK | 480 |

TABLE 14-continued

| | | |
|---|---|---|
| Q09666 | VDINAPDVEVHGPDWHLK | 481 |
| Q09666 | ADLGVSGPK | 482 |
| Q09666 | VDIDVPDVNLEAPEGK | 483 |
| Q09666 | TDVDVSLPK | 484 |
| Q09666 | VEGDLK | 485 |
| Q09666 | GPEIDVK | 486 |
| Q09666 | VDIDAPDVEVHDPDWHLK | 487 |
| Q09666 | ADIDVSGPSVDTDAPDLDIEGPEGK | 488 |
| Q09666 | GEIDASVPELEGDLR | 489 |
| Q09666 | GDADVSVPK | 490 |
| Q09666 | GDVDVSLPK | 491 |
| Q09666 | VPDVDIR | 492 |
| Q09666 | GDVDVSAPK | 493 |
| Q09666 | GPELDVK | 494 |
| Q09666 | GEVDVDVPK | 495 |
| Q09666 | GPHVDVSGPDIDIEGPEGK | 496 |
| Q09666 | GDVDVSVPEVEGK | 497 |
| Q09666 | VDVNAPDVQAPDWHLK | 498 |
| Q09666 | VDIEGPDVNIEGPEGK | 499 |
| Q09666 | GPEVDIK | 500 |
| Q09666 | VDINAPDVGVQGPDWHLK | 501 |
| Q09666 | GEGPDGDVK | 502 |
| Q09666 | GEGPDVDVNLPK | 503 |
| Q09666 | GDVDVTGPK | 504 |
| Q09666 | GPEVDLK | 505 |
| Q09666 | VDIDVPDVNVQGPDWHLK | 506 |
| Q09666 | VDVEGPDVNIEGPEGK | 507 |
| Q09666 | GDVDISLPK | 508 |
| Q09666 | GPEVDIR | 509 |
| Q09666 | GPQVDIDVPDVGVQGPDWHLK | 510 |
| Q09666 | ADLDVSGPK | 511 |
| Q09666 | VDIDVPDVNIEGPEGK | 512 |
| Q09666 | VDINAPDVDVQGPDWHLK | 513 |
| Q09666 | VDVDVPDVNIEGPDAK | 514 |
| Q09666 | GEVDVSLANVEGDLK | 515 |
| Q09666 | GPALDIK | 516 |
| Q09666 | IDVDAPDIDIHGPDAK | 517 |
| Q09666 | GDVDVSGPK | 518 |
| Q09666 | APSLDIK | 519 |
| Q09666 | GPEVDVSGPK | 520 |
| Q09666 | LNIEGK | 521 |
| Q09666 | FNFSGSK | 522 |
| Q09666 | VQTPEVDVK | 523 |
| Q09666 | KPDIDITGPK | 524 |
| Q09666 | VDINAPDVEVQGK | 525 |
| Q09666 | GDLDIAGPNLEGDFK | 526 |
| Q09666 | APEVNLNAPDVDVHGPDWNLK | 527 |
| Q09666 | AEGPDVAVDLPK | 528 |
| Q09666 | VDINAPDVDVHGPDWHLK | 529 |
| Q09666 | GEGPEVDVTLPK | 530 |
| Q09666 | ADIDISGPNVDVDVPDVNIEGPDAK | 531 |
| Q09666 | GDVVVSLPK | 532 |
| Q09666 | VDIDTPDINIEGSEGK | 533 |
| Q09666 | VDINAPDVDVR | 534 |
| Q09666 | GPDWHLK | 535 |
| Q09666 | APEVDIK | 536 |
| Q09666 | VDIDTPDIDIHGPEGK | 537 |
| Q09666 | VDIDVPDVDVQGPDWHLK | 538 |
| Q09666 | VDIDVPDVNIEGPDAK | 539 |
| Q09666 | GEGPDVDVTLPK | 540 |
| Q09666 | ADIEISGPK | 541 |
| Q09666 | VDIDAPDVSIEGPDAK | 542 |
| Q09666 | GPSLDIDTPDVNIEGPEGK | 543 |
| Q09666 | GPEVDIEGPEGK | 544 |
| Q09666 | VGIDTPDIDIHGPEGK | 545 |
| Q09666 | GDVDVTLPK | 546 |
| Q09666 | GPEADIK | 547 |
| Q09666 | VDINTPDVDVHGPDWHLK | 548 |
| Q09666 | GEGPDVDVSLPK | 549 |
| Q09666 | VDVDIPDVNIEGPDAK | 550 |
| Q09666 | ISIPDVDLDLK | 551 |
| Q09666 | GDFDVSVPK | 552 |
| Q09666 | VEGTLK | 553 |
| Q09666 | LDFEGPDAK | 554 |
| Q09666 | LSGPSLK | 555 |
| Q09666 | VTAPDVDLHLK | 556 |
| Q09666 | IGFSGPK | 557 |
| Q09666 | LEGGEVDLK | 558 |
| Q09666 | FGFGAK | 559 |
| Q09666 | SPSLDVTVPEAELNLETPEISVGGK | 560 |

TABLE 14-continued

| | | |
|---|---|---|
| Q09666 | QGFDLNVPGGEIDASLK | 561 |
| Q09666 | APDVDVNIAGPDAALK | 562 |
| Q09666 | AEAPLPSPK | 563 |
| Q09666 | LEGELQAPDLELSLPAIHVEGLDIK | 564 |
| Q09666 | IEGDLK | 565 |
| Q09666 | VQANLGAPDINIEGLDAK | 566 |
| Q09666 | TPSFGISAPQVSIPDVNVNLK | 567 |
| Q09666 | GDVPSVGLEGPDVDLQGPEAK | 568 |
| Q09666 | IGIPGVK | 569 |
| Q09666 | LEGPDVSLK | 570 |
| Q09666 | VSGPDLDLNLK | 571 |
| Q09666 | VHAPGLNLSGVGGK | 572 |
| Q09666 | VPGIDATTK | 573 |
| Q09666 | LNVGAPDVTLR | 574 |
| Q09666 | GPSLQGDLAVSGDIK | 575 |
| Q09666 | VSVGAPDLSLEASEGSIK | 576 |
| Q09666 | LPQFGISTPGSDLHVNAK | 577 |
| Q09666 | GPQVSGELK | 578 |
| Q09666 | GPGVDVNLK | 579 |
| Q09666 | ISAPNVDFNLEGPK | 580 |
| Q09666 | GSLGATGEIK | 581 |
| Q09666 | LPTGQISGPEIK | 582 |
| Q09666 | GSEVGFHGAAPDISVK | 583 |
| Q09666 | GGADVSGGVSAPDISLGEGHLSVK | 584 |
| Q09666 | GSGGEWK | 585 |
| Q09666 | GPQVSSALNLDTSK | 586 |
| Q09666 | FAGGLHFSGPK | 587 |
| Q09666 | VEGGVK | 588 |
| Q09666 | FTFSGR | 589 |
| Q09666 | AEASIQAGAGDGEWEESEVK | 590 |
| Q09666 | FNFSKPK | 591 |
| Q09666 | GGVTGSPEASISGSK | 592 |
| Q09666 | ASLGSLEGEAEAEASSPK | 593 |
| Q09666 | SNSFSDER | 594 |
| Q09666 | EFSGPSTPTGTLEFEGGEVSLEGGK | 595 |
| Q09666 | FGTFGGLGSK | 596 |
| Q09666 | GHYEVTGSDDETGK | 597 |
| Q09666 | LQGSGVSLASK | 598 |
| Q09666 | LSSSSSNDSGNK | 599 |
| Q09666 | VGIQLPEVELSVSTK | 600 |
| Q15485 | VDGSVDFYR | 601 |
| Q15485 | DWATYK | 602 |
| Q15485 | LGEFWLGNDNIHALTAQGTSELR | 603 |
| Q15485 | VDLVDFEDNYQFAK | 604 |
| Q15485 | GTHGSFANGINWK | 605 |
| Q15485 | GYNYSYK | 606 |
| Q15485 | GEAGTNGK | 607 |
| Q15746 | LVASSHISK | 608 |
| Q15746 | TSLSVDPSR | 609 |
| Q15746 | GYPEPQVTWHR | 610 |
| Q15746 | NGQPITSGGR | 611 |
| Q15746 | GTFSLVIHAVHEEDR | 612 |
| Q15746 | QVTVELTVEGSFAK | 613 |
| Q15746 | QLGQPVVSK | 614 |
| Q15746 | ITGRPQPQVTWLK | 615 |
| Q15746 | GNVPLQPSAR | 616 |
| Q15746 | VSVSEK | 617 |
| Q15746 | ATNSDVR | 618 |
| Q15746 | EVTNVISK | 619 |
| Q15746 | LDSLEAAAK | 620 |
| Q15746 | GGSPPWAANSQPQPPR | 621 |
| Q15746 | TAPQTPVLQK | 622 |
| Q15746 | TSSSITLQAAR | 623 |
| Q15746 | VQPEPR | 624 |
| Q15746 | APGLGVLSPSGEER | 625 |
| Q15746 | RPAPPRPATFPTR | 626 |
| Q15746 | QPGLGSQDVVSK | 627 |
| Q15746 | DSAFPK | 628 |
| Q15746 | FESKPQSQEVK | 629 |
| Q15746 | ENQTVK | 630 |
| Q15746 | ITWLLNGQPIQYAR | 631 |
| Q15746 | SEYLLPVAPSKPTAPIFLQGLSDLK | 632 |
| Q15746 | TQAVLTVQEPHDGTQPWFISKPR | 633 |
| Q15746 | DTGHFEVLQNEDVFTLVLK | 634 |
| Q15746 | VQPWHAGQYEILLK | 635 |
| Q15746 | YGSLRPGWPAR | 636 |
| Q15746 | GQGWLEEEDGEDVR | 637 |
| Q15746 | QHTEEAIR | 638 |
| Q15746 | QQEVEQLDFR | 639 |
| Q15746 | TLSEDDLK | 640 |

TABLE 14-continued

| | | |
|---|---|---|
| Q15746 | TVSEEER | 641 |
| Q15746 | VHSPQQVDFR | 642 |
| Q15746 | VPPPKPATPDFR | 643 |
| Q15746 | LPAENGSSSAETLNAK | 644 |
| Q15746 | GHAGTTDNEK | 645 |
| Q15746 | SESQGTAPAFK | 646 |
| Q15746 | LQDVHVAEGK | 647 |
| Q15746 | ALPEDR | 648 |
| Q15746 | SSLPPVLGTESDATVK | 649 |
| Q15746 | AGESVELFGK | 650 |
| Q15746 | VENSENGSK | 651 |
| Q15746 | LTILAAR | 652 |
| Q15746 | STSFNVQDLLPDHEYK | 653 |
| Q15746 | DEVEVSDDDEK | 654 |
| Q15746 | EPEVDYR | 655 |
| Q15746 | TVTINTEQK | 656 |
| Q15746 | VSDFYDIEER | 657 |
| Q15746 | IIDEDFELTER | 658 |
| Q15746 | QISEGVEYIHK | 659 |
| Q15746 | LIDFGLAR | 660 |
| Q15746 | LENAGSLK | 661 |
| Q15746 | DFISNLLK | 662 |
| Q15746 | TGNAVR | 663 |
| Q15746 | SSTGSPTSPLNAEK | 664 |
| Q15746 | DLEVVEGSAAR | 665 |
| Q15746 | IEGYPDPEVVWFK | 666 |
| Q15746 | DDQSIR | 667 |
| Q6UWP8 | VIEGINR | 668 |
| Q6UWP8 | GLSNAER | 669 |
| Q6UWP8 | ALDGINSGITHAGR | 670 |
| Q6UWP8 | VAHEINHGIGQAGK | 671 |
| Q6UWP8 | AVQGFHTGVHQAGK | 672 |
| Q6UWP8 | LGQGVNHAADQAGK | 673 |
| Q6UWP8 | LGQGAHHAAGQAGK | 674 |
| Q6UWP8 | ELQNAHNGVNQASK | 675 |
| Q6UWP8 | LGHGVNNAAGQVGK | 676 |
| Q6UWP8 | LIHHGVHHGANQAGSEAGK | 677 |
| Q6UWP8 | FGQGVDNAAGQAGNEAGR | 678 |
| Q6UWP8 | FGQGVHHAAGQAGNEAGR | 679 |
| Q6UWP8 | FGQGAHHGLSEGWK | 680 |
| Q6UWP8 | FGQGIHHAAGQVGK | 681 |
| Q6UWP8 | FGQGAHHAAGQAGNEAGR | 682 |
| Q6UWP8 | FGQGVHHGLSEGWK | 683 |
| Q6UWP8 | FGQGVHHTAGQVGK | 684 |
| Q6UWP8 | FGQGVHHAASQFGK | 685 |
| Q6UWP8 | LGHGVHHGVNEAWK | 686 |
| Q6UWP8 | FGQGVHHAASQVGK | 687 |
| Q6UWP8 | VVQGLHHGVSQAGR | 688 |
| Q6UWP8 | EAGQFGHDIHHTAGQAGK | 689 |
| Q6UWP8 | EGDIAVHGVQPGVHEAGK | 690 |
| Q6UWP8 | EAGQFGQGVHHTLEQAGK | 691 |
| Q96IU4 | INAANYASVK | 692 |
| Q96IU4 | QLPNHR | 693 |
| Q96IU4 | EGTIQVQGQALFFR | 694 |
| Q96IU4 | EALPGSGQAR | 695 |
| Q96IU4 | FSVLLLHGIR | 696 |
| Q96IU4 | FSSETWQNLGTLHR | 697 |
| Q96IU4 | AVAIDLPGLGHSK | 698 |

TABLE 15

Rule-In TBI Biomarkers - Unsupervised Analysis

| Unique Protein | Abbreviated Name | Descriptor | UniProt Primary Accession Number | SEQ ID NO: |
|---|---|---|---|---|
| | CAND1 | CAND1_HUMAN | Q86VP6 | |
| | SYEP | SYEP_HUMAN | P07814 | |
| | GLO2 | GLO2_HUMAN | Q16775 | |
| | DIAP1 | DIAP1_HUMAN | O60610 | |
| | DYL1 | DYL1_HUMAN | P63167 | |
| | PSA | PSA_HUMAN | P55786 | |
| | EPHB4 | EPHB4_HUMAN | P54760 | |
| | PLOD1 | PLOD1_HUMAN | Q02809 | |
| | FBLN3 | FBLN3_HUMAN | Q12805 | |
| | HV103 | HV103_HUMAN | A0A0C4DH29 | |

TABLE 15-continued

| | | | |
|---|---|---|---|
| | IGHD | IGHD_HUMAN | P01880 |
| | THIM | THIM_HUMAN | P42765 |
| | IGHA2 | IGHA2_HUMAN | P01877 |
| | KV105 | KV105_HUMAN | P01602 |
| | MASP2 | MASP2_HUMAN | O00187 |

| Protein | Peptide Sequence | |
|---|---|---|
| A0A0C4DH29 | QAPGQR | 699 |
| O00187 | WPEPVFGR | 700 |
| O00187 | LASPGFPGEYANDQER | 701 |
| O00187 | WTLTAPPGYR | 702 |
| O00187 | DTFYSLGSSLDITFR | 703 |
| O00187 | AGYVLHR | 704 |
| O00187 | SGELSSPEYPRPYPK | 705 |
| O00187 | SNTVTITFVTDESGDHTGWK | 706 |
| O00187 | VEYITGPGVTTYK | 707 |
| O00187 | IYGGQK | 708 |
| O00187 | HDASALDIR | 709 |
| O00187 | TDDIGTASGWGLTQR | 710 |
| O00187 | GDSGGALVFLDSETER | 711 |
| O00187 | VINYIPWIENIISDF | 712 |
| O60610 | SPDELPSAGGDGGK | 713 |
| O60610 | EKPNSAHR | 714 |
| O60610 | EETAGSYDSR | 715 |
| O60610 | FQPLLDGLK | 716 |
| O60610 | SGTTIALK | 717 |
| O60610 | LGLHQVLQDLR | 718 |
| O60610 | VQLNVFDEQGEEDSYDLK | 719 |
| O60610 | AEPHFLSILQHLLLVR | 720 |
| O60610 | NDYEARPQYYK | 721 |
| O60610 | NGADPDFK | 722 |
| O60610 | LQDLQGEK | 723 |
| O60610 | DALHSEK | 724 |
| O60610 | QQIATEK | 725 |
| O60610 | QDLEAEVSQLTGEVAK | 726 |
| O60610 | LYKPEVQLR | 727 |
| O60610 | RPNWSK | 728 |
| O60610 | FENNELFAK | 729 |
| O60610 | LTLTFSAQTK | 730 |
| O60610 | DQEGGEEK | 731 |
| O60610 | TAQNLSIFLGSFR | 732 |
| O60610 | LNAILFK | 733 |
| O60610 | FPDELAHVEK | 734 |
| O60610 | VSAENLQK | 735 |
| O60610 | QISDVER | 736 |
| O60610 | DVQNFPAATDEK | 737 |
| O60610 | DAQEQYNK | 738 |
| O60610 | ELGEYFLFDPK | 739 |
| O60610 | NSETFPTILEEAK | 740 |
| P01602 | VPAQLLGLLLLWLPGAK | 741 |
| P01602 | ASQSISSWLAWYQQKPGK | 742 |
| P01880 | EVNTSGFAPARPPPQPR | 743 |
| P07814 | DDVSISVEEGK | 744 |
| P07814 | ENILHVSENVIFTDVNSILR | 745 |
| P07814 | GNAAWQEQLK | 746 |
| P07814 | APVHVK | 747 |
| P07814 | WFGFLEAQQAFQSVGTK | 748 |
| P07814 | WDVSTTK | 749 |
| P07814 | FPPEASGYLHIGHAK | 750 |
| P07814 | AALLNQHYQVNFK | 751 |
| P07814 | IQPHPR | 752 |
| P07814 | TTEYHDR | 753 |
| P07814 | DEQFYWIIEALGIR | 754 |
| P07814 | KPYIWEYSR | 755 |
| P07814 | LNLNNTVLSK | 756 |
| P07814 | LTWFVNEGLVDGWDDPR | 757 |
| P07814 | QFIAAQGSSR | 758 |
| P07814 | IWAFNK | 759 |
| P07814 | VIDPVAPR | 760 |
| P07814 | YVALLK | 761 |
| P07814 | NPEVGLKPVWYSPK | 762 |
| P07814 | IISLDAK | 763 |
| P07814 | LNLENK | 764 |
| P07814 | GDIIQLQR | 765 |
| P07814 | NETSAPFK | 766 |
| P07814 | VAVQGDVVR | 767 |
| P07814 | EDVDAAVK | 768 |
| P07814 | QLLSLK | 769 |
| P07814 | SLYDEVAAQGEVVR | 770 |

TABLE 15-continued

| | | |
|---|---|---|
| P07814 | EYIPGQPPLSQSSDSSPTR | 771 |
| P07814 | NSEPAGLETPEAK | 772 |
| P07814 | VASQGEVVR | 773 |
| P07814 | DQVDIAVQELLQLK | 774 |
| P07814 | SLIGVEYKPVSATGAEDK | 775 |
| P07814 | QNKPQK | 776 |
| P07814 | QNDGQR | 777 |
| P07814 | NQGGGLSSSGAGEGQGPK | 778 |
| P07814 | EENLADWYSQVITK | 779 |
| P07814 | DFFDAEIK | 780 |
| P07814 | THVADFAPEVAWVTR | 781 |
| P07814 | WVQSHR | 782 |
| P07814 | HPQPFLR | 783 |
| P07814 | FAGGDYTTTIEAFISASGR | 784 |
| P07814 | AIQGGTSHHLGQNFSK | 785 |
| P07814 | QFAYQNSWGLTTR | 786 |
| P07814 | EALIAK | 787 |
| P07814 | LLSVNIR | 788 |
| P07814 | DNYSPGWK | 789 |
| P07814 | FNHWELK | 790 |
| P07814 | LTVAENEAETK | 791 |
| P07814 | LQAILEDIQVTLFTR | 792 |
| P07814 | YYTLFGR | 793 |
| P42765 | GVFVVAAK | 794 |
| P42765 | TPFGAYGGLLK | 795 |
| P42765 | DFTATDLSEFAAK | 796 |
| P42765 | ETPALTINR | 797 |
| P42765 | YALOSQQR | 798 |
| P42765 | HNFTPLAR | 799 |
| P42765 | SLDLDISK | 800 |
| P42765 | TNVNGGAIALGHPLGGSGSR | 801 |
| P42765 | ITAHLVHELR | 802 |
| P54760 | LETADLK | 803 |
| P54760 | WVTFPQVDGQWEELSGLDEEQHSVR | 804 |
| P54760 | APGQAHWLR | 805 |
| P54760 | TGWVPR | 806 |
| P54760 | GAVHVYATLR | 807 |
| P54760 | VDTVAAEHLTR | 808 |
| P54760 | RPGAEATGK | 809 |
| P54760 | LGPLSK | 810 |
| P54760 | FPETVPR | 811 |
| P54760 | LNGSSLHLEWSAPLESGGR | 812 |
| P54760 | EDLTYALR | 813 |
| P54760 | DLVEPWVVVR | 814 |
| P54760 | EVPPAVSDIR | 815 |
| P54760 | SSPSSLSLAWAVPR | 816 |
| P54760 | APSGAVLDYEVK | 817 |
| P54760 | GAEGPSSVR | 818 |
| P54760 | GASYLVQVR | 819 |
| P54760 | SEAGYGPFGQEHHSQTQLDESEGWR | 820 |
| P54760 | EAEYSDK | 821 |
| P54760 | HGQYLIGHGTK | 822 |
| P54760 | EIDVSYVK | 823 |
| P54760 | GGYTER | 824 |
| P54760 | FLEENSSDPTYTSSLGGK | 825 |
| P54760 | FPQVVSALDK | 826 |
| P54760 | ENGGASHPLLDQR | 827 |
| P54760 | QPHYSAFGSVGEWLR | 828 |
| P54760 | SQAKPGTPGGTGGPAPQY | 829 |
| P55786 | NVKPDQWVK | 830 |
| P55786 | LNLGTVGFYR | 831 |
| P55786 | DLSLPPVDR | 832 |
| P55786 | LGLQNDLFSLAR | 833 |
| P55786 | AGIISTVEVLK | 834 |
| P55786 | DVFSPIGER | 835 |
| P55786 | LGWDPKPGEGHLDALLR | 836 |
| P55786 | GLVLGK | 837 |
| P55786 | ATLEEAR | 838 |
| P55786 | DHVEGK | 839 |
| P55786 | QILSADLR | 840 |
| P55786 | SPVYLTVLK | 841 |
| P55786 | VLGATLLPDLIQK | 842 |
| P55786 | DNWEELYNR | 843 |
| P55786 | YQGGFLISR | 844 |
| P55786 | LSVEGFAVDK | 845 |
| P55786 | AFFESHPAPSAER | 846 |
| P55786 | DAESIHQYLLQR | 847 |
| P63167 | DIAAHIK | 848 |
| Q02809 | ETEGFR | 849 |
| Q02809 | SAQFFNYK | 850 |

TABLE 15-continued

| | | |
|---|---|---|
| Q02809 | IQALGLGEDWNVEK | 851 |
| Q02809 | GTSAGGGQK | 852 |
| Q02809 | EDLVILFADSYDVLFASGPR | 853 |
| Q02809 | SQVVFSAEELIYPDR | 854 |
| Q02809 | YPVVSDGK | 855 |
| Q02809 | FLGSGGFIGYAPNLSK | 856 |
| Q02809 | LVAEWEGQDSDSDQLFYTK | 857 |
| Q02809 | IFLDPEK | 858 |
| Q02809 | EQINITLDHR | 859 |
| Q02809 | IFQNLDGALDEVVLK | 860 |
| Q02809 | NLAYDTLPVLIHGNGPTK | 861 |
| Q02809 | LQLNYLGNYIPR | 862 |
| Q02809 | LHYPQK | 863 |
| Q02809 | LFIHNHEQHHK | 864 |
| Q02809 | AQVEEFLAQHGSEYQSVK | 865 |
| Q02809 | LLIQQNK | 866 |
| Q02809 | LWSNFWGALSADGYYAR | 867 |
| Q02809 | SEDYVDIVQGR | 868 |
| Q02809 | VGVWNVPYISNIYLIK | 869 |
| Q02809 | GELQSSDLFHHSK | 870 |
| Q02809 | HTLGHLLSLDSYR | 871 |
| Q02809 | TTHLHNDLWEVFSNPEDWK | 872 |
| Q02809 | YIHQNYTK | 873 |
| Q02809 | LYPGYYTR | 874 |
| Q02809 | AQFDLAFVVR | 875 |
| Q02809 | LTHYHEGLPTTR | 876 |
| Q02809 | YIAVSFVDP | 877 |
| Q02809 | GDAKPEDNLLVLTVATK | 878 |
| Q12805 | NNFVIR | 879 |
| Q12805 | NPADPQR | 880 |
| Q12805 | IPSNPSHR | 881 |
| Q12805 | ELPQSIVYK | 882 |
| Q12805 | SVPSDIFQIQATTIYANTINTFR | 883 |
| Q12805 | SGNENGEFYLR | 884 |
| Q12805 | LTIIVGPFSF | 885 |
| Q16775 | EAAIVDPVQPQK | 886 |
| Q16775 | LTTVLTTHHHWDHAGGNEK | 887 |
| Q16775 | LESGLK | 888 |
| Q16775 | VYGGDDR | 889 |
| Q16775 | IGALTHK | 890 |
| Q16775 | ITHLSTLQVGSLNVK | 891 |
| Q16775 | ALLEVLGR | 892 |
| Q16775 | HVEPGNAAIR | 893 |
| Q86VP6 | LDDDSER | 894 |
| Q86VP6 | DISSIGLK | 895 |
| Q86VP6 | LTSAIAK | 896 |
| Q86VP6 | IGEYLEK | 897 |
| Q86VP6 | TVSPALISR | 898 |
| Q86VP6 | ADVFHAYLSLLK | 899 |
| Q86VP6 | ITSEALLVTQQLVK | 900 |
| Q86VP6 | ALTLIAGSPLK | 901 |
| Q86VP6 | IDLRPVLGEGVPILASFLR | 902 |
| Q86VP6 | LGTLSALDILIK | 903 |
| Q86VP6 | VYPSSLSK | 904 |
| Q86VP6 | ISGSILNELIGLVR | 905 |
| Q86VP6 | QSYYSIAK | 906 |
| Q86VP6 | EGPAVVGQFIQDVK | 907 |
| Q86VP6 | STDSIR | 908 |
| Q86VP6 | LLALLSLGEVGHHIDLSGQLELK | 909 |
| Q86VP6 | SVILEAFSSPSEEVK | 910 |
| Q86VP6 | QYLLLHSLK | 911 |
| Q86VP6 | EIISSASVVGLKPYVENIWALLLK | 912 |
| Q86VP6 | LTLIDPETLLPR | 913 |
| Q86VP6 | GYLISGSSYAR | 914 |
| Q86VP6 | SSVVTAVK | 915 |
| Q86VP6 | FTISDHPQPIDPLLK | 916 |
| Q86VP6 | TLEDPDLNVR | 917 |
| Q86VP6 | VALVTFNSAAHNKPSLIR | 918 |
| Q86VP6 | DLLDTVLPHLYNETK | 919 |
| Q86VP6 | HTVDDGLDIR | 920 |
| Q86VP6 | LDIFEFLNHVEDGLK | 921 |
| Q86VP6 | DHYDIK | 922 |
| Q86VP6 | LVEPLR | 923 |
| Q86VP6 | AVAALLTIPEAEK | 924 |
| Q86VP6 | VIRPLDQPSSFDATPYIK | 925 |
| Q86VP6 | AADIDQEVK | 926 |

TABLE 16

Rule-In TBI Biomarkers-Bootstrapping Analysis

| Unique Protein | Abbreviated Name | Descriptor | UniProt Primary Accession Number | SEQ ID NO: |
|---|---|---|---|---|
| | SAMP | SAMP_HUMAN | P02743 | |
| | 1433B | 1433B_HUMAN | P31946 | |
| | FIBB | FIBB_HUMAN | P02675 | |
| | RS28 | RS28_HUMAN | P62857 | |
| | TRFE | TRFE_HUMAN | P02787 | |

| Protein | Peptide Sequence | | | |
|---|---|---|---|---|
| P02675 | SQGVNDNEEGFFSAR | | | 927 |
| P02675 | GHRPLDK | | | 928 |
| P02675 | EEAPSLRPAPPPISGGGYR | | | 929 |
| P02675 | DNENVVNEYSSELEK | | | 930 |
| P02675 | HQLYIDETVNSNIPTNLR | | | 931 |
| P02675 | SILENLR | | | 932 |
| P02675 | QDGSVDFGR | | | 933 |
| P02675 | QGFGNVATNTDGK | | | 934 |
| P02675 | AHYGGFTVQNEANK | | | 935 |
| P02675 | YQISVNK | | | 936 |
| P02675 | DNDGWLTSDPR | | | 937 |
| P02675 | EDGGGWWYNR | | | 938 |
| P02675 | IRPFFPQQ | | | 939 |
| P02743 | VFVFPR | | | 940 |
| P02743 | AYSDLSR | | | 941 |
| P02743 | AYSLFSYNTQGR | | | 942 |
| P02743 | DNELLVYK | | | 943 |
| P02743 | VGEYSLYIGR | | | 944 |
| P02743 | QGYFVEAQPK | | | 945 |
| P02743 | IVLGQEQDSYGGK | | | 946 |
| P02743 | GYVIIKPLVWV | | | 947 |
| P02787 | EDPQTFYYAVAVVK | | | 948 |
| P02787 | DGAGDVAFVK | | | 949 |
| P02787 | HSTIFENLANK | | | 950 |
| P02787 | KPVDEYK | | | 951 |
| P02787 | EDLIWELLNQAQEHFGK | | | 952 |
| P02787 | EFQLFSSPHGK | | | 953 |
| P02787 | DSAHGFLK | | | 954 |
| P02787 | SASDLTWDNLK | | | 955 |
| P02787 | EGYYGYTGAFR | | | 956 |
| P02787 | HQTVPQNTGGK | | | 957 |
| P02787 | NPDPWAK | | | 958 |
| P02787 | APNHAVVTR | | | 959 |
| P02787 | YLGEEYVK | | | 960 |
| P02787 | AVGNLR | | | 961 |
| P31946 | AVTEQGHELSNEER | | | 962 |
| P31946 | YLIPNATQPESK | | | 963 |
| P31946 | YLSEVASGDNK | | | 964 |
| P31946 | QTTVSNSQQAYQEAFEISK | | | 965 |
| P31946 | TAFDEAIAELDTLNEESYK | | | 966 |
| P31946 | DNLTLWTSENQGDEGDAGEGEN | | | 967 |
| P62857 | EGDVLTLLESER | | | 968 |

TABLE 17

Rule-In Mild TBI Biomarkers-Unique

| Unique Protein | Abbreviated Name | Descriptor | UniProt Primary Accession Number | SEQ ID NO: |
|---|---|---|---|---|
| | DYL1 | DYL1_HUMAN | P63167 | |
| | FBLN3 | FBLN3_HUMAN | Q12805 | |
| | PSA | PSA_HUMAN | P55786 | |
| | HV103 | HV103_HUMAN | A0A0C4DH29 | |
| | IGHD | IGHD_HUMAN | P01880 | |

TABLE 17-continued

Rule-In Mild TBI Biomarkers-Unique

| Protein | Peptide Sequence | |
|---|---|---|
| A0A0C4DH29 | QAPGQR | 969 |
| P01880 | EVNTSGFAPARPPPQPR | 970 |
| P55786 | NVKPDQWVK | 971 |
| P55786 | LNLGTVGFYR | 972 |
| P55786 | DLSLPPVDR | 973 |
| P55786 | LGLQNDLFSLAR | 974 |
| P55786 | AGIISTVEVLK | 975 |
| P55786 | DVFSPIGER | 976 |
| P55786 | LGWDPKPGEGHLDALLR | 977 |
| P55786 | GLVLGK | 978 |
| P55786 | ATLEEAR | 979 |
| P55786 | DHVEGK | 980 |
| P55786 | QILSADLR | 981 |
| P55786 | SPVYLTVLK | 982 |
| P55786 | VLGATLLPDLIQK | 983 |
| P55786 | DNWEELYNR | 984 |
| P55786 | YQGGFLISR | 985 |
| P55786 | LSVEGFAVDK | 986 |
| P55786 | AFFESHPAPSAER | 987 |
| P55786 | DAESIHQYLLQR | 988 |
| P63167 | DIAAHIK | 989 |
| Q12805 | NNFVIR | 990 |
| Q12805 | NPADPQR | 991 |
| Q12805 | IPSNPSHR | 992 |
| Q12805 | ELPQSIVYK | 993 |
| Q12805 | SVPSDIFQIQATTIYANTINTFR | 994 |
| Q12805 | SGNENGEFYLR | 995 |
| Q12805 | LTIIVGPFSF | 996 |

TABLE 18

Rule-In Mild TBI Biomarkers-Supervised Analysis

| Unique Protein | Abbreviated Name | Descriptor | UniProt Primary Accession Number |
|---|---|---|---|
| | FCN2 | FCN2_HUMAN | Q15485 |
| | HBA | HBA_HUMAN | P69905 |
| | AHNK | AHNK_HUMAN | Q09666 |

| Protein | Peptide Sequence | |
|---|---|---|
| P69905 | VGAHAGEYGAEALER | 997 |
| P69905 | TYFPHFDLSHGSAQVK | 998 |
| P69905 | FLASVSTVLTSK | 999 |
| Q09666 | ELLLPNWQGSGSHGLTIAQR | 1000 |
| Q09666 | DDGVFVQEVTQNSPAAR | 1001 |
| Q09666 | SPEPGQTWTR | 1002 |
| Q09666 | SEDGVEGDLGETQSR | 1003 |
| Q09666 | TITVTR | 1004 |
| Q09666 | VTAYTVDVTGR | 1005 |
| Q09666 | DIDISSPEFK | 1006 |
| Q09666 | HELTEISNVDVETQSGK | 1007 |
| Q09666 | LPSGSGAASPTGSAVDIR | 1008 |
| Q09666 | AGAISASGPELQGAGHSK | 1009 |
| Q09666 | VGGSGVNVNAK | 1010 |
| Q09666 | GLDLGGR | 1011 |
| Q09666 | GGVQVPAVDISSSLGGR | 1012 |
| Q09666 | AVEVOGPSLESGDHGK | 1013 |
| Q09666 | FGVSTGR | 1014 |
| Q09666 | EGQTPK | 1015 |
| Q09666 | VSAPEVSVGHK | 1016 |
| Q09666 | GPQITGPSLEGDLGLK | 1017 |
| Q09666 | FSVSGAK | 1018 |
| Q09666 | VSAPGVQGDVK | 1019 |
| Q09666 | GPQVALK | 1020 |
| Q09666 | VDIETPNLEGTLTGPR | 1021 |
| Q09666 | LGSPSGK | 1022 |
| Q09666 | GGVDVTLPR | 1023 |
| Q09666 | VPEVDVR | 1024 |
| Q09666 | VDVSAPDVEAHGPEWNLK | 1025 |
| Q09666 | GDISISGPK | 1026 |
| Q09666 | VNVEAPDVNLEGLGGK | 1027 |
| Q09666 | GEYDVTVPK | 1028 |
| Q09666 | VDIDAPDVDVHGPDWHLK | 1029 |
| Q09666 | FSVPGFK | 1030 |
| Q09666 | AEGPEVDVNLPK | 1031 |
| Q09666 | ADVDISGPK | 1032 |
| Q09666 | IDVTAPDVSIEEPEGK | 1033 |
| Q09666 | VPDVELK | 1034 |
| Q09666 | VGVEVPDVNIEGPEGK | 1035 |
| Q09666 | GEGPEFDVNLSK | 1036 |
| Q09666 | ANVDISAPK | 1037 |
| Q09666 | VDTNAPDLSLEGPEGK | 1038 |
| Q09666 | GNVDISAPK | 1039 |
| Q09666 | APDVEGQGLDWSLK | 1040 |
| Q09666 | GEGPEVDVNLPK | 1041 |
| Q09666 | ADVVVSGPK | 1042 |
| Q09666 | VDIEAPDVSLEGPEGK | 1043 |
| Q09666 | GDVDVSVPK | 1044 |
| Q09666 | VPDVEIK | 1045 |
| Q09666 | EVDVNLPK | 1046 |
| Q09666 | ADIDVSGPK | 1047 |
| Q09666 | VDVEVPDVSLEGPEGK | 1048 |
| Q09666 | VDISAPDVDVHGPDWHLK | 1049 |
| Q09666 | GEGPEVDVK | 1050 |
| Q09666 | ADVDVSGPK | 1051 |
| Q09666 | ISIPDVGLHLK | 1052 |
| Q09666 | GDYDVTVPK | 1053 |
| Q09666 | VEGEIK | 1054 |
| Q09666 | APDVDIK | 1055 |
| Q09666 | VDINAPDVEVHGPDWHLK | 1056 |
| Q09666 | ADLGVSGPK | 1057 |
| Q09666 | VDIDVPDVNLEAPEGK | 1058 |
| Q09666 | TDVDVSLPK | 1059 |
| Q09666 | VEGDLK | 1060 |
| Q09666 | GPEIDVK | 1061 |
| Q09666 | VDIDAPDVEVHDPDWHLK | 1062 |

TABLE 18-continued

Rule-In Mild TBI Biomarkers-Supervised Analysis

| | | |
|---|---|---|
| Q09666 | ADIDVSGPSVDTDAPDLDIEGPEGK | 1063 |
| Q09666 | GEIDASVPELEGDLR | 1064 |
| Q09666 | GDADVSVPK | 1065 |
| Q09666 | GDVDVSLPK | 1066 |
| Q09666 | VPDVDIR | 1067 |
| Q09666 | GDVDVSAPK | 1068 |
| Q09666 | GPELDVK | 1069 |
| Q09666 | GEVDVDVPK | 1070 |
| Q09666 | GPHVDVSGPDIDIEGPEGK | 1071 |
| Q09666 | GDVDVSVPEVEGK | 1072 |
| Q09666 | VDVNAPDVQAPDWHLK | 1073 |
| Q09666 | VDIEGPDVNIEGPEGK | 1074 |
| Q09666 | GPEVDIK | 1075 |
| Q09666 | VDINAPDVGVQGPDWHLK | 1076 |
| Q09666 | GEGPDGDVK | 1077 |
| Q09666 | GEGPDVDVNLPK | 1078 |
| Q09666 | GDVDVTGPK | 1079 |
| Q09666 | GPEVDLK | 1080 |
| Q09666 | VDIDVPDVNVQGPDWHLK | 1081 |
| Q09666 | VDVEGPDVNIEGPEGK | 1082 |
| Q09666 | GDVDISLPK | 1083 |
| Q09666 | GPEVDIR | 1084 |
| Q09666 | GPQVDIDVPDVGVQGPDWHLK | 1085 |
| Q09666 | ADLDVSGPK | 1086 |
| Q09666 | VDIDVPDVNIEGPEGK | 1087 |
| Q09666 | VDINAPDVDVQGPDWHLK | 1088 |
| Q09666 | VDVDVPDVNIEGPDAK | 1089 |
| Q09666 | GEVDVSLANVEGDLK | 1090 |
| Q09666 | GPALDIK | 1091 |
| Q09666 | IDVDAPDIDIHGPDAK | 1092 |
| Q09666 | GDVDVSGPK | 1093 |
| Q09666 | APSLDIK | 1094 |
| Q09666 | GPEVDVSGPK | 1095 |
| Q09666 | LNIEGK | 1096 |
| Q09666 | FNFSGSK | 1097 |
| Q09666 | VQTPEVDVK | 1098 |
| Q09666 | KPDIDITGPK | 1099 |
| Q09666 | VDINAPDVEVQGK | 1100 |
| Q09666 | GDLDIAGPNLEGDFK | 1101 |
| Q09666 | APEVNLNAPDVDVHGPDWNLK | 1102 |
| Q09666 | AEGPDVAVDLPK | 1103 |
| Q09666 | VDINAPDVDVHGPDWHLK | 1104 |
| Q09666 | GEGPEVDVTLPK | 1105 |
| Q09666 | ADIDISGPNVDVDVPDVNIEGPDAK | 1106 |
| Q09666 | GDVVVSLPK | 1107 |
| Q09666 | VDIDTPDINIEGSEGK | 1108 |
| Q09666 | VDINAPDVDVR | 1109 |
| Q09666 | GPDWHLK | 1110 |
| Q09666 | APEVDIK | 1111 |
| Q09666 | VDIDTPDIDIHGPEGK | 1112 |
| Q09666 | VDIDVPDVDVQGPDWHLK | 1113 |
| Q09666 | VDVVPDVNIEGPDAK | 1114 |
| Q09666 | GEGPDVDVTLPK | 1115 |
| Q09666 | ADIESGPK | 1116 |
| Q09666 | VDIDAPDVSIEGPDAK | 1117 |
| Q09666 | GPSLDIDTPDVNIEGPEGK | 1118 |
| Q09666 | GPEVDIEGPEGK | 1119 |
| Q09666 | VGIDTPDIDIHGPEGK | 1120 |
| Q09666 | GDVDVTLPK | 1121 |
| Q09666 | GPEADIK | 1122 |
| Q09666 | VDINTPDVDVHGPDWHLK | 1123 |
| Q09666 | GEGPDVDVSLPK | 1124 |
| Q09666 | VDVDIPDVNIEGPDAK | 1125 |
| Q09666 | ISIPDVDLDLK | 1126 |
| Q09666 | GDFDVSVPK | 1127 |
| Q09666 | VEGTLK | 1128 |
| Q09666 | LDFEGPDAK | 1129 |
| Q09666 | LSGPSLK | 1130 |
| Q09666 | VTAPDVDLHLK | 1131 |
| Q09666 | IGFSGPK | 1132 |
| Q09666 | LEGGEVDLK | 1133 |
| Q09666 | FGFGAK | 1134 |
| Q09666 | SPSLDVTVPEAELNLETPEISVGGK | 1135 |
| Q09666 | QGFDLNVPGGEIDASLK | 1136 |
| Q09666 | APDVDVNIAGPDAALK | 1137 |
| Q09666 | AEAPLPSPK | 1138 |
| Q09666 | LEGELQAPDLELSLPAIHVEGLDIK | 1139 |
| Q09666 | IEGDLK | 1140 |
| Q09666 | VQANLGAPDINIEGLDAK | 1141 |
| Q09666 | TPSFGISAPQVSIPDVNVNLK | 1142 |
| Q09666 | GDVPSVGLEGPDVDLQGPEAK | 1143 |
| Q09666 | IGIPGVK | 1144 |
| Q09666 | LEGPDVSLK | 1145 |
| Q09666 | VSGPDLDLNLK | 1146 |
| Q09666 | VHAPGLNLSGVGGK | 1147 |
| Q09666 | VPGIDATTK | 1148 |
| Q09666 | LNVGAPDVTLR | 1149 |
| Q09666 | GPSLQGDLAVSGDIK | 1150 |
| Q09666 | VSVGAPDLSLEASEGSIK | 1151 |
| Q09666 | LPQFGISTPGSDLHVNAK | 1152 |
| Q09666 | GPQVSGELK | 1153 |
| Q09666 | GPGVDVNLK | 1154 |
| Q09666 | ISAPNVDFNLEGPK | 1155 |
| Q09666 | GSLGATGEIK | 1156 |
| Q09666 | LPTGQISGPEIK | 1157 |
| Q09666 | GSEVGFHGAAAPDISVK | 1158 |
| Q09666 | GGADVSGGVSAPDISLGEGHLSVK | 1159 |
| Q09666 | GSGGEWK | 1160 |
| Q09666 | GPQVSSALNLDTSK | 1161 |
| Q09666 | FAGGLHFSGPK | 1162 |
| Q09666 | VEGGVK | 1163 |
| Q09666 | FTFSGR | 1164 |
| Q09666 | AEASIQAGAGDGEWEESEVK | 1165 |
| Q09666 | FNFSKPK | 1166 |
| Q09666 | GGVTGSPEASISGSK | 1167 |
| Q09666 | ASLGSLEGEAEAEASSPK | 1168 |
| Q09666 | SNSFSDER | 1169 |
| Q09666 | EFSGPSTPTGTLEFEGGEVSLEGGK | 1170 |
| Q09666 | FGTFGGLGSK | 1171 |
| Q09666 | GHYEVTGSDDETGK | 1172 |
| Q09666 | LQGSGVSLASK | 1173 |
| Q09666 | LSSSSSNDSGNK | 1174 |
| Q09666 | VGIQLPEVELSVSTK | 1175 |
| Q15485 | VDGSVDFYR | 1176 |
| Q15485 | DWATYK | 1177 |
| Q15485 | LGEFWLGNDNIHALTAQGTSELR | 1178 |
| Q15485 | VDLVDFEDNYQFAK | 1179 |
| Q15485 | GTHGSFANGINWK | 1180 |
| Q15485 | GYNYSYK | 1181 |
| Q15485 | GEAGTNGK | 1182 |

TABLE 19

Rule-In Mild TBI Biomarkers-Unsupervised Analysis

| Unique Protein | Abbreviated Name | Descriptor | UniProt Primary Accession Number | SEQ ID NO: |
|---|---|---|---|---|
| | HV103 | HV103_HUMAN | A0A0C4DH29 | |
| | IGHD | IGHD_HUMAN | P01880 | |
| | THIM | THIM_HUMAN | P42765 | |
| | IGHA2 | IGHA2_HUMAN | P01877 | |
| | KV105 | KV105_HUMAN | P01602 | |
| | MASP2 | MASP2_HUMAN | O00187 | |
| | DIAP1 | DIAP1_HUMAN | O60610 | |

TABLE 19-continued

Rule-In Mild TBI Biomarkers-Unsupervised Analysis

| | | | |
|---|---|---|---|
| | PLOD1 | PLOD1_HUMAN | Q02809 |
| | EPHB4 | EPHB4_HUMAN | P54760 |
| | FBLN3 | FBLN3_HUMAN | Q12805 |
| | DYL1 | DYL1_HUMAN | P63167 |
| | PSA | PSA_HUMAN | P55786 |

| Protein | Peptide Sequence | |
|---|---|---|
| A0A0C4DH29 | QAPGQR | 1183 |
| O00187 | WPEPVFGR | 1184 |
| O00187 | LASPGFPGEYANDQER | 1185 |
| O00187 | WTLTAPPGYR | 1186 |
| O00187 | DTFYSLGSSLDITFR | 1187 |
| O00187 | AGYVLHR | 1188 |
| O00187 | SGELSSPEYPRPYPK | 1189 |
| O00187 | SNTVTITFVTDESGDHTGWK | 1190 |
| O00187 | VEYITGPGVTTYK | 1191 |
| O00187 | IYGGQK | 1192 |
| O00187 | HDASALDIR | 1193 |
| O00187 | TDDIGTASGWGLTQR | 1194 |
| O00187 | GDSGGALVFLDSETER | 1195 |
| O00187 | VINYIPWIENIISDF | 1196 |
| O60610 | SPDELPSAGGDGGK | 1197 |
| O60610 | EKPNSAHR | 1198 |
| O60610 | EETAGSYDSR | 1199 |
| O60610 | FQPLLDGLK | 1200 |
| O60610 | SGTTIALK | 1201 |
| O60610 | LGLHQVLQDLR | 1202 |
| O60610 | VQLNVFDEQGEEDSYDLK | 1203 |
| O60610 | AEPHFLSILQHLLLVR | 1204 |
| O60610 | NDYEARPQYYK | 1205 |
| O60610 | NGADPDFK | 1206 |
| O60610 | LQDLQGEK | 1207 |
| O60610 | DALHSEK | 1208 |
| O60610 | QQIATEK | 1209 |
| O60610 | QDLEAEVSQLTGEVAK | 1210 |
| O60610 | LYKPEVQLR | 1211 |
| O60610 | RPNWSK | 1212 |
| O60610 | FENNELFAK | 1213 |
| O60610 | LTLTFSAQTK | 1214 |
| O60610 | DQEGGEEK | 1215 |
| O60610 | TAQNLSIFLGSFR | 1216 |
| O60610 | LNAILFK | 1217 |
| O60610 | FPDELAHVEK | 1218 |
| O60610 | VSAENLQK | 1219 |
| O60610 | QISDVER | 1220 |
| O60610 | DVQNFPAATDEK | 1221 |
| O60610 | DAQEQYNK | 1222 |
| O60610 | ELGEYFLFDPK | 1223 |
| O60610 | NSETFPTILEEAK | 1224 |
| P01602 | VPAQLLGLLLLWLPGAK | 1225 |
| P01602 | ASQSISSWLAWYQQKPGK | 1226 |
| P01880 | EVNTSGFAPARPPPQPR | 1227 |
| P42765 | GVFVVAAK | 1228 |
| P42765 | TPFGAYGGLLK | 1229 |
| P42765 | DFTATDLSEFAAK | 1230 |
| P42765 | ETPALTINR | 1231 |
| P42765 | YALQSQQR | 1232 |
| P42765 | HNFTPLAR | 1233 |
| P42765 | SLDLDISK | 1234 |
| P42765 | TNVNGGAIALGHPLGGSGSR | 1235 |
| P42765 | ITAHLVHELR | 1236 |
| P54760 | LETADLK | 1237 |
| P54760 | WVTFPQVDGQWEELSGLDEEQHSVR | 1238 |
| P54760 | APGQAHWLR | 1239 |
| P54760 | TGWVPR | 1240 |
| P54760 | GAVHVYATLR | 1241 |
| P54760 | VDTVAAEHLTR | 1242 |
| P54760 | RPGAEATGK | 1243 |
| P54760 | LGPLSK | 1244 |
| P54760 | FPETVPR | 1245 |
| P54760 | LNGSSLHLEWSAPLESGGR | 1246 |
| P54760 | EDLTYALR | 1247 |
| P54760 | DLVEPWVVVR | 1248 |
| P54760 | EVPPAVSDIR | 1249 |
| P54760 | SSPSSLSLAWAVPR | 1250 |
| P54760 | APSGAVLDYEVK | 1251 |
| P54760 | GAEGPSSVR | 1252 |

TABLE 19-continued

Rule-In Mild TBI Biomarkers-Unsupervised Analysis

| | | |
|---|---|---|
| P54760 | GASYLVQVR | 1253 |
| P54760 | SEAGYGPFGQEHHSQTQLDESEGWR | 1254 |
| P54760 | EAEYSDK | 1255 |
| P54760 | HGQYLIGHGTK | 1256 |
| P54760 | EIDVSYVK | 1257 |
| P54760 | GGYTER | 1258 |
| P54760 | FLEENSSDPTYTSSLGGK | 1259 |
| P54760 | FPQVVSALDK | 1260 |
| P54760 | ENGGASHPLLDQR | 1261 |
| P54760 | QPHYSAFGSVGEWLR | 1262 |
| P54760 | SQAKPGTPGGTGGPAPQY | 1263 |
| P55786 | NVKPDQWVK | 1264 |
| P55786 | LNLGTVGFYR | 1265 |
| P55786 | DLSLPPVDR | 1266 |
| P55786 | LGLQNDLFSLAR | 1267 |
| P55786 | AGIISTVEVLK | 1268 |
| P55786 | DVFSPIGER | 1269 |
| P55786 | LGWDPKPGEGHLDALLR | 1270 |
| P55786 | GLVLGK | 1271 |
| P55786 | ATLEEAR | 1272 |
| P55786 | DHVEGK | 1273 |
| P55786 | QILSADLR | 1274 |
| P55786 | SPVYLTVLK | 1275 |
| P55786 | VLGATLLPDLIQK | 1276 |
| P55786 | DNWEELYNR | 1277 |
| P55786 | YQGGFLISR | 1278 |
| P55786 | LSVEGFAVDK | 1279 |
| P55786 | AFFESHPAPSAER | 1280 |
| P55786 | DAESIHQYLLQR | 1281 |
| P63167 | DIAAHIK | 1282 |
| Q02809 | ETEGFR | 1283 |
| Q02809 | SAQFFNYK | 1284 |
| Q02809 | IQALGLGEDWNVEK | 1285 |
| Q02809 | GTSAGGGQK | 1286 |
| Q02809 | EDLVILFADSYDVLFASGPR | 1287 |
| Q02809 | SQVVFSAEELIYPDR | 1288 |
| Q02809 | YPVVSDGK | 1289 |
| Q02809 | FLGSGGFIGYAPNLSK | 1290 |
| Q02809 | LVAEWEGQDSDSDQLFYTK | 1291 |
| Q02809 | IFLDPEK | 1292 |
| Q02809 | EQINITLDHR | 1293 |
| Q02809 | IFQNLDGALDEVVLK | 1294 |
| Q02809 | NLAYDTLPVLIHGNGPTK | 1295 |
| Q02809 | LOLNYLGNYIPR | 1296 |
| Q02809 | LHYPQK | 1297 |
| Q02809 | LFIHNHEQHHK | 1298 |
| Q02809 | AQVEEFLAQHGSEYQSVK | 1299 |
| Q02809 | LLIQQNK | 1300 |
| Q02809 | LWSNFWGALSADGYYAR | 1301 |
| Q02809 | SEDYVDIVQGR | 1302 |
| Q02809 | VGVWNVPYISNIYLIK | 1303 |
| Q02809 | GELQSSDLFHHSK | 1304 |
| Q02809 | HTLGHLLSLDSYR | 1305 |
| Q02809 | TTHLHNDLWEVFSNPEDWK | 1306 |
| Q02809 | YIHQNYTK | 1307 |
| Q02809 | LYPGYYTR | 1308 |
| Q02809 | AQFDLAFVVR | 1309 |
| Q02809 | LTHYHEGLPTTR | 1310 |
| Q02809 | YIAVSFVDP | 1311 |
| Q02809 | GDAKPEDNLLVLTVATK | 1312 |
| Q12805 | NNFVIR | 1313 |
| Q12805 | NPADPQR | 1314 |
| Q12805 | IPSNPSHR | 1315 |
| Q12805 | ELPQSIVYK | 1316 |
| Q12805 | SVPSDIFQIQATTIYANTINTFR | 1317 |
| Q12805 | SGNENGEFYLR | 1318 |
| Q12805 | LTIIVGPFSF | 1319 |

TABLE 20

| | Rule-In Severe TBI Biomarkers | | | |
|---|---|---|---|---|
| Unique Protein | Abbreviated Name | Descriptor | UniProt Primary Accession Number | SEQ ID NO: |
| | CAND1 | CAND1_HUMAN | Q86VP6 | |
| | GLO2 | GLO2_HUMAN | Q16775 | |
| | ERAP1 | ERAP1_HUMAN | Q9NZ08 | |
| | SYYC | SYYC_HUMAN | P54577 | |
| | C1RL | C1RL_HUMAN | Q9NZP8 | |
| | ATPG | ATPG_HUMAN | P36542 | |

| Protein | Peptide Sequence | SEQ ID NO: |
|---|---|---|
| P36542 | AGVAGLSAWTLQPQWIQVR | 1320 |
| P36542 | IYGLGSLALYEK | 1321 |
| P36542 | HLLIGVSSDR | 1322 |
| P36542 | SEVATLTAAGK | 1323 |
| P36542 | THSDQFLVAFK | 1324 |
| P36542 | SVISYK | 1325 |
| P36542 | ESTTSEQSAR | 1326 |
| P36542 | LTLTFNR | 1327 |
| P36542 | QAVITK | 1328 |
| P36542 | ELIEIISGAAALD | 1329 |
| P54577 | LHLITR | 1330 |
| P54577 | NLQEVLGEEK | 1331 |
| P54577 | IADFLK | 1332 |
| P54577 | APWELLELR | 1333 |
| P54577 | VSYYENVIK | 1334 |
| P54577 | GTDYQLSK | 1335 |
| P54577 | EYTLDVYR | 1336 |
| P54577 | LSSVVTQHDSK | 1337 |
| P54577 | AGAEVVK | 1338 |
| P54577 | QVEHPLLSGLLYPGLQALDEEYLK | 1339 |
| P54577 | VDAQFGGIDQR | 1340 |
| P54577 | IFTFAEK | 1341 |
| P54577 | YLPALGYSK | 1342 |
| P54577 | HVLFPLK | 1343 |
| P54577 | SEFVILR | 1344 |
| P54577 | TYTAYVDLEK | 1345 |
| P54577 | DFAAEVVHPGDLK | 1346 |
| P54577 | NSVEVALNK | 1347 |
| P54577 | LLDPIR | 1348 |
| P54577 | FNTPALK | 1349 |
| P54577 | LASAAYPDPSK | 1350 |
| P54577 | NSEPEEVIPSR | 1351 |
| P54577 | IITVEK | 1352 |
| P54577 | HPDADSLYVEK | 1353 |
| P54577 | IDVGEAEPR | 1354 |
| P54577 | TVVSGLVQFVPK | 1355 |
| P54577 | QVEPLDPPAGSAPGEHVFVK | 1356 |
| P54577 | GQPDEELKPK | 1357 |
| P54577 | LQADFK | 1358 |
| Q16775 | EAAIVDPVQPQK | 1359 |
| Q16775 | LTTVLTTHHHWDHAGGNEK | 1360 |
| Q16775 | LESGLK | 1361 |
| Q16775 | VYGGDDR | 1362 |
| Q16775 | IGALTHK | 1363 |
| Q16775 | ITHLSTLQVGSLNVK | 1364 |
| Q16775 | ALLEVLGR | 1365 |
| Q16775 | HVEPGNAAIR | 1366 |
| Q86VP6 | LDDDSER | 1367 |
| Q86VP6 | DISSIGLK | 1368 |
| Q86VP6 | LTSAIAK | 1369 |
| Q86VP6 | IGEYLEK | 1370 |
| Q86VP6 | TVSPALISR | 1371 |
| Q86VP6 | ADVFHAYLSLLK | 1372 |
| Q86VP6 | ITSEALLVTQQLVK | 1373 |
| Q86VP6 | ALTLIAGSPLK | 1374 |
| Q86VP6 | IDLRPVLGEGVPILASFLR | 1375 |
| Q86VP6 | LGTLSALDILIK | 1376 |
| Q86VP6 | VYPSSLSK | 1377 |
| Q86VP6 | ISGSILNELIGLVR | 1378 |
| Q86VP6 | QSYYSIAK | 1379 |
| Q86VP6 | EGPAVVGQFIQDVK | 1380 |
| Q86VP6 | STDSIR | 1381 |
| Q86VP6 | LLALLSLGEVGHHIDLSGQLELK | 1382 |
| Q86VP6 | SVILEAFSSPSEEVK | 1383 |

TABLE 20-continued

| | Rule-In Severe TBI Biomarkers | |
|---|---|---|
| Q86VP6 | QYLLLHSLK | 1384 |
| Q86VP6 | EIISSASVVGLKPYVENIWALLLK | 1385 |
| Q86VP6 | LTLIDPETLLPR | 1386 |
| Q86VP6 | GYLISGSSYAR | 1387 |
| Q86VP6 | SSVVTAVK | 1388 |
| Q86VP6 | FTISDHPQPIDPLLK | 1389 |
| Q86VP6 | TLEDPDLNVR | 1390 |
| Q86VP6 | VALVTFNSAAHNKPSLIR | 1391 |
| Q86VP6 | DLLDTVLPHLYNETK | 1392 |
| Q86VP6 | HTVDDGLDIR | 1393 |
| Q86VP6 | LDIFEFLNHVEDGLK | 1394 |
| Q86VP6 | DHYDIK | 1395 |
| Q86VP6 | LVEPLR | 1396 |
| Q86VP6 | AVAALLTIPEAEK | 1397 |
| Q86VP6 | VIRPLDQPSSFDATPYIK | 1398 |
| Q86VP6 | AADIDQEVK | 1399 |
| Q9NZ08 | SDGTPFPWNK | 1400 |
| Q9NZ08 | VEITASQPTSTIILHSHHLQISR | 1401 |
| Q9NZ08 | LSEEPLQVLEHPR | 1402 |
| Q9NZ08 | ILASTQFEPTAAR | 1403 |
| Q9NZ08 | ASFSIK | 1404 |
| Q9NZ08 | SVTVAEGLIEDHFDVTVK | 1405 |
| Q9NZ08 | VSVYAVPDK | 1406 |
| Q9NZ08 | ESALLFDAEK | 1407 |
| Q9NZ08 | VGDYFFGK | 1408 |
| Q9NZ08 | EYLSADAFK | 1409 |
| Q9NZ08 | SGIVQYLQK | 1410 |
| Q9NZ08 | SQHSSSSHWHQEGVDVK | 1411 |
| Q9NZ08 | GFPLITITVR | 1412 |
| Q9NZ08 | GSDGAPDTGYLWHVPLTFITSK | 1413 |
| Q9NZ08 | TDVLILPEEVEWIK | 1414 |
| Q9NZ08 | GTHTAVSSNDR | 1415 |
| Q9NZ08 | ASLINNAFQLVSIGK | 1416 |
| Q9NZ08 | ALDLSLYLK | 1417 |
| Q9NZ08 | QTWTDEGSVSER | 1418 |
| Q9NZ08 | YQFSLSSTEK | 1419 |
| Q9NZ08 | LQWLLDESFK | 1420 |
| Q9NZ08 | TQEFPQILTLIGR | 1421 |
| Q9NZ08 | NPVGYPLAWQFLR | 1422 |
| Q9NZ08 | GFFSSLK | 1423 |
| Q9NZ08 | ENGSQLR | 1424 |
| Q9NZ08 | VWLQSEK | 1425 |
| Q9NZP8 | GSVLLAQELPQQLTSPGYPEPYGK | 1426 |
| Q9NZP8 | GQESSTDIK | 1427 |
| Q9NZP8 | APEGFAVR | 1428 |
| Q9NZP8 | EFVSSGR | 1429 |
| Q9NZP8 | TQPSSENK | 1430 |
| Q9NZP8 | TAHLHK | 1431 |
| Q9NZP8 | GFLALYQTVAVNYSQPISEASR | 1432 |
| Q9NZP8 | GSEAINAPGDNPAK | 1433 |
| Q9NZP8 | LGNFPWQAFTSIHGR | 1434 |
| Q9NZP8 | WILTAAHTIYPK | 1435 |
| Q9NZP8 | LGNHPVHR | 1436 |
| Q9NZP8 | VVVHPDYR | 1437 |
| Q9NZP8 | VLSYVDWIK | 1438 |

TABLE 21

| | Rule-Out TBI Biomarkers | | |
|---|---|---|---|
| Unique Protein | Abbreviated Name | Descriptor | UniProt Primary Accession Number | SEQ ID NO: |
| | ACTBL | ACTBL_HUMAN | Q562R1 | |
| | ALDH2 | ALDH2_HUMAN | P05091 | |
| | ANXA5 | ANXA5_HUMAN | P08758 | |
| | CAMP | CAMP_HUMAN | P49913 | |
| | CPNE3 | CPNE3_HUMAN | O75131 | |
| | CRAC1 | CRAC1_HUMAN | Q9NQ79 | |
| | CYTC | CYTC_HUMAN | P01034 | |
| | DNPEP | DNPEP_HUMAN | Q9ULA0 | |
| | EIF3I | EIF3I_HUMAN | Q13347 | |
| | GSHB | GSHB_HUMAN | P48637 | |
| | ICAM1 | ICAM1_HUMAN | P05362 | |
| | HV323 | HV323_HUMAN | P01764 | |

TABLE 21-continued

| Rule-Out TBI Biomarkers | | |
|---|---|---|
| HNRPD | HNRPD_HUMAN | Q14103 |
| KVD33 | KVD33_HUMAN | P01593 |
| FA9 | FA9_HUMAN | P00740 |
| FHR4 | FHR4_HUMAN | Q92496 |
| FRPD1 | FRPD1_HUMAN | Q5SYB0 |
| HS90B | HS90B_HUMAN | P08238 |
| MA2A1 | MA2A1_HUMAN | Q16706 |
| PCYOX | PCYOX_HUMAN | Q9UHG3 |
| PNPH | PNPH_HUMAN | P00491 |
| PROC | PROC_HUMAN | P04070 |
| RL3 | RL3_HUMAN | P39023 |
| SH3L3 | SH3L3_HUMAN | Q9H299 |
| SRRM2 | SRRM2_HUMAN | Q9UQ35 |
| TBB1 | TBB1_HUMAN | Q9H4B7 |
| TENA | TENA_HUMAN | P24821 |
| TRAP1 | TRAP1_HUMAN | Q12931 |

| Protein | Peptide Sequence | |
|---|---|---|
| O75131 | TFIIDYYFEVVQK | 1439 |
| O75131 | FGVYDIDNK | 1441 |
| O75131 | TGRPAGK | 1442 |
| O75131 | GSITISAEEIK | 1443 |
| O75131 | SDPYLEFHK | 1444 |
| O75131 | NNLNPVWRPFK | 1445 |
| O75131 | NSGVISVK | 1446 |
| O75131 | LYGPTNFSPIINHVAR | 1447 |
| O75131 | QAIVNASR | 1448 |
| O75131 | SPLGEVAIR | 1449 |
| O75131 | QFQNAPK | 1450 |
| P00491 | NTAEWLLSHTK | 1451 |
| P00491 | LTQAQIFDYGEIPNFPR | 1452 |
| P00491 | STVPGHAGR | 1453 |
| P00491 | LVFGFLNGR | 1454 |
| P00491 | VFHLLGVDTLVVTNAAGGLNPK | 1455 |
| P00491 | DHINLPGFSGQNPLR | 1456 |
| P00491 | GPNDER | 1457 |
| P00491 | ALSTWK | 1458 |
| P00491 | VFGFSLITNK | 1459 |
| P00491 | ANHEEVLAAGK | 1460 |
| P00740 | ILNRPK | 1461 |
| P00740 | LEEFVQGNLER | 1462 |
| P00740 | EVFENTER | 1463 |
| P00740 | TTEFWK | 1464 |
| P00740 | NSADNK | 1465 |
| P00740 | LAENQK | 1466 |
| P00740 | VSVSQTSK | 1467 |
| P00740 | VVGGEDAKPGQFPWQVVLNGK | 1468 |
| P00740 | ITVVAGEHNIEETEHTEQK | 1469 |
| P00740 | IIPHHNYNAAINK | 1470 |
| P00740 | EYTNIFLK | 1471 |
| P00740 | FGSGYVSGWGR | 1472 |
| P00740 | SALVLQYLR | 1473 |
| P00740 | VPLVDR | 1474 |
| P01034 | ALDFAVGEYNK | 1475 |
| P01034 | QIVAGVNYFLDVELGR | 1476 |
| P01593 | VPAQLLGLLLLWLSGAR | 1477 |
| P01593 | LLIYDASNLETGVPSR | 1478 |
| P01764 | GLEWVSAISGSGGSTYYADSVK | 1479 |
| P04070 | AHQVLR | 1480 |
| P04070 | ANSFLEELR | 1481 |
| P04070 | EIFQNVDDTLAFWSK | 1482 |
| P04070 | SGWEGR | 1483 |
| P04070 | DTEDQEDQVDPR | 1484 |
| P04070 | GDSPWQVVLLDSK | 1485 |
| P04070 | LGEYDLR | 1486 |
| P04070 | WELDLDIK | 1487 |
| P04070 | EVFVHPNYSK | 1488 |
| P04070 | ELNQAGQETLVTGWGYHSSR | 1489 |
| P04070 | TFVLNFIK | 1490 |
| P04070 | YLDWIHGHIR | 1491 |
| P05091 | TIPIDGDFFSYTR | 1492 |
| P05091 | VAEQTPLTALYVANLIK | 1493 |
| P05091 | VAFTGSTEIGR | 1494 |
| P05091 | VIQVAAGSSNLK | 1495 |
| P05091 | TFVQEDIYDEFVER | 1496 |
| P05091 | VVGNPFDSK | 1497 |
| P05091 | TEQGPQVDETQFK | 1498 |

TABLE 21-continued

| Rule-Out TBI Biomarkers | | |
|---|---|---|
| P05091 | ILGYINTGK | 1499 |
| P05091 | TIEEVVGR | 1500 |
| P05091 | ANNSTYGLAAAVFTK | 1501 |
| P05091 | ELGEYGLQAYTEVK | 1502 |
| P05091 | AAFQLGSPWR | 1503 |
| P05362 | LLGIETPLPK | 1504 |
| P05362 | ELLLPGNNR | 1505 |
| P05362 | TFLTVYWTPER | 1506 |
| P05362 | VELAPLPSWQPVGK | 1507 |
| P05362 | ANLTVVLLR | 1508 |
| P05362 | EPAVGEPAEVTTTVLVR | 1509 |
| P05362 | LNPTVTYGNDSFSAK | 1510 |
| P05362 | ASVSVTAEDEGTQR | 1511 |
| P05362 | VTLNGVPAQPLGPR | 1512 |
| P05362 | AQLLLK | 1513 |
| P05362 | ATPEDNGR | 1514 |
| P05362 | VLYGPR | 1515 |
| P05362 | DGTFPLPIGESVTVTR | 1516 |
| P05362 | STQGEVTR | 1517 |
| P05362 | VTVNVLSPR | 1518 |
| P08238 | VVVITK | 1519 |
| P08238 | NPDDITQEEYGEFYK | 1520 |
| P08238 | ALLFIPR | 1521 |
| P08238 | FYEAFSK | 1522 |
| P08238 | LGIHEDSTNR | 1523 |
| P08238 | HLEINPDHPIVETLR | 1524 |
| P08758 | GTVTDFPGFDER | 1525 |
| P08758 | ADAETLR | 1526 |
| P08758 | GLGTDEESILTLLTSR | 1527 |
| P08758 | QEISAAFK | 1528 |
| P08758 | DLLDDLK | 1529 |
| P08758 | SELTGK | 1530 |
| P08758 | LYDAYELK | 1531 |
| P08758 | GAGTNEK | 1532 |
| P08758 | VLTEIIASR | 1533 |
| P08758 | QVYEEEYGSSLEDDVVGDTSGYYQR | 1534 |
| P08758 | DPDAGIDEAQVEQDAQALFQAGELK | 1535 |
| P08758 | WGTDEEK | 1536 |
| P08758 | FITIFGTR | 1537 |
| P08758 | ETSGNLEQLLLAVVK | 1538 |
| P08758 | GAGTDDHTLIR | 1539 |
| P08758 | SEIDLFNIR | 1540 |
| P08758 | GDTSGDYK | 1541 |
| P24821 | QSGVNATLPEENQPVVFNHVYNIK | 1542 |
| P24821 | LEELENLVSSLR | 1543 |
| P24821 | VPGDQTSTIIQELEPGVEYFIR | 1544 |
| P24821 | VFAILENK | 1545 |
| P24821 | SIPVSAR | 1546 |
| P24821 | VATYLPAPEGLK | 1547 |
| P24821 | ETSVEVEWDPLDIAFETWEIIFR | 1548 |
| P24821 | EDEGEITK | 1549 |
| P24821 | RPETSYR | 1550 |
| P24821 | QTGLAPGQEYEISLHIVK | 1551 |
| P24821 | LDAPSQIEVK | 1552 |
| P24821 | ETFTTGLDAPR | 1553 |
| P24821 | VSQTDNSITLEWR | 1554 |
| P24821 | AAIDSYR | 1555 |
| P24821 | YAPISGGDHAEVDVPK | 1556 |
| P24821 | SQQATTK | 1557 |
| P24821 | TTLTGLRPGTEYGIGVSAVK | 1558 |
| P24821 | ESNPATINAATELDTPK | 1559 |
| P24821 | DLQVSETAETSLTLLWK | 1560 |
| P24821 | LNYSLPTGQWVGVQLPR | 1561 |
| P24821 | NTTSYVLR | 1562 |
| P24821 | GLEPGQEYNVLLTAEK | 1563 |
| P24821 | ASTEQAPELENLTVTEVGWDGLR | 1564 |
| P24821 | LNWTAADQAYEHFIIQVQEANK | 1565 |
| P24821 | NLTVPGSLR | 1566 |
| P24821 | AVDIPGLK | 1567 |
| P24821 | AATPYTVSIYGVIQGYR | 1568 |
| P24821 | STDLPGLK | 1569 |
| P24821 | AATHYTITIR | 1570 |
| P24821 | AGTPYTVTLHGEVR | 1571 |
| P24821 | LNWTAADNAYEHFVIQVQEVNK | 1572 |
| P24821 | VEAAQNLTLPGSLR | 1573 |
| P24821 | AVDIPGLEAATPYR | 1574 |
| P24821 | VSIYGVIR | 1575 |
| P24821 | TPVLSAEASTAK | 1576 |

TABLE 21-continued

| Rule-Out TBI Biomarkers | | |
|---|---|---|
| P24821 | LLETVEYNISGAER | 1577 |
| P24821 | TAHISGLPPSTDFIVYLSGLAPSIR | 1578 |
| P24821 | LLDPQEFTLSGTQR | 1579 |
| P24821 | AEIVTEAEPEVDNLLVSDATPDGFR | 1580 |
| P24821 | LSWTADEGVFDNFVLK | 1581 |
| P24821 | QSEPLEITLLAPER | 1582 |
| P24821 | EATEYEIELYGISK | 1583 |
| P24821 | EVIFSDITENSATVSWR | 1584 |
| P24821 | APTAQVESFR | 1585 |
| P24821 | WQPAIATVDSYVISYTGEK | 1586 |
| P24821 | VPEITR | 1587 |
| P24821 | TVSGNTVEYALTDLEPATEYTLR | 1588 |
| P24821 | SSTITAK | 1589 |
| P24821 | FTTDLDSPR | 1590 |
| P24821 | DLTATEVQSETALLTWRPPR | 1591 |
| P24821 | ASVTGYLLVYESVDGTVK | 1592 |
| P24821 | EVIVGPDTTSYSLADLSPSTHYTAK | 1593 |
| P24821 | IQALNGPLR | 1594 |
| P24821 | ENFYQNWK | 1595 |
| P24821 | AYAAGFGDR | 1596 |
| P24821 | EEFWLGLDNLNK | 1597 |
| P24821 | ITAQGQYELR | 1598 |
| P24821 | DHGETAFAVYDK | 1599 |
| P24821 | FSVGDAK | 1600 |
| P24821 | SFSTFDK | 1601 |
| P24821 | GAFWYR | 1602 |
| P24821 | YGDNNHSQGVNWFHWK | 1603 |
| P39023 | HGSLGFLPR | 1604 |
| P39023 | DDPSKPVHLTAFLGYK | 1605 |
| P39023 | EVDRPGSK | 1606 |
| P39023 | WQDEDGK | 1607 |
| P39023 | VAFSVAR | 1608 |
| P39023 | IGQGYLIK | 1609 |
| P39023 | NNASTDYDLSDK | 1610 |
| P39023 | SLLVQTK | 1611 |
| P48637 | QQLEELAR | 1612 |
| P48637 | ALAEGVLLR | 1613 |
| P48637 | NIFDQR | 1614 |
| P48637 | AIENELLAR | 1615 |
| P48637 | NIHVIR | 1616 |
| P48637 | TFEDISEK | 1617 |
| P48637 | GSLDQDR | 1618 |
| P48637 | LFVDGQEIAVVYFR | 1619 |
| P48637 | QYSLQNWEAR | 1620 |
| P48637 | FVLKPQR | 1621 |
| P48637 | HVGHLLR | 1622 |
| P48637 | AIEHADGGVAAGVAVLDNPYPV | 1623 |
| P48637 | QDDFTAR | 1624 |
| P48637 | EGIAQTVFLGLNR | 1625 |
| P48637 | SADGSPALK | 1626 |
| P48637 | QIEINTISASFGGLASR | 1627 |
| P48637 | TPAVHR | 1628 |
| P48637 | HVLSVLSK | 1629 |
| P48637 | ILSNNPSK | 1630 |
| P48637 | GLALGIAK | 1631 |
| P48637 | AWELYGSPNALVLLIAQEK | 1632 |
| P49913 | DGHSLGR | 1633 |
| P49913 | AIDGINQR | 1634 |
| P49913 | SSDANLYR | 1635 |
| P49913 | FALLGDFFR | 1636 |
| Q12931 | ALLLWGR | 1637 |
| Q12931 | HEFQAETK | 1638 |
| Q12931 | LLDIVAR | 1639 |
| Q12931 | SLYSEK | 1640 |
| Q12931 | ELISNASDALEK | 1641 |
| Q12931 | AFLDALONQAEASSK | 1642 |
| Q12931 | IIIHLK | 1643 |
| Q12931 | EFSSEAR | 1644 |
| Q12931 | YSNFVSFPLYLNGR | 1645 |
| Q12931 | EWQHEEFYR | 1646 |
| Q12931 | YVAQAHDKPR | 1647 |
| Q12931 | YTLHYK | 1648 |
| Q12931 | TDAPLNIR | 1649 |
| Q12931 | ELGSSVALYSR | 1650 |
| Q12931 | VLIQTK | 1651 |
| Q12931 | ATDILPK | 1652 |
| Q12931 | GVVDSEDIPLNLSR | 1653 |
| Q12931 | ELLQESALIR | 1654 |

TABLE 21-continued

| Rule-Out TBI Biomarkers | | |
|---|---|---|
| Q12931 | FFIDQSK | 1655 |
| Q12931 | EGIVTATEQEVK | 1656 |
| Q12931 | YESSALPSGQLTSLSEYASR | 1657 |
| Q12931 | LISVETDIVVDHYK | 1658 |
| Q12931 | NVLGSR | 1659 |
| Q12931 | AQLLQPTLEINPR | 1660 |
| Q12931 | LNELLVK | 1661 |
| Q12931 | TTAQLGPR | 1662 |
| Q12931 | NPAWSLQAGR | 1663 |
| Q12931 | LFSTQTAEDK | 1664 |
| Q12931 | EEPLHSIISSTESVQGSTSK | 1665 |
| Q13347 | SITQIK | 1666 |
| Q13347 | EGDLLFTVAK | 1667 |
| Q13347 | DPIVNVWYSVNGER | 1668 |
| Q13347 | TNSAVR | 1669 |
| Q13347 | SGEVLVNVK | 1670 |
| Q13347 | QINDIQLSR | 1671 |
| Q13347 | LFDSTTLEHQK | 1672 |
| Q13347 | FFHLAFEEEFGR | 1673 |
| Q13347 | GHFGPINSVAFHPDGK | 1674 |
| Q13347 | SYSSGGEDGYVR | 1675 |
| Q13347 | IHYFDPQYFEFEFEA | 1676 |
| Q14103 | NEEDEGHSNSSPR | 1677 |
| Q14103 | HSEAATAQR | 1678 |
| Q14103 | LDPITGR | 1679 |
| Q14103 | ESESVDK | 1680 |
| Q14103 | IFVGGLSPDTPEEK | 1681 |
| Q14103 | YHNVGLSK | 1682 |
| Q14103 | EQYQQQQQWGSR | 1683 |
| Q14103 | GGHQNSYKPY | 1684 |
| Q16706 | GHLDYPR | 1685 |
| Q16706 | IDHLER | 1686 |
| Q16706 | LLAENNEIISNIR | 1687 |
| Q16706 | DSVINLSESVEDGPK | 1688 |
| Q16706 | TFNDYFR | 1689 |
| Q16706 | FIWSEISYLSK | 1690 |
| Q16706 | WWDIIDIQK | 1691 |
| Q16706 | VHYAVK | 1692 |
| Q16706 | HFALHK | 1693 |
| Q16706 | TLEFFWR | 1694 |
| Q16706 | VLLAPLGDDFR | 1695 |
| Q16706 | IQFGTLSDFFDALDK | 1696 |
| Q16706 | ADETQR | 1697 |
| Q16706 | DDHYWSGYFTSRPFYK | 1698 |
| Q16706 | AAEILYYFALR | 1699 |
| Q16706 | FLSSSLYTALTEAR | 1700 |
| Q16706 | NLGLFQHHDAITGTAK | 1701 |
| Q16706 | DWVVVDYGTR | 1702 |
| Q16706 | IIGNSAFLLILK | 1703 |
| Q16706 | SQDSLPQK | 1704 |
| Q16706 | YLVVYNPLEQDR | 1705 |
| Q16706 | AHIPPLGLK | 1706 |
| Q16706 | ILESASSNSHLADYVLYK | 1707 |
| Q16706 | VEDSGIFTIK | 1708 |
| Q16706 | HHEVNVQFSWYGTTIK | 1709 |
| Q16706 | SGAYLFLPDGNAKPYVYTTPPFVR | 1710 |
| Q16706 | LYHIQGIEGQSVEVSNIVDIR | 1711 |
| Q16706 | ISSDIK | 1712 |
| Q16706 | FYTDLNGYQIQPR | 1713 |
| Q16706 | GLEQGIQDNK | 1714 |
| Q16706 | ITANLFR | 1715 |
| Q16706 | SAVNTEEEK | 1716 |
| Q16706 | VGNGHSNEAALILHR | 1717 |
| Q562R1 | AGFGGDDAPR | 1718 |
| Q562R1 | IWYHTFYNELR | 1719 |
| Q562R1 | VAPDEHPILLTEAPLNPK | 1720 |
| Q562R1 | GYNFTTTAER | 1721 |
| Q562R1 | AAASSSPER | 1722 |
| Q562R1 | QEYDEAGPPIVHR | 1723 |
| Q5SYB0 | SSFLTEEK | 1724 |
| Q5SYB0 | LYLENGQTK | 1725 |
| Q5SYB0 | FEANTTVK | 1726 |
| Q5SYB0 | DIILTVK | 1727 |
| Q5SYB0 | SIEYFALALEEQYSISR | 1728 |
| Q5SYB0 | LHLLHEEELIQQVVER | 1729 |
| Q5SYB0 | EESHDYR | 1730 |
| Q5SYB0 | DPLDLLK | 1731 |
| Q5SYB0 | LAALHIQER | 1732 |

TABLE 21-continued

| Rule-Out TBI Biomarkers | | |
|---|---|---|
| Q5SYB0 | DWGIENFISPTLLR | 1733 |
| Q5SYB0 | NQNLLEPR | 1734 |
| Q5SYB0 | QLISAAQLR | 1735 |
| Q5SYB0 | LNYLQILGELK | 1736 |
| Q5SYB0 | ESYIALLVGAK | 1737 |
| Q5SYB0 | YGISQVINSK | 1738 |
| Q5SYB0 | VELTEESEK | 1739 |
| Q5SYB0 | VYLQDVK | 1740 |
| Q5SYB0 | VLTLLLESNSAK | 1741 |
| Q5SYB0 | LLVDPVTSIFLWPGNK | 1742 |
| Q5SYB0 | VSAEEGYESR | 1743 |
| Q5SYB0 | EEQPPGNSPTPEVAR | 1744 |
| Q5SYB0 | STFFHFGSPGLAESIDSDSQEER | 1745 |
| Q5SYB0 | TEFSESAALETFGWAPELSTVR | 1746 |
| Q5SYB0 | VAAADGPAR | 1747 |
| Q5SYB0 | NPTQTLIPVR | 1748 |
| Q5SYB0 | AVDILR | 1749 |
| Q5SYB0 | EAEDSLSITVVR | 1750 |
| Q5SYB0 | LTPPGPPSGPR | 1751 |
| Q5SYB0 | DVSTAEPSATSLQNK | 1752 |
| Q5SYB0 | ALGLLAPLR | 1753 |
| Q5SYB0 | STNPASR | 1754 |
| Q5SYB0 | SVIDSR | 1755 |
| Q5SYB0 | VSSISAIR | 1756 |
| Q5SYB0 | IDPNNK | 1757 |
| Q5SYB0 | EPTIEHGDSSFSLSSGDPNPDR | 1758 |
| Q5SYB0 | YTEPLLSPR | 1759 |
| Q5SYB0 | IASIPTK | 1760 |
| Q5SYB0 | EEPQGQLSLER | 1761 |
| Q5SYB0 | NGTNVFQEESR | 1762 |
| Q5SYB0 | DSGDSPGDVSNNVSQTLDISSPAGK | 1763 |
| Q5SYB0 | IVTSLSLDAPVTGTEQIPPHPPR | 1764 |
| Q5SYB0 | DPQGQSR | 1765 |
| Q5SYB0 | LFVELDLDPDFFLGK | 1766 |
| Q5SYB0 | QTVSPAVPPEGIK | 1767 |
| Q5SYB0 | AEAPNHVTGQDIAPR | 1768 |
| Q5SYB0 | GPQPETEEEDR | 1769 |
| Q5SYB0 | EAAGNLR | 1770 |
| Q5SYB0 | DVVYTYHQFIEAAK | 1771 |
| Q5SYB0 | GYHDLSVK | 1772 |
| Q92496 | VYLPWSR | 1773 |
| Q9H299 | VYSTSVTGSR | 1774 |
| Q9H299 | SQQSEVTR | 1775 |
| Q9H299 | IQYQLVDISQDNALR | 1776 |
| Q9H4B7 | GASALQLER | 1777 |
| Q9H4B7 | ISVYYNEAYGR | 1778 |
| Q9H4B7 | LGALFQPDSFVHGNSGAGNNWAK | 1779 |
| Q9H4B7 | GHYTEGAELIENVLEVVR | 1780 |
| Q9H4B7 | EVDQQLLSVQTR | 1781 |
| Q9NQ79 | LVNIAVDER | 1782 |
| Q9NQ79 | SSPYYALR | 1783 |
| Q9NQ79 | EEIYFLNTNNAFSGVATYTDK | 1784 |
| Q9NQ79 | WEDILSDEVNVAR | 1785 |
| Q9NQ79 | GVASLFAGR | 1786 |
| Q9NQ79 | GILALR | 1787 |
| Q9NQ79 | DVAAEAGVSK | 1788 |
| Q9NQ79 | GDGTFVDAAASAGVDDPHQHGR | 1789 |
| Q9NQ79 | GVALADFNR | 1790 |
| Q9NQ79 | VDIVYGNWNGPHR | 1791 |
| Q9NQ79 | DIASPK | 1792 |
| Q9NQ79 | TVITADFDNDQELEIFFNNIAYR | 1793 |
| Q9NQ79 | SSSANR | 1794 |
| Q9NQ79 | EHGDPLIEELNPGDALEPEGR | 1795 |
| Q9NQ79 | GNQGFNNNWLR | 1796 |
| Q9NQ79 | FGAFAR | 1797 |
| Q9NQ79 | VVLYTK | 1798 |
| Q9NQ79 | SGAHLR | 1799 |
| Q9NQ79 | DEASSVEVTWPDGK | 1800 |
| Q9UHG3 | YGFQSLR | 1801 |
| Q9UHG3 | YQSHDYAFSSVEK | 1802 |
| Q9UHG3 | TLLETLOK | 1803 |
| Q9UHG3 | AGFSEK | 1804 |
| Q9UHG3 | YTGNPTK | 1805 |
| Q9UHG3 | SDFYDIVLVATPLNR | 1806 |
| Q9UHG3 | GELNTSIFSSRPIDK | 1807 |
| Q9UHG3 | EDPEPSTDGTYVWK | 1808 |
| Q9UHG3 | IFSQETLTK | 1809 |
| Q9UHG3 | LFLSYDYAVK | 1810 |

TABLE 21-continued

| Rule-Out TBI Biomarkers | | |
|---|---|---|
| Q9UHG3 | KPWLAYPHYKPPEK | 1811 |
| Q9UHG3 | IAIIGAGIGGTSAAYYLR | 1812 |
| Q9UHG3 | IDLFER | 1813 |
| Q9UHG3 | EEVGGR | 1814 |
| Q9ULA0 | EAVQTAAK | 1815 |
| Q9ULA0 | LLQAGFSELK | 1816 |
| Q9ULA0 | WNIKPESK | 1817 |
| Q9ULA0 | SQVGFQQVGVETYGGGIWSTWFDR | 1818 |
| Q9ULA0 | DLTLAGR | 1819 |
| Q9ULA0 | LEQQLVHVERPILR | 1820 |
| Q9ULA0 | IPHLAIHLQR | 1821 |
| Q9ULA0 | GTPEPGPLNAVDER | 1822 |
| Q9ULA0 | HEENHRPLFHK | 1823 |
| Q9ULA0 | YASNAVSEALIR | 1824 |
| Q9ULA0 | GFFELFPSLSHNLLVD | 1825 |
| Q9UQ35 | GSGTNGYVQR | 1826 |
| Q9UQ35 | NLSLVR | 1827 |
| Q9UQ35 | GERPDYK | 1828 |
| Q9UQ35 | LEAALVK | 1829 |
| Q9UQ35 | RPNPDILDHER | 1830 |
| Q9UQ35 | DVNPGGK | 1831 |
| Q9UQ35 | EETPGQRPAVTETHQLAELNEK | 1832 |
| Q9UQ35 | AAFGISDSYVDGSSFDPQR | 1833 |
| Q9UQ35 | QPAPEPPKPYSLVR | 1834 |
| Q9UQ35 | STTPAPK | 1835 |
| Q9UQ35 | STSADSASSSDTSR | 1836 |
| Q9UQ35 | THTTALAGR | 1837 |
| Q9UQ35 | SPSPASGR | 1838 |
| Q9UQ35 | QPSSPYEDK | 1839 |
| Q9UQ35 | SATRPSPSPER | 1840 |
| Q9UQ35 | SSTGPEPPAPTPLLAER | 1841 |
| Q9UQ35 | LPQSSSSESSPPSPQPTK | 1842 |
| Q9UQ35 | HASSSPESPKPAPAPGSHR | 1843 |
| Q9UQ35 | EISSSPTSK | 1844 |
| Q9UQ35 | SHSHTPSR | 1845 |
| Q9UQ35 | SPATAK | 1846 |
| Q9UQ35 | SPQRPGWSR | 1847 |
| Q9UQ35 | SGSSQPK | 1848 |
| Q9UQ35 | SSSSPPPK | 1849 |
| Q9UQ35 | QSHSSSSPHPK | 1850 |
| Q9UQ35 | SGTPPR | 1851 |
| Q9UQ35 | QGSITSPQANEQSVTPQR | 1852 |
| Q9UQ35 | AIISPR | 1853 |
| Q9UQ35 | SHSGSSSPSPSR | 1854 |
| Q9UQ35 | YSHSGSSSPDTK | 1855 |
| Q9UQ35 | VKPETPPR | 1856 |
| Q9UQ35 | QSHSGSISPYPK | 1857 |
| Q9UQ35 | AQTPPGPSLSGSK | 1858 |
| Q9UQ35 | SSTPPGESYFGVSSLQLK | 1859 |
| Q9UQ35 | GQSQTSPDHR | 1860 |
| Q9UQ35 | SDTSSPEVR | 1861 |
| Q9UQ35 | QSHSESPSLQSK | 1862 |
| Q9UQ35 | SQTSPK | 1863 |
| Q9UQ35 | SSSPVTELASR | 1864 |
| Q9UQ35 | FQSDSSSYPTVDSNSLLGQSR | 1865 |
| Q9UQ35 | LETAESK | 1866 |
| Q9UQ35 | FSPFPVQDRPESSLVFK | 1867 |
| Q9UQ35 | SGAGSSPETK | 1868 |
| Q9UQ35 | SEEPAGQILSHLSSELK | 1869 |
| Q9UQ35 | ELSNSPLR | 1870 |
| Q9UQ35 | ENSFGSPLEFR | 1871 |
| Q9UQ35 | SSGHSSSELSPDAVEK | 1872 |
| Q9UQ35 | SGSSPGLR | 1873 |
| Q9UQ35 | DGSGTPSR | 1874 |
| Q9UQ35 | ALPQTPRPR | 1875 |
| Q9UQ35 | SPSSPELNNK | 1876 |
| Q9UQ35 | SGSESSVDQK | 1877 |
| Q9UQ35 | TPLGQR | 1878 |
| Q9UQ35 | SGSSQELDVKPSASPQER | 1879 |
| Q9UQ35 | SESDSSPDSK | 1880 |
| Q9UQ35 | SGSSPEVDSK | 1881 |
| Q9UQ35 | SGSSPEVK | 1882 |
| Q9UQ35 | AQSGSDSSPEPK | 1883 |
| Q9UQ35 | GPSPEGSSSTESSPEHPPK | 1884 |
| Q9UQ35 | SSPELTR | 1885 |
| Q9UQ35 | SASSSPETR | 1886 |
| Q9UQ35 | SPSVSSPEPAEK | 1887 |
| Q9UQ35 | SPSPKPR | 1888 |

TABLE 21-continued

Rule-Out TBI Biomarkers

| | | |
|---|---|---|
| Q9UQ35 | SGSSQSTSR | 1889 |
| Q9UQ35 | GGSGYHSR | 1890 |
| Q9UQ35 | TSPAPWK | 1891 |
| Q9UQ35 | ASPATHR | 1892 |
| Q9UQ35 | TPLISR | 1893 |
| Q9UQ35 | TPPVTR | 1894 |
| Q9UQ35 | TSPITR | 1895 |
| Q9UQ35 | SPVPSAFSDQSR | 1896 |
| Q9UQ35 | VPSPTPAPK | 1897 |
| Q9UQ35 | EGRPPEPTPAK | 1898 |
| Q9UQ35 | KPPPGER | 1899 |
| Q9UQ35 | KPIDSLR | 1900 |
| Q9UQ35 | SLSYSPVER | 1901 |
| Q9UQ35 | RPSPQPSPR | 1902 |
| Q9UQ35 | DQQSSSSER | 1903 |
| Q9UQ35 | TPPAIR | 1904 |
| Q9UQ35 | SPLAIR | 1905 |
| Q9UQ35 | SPPAIR | 1906 |
| Q9UQ35 | SASGSSSDR | 1907 |
| Q9UQ35 | SATPPATR | 1908 |
| Q9UQ35 | NHSGSR | 1909 |
| Q9UQ35 | TPPVALNSSR | 1910 |
| Q9UQ35 | IPDHQR | 1911 |
| Q9UQ35 | TSVPENHAQSR | 1912 |
| Q9UQ35 | TAPAANLASR | 1913 |
| Q9UQ35 | TPAIPTAVNLADSR | 1914 |
| Q9UQ35 | TAVAPSAVNLADPR | 1915 |
| Q9UQ35 | TPTAPAVNLAGAR | 1916 |
| Q9UQ35 | TPQAPASANLVGPR | 1917 |
| Q9UQ35 | SAHATAPVNIAGSR | 1918 |
| Q9UQ35 | TAAALAPASLTSAR | 1919 |
| Q9UQ35 | VPLSAYER | 1920 |
| Q9UQ35 | TSPPLLDR | 1921 |
| Q9UQ35 | TPPSAPSQSR | 1922 |
| Q9UQ35 | APSPSSR | 1923 |

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

Clause 1. A method of measuring or detecting at least one biomarker, the method comprising: testing a sample obtained from a subject; and measuring or detecting at least one biomarker or fragment thereof selected from the group consisting of AL9A1, ATPG, C1 RL, CAND1, EPIPL, GLO2, IGHA2, PZP, SYTC, SYYC, or any combinations thereof in the sample; and/or measuring or detecting at least one biomarker of fragment thereof selected from the group consisting of ABHEB, AL9A1, DNM1L, FCN2, INF2, K22E, M3K5, NCOR1, SBSN, SYEP, TPP2, or any combinations thereof in the sample; wherein the measurement or detection of the at least one biomarker indicates that the subject has sustained or may have sustained a traumatic brain injury (TBI).

Clause 2. The method of clause 1, wherein the at least one biomarker or fragment thereof is selected from the group consisting of AL9A1, ATPG, C1RL, EPIPL, IGHA2, PZP, SYTC, SYYC, or any combinations thereof; and wherein the at least one biomarker is not detectable in a sample obtained from a healthy subject.

Clause 3. The method of either clause 1 or clause 2, wherein the at least one biomarker or fragment thereof is selected from the group consisting of ATPG, C1RL, SYYC, or any combinations thereof.

Clause 4. The method of clause 1, wherein the at least one biomarker or fragment thereof is selected from the group consisting of CAND1, GLO2, or the combination thereof, wherein levels of CAND1 and GLO2 are higher compared to levels of CAND1 and GLO2 in a sample obtained from a healthy subject.

Clause 5. The method of clause 1, wherein the at least one biomarker or fragment thereof is selected from the group consisting of ABHEB, AL9A1, DNM1L, or combinations thereof; wherein levels of ABHEB are higher compared to levels of ABHEB in a sample obtained from a healthy subject; and/or wherein levels of AL9A1 and DNM1L are lower compared to levels of AL9A1 and DNM1L in a sample obtained from a healthy subject.

Clause 6. The method of clause 1, wherein the at least one biomarker or fragment thereof is selected from the group consisting of M3K5, SBSN, SYEP, or combinations thereof; and wherein the measurement or detection of the at least one biomarker indicates that the subject has sustained or may have sustained a mild TBI.

Clause 7. The method of clause 1 or clause 6, wherein levels of SBSN and SYEP are higher compared to levels of SBSN and SYEP in a sample obtained from a healthy subject; and/or wherein levels of M3K5 are lower compared to levels of M3K5 in a sample obtained from a healthy subject.

Clause 8. The method of clause 1, wherein the at least one biomarker or fragment thereof is selected from the group consisting of INF2, SYEP, or combinations thereof.

Clause 9. The method of clause 1, wherein the at least one biomarker or fragment thereof further comprises at least one biomarker selected from the group consisting of ANXA6, ERAP1, EZRI, FA5, G6PI, MYLK, SAMP, or combinations thereof.

Clause 10. A method of measuring or detecting at least one biomarker, the method comprising: testing a sample obtained from a subject; and measuring or detecting at least one biomarker or fragment thereof selected from the group consisting of 1433G, ACK1, ACY1, AKAl2, ARGI1, CADH5, CLH1, COPG2, DPOD2, DSG2, HV307, IQGA2, K1C14, K1C19, KV105, LAMC1, MDHM, NQO2, PERM, PLST, PNCB, PTPRC, SEPT7, SYRC, TRXR2, TXNL1, UGGG1, WDR1 or any combinations thereof in the sample; wherein the measurement or detection of the at least one biomarker indicates that the subject has sustained or may have sustained a mild traumatic brain injury (mTBI).

Clause 11. The method of clause 10, wherein the at least one biomarker is not detectable in a sample obtained from a healthy subject.

Clause 12. The method of clause 10, wherein the at least one biomarker is not detectable in a sample obtained from a subject that has sustained a severe TBI (sTBI).

Clause 13. The method of any of clauses 10 to 12, wherein the at least one biomarker or fragment thereof is selected from the group consisting of ACK1, ACY1, PLST, PNCB, PTPRC, UGGG1, or any combinations thereof in the sample; wherein the measurement or detection of the at least one biomarker indicates that the subject has sustained or may have sustained an mTBI of subclass 1.

Clause 14. The method of any of clauses 10 to 12, wherein the at least one biomarker or fragment thereof is selected from the group consisting of AKAl2, HV307, PERM, KV105, NQO2, SEPT7, SYRC, TRXR2, or any combinations thereof in the sample; wherein the measurement or detection of the at least one biomarker indicates that the subject has sustained or may have sustained an mTBI of subclass 2.

Clause 15. The method of any of clauses 10 to 12, wherein the at least one biomarker or fragment thereof is selected from the group consisting of 1433B, ARGI1, CADH5, CLH1, COPG2, DPOD2, DSG2, IQGA2, K1C14, LAMC1, MDHM, TXNL1, or any combinations thereof in the sample; wherein the measurement or detection of the at least one biomarker indicates that the subject has sustained or may have sustained an mTBI of subclass 3.

Clause 16. The method of clause 10, wherein the at least one biomarker or fragment thereof further comprises at least one biomarker selected from the group consisting of AHNK, AL1A1, AMPN, CAPZB, CATD, CLIP2, CMGA, FSCN1, GMPR2, GRP78, GSH1, IDHC, K1C20, KRR1, MBL2, NTF2, PCBP2, PGK1, SAA1, TFR1, or combinations thereof.

Clause 17. A biomarker panel for determining traumatic brain injury (TBI) status of a subject, the panel comprising at least one of the following biomarkers: TPP2, CAND1, NCOR1, K22E, AL9A1, ABHEB, DNM1L, INF2, or any combinations thereof; wherein measurement or detection of the at least one biomarker indicates that the subject has sustained or may have sustained a mild TBI of subclass 4.

Clause 18. The biomarker panel of clause 17, wherein levels of CAND1, NCOR1, K22E, ABHEB, and DNM1L are higher compared to levels of CAND1, NCOR1, K22E, ABHEB, and DNM1L in a sample obtained from a healthy subject; and/or wherein levels of TPP2, AL9A1, and INF2 are lower compared to levels of TPP2, AL9A1, and INF2 in a sample obtained from a healthy subject.

Clause 19. A biomarker panel for determining traumatic brain injury (TBI) status of a subject, the panel comprising at least one of the following biomarkers: TPP2, NCOR1, HV103, INF2, IGHD, CK054, M3K5, ABHEB, AL9A1, DNM1L, or any combinations thereof; wherein measurement or detection of the at least one biomarker indicates that the subject has sustained or may have sustained a mild TBI of subclass 3.

Clause 20. The biomarker panel of clause 19, wherein levels of NCOR1, HV103, IGHD, ABHEB, and DNM1L are higher compared to levels of NCOR1, HV103, IGHD, ABHEB, and DNM1L in a sample obtained from a healthy subject; and/or wherein levels of TPP2, IGHD, CK054, M3K5, and AL9A1 are lower compared to levels of TPP2, IGHD, CK054, M3K5, and AL9A1 in a sample obtained from a healthy subject.

Clause 21. A biomarker panel for determining traumatic brain injury (TBI) status of a subject, the panel comprising at least one of the following biomarkers: NCOR1, TPP2, K22E, ABHEB, INF2, SBSN, AL9A1, MA2B2, or any combinations thereof; wherein measurement or detection of the at least one biomarker indicates that the subject has sustained or may have sustained a mild TBI of subclass 2.

Clause 22. The biomarker panel of clause 21, wherein levels of NCOR1, K22E, ABHEB, and SBSN are higher compared to levels of NCOR1, K22E, ABHEB, and SBSN in a sample obtained from a healthy subject; and/or wherein levels of TPP2, INF2, AL9A1, and MA2B2 are lower compared to levels of TPP2, INF2, AL9A1, and MA2B2 in a sample obtained from a healthy subject.

Clause 23. A biomarker panel for determining traumatic brain injury (TBI) status of a subject, the panel comprising at least one of the following biomarkers: K22E, DNM1L, DIAP1, ABHEB, PLOD1, SYEP, KV133, AL9A1, EPHB4, or any combinations thereof; wherein measurement or detection of the at least one biomarker indicates that the subject has sustained or may have sustained a mild TBI of subclass 1.

Clause 24. The biomarker panel of clause 23, wherein levels of K22E, DNM1L, DIAP1, ABHEB, PLOD1, SYEP, and EPHB4 are higher compared to levels of K22E, DNMIL, DIAP1, ABHEB, PLOD1, SYEP, and EPHB4 in a sample obtained from a healthy subject; and/or wherein levels of KV133 and AL9A1 are lower compared to levels of KV133 and AL9A1 in a sample obtained from a healthy subject.

Clause 25. The method of clause 1, wherein the at least one biomarker or fragment thereof further comprises at least one biomarker selected from the group consisting of MYLK, SAMP, or a combination thereof.

Clause 26. A biomarker panel for determining traumatic brain injury (TBI) status of a subject, the panel comprising at least one of the following biomarkers: CAND1, NCOR1, K22E, ABHEB, DNM1L, SBSN, GLO2, SYEP, or any combinations thereof; wherein measurement or detection of higher levels of the at least one biomarker in the subject as compared to levels of the at least one biomarkers in a healthy subject indicates that the subject has sustained or may have sustained a mild TBI of subclass 4.

Clause 27. A biomarker panel for determining traumatic brain injury (TBI) status of a subject, the panel comprising at least one of the following biomarkers: NCOR1, HV103, IGHD, ABHEB, DNM1L, ALBU, THIM, IGHA2, KV139, and, or any combinations thereof; wherein measurement or detection of higher levels of the at least one biomarker in the subject as compared to levels of the at least one biomarkers in a healthy subject indicates that the subject has sustained or may have sustained a mild TBI of subclass 3.

Clause 28. A biomarker panel for determining traumatic brain injury (TBI) status of a subject, the panel comprising at least one of the following biomarkers: NCOR1, K22E, ABHEB, SBSN, DNM1L, DIAP1, DYL1, PSA, EPHB4, or any combinations thereof; wherein measurement or detection of higher levels of the at least one biomarker in the subject as compared to levels of the at least one biomarkers in a healthy subject indicates that the subject has sustained or may have sustained a mild TBI of subclass 2.

Clause 29. A biomarker panel for determining traumatic brain injury (TBI) status of a subject, the panel comprising at least one of the following biomarkers: K22E, DNM1L, DIAP1, ABHEB, PLOD I, SYEP, EPHB4, FBLN3, or any combinations thereof; wherein measurement or detection of higher levels of the at least one biomarker in the subject as compared to levels of the at least one biomarkers in a healthy subject indicates that the subject has sustained or may have sustained a mild TBI of subclass 1.

Clause 30. The method of clause 10, wherein the at least one biomarker or fragment thereof further comprises at least one biomarker selected from the group consisting of ANXA6, MASP2, MYLK, SAMP, or a combination thereof.

Clause 31. A biomarker panel for determining that a subject has not sustained a traumatic brain injury (TBI), the panel comprising at least one of the following biomarkers: ACTBL, ALDH2, ANXA5, CAMP, CPNE3, CRAC1, CYTC, DNPEP, EIF3I, GSHB, ICAM1, HV323, HNRPD, KVD33, FA9, FHR4, FRPD1, HS90B, MA2A1, PCYOX, PNPH, PROC, RL3, SH3L3, SRRM2, TBB1, TENA, TRAP1 or any combinations thereof; wherein measurement or detection of the at least one biomarker in the subject indicates that the subject has not sustained a TBI.

Clause 32. A method of measuring or detecting at least one biomarker, the method comprising: obtaining a sample from a subject after an actual or suspected head injury; and measuring or detecting at least one biomarker or fragment thereof selected from the group consisting of AL9A1, ATPG, CTRL, CAND1, EPIPL, GLO2, IGHA2, PZP, SYTC, SYYC, or any combinations thereof in the sample; and/or measuring or detecting at least one biomarker of fragment thereof selected from the group consisting of ABHEB, AL9A1, DNM1L, FCN2, INF2, K22E, M3K5, NCOR1, SBSN, SYEP, TPP2, or any combinations thereof in the sample.

Clause 33. The method according to clause 32, wherein the measurement or detection of the at least one biomarker indicates that the subject has sustained a traumatic brain injury (TBI).

Clause 34. The method according to clause 32 or clause 33, wherein the at least one biomarker or fragment thereof is selected from the group consisting of AL9A1, ATPG, C1RL, EPIPL, IGHA2, PZP, SYTC, SYYC, or any combinations thereof; and wherein the at least one biomarker is not detectable in a sample obtained from a healthy subject.

Clause 35. The method according to any of clauses 32 to 34, wherein the at least one biomarker or fragment thereof is selected from the group consisting of ATPG, C1RL, SYYC, or any combinations thereof.

Clause 36. The method according to clause 32 or clause 33, wherein the at least one biomarker or fragment thereof is selected from the group consisting of CAND1, GLO2, or the combination thereof; and wherein levels of CAND1 and GLO2 are higher compared to levels of CAND1 and GLO2 in a sample obtained from a healthy subject.

Clause 37. The method according to clause 32 or clause 33, wherein the at least one biomarker or fragment thereof is selected from the group consisting of ABHEB, AL9A1, DNM1L, or combinations thereof; wherein levels of ABHEB are higher compared to levels of ABHEB in a sample obtained from a healthy subject; and/or wherein levels of AL9A1 and DNM1L are lower compared to levels of AL9A1 and DNM1L in a sample obtained from a healthy subject.

Clause 38. The method according to clause 32 or clause 33, wherein the at least one biomarker or fragment thereof is selected from the group consisting of M3K5, SBSN, SYEP, or combinations thereof; wherein levels of SBSN and SYEP are higher compared to levels of SBSN and SYEP in a sample obtained from a healthy subject; and/or wherein levels of M3K5 are lower compared to levels of M3K5 in a sample obtained from a healthy subject.

Clause 39. The method according to clause 32 or clause 33, wherein the at least one biomarker or fragment thereof is selected from the group consisting of INF2, SYEP, or combinations thereof.

Clause 40. The method according to any of clauses 32 to 39, wherein the at least one biomarker or fragment thereof further comprises at least one biomarker selected from the group consisting of ANXA6, ERAP1, EZRI, FA5, G6PI, MYLK, SAMP, or combinations thereof.

Clause 41. The method according to any of clauses 32 to 39, wherein the at least one biomarker or fragment thereof further comprises at least one biomarker selected from the group consisting of MYLK, SAMP, or a combination thereof.

Clause 42. A method of measuring or detecting at least one biomarker, the method comprising: obtaining a sample from a subject after an actual or suspected head injury; and measuring or detecting at least one biomarker or fragment thereof selected from the group consisting of 1433G, ACK1, ACY1, AKAl2, ARGI1, CADH5, CLH1, COPG2, DPOD2, DSG2, HV319, IQGA2, K1C14, K1C19, KV105, LAMC1, MDHM, NQO2, PERM, PLST, PNCB, PTPRC, SEPT7, SYRC, TRXR2, TXNL1, UGGG1, WDR1 or any combinations thereof in the sample.

Clause 43. The method according to clause 42, wherein the measurement or detection of the at least one biomarker indicates that the subject has sustained a traumatic brain injury (TBI).

Clause 44. The method according to clause 42 or clause 43, wherein the at least one biomarker is not detectable in a sample obtained from a healthy subject.

Clause 45. The method according to any of clauses 42 to 44, wherein the at least one biomarker is not detectable in a sample obtained from a subject that has sustained a severe TBI.

Clause 46. The method according to any of clauses 42 to 44, wherein the at least one biomarker or fragment thereof is selected from the group consisting of ACK1, ACY1, PLST, PNCB, PTPRC, UGGG1, or any combinations thereof in the sample; wherein the measurement or detection of the at least one biomarker indicates that the subject has sustained a mild TBI of subclass 1.

Clause 47. The method according to any of clauses 42 to 44, wherein the at least one biomarker or fragment thereof is selected from the group consisting of AKAl2, HV319, PERM, KV105, NQO2, SEPT7, SYRC, TRXR2, or any combinations thereof in the sample; wherein the measurement or detection of the at least one biomarker indicates that the subject has sustained a mild TBI of subclass 2.

Clause 48. The method according to any of clauses 42 to 44, wherein the at least one biomarker or fragment thereof is selected from the group consisting of 1433B, ARGI1, CADH5, CLH1, COPG2, DPOD2, DSG2, IQGA2, K1C14, LAMC1, MDHM, TXNL1, or any combinations thereof in the sample; wherein the measurement or detection of the at least one biomarker indicates that the subject has sustained a mild TBI of subclass 3.

Clause 49. The method according to any of clauses 42 to 48, wherein the at least one biomarker or fragment thereof further comprises at least one biomarker selected from the group consisting of AHNK, AL1A1, AMPN, CAPZB, CATD, CLIP2, CMGA, FSCN1, GMPR2, GRP78, GSH1, IDHC, K1C20, KRR1, MBL2, NTF2, PCBP2, PGK1, SAA1, TFR1, or combinations thereof.

Clause 50. The method according to any of clauses 42 to 48, wherein the at least one biomarker or fragment thereof further comprises at least one biomarker selected from the group consisting of ANXA6, MASP2, MYLK, SAMP, or a combination thereof.

Clause 51. A biomarker panel for determining traumatic brain injury (TBI) status of a subject, the panel comprising at least one of the following biomarkers: TPP2, CAND1, NCOR1, K22E, AL9A1, ABHEB, DNM1L, INF2, or any combinations thereof; wherein measurement or detection of the at least one biomarker indicates that the subject has sustained a mild TBI of subclass 4.

Clause 52. The biomarker panel according to clause 51, wherein levels of CAND1, NCOR1, K22E, ABHEB, and DNM1L are higher compared to levels of CAND1, NCOR1, K22E, ABHEB, and DNM1L in a sample obtained from a healthy subject; and/or wherein levels of TPP2, AL9A1, and INF2 are lower compared to levels of TPP2, AL9A1, and INF2 in a sample obtained from a healthy subject.

Clause 53. A biomarker panel for determining traumatic brain injury (TBI) status of a subject, the panel comprising at least one of the following biomarkers: TPP2, NCOR1, HV103, INF2, IGHD, CK054, M3K5, ABHEB, AL9A1, DNM1L, or any combinations thereof; wherein measurement or detection of the at least one biomarker indicates that the subject has sustained a mild TBI of subclass 3.

Clause 54. The biomarker panel according to clause 53, wherein levels of NCOR1, HV103, IGHD, ABHEB, and DNM1L are higher compared to levels of NCOR1, HV103, IGHD, ABHEB, and DNM1L in a sample obtained from a healthy subject; and/or wherein levels of TPP2, IGHD, CK054, M3K5, and AL9A1 are lower compared to levels of TPP2, IGHD, CK054, M3K5, and AL9A1 in a sample obtained from a healthy subject.

Clause 55. A biomarker panel for determining traumatic brain injury (TBI) status of a subject, the panel comprising at least one of the following biomarkers: NCOR1, TPP2, K22E, ABHEB, INF2, SBSN, AL9A1, MA2B2, or any combinations thereof; wherein measurement or detection of the at least one biomarker indicates that the subject has sustained a mild TBI of subclass 2.

Clause 56. The biomarker panel according to clause 55, wherein levels of NCOR1, K22E, ABHEB, and SBSN are higher compared to levels of NCOR1, K22E, ABHEB, and SBSN in a sample obtained from a healthy subject; and/or wherein levels of TPP2, INF2, AL9A1, and MA2B2 are lower compared to levels of TPP2, INF2, AL9A1, and MA2B2 in a sample obtained from a healthy subject.

Clause 57. A biomarker panel for determining traumatic brain injury (TBI) status of a subject, the panel comprising at least one of the following biomarkers: K22E, DNM1L, DIAP1, ABHEB, PLOD1, SYEP, KV102, AL9A1, EPHB4, or any combinations thereof; wherein measurement or detection of the at least one biomarker indicates that the subject has sustained a mild TBI of subclass 1.

Clause 58. The biomarker panel according to clause 57, wherein levels of K22E, DNM1L, DIAP1, ABHEB, PLOD1, SYEP, and EPHB4 are higher compared to levels of K22E, DNM1L, DIAP1, ABHEB, PLOD1, SYEP, and EPHB4 in a sample obtained from a healthy subject; and/or wherein levels of KV102 and AL9A1 are lower compared to levels of KV102 and AL9A1 in a sample obtained from a healthy subject.

Clause 59. A biomarker panel for determining traumatic brain injury (TBI) status of a subject, the panel comprising at least one of the following biomarkers: CAND1, NCOR1, K22E, ABHEB, DNM1L, SBSN, GLO2, SYEP, or any combinations thereof; wherein measurement or detection of higher levels of the at least one biomarker in the subject as compared to levels of the at least one biomarkers in a healthy subject indicates that the subject has sustained a mild TBI of subclass 4.

Clause 60. A biomarker panel for determining traumatic brain injury (TBI) status of a subject, the panel comprising at least one of the following biomarkers: NCOR1, HV103, IGHD, ABHEB, DNM1L, ALBU, THIM, IGHA2, KV139, and, or any combinations thereof; wherein measurement or detection of higher levels of the at least one biomarker in the subject as compared to levels of the at least one biomarkers in a healthy subject indicates that the subject has sustained a mild TBI of subclass 3.

Clause 61. A biomarker panel for determining traumatic brain injury (TBI) status of a subject, the panel comprising at least one of the following biomarkers: NCOR1, K22E, ABHEB, SBSN, DNM1L, DIAP1, DYL1, PSA, EPHB4, or any combinations thereof; wherein measurement or detection of higher levels of the at least one biomarker in the subject as compared to levels of the at least one biomarkers in a healthy subject indicates that the subject has sustained a mild TBI of subclass 2.

Clause 62. A biomarker panel for determining traumatic brain injury (TBI) status of a subject, the panel comprising at least one of the following biomarkers: K22E, DNM1L, DIAP1, ABHEB, PLOD1, SYEP, EPHB4, FBLN3, or any combinations thereof; wherein measurement or detection of higher levels of the at least one biomarker in the subject as compared to levels of the at least one biomarkers in a healthy subject indicates that the subject has sustained a mild TBI of subclass 1.

Clause 63. A biomarker panel for determining that a subject has not sustained a traumatic brain injury (TBI), the panel comprising at least one of the following biomarkers: ACTBL, ALDH2, ANXA5, CAMP, CPNE3, CRAC1, CYTC, DNPEP, EIF3I, GSHB, ICAM1, HV303, HNRPD, KV121, FA9, FHR4, FRPD1, HS90B, MA2A1, PCYOX, PNPH, PROC, RL3, SH3L3, SRRM2, TBB1, TENA, TRAP1 or any combinations thereof; wherein measurement or detection of the at least one biomarker in the subject indicates that the subject has not sustained a TBI.

Clause 64. A method of measuring or detecting at least one biomarker, the method comprising: obtaining a sample from a subject after an actual or suspected head injury; and measuring or detecting at least one peptide of at least one biomarker or fragment thereof selected from the group consisting of PZP, EPIPL, IGHA2, AL9A1, G6PI, SYTC, EZRI, FA5, or any combinations thereof in the sample; wherein the at least one peptide of the at least one biomarker is selected from the group consisting of SEQ ID NOs: 4-260.

Clause 65. Use of at least one peptide selected from the group consisting of SEQ ID NOs: 4-260 to isolate or identify at least one biomarker or fragment thereof selected from the group consisting of PZP, EPIPL, IGHA2, AL9A1, G6PI, SYTC, EZRI, FA5, or any combinations thereof.

Clause 66. A method of measuring or detecting at least one biomarker, the method comprising: obtaining a sample from a subject after an actual or suspected head injury; and measuring or detecting at least one peptide of at least one biomarker or fragment thereof selected from the group consisting of NCOR1, ABHEB, ANXA6, DNM1L, FCN2, HBA, MYLK, SBSN, AHNK, K22E, or any combinations thereof in the sample; wherein the at least one peptide of the at least one biomarker is selected from the group consisting of SEQ ID NOs: 261-698.

Clause 67. Use of at least one peptide selected from the group consisting of SEQ ID NOs: 261-698 to isolate or identify at least one biomarker or fragment thereof selected from the group consisting of NCOR1, ABHEB, ANXA6, DNM1L, FCN2, HBA, MYLK, SBSN, AHNK, K22E, or any combinations thereof.

Clause 68. A method of measuring or detecting at least one biomarker, the method comprising: obtaining a sample from a subject after an actual or suspected head injury; and measuring or detecting at least one peptide of at least one biomarker or fragment thereof selected from the group consisting of CAND1, SYEP, GLO2, DIAP1, DYL1, PSA, EPHB4, PLOD1, FBLN3, HV103, IGHD, THIM, IGHA2, KV105, MASP2, or any combinations thereof in the sample; wherein the at least one peptide of the at least one biomarker is selected from the group consisting of SEQ ID NOs: 699-926.

Clause 69. Use of at least one peptide selected from the group consisting of SEQ ID NOs: 699-926 to isolate or identify at least one biomarker or fragment thereof selected from the group consisting of CAND1, SYEP, GLO2, DIAP1, DYL1, PSA, EPHB4, PLOD1, FBLN3, HV103, IGHD, THIM, IGHA2, KV105, MASP2, or any combinations thereof.

Clause 70. A method of measuring or detecting at least one biomarker, the method comprising: obtaining a sample from a subject after an actual or suspected head injury; and measuring or detecting at least one peptide of at least one biomarker or fragment thereof selected from the group consisting of SAMP, 1433B, FIBB, RS28, TRFE, or any combinations thereof in the sample; wherein the at least one peptide of the at least one biomarker is selected from the group consisting of SEQ ID NOs: 927-968.

Clause 71. Use of at least one peptide selected from the group consisting of SEQ ID NOs: 927-968 to isolate or identify at least one biomarker or fragment thereof selected from the group consisting of SAMP, 1433B, FIBB, RS28, TRFE, or any combinations thereof.

Clause 72. A method of measuring or detecting at least one biomarker, the method comprising: obtaining a sample from a subject after an actual or suspected head injury; and measuring or detecting at least one peptide of at least one biomarker or fragment thereof selected from the group consisting of DYL1, FBLN3, PSA, HV103, IGHD, or any combinations thereof in the sample; wherein the at least one peptide of the at least one biomarker is selected from the group consisting of SEQ ID NOs: 969-996.

Clause 73. Use of at least one peptide selected from the group consisting of SEQ ID NOs: 969-996 to isolate or identify at least one biomarker or fragment thereof selected from the group consisting of DYL1, FBLN3, PSA, HV103, IGHD, or any combinations thereof.

Clause 74. A method of measuring or detecting at least one biomarker, the method comprising: obtaining a sample from a subject after an actual or suspected head injury; and measuring or detecting at least one peptide of at least one biomarker or fragment thereof selected from the group consisting of FCN2, HBA, AHNK, or any combinations thereof in the sample; wherein the at least one peptide of the at least one biomarker is selected from the group consisting of SEQ ID NOs: 997-1182.

Clause 75. Use of at least one peptide selected from the group consisting of SEQ ID NOs: 997-1182 to isolate or identify at least one biomarker or fragment thereof selected from the group consisting of FCN2, HBA, AHNK, or any combinations thereof.

Clause 76. A method of measuring or detecting at least one biomarker, the method comprising: obtaining a sample from a subject after an actual or suspected head injury; and measuring or detecting at least one peptide of at least one biomarker or fragment thereof selected from the group consisting of HV103, IGHD, THIM, IGHA2, KV105, MASP2, DIAP1, PLOD1, EPHB4, FBLN3, DYL1, PSA, or any combinations thereof in the sample; wherein the at least one peptide of the at least one biomarker is selected from the group consisting of SEQ ID NOs: 1183-1319.

Clause 77. Use of at least one peptide selected from the group consisting of SEQ ID NOs: 1183-1319 to isolate or identify at least one biomarker or fragment thereof selected from the group consisting of HV103, IGHD, THIM, IGHA2, KV105, MASP2, DIAP1, PLOD1, EPHB4, FBLN3, DYL1, PSA, or any combinations thereof.

Clause 78. A method of measuring or detecting at least one biomarker, the method comprising: obtaining a sample from a subject after an actual or suspected head injury; and measuring or detecting at least one peptide of at least one biomarker or fragment thereof selected from the group consisting of CAND1, GLO2, ERAP1, SYYC, C1RL, ATPG, or any combinations thereof in the sample; wherein the at least one peptide of the at least one biomarker is selected from the group consisting of SEQ ID NOs: 1320-1438.

Clause 79. Use of at least one peptide selected from the group consisting of SEQ ID NOs: 1320-1438 to isolate or identify at least one biomarker or fragment thereof selected from the group consisting of CAND1, GLO2, ERAP1, SYYC, C1RL, ATPG, or any combinations thereof.

Clause 80. A method of measuring or detecting at least one biomarker, the method comprising: obtaining a sample from a subject after an actual or suspected head injury; and measuring or detecting at least one peptide of at least one biomarker or fragment thereof selected from the group consisting of ACTBL, ALDH2, ANXA5, CAMP, CPNE3, CRAC1, CYTC, DNPEP, EIF3I, GSHB, ICAM1, HV323, HNRPD, KVD33, FA9, FHR4, FRPD1, HS90B, MA2A1, PCYOX, PNPH, PROC, RL3, SH3L3, SRRM2, TBB1, TENA, TRAP1, or any combinations thereof in the sample; wherein the at least one peptide of the at least one biomarker is selected from the group consisting of SEQ ID NOs: 1439-1923.

Clause 81. Use of at least one peptide selected from the group consisting of SEQ ID NOs: 1439-1923 to isolate or identify at least one biomarker or fragment thereof selected from the group consisting of ACTBL, ALDH2, ANXA5, CAMP, CPNE3, CRAC1, CYTC, DNPEP, EIF3I, GSHB, ICAM1, HV323, HNRPD, KVD33, FA9, FHR4, FRPD1, HS90B, MA2A1, PCYOX, PNPH, PROC, RL3, SH3L3, SRRM2, TBB1, TENA, TRAP1, or any combinations thereof.

What is claimed is:

1. A method comprising:
   (A) measuring or detecting a level of at least one biomarker in a biological sample obtained from a subject, wherein the at least one biomarker comprises Aldehyde Dehydrogenase 9 Family Member A1 (AL9A1), wherein measuring or detecting the level of the at least one biomarker determines whether the subject has sustained a mild traumatic brain injury (mTBI) of any of subclasses 1, 2, 3, or 4, wherein the subject is determined to have a mTBI when the level of AL9A1 is lower compared to a level of AL9A1 obtained from a healthy subject; and
   (B) treating the subject for a mTBI, wherein treating the subject for a mTBI comprises: treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v).

2. The method of claim 1, wherein measuring or detecting a level of the at least one biomarker comprises performing an immunoassay, a clinical chemistry assay, a single molecule detection assay, a point-of-care assay, and/or mass spectroscopy.

3. The method of claim 1, wherein the at least one biomarker further comprises a biomarker selected from the group consisting of: Tripeptidyl Peptidase 2 (TPP2), Keratin 2 (K22E), and Dynamin 1 Like (DNM1L).

4. The method of claim 3, wherein:
   (i) the biomarker is DNM1L and the mTBI subclass is any one of subclasses 1, 3, or 4; and wherein the level of DNM1L is higher compared to a level of DNM1L obtained from a healthy subject;
   (ii) the biomarker is TPP2 and the mTBI subclass is any one of subclasses 2, 3, or 4; and wherein the level of TPP2 is lower compared to a level of TPP2 obtained from a healthy subject; or
   (iii) the biomarker is K22E and the mTBI subclass is any one of subclasses 1, 2, or 4; and wherein the level of K22E is higher compared to a level of K22E obtained from a healthy subject.

5. A method comprising:
   (A) measuring or detecting a level of at least one biomarker in a biological sample obtained from a subject wherein:
      (i) the at least one biomarker comprises Aldehyde Dehydrogenase 9 Family Member A1 (AL9A1), and measuring or detecting the level of AL9A1 determines whether the subject has sustained a mild traumatic brain injury (mTBI) of any of subclasses 1, 2, 3, or 4, wherein the subject is determined to have a mTBI when the level of AL9A1 is lower compared to a level of AL9A1 obtained from a healthy subject;
      (ii) the at least one biomarker comprises Dynamin 1 Like (DNM1L), and measuring or detecting the level of DNM1L determines whether the subject has sustained an mTBI of any of subclasses 1, 2, 3, or 4, wherein the subject is determined to have a mTBI when the level of DNM1L is higher compared to a level of DNM1L obtained from a healthy subject;
      (iii) the at least one biomarker comprises Tripeptidyl Peptidase 2 (TPP2), and measuring or detecting the level of TPP2 determines whether the subject has sustained a mTBI of any of subclasses 2, 3, or 4, wherein the subject is determined to have a mTBI when the level of TPP2 is lower compared to a level of TPP2 obtained from a healthy subject; or
      (iv) the at least one biomarker comprises Keratin 2 (K22E), and measuring or detecting the level of K22E determines whether the subject has sustained a mTBI of any of subclasses 1, 2, or 4, wherein the subject is determined to have a mTBI when the level of K22E is higher compared to a level of AL9A1 obtained from a healthy subject; and
   (B) treating the subject for a mTBI, wherein treating the subject for a mTBI comprises: treatment (i) with rest; (ii) by abstaining from physical activities; (iii) by avoiding light; (iv) by wearing protective eyewear when in light; (v) with one or more therapeutic agents selected from the group consisting of a medication for relief of a headache or migraine, and an anti-nausea medication, or combinations thereof; or (vi) with any combination of (i)-(v).

6. The method of claim 5, wherein measuring or detecting a level of the at least one biomarker comprises performing an immunoassay, a clinical chemistry assay, a single molecule detection assay, a point-of-care assay, and/or mass spectroscopy.

7. The method of claim 5, wherein the at least one biomarker further comprises a biomarker selected from the group consisting of:
   (i) Cullin-Associated NEDD8-Dissociated Protein 1 (CAND1), Nuclear Receptor Corepressor 1 (NCOR1), Protein ABHD14B (ABHEB), or Inverted Formin 2 (INF2), wherein measurement or detection of the biomarker indicates that the subject has sustained an mTBI of subclass 4;
   (ii) NCOR1, Immunoglobulin Heavy Variable 1-3 (HV103), INF2, Immunoglobulin Heavy Constant Delta (IGHD), Ester Hydrolase C11orf54(CK054), Mitogen-Activated Protein Kinase Kinase Kinase 5 (M3K5), or ABHEB, but not Keratin, Type II Cytoskeletal 2 Epidermal (K22E), wherein measurement or detection of the biomarker indicates that the subject has sustained an mTBI of subclass 3;

(iii) NCOR1, ABHEB, INF2, Suprabasin (SBSN), or Epididymis-Specific Alpha-Mannosidase (MA2B2), wherein measurement or detection of the biomarker indicates that the subject has sustained an mTBI of subclass 2; or (iv) Protein Diaphanous Homolog 1 (DIAP1), ABHEB, Procollagen-Lysine, 2-Oxoglutarate 5-Dioxygenase 1 (PLOD1), Bifunctional Glutamate/Proline-tRNA Ligase (SYEP), Immunoglobulin Kappa Variable 1-33 (KV133), or Ephrin Type-B Receptor 4 (EPHB4), but not TPP2, wherein measurement or detection of the biomarker indicates that the subject has sustained an mTBI of subclass 1.

* * * * *

SEQUENCE LISTING

<160> NUMBER OF SEQ ID NOS: 1923

<210> SEQ ID NO 1
<211> LENGTH: 6
<212> TYPE: PRT
<213> ORGANISM: Artificial sequence
<220> FEATURE:
<223> OTHER INFORMATION: Synthetic

<400> SEQUENCE: 1

His His His His His His
1               5

<210> SEQ ID NO 2
<211> LENGTH: 5
<212> TYPE: PRT
<213> ORGANISM: Artificial sequence
<220> FEATURE:
<223> OTHER INFORMATION: Synthetic

<400> SEQUENCE: 2

Asp Asp Asp Asp Lys
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic

<400> SEQUENCE: 3

Ala Asp Asp Asp Asp Lys
1               5

<210> SEQ ID NO 4
<211> LENGTH: 6
<212> TYPE: PRT
<213> ORGANISM: Homo sapiens

<400> SEQUENCE: 4

Asp Pro Gln Phe Gln Lys
1               5

<210> SEQ ID NO 5
<211> LENGTH: 6
<212> TYPE: PRT
<213> ORGANISM: Homo sapiens

<400> SEQUENCE: 5

Leu Gln Gln Trp Tyr Arg
1               5

<210> SEQ ID NO 6
<211> LENGTH: 6
<212> TYPE: PRT
<213> ORGANISM: Homo sapiens

<400> SEQUENCE: 6

Ser Glu Leu Asn Leu Arg
1               5

<210> SEQ ID NO 7
<211> LENGTH: 21
<212> TYPE: PRT
<213> ORGANISM: Homo sapiens

```
<400> SEQUENCE: 7

Phe Asn His Phe Ser Leu Thr Leu Asn Thr Asn His Gly His Ile Leu
1               5                   10                  15

Val Asp Tyr Ser Lys
            20

<210> SEQ ID NO 8
<211> LENGTH: 7
<212> TYPE: PRT
<213> ORGANISM: Homo sapiens

<400> SEQUENCE: 8

Ile Asn Tyr Thr Glu Gly Arg
1               5

<210> SEQ ID NO 9
<211> LENGTH: 8
<212> TYPE: PRT
<213> ORGANISM: Homo sapiens

<400> SEQUENCE: 9

Ala Val Leu His Val Ala Leu Arg
1               5

<210> SEQ ID NO 10
<211> LENGTH: 10
<212> TYPE: PRT
<213> ORGANISM: Homo sapiens

<400> SEQUENCE: 10

Ser Asn Thr Pro Ile Leu Val Asp Gly Lys
1               5                   10

<210> SEQ ID NO 11
<211> LENGTH: 14
<212> TYPE: PRT
<213> ORGANISM: Homo sapiens

<400> SEQUENCE: 11

Val Trp Tyr Val Ser Asn Ile Asp Gly Thr His Ile Ala Lys
1               5                   10

<210> SEQ ID NO 12
<211> LENGTH: 17
<212> TYPE: PRT
<213> ORGANISM: Homo sapiens

<400> SEQUENCE: 12

Thr Leu Ala Gln Leu Asn Pro Glu Ser Ser Leu Phe Ile Ile Ala Ser
1               5                   10                  15

Lys

<210> SEQ ID NO 13
<211> LENGTH: 15
<212> TYPE: PRT
<213> ORGANISM: Homo sapiens

<400> SEQUENCE: 13

Thr Phe Thr Thr Gln Glu Thr Ile Thr Asn Ala Glu Thr Ala Lys
1               5                   10                  15

<210> SEQ ID NO 14
```

```
<211> LENGTH: 8
<212> TYPE: PRT
<213> ORGANISM: Homo sapiens

<400> SEQUENCE: 14

Glu Trp Phe Leu Gln Ala Ala Lys
1               5

<210> SEQ ID NO 15
<211> LENGTH: 7
<212> TYPE: PRT
<213> ORGANISM: Homo sapiens

<400> SEQUENCE: 15

Asp Pro Ser Ala Val Ala Lys
1               5

<210> SEQ ID NO 16
<211> LENGTH: 11
<212> TYPE: PRT
<213> ORGANISM: Homo sapiens

<400> SEQUENCE: 16

His Phe Val Ala Leu Ser Thr Asn Thr Thr Lys
1               5                   10

<210> SEQ ID NO 17
<211> LENGTH: 7
<212> TYPE: PRT
<213> ORGANISM: Homo sapiens

<400> SEQUENCE: 17

Glu Leu Gln Ala Ala Gly Lys
1               5

<210> SEQ ID NO 18
<211> LENGTH: 15
<212> TYPE: PRT
<213> ORGANISM: Homo sapiens

<400> SEQUENCE: 18

Val Phe Glu Gly Asn Arg Pro Thr Asn Ser Ile Val Phe Thr Lys
1               5                   10                  15

<210> SEQ ID NO 19
<211> LENGTH: 22
<212> TYPE: PRT
<213> ORGANISM: Homo sapiens

<400> SEQUENCE: 19

Ile Phe Val Gln Gly Ile Ile Trp Asp Ile Asn Ser Phe Asp Gln Trp
1               5                   10                  15

Gly Val Glu Leu Gly Lys
            20

<210> SEQ ID NO 20
<211> LENGTH: 25
<212> TYPE: PRT
<213> ORGANISM: Homo sapiens

<400> SEQUENCE: 20

Leu Trp Val Leu Val Val Leu Gly Thr Ser Trp Val Gly Trp Gly Ser
1               5                   10                  15

Gln Gly Thr Glu Ala Ala Gln Leu Arg
```

<210> SEQ ID NO 21
<211> LENGTH: 7
<212> TYPE: PRT
<213> ORGANISM: Homo sapiens

<400> SEQUENCE: 21

Glu Tyr Glu Pro Tyr Phe Lys
1               5

<210> SEQ ID NO 22
<211> LENGTH: 24
<212> TYPE: PRT
<213> ORGANISM: Homo sapiens

<400> SEQUENCE: 22

Glu Lys Pro Gln Ser Thr Ile Ser Gly Leu Leu Gly Pro Thr Leu Tyr
1               5                   10                  15

Ala Glu Val Gly Asp Ile Ile Lys
            20

<210> SEQ ID NO 23
<211> LENGTH: 13
<212> TYPE: PRT
<213> ORGANISM: Homo sapiens

<400> SEQUENCE: 23

Ala Asp Lys Pro Leu Ser Ile His Pro Gln Gly Ile Arg
1               5                   10

<210> SEQ ID NO 24
<211> LENGTH: 16
<212> TYPE: PRT
<213> ORGANISM: Homo sapiens

<400> SEQUENCE: 24

Leu Ser Glu Gly Ala Ser Tyr Leu Asp His Thr Phe Pro Ala Glu Lys
1               5                   10                  15

<210> SEQ ID NO 25
<211> LENGTH: 10
<212> TYPE: PRT
<213> ORGANISM: Homo sapiens

<400> SEQUENCE: 25

Gly Thr Leu Thr Glu Gly Gly Thr Gln Lys
1               5                   10

<210> SEQ ID NO 26
<211> LENGTH: 13
<212> TYPE: PRT
<213> ORGANISM: Homo sapiens

<400> SEQUENCE: 26

Gln Ile Val Leu Leu Phe Ala Val Phe Asp Glu Ser Lys
1               5                   10

<210> SEQ ID NO 27
<211> LENGTH: 9
<212> TYPE: PRT
<213> ORGANISM: Homo sapiens

<400> SEQUENCE: 27

Trp Ile Ile Ser Ser Leu Thr Pro Lys
1               5

<210> SEQ ID NO 28
<211> LENGTH: 13
<212> TYPE: PRT
<213> ORGANISM: Homo sapiens

<400> SEQUENCE: 28

Ser Gln His Leu Asp Asn Phe Ser Asn Gln Ile Gly Lys
1               5                   10

<210> SEQ ID NO 29
<211> LENGTH: 10
<212> TYPE: PRT
<213> ORGANISM: Homo sapiens

<400> SEQUENCE: 29

Glu Asp Gly Ile Leu Gly Pro Ile Ile Arg
1               5                   10

<210> SEQ ID NO 30
<211> LENGTH: 11
<212> TYPE: PRT
<213> ORGANISM: Homo sapiens

<400> SEQUENCE: 30

Ala Val Gln Pro Gly Glu Thr Tyr Thr Tyr Lys
1               5                   10

<210> SEQ ID NO 31
<211> LENGTH: 17
<212> TYPE: PRT
<213> ORGANISM: Homo sapiens

<400> SEQUENCE: 31

Ala Ala Asp Ile Glu Gln Gln Ala Val Phe Ala Val Phe Asp Glu Asn
1               5                   10                  15

Lys

<210> SEQ ID NO 32
<211> LENGTH: 10
<212> TYPE: PRT
<213> ORGANISM: Homo sapiens

<400> SEQUENCE: 32

Ser Trp Tyr Leu Glu Asp Asn Ile Asn Lys
1               5                   10

<210> SEQ ID NO 33
<211> LENGTH: 17
<212> TYPE: PRT
<213> ORGANISM: Homo sapiens

<400> SEQUENCE: 33

Leu Glu Pro Glu Asp Glu Glu Ser Asp Ala Asp Tyr Asp Tyr Gln Asn
1               5                   10                  15

Arg

<210> SEQ ID NO 34
<211> LENGTH: 8
<212> TYPE: PRT
<213> ORGANISM: Homo sapiens

```
<400> SEQUENCE: 34

Leu Ala Ala Ala Leu Gly Ile Arg
1               5

<210> SEQ ID NO 35
<211> LENGTH: 11
<212> TYPE: PRT
<213> ORGANISM: Homo sapiens

<400> SEQUENCE: 35

Phe Thr Val Asn Asn Leu Ala Glu Pro Gln Lys
1               5                   10

<210> SEQ ID NO 36
<211> LENGTH: 15
<212> TYPE: PRT
<213> ORGANISM: Homo sapiens

<400> SEQUENCE: 36

Ala Pro Ser His Gln Gln Ala Thr Thr Ala Gly Ser Pro Leu Arg
1               5                   10                  15

<210> SEQ ID NO 37
<211> LENGTH: 10
<212> TYPE: PRT
<213> ORGANISM: Homo sapiens

<400> SEQUENCE: 37

Leu Leu Ser Leu Gly Ala Gly Glu Phe Lys
1               5                   10

<210> SEQ ID NO 38
<211> LENGTH: 6
<212> TYPE: PRT
<213> ORGANISM: Homo sapiens

<400> SEQUENCE: 38

Ser Gln Glu His Ala Lys
1               5

<210> SEQ ID NO 39
<211> LENGTH: 10
<212> TYPE: PRT
<213> ORGANISM: Homo sapiens

<400> SEQUENCE: 39

Asp Pro Pro Ser Asp Leu Leu Leu Leu Lys
1               5                   10

<210> SEQ ID NO 40
<211> LENGTH: 6
<212> TYPE: PRT
<213> ORGANISM: Homo sapiens

<400> SEQUENCE: 40

Gln Ser Asn Ser Ser Lys
1               5

<210> SEQ ID NO 41
<211> LENGTH: 7
<212> TYPE: PRT
<213> ORGANISM: Homo sapiens

<400> SEQUENCE: 41
```

```
Trp His Leu Ala Ser Glu Lys
1               5

<210> SEQ ID NO 42
<211> LENGTH: 14
<212> TYPE: PRT
<213> ORGANISM: Homo sapiens

<400> SEQUENCE: 42

Ala Trp Gly Glu Ser Thr Pro Leu Ala Asn Lys Pro Gly Lys
1               5                   10

<210> SEQ ID NO 43
<211> LENGTH: 6
<212> TYPE: PRT
<213> ORGANISM: Homo sapiens

<400> SEQUENCE: 43

Gln Ser Gly His Pro Lys
1               5

<210> SEQ ID NO 44
<211> LENGTH: 6
<212> TYPE: PRT
<213> ORGANISM: Homo sapiens

<400> SEQUENCE: 44

Ser Gln Phe Leu Ile Lys
1               5

<210> SEQ ID NO 45
<211> LENGTH: 10
<212> TYPE: PRT
<213> ORGANISM: Homo sapiens

<400> SEQUENCE: 45

His Thr His His Ala Pro Leu Ser Pro Arg
1               5                   10

<210> SEQ ID NO 46
<211> LENGTH: 6
<212> TYPE: PRT
<213> ORGANISM: Homo sapiens

<400> SEQUENCE: 46

Thr Phe His Pro Leu Arg
1               5

<210> SEQ ID NO 47
<211> LENGTH: 10
<212> TYPE: PRT
<213> ORGANISM: Homo sapiens

<400> SEQUENCE: 47

Ser Glu Ala Tyr Asn Thr Phe Ser Glu Arg
1               5                   10

<210> SEQ ID NO 48
<211> LENGTH: 7
<212> TYPE: PRT
<213> ORGANISM: Homo sapiens

<400> SEQUENCE: 48

His Ser Leu Val Leu His Lys
1               5
```

```
<210> SEQ ID NO 49
<211> LENGTH: 12
<212> TYPE: PRT
<213> ORGANISM: Homo sapiens

<400> SEQUENCE: 49

Glu Phe Asn Pro Leu Val Ile Val Gly Leu Ser Lys
1               5                   10

<210> SEQ ID NO 50
<211> LENGTH: 11
<212> TYPE: PRT
<213> ORGANISM: Homo sapiens

<400> SEQUENCE: 50

Asp Gly Thr Asp Tyr Ile Glu Ile Ile Pro Lys
1               5                   10

<210> SEQ ID NO 51
<211> LENGTH: 23
<212> TYPE: PRT
<213> ORGANISM: Homo sapiens

<400> SEQUENCE: 51

Glu Glu Val Gln Ser Ser Glu Asp Asp Tyr Ala Glu Ile Asp Tyr Val
1               5                   10                  15

Pro Tyr Asp Asp Pro Tyr Lys
            20

<210> SEQ ID NO 52
<211> LENGTH: 7
<212> TYPE: PRT
<213> ORGANISM: Homo sapiens

<400> SEQUENCE: 52

Thr Asn Ile Asn Ser Ser Arg
1               5

<210> SEQ ID NO 53
<211> LENGTH: 11
<212> TYPE: PRT
<213> ORGANISM: Homo sapiens

<400> SEQUENCE: 53

Asp Pro Asp Asn Ile Ala Ala Trp Tyr Leu Arg
1               5                   10

<210> SEQ ID NO 54
<211> LENGTH: 6
<212> TYPE: PRT
<213> ORGANISM: Homo sapiens

<400> SEQUENCE: 54

Ser Asn Asn Gly Asn Arg
1               5

<210> SEQ ID NO 55
<211> LENGTH: 19
<212> TYPE: PRT
<213> ORGANISM: Homo sapiens

<400> SEQUENCE: 55

Asn Tyr Tyr Ile Ala Ala Glu Glu Ile Ser Trp Asp Tyr Ser Glu Phe
```

Val Gln Arg

<210> SEQ ID NO 56
<211> LENGTH: 17
<212> TYPE: PRT
<213> ORGANISM: Homo sapiens

<400> SEQUENCE: 56

Glu Thr Asp Ile Glu Asp Ser Asp Asp Ile Pro Glu Asp Thr Thr Tyr
1               5                   10                  15

Lys

<210> SEQ ID NO 57
<211> LENGTH: 8
<212> TYPE: PRT
<213> ORGANISM: Homo sapiens

<400> SEQUENCE: 57

Tyr Leu Asp Ser Thr Phe Thr Lys
1               5

<210> SEQ ID NO 58
<211> LENGTH: 15
<212> TYPE: PRT
<213> ORGANISM: Homo sapiens

<400> SEQUENCE: 58

Gly Glu Tyr Glu Glu His Leu Gly Ile Leu Gly Pro Ile Ile Arg
1               5                   10                  15

<210> SEQ ID NO 59
<211> LENGTH: 10
<212> TYPE: PRT
<213> ORGANISM: Homo sapiens

<400> SEQUENCE: 59

Ala Glu Val Asp Asp Val Ile Gln Val Arg
1               5                   10

<210> SEQ ID NO 60
<211> LENGTH: 18
<212> TYPE: PRT
<213> ORGANISM: Homo sapiens

<400> SEQUENCE: 60

Asn Leu Ala Ser Arg Pro Tyr Ser Leu His Ala His Gly Leu Ser Tyr
1               5                   10                  15

Glu Lys

<210> SEQ ID NO 61
<211> LENGTH: 11
<212> TYPE: PRT
<213> ORGANISM: Homo sapiens

<400> SEQUENCE: 61

Thr Tyr Glu Asp Asp Ser Pro Glu Trp Phe Lys
1               5                   10

<210> SEQ ID NO 62
<211> LENGTH: 20
<212> TYPE: PRT
<213> ORGANISM: Homo sapiens

<400> SEQUENCE: 62

Glu Asp Asn Ala Val Gln Pro Asn Ser Ser Tyr Thr Tyr Val Trp His
1               5                   10                  15

Ala Thr Glu Arg
            20

<210> SEQ ID NO 63
<211> LENGTH: 12
<212> TYPE: PRT
<213> ORGANISM: Homo sapiens

<400> SEQUENCE: 63

Ala Trp Ala Tyr Tyr Ser Ala Val Asn Pro Glu Lys
1               5                   10

<210> SEQ ID NO 64
<211> LENGTH: 6
<212> TYPE: PRT
<213> ORGANISM: Homo sapiens

<400> SEQUENCE: 64

Ser Trp Tyr Tyr Glu Lys
1               5

<210> SEQ ID NO 65
<211> LENGTH: 15
<212> TYPE: PRT
<213> ORGANISM: Homo sapiens

<400> SEQUENCE: 65

Gln His Gln Leu Gly Val Trp Pro Leu Leu Pro Gly Ser Phe Lys
1               5                   10                  15

<210> SEQ ID NO 66
<211> LENGTH: 18
<212> TYPE: PRT
<213> ORGANISM: Homo sapiens

<400> SEQUENCE: 66

Ala Ser Lys Pro Gly Trp Trp Leu Leu Asn Thr Glu Val Gly Glu Asn
1               5                   10                  15

Gln Arg

<210> SEQ ID NO 67
<211> LENGTH: 11
<212> TYPE: PRT
<213> ORGANISM: Homo sapiens

<400> SEQUENCE: 67

Ala Ser Glu Phe Leu Gly Tyr Trp Glu Pro Arg
1               5                   10

<210> SEQ ID NO 68
<211> LENGTH: 14
<212> TYPE: PRT
<213> ORGANISM: Homo sapiens

<400> SEQUENCE: 68

Leu Asn Asn Gly Gly Ser Tyr Asn Ala Trp Ser Val Glu Lys
1               5                   10

<210> SEQ ID NO 69

```
<211> LENGTH: 13
<212> TYPE: PRT
<213> ORGANISM: Homo sapiens

<400> SEQUENCE: 69

Glu Val Ile Ile Thr Gly Ile Gln Thr Gln Gly Ala Lys
1               5                   10

<210> SEQ ID NO 70
<211> LENGTH: 11
<212> TYPE: PRT
<213> ORGANISM: Homo sapiens

<400> SEQUENCE: 70

Glu Asn Gln Phe Asp Pro Pro Ile Val Ala Arg
1               5                   10

<210> SEQ ID NO 71
<211> LENGTH: 8
<212> TYPE: PRT
<213> ORGANISM: Homo sapiens

<400> SEQUENCE: 71

Ala Tyr Asn Arg Pro Thr Leu Arg
1               5

<210> SEQ ID NO 72
<211> LENGTH: 8
<212> TYPE: PRT
<213> ORGANISM: Homo sapiens

<400> SEQUENCE: 72

Gln Ile Thr Ala Ser Ser Phe Lys
1               5

<210> SEQ ID NO 73
<211> LENGTH: 11
<212> TYPE: PRT
<213> ORGANISM: Homo sapiens

<400> SEQUENCE: 73

Ser Trp Trp Gly Asp Tyr Trp Glu Pro Phe Arg
1               5                   10

<210> SEQ ID NO 74
<211> LENGTH: 7
<212> TYPE: PRT
<213> ORGANISM: Homo sapiens

<400> SEQUENCE: 74

Val Asn Ala Trp Gln Ala Lys
1               5

<210> SEQ ID NO 75
<211> LENGTH: 9
<212> TYPE: PRT
<213> ORGANISM: Homo sapiens

<400> SEQUENCE: 75

Gln Trp Leu Glu Ile Asp Leu Leu Lys
1               5

<210> SEQ ID NO 76
<211> LENGTH: 17
<212> TYPE: PRT
```

<213> ORGANISM: Homo sapiens

<400> SEQUENCE: 76

Ser Tyr Thr Ile His Tyr Ser Glu Gln Gly Val Glu Trp Lys Pro Tyr
1               5                   10                  15
Arg

<210> SEQ ID NO 77
<211> LENGTH: 9
<212> TYPE: PRT
<213> ORGANISM: Homo sapiens

<400> SEQUENCE: 77

Ile Phe Glu Gly Asn Thr Asn Thr Lys
1               5

<210> SEQ ID NO 78
<211> LENGTH: 10
<212> TYPE: PRT
<213> ORGANISM: Homo sapiens

<400> SEQUENCE: 78

Asn Phe Phe Asn Pro Pro Ile Ile Ser Arg
1               5                   10

<210> SEQ ID NO 79
<211> LENGTH: 9
<212> TYPE: PRT
<213> ORGANISM: Homo sapiens

<400> SEQUENCE: 79

Thr Trp Asn Gln Ser Ile Ala Leu Arg
1               5

<210> SEQ ID NO 80
<211> LENGTH: 13
<212> TYPE: PRT
<213> ORGANISM: Homo sapiens

<400> SEQUENCE: 80

Glu Val Trp Tyr Phe Gly Leu His Tyr Val Asp Asn Lys
1               5                   10

<210> SEQ ID NO 81
<211> LENGTH: 7
<212> TYPE: PRT
<213> ORGANISM: Homo sapiens

<400> SEQUENCE: 81

Gly Phe Pro Thr Trp Leu Lys
1               5

<210> SEQ ID NO 82
<211> LENGTH: 7
<212> TYPE: PRT
<213> ORGANISM: Homo sapiens

<400> SEQUENCE: 82

Val Ser Ala Gln Glu Val Arg
1               5

<210> SEQ ID NO 83
<211> LENGTH: 17
<212> TYPE: PRT

```
<213> ORGANISM: Homo sapiens

<400> SEQUENCE: 83

Phe Tyr Pro Glu Asp Val Ala Glu Glu Leu Ile Gln Asp Ile Thr Gln
1               5                   10                  15

Lys

<210> SEQ ID NO 84
<211> LENGTH: 6
<212> TYPE: PRT
<213> ORGANISM: Homo sapiens

<400> SEQUENCE: 84

Phe Gly Asp Tyr Asn Lys
1               5

<210> SEQ ID NO 85
<211> LENGTH: 8
<212> TYPE: PRT
<213> ORGANISM: Homo sapiens

<400> SEQUENCE: 85

Ser Gly Tyr Leu Ser Ser Glu Arg
1               5

<210> SEQ ID NO 86
<211> LENGTH: 6
<212> TYPE: PRT
<213> ORGANISM: Homo sapiens

<400> SEQUENCE: 86

Asp Gln Trp Glu Asp Arg
1               5

<210> SEQ ID NO 87
<211> LENGTH: 9
<212> TYPE: PRT
<213> ORGANISM: Homo sapiens

<400> SEQUENCE: 87

Ile Gln Val Trp His Ala Glu His Arg
1               5

<210> SEQ ID NO 88
<211> LENGTH: 18
<212> TYPE: PRT
<213> ORGANISM: Homo sapiens

<400> SEQUENCE: 88

Gly Thr Asp Leu Trp Leu Gly Val Asp Ala Leu Gly Leu Asn Ile Tyr
1               5                   10                  15

Glu Lys

<210> SEQ ID NO 89
<211> LENGTH: 7
<212> TYPE: PRT
<213> ORGANISM: Homo sapiens

<400> SEQUENCE: 89

Gln Gln Leu Glu Thr Glu Lys
1               5

<210> SEQ ID NO 90
```

```
<211> LENGTH: 7
<212> TYPE: PRT
<213> ORGANISM: Homo sapiens

<400> SEQUENCE: 90

Leu Gln Asp Tyr Glu Glu Lys
1               5

<210> SEQ ID NO 91
<211> LENGTH: 8
<212> TYPE: PRT
<213> ORGANISM: Homo sapiens

<400> SEQUENCE: 91

Glu Leu Ser Glu Gln Ile Gln Arg
1               5

<210> SEQ ID NO 92
<211> LENGTH: 8
<212> TYPE: PRT
<213> ORGANISM: Homo sapiens

<400> SEQUENCE: 92

Ala Leu Gln Leu Glu Glu Glu Arg
1               5

<210> SEQ ID NO 93
<211> LENGTH: 7
<212> TYPE: PRT
<213> ORGANISM: Homo sapiens

<400> SEQUENCE: 93

Gln Ala Val Asp Gln Ile Lys
1               5

<210> SEQ ID NO 94
<211> LENGTH: 15
<212> TYPE: PRT
<213> ORGANISM: Homo sapiens

<400> SEQUENCE: 94

Ser Gln Glu Gln Leu Ala Ala Glu Leu Ala Glu Tyr Thr Ala Lys
1               5                   10                  15

<210> SEQ ID NO 95
<211> LENGTH: 8
<212> TYPE: PRT
<213> ORGANISM: Homo sapiens

<400> SEQUENCE: 95

Ile Ala Leu Leu Glu Glu Ala Arg
1               5

<210> SEQ ID NO 96
<211> LENGTH: 10
<212> TYPE: PRT
<213> ORGANISM: Homo sapiens

<400> SEQUENCE: 96

Glu Asp Glu Val Glu Glu Trp Gln His Arg
1               5                   10

<210> SEQ ID NO 97
<211> LENGTH: 8
<212> TYPE: PRT
```

<213> ORGANISM: Homo sapiens

<400> SEQUENCE: 97

Glu Ala Gln Asp Asp Leu Val Lys
1               5

<210> SEQ ID NO 98
<211> LENGTH: 13
<212> TYPE: PRT
<213> ORGANISM: Homo sapiens

<400> SEQUENCE: 98

Gln Leu Leu Thr Leu Ser Ser Glu Leu Ser Gln Ala Arg
1               5                   10

<210> SEQ ID NO 99
<211> LENGTH: 7
<212> TYPE: PRT
<213> ORGANISM: Homo sapiens

<400> SEQUENCE: 99

Ile Asp Glu Phe Glu Ala Leu
1               5

<210> SEQ ID NO 100
<211> LENGTH: 11
<212> TYPE: PRT
<213> ORGANISM: Homo sapiens

<400> SEQUENCE: 100

Val Val Ser Val Asp Glu Asn Phe Arg Pro Arg
1               5                   10

<210> SEQ ID NO 101
<211> LENGTH: 13
<212> TYPE: PRT
<213> ORGANISM: Homo sapiens

<400> SEQUENCE: 101

Asn Glu Leu Ile Pro Leu Ile Tyr Leu Glu Asn Pro Arg
1               5                   10

<210> SEQ ID NO 102
<211> LENGTH: 8
<212> TYPE: PRT
<213> ORGANISM: Homo sapiens

<400> SEQUENCE: 102

Ile Ala Gln Trp Gln Ser Leu Lys
1               5

<210> SEQ ID NO 103
<211> LENGTH: 22
<212> TYPE: PRT
<213> ORGANISM: Homo sapiens

<400> SEQUENCE: 103

Leu Glu Ala Gly Ile Asn Gln Leu Ser Phe Pro Leu Ser Ser Glu Pro
1               5                   10                  15

Ile Gln Gly Ser Tyr Arg
            20

<210> SEQ ID NO 104
<211> LENGTH: 10

```
<212> TYPE: PRT
<213> ORGANISM: Homo sapiens

<400> SEQUENCE: 104

Val Val Val Gln Thr Glu Ser Gly Gly Arg
1               5                   10

<210> SEQ ID NO 105
<211> LENGTH: 14
<212> TYPE: PRT
<213> ORGANISM: Homo sapiens

<400> SEQUENCE: 105

Ile Gln His Pro Phe Thr Val Glu Glu Phe Val Leu Pro Lys
1               5                   10

<210> SEQ ID NO 106
<211> LENGTH: 12
<212> TYPE: PRT
<213> ORGANISM: Homo sapiens

<400> SEQUENCE: 106

Glu Glu Gly Thr Asp Leu Glu Val Thr Ala Asn Arg
1               5                   10

<210> SEQ ID NO 107
<211> LENGTH: 10
<212> TYPE: PRT
<213> ORGANISM: Homo sapiens

<400> SEQUENCE: 107

Ile Ser Glu Ile Thr Asn Ile Val Ser Lys
1               5                   10

<210> SEQ ID NO 108
<211> LENGTH: 15
<212> TYPE: PRT
<213> ORGANISM: Homo sapiens

<400> SEQUENCE: 108

Gln Gly Ile Pro Phe Phe Ala Gln Val Leu Leu Val Asp Gly Lys
1               5                   10                  15

<210> SEQ ID NO 109
<211> LENGTH: 18
<212> TYPE: PRT
<213> ORGANISM: Homo sapiens

<400> SEQUENCE: 109

Gly Ser Phe Ala Leu Ser Phe Pro Val Glu Ser Asp Val Ala Pro Ile
1               5                   10                  15

Ala Arg

<210> SEQ ID NO 110
<211> LENGTH: 6
<212> TYPE: PRT
<213> ORGANISM: Homo sapiens

<400> SEQUENCE: 110

Val Phe Thr Asn Ser Lys
1               5

<210> SEQ ID NO 111
<211> LENGTH: 7
```

-continued

```
<212> TYPE: PRT
<213> ORGANISM: Homo sapiens

<400> SEQUENCE: 111

Gly Glu Val Phe Thr Leu Lys
1               5

<210> SEQ ID NO 112
<211> LENGTH: 7
<212> TYPE: PRT
<213> ORGANISM: Homo sapiens

<400> SEQUENCE: 112

Leu Pro Ser Asn Val Val Lys
1               5

<210> SEQ ID NO 113
<211> LENGTH: 11
<212> TYPE: PRT
<213> ORGANISM: Homo sapiens

<400> SEQUENCE: 113

Ala Val Gly Tyr Leu Ile Thr Gly Tyr Gln Arg
1               5                   10

<210> SEQ ID NO 114
<211> LENGTH: 12
<212> TYPE: PRT
<213> ORGANISM: Homo sapiens

<400> SEQUENCE: 114

His Gln Asp Gly Ser Tyr Ser Thr Phe Gly Glu Arg
1               5                   10

<210> SEQ ID NO 115
<211> LENGTH: 11
<212> TYPE: PRT
<213> ORGANISM: Homo sapiens

<400> SEQUENCE: 115

Glu Gly Thr His Gly Ser His Val Tyr Thr Lys
1               5                   10

<210> SEQ ID NO 116
<211> LENGTH: 12
<212> TYPE: PRT
<213> ORGANISM: Homo sapiens

<400> SEQUENCE: 116

Ala Leu Leu Ala Tyr Ala Phe Ser Leu Leu Gly Lys
1               5                   10

<210> SEQ ID NO 117
<211> LENGTH: 8
<212> TYPE: PRT
<213> ORGANISM: Homo sapiens

<400> SEQUENCE: 117

Glu Ile Leu Asn Ser Leu Asp Lys
1               5

<210> SEQ ID NO 118
<211> LENGTH: 14
<212> TYPE: PRT
<213> ORGANISM: Homo sapiens
```

```
<400> SEQUENCE: 118

Glu Asp Asn Leu Val His Trp Glu Arg Pro Gln Arg Pro Lys
1               5                   10

<210> SEQ ID NO 119
<211> LENGTH: 23
<212> TYPE: PRT
<213> ORGANISM: Homo sapiens

<400> SEQUENCE: 119

Gln Gln Asn Ala Gln Gly Gly Phe Ser Ser Thr Gln Asp Thr Val Val
1               5                   10                  15

Ala Leu His Ala Leu Ser Arg
            20

<210> SEQ ID NO 120
<211> LENGTH: 8
<212> TYPE: PRT
<213> ORGANISM: Homo sapiens

<400> SEQUENCE: 120

Glu Asp Ser Pro Phe Ala Leu Lys
1               5

<210> SEQ ID NO 121
<211> LENGTH: 10
<212> TYPE: PRT
<213> ORGANISM: Homo sapiens

<400> SEQUENCE: 121

Ser Leu Phe Thr Asp Leu Val Ala Glu Lys
1               5                   10

<210> SEQ ID NO 122
<211> LENGTH: 15
<212> TYPE: PRT
<213> ORGANISM: Homo sapiens

<400> SEQUENCE: 122

Ile Ser Ala Ser Ser Glu Val Ala Phe Leu Ser Ile Gln Ile Lys
1               5                   10                  15

<210> SEQ ID NO 123
<211> LENGTH: 7
<212> TYPE: PRT
<213> ORGANISM: Homo sapiens

<400> SEQUENCE: 123

Gly Pro Thr Gln Asp Phe Arg
1               5

<210> SEQ ID NO 124
<211> LENGTH: 6
<212> TYPE: PRT
<213> ORGANISM: Homo sapiens

<400> SEQUENCE: 124

Val Ser Val Gln Leu Lys
1               5

<210> SEQ ID NO 125
<211> LENGTH: 12
<212> TYPE: PRT
```

```
<213> ORGANISM: Homo sapiens

<400> SEQUENCE: 125

Ala Ser Pro Ala Phe Leu Ala Ser Gln Asn Thr Lys
1               5                   10

<210> SEQ ID NO 126
<211> LENGTH: 10
<212> TYPE: PRT
<213> ORGANISM: Homo sapiens

<400> SEQUENCE: 126

Gln Thr Leu Ser Trp Thr Val Thr Pro Lys
1               5                   10

<210> SEQ ID NO 127
<211> LENGTH: 13
<212> TYPE: PRT
<213> ORGANISM: Homo sapiens

<400> SEQUENCE: 127

Thr Leu Leu Val Glu Ala Glu Gly Ile Glu Gln Glu Lys
1               5                   10

<210> SEQ ID NO 128
<211> LENGTH: 7
<212> TYPE: PRT
<213> ORGANISM: Homo sapiens

<400> SEQUENCE: 128

Ala Ser Ser Pro Ser Gly Lys
1               5

<210> SEQ ID NO 129
<211> LENGTH: 8
<212> TYPE: PRT
<213> ORGANISM: Homo sapiens

<400> SEQUENCE: 129

Glu Gly Ser Gly Asp Gly Gly Arg
1               5

<210> SEQ ID NO 130
<211> LENGTH: 13
<212> TYPE: PRT
<213> ORGANISM: Homo sapiens

<400> SEQUENCE: 130

Ala Glu Leu Asn Pro Trp Pro Glu Tyr Ile Tyr Thr Arg
1               5                   10

<210> SEQ ID NO 131
<211> LENGTH: 10
<212> TYPE: PRT
<213> ORGANISM: Homo sapiens

<400> SEQUENCE: 131

Ala Glu His Asp Ser Ile Leu Ala Glu Lys
1               5                   10

<210> SEQ ID NO 132
<211> LENGTH: 6
<212> TYPE: PRT
<213> ORGANISM: Homo sapiens
```

```
<400> SEQUENCE: 132

Asp Ser Lys Pro Ile Lys
1               5

<210> SEQ ID NO 133
<211> LENGTH: 7
<212> TYPE: PRT
<213> ORGANISM: Homo sapiens

<400> SEQUENCE: 133

Val Thr Leu Pro Asp Gly Lys
1               5

<210> SEQ ID NO 134
<211> LENGTH: 8
<212> TYPE: PRT
<213> ORGANISM: Homo sapiens

<400> SEQUENCE: 134

Gln Val Asp Ala Glu Ser Trp Lys
1               5

<210> SEQ ID NO 135
<211> LENGTH: 10
<212> TYPE: PRT
<213> ORGANISM: Homo sapiens

<400> SEQUENCE: 135

Val Asn Thr Pro Thr Thr Thr Val Tyr Arg
1               5                   10

<210> SEQ ID NO 136
<211> LENGTH: 9
<212> TYPE: PRT
<213> ORGANISM: Homo sapiens

<400> SEQUENCE: 136

Asn Ser Ser Thr Tyr Trp Glu Gly Lys
1               5

<210> SEQ ID NO 137
<211> LENGTH: 10
<212> TYPE: PRT
<213> ORGANISM: Homo sapiens

<400> SEQUENCE: 137

Ile Tyr Gly Ile Ser Phe Pro Asp Pro Lys
1               5                   10

<210> SEQ ID NO 138
<211> LENGTH: 13
<212> TYPE: PRT
<213> ORGANISM: Homo sapiens

<400> SEQUENCE: 138

Gly Ala Tyr Ile Tyr Asn Ala Leu Ile Glu Phe Ile Arg
1               5                   10

<210> SEQ ID NO 139
<211> LENGTH: 14
<212> TYPE: PRT
<213> ORGANISM: Homo sapiens

<400> SEQUENCE: 139
```

Gly Phe Gln Glu Val Val Thr Pro Asn Ile Phe Asn Ser Arg
1               5                   10

<210> SEQ ID NO 140
<211> LENGTH: 9
<212> TYPE: PRT
<213> ORGANISM: Homo sapiens

<400> SEQUENCE: 140

Leu Ala Asp Phe Gly Val Leu His Arg
1               5

<210> SEQ ID NO 141
<211> LENGTH: 12
<212> TYPE: PRT
<213> ORGANISM: Homo sapiens

<400> SEQUENCE: 141

Asn Glu Leu Ser Gly Ala Leu Thr Gly Leu Thr Arg
1               5                   10

<210> SEQ ID NO 142
<211> LENGTH: 11
<212> TYPE: PRT
<213> ORGANISM: Homo sapiens

<400> SEQUENCE: 142

Thr Val Tyr Ser Val Phe Gly Phe Ser Phe Lys
1               5                   10

<210> SEQ ID NO 143
<211> LENGTH: 9
<212> TYPE: PRT
<213> ORGANISM: Homo sapiens

<400> SEQUENCE: 143

Leu Asn Leu Ser Thr Arg Pro Glu Lys
1               5

<210> SEQ ID NO 144
<211> LENGTH: 13
<212> TYPE: PRT
<213> ORGANISM: Homo sapiens

<400> SEQUENCE: 144

Phe Leu Gly Asp Ile Glu Val Trp Asp Gln Ala Glu Lys
1               5                   10

<210> SEQ ID NO 145
<211> LENGTH: 12
<212> TYPE: PRT
<213> ORGANISM: Homo sapiens

<400> SEQUENCE: 145

Gln Leu Glu Asn Ser Leu Asn Glu Phe Gly Glu Lys
1               5                   10

<210> SEQ ID NO 146
<211> LENGTH: 14
<212> TYPE: PRT
<213> ORGANISM: Homo sapiens

<400> SEQUENCE: 146

Trp Glu Leu Asn Ser Gly Asp Gly Ala Phe Tyr Gly Pro Lys
1               5                   10

<210> SEQ ID NO 147
<211> LENGTH: 6
<212> TYPE: PRT
<213> ORGANISM: Homo sapiens

<400> SEQUENCE: 147

Ile Asp Ile Gln Ile Lys
1               5

<210> SEQ ID NO 148
<211> LENGTH: 13
<212> TYPE: PRT
<213> ORGANISM: Homo sapiens

<400> SEQUENCE: 148

Phe Asn Leu Thr Tyr Val Ser His Asp Gly Asp Asp Lys
1               5                   10

<210> SEQ ID NO 149
<211> LENGTH: 7
<212> TYPE: PRT
<213> ORGANISM: Homo sapiens

<400> SEQUENCE: 149

Arg Pro Val Ile Val His Arg
1               5

<210> SEQ ID NO 150
<211> LENGTH: 7
<212> TYPE: PRT
<213> ORGANISM: Homo sapiens

<400> SEQUENCE: 150

Gln Gln Phe His Asp Ala Lys
1               5

<210> SEQ ID NO 151
<211> LENGTH: 8
<212> TYPE: PRT
<213> ORGANISM: Homo sapiens

<400> SEQUENCE: 151

Ile Ser Gly Thr Val Asn Ile Arg
1               5

<210> SEQ ID NO 152
<211> LENGTH: 8
<212> TYPE: PRT
<213> ORGANISM: Homo sapiens

<400> SEQUENCE: 152

Thr Ile Ser Glu Thr Ile Glu Arg
1               5

<210> SEQ ID NO 153
<211> LENGTH: 7
<212> TYPE: PRT
<213> ORGANISM: Homo sapiens

<400> SEQUENCE: 153

Ile Leu Leu Glu Ala Ala Arg
1               5

```
<210> SEQ ID NO 154
<211> LENGTH: 6
<212> TYPE: PRT
<213> ORGANISM: Homo sapiens

<400> SEQUENCE: 154

Ser Ile Phe Glu Ala Arg
1               5

<210> SEQ ID NO 155
<211> LENGTH: 12
<212> TYPE: PRT
<213> ORGANISM: Homo sapiens

<400> SEQUENCE: 155

Gly Ile Lys Pro Val Thr Leu Glu Leu Gly Gly Lys
1               5                   10

<210> SEQ ID NO 156
<211> LENGTH: 7
<212> TYPE: PRT
<213> ORGANISM: Homo sapiens

<400> SEQUENCE: 156

Phe Thr Glu Glu Val Val Lys
1               5

<210> SEQ ID NO 157
<211> LENGTH: 10
<212> TYPE: PRT
<213> ORGANISM: Homo sapiens

<400> SEQUENCE: 157

Ile Gly Asp Pro Leu Leu Glu Asp Thr Arg
1               5                   10

<210> SEQ ID NO 158
<211> LENGTH: 6
<212> TYPE: PRT
<213> ORGANISM: Homo sapiens

<400> SEQUENCE: 158

Val Leu Gly Phe Val Lys
1               5

<210> SEQ ID NO 159
<211> LENGTH: 15
<212> TYPE: PRT
<213> ORGANISM: Homo sapiens

<400> SEQUENCE: 159

Ala Asn Asp Thr Thr Phe Gly Leu Ala Ala Gly Val Phe Thr Arg
1               5                   10                  15

<210> SEQ ID NO 160
<211> LENGTH: 10
<212> TYPE: PRT
<213> ORGANISM: Homo sapiens

<400> SEQUENCE: 160

Val Thr Ile Glu Tyr Tyr Ser Gln Leu Lys
1               5                   10

<210> SEQ ID NO 161
<211> LENGTH: 11
```

```
<212> TYPE: PRT
<213> ORGANISM: Homo sapiens

<400> SEQUENCE: 161

Val Glu Pro Ala Asp Ala Ser Gly Thr Glu Lys
1               5                   10

<210> SEQ ID NO 162
<211> LENGTH: 8
<212> TYPE: PRT
<213> ORGANISM: Homo sapiens

<400> SEQUENCE: 162

Ala Phe Glu Pro Ala Thr Gly Arg
1               5

<210> SEQ ID NO 163
<211> LENGTH: 10
<212> TYPE: PRT
<213> ORGANISM: Homo sapiens

<400> SEQUENCE: 163

Glu Val Asn Leu Ala Val Gln Asn Ala Lys
1               5                   10

<210> SEQ ID NO 164
<211> LENGTH: 8
<212> TYPE: PRT
<213> ORGANISM: Homo sapiens

<400> SEQUENCE: 164

Gly Gln Leu Leu Pro Val Ser Lys
1               5

<210> SEQ ID NO 165
<211> LENGTH: 12
<212> TYPE: PRT
<213> ORGANISM: Homo sapiens

<400> SEQUENCE: 165

Ala Leu Gln Gln Gly Leu Val Gly Leu Glu Leu Lys
1               5                   10

<210> SEQ ID NO 166
<211> LENGTH: 13
<212> TYPE: PRT
<213> ORGANISM: Homo sapiens

<400> SEQUENCE: 166

Ala Thr Thr Gly Tyr Pro Asp Pro Tyr Gly Gly Glu Lys
1               5                   10

<210> SEQ ID NO 167
<211> LENGTH: 9
<212> TYPE: PRT
<213> ORGANISM: Homo sapiens

<400> SEQUENCE: 167

Leu Ala Leu Phe Gln Ala Ile Gly Lys
1               5

<210> SEQ ID NO 168
<211> LENGTH: 12
<212> TYPE: PRT
<213> ORGANISM: Homo sapiens
```

```
<400> SEQUENCE: 168

Leu Ser Glu Leu Glu Pro Gly Thr Gly Asp Leu Arg
1               5                   10

<210> SEQ ID NO 169
<211> LENGTH: 9
<212> TYPE: PRT
<213> ORGANISM: Homo sapiens

<400> SEQUENCE: 169

Phe Leu Asn Pro Asn Thr Leu Glu Arg
1               5

<210> SEQ ID NO 170
<211> LENGTH: 9
<212> TYPE: PRT
<213> ORGANISM: Homo sapiens

<400> SEQUENCE: 170

Leu Thr Tyr His Gln Leu Leu Glu Arg
1               5

<210> SEQ ID NO 171
<211> LENGTH: 12
<212> TYPE: PRT
<213> ORGANISM: Homo sapiens

<400> SEQUENCE: 171

Ala Pro Gly Ser Gly Leu Ala Leu Leu Pro Leu Lys
1               5                   10

<210> SEQ ID NO 172
<211> LENGTH: 9
<212> TYPE: PRT
<213> ORGANISM: Homo sapiens

<400> SEQUENCE: 172

Leu Ala Ala Val Asp Val Ser Ala Arg
1               5

<210> SEQ ID NO 173
<211> LENGTH: 19
<212> TYPE: PRT
<213> ORGANISM: Homo sapiens

<400> SEQUENCE: 173

Tyr Leu Glu Gly Thr Gly Ser Val Ala Gly Val Val Leu Leu Pro Glu
1               5                   10                  15

Gly His Lys

<210> SEQ ID NO 174
<211> LENGTH: 8
<212> TYPE: PRT
<213> ORGANISM: Homo sapiens

<400> SEQUENCE: 174

Leu Trp Val Asp Glu Ala Val Arg
1               5

<210> SEQ ID NO 175
<211> LENGTH: 10
<212> TYPE: PRT
<213> ORGANISM: Homo sapiens
```

<400> SEQUENCE: 175

Gly Leu Val Asp Arg Pro Leu Ala Leu Arg
1               5                   10

<210> SEQ ID NO 176
<211> LENGTH: 8
<212> TYPE: PRT
<213> ORGANISM: Homo sapiens

<400> SEQUENCE: 176

Leu Pro Leu Glu Ala Ala Leu Arg
1               5

<210> SEQ ID NO 177
<211> LENGTH: 17
<212> TYPE: PRT
<213> ORGANISM: Homo sapiens

<400> SEQUENCE: 177

Gln Leu Ser Gln Ala Gly Ser Phe Ser Asp Gly Thr His Gly Gly Leu
1               5                   10                  15

Arg

<210> SEQ ID NO 178
<211> LENGTH: 11
<212> TYPE: PRT
<213> ORGANISM: Homo sapiens

<400> SEQUENCE: 178

Gly Gly Glu Pro Gln Gly Pro Pro Phe Ile Lys
1               5                   10

<210> SEQ ID NO 179
<211> LENGTH: 14
<212> TYPE: PRT
<213> ORGANISM: Homo sapiens

<400> SEQUENCE: 179

Gln Ala Leu Ser Thr Ala Thr Ala Thr Val Ser Val Gly Lys
1               5                   10

<210> SEQ ID NO 180
<211> LENGTH: 20
<212> TYPE: PRT
<213> ORGANISM: Homo sapiens

<400> SEQUENCE: 180

Gly Arg Pro Val Ser Leu Trp Glu Leu Leu Phe Ser Glu Ala Ile Ser
1               5                   10                  15

Ser Glu Gln Arg
            20

<210> SEQ ID NO 181
<211> LENGTH: 17
<212> TYPE: PRT
<213> ORGANISM: Homo sapiens

<400> SEQUENCE: 181

Leu Ala Ala Glu Leu Ser Ala Thr Leu Glu Gln Ala Ala Ala Thr Ala
1               5                   10                  15

Arg

```
<210> SEQ ID NO 182
<211> LENGTH: 7
<212> TYPE: PRT
<213> ORGANISM: Homo sapiens

<400> SEQUENCE: 182

Val Thr Phe Ser Gly Leu Arg
1               5

<210> SEQ ID NO 183
<211> LENGTH: 10
<212> TYPE: PRT
<213> ORGANISM: Homo sapiens

<400> SEQUENCE: 183

Asp Thr Val Thr Pro Gly Glu Leu Leu Lys
1               5                   10

<210> SEQ ID NO 184
<211> LENGTH: 11
<212> TYPE: PRT
<213> ORGANISM: Homo sapiens

<400> SEQUENCE: 184

Ala Glu Ile Ile Asp Gln Asp Leu Tyr Glu Arg
1               5                   10

<210> SEQ ID NO 185
<211> LENGTH: 9
<212> TYPE: PRT
<213> ORGANISM: Homo sapiens

<400> SEQUENCE: 185

Leu Glu His Gly Gln Ala Thr Ala Lys
1               5

<210> SEQ ID NO 186
<211> LENGTH: 10
<212> TYPE: PRT
<213> ORGANISM: Homo sapiens

<400> SEQUENCE: 186

Asp Val Gly Ser Leu Ala Ser Ala Gln Arg
1               5                   10

<210> SEQ ID NO 187
<211> LENGTH: 7
<212> TYPE: PRT
<213> ORGANISM: Homo sapiens

<400> SEQUENCE: 187

Leu Ser Ile Tyr Glu Ala Arg
1               5

<210> SEQ ID NO 188
<211> LENGTH: 25
<212> TYPE: PRT
<213> ORGANISM: Homo sapiens

<400> SEQUENCE: 188

Gly Leu Leu Arg Pro Gly Thr Ala Leu Ile Leu Leu Glu Ala Gln Ala
1               5                   10                  15

Ala Thr Gly Phe Ile Ile Asp Pro Lys
            20                  25
```

```
<210> SEQ ID NO 189
<211> LENGTH: 9
<212> TYPE: PRT
<213> ORGANISM: Homo sapiens

<400> SEQUENCE: 189

Gly His Ser Val Glu Glu Ala Leu Arg
1               5

<210> SEQ ID NO 190
<211> LENGTH: 11
<212> TYPE: PRT
<213> ORGANISM: Homo sapiens

<400> SEQUENCE: 190

Ala Ala Val Ile Gly Pro Asp Val Phe Ala Lys
1               5                   10

<210> SEQ ID NO 191
<211> LENGTH: 16
<212> TYPE: PRT
<213> ORGANISM: Homo sapiens

<400> SEQUENCE: 191

Val Ser Ala Trp Glu Leu Ile Asn Ser Glu Tyr Phe Ser Glu Gly Arg
1               5                   10                  15

<210> SEQ ID NO 192
<211> LENGTH: 9
<212> TYPE: PRT
<213> ORGANISM: Homo sapiens

<400> SEQUENCE: 192

Glu Val Thr Leu Gly Gln Val Ala Lys
1               5

<210> SEQ ID NO 193
<211> LENGTH: 8
<212> TYPE: PRT
<213> ORGANISM: Homo sapiens

<400> SEQUENCE: 193

Leu Leu Glu Ala Glu Thr Gln Arg
1               5

<210> SEQ ID NO 194
<211> LENGTH: 10
<212> TYPE: PRT
<213> ORGANISM: Homo sapiens

<400> SEQUENCE: 194

Gly Val Val Gly Pro Glu Leu Tyr Gly Arg
1               5                   10

<210> SEQ ID NO 195
<211> LENGTH: 9
<212> TYPE: PRT
<213> ORGANISM: Homo sapiens

<400> SEQUENCE: 195

Ala Glu Gly Ala Ile Ala Gly Phe Arg
1               5
```

```
<210> SEQ ID NO 196
<211> LENGTH: 10
<212> TYPE: PRT
<213> ORGANISM: Homo sapiens

<400> SEQUENCE: 196

Gly Leu Ile Pro Trp Glu Gln Ala Ala Arg
1               5                   10

<210> SEQ ID NO 197
<211> LENGTH: 9
<212> TYPE: PRT
<213> ORGANISM: Homo sapiens

<400> SEQUENCE: 197

Ser Leu Gln Ala Val Pro Gly Ala Lys
1               5

<210> SEQ ID NO 198
<211> LENGTH: 10
<212> TYPE: PRT
<213> ORGANISM: Homo sapiens

<400> SEQUENCE: 198

Gly Leu Leu Glu Asp Val Gln Glu Gly Arg
1               5                   10

<210> SEQ ID NO 199
<211> LENGTH: 12
<212> TYPE: PRT
<213> ORGANISM: Homo sapiens

<400> SEQUENCE: 199

Thr Thr Val Pro Gln Leu Leu Ala Ser Val Gln Arg
1               5                   10

<210> SEQ ID NO 200
<211> LENGTH: 8
<212> TYPE: PRT
<213> ORGANISM: Homo sapiens

<400> SEQUENCE: 200

Ala Ser Ile Ala Gln Ala Val Arg
1               5

<210> SEQ ID NO 201
<211> LENGTH: 11
<212> TYPE: PRT
<213> ORGANISM: Homo sapiens

<400> SEQUENCE: 201

Asp Gly Leu Leu Pro Thr Gly Leu Gly Gln Arg
1               5                   10

<210> SEQ ID NO 202
<211> LENGTH: 19
<212> TYPE: PRT
<213> ORGANISM: Homo sapiens

<400> SEQUENCE: 202

Leu Leu Glu Ala Gln Val Ala Ser Gly Phe Leu Val Asp Pro Leu Asn
1               5                   10                  15

Asn Gln Arg
```

```
<210> SEQ ID NO 203
<211> LENGTH: 8
<212> TYPE: PRT
<213> ORGANISM: Homo sapiens

<400> SEQUENCE: 203

Leu Ser Val Glu Asp Ala Val Lys
1               5

<210> SEQ ID NO 204
<211> LENGTH: 6
<212> TYPE: PRT
<213> ORGANISM: Homo sapiens

<400> SEQUENCE: 204

Val Gly Leu Val Gly Arg
1               5

<210> SEQ ID NO 205
<211> LENGTH: 11
<212> TYPE: PRT
<213> ORGANISM: Homo sapiens

<400> SEQUENCE: 205

Glu Leu Ser Glu Gln Leu Gly Gln Ala Glu Arg
1               5                   10

<210> SEQ ID NO 206
<211> LENGTH: 11
<212> TYPE: PRT
<213> ORGANISM: Homo sapiens

<400> SEQUENCE: 206

Ala Ala Ala Gly Tyr Pro Asp Pro Tyr Ser Arg
1               5                   10

<210> SEQ ID NO 207
<211> LENGTH: 17
<212> TYPE: PRT
<213> ORGANISM: Homo sapiens

<400> SEQUENCE: 207

Leu Gly Leu Leu Asp Thr Gln Thr Ser Gln Val Leu Thr Ala Val Asp
1               5                   10                  15

Lys

<210> SEQ ID NO 208
<211> LENGTH: 8
<212> TYPE: PRT
<213> ORGANISM: Homo sapiens

<400> SEQUENCE: 208

Phe Phe Phe Asp Pro Ser Ala Arg
1               5

<210> SEQ ID NO 209
<211> LENGTH: 9
<212> TYPE: PRT
<213> ORGANISM: Homo sapiens

<400> SEQUENCE: 209

Asp Gln Val Thr Tyr Gln Gln Leu Arg
1               5
```

```
<210> SEQ ID NO 210
<211> LENGTH: 7
<212> TYPE: PRT
<213> ORGANISM: Homo sapiens

<400> SEQUENCE: 210

Val Pro Val Ser Thr Gly Arg
1               5

<210> SEQ ID NO 211
<211> LENGTH: 15
<212> TYPE: PRT
<213> ORGANISM: Homo sapiens

<400> SEQUENCE: 211

Gln Val Val Ser Ala Val Thr Ala Leu Val Glu Ala Ala Glu Arg
1               5                   10                  15

<210> SEQ ID NO 212
<211> LENGTH: 8
<212> TYPE: PRT
<213> ORGANISM: Homo sapiens

<400> SEQUENCE: 212

Gln Pro Leu Gln Ala Thr Phe Arg
1               5

<210> SEQ ID NO 213
<211> LENGTH: 13
<212> TYPE: PRT
<213> ORGANISM: Homo sapiens

<400> SEQUENCE: 213

Thr Leu Asp Glu Leu Ser Gln Gly Thr Thr Thr Val Lys
1               5                   10

<210> SEQ ID NO 214
<211> LENGTH: 19
<212> TYPE: PRT
<213> ORGANISM: Homo sapiens

<400> SEQUENCE: 214

Ser Leu Glu Gly Gly Asn Phe Ile Ala Gly Val Leu Ile Gln Gly Thr
1               5                   10                  15

Gln Glu Arg

<210> SEQ ID NO 215
<211> LENGTH: 8
<212> TYPE: PRT
<213> ORGANISM: Homo sapiens

<400> SEQUENCE: 215

Leu Thr Val Glu Glu Ala Phe Lys
1               5

<210> SEQ ID NO 216
<211> LENGTH: 10
<212> TYPE: PRT
<213> ORGANISM: Homo sapiens

<400> SEQUENCE: 216

Ile Leu Ala Asp Pro Ser Asp Asp Thr Lys
1               5                   10
```

```
<210> SEQ ID NO 217
<211> LENGTH: 12
<212> TYPE: PRT
<213> ORGANISM: Homo sapiens

<400> SEQUENCE: 217

Gly Glu Asn Tyr Val Tyr Ile Asn Glu Ala Thr Arg
1               5                   10

<210> SEQ ID NO 218
<211> LENGTH: 21
<212> TYPE: PRT
<213> ORGANISM: Homo sapiens

<400> SEQUENCE: 218

Phe Ala Asp Gln Val Val Ser Phe Trp Asp Leu Leu Ser Ser Pro Tyr
1               5                   10                  15

Phe Thr Glu Asp Arg
            20

<210> SEQ ID NO 219
<211> LENGTH: 15
<212> TYPE: PRT
<213> ORGANISM: Homo sapiens

<400> SEQUENCE: 219

Glu Leu Ile Gln Glu Tyr Gly Ala Gln Ser Gly Gly Leu Glu Lys
1               5                   10                  15

<210> SEQ ID NO 220
<211> LENGTH: 20
<212> TYPE: PRT
<213> ORGANISM: Homo sapiens

<400> SEQUENCE: 220

Leu Leu Glu Ile Ile Thr Thr Thr Ile Glu Glu Thr Glu Thr Gln Asn
1               5                   10                  15

Gln Gly Ile Lys
            20

<210> SEQ ID NO 221
<211> LENGTH: 12
<212> TYPE: PRT
<213> ORGANISM: Homo sapiens

<400> SEQUENCE: 221

Gly Glu Val Thr Ala Ala Asp Leu Phe Asn Ser Arg
1               5                   10

<210> SEQ ID NO 222
<211> LENGTH: 6
<212> TYPE: PRT
<213> ORGANISM: Homo sapiens

<400> SEQUENCE: 222

Thr Leu His Thr Leu Arg
1               5

<210> SEQ ID NO 223
<211> LENGTH: 17
<212> TYPE: PRT
<213> ORGANISM: Homo sapiens

<400> SEQUENCE: 223
```

```
Leu Ser Val Asp Glu Ala Val Asp Val Gly Leu Val Asn Glu Glu Leu
1               5                   10                  15

Arg

<210> SEQ ID NO 224
<211> LENGTH: 6
<212> TYPE: PRT
<213> ORGANISM: Homo sapiens

<400> SEQUENCE: 224

Ala Ala Thr Gly Tyr Arg
1               5

<210> SEQ ID NO 225
<211> LENGTH: 19
<212> TYPE: PRT
<213> ORGANISM: Homo sapiens

<400> SEQUENCE: 225

Leu Leu Glu Val Gln Val Ala Thr Gly Gly Val Ile Asp Pro Gln His
1               5                   10                  15

His His Arg

<210> SEQ ID NO 226
<211> LENGTH: 8
<212> TYPE: PRT
<213> ORGANISM: Homo sapiens

<400> SEQUENCE: 226

Leu Pro Leu Glu Thr Ala Tyr Arg
1               5

<210> SEQ ID NO 227
<211> LENGTH: 10
<212> TYPE: PRT
<213> ORGANISM: Homo sapiens

<400> SEQUENCE: 227

Asp Ile Tyr Ala Leu Ile Ser Asp Gln Lys
1               5                   10

<210> SEQ ID NO 228
<211> LENGTH: 9
<212> TYPE: PRT
<213> ORGANISM: Homo sapiens

<400> SEQUENCE: 228

Phe Val Asp Pro Asn Thr Gln Glu Lys
1               5

<210> SEQ ID NO 229
<211> LENGTH: 10
<212> TYPE: PRT
<213> ORGANISM: Homo sapiens

<400> SEQUENCE: 229

Asp Ser Glu His Ile Asp Asp Glu Thr Arg
1               5                   10

<210> SEQ ID NO 230
<211> LENGTH: 13
<212> TYPE: PRT
<213> ORGANISM: Homo sapiens
```

-continued

```
<400> SEQUENCE: 230

Ala Leu Glu Ala Glu Gln Val Glu Ile Thr Val Gly Arg
1               5                   10

<210> SEQ ID NO 231
<211> LENGTH: 19
<212> TYPE: PRT
<213> ORGANISM: Homo sapiens

<400> SEQUENCE: 231

Gly Gln Lys Pro Thr Leu Trp Ala Leu Leu Asn Ser Glu Tyr Val Thr
1               5                   10                  15

Glu Glu Lys

<210> SEQ ID NO 232
<211> LENGTH: 15
<212> TYPE: PRT
<213> ORGANISM: Homo sapiens

<400> SEQUENCE: 232

Ala Leu Gln Thr Val Ala Gln Leu Ile Leu Glu Leu Ile Glu Lys
1               5                   10                  15

<210> SEQ ID NO 233
<211> LENGTH: 6
<212> TYPE: PRT
<213> ORGANISM: Homo sapiens

<400> SEQUENCE: 233

Gln Glu Thr Ser Asn Lys
1               5

<210> SEQ ID NO 234
<211> LENGTH: 8
<212> TYPE: PRT
<213> ORGANISM: Homo sapiens

<400> SEQUENCE: 234

His Leu Trp Phe Gln Gly Ile Arg
1               5

<210> SEQ ID NO 235
<211> LENGTH: 19
<212> TYPE: PRT
<213> ORGANISM: Homo sapiens

<400> SEQUENCE: 235

Leu Ser Val Glu Glu Pro Val Pro Ala Gly Val Val Gly Ser Glu Ile
1               5                   10                  15

Gln Glu Lys

<210> SEQ ID NO 236
<211> LENGTH: 18
<212> TYPE: PRT
<213> ORGANISM: Homo sapiens

<400> SEQUENCE: 236

Gly Phe Phe Asp Pro Asn Thr His Glu Asn Leu Thr Tyr Val Gln Leu
1               5                   10                  15

Leu Arg

<210> SEQ ID NO 237
```

-continued

```
<211> LENGTH: 12
<212> TYPE: PRT
<213> ORGANISM: Homo sapiens

<400> SEQUENCE: 237

Gly Ser Ala Val His Gln Leu Ser Glu Glu Leu Arg
1               5                   10

<210> SEQ ID NO 238
<211> LENGTH: 22
<212> TYPE: PRT
<213> ORGANISM: Homo sapiens

<400> SEQUENCE: 238

Val Thr Pro Gly Ser Gly Ala Leu Gln Gly Gln Ser Val Ser Val Trp
1               5                   10                  15

Glu Leu Leu Phe Tyr Arg
            20

<210> SEQ ID NO 239
<211> LENGTH: 6
<212> TYPE: PRT
<213> ORGANISM: Homo sapiens

<400> SEQUENCE: 239

Glu Val Ser Glu Asp Arg
1               5

<210> SEQ ID NO 240
<211> LENGTH: 25
<212> TYPE: PRT
<213> ORGANISM: Homo sapiens

<400> SEQUENCE: 240

Ala Gly Thr Leu Thr Val Glu Glu Leu Gly Ala Thr Leu Thr Ser Leu
1               5                   10                  15

Leu Ala Gln Ala Gln Ala Gln Ala Arg
            20                  25

<210> SEQ ID NO 241
<211> LENGTH: 13
<212> TYPE: PRT
<213> ORGANISM: Homo sapiens

<400> SEQUENCE: 241

Ala Glu Ala Glu Ala Gly Ser Pro Arg Pro Asp Pro Arg
1               5                   10

<210> SEQ ID NO 242
<211> LENGTH: 15
<212> TYPE: PRT
<213> ORGANISM: Homo sapiens

<400> SEQUENCE: 242

Ala Val Pro Val Trp Asp Val Leu Ala Ser Gly Tyr Val Ser Arg
1               5                   10                  15

<210> SEQ ID NO 243
<211> LENGTH: 19
<212> TYPE: PRT
<213> ORGANISM: Homo sapiens

<400> SEQUENCE: 243

Glu Glu Leu Leu Ala Glu Phe Gly Ser Gly Thr Leu Asp Leu Pro Ala
```

```
1               5                   10                  15
Leu Thr Arg

<210> SEQ ID NO 244
<211> LENGTH: 22
<212> TYPE: PRT
<213> ORGANISM: Homo sapiens

<400> SEQUENCE: 244

Leu Thr Ala Ile Ile Glu Glu Ala Glu Glu Ala Pro Gly Ala Arg Pro
1               5                   10                  15

Gln Leu Gln Asp Ala Arg
            20

<210> SEQ ID NO 245
<211> LENGTH: 7
<212> TYPE: PRT
<213> ORGANISM: Homo sapiens

<400> SEQUENCE: 245

Glu Pro Gly Pro Ala Gly Arg
1               5

<210> SEQ ID NO 246
<211> LENGTH: 7
<212> TYPE: PRT
<213> ORGANISM: Homo sapiens

<400> SEQUENCE: 246

Gly Asp Gly Asp Ser Gly Arg
1               5

<210> SEQ ID NO 247
<211> LENGTH: 19
<212> TYPE: PRT
<213> ORGANISM: Homo sapiens

<400> SEQUENCE: 247

Glu Gly Gln Gly Glu Gly Glu Thr Gln Glu Ala Ala Ala Ala Ala
1               5                   10                  15

Ala Ala Arg

<210> SEQ ID NO 248
<211> LENGTH: 6
<212> TYPE: PRT
<213> ORGANISM: Homo sapiens

<400> SEQUENCE: 248

Gln Glu Gln Thr Leu Arg
1               5

<210> SEQ ID NO 249
<211> LENGTH: 23
<212> TYPE: PRT
<213> ORGANISM: Homo sapiens

<400> SEQUENCE: 249

Gly Gln Phe Gln Gly Arg Pro Val Ser Val Trp Asp Val Leu Phe Ser
1               5                   10                  15

Ser Tyr Leu Ser Glu Ala Arg
            20
```

<210> SEQ ID NO 250
<211> LENGTH: 23
<212> TYPE: PRT
<213> ORGANISM: Homo sapiens

<400> SEQUENCE: 250

Asp Glu Leu Leu Ala Gln His Ala Ala Gly Ala Leu Gly Leu Pro Asp
1               5                   10                  15

Leu Val Ala Val Leu Thr Arg
            20

<210> SEQ ID NO 251
<211> LENGTH: 8
<212> TYPE: PRT
<213> ORGANISM: Homo sapiens

<400> SEQUENCE: 251

Val Ile Glu Glu Thr Glu Glu Arg
1               5

<210> SEQ ID NO 252
<211> LENGTH: 19
<212> TYPE: PRT
<213> ORGANISM: Homo sapiens

<400> SEQUENCE: 252

Gln Val Ser Ala Ser Glu Leu His Thr Ser Gly Ile Leu Gly Pro Glu
1               5                   10                  15

Thr Leu Arg

<210> SEQ ID NO 253
<211> LENGTH: 7
<212> TYPE: PRT
<213> ORGANISM: Homo sapiens

<400> SEQUENCE: 253

Asp Leu Ala Gln Gly Thr Lys
1               5

<210> SEQ ID NO 254
<211> LENGTH: 19
<212> TYPE: PRT
<213> ORGANISM: Homo sapiens

<400> SEQUENCE: 254

Leu Ser Val Glu Glu Ala Val Ala Ala Gly Val Val Gly Gly Glu Ile
1               5                   10                  15

Gln Glu Lys

<210> SEQ ID NO 255
<211> LENGTH: 18
<212> TYPE: PRT
<213> ORGANISM: Homo sapiens

<400> SEQUENCE: 255

Ala Val Pro Val Trp Asp Val Leu Ala Ser Gly Tyr Val Ser Gly Ala
1               5                   10                  15

Ala Arg

<210> SEQ ID NO 256
<211> LENGTH: 23
<212> TYPE: PRT
<213> ORGANISM: Homo sapiens -continued

```
<400> SEQUENCE: 256

Leu Thr Ala Ile Ile Glu Glu Ala Glu Ala Pro Gly Ala Arg Pro
1               5                   10                  15

Gln Leu Gln Asp Ala Trp Arg
            20

<210> SEQ ID NO 257
<211> LENGTH: 25
<212> TYPE: PRT
<213> ORGANISM: Homo sapiens

<400> SEQUENCE: 257

Ala Ser Thr Leu Thr Val Glu Glu Leu Gly Ala Thr Leu Thr Ser Leu
1               5                   10                  15

Leu Ala Gln Ala Gln Ala Gln Ala Arg
            20                  25

<210> SEQ ID NO 258
<211> LENGTH: 19
<212> TYPE: PRT
<213> ORGANISM: Homo sapiens

<400> SEQUENCE: 258

Glu Gly Gln Gly Glu Gly Glu Thr Gln Glu Ala Ala Ala Ala Thr Ala
1               5                   10                  15

Ala Ala Arg

<210> SEQ ID NO 259
<211> LENGTH: 19
<212> TYPE: PRT
<213> ORGANISM: Homo sapiens

<400> SEQUENCE: 259

Gly Phe Phe Asp Pro Asn Thr His Glu Asn Leu Thr Tyr Leu Gln Leu
1               5                   10                  15

Leu Gln Arg

<210> SEQ ID NO 260
<211> LENGTH: 17
<212> TYPE: PRT
<213> ORGANISM: Homo sapiens

<400> SEQUENCE: 260

Ala Thr Leu Asp Pro Glu Thr Gly Leu Leu Phe Leu Ser Leu Ser Leu
1               5                   10                  15

Gln

<210> SEQ ID NO 261
<211> LENGTH: 10
<212> TYPE: PRT
<213> ORGANISM: Homo sapiens

<400> SEQUENCE: 261

Ser Ser Val Leu Glu Ser Leu Val Gly Arg
1               5                   10

<210> SEQ ID NO 262
<211> LENGTH: 7
<212> TYPE: PRT
<213> ORGANISM: Homo sapiens
```

<400> SEQUENCE: 262

Gly Thr Gly Ile Val Thr Arg
1               5

<210> SEQ ID NO 263
<211> LENGTH: 15
<212> TYPE: PRT
<213> ORGANISM: Homo sapiens

<400> SEQUENCE: 263

Arg Pro Leu Ile Leu Gln Leu Val His Val Ser Gln Glu Asp Lys
1               5                   10                  15

<210> SEQ ID NO 264
<211> LENGTH: 15
<212> TYPE: PRT
<213> ORGANISM: Homo sapiens

<400> SEQUENCE: 264

Thr Thr Gly Glu Glu Asn Gly Val Glu Ala Glu Glu Trp Gly Lys
1               5                   10                  15

<210> SEQ ID NO 265
<211> LENGTH: 9
<212> TYPE: PRT
<213> ORGANISM: Homo sapiens

<400> SEQUENCE: 265

Leu Tyr Thr Asp Phe Asp Glu Ile Arg
1               5

<210> SEQ ID NO 266
<211> LENGTH: 9
<212> TYPE: PRT
<213> ORGANISM: Homo sapiens

<400> SEQUENCE: 266

Gln Glu Ile Glu Asn Glu Thr Glu Arg
1               5

<210> SEQ ID NO 267
<211> LENGTH: 6
<212> TYPE: PRT
<213> ORGANISM: Homo sapiens

<400> SEQUENCE: 267

Ile Ser Gly Asn Asn Lys
1               5

<210> SEQ ID NO 268
<211> LENGTH: 10
<212> TYPE: PRT
<213> ORGANISM: Homo sapiens

<400> SEQUENCE: 268

Gly Val Ser Pro Glu Pro Ile His Leu Lys
1               5                   10

<210> SEQ ID NO 269
<211> LENGTH: 8
<212> TYPE: PRT
<213> ORGANISM: Homo sapiens

<400> SEQUENCE: 269

Val Pro Val Gly Asp Gln Pro Lys
1               5

<210> SEQ ID NO 270
<211> LENGTH: 7
<212> TYPE: PRT
<213> ORGANISM: Homo sapiens

<400> SEQUENCE: 270

Asp Ile Glu Leu Gln Ile Arg
1               5

<210> SEQ ID NO 271
<211> LENGTH: 7
<212> TYPE: PRT
<213> ORGANISM: Homo sapiens

<400> SEQUENCE: 271

Glu Val Asp Pro Asp Gly Arg
1               5

<210> SEQ ID NO 272
<211> LENGTH: 7
<212> TYPE: PRT
<213> ORGANISM: Homo sapiens

<400> SEQUENCE: 272

Thr Leu Ala Val Ile Thr Lys
1               5

<210> SEQ ID NO 273
<211> LENGTH: 9
<212> TYPE: PRT
<213> ORGANISM: Homo sapiens

<400> SEQUENCE: 273

Leu Gly Ile Ile Gly Val Val Asn Arg
1               5

<210> SEQ ID NO 274
<211> LENGTH: 8
<212> TYPE: PRT
<213> ORGANISM: Homo sapiens

<400> SEQUENCE: 274

Ser Gln Leu Asp Ile Asn Asn Lys
1               5

<210> SEQ ID NO 275
<211> LENGTH: 7
<212> TYPE: PRT
<213> ORGANISM: Homo sapiens

<400> SEQUENCE: 275

Ser Val Thr Asp Ser Ile Arg
1               5

<210> SEQ ID NO 276
<211> LENGTH: 8
<212> TYPE: PRT
<213> ORGANISM: Homo sapiens

<400> SEQUENCE: 276

Asp Glu Tyr Ala Phe Leu Gln Lys
1               5

<210> SEQ ID NO 277
<211> LENGTH: 7
<212> TYPE: PRT
<213> ORGANISM: Homo sapiens

<400> SEQUENCE: 277

Tyr Pro Ser Leu Ala Asn Arg
1               5

<210> SEQ ID NO 278
<211> LENGTH: 22
<212> TYPE: PRT
<213> ORGANISM: Homo sapiens

<400> SEQUENCE: 278

Ile Asn Val Leu Ala Ala Gln Tyr Gln Ser Leu Leu Asn Ser Tyr Gly
1               5                   10                  15

Glu Pro Val Asp Asp Lys
            20

<210> SEQ ID NO 279
<211> LENGTH: 10
<212> TYPE: PRT
<213> ORGANISM: Homo sapiens

<400> SEQUENCE: 279

Ser Ala Thr Leu Leu Gln Leu Ile Thr Lys
1               5                   10

<210> SEQ ID NO 280
<211> LENGTH: 21
<212> TYPE: PRT
<213> ORGANISM: Homo sapiens

<400> SEQUENCE: 280

Thr Leu Glu Ser Val Asp Pro Leu Gly Gly Leu Asn Thr Ile Asp Ile
1               5                   10                  15

Leu Thr Ala Ile Arg
            20

<210> SEQ ID NO 281
<211> LENGTH: 21
<212> TYPE: PRT
<213> ORGANISM: Homo sapiens

<400> SEQUENCE: 281

Asn Ala Thr Gly Pro Arg Pro Ala Leu Phe Val Pro Glu Val Ser Phe
1               5                   10                  15

Glu Leu Leu Val Lys
            20

<210> SEQ ID NO 282
<211> LENGTH: 7
<212> TYPE: PRT
<213> ORGANISM: Homo sapiens

<400> SEQUENCE: 282

Leu Glu Glu Pro Ser Leu Arg
1               5

<210> SEQ ID NO 283
<211> LENGTH: 8

```
<212> TYPE: PRT
<213> ORGANISM: Homo sapiens

<400> SEQUENCE: 283

Glu Leu Pro Ser Ala Val Ser Arg
1               5

<210> SEQ ID NO 284
<211> LENGTH: 23
<212> TYPE: PRT
<213> ORGANISM: Homo sapiens

<400> SEQUENCE: 284

Val Pro Ser Ala Leu Ala Pro Ala Ser Gln Glu Pro Ser Pro Ala Ala
1               5                   10                  15

Ser Ala Glu Ala Asp Gly Lys
            20

<210> SEQ ID NO 285
<211> LENGTH: 6
<212> TYPE: PRT
<213> ORGANISM: Homo sapiens

<400> SEQUENCE: 285

Leu Ile Gln Asp Ser Arg
1               5

<210> SEQ ID NO 286
<211> LENGTH: 22
<212> TYPE: PRT
<213> ORGANISM: Homo sapiens

<400> SEQUENCE: 286

Asn Val Ala Ser Gly Gly Gly Gly Val Gly Asp Gly Val Gln Glu Pro
1               5                   10                  15

Thr Thr Gly Asn Trp Arg
            20

<210> SEQ ID NO 287
<211> LENGTH: 9
<212> TYPE: PRT
<213> ORGANISM: Homo sapiens

<400> SEQUENCE: 287

Ala Glu Glu Leu Leu Ala Glu Glu Lys
1               5

<210> SEQ ID NO 288
<211> LENGTH: 15
<212> TYPE: PRT
<213> ORGANISM: Homo sapiens

<400> SEQUENCE: 288

Gly His Ala Val Asn Leu Leu Asp Val Pro Val Pro Val Ala Arg
1               5                   10                  15

<210> SEQ ID NO 289
<211> LENGTH: 7
<212> TYPE: PRT
<213> ORGANISM: Homo sapiens

<400> SEQUENCE: 289

Ser Tyr Phe Leu Ile Val Arg
1               5
```

```
<210> SEQ ID NO 290
<211> LENGTH: 8
<212> TYPE: PRT
<213> ORGANISM: Homo sapiens

<400> SEQUENCE: 290

Asn Ile Gln Asp Ser Val Pro Lys
1               5

<210> SEQ ID NO 291
<211> LENGTH: 13
<212> TYPE: PRT
<213> ORGANISM: Homo sapiens

<400> SEQUENCE: 291

Asp Thr Leu Gln Ser Glu Leu Val Gly Gln Leu Tyr Lys
1               5                   10

<210> SEQ ID NO 292
<211> LENGTH: 13
<212> TYPE: PRT
<213> ORGANISM: Homo sapiens

<400> SEQUENCE: 292

Ala Leu Gln Gly Ala Ser Gln Ile Ile Ala Glu Ile Arg
1               5                   10

<210> SEQ ID NO 293
<211> LENGTH: 14
<212> TYPE: PRT
<213> ORGANISM: Homo sapiens

<400> SEQUENCE: 293

Tyr Pro Pro His Ser Val Gln Tyr Thr Phe Pro Asn Thr Arg
1               5                   10

<210> SEQ ID NO 294
<211> LENGTH: 11
<212> TYPE: PRT
<213> ORGANISM: Homo sapiens

<400> SEQUENCE: 294

His Gln Gln Glu Phe Ala Val Pro Asp Tyr Arg
1               5                   10

<210> SEQ ID NO 295
<211> LENGTH: 22
<212> TYPE: PRT
<213> ORGANISM: Homo sapiens

<400> SEQUENCE: 295

Ser Ser His Leu Glu Val Ser Gln Ala Ser Gln Leu Leu Gln Gln Gln
1               5                   10                  15

Gln Gln Gln Gln Leu Arg
            20

<210> SEQ ID NO 296
<211> LENGTH: 18
<212> TYPE: PRT
<213> ORGANISM: Homo sapiens

<400> SEQUENCE: 296

Arg Pro Ser Leu Leu Ser Glu Phe His Pro Gly Ser Asp Arg Pro Gln
```

-continued

```
1               5                   10                  15

Glu Arg

<210> SEQ ID NO 297
<211> LENGTH: 21
<212> TYPE: PRT
<213> ORGANISM: Homo sapiens

<400> SEQUENCE: 297

Thr Ser Tyr Glu Pro Phe His Pro Gly Pro Ser Pro Val Asp His Asp
1               5                   10                  15

Ser Leu Glu Ser Lys
            20

<210> SEQ ID NO 298
<211> LENGTH: 11
<212> TYPE: PRT
<213> ORGANISM: Homo sapiens

<400> SEQUENCE: 298

Leu Glu Gln Val Ser Asp Ser His Phe Gln Arg
1               5                   10

<210> SEQ ID NO 299
<211> LENGTH: 17
<212> TYPE: PRT
<213> ORGANISM: Homo sapiens

<400> SEQUENCE: 299

Val Ser Ala Ala Val Leu Pro Leu Val His Pro Leu Pro Glu Gly Leu
1               5                   10                  15

Arg

<210> SEQ ID NO 300
<211> LENGTH: 6
<212> TYPE: PRT
<213> ORGANISM: Homo sapiens

<400> SEQUENCE: 300

Ala Ser Ala Asp Ala Lys
1               5

<210> SEQ ID NO 301
<211> LENGTH: 11
<212> TYPE: PRT
<213> ORGANISM: Homo sapiens

<400> SEQUENCE: 301

Ser Ile Val Gln Ile Ile Tyr Asp Glu Asn Arg
1               5                   10

<210> SEQ ID NO 302
<211> LENGTH: 8
<212> TYPE: PRT
<213> ORGANISM: Homo sapiens

<400> SEQUENCE: 302

Ile Phe Glu Gly Leu Gly Pro Lys
1               5

<210> SEQ ID NO 303
<211> LENGTH: 13
<212> TYPE: PRT
```

```
<213> ORGANISM: Homo sapiens

<400> SEQUENCE: 303

Val Glu Leu Pro Leu Tyr Asn Gln Pro Ser Asp Thr Lys
1               5                   10

<210> SEQ ID NO 304
<211> LENGTH: 7
<212> TYPE: PRT
<213> ORGANISM: Homo sapiens

<400> SEQUENCE: 304

Val Tyr His Glu Asn Ile Lys
1               5

<210> SEQ ID NO 305
<211> LENGTH: 6
<212> TYPE: PRT
<213> ORGANISM: Homo sapiens

<400> SEQUENCE: 305

Leu Ile Leu Phe Phe Lys
1               5

<210> SEQ ID NO 306
<211> LENGTH: 10
<212> TYPE: PRT
<213> ORGANISM: Homo sapiens

<400> SEQUENCE: 306

Gly Ala Gly Leu Ser Ala Thr Ile Ala Arg
1               5                   10

<210> SEQ ID NO 307
<211> LENGTH: 20
<212> TYPE: PRT
<213> ORGANISM: Homo sapiens

<400> SEQUENCE: 307

Ser Glu His Glu Ile Ser Glu Ile Ile Asp Gly Leu Ser Glu Gln Glu
1               5                   10                  15

Asn Asn Glu Lys
            20

<210> SEQ ID NO 308
<211> LENGTH: 6
<212> TYPE: PRT
<213> ORGANISM: Homo sapiens

<400> SEQUENCE: 308

Phe Ile Gln His Pro Lys
1               5

<210> SEQ ID NO 309
<211> LENGTH: 11
<212> TYPE: PRT
<213> ORGANISM: Homo sapiens

<400> SEQUENCE: 309

Asn Phe Gly Leu Ile Ala Ser Tyr Leu Glu Arg
1               5                   10

<210> SEQ ID NO 310
<211> LENGTH: 12
```

<212> TYPE: PRT
<213> ORGANISM: Homo sapiens

<400> SEQUENCE: 310

Asn Gln Gln Ile Ala Arg Pro Ser Gln Glu Glu Lys
1               5                   10

<210> SEQ ID NO 311
<211> LENGTH: 11
<212> TYPE: PRT
<213> ORGANISM: Homo sapiens

<400> SEQUENCE: 311

Ile Asp Gly Thr Ala Glu Glu Thr Glu Glu Arg
1               5                   10

<210> SEQ ID NO 312
<211> LENGTH: 6
<212> TYPE: PRT
<213> ORGANISM: Homo sapiens

<400> SEQUENCE: 312

Glu Gln Ala Thr Pro Arg
1               5

<210> SEQ ID NO 313
<211> LENGTH: 7
<212> TYPE: PRT
<213> ORGANISM: Homo sapiens

<400> SEQUENCE: 313

Gly Leu Val Glu His Gly Arg
1               5

<210> SEQ ID NO 314
<211> LENGTH: 7
<212> TYPE: PRT
<213> ORGANISM: Homo sapiens

<400> SEQUENCE: 314

Asn Trp Ala Ala Ile Ala Lys
1               5

<210> SEQ ID NO 315
<211> LENGTH: 11
<212> TYPE: PRT
<213> ORGANISM: Homo sapiens

<400> SEQUENCE: 315

His Asn Leu Asp Asn Leu Leu Gln Gln His Lys
1               5                   10

<210> SEQ ID NO 316
<211> LENGTH: 9
<212> TYPE: PRT
<213> ORGANISM: Homo sapiens

<400> SEQUENCE: 316

Ala Asp Ser Val Asp Val Glu Val Arg
1               5

<210> SEQ ID NO 317
<211> LENGTH: 8
<212> TYPE: PRT
<213> ORGANISM: Homo sapiens

```
<400> SEQUENCE: 317

Val Pro Glu Asn His Ala Ser Lys
1               5

<210> SEQ ID NO 318
<211> LENGTH: 7
<212> TYPE: PRT
<213> ORGANISM: Homo sapiens

<400> SEQUENCE: 318

Val Glu Gly Asp Asn Thr Lys
1               5

<210> SEQ ID NO 319
<211> LENGTH: 21
<212> TYPE: PRT
<213> ORGANISM: Homo sapiens

<400> SEQUENCE: 319

Glu Trp Glu Val Leu Gln Pro Ala Pro His Gln Val Ile Thr Asn Leu
1               5                   10                  15

Pro Glu Gly Val Arg
            20

<210> SEQ ID NO 320
<211> LENGTH: 18
<212> TYPE: PRT
<213> ORGANISM: Homo sapiens

<400> SEQUENCE: 320

Leu Pro Thr Thr Arg Pro Thr Arg Pro Pro Pro Leu Ile Pro Ser
1               5                   10                  15

Ser Lys

<210> SEQ ID NO 321
<211> LENGTH: 6
<212> TYPE: PRT
<213> ORGANISM: Homo sapiens

<400> SEQUENCE: 321

Gln Gln Glu Ser Ala Lys
1               5

<210> SEQ ID NO 322
<211> LENGTH: 8
<212> TYPE: PRT
<213> ORGANISM: Homo sapiens

<400> SEQUENCE: 322

Ser Ala Thr Leu Pro Tyr Ile Lys
1               5

<210> SEQ ID NO 323
<211> LENGTH: 7
<212> TYPE: PRT
<213> ORGANISM: Homo sapiens

<400> SEQUENCE: 323

Gln Glu Glu Phe Ser Pro Arg
1               5

<210> SEQ ID NO 324
```

```
<211> LENGTH: 12
<212> TYPE: PRT
<213> ORGANISM: Homo sapiens

<400> SEQUENCE: 324

Ser Gln Asn Ser Gln Pro Glu Gly Leu Leu Val Arg
1               5                   10

<210> SEQ ID NO 325
<211> LENGTH: 8
<212> TYPE: PRT
<213> ORGANISM: Homo sapiens

<400> SEQUENCE: 325

Ala Gln His Glu Gly Val Val Arg
1               5

<210> SEQ ID NO 326
<211> LENGTH: 13
<212> TYPE: PRT
<213> ORGANISM: Homo sapiens

<400> SEQUENCE: 326

Gly Thr Ala Gly Ala Ile Gln Glu Gly Ser Ile Thr Arg
1               5                   10

<210> SEQ ID NO 327
<211> LENGTH: 10
<212> TYPE: PRT
<213> ORGANISM: Homo sapiens

<400> SEQUENCE: 327

Ile Ser Val Glu Ser Ile Pro Ser Leu Arg
1               5                   10

<210> SEQ ID NO 328
<211> LENGTH: 22
<212> TYPE: PRT
<213> ORGANISM: Homo sapiens

<400> SEQUENCE: 328

Gly Ser Ile Thr Gln Gly Thr Pro Ala Leu Pro Gln Thr Gly Ile Pro
1               5                   10                  15

Thr Glu Ala Leu Val Lys
            20

<210> SEQ ID NO 329
<211> LENGTH: 11
<212> TYPE: PRT
<213> ORGANISM: Homo sapiens

<400> SEQUENCE: 329

Ser Gly His Ile Leu Ser Tyr Asp Asn Ile Lys
1               5                   10

<210> SEQ ID NO 330
<211> LENGTH: 8
<212> TYPE: PRT
<213> ORGANISM: Homo sapiens

<400> SEQUENCE: 330

Thr Ala His Glu Ile Ser Leu Lys
1               5
```

```
<210> SEQ ID NO 331
<211> LENGTH: 10
<212> TYPE: PRT
<213> ORGANISM: Homo sapiens

<400> SEQUENCE: 331

Ser Tyr Glu Ser Val Glu Gly Asn Ile Lys
1               5                   10

<210> SEQ ID NO 332
<211> LENGTH: 8
<212> TYPE: PRT
<213> ORGANISM: Homo sapiens

<400> SEQUENCE: 332

Gly Ser Pro His Ser Asp Leu Lys
1               5

<210> SEQ ID NO 333
<211> LENGTH: 11
<212> TYPE: PRT
<213> ORGANISM: Homo sapiens

<400> SEQUENCE: 333

Ala Thr Thr Glu Ser Phe Glu Asp Gly Leu Lys
1               5                   10

<210> SEQ ID NO 334
<211> LENGTH: 6
<212> TYPE: PRT
<213> ORGANISM: Homo sapiens

<400> SEQUENCE: 334

Glu Ser Pro Pro Ile Arg
1               5

<210> SEQ ID NO 335
<211> LENGTH: 8
<212> TYPE: PRT
<213> ORGANISM: Homo sapiens

<400> SEQUENCE: 335

Ala Phe Glu Gly Ala Ile Thr Lys
1               5

<210> SEQ ID NO 336
<211> LENGTH: 11
<212> TYPE: PRT
<213> ORGANISM: Homo sapiens

<400> SEQUENCE: 336

Gly Lys Pro Tyr Asp Gly Ile Thr Thr Ile Lys
1               5                   10

<210> SEQ ID NO 337
<211> LENGTH: 9
<212> TYPE: PRT
<213> ORGANISM: Homo sapiens

<400> SEQUENCE: 337

Gln Asp Ile Leu Thr Gln Glu Ser Arg
1               5

<210> SEQ ID NO 338
<211> LENGTH: 23
```

```
<212> TYPE: PRT
<213> ORGANISM: Homo sapiens

<400> SEQUENCE: 338

Thr Pro Glu Val Val Gln Ser Thr Arg Pro Ile Ile Glu Gly Ser Ile
1               5                   10                  15

Ser Gln Gly Thr Pro Ile Lys
            20

<210> SEQ ID NO 339
<211> LENGTH: 11
<212> TYPE: PRT
<213> ORGANISM: Homo sapiens

<400> SEQUENCE: 339

Phe Asp Asn Asn Ser Gly Gln Ser Ala Ile Lys
1               5                   10

<210> SEQ ID NO 340
<211> LENGTH: 8
<212> TYPE: PRT
<213> ORGANISM: Homo sapiens

<400> SEQUENCE: 340

Ser Leu Ile Thr Gly Pro Ser Lys
1               5

<210> SEQ ID NO 341
<211> LENGTH: 6
<212> TYPE: PRT
<213> ORGANISM: Homo sapiens

<400> SEQUENCE: 341

Ala Gly Glu Thr Val Arg
1               5

<210> SEQ ID NO 342
<211> LENGTH: 13
<212> TYPE: PRT
<213> ORGANISM: Homo sapiens

<400> SEQUENCE: 342

His Thr Ser Val Val Ser Ser Gly Pro Ser Val Leu Arg
1               5                   10

<210> SEQ ID NO 343
<211> LENGTH: 8
<212> TYPE: PRT
<213> ORGANISM: Homo sapiens

<400> SEQUENCE: 343

Ser Thr Leu His Glu Ala Pro Lys
1               5

<210> SEQ ID NO 344
<211> LENGTH: 14
<212> TYPE: PRT
<213> ORGANISM: Homo sapiens

<400> SEQUENCE: 344

Ala Gln Leu Ser Pro Gly Ile Tyr Asp Asp Thr Ser Ala Arg
1               5                   10

<210> SEQ ID NO 345
```

```
<211> LENGTH: 10
<212> TYPE: PRT
<213> ORGANISM: Homo sapiens

<400> SEQUENCE: 345

Thr Ser Asp Val Thr Ile Ser Ser Asn Lys
1               5                   10

<210> SEQ ID NO 346
<211> LENGTH: 6
<212> TYPE: PRT
<213> ORGANISM: Homo sapiens

<400> SEQUENCE: 346

Ser Thr Asn His Glu Arg
1               5

<210> SEQ ID NO 347
<211> LENGTH: 8
<212> TYPE: PRT
<213> ORGANISM: Homo sapiens

<400> SEQUENCE: 347

Ser Thr Leu Thr Pro Thr Gln Arg
1               5

<210> SEQ ID NO 348
<211> LENGTH: 6
<212> TYPE: PRT
<213> ORGANISM: Homo sapiens

<400> SEQUENCE: 348

Glu Ser Ile Pro Ala Lys
1               5

<210> SEQ ID NO 349
<211> LENGTH: 20
<212> TYPE: PRT
<213> ORGANISM: Homo sapiens

<400> SEQUENCE: 349

Ser Pro Val Pro Gly Val Asp Pro Val Ser His Ser Pro Phe Asp
1               5                   10                  15
Pro His His Arg
            20

<210> SEQ ID NO 350
<211> LENGTH: 9
<212> TYPE: PRT
<213> ORGANISM: Homo sapiens

<400> SEQUENCE: 350

Gly Ser Thr Ala Gly Glu Val Tyr Arg
1               5

<210> SEQ ID NO 351
<211> LENGTH: 13
<212> TYPE: PRT
<213> ORGANISM: Homo sapiens

<400> SEQUENCE: 351

Ala Leu Asp Pro Ala Ala Ala Ala Tyr Leu Phe Gln Arg
1               5                   10
```

```
<210> SEQ ID NO 352
<211> LENGTH: 12
<212> TYPE: PRT
<213> ORGANISM: Homo sapiens

<400> SEQUENCE: 352

Glu Gln Pro Leu Gly Leu Pro Tyr Pro Ala Thr Arg
1               5                   10

<210> SEQ ID NO 353
<211> LENGTH: 23
<212> TYPE: PRT
<213> ORGANISM: Homo sapiens

<400> SEQUENCE: 353

Tyr Glu Thr Pro Ser Asp Ala Ile Glu Val Ile Ser Pro Ala Ser Ser
1               5                   10                  15

Pro Ala Pro Pro Gln Glu Lys
            20

<210> SEQ ID NO 354
<211> LENGTH: 10
<212> TYPE: PRT
<213> ORGANISM: Homo sapiens

<400> SEQUENCE: 354

Leu Gln Thr Tyr Gln Pro Glu Val Val Lys
1               5                   10

<210> SEQ ID NO 355
<211> LENGTH: 10
<212> TYPE: PRT
<213> ORGANISM: Homo sapiens

<400> SEQUENCE: 355

Ala Asn Gln Ala Glu Asn Asp Pro Thr Arg
1               5                   10

<210> SEQ ID NO 356
<211> LENGTH: 18
<212> TYPE: PRT
<213> ORGANISM: Homo sapiens

<400> SEQUENCE: 356

Tyr Ser Pro Glu Ser Gln Ala Gln Ser Val His His Gln Arg Pro Gly
1               5                   10                  15

Ser Arg

<210> SEQ ID NO 357
<211> LENGTH: 9
<212> TYPE: PRT
<213> ORGANISM: Homo sapiens

<400> SEQUENCE: 357

Val Ser Pro Glu Asn Leu Val Asp Lys
1               5

<210> SEQ ID NO 358
<211> LENGTH: 22
<212> TYPE: PRT
<213> ORGANISM: Homo sapiens

<400> SEQUENCE: 358

Ser His Val Ser Ser Glu Pro Tyr Glu Pro Ile Ser Pro Pro Gln Val
```

```
1               5               10              15
Pro Val Val His Glu Lys
                20

<210> SEQ ID NO 359
<211> LENGTH: 10
<212> TYPE: PRT
<213> ORGANISM: Homo sapiens

<400> SEQUENCE: 359

Gln Asp Ser Leu Leu Leu Ser Gln Arg
1               5               10

<210> SEQ ID NO 360
<211> LENGTH: 8
<212> TYPE: PRT
<213> ORGANISM: Homo sapiens

<400> SEQUENCE: 360

Gly Ala Glu Pro Ala Glu Gln Arg
1               5

<210> SEQ ID NO 361
<211> LENGTH: 14
<212> TYPE: PRT
<213> ORGANISM: Homo sapiens

<400> SEQUENCE: 361

Ser Pro Gly Ser Ile Ser Tyr Leu Pro Ser Phe Phe Thr Lys
1               5               10

<210> SEQ ID NO 362
<211> LENGTH: 18
<212> TYPE: PRT
<213> ORGANISM: Homo sapiens

<400> SEQUENCE: 362

Gly His Ser Phe Ala Asp Pro Ala Ser Asn Leu Gly Leu Glu Asp Ile
1               5               10              15

Ile Arg

<210> SEQ ID NO 363
<211> LENGTH: 18
<212> TYPE: PRT
<213> ORGANISM: Homo sapiens

<400> SEQUENCE: 363

Glu Pro Ala Pro Leu Leu Ser Ala Gln Tyr Glu Thr Leu Ser Asp Ser
1               5               10              15

Asp Asp

<210> SEQ ID NO 364
<211> LENGTH: 13
<212> TYPE: PRT
<213> ORGANISM: Homo sapiens

<400> SEQUENCE: 364

Ser Ala Ala Val Ser Glu Gln Gln Gln Leu Glu Gln Lys
1               5               10

<210> SEQ ID NO 365
<211> LENGTH: 6
<212> TYPE: PRT
```

```
<213> ORGANISM: Homo sapiens

<400> SEQUENCE: 365

Thr Leu Glu Val Glu Lys
1               5

<210> SEQ ID NO 366
<211> LENGTH: 15
<212> TYPE: PRT
<213> ORGANISM: Homo sapiens

<400> SEQUENCE: 366

Thr Thr Ile Thr Ala Ala Asn Phe Ile Asp Val Ile Ile Thr Arg
1               5                   10                  15

<210> SEQ ID NO 367
<211> LENGTH: 6
<212> TYPE: PRT
<213> ORGANISM: Homo sapiens

<400> SEQUENCE: 367

Gln Ile Ala Ser Asp Lys
1               5

<210> SEQ ID NO 368
<211> LENGTH: 15
<212> TYPE: PRT
<213> ORGANISM: Homo sapiens

<400> SEQUENCE: 368

Gly Ser Gln Ser Ser Asp Ser Ser Ser Leu Ser Ser His Arg
1               5                   10                  15

<210> SEQ ID NO 369
<211> LENGTH: 6
<212> TYPE: PRT
<213> ORGANISM: Homo sapiens

<400> SEQUENCE: 369

Gly Phe Gly Ser Asp Lys
1               5

<210> SEQ ID NO 370
<211> LENGTH: 10
<212> TYPE: PRT
<213> ORGANISM: Homo sapiens

<400> SEQUENCE: 370

Glu Ala Ile Leu Asp Ile Ile Thr Ser Arg
1               5                   10

<210> SEQ ID NO 371
<211> LENGTH: 7
<212> TYPE: PRT
<213> ORGANISM: Homo sapiens

<400> SEQUENCE: 371

Asp Leu Ile Ala Asp Leu Lys
1               5

<210> SEQ ID NO 372
<211> LENGTH: 6
<212> TYPE: PRT
<213> ORGANISM: Homo sapiens
```

```
<400> SEQUENCE: 372

Tyr Glu Leu Thr Gly Lys
1               5

<210> SEQ ID NO 373
<211> LENGTH: 11
<212> TYPE: PRT
<213> ORGANISM: Homo sapiens

<400> SEQUENCE: 373

Asp Ala Ile Ser Gly Ile Gly Thr Asp Glu Lys
1               5                   10

<210> SEQ ID NO 374
<211> LENGTH: 16
<212> TYPE: PRT
<213> ORGANISM: Homo sapiens

<400> SEQUENCE: 374

Asp Leu Glu Ala Asp Ile Ile Gly Asp Thr Ser Gly His Phe Gln Lys
1               5                   10                  15

<210> SEQ ID NO 375
<211> LENGTH: 25
<212> TYPE: PRT
<213> ORGANISM: Homo sapiens

<400> SEQUENCE: 375

Glu Glu Asp Asp Val Val Ser Glu Asp Leu Val Gln Gln Asp Val Gln
1               5                   10                  15

Asp Leu Tyr Glu Ala Gly Glu Leu Lys
            20                  25

<210> SEQ ID NO 376
<211> LENGTH: 15
<212> TYPE: PRT
<213> ORGANISM: Homo sapiens

<400> SEQUENCE: 376

Trp Gly Thr Asp Glu Ala Gln Phe Ile Tyr Ile Leu Gly Asn Arg
1               5                   10                  15

<210> SEQ ID NO 377
<211> LENGTH: 8
<212> TYPE: PRT
<213> ORGANISM: Homo sapiens

<400> SEQUENCE: 377

Leu Val Phe Asp Glu Tyr Leu Lys
1               5

<210> SEQ ID NO 378
<211> LENGTH: 11
<212> TYPE: PRT
<213> ORGANISM: Homo sapiens

<400> SEQUENCE: 378

Thr Thr Gly Lys Pro Ile Glu Ala Ser Ile Arg
1               5                   10

<210> SEQ ID NO 379
<211> LENGTH: 9
<212> TYPE: PRT
<213> ORGANISM: Homo sapiens
```

<400> SEQUENCE: 379

Gly Glu Leu Ser Gly Asp Phe Glu Lys
1               5

<210> SEQ ID NO 380
<211> LENGTH: 9
<212> TYPE: PRT
<213> ORGANISM: Homo sapiens

<400> SEQUENCE: 380

Ser Thr Pro Glu Tyr Phe Ala Glu Arg
1               5

<210> SEQ ID NO 381
<211> LENGTH: 8
<212> TYPE: PRT
<213> ORGANISM: Homo sapiens

<400> SEQUENCE: 381

Asn Asp Thr Ser Gly Glu Tyr Lys
1               5

<210> SEQ ID NO 382
<211> LENGTH: 16
<212> TYPE: PRT
<213> ORGANISM: Homo sapiens

<400> SEQUENCE: 382

Gly Thr Val Arg Pro Ala Asn Asp Phe Asn Pro Asp Ala Asp Ala Lys
1               5                   10                  15

<210> SEQ ID NO 383
<211> LENGTH: 16
<212> TYPE: PRT
<213> ORGANISM: Homo sapiens

<400> SEQUENCE: 383

Gly Leu Gly Thr Asp Glu Asp Thr Ile Ile Asp Ile Ile Thr His Arg
1               5                   10                  15

<210> SEQ ID NO 384
<211> LENGTH: 9
<212> TYPE: PRT
<213> ORGANISM: Homo sapiens

<400> SEQUENCE: 384

Ser Glu Ile Ser Gly Asp Leu Ala Arg
1               5

<210> SEQ ID NO 385
<211> LENGTH: 9
<212> TYPE: PRT
<213> ORGANISM: Homo sapiens

<400> SEQUENCE: 385

Ala Leu Ile Glu Ile Leu Ala Thr Arg
1               5

<210> SEQ ID NO 386
<211> LENGTH: 6
<212> TYPE: PRT
<213> ORGANISM: Homo sapiens

<400> SEQUENCE: 386

Thr Asn Ala Glu Ile Arg
1               5

<210> SEQ ID NO 387
<211> LENGTH: 7
<212> TYPE: PRT
<213> ORGANISM: Homo sapiens

<400> SEQUENCE: 387

Ala Ile Asn Glu Ala Tyr Lys
1               5

<210> SEQ ID NO 388
<211> LENGTH: 15
<212> TYPE: PRT
<213> ORGANISM: Homo sapiens

<400> SEQUENCE: 388

Ser Leu Glu Asp Ala Leu Ser Ser Asp Thr Ser Gly His Phe Arg
1               5                   10                  15

<210> SEQ ID NO 389
<211> LENGTH: 10
<212> TYPE: PRT
<213> ORGANISM: Homo sapiens

<400> SEQUENCE: 389

Ile Leu Ile Ser Leu Ala Thr Gly His Arg
1               5                   10

<210> SEQ ID NO 390
<211> LENGTH: 11
<212> TYPE: PRT
<213> ORGANISM: Homo sapiens

<400> SEQUENCE: 390

Glu Glu Gly Gly Glu Asn Leu Asp Gln Ala Arg
1               5                   10

<210> SEQ ID NO 391
<211> LENGTH: 20
<212> TYPE: PRT
<213> ORGANISM: Homo sapiens

<400> SEQUENCE: 391

Glu Asp Ala Gln Val Ala Ala Glu Ile Leu Glu Ile Ala Asp Thr Pro
1               5                   10                  15

Ser Gly Asp Lys
            20

<210> SEQ ID NO 392
<211> LENGTH: 6
<212> TYPE: PRT
<213> ORGANISM: Homo sapiens

<400> SEQUENCE: 392

Ser Tyr Pro His Leu Arg
1               5

<210> SEQ ID NO 393
<211> LENGTH: 7
<212> TYPE: PRT
<213> ORGANISM: Homo sapiens -continued

```
<400> SEQUENCE: 393

Val Phe Gln Glu Phe Ile Lys
1               5

<210> SEQ ID NO 394
<211> LENGTH: 11
<212> TYPE: PRT
<213> ORGANISM: Homo sapiens

<400> SEQUENCE: 394

Asp Ala Phe Val Ala Ile Val Gln Ser Val Lys
1               5                   10

<210> SEQ ID NO 395
<211> LENGTH: 9
<212> TYPE: PRT
<213> ORGANISM: Homo sapiens

<400> SEQUENCE: 395

Asn Lys Pro Leu Phe Phe Ala Asp Lys
1               5

<210> SEQ ID NO 396
<211> LENGTH: 7
<212> TYPE: PRT
<213> ORGANISM: Homo sapiens

<400> SEQUENCE: 396

Gly Ala Gly Thr Asp Glu Lys
1               5

<210> SEQ ID NO 397
<211> LENGTH: 9
<212> TYPE: PRT
<213> ORGANISM: Homo sapiens

<400> SEQUENCE: 397

Ser Glu Ile Asp Leu Leu Asn Ile Arg
1               5

<210> SEQ ID NO 398
<211> LENGTH: 16
<212> TYPE: PRT
<213> ORGANISM: Homo sapiens

<400> SEQUENCE: 398

Ser Leu His Gln Ala Ile Glu Gly Asp Thr Ser Gly Asp Phe Leu Lys
1               5                   10                  15

<210> SEQ ID NO 399
<211> LENGTH: 14
<212> TYPE: PRT
<213> ORGANISM: Homo sapiens

<400> SEQUENCE: 399

Gly Phe Ser Ser Gly Ser Ala Val Val Ser Gly Gly Ser Arg
1               5                   10

<210> SEQ ID NO 400
<211> LENGTH: 16
<212> TYPE: PRT
<213> ORGANISM: Homo sapiens

<400> SEQUENCE: 400
```

His Gly Gly Gly Gly Gly Phe Gly Gly Gly Phe Gly Ser Arg
1               5                   10                  15

<210> SEQ ID NO 401
<211> LENGTH: 9
<212> TYPE: PRT
<213> ORGANISM: Homo sapiens

<400> SEQUENCE: 401

Ser Leu Val Gly Leu Gly Gly Thr Lys
1               5

<210> SEQ ID NO 402
<211> LENGTH: 22
<212> TYPE: PRT
<213> ORGANISM: Homo sapiens

<400> SEQUENCE: 402

Ser Ile Ser Ile Ser Val Ala Gly Gly Gly Gly Phe Gly Ala Ala
1               5                   10                  15

Gly Gly Phe Gly Gly Arg
            20

<210> SEQ ID NO 403
<211> LENGTH: 9
<212> TYPE: PRT
<213> ORGANISM: Homo sapiens

<400> SEQUENCE: 403

Val Asp Pro Glu Ile Gln Asn Val Lys
1               5

<210> SEQ ID NO 404
<211> LENGTH: 9
<212> TYPE: PRT
<213> ORGANISM: Homo sapiens

<400> SEQUENCE: 404

Tyr Leu Asp Gly Leu Thr Ala Glu Arg
1               5

<210> SEQ ID NO 405
<211> LENGTH: 11
<212> TYPE: PRT
<213> ORGANISM: Homo sapiens

<400> SEQUENCE: 405

Thr Ala Ala Glu Asn Asp Phe Val Thr Leu Lys
1               5                   10

<210> SEQ ID NO 406
<211> LENGTH: 6
<212> TYPE: PRT
<213> ORGANISM: Homo sapiens

<400> SEQUENCE: 406

Val Glu Leu Gln Ser Lys
1               5

<210> SEQ ID NO 407
<211> LENGTH: 12
<212> TYPE: PRT
<213> ORGANISM: Homo sapiens

<400> SEQUENCE: 407

```
Val Asp Leu Leu Asn Gln Glu Ile Glu Phe Leu Lys
1               5                   10
```

<210> SEQ ID NO 408
<211> LENGTH: 10
<212> TYPE: PRT
<213> ORGANISM: Homo sapiens

<400> SEQUENCE: 408

```
Glu Glu Ala Glu Ala Leu Tyr His Ser Lys
1               5                   10
```

<210> SEQ ID NO 409
<211> LENGTH: 10
<212> TYPE: PRT
<213> ORGANISM: Homo sapiens

<400> SEQUENCE: 409

```
Tyr Glu Glu Leu Gln Val Thr Val Gly Arg
1               5                   10
```

<210> SEQ ID NO 410
<211> LENGTH: 9
<212> TYPE: PRT
<213> ORGANISM: Homo sapiens

<400> SEQUENCE: 410

```
Leu Gln Gly Glu Ile Ala His Val Lys
1               5
```

<210> SEQ ID NO 411
<211> LENGTH: 12
<212> TYPE: PRT
<213> ORGANISM: Homo sapiens

<400> SEQUENCE: 411

```
Asn Val Gln Asp Ala Ile Ala Asp Ala Glu Gln Arg
1               5                   10
```

<210> SEQ ID NO 412
<211> LENGTH: 6
<212> TYPE: PRT
<213> ORGANISM: Homo sapiens

<400> SEQUENCE: 412

```
Gly Glu His Ala Leu Lys
1               5
```

<210> SEQ ID NO 413
<211> LENGTH: 12
<212> TYPE: PRT
<213> ORGANISM: Homo sapiens

<400> SEQUENCE: 413

```
Leu Asn Asp Leu Glu Glu Ala Leu Gln Gln Ala Lys
1               5                   10
```

<210> SEQ ID NO 414
<211> LENGTH: 9
<212> TYPE: PRT
<213> ORGANISM: Homo sapiens

<400> SEQUENCE: 414

```
Ala Ala Phe Gly Gly Ser Gly Gly Arg
```

```
<210> SEQ ID NO 415
<211> LENGTH: 20
<212> TYPE: PRT
<213> ORGANISM: Homo sapiens

<400> SEQUENCE: 415

Gly Ser Ser Ser Gly Gly Gly Tyr Ser Gly Ser Ser Ser Tyr Gly
1               5                   10                  15

Ser Gly Gly Arg
            20

<210> SEQ ID NO 416
<211> LENGTH: 23
<212> TYPE: PRT
<213> ORGANISM: Homo sapiens

<400> SEQUENCE: 416

Gly Gly Ser Gly Gly Gly Gly Ser Ile Ser Gly Gly Tyr Gly Ser
1               5                   10                  15

Gly Gly Gly Ser Gly Gly Arg
            20

<210> SEQ ID NO 417
<211> LENGTH: 8
<212> TYPE: PRT
<213> ORGANISM: Homo sapiens

<400> SEQUENCE: 417

Tyr Gly Ser Gly Gly Gly Ser Lys
1               5

<210> SEQ ID NO 418
<211> LENGTH: 15
<212> TYPE: PRT
<213> ORGANISM: Homo sapiens

<400> SEQUENCE: 418

Gly Gly Ser Ile Ser Gly Gly Gly Tyr Gly Ser Gly Gly Gly Lys
1               5                   10                  15

<210> SEQ ID NO 419
<211> LENGTH: 8
<212> TYPE: PRT
<213> ORGANISM: Homo sapiens

<400> SEQUENCE: 419

His Ser Ser Gly Gly Gly Ser Arg
1               5

<210> SEQ ID NO 420
<211> LENGTH: 20
<212> TYPE: PRT
<213> ORGANISM: Homo sapiens

<400> SEQUENCE: 420

Gly Gly Ser Ser Ser Gly Gly Gly Tyr Gly Ser Gly Gly Gly Ser
1               5                   10                  15

Ser Ser Val Lys
            20

<210> SEQ ID NO 421
```

```
<211> LENGTH: 16
<212> TYPE: PRT
<213> ORGANISM: Homo sapiens

<400> SEQUENCE: 421

Gly Ser Ser Gly Glu Ala Phe Gly Ser Ser Val Thr Phe Ser Phe Arg
1               5                   10                  15

<210> SEQ ID NO 422
<211> LENGTH: 15
<212> TYPE: PRT
<213> ORGANISM: Homo sapiens

<400> SEQUENCE: 422

Val Gly Ala His Ala Gly Glu Tyr Gly Ala Glu Ala Leu Glu Arg
1               5                   10                  15

<210> SEQ ID NO 423
<211> LENGTH: 16
<212> TYPE: PRT
<213> ORGANISM: Homo sapiens

<400> SEQUENCE: 423

Thr Tyr Phe Pro His Phe Asp Leu Ser His Gly Ser Ala Gln Val Lys
1               5                   10                  15

<210> SEQ ID NO 424
<211> LENGTH: 12
<212> TYPE: PRT
<213> ORGANISM: Homo sapiens

<400> SEQUENCE: 424

Phe Leu Ala Ser Val Ser Thr Val Leu Thr Ser Lys
1               5                   10

<210> SEQ ID NO 425
<211> LENGTH: 20
<212> TYPE: PRT
<213> ORGANISM: Homo sapiens

<400> SEQUENCE: 425

Glu Leu Leu Leu Pro Asn Trp Gln Gly Ser Gly Ser His Gly Leu Thr
1               5                   10                  15

Ile Ala Gln Arg
            20

<210> SEQ ID NO 426
<211> LENGTH: 17
<212> TYPE: PRT
<213> ORGANISM: Homo sapiens

<400> SEQUENCE: 426

Asp Asp Gly Val Phe Val Gln Glu Val Thr Gln Asn Ser Pro Ala Ala
1               5                   10                  15

Arg

<210> SEQ ID NO 427
<211> LENGTH: 10
<212> TYPE: PRT
<213> ORGANISM: Homo sapiens

<400> SEQUENCE: 427

Ser Pro Glu Pro Gly Gln Thr Trp Thr Arg
1               5                   10
```

<210> SEQ ID NO 428
<211> LENGTH: 15
<212> TYPE: PRT
<213> ORGANISM: Homo sapiens

<400> SEQUENCE: 428

Ser Glu Asp Gly Val Glu Gly Asp Leu Gly Glu Thr Gln Ser Arg
1               5                   10                  15

<210> SEQ ID NO 429
<211> LENGTH: 6
<212> TYPE: PRT
<213> ORGANISM: Homo sapiens

<400> SEQUENCE: 429

Thr Ile Thr Val Thr Arg
1               5

<210> SEQ ID NO 430
<211> LENGTH: 11
<212> TYPE: PRT
<213> ORGANISM: Homo sapiens

<400> SEQUENCE: 430

Val Thr Ala Tyr Thr Val Asp Val Thr Gly Arg
1               5                   10

<210> SEQ ID NO 431
<211> LENGTH: 10
<212> TYPE: PRT
<213> ORGANISM: Homo sapiens

<400> SEQUENCE: 431

Asp Ile Asp Ile Ser Ser Pro Glu Phe Lys
1               5                   10

<210> SEQ ID NO 432
<211> LENGTH: 17
<212> TYPE: PRT
<213> ORGANISM: Homo sapiens

<400> SEQUENCE: 432

His Glu Leu Thr Glu Ile Ser Asn Val Asp Val Glu Thr Gln Ser Gly
1               5                   10                  15

Lys

<210> SEQ ID NO 433
<211> LENGTH: 18
<212> TYPE: PRT
<213> ORGANISM: Homo sapiens

<400> SEQUENCE: 433

Leu Pro Ser Gly Ser Gly Ala Ala Ser Pro Thr Gly Ser Ala Val Asp
1               5                   10                  15

Ile Arg

<210> SEQ ID NO 434
<211> LENGTH: 18
<212> TYPE: PRT
<213> ORGANISM: Homo sapiens

<400> SEQUENCE: 434

```
Ala Gly Ala Ile Ser Ala Ser Gly Pro Glu Leu Gln Gly Ala Gly His
1               5                   10                  15

Ser Lys

<210> SEQ ID NO 435
<211> LENGTH: 11
<212> TYPE: PRT
<213> ORGANISM: Homo sapiens

<400> SEQUENCE: 435

Val Gly Gly Ser Gly Val Asn Val Asn Ala Lys
1               5                   10

<210> SEQ ID NO 436
<211> LENGTH: 7
<212> TYPE: PRT
<213> ORGANISM: Homo sapiens

<400> SEQUENCE: 436

Gly Leu Asp Leu Gly Gly Arg
1               5

<210> SEQ ID NO 437
<211> LENGTH: 17
<212> TYPE: PRT
<213> ORGANISM: Homo sapiens

<400> SEQUENCE: 437

Gly Gly Val Gln Val Pro Ala Val Asp Ile Ser Ser Ser Leu Gly Gly
1               5                   10                  15

Arg

<210> SEQ ID NO 438
<211> LENGTH: 16
<212> TYPE: PRT
<213> ORGANISM: Homo sapiens

<400> SEQUENCE: 438

Ala Val Glu Val Gln Gly Pro Ser Leu Glu Ser Gly Asp His Gly Lys
1               5                   10                  15

<210> SEQ ID NO 439
<211> LENGTH: 7
<212> TYPE: PRT
<213> ORGANISM: Homo sapiens

<400> SEQUENCE: 439

Phe Gly Val Ser Thr Gly Arg
1               5

<210> SEQ ID NO 440
<211> LENGTH: 6
<212> TYPE: PRT
<213> ORGANISM: Homo sapiens

<400> SEQUENCE: 440

Glu Gly Gln Thr Pro Lys
1               5

<210> SEQ ID NO 441
<211> LENGTH: 11
<212> TYPE: PRT
<213> ORGANISM: Homo sapiens
```

```
<400> SEQUENCE: 441

Val Ser Ala Pro Glu Val Ser Val Gly His Lys
1               5                   10

<210> SEQ ID NO 442
<211> LENGTH: 16
<212> TYPE: PRT
<213> ORGANISM: Homo sapiens

<400> SEQUENCE: 442

Gly Pro Gln Ile Thr Gly Pro Ser Leu Glu Gly Asp Leu Gly Leu Lys
1               5                   10                  15

<210> SEQ ID NO 443
<211> LENGTH: 7
<212> TYPE: PRT
<213> ORGANISM: Homo sapiens

<400> SEQUENCE: 443

Phe Ser Val Ser Gly Ala Lys
1               5

<210> SEQ ID NO 444
<211> LENGTH: 11
<212> TYPE: PRT
<213> ORGANISM: Homo sapiens

<400> SEQUENCE: 444

Val Ser Ala Pro Gly Val Gln Gly Asp Val Lys
1               5                   10

<210> SEQ ID NO 445
<211> LENGTH: 7
<212> TYPE: PRT
<213> ORGANISM: Homo sapiens

<400> SEQUENCE: 445

Gly Pro Gln Val Ala Leu Lys
1               5

<210> SEQ ID NO 446
<211> LENGTH: 16
<212> TYPE: PRT
<213> ORGANISM: Homo sapiens

<400> SEQUENCE: 446

Val Asp Ile Glu Thr Pro Asn Leu Glu Gly Thr Leu Thr Gly Pro Arg
1               5                   10                  15

<210> SEQ ID NO 447
<211> LENGTH: 7
<212> TYPE: PRT
<213> ORGANISM: Homo sapiens

<400> SEQUENCE: 447

Leu Gly Ser Pro Ser Gly Lys
1               5

<210> SEQ ID NO 448
<211> LENGTH: 9
<212> TYPE: PRT
<213> ORGANISM: Homo sapiens

<400> SEQUENCE: 448
```

Gly Gly Val Asp Val Thr Leu Pro Arg
1               5

<210> SEQ ID NO 449
<211> LENGTH: 7
<212> TYPE: PRT
<213> ORGANISM: Homo sapiens

<400> SEQUENCE: 449

Val Pro Glu Val Asp Val Arg
1               5

<210> SEQ ID NO 450
<211> LENGTH: 18
<212> TYPE: PRT
<213> ORGANISM: Homo sapiens

<400> SEQUENCE: 450

Val Asp Val Ser Ala Pro Asp Val Glu Ala His Gly Pro Glu Trp Asn
1               5                   10                  15

Leu Lys

<210> SEQ ID NO 451
<211> LENGTH: 9
<212> TYPE: PRT
<213> ORGANISM: Homo sapiens

<400> SEQUENCE: 451

Gly Asp Ile Ser Ile Ser Gly Pro Lys
1               5

<210> SEQ ID NO 452
<211> LENGTH: 16
<212> TYPE: PRT
<213> ORGANISM: Homo sapiens

<400> SEQUENCE: 452

Val Asn Val Glu Ala Pro Asp Val Asn Leu Glu Gly Leu Gly Gly Lys
1               5                   10                  15

<210> SEQ ID NO 453
<211> LENGTH: 9
<212> TYPE: PRT
<213> ORGANISM: Homo sapiens

<400> SEQUENCE: 453

Gly Glu Tyr Asp Val Thr Val Pro Lys
1               5

<210> SEQ ID NO 454
<211> LENGTH: 18
<212> TYPE: PRT
<213> ORGANISM: Homo sapiens

<400> SEQUENCE: 454

Val Asp Ile Asp Ala Pro Asp Val Asp Val His Gly Pro Asp Trp His
1               5                   10                  15

Leu Lys

<210> SEQ ID NO 455
<211> LENGTH: 7
<212> TYPE: PRT
<213> ORGANISM: Homo sapiens

```
<400> SEQUENCE: 455

Phe Ser Val Pro Gly Phe Lys
1               5

<210> SEQ ID NO 456
<211> LENGTH: 12
<212> TYPE: PRT
<213> ORGANISM: Homo sapiens

<400> SEQUENCE: 456

Ala Glu Gly Pro Glu Val Asp Val Asn Leu Pro Lys
1               5                   10

<210> SEQ ID NO 457
<211> LENGTH: 9
<212> TYPE: PRT
<213> ORGANISM: Homo sapiens

<400> SEQUENCE: 457

Ala Asp Val Asp Ile Ser Gly Pro Lys
1               5

<210> SEQ ID NO 458
<211> LENGTH: 16
<212> TYPE: PRT
<213> ORGANISM: Homo sapiens

<400> SEQUENCE: 458

Ile Asp Val Thr Ala Pro Asp Val Ser Ile Glu Gly Pro Glu Gly Lys
1               5                   10                  15

<210> SEQ ID NO 459
<211> LENGTH: 7
<212> TYPE: PRT
<213> ORGANISM: Homo sapiens

<400> SEQUENCE: 459

Val Pro Asp Val Glu Leu Lys
1               5

<210> SEQ ID NO 460
<211> LENGTH: 16
<212> TYPE: PRT
<213> ORGANISM: Homo sapiens

<400> SEQUENCE: 460

Val Gly Val Glu Val Pro Asp Val Asn Ile Glu Gly Pro Glu Gly Lys
1               5                   10                  15

<210> SEQ ID NO 461
<211> LENGTH: 12
<212> TYPE: PRT
<213> ORGANISM: Homo sapiens

<400> SEQUENCE: 461

Gly Glu Gly Pro Glu Phe Asp Val Asn Leu Ser Lys
1               5                   10

<210> SEQ ID NO 462
<211> LENGTH: 9
<212> TYPE: PRT
<213> ORGANISM: Homo sapiens

<400> SEQUENCE: 462
```

Ala Asn Val Asp Ile Ser Ala Pro Lys
1               5

<210> SEQ ID NO 463
<211> LENGTH: 16
<212> TYPE: PRT
<213> ORGANISM: Homo sapiens

<400> SEQUENCE: 463

Val Asp Thr Asn Ala Pro Asp Leu Ser Leu Glu Gly Pro Glu Gly Lys
1               5                   10                  15

<210> SEQ ID NO 464
<211> LENGTH: 9
<212> TYPE: PRT
<213> ORGANISM: Homo sapiens

<400> SEQUENCE: 464

Gly Asn Val Asp Ile Ser Ala Pro Lys
1               5

<210> SEQ ID NO 465
<211> LENGTH: 14
<212> TYPE: PRT
<213> ORGANISM: Homo sapiens

<400> SEQUENCE: 465

Ala Pro Asp Val Glu Gly Gln Gly Leu Asp Trp Ser Leu Lys
1               5                   10

<210> SEQ ID NO 466
<211> LENGTH: 12
<212> TYPE: PRT
<213> ORGANISM: Homo sapiens

<400> SEQUENCE: 466

Gly Glu Gly Pro Glu Val Asp Val Asn Leu Pro Lys
1               5                   10

<210> SEQ ID NO 467
<211> LENGTH: 9
<212> TYPE: PRT
<213> ORGANISM: Homo sapiens

<400> SEQUENCE: 467

Ala Asp Val Val Val Ser Gly Pro Lys
1               5

<210> SEQ ID NO 468
<211> LENGTH: 16
<212> TYPE: PRT
<213> ORGANISM: Homo sapiens

<400> SEQUENCE: 468

Val Asp Ile Glu Ala Pro Asp Val Ser Leu Glu Gly Pro Glu Gly Lys
1               5                   10                  15

<210> SEQ ID NO 469
<211> LENGTH: 9
<212> TYPE: PRT
<213> ORGANISM: Homo sapiens

<400> SEQUENCE: 469

Gly Asp Val Asp Val Ser Val Pro Lys
1               5

```
<210> SEQ ID NO 470
<211> LENGTH: 7
<212> TYPE: PRT
<213> ORGANISM: Homo sapiens

<400> SEQUENCE: 470

Val Pro Asp Val Glu Ile Lys
1               5

<210> SEQ ID NO 471
<211> LENGTH: 8
<212> TYPE: PRT
<213> ORGANISM: Homo sapiens

<400> SEQUENCE: 471

Glu Val Asp Val Asn Leu Pro Lys
1               5

<210> SEQ ID NO 472
<211> LENGTH: 9
<212> TYPE: PRT
<213> ORGANISM: Homo sapiens

<400> SEQUENCE: 472

Ala Asp Ile Asp Val Ser Gly Pro Lys
1               5

<210> SEQ ID NO 473
<211> LENGTH: 16
<212> TYPE: PRT
<213> ORGANISM: Homo sapiens

<400> SEQUENCE: 473

Val Asp Val Glu Val Pro Asp Val Ser Leu Glu Gly Pro Glu Gly Lys
1               5                   10                  15

<210> SEQ ID NO 474
<211> LENGTH: 18
<212> TYPE: PRT
<213> ORGANISM: Homo sapiens

<400> SEQUENCE: 474

Val Asp Ile Ser Ala Pro Asp Val His Gly Pro Asp Trp His
1               5                   10                  15

Leu Lys

<210> SEQ ID NO 475
<211> LENGTH: 9
<212> TYPE: PRT
<213> ORGANISM: Homo sapiens

<400> SEQUENCE: 475

Gly Glu Gly Pro Glu Val Asp Val Lys
1               5

<210> SEQ ID NO 476
<211> LENGTH: 9
<212> TYPE: PRT
<213> ORGANISM: Homo sapiens

<400> SEQUENCE: 476

Ala Asp Val Asp Val Ser Gly Pro Lys
1               5
```

<210> SEQ ID NO 477
<211> LENGTH: 11
<212> TYPE: PRT
<213> ORGANISM: Homo sapiens

<400> SEQUENCE: 477

Ile Ser Ile Pro Asp Val Gly Leu His Leu Lys
1               5                   10

<210> SEQ ID NO 478
<211> LENGTH: 9
<212> TYPE: PRT
<213> ORGANISM: Homo sapiens

<400> SEQUENCE: 478

Gly Asp Tyr Asp Val Thr Val Pro Lys
1               5

<210> SEQ ID NO 479
<211> LENGTH: 6
<212> TYPE: PRT
<213> ORGANISM: Homo sapiens

<400> SEQUENCE: 479

Val Glu Gly Glu Ile Lys
1               5

<210> SEQ ID NO 480
<211> LENGTH: 7
<212> TYPE: PRT
<213> ORGANISM: Homo sapiens

<400> SEQUENCE: 480

Ala Pro Asp Val Asp Ile Lys
1               5

<210> SEQ ID NO 481
<211> LENGTH: 18
<212> TYPE: PRT
<213> ORGANISM: Homo sapiens

<400> SEQUENCE: 481

Val Asp Ile Asn Ala Pro Asp Val Glu Val His Gly Pro Asp Trp His
1               5                   10                  15

Leu Lys

<210> SEQ ID NO 482
<211> LENGTH: 9
<212> TYPE: PRT
<213> ORGANISM: Homo sapiens

<400> SEQUENCE: 482

Ala Asp Leu Gly Val Ser Gly Pro Lys
1               5

<210> SEQ ID NO 483
<211> LENGTH: 16
<212> TYPE: PRT
<213> ORGANISM: Homo sapiens

<400> SEQUENCE: 483

Val Asp Ile Asp Val Pro Asp Val Asn Leu Glu Ala Pro Glu Gly Lys
1               5                   10                  15

<210> SEQ ID NO 484
<211> LENGTH: 9
<212> TYPE: PRT
<213> ORGANISM: Homo sapiens

<400> SEQUENCE: 484

Thr Asp Val Asp Val Ser Leu Pro Lys
1               5

<210> SEQ ID NO 485
<211> LENGTH: 6
<212> TYPE: PRT
<213> ORGANISM: Homo sapiens

<400> SEQUENCE: 485

Val Glu Gly Asp Leu Lys
1               5

<210> SEQ ID NO 486
<211> LENGTH: 7
<212> TYPE: PRT
<213> ORGANISM: Homo sapiens

<400> SEQUENCE: 486

Gly Pro Glu Ile Asp Val Lys
1               5

<210> SEQ ID NO 487
<211> LENGTH: 18
<212> TYPE: PRT
<213> ORGANISM: Homo sapiens

<400> SEQUENCE: 487

Val Asp Ile Asp Ala Pro Asp Val Glu Val His Asp Pro Asp Trp His
1               5                   10                  15

Leu Lys

<210> SEQ ID NO 488
<211> LENGTH: 25
<212> TYPE: PRT
<213> ORGANISM: Homo sapiens

<400> SEQUENCE: 488

Ala Asp Ile Asp Val Ser Gly Pro Ser Val Asp Thr Asp Ala Pro Asp
1               5                   10                  15

Leu Asp Ile Glu Gly Pro Glu Gly Lys
            20                  25

<210> SEQ ID NO 489
<211> LENGTH: 15
<212> TYPE: PRT
<213> ORGANISM: Homo sapiens

<400> SEQUENCE: 489

Gly Glu Ile Asp Ala Ser Val Pro Glu Leu Glu Gly Asp Leu Arg
1               5                   10                  15

<210> SEQ ID NO 490
<211> LENGTH: 9
<212> TYPE: PRT
<213> ORGANISM: Homo sapiens

<400> SEQUENCE: 490

Gly Asp Ala Asp Val Ser Val Pro Lys
1               5

<210> SEQ ID NO 491
<211> LENGTH: 9
<212> TYPE: PRT
<213> ORGANISM: Homo sapiens

<400> SEQUENCE: 491

Gly Asp Val Asp Val Ser Leu Pro Lys
1               5

<210> SEQ ID NO 492
<211> LENGTH: 7
<212> TYPE: PRT
<213> ORGANISM: Homo sapiens

<400> SEQUENCE: 492

Val Pro Asp Val Asp Ile Arg
1               5

<210> SEQ ID NO 493
<211> LENGTH: 9
<212> TYPE: PRT
<213> ORGANISM: Homo sapiens

<400> SEQUENCE: 493

Gly Asp Val Asp Val Ser Ala Pro Lys
1               5

<210> SEQ ID NO 494
<211> LENGTH: 7
<212> TYPE: PRT
<213> ORGANISM: Homo sapiens

<400> SEQUENCE: 494

Gly Pro Glu Leu Asp Val Lys
1               5

<210> SEQ ID NO 495
<211> LENGTH: 9
<212> TYPE: PRT
<213> ORGANISM: Homo sapiens

<400> SEQUENCE: 495

Gly Glu Val Asp Val Asp Val Pro Lys
1               5

<210> SEQ ID NO 496
<211> LENGTH: 19
<212> TYPE: PRT
<213> ORGANISM: Homo sapiens

<400> SEQUENCE: 496

Gly Pro His Val Asp Val Ser Gly Pro Asp Ile Asp Ile Glu Gly Pro
1               5                   10                  15

Glu Gly Lys

<210> SEQ ID NO 497
<211> LENGTH: 13
<212> TYPE: PRT
<213> ORGANISM: Homo sapiens

<400> SEQUENCE: 497

```
Gly Asp Val Asp Val Ser Val Pro Glu Val Glu Gly Lys
1               5                   10

<210> SEQ ID NO 498
<211> LENGTH: 16
<212> TYPE: PRT
<213> ORGANISM: Homo sapiens

<400> SEQUENCE: 498

Val Asp Val Asn Ala Pro Asp Val Gln Ala Pro Asp Trp His Leu Lys
1               5                   10                  15

<210> SEQ ID NO 499
<211> LENGTH: 16
<212> TYPE: PRT
<213> ORGANISM: Homo sapiens

<400> SEQUENCE: 499

Val Asp Ile Glu Gly Pro Asp Val Asn Ile Glu Gly Pro Glu Gly Lys
1               5                   10                  15

<210> SEQ ID NO 500
<211> LENGTH: 7
<212> TYPE: PRT
<213> ORGANISM: Homo sapiens

<400> SEQUENCE: 500

Gly Pro Glu Val Asp Ile Lys
1               5

<210> SEQ ID NO 501
<211> LENGTH: 18
<212> TYPE: PRT
<213> ORGANISM: Homo sapiens

<400> SEQUENCE: 501

Val Asp Ile Asn Ala Pro Asp Val Gly Val Gln Gly Pro Asp Trp His
1               5                   10                  15

Leu Lys

<210> SEQ ID NO 502
<211> LENGTH: 9
<212> TYPE: PRT
<213> ORGANISM: Homo sapiens

<400> SEQUENCE: 502

Gly Glu Gly Pro Asp Gly Asp Val Lys
1               5

<210> SEQ ID NO 503
<211> LENGTH: 12
<212> TYPE: PRT
<213> ORGANISM: Homo sapiens

<400> SEQUENCE: 503

Gly Glu Gly Pro Asp Val Asp Val Asn Leu Pro Lys
1               5                   10

<210> SEQ ID NO 504
<211> LENGTH: 9
<212> TYPE: PRT
<213> ORGANISM: Homo sapiens

<400> SEQUENCE: 504
```

-continued

```
Gly Asp Val Asp Val Thr Gly Pro Lys
1               5

<210> SEQ ID NO 505
<211> LENGTH: 7
<212> TYPE: PRT
<213> ORGANISM: Homo sapiens

<400> SEQUENCE: 505

Gly Pro Glu Val Asp Leu Lys
1               5

<210> SEQ ID NO 506
<211> LENGTH: 18
<212> TYPE: PRT
<213> ORGANISM: Homo sapiens

<400> SEQUENCE: 506

Val Asp Ile Asp Val Pro Asp Val Asn Val Gln Gly Pro Asp Trp His
1               5                   10                  15

Leu Lys

<210> SEQ ID NO 507
<211> LENGTH: 16
<212> TYPE: PRT
<213> ORGANISM: Homo sapiens

<400> SEQUENCE: 507

Val Asp Val Glu Gly Pro Asp Val Asn Ile Glu Gly Pro Glu Gly Lys
1               5                   10                  15

<210> SEQ ID NO 508
<211> LENGTH: 9
<212> TYPE: PRT
<213> ORGANISM: Homo sapiens

<400> SEQUENCE: 508

Gly Asp Val Asp Ile Ser Leu Pro Lys
1               5

<210> SEQ ID NO 509
<211> LENGTH: 7
<212> TYPE: PRT
<213> ORGANISM: Homo sapiens

<400> SEQUENCE: 509

Gly Pro Glu Val Asp Ile Arg
1               5

<210> SEQ ID NO 510
<211> LENGTH: 21
<212> TYPE: PRT
<213> ORGANISM: Homo sapiens

<400> SEQUENCE: 510

Gly Pro Gln Val Asp Ile Asp Val Pro Asp Val Gly Val Gln Gly Pro
1               5                   10                  15

Asp Trp His Leu Lys
            20

<210> SEQ ID NO 511
<211> LENGTH: 9
<212> TYPE: PRT
```

```
<213> ORGANISM: Homo sapiens

<400> SEQUENCE: 511

Ala Asp Leu Asp Val Ser Gly Pro Lys
1               5

<210> SEQ ID NO 512
<211> LENGTH: 16
<212> TYPE: PRT
<213> ORGANISM: Homo sapiens

<400> SEQUENCE: 512

Val Asp Ile Asp Val Pro Asp Val Asn Ile Glu Gly Pro Glu Gly Lys
1               5                   10                  15

<210> SEQ ID NO 513
<211> LENGTH: 18
<212> TYPE: PRT
<213> ORGANISM: Homo sapiens

<400> SEQUENCE: 513

Val Asp Ile Asn Ala Pro Asp Val Asp Val Gln Gly Pro Asp Trp His
1               5                   10                  15

Leu Lys

<210> SEQ ID NO 514
<211> LENGTH: 16
<212> TYPE: PRT
<213> ORGANISM: Homo sapiens

<400> SEQUENCE: 514

Val Asp Val Asp Val Pro Asp Val Asn Ile Glu Gly Pro Asp Ala Lys
1               5                   10                  15

<210> SEQ ID NO 515
<211> LENGTH: 15
<212> TYPE: PRT
<213> ORGANISM: Homo sapiens

<400> SEQUENCE: 515

Gly Glu Val Asp Val Ser Leu Ala Asn Val Glu Gly Asp Leu Lys
1               5                   10                  15

<210> SEQ ID NO 516
<211> LENGTH: 7
<212> TYPE: PRT
<213> ORGANISM: Homo sapiens

<400> SEQUENCE: 516

Gly Pro Ala Leu Asp Ile Lys
1               5

<210> SEQ ID NO 517
<211> LENGTH: 16
<212> TYPE: PRT
<213> ORGANISM: Homo sapiens

<400> SEQUENCE: 517

Ile Asp Val Asp Ala Pro Asp Ile Asp Ile His Gly Pro Asp Ala Lys
1               5                   10                  15

<210> SEQ ID NO 518
<211> LENGTH: 9
<212> TYPE: PRT
```

<213> ORGANISM: Homo sapiens

<400> SEQUENCE: 518

Gly Asp Val Asp Val Ser Gly Pro Lys
1               5

<210> SEQ ID NO 519
<211> LENGTH: 7
<212> TYPE: PRT
<213> ORGANISM: Homo sapiens

<400> SEQUENCE: 519

Ala Pro Ser Leu Asp Ile Lys
1               5

<210> SEQ ID NO 520
<211> LENGTH: 10
<212> TYPE: PRT
<213> ORGANISM: Homo sapiens

<400> SEQUENCE: 520

Gly Pro Glu Val Asp Val Ser Gly Pro Lys
1               5                   10

<210> SEQ ID NO 521
<211> LENGTH: 6
<212> TYPE: PRT
<213> ORGANISM: Homo sapiens

<400> SEQUENCE: 521

Leu Asn Ile Glu Gly Lys
1               5

<210> SEQ ID NO 522
<211> LENGTH: 7
<212> TYPE: PRT
<213> ORGANISM: Homo sapiens

<400> SEQUENCE: 522

Phe Asn Phe Ser Gly Ser Lys
1               5

<210> SEQ ID NO 523
<211> LENGTH: 9
<212> TYPE: PRT
<213> ORGANISM: Homo sapiens

<400> SEQUENCE: 523

Val Gln Thr Pro Glu Val Asp Val Lys
1               5

<210> SEQ ID NO 524
<211> LENGTH: 10
<212> TYPE: PRT
<213> ORGANISM: Homo sapiens

<400> SEQUENCE: 524

Lys Pro Asp Ile Asp Ile Thr Gly Pro Lys
1               5                   10

<210> SEQ ID NO 525
<211> LENGTH: 13
<212> TYPE: PRT
<213> ORGANISM: Homo sapiens -continued

<400> SEQUENCE: 525

Val Asp Ile Asn Ala Pro Asp Val Glu Val Gln Gly Lys
1               5                   10

<210> SEQ ID NO 526
<211> LENGTH: 15
<212> TYPE: PRT
<213> ORGANISM: Homo sapiens

<400> SEQUENCE: 526

Gly Asp Leu Asp Ile Ala Gly Pro Asn Leu Glu Gly Asp Phe Lys
1               5                   10                  15

<210> SEQ ID NO 527
<211> LENGTH: 21
<212> TYPE: PRT
<213> ORGANISM: Homo sapiens

<400> SEQUENCE: 527

Ala Pro Glu Val Asn Leu Asn Ala Pro Asp Val Asp Val His Gly Pro
1               5                   10                  15

Asp Trp Asn Leu Lys
            20

<210> SEQ ID NO 528
<211> LENGTH: 12
<212> TYPE: PRT
<213> ORGANISM: Homo sapiens

<400> SEQUENCE: 528

Ala Glu Gly Pro Asp Val Ala Val Asp Leu Pro Lys
1               5                   10

<210> SEQ ID NO 529
<211> LENGTH: 18
<212> TYPE: PRT
<213> ORGANISM: Homo sapiens

<400> SEQUENCE: 529

Val Asp Ile Asn Ala Pro Asp Val Asp Val His Gly Pro Asp Trp His
1               5                   10                  15

Leu Lys

<210> SEQ ID NO 530
<211> LENGTH: 12
<212> TYPE: PRT
<213> ORGANISM: Homo sapiens

<400> SEQUENCE: 530

Gly Glu Gly Pro Glu Val Asp Val Thr Leu Pro Lys
1               5                   10

<210> SEQ ID NO 531
<211> LENGTH: 25
<212> TYPE: PRT
<213> ORGANISM: Homo sapiens

<400> SEQUENCE: 531

Ala Asp Ile Asp Ile Ser Gly Pro Asn Val Asp Val Asp Val Pro Asp
1               5                   10                  15

Val Asn Ile Glu Gly Pro Asp Ala Lys
            20                  25

<210> SEQ ID NO 532
<211> LENGTH: 9
<212> TYPE: PRT
<213> ORGANISM: Homo sapiens

<400> SEQUENCE: 532

Gly Asp Val Val Val Ser Leu Pro Lys
1               5

<210> SEQ ID NO 533
<211> LENGTH: 16
<212> TYPE: PRT
<213> ORGANISM: Homo sapiens

<400> SEQUENCE: 533

Val Asp Ile Asp Thr Pro Asp Ile Asn Ile Glu Gly Ser Glu Gly Lys
1               5                   10                  15

<210> SEQ ID NO 534
<211> LENGTH: 11
<212> TYPE: PRT
<213> ORGANISM: Homo sapiens

<400> SEQUENCE: 534

Val Asp Ile Asn Ala Pro Asp Val Asp Val Arg
1               5                   10

<210> SEQ ID NO 535
<211> LENGTH: 7
<212> TYPE: PRT
<213> ORGANISM: Homo sapiens

<400> SEQUENCE: 535

Gly Pro Asp Trp His Leu Lys
1               5

<210> SEQ ID NO 536
<211> LENGTH: 7
<212> TYPE: PRT
<213> ORGANISM: Homo sapiens

<400> SEQUENCE: 536

Ala Pro Glu Val Asp Ile Lys
1               5

<210> SEQ ID NO 537
<211> LENGTH: 16
<212> TYPE: PRT
<213> ORGANISM: Homo sapiens

<400> SEQUENCE: 537

Val Asp Ile Asp Thr Pro Asp Ile Asp Ile His Gly Pro Glu Gly Lys
1               5                   10                  15

<210> SEQ ID NO 538
<211> LENGTH: 18
<212> TYPE: PRT
<213> ORGANISM: Homo sapiens

<400> SEQUENCE: 538

Val Asp Ile Asp Val Pro Asp Val Asp Val Gln Gly Pro Asp Trp His
1               5                   10                  15

Leu Lys

```
<210> SEQ ID NO 539
<211> LENGTH: 16
<212> TYPE: PRT
<213> ORGANISM: Homo sapiens

<400> SEQUENCE: 539

Val Asp Ile Asp Val Pro Asp Val Asn Ile Glu Gly Pro Asp Ala Lys
1               5                   10                  15

<210> SEQ ID NO 540
<211> LENGTH: 12
<212> TYPE: PRT
<213> ORGANISM: Homo sapiens

<400> SEQUENCE: 540

Gly Glu Gly Pro Asp Val Asp Val Thr Leu Pro Lys
1               5                   10

<210> SEQ ID NO 541
<211> LENGTH: 9
<212> TYPE: PRT
<213> ORGANISM: Homo sapiens

<400> SEQUENCE: 541

Ala Asp Ile Glu Ile Ser Gly Pro Lys
1               5

<210> SEQ ID NO 542
<211> LENGTH: 16
<212> TYPE: PRT
<213> ORGANISM: Homo sapiens

<400> SEQUENCE: 542

Val Asp Ile Asp Ala Pro Asp Val Ser Ile Glu Gly Pro Asp Ala Lys
1               5                   10                  15

<210> SEQ ID NO 543
<211> LENGTH: 19
<212> TYPE: PRT
<213> ORGANISM: Homo sapiens

<400> SEQUENCE: 543

Gly Pro Ser Leu Asp Ile Asp Thr Pro Asp Val Asn Ile Glu Gly Pro
1               5                   10                  15

Glu Gly Lys

<210> SEQ ID NO 544
<211> LENGTH: 12
<212> TYPE: PRT
<213> ORGANISM: Homo sapiens

<400> SEQUENCE: 544

Gly Pro Glu Val Asp Ile Glu Gly Pro Glu Gly Lys
1               5                   10

<210> SEQ ID NO 545
<211> LENGTH: 16
<212> TYPE: PRT
<213> ORGANISM: Homo sapiens

<400> SEQUENCE: 545

Val Gly Ile Asp Thr Pro Asp Ile Asp Ile His Gly Pro Glu Gly Lys
1               5                   10                  15
```

```
<210> SEQ ID NO 546
<211> LENGTH: 9
<212> TYPE: PRT
<213> ORGANISM: Homo sapiens

<400> SEQUENCE: 546

Gly Asp Val Asp Val Thr Leu Pro Lys
1               5

<210> SEQ ID NO 547
<211> LENGTH: 7
<212> TYPE: PRT
<213> ORGANISM: Homo sapiens

<400> SEQUENCE: 547

Gly Pro Glu Ala Asp Ile Lys
1               5

<210> SEQ ID NO 548
<211> LENGTH: 18
<212> TYPE: PRT
<213> ORGANISM: Homo sapiens

<400> SEQUENCE: 548

Val Asp Ile Asn Thr Pro Asp Val Asp Val His Gly Pro Asp Trp His
1               5                   10                  15

Leu Lys

<210> SEQ ID NO 549
<211> LENGTH: 12
<212> TYPE: PRT
<213> ORGANISM: Homo sapiens

<400> SEQUENCE: 549

Gly Glu Gly Pro Asp Val Asp Val Ser Leu Pro Lys
1               5                   10

<210> SEQ ID NO 550
<211> LENGTH: 16
<212> TYPE: PRT
<213> ORGANISM: Homo sapiens

<400> SEQUENCE: 550

Val Asp Val Asp Ile Pro Asp Val Asn Ile Glu Gly Pro Asp Ala Lys
1               5                   10                  15

<210> SEQ ID NO 551
<211> LENGTH: 11
<212> TYPE: PRT
<213> ORGANISM: Homo sapiens

<400> SEQUENCE: 551

Ile Ser Ile Pro Asp Val Asp Leu Asp Leu Lys
1               5                   10

<210> SEQ ID NO 552
<211> LENGTH: 9
<212> TYPE: PRT
<213> ORGANISM: Homo sapiens

<400> SEQUENCE: 552

Gly Asp Phe Asp Val Ser Val Pro Lys
1               5
```

<210> SEQ ID NO 553
<211> LENGTH: 6
<212> TYPE: PRT
<213> ORGANISM: Homo sapiens

<400> SEQUENCE: 553

Val Glu Gly Thr Leu Lys
1               5

<210> SEQ ID NO 554
<211> LENGTH: 9
<212> TYPE: PRT
<213> ORGANISM: Homo sapiens

<400> SEQUENCE: 554

Leu Asp Phe Glu Gly Pro Asp Ala Lys
1               5

<210> SEQ ID NO 555
<211> LENGTH: 7
<212> TYPE: PRT
<213> ORGANISM: Homo sapiens

<400> SEQUENCE: 555

Leu Ser Gly Pro Ser Leu Lys
1               5

<210> SEQ ID NO 556
<211> LENGTH: 11
<212> TYPE: PRT
<213> ORGANISM: Homo sapiens

<400> SEQUENCE: 556

Val Thr Ala Pro Asp Val Asp Leu His Leu Lys
1               5                   10

<210> SEQ ID NO 557
<211> LENGTH: 7
<212> TYPE: PRT
<213> ORGANISM: Homo sapiens

<400> SEQUENCE: 557

Ile Gly Phe Ser Gly Pro Lys
1               5

<210> SEQ ID NO 558
<211> LENGTH: 9
<212> TYPE: PRT
<213> ORGANISM: Homo sapiens

<400> SEQUENCE: 558

Leu Glu Gly Gly Glu Val Asp Leu Lys
1               5

<210> SEQ ID NO 559
<211> LENGTH: 6
<212> TYPE: PRT
<213> ORGANISM: Homo sapiens

<400> SEQUENCE: 559

Phe Gly Phe Gly Ala Lys
1               5

<210> SEQ ID NO 560

```
<211> LENGTH: 25
<212> TYPE: PRT
<213> ORGANISM: Homo sapiens

<400> SEQUENCE: 560

Ser Pro Ser Leu Asp Val Thr Val Pro Glu Ala Glu Leu Asn Leu Glu
1               5                   10                  15

Thr Pro Glu Ile Ser Val Gly Gly Lys
            20                  25

<210> SEQ ID NO 561
<211> LENGTH: 17
<212> TYPE: PRT
<213> ORGANISM: Homo sapiens

<400> SEQUENCE: 561

Gln Gly Phe Asp Leu Asn Val Pro Gly Gly Glu Ile Asp Ala Ser Leu
1               5                   10                  15

Lys

<210> SEQ ID NO 562
<211> LENGTH: 16
<212> TYPE: PRT
<213> ORGANISM: Homo sapiens

<400> SEQUENCE: 562

Ala Pro Asp Val Asp Val Asn Ile Ala Gly Pro Asp Ala Ala Leu Lys
1               5                   10                  15

<210> SEQ ID NO 563
<211> LENGTH: 9
<212> TYPE: PRT
<213> ORGANISM: Homo sapiens

<400> SEQUENCE: 563

Ala Glu Ala Pro Leu Pro Ser Pro Lys
1               5

<210> SEQ ID NO 564
<211> LENGTH: 25
<212> TYPE: PRT
<213> ORGANISM: Homo sapiens

<400> SEQUENCE: 564

Leu Glu Gly Glu Leu Gln Ala Pro Asp Leu Glu Leu Ser Leu Pro Ala
1               5                   10                  15

Ile His Val Glu Gly Leu Asp Ile Lys
            20                  25

<210> SEQ ID NO 565
<211> LENGTH: 6
<212> TYPE: PRT
<213> ORGANISM: Homo sapiens

<400> SEQUENCE: 565

Ile Glu Gly Asp Leu Lys
1               5

<210> SEQ ID NO 566
<211> LENGTH: 18
<212> TYPE: PRT
<213> ORGANISM: Homo sapiens

<400> SEQUENCE: 566
```

```
Val Gln Ala Asn Leu Gly Ala Pro Asp Ile Asn Ile Glu Gly Leu Asp
1               5                   10                  15

Ala Lys

<210> SEQ ID NO 567
<211> LENGTH: 21
<212> TYPE: PRT
<213> ORGANISM: Homo sapiens

<400> SEQUENCE: 567

Thr Pro Ser Phe Gly Ile Ser Ala Pro Gln Val Ser Ile Pro Asp Val
1               5                   10                  15

Asn Val Asn Leu Lys
            20

<210> SEQ ID NO 568
<211> LENGTH: 21
<212> TYPE: PRT
<213> ORGANISM: Homo sapiens

<400> SEQUENCE: 568

Gly Asp Val Pro Ser Val Gly Leu Glu Gly Pro Asp Val Asp Leu Gln
1               5                   10                  15

Gly Pro Glu Ala Lys
            20

<210> SEQ ID NO 569
<211> LENGTH: 7
<212> TYPE: PRT
<213> ORGANISM: Homo sapiens

<400> SEQUENCE: 569

Ile Gly Ile Pro Gly Val Lys
1               5

<210> SEQ ID NO 570
<211> LENGTH: 9
<212> TYPE: PRT
<213> ORGANISM: Homo sapiens

<400> SEQUENCE: 570

Leu Glu Gly Pro Asp Val Ser Leu Lys
1               5

<210> SEQ ID NO 571
<211> LENGTH: 11
<212> TYPE: PRT
<213> ORGANISM: Homo sapiens

<400> SEQUENCE: 571

Val Ser Gly Pro Asp Leu Asp Leu Asn Leu Lys
1               5                   10

<210> SEQ ID NO 572
<211> LENGTH: 14
<212> TYPE: PRT
<213> ORGANISM: Homo sapiens

<400> SEQUENCE: 572

Val His Ala Pro Gly Leu Asn Leu Ser Gly Val Gly Gly Lys
1               5                   10
```

```
<210> SEQ ID NO 573
<211> LENGTH: 9
<212> TYPE: PRT
<213> ORGANISM: Homo sapiens

<400> SEQUENCE: 573

Val Pro Gly Ile Asp Ala Thr Thr Lys
1               5

<210> SEQ ID NO 574
<211> LENGTH: 11
<212> TYPE: PRT
<213> ORGANISM: Homo sapiens

<400> SEQUENCE: 574

Leu Asn Val Gly Ala Pro Asp Val Thr Leu Arg
1               5                   10

<210> SEQ ID NO 575
<211> LENGTH: 15
<212> TYPE: PRT
<213> ORGANISM: Homo sapiens

<400> SEQUENCE: 575

Gly Pro Ser Leu Gln Gly Asp Leu Ala Val Ser Gly Asp Ile Lys
1               5                   10                  15

<210> SEQ ID NO 576
<211> LENGTH: 18
<212> TYPE: PRT
<213> ORGANISM: Homo sapiens

<400> SEQUENCE: 576

Val Ser Val Gly Ala Pro Asp Leu Ser Leu Glu Ala Ser Glu Gly Ser
1               5                   10                  15

Ile Lys

<210> SEQ ID NO 577
<211> LENGTH: 18
<212> TYPE: PRT
<213> ORGANISM: Homo sapiens

<400> SEQUENCE: 577

Leu Pro Gln Phe Gly Ile Ser Thr Pro Gly Ser Asp Leu His Val Asn
1               5                   10                  15

Ala Lys

<210> SEQ ID NO 578
<211> LENGTH: 9
<212> TYPE: PRT
<213> ORGANISM: Homo sapiens

<400> SEQUENCE: 578

Gly Pro Gln Val Ser Gly Glu Leu Lys
1               5

<210> SEQ ID NO 579
<211> LENGTH: 9
<212> TYPE: PRT
<213> ORGANISM: Homo sapiens

<400> SEQUENCE: 579

Gly Pro Gly Val Asp Val Asn Leu Lys
1               5
```

<210> SEQ ID NO 580
<211> LENGTH: 14
<212> TYPE: PRT
<213> ORGANISM: Homo sapiens

<400> SEQUENCE: 580

Ile Ser Ala Pro Asn Val Asp Phe Asn Leu Glu Gly Pro Lys
1               5                   10

<210> SEQ ID NO 581
<211> LENGTH: 10
<212> TYPE: PRT
<213> ORGANISM: Homo sapiens

<400> SEQUENCE: 581

Gly Ser Leu Gly Ala Thr Gly Glu Ile Lys
1               5                   10

<210> SEQ ID NO 582
<211> LENGTH: 12
<212> TYPE: PRT
<213> ORGANISM: Homo sapiens

<400> SEQUENCE: 582

Leu Pro Thr Gly Gln Ile Ser Gly Pro Glu Ile Lys
1               5                   10

<210> SEQ ID NO 583
<211> LENGTH: 16
<212> TYPE: PRT
<213> ORGANISM: Homo sapiens

<400> SEQUENCE: 583

Gly Ser Glu Val Gly Phe His Gly Ala Ala Pro Asp Ile Ser Val Lys
1               5                   10                  15

<210> SEQ ID NO 584
<211> LENGTH: 24
<212> TYPE: PRT
<213> ORGANISM: Homo sapiens

<400> SEQUENCE: 584

Gly Gly Ala Asp Val Ser Gly Gly Val Ser Ala Pro Asp Ile Ser Leu
1               5                   10                  15

Gly Glu Gly His Leu Ser Val Lys
            20

<210> SEQ ID NO 585
<211> LENGTH: 7
<212> TYPE: PRT
<213> ORGANISM: Homo sapiens

<400> SEQUENCE: 585

Gly Ser Gly Gly Glu Trp Lys
1               5

<210> SEQ ID NO 586
<211> LENGTH: 14
<212> TYPE: PRT
<213> ORGANISM: Homo sapiens

<400> SEQUENCE: 586

Gly Pro Gln Val Ser Ser Ala Leu Asn Leu Asp Thr Ser Lys 1               5                   10

<210> SEQ ID NO 587
<211> LENGTH: 11
<212> TYPE: PRT
<213> ORGANISM: Homo sapiens

<400> SEQUENCE: 587

Phe Ala Gly Gly Leu His Phe Ser Gly Pro Lys
1               5                   10

<210> SEQ ID NO 588
<211> LENGTH: 6
<212> TYPE: PRT
<213> ORGANISM: Homo sapiens

<400> SEQUENCE: 588

Val Glu Gly Gly Val Lys
1               5

<210> SEQ ID NO 589
<211> LENGTH: 6
<212> TYPE: PRT
<213> ORGANISM: Homo sapiens

<400> SEQUENCE: 589

Phe Thr Phe Ser Gly Arg
1               5

<210> SEQ ID NO 590
<211> LENGTH: 20
<212> TYPE: PRT
<213> ORGANISM: Homo sapiens

<400> SEQUENCE: 590

Ala Glu Ala Ser Ile Gln Ala Gly Ala Gly Asp Gly Glu Trp Glu Glu
1               5                   10                  15

Ser Glu Val Lys
            20

<210> SEQ ID NO 591
<211> LENGTH: 7
<212> TYPE: PRT
<213> ORGANISM: Homo sapiens

<400> SEQUENCE: 591

Phe Asn Phe Ser Lys Pro Lys
1               5

<210> SEQ ID NO 592
<211> LENGTH: 15
<212> TYPE: PRT
<213> ORGANISM: Homo sapiens

<400> SEQUENCE: 592

Gly Gly Val Thr Gly Ser Pro Glu Ala Ser Ile Ser Gly Ser Lys
1               5                   10                  15

<210> SEQ ID NO 593
<211> LENGTH: 18
<212> TYPE: PRT
<213> ORGANISM: Homo sapiens

<400> SEQUENCE: 593

```
Ala Ser Leu Gly Ser Leu Glu Gly Glu Ala Glu Ala Glu Ala Ser Ser
1               5                   10                  15

Pro Lys

<210> SEQ ID NO 594
<211> LENGTH: 8
<212> TYPE: PRT
<213> ORGANISM: Homo sapiens

<400> SEQUENCE: 594

Ser Asn Ser Phe Ser Asp Glu Arg
1               5

<210> SEQ ID NO 595
<211> LENGTH: 25
<212> TYPE: PRT
<213> ORGANISM: Homo sapiens

<400> SEQUENCE: 595

Glu Phe Ser Gly Pro Ser Thr Pro Thr Gly Thr Leu Glu Phe Glu Gly
1               5                   10                  15

Gly Glu Val Ser Leu Glu Gly Gly Lys
            20                  25

<210> SEQ ID NO 596
<211> LENGTH: 10
<212> TYPE: PRT
<213> ORGANISM: Homo sapiens

<400> SEQUENCE: 596

Phe Gly Thr Phe Gly Gly Leu Gly Ser Lys
1               5                   10

<210> SEQ ID NO 597
<211> LENGTH: 14
<212> TYPE: PRT
<213> ORGANISM: Homo sapiens

<400> SEQUENCE: 597

Gly His Tyr Glu Val Thr Gly Ser Asp Asp Glu Thr Gly Lys
1               5                   10

<210> SEQ ID NO 598
<211> LENGTH: 11
<212> TYPE: PRT
<213> ORGANISM: Homo sapiens

<400> SEQUENCE: 598

Leu Gln Gly Ser Gly Val Ser Leu Ala Ser Lys
1               5                   10

<210> SEQ ID NO 599
<211> LENGTH: 12
<212> TYPE: PRT
<213> ORGANISM: Homo sapiens

<400> SEQUENCE: 599

Leu Ser Ser Ser Ser Ser Asn Asp Ser Gly Asn Lys
1               5                   10

<210> SEQ ID NO 600
<211> LENGTH: 15
<212> TYPE: PRT
<213> ORGANISM: Homo sapiens
```

```
<400> SEQUENCE: 600

Val Gly Ile Gln Leu Pro Glu Val Glu Leu Ser Val Ser Thr Lys
1               5                   10                  15

<210> SEQ ID NO 601
<211> LENGTH: 9
<212> TYPE: PRT
<213> ORGANISM: Homo sapiens

<400> SEQUENCE: 601

Val Asp Gly Ser Val Asp Phe Tyr Arg
1               5

<210> SEQ ID NO 602
<211> LENGTH: 6
<212> TYPE: PRT
<213> ORGANISM: Homo sapiens

<400> SEQUENCE: 602

Asp Trp Ala Thr Tyr Lys
1               5

<210> SEQ ID NO 603
<211> LENGTH: 23
<212> TYPE: PRT
<213> ORGANISM: Homo sapiens

<400> SEQUENCE: 603

Leu Gly Glu Phe Trp Leu Gly Asn Asp Asn Ile His Ala Leu Thr Ala
1               5                   10                  15

Gln Gly Thr Ser Glu Leu Arg
            20

<210> SEQ ID NO 604
<211> LENGTH: 14
<212> TYPE: PRT
<213> ORGANISM: Homo sapiens

<400> SEQUENCE: 604

Val Asp Leu Val Asp Phe Glu Asp Asn Tyr Gln Phe Ala Lys
1               5                   10

<210> SEQ ID NO 605
<211> LENGTH: 13
<212> TYPE: PRT
<213> ORGANISM: Homo sapiens

<400> SEQUENCE: 605

Gly Thr His Gly Ser Phe Ala Asn Gly Ile Asn Trp Lys
1               5                   10

<210> SEQ ID NO 606
<211> LENGTH: 7
<212> TYPE: PRT
<213> ORGANISM: Homo sapiens

<400> SEQUENCE: 606

Gly Tyr Asn Tyr Ser Tyr Lys
1               5

<210> SEQ ID NO 607
<211> LENGTH: 8
<212> TYPE: PRT
```

<213> ORGANISM: Homo sapiens

<400> SEQUENCE: 607

Gly Glu Ala Gly Thr Asn Gly Lys
1               5

<210> SEQ ID NO 608
<211> LENGTH: 9
<212> TYPE: PRT
<213> ORGANISM: Homo sapiens

<400> SEQUENCE: 608

Leu Val Ala Ser Ser His Ile Ser Lys
1               5

<210> SEQ ID NO 609
<211> LENGTH: 9
<212> TYPE: PRT
<213> ORGANISM: Homo sapiens

<400> SEQUENCE: 609

Thr Ser Leu Ser Val Asp Pro Ser Arg
1               5

<210> SEQ ID NO 610
<211> LENGTH: 11
<212> TYPE: PRT
<213> ORGANISM: Homo sapiens

<400> SEQUENCE: 610

Gly Tyr Pro Glu Pro Gln Val Thr Trp His Arg
1               5                   10

<210> SEQ ID NO 611
<211> LENGTH: 10
<212> TYPE: PRT
<213> ORGANISM: Homo sapiens

<400> SEQUENCE: 611

Asn Gly Gln Pro Ile Thr Ser Gly Gly Arg
1               5                   10

<210> SEQ ID NO 612
<211> LENGTH: 15
<212> TYPE: PRT
<213> ORGANISM: Homo sapiens

<400> SEQUENCE: 612

Gly Thr Phe Ser Leu Val Ile His Ala Val His Glu Glu Asp Arg
1               5                   10                  15

<210> SEQ ID NO 613
<211> LENGTH: 14
<212> TYPE: PRT
<213> ORGANISM: Homo sapiens

<400> SEQUENCE: 613

Gln Val Thr Val Glu Leu Thr Val Glu Gly Ser Phe Ala Lys
1               5                   10

<210> SEQ ID NO 614
<211> LENGTH: 9
<212> TYPE: PRT
<213> ORGANISM: Homo sapiens

```
<400> SEQUENCE: 614

Gln Leu Gly Gln Pro Val Val Ser Lys
1               5

<210> SEQ ID NO 615
<211> LENGTH: 13
<212> TYPE: PRT
<213> ORGANISM: Homo sapiens

<400> SEQUENCE: 615

Ile Thr Gly Arg Pro Gln Pro Gln Val Thr Trp Leu Lys
1               5                   10

<210> SEQ ID NO 616
<211> LENGTH: 10
<212> TYPE: PRT
<213> ORGANISM: Homo sapiens

<400> SEQUENCE: 616

Gly Asn Val Pro Leu Gln Pro Ser Ala Arg
1               5                   10

<210> SEQ ID NO 617
<211> LENGTH: 6
<212> TYPE: PRT
<213> ORGANISM: Homo sapiens

<400> SEQUENCE: 617

Val Ser Val Ser Glu Lys
1               5

<210> SEQ ID NO 618
<211> LENGTH: 7
<212> TYPE: PRT
<213> ORGANISM: Homo sapiens

<400> SEQUENCE: 618

Ala Thr Asn Ser Asp Val Arg
1               5

<210> SEQ ID NO 619
<211> LENGTH: 8
<212> TYPE: PRT
<213> ORGANISM: Homo sapiens

<400> SEQUENCE: 619

Glu Val Thr Asn Val Ile Ser Lys
1               5

<210> SEQ ID NO 620
<211> LENGTH: 9
<212> TYPE: PRT
<213> ORGANISM: Homo sapiens

<400> SEQUENCE: 620

Leu Asp Ser Leu Glu Ala Ala Ala Lys
1               5

<210> SEQ ID NO 621
<211> LENGTH: 16
<212> TYPE: PRT
<213> ORGANISM: Homo sapiens

<400> SEQUENCE: 621
```

-continued

Gly Gly Ser Pro Pro Trp Ala Ala Asn Ser Gln Pro Gln Pro Pro Arg
1               5                   10                  15

<210> SEQ ID NO 622
<211> LENGTH: 10
<212> TYPE: PRT
<213> ORGANISM: Homo sapiens

<400> SEQUENCE: 622

Thr Ala Pro Gln Thr Pro Val Leu Gln Lys
1               5                   10

<210> SEQ ID NO 623
<211> LENGTH: 11
<212> TYPE: PRT
<213> ORGANISM: Homo sapiens

<400> SEQUENCE: 623

Thr Ser Ser Ser Ile Thr Leu Gln Ala Ala Arg
1               5                   10

<210> SEQ ID NO 624
<211> LENGTH: 6
<212> TYPE: PRT
<213> ORGANISM: Homo sapiens

<400> SEQUENCE: 624

Val Gln Pro Glu Pro Arg
1               5

<210> SEQ ID NO 625
<211> LENGTH: 14
<212> TYPE: PRT
<213> ORGANISM: Homo sapiens

<400> SEQUENCE: 625

Ala Pro Gly Leu Gly Val Leu Ser Pro Ser Gly Glu Glu Arg
1               5                   10

<210> SEQ ID NO 626
<211> LENGTH: 13
<212> TYPE: PRT
<213> ORGANISM: Homo sapiens

<400> SEQUENCE: 626

Arg Pro Ala Pro Pro Arg Pro Ala Thr Phe Pro Thr Arg
1               5                   10

<210> SEQ ID NO 627
<211> LENGTH: 12
<212> TYPE: PRT
<213> ORGANISM: Homo sapiens

<400> SEQUENCE: 627

Gln Pro Gly Leu Gly Ser Gln Asp Val Val Ser Lys
1               5                   10

<210> SEQ ID NO 628
<211> LENGTH: 6
<212> TYPE: PRT
<213> ORGANISM: Homo sapiens

<400> SEQUENCE: 628

Asp Ser Ala Phe Pro Lys
1               5

<210> SEQ ID NO 629
<211> LENGTH: 11
<212> TYPE: PRT
<213> ORGANISM: Homo sapiens

<400> SEQUENCE: 629

Phe Glu Ser Lys Pro Gln Ser Gln Glu Val Lys
1               5                   10

<210> SEQ ID NO 630
<211> LENGTH: 6
<212> TYPE: PRT
<213> ORGANISM: Homo sapiens

<400> SEQUENCE: 630

Glu Asn Gln Thr Val Lys
1               5

<210> SEQ ID NO 631
<211> LENGTH: 14
<212> TYPE: PRT
<213> ORGANISM: Homo sapiens

<400> SEQUENCE: 631

Ile Thr Trp Leu Leu Asn Gly Gln Pro Ile Gln Tyr Ala Arg
1               5                   10

<210> SEQ ID NO 632
<211> LENGTH: 25
<212> TYPE: PRT
<213> ORGANISM: Homo sapiens

<400> SEQUENCE: 632

Ser Glu Tyr Leu Leu Pro Val Ala Pro Ser Lys Pro Thr Ala Pro Ile
1               5                   10                  15

Phe Leu Gln Gly Leu Ser Asp Leu Lys
            20                  25

<210> SEQ ID NO 633
<211> LENGTH: 23
<212> TYPE: PRT
<213> ORGANISM: Homo sapiens

<400> SEQUENCE: 633

Thr Gln Ala Val Leu Thr Val Gln Glu Pro His Asp Gly Thr Gln Pro
1               5                   10                  15

Trp Phe Ile Ser Lys Pro Arg
            20

<210> SEQ ID NO 634
<211> LENGTH: 19
<212> TYPE: PRT
<213> ORGANISM: Homo sapiens

<400> SEQUENCE: 634

Asp Thr Gly His Phe Glu Val Leu Gln Asn Glu Asp Val Phe Thr Leu
1               5                   10                  15

Val Leu Lys

<210> SEQ ID NO 635
<211> LENGTH: 14
<212> TYPE: PRT

<213> ORGANISM: Homo sapiens

<400> SEQUENCE: 635

Val Gln Pro Trp His Ala Gly Gln Tyr Glu Ile Leu Leu Lys
1               5                   10

<210> SEQ ID NO 636
<211> LENGTH: 11
<212> TYPE: PRT
<213> ORGANISM: Homo sapiens

<400> SEQUENCE: 636

Tyr Gly Ser Leu Arg Pro Gly Trp Pro Ala Arg
1               5                   10

<210> SEQ ID NO 637
<211> LENGTH: 14
<212> TYPE: PRT
<213> ORGANISM: Homo sapiens

<400> SEQUENCE: 637

Gly Gln Gly Trp Leu Glu Glu Asp Gly Glu Asp Val Arg
1               5                   10

<210> SEQ ID NO 638
<211> LENGTH: 8
<212> TYPE: PRT
<213> ORGANISM: Homo sapiens

<400> SEQUENCE: 638

Gln His Thr Glu Glu Ala Ile Arg
1               5

<210> SEQ ID NO 639
<211> LENGTH: 10
<212> TYPE: PRT
<213> ORGANISM: Homo sapiens

<400> SEQUENCE: 639

Gln Gln Glu Val Glu Gln Leu Asp Phe Arg
1               5                   10

<210> SEQ ID NO 640
<211> LENGTH: 8
<212> TYPE: PRT
<213> ORGANISM: Homo sapiens

<400> SEQUENCE: 640

Thr Leu Ser Glu Asp Asp Leu Lys
1               5

<210> SEQ ID NO 641
<211> LENGTH: 7
<212> TYPE: PRT
<213> ORGANISM: Homo sapiens

<400> SEQUENCE: 641

Thr Val Ser Glu Glu Glu Arg
1               5

<210> SEQ ID NO 642
<211> LENGTH: 10
<212> TYPE: PRT
<213> ORGANISM: Homo sapiens

<400> SEQUENCE: 642

Val His Ser Pro Gln Gln Val Asp Phe Arg
1               5                   10

<210> SEQ ID NO 643
<211> LENGTH: 12
<212> TYPE: PRT
<213> ORGANISM: Homo sapiens

<400> SEQUENCE: 643

Val Pro Pro Pro Lys Pro Ala Thr Pro Asp Phe Arg
1               5                   10

<210> SEQ ID NO 644
<211> LENGTH: 16
<212> TYPE: PRT
<213> ORGANISM: Homo sapiens

<400> SEQUENCE: 644

Leu Pro Ala Glu Asn Gly Ser Ser Ser Ala Glu Thr Leu Asn Ala Lys
1               5                   10                  15

<210> SEQ ID NO 645
<211> LENGTH: 10
<212> TYPE: PRT
<213> ORGANISM: Homo sapiens

<400> SEQUENCE: 645

Gly His Ala Gly Thr Thr Asp Asn Glu Lys
1               5                   10

<210> SEQ ID NO 646
<211> LENGTH: 11
<212> TYPE: PRT
<213> ORGANISM: Homo sapiens

<400> SEQUENCE: 646

Ser Glu Ser Gln Gly Thr Ala Pro Ala Phe Lys
1               5                   10

<210> SEQ ID NO 647
<211> LENGTH: 10
<212> TYPE: PRT
<213> ORGANISM: Homo sapiens

<400> SEQUENCE: 647

Leu Gln Asp Val His Val Ala Glu Gly Lys
1               5                   10

<210> SEQ ID NO 648
<211> LENGTH: 6
<212> TYPE: PRT
<213> ORGANISM: Homo sapiens

<400> SEQUENCE: 648

Ala Leu Pro Glu Asp Arg
1               5

<210> SEQ ID NO 649
<211> LENGTH: 16
<212> TYPE: PRT
<213> ORGANISM: Homo sapiens

<400> SEQUENCE: 649

```
Ser Ser Leu Pro Pro Val Leu Gly Thr Glu Ser Asp Ala Thr Val Lys
1               5                   10                  15
```

<210> SEQ ID NO 650
<211> LENGTH: 10
<212> TYPE: PRT
<213> ORGANISM: Homo sapiens

<400> SEQUENCE: 650

```
Ala Gly Glu Ser Val Glu Leu Phe Gly Lys
1               5                   10
```

<210> SEQ ID NO 651
<211> LENGTH: 9
<212> TYPE: PRT
<213> ORGANISM: Homo sapiens

<400> SEQUENCE: 651

```
Val Glu Asn Ser Glu Asn Gly Ser Lys
1               5
```

<210> SEQ ID NO 652
<211> LENGTH: 7
<212> TYPE: PRT
<213> ORGANISM: Homo sapiens

<400> SEQUENCE: 652

```
Leu Thr Ile Leu Ala Ala Arg
1               5
```

<210> SEQ ID NO 653
<211> LENGTH: 16
<212> TYPE: PRT
<213> ORGANISM: Homo sapiens

<400> SEQUENCE: 653

```
Ser Thr Ser Phe Asn Val Gln Asp Leu Leu Pro Asp His Glu Tyr Lys
1               5                   10                  15
```

<210> SEQ ID NO 654
<211> LENGTH: 11
<212> TYPE: PRT
<213> ORGANISM: Homo sapiens

<400> SEQUENCE: 654

```
Asp Glu Val Glu Val Ser Asp Asp Glu Gly Lys
1               5                   10
```

<210> SEQ ID NO 655
<211> LENGTH: 7
<212> TYPE: PRT
<213> ORGANISM: Homo sapiens

<400> SEQUENCE: 655

```
Glu Pro Glu Val Asp Tyr Arg
1               5
```

<210> SEQ ID NO 656
<211> LENGTH: 9
<212> TYPE: PRT
<213> ORGANISM: Homo sapiens

<400> SEQUENCE: 656

```
Thr Val Thr Ile Asn Thr Glu Gln Lys
1               5
```

```
<210> SEQ ID NO 657
<211> LENGTH: 10
<212> TYPE: PRT
<213> ORGANISM: Homo sapiens

<400> SEQUENCE: 657

Val Ser Asp Phe Tyr Asp Ile Glu Glu Arg
1               5                   10

<210> SEQ ID NO 658
<211> LENGTH: 11
<212> TYPE: PRT
<213> ORGANISM: Homo sapiens

<400> SEQUENCE: 658

Ile Ile Asp Glu Asp Phe Glu Leu Thr Glu Arg
1               5                   10

<210> SEQ ID NO 659
<211> LENGTH: 11
<212> TYPE: PRT
<213> ORGANISM: Homo sapiens

<400> SEQUENCE: 659

Gln Ile Ser Glu Gly Val Glu Tyr Ile His Lys
1               5                   10

<210> SEQ ID NO 660
<211> LENGTH: 8
<212> TYPE: PRT
<213> ORGANISM: Homo sapiens

<400> SEQUENCE: 660

Leu Ile Asp Phe Gly Leu Ala Arg
1               5

<210> SEQ ID NO 661
<211> LENGTH: 8
<212> TYPE: PRT
<213> ORGANISM: Homo sapiens

<400> SEQUENCE: 661

Leu Glu Asn Ala Gly Ser Leu Lys
1               5

<210> SEQ ID NO 662
<211> LENGTH: 8
<212> TYPE: PRT
<213> ORGANISM: Homo sapiens

<400> SEQUENCE: 662

Asp Phe Ile Ser Asn Leu Leu Lys
1               5

<210> SEQ ID NO 663
<211> LENGTH: 6
<212> TYPE: PRT
<213> ORGANISM: Homo sapiens

<400> SEQUENCE: 663

Thr Gly Asn Ala Val Arg
1               5
```

```
<210> SEQ ID NO 664
<211> LENGTH: 14
<212> TYPE: PRT
<213> ORGANISM: Homo sapiens

<400> SEQUENCE: 664

Ser Ser Thr Gly Ser Pro Thr Ser Pro Leu Asn Ala Glu Lys
1               5                   10

<210> SEQ ID NO 665
<211> LENGTH: 11
<212> TYPE: PRT
<213> ORGANISM: Homo sapiens

<400> SEQUENCE: 665

Asp Leu Glu Val Val Glu Gly Ser Ala Ala Arg
1               5                   10

<210> SEQ ID NO 666
<211> LENGTH: 13
<212> TYPE: PRT
<213> ORGANISM: Homo sapiens

<400> SEQUENCE: 666

Ile Glu Gly Tyr Pro Asp Pro Glu Val Val Trp Phe Lys
1               5                   10

<210> SEQ ID NO 667
<211> LENGTH: 6
<212> TYPE: PRT
<213> ORGANISM: Homo sapiens

<400> SEQUENCE: 667

Asp Asp Gln Ser Ile Arg
1               5

<210> SEQ ID NO 668
<211> LENGTH: 7
<212> TYPE: PRT
<213> ORGANISM: Homo sapiens

<400> SEQUENCE: 668

Val Ile Glu Gly Ile Asn Arg
1               5

<210> SEQ ID NO 669
<211> LENGTH: 7
<212> TYPE: PRT
<213> ORGANISM: Homo sapiens

<400> SEQUENCE: 669

Gly Leu Ser Asn Ala Glu Arg
1               5

<210> SEQ ID NO 670
<211> LENGTH: 14
<212> TYPE: PRT
<213> ORGANISM: Homo sapiens

<400> SEQUENCE: 670

Ala Leu Asp Gly Ile Asn Ser Gly Ile Thr His Ala Gly Arg
1               5                   10

<210> SEQ ID NO 671
<211> LENGTH: 14
```

<212> TYPE: PRT
<213> ORGANISM: Homo sapiens

<400> SEQUENCE: 671

Val Ala His Glu Ile Asn His Gly Ile Gly Gln Ala Gly Lys
1               5                   10

<210> SEQ ID NO 672
<211> LENGTH: 14
<212> TYPE: PRT
<213> ORGANISM: Homo sapiens

<400> SEQUENCE: 672

Ala Val Gln Gly Phe His Thr Gly Val His Gln Ala Gly Lys
1               5                   10

<210> SEQ ID NO 673
<211> LENGTH: 14
<212> TYPE: PRT
<213> ORGANISM: Homo sapiens

<400> SEQUENCE: 673

Leu Gly Gln Gly Val Asn His Ala Ala Asp Gln Ala Gly Lys
1               5                   10

<210> SEQ ID NO 674
<211> LENGTH: 14
<212> TYPE: PRT
<213> ORGANISM: Homo sapiens

<400> SEQUENCE: 674

Leu Gly Gln Gly Ala His His Ala Ala Gly Gln Ala Gly Lys
1               5                   10

<210> SEQ ID NO 675
<211> LENGTH: 14
<212> TYPE: PRT
<213> ORGANISM: Homo sapiens

<400> SEQUENCE: 675

Glu Leu Gln Asn Ala His Asn Gly Val Asn Gln Ala Ser Lys
1               5                   10

<210> SEQ ID NO 676
<211> LENGTH: 14
<212> TYPE: PRT
<213> ORGANISM: Homo sapiens

<400> SEQUENCE: 676

Leu Gly His Gly Val Asn Asn Ala Ala Gly Gln Val Gly Lys
1               5                   10

<210> SEQ ID NO 677
<211> LENGTH: 19
<212> TYPE: PRT
<213> ORGANISM: Homo sapiens

<400> SEQUENCE: 677

Leu Ile His His Gly Val His His Gly Ala Asn Gln Ala Gly Ser Glu
1               5                   10                  15

Ala Gly Lys

<210> SEQ ID NO 678
<211> LENGTH: 18

```
<212> TYPE: PRT
<213> ORGANISM: Homo sapiens

<400> SEQUENCE: 678

Phe Gly Gln Gly Val Asp Asn Ala Ala Gly Gln Ala Gly Asn Glu Ala
1               5                   10                  15

Gly Arg

<210> SEQ ID NO 679
<211> LENGTH: 18
<212> TYPE: PRT
<213> ORGANISM: Homo sapiens

<400> SEQUENCE: 679

Phe Gly Gln Gly Val His His Ala Ala Gly Gln Ala Gly Asn Glu Ala
1               5                   10                  15

Gly Arg

<210> SEQ ID NO 680
<211> LENGTH: 14
<212> TYPE: PRT
<213> ORGANISM: Homo sapiens

<400> SEQUENCE: 680

Phe Gly Gln Gly Ala His His Gly Leu Ser Glu Gly Trp Lys
1               5                   10

<210> SEQ ID NO 681
<211> LENGTH: 14
<212> TYPE: PRT
<213> ORGANISM: Homo sapiens

<400> SEQUENCE: 681

Phe Gly Gln Gly Ile His His Ala Ala Gly Gln Val Gly Lys
1               5                   10

<210> SEQ ID NO 682
<211> LENGTH: 18
<212> TYPE: PRT
<213> ORGANISM: Homo sapiens

<400> SEQUENCE: 682

Phe Gly Gln Gly Ala His His Ala Ala Gly Gln Ala Gly Asn Glu Ala
1               5                   10                  15

Gly Arg

<210> SEQ ID NO 683
<211> LENGTH: 14
<212> TYPE: PRT
<213> ORGANISM: Homo sapiens

<400> SEQUENCE: 683

Phe Gly Gln Gly Val His His Gly Leu Ser Glu Gly Trp Lys
1               5                   10

<210> SEQ ID NO 684
<211> LENGTH: 14
<212> TYPE: PRT
<213> ORGANISM: Homo sapiens

<400> SEQUENCE: 684

Phe Gly Gln Gly Val His His Thr Ala Gly Gln Val Gly Lys
1               5                   10
```

```
<210> SEQ ID NO 685
<211> LENGTH: 14
<212> TYPE: PRT
<213> ORGANISM: Homo sapiens

<400> SEQUENCE: 685

Phe Gly Gln Gly Val His His Ala Ala Ser Gln Phe Gly Lys
1               5                   10

<210> SEQ ID NO 686
<211> LENGTH: 14
<212> TYPE: PRT
<213> ORGANISM: Homo sapiens

<400> SEQUENCE: 686

Leu Gly His Gly Val His His Gly Val Asn Glu Ala Trp Lys
1               5                   10

<210> SEQ ID NO 687
<211> LENGTH: 14
<212> TYPE: PRT
<213> ORGANISM: Homo sapiens

<400> SEQUENCE: 687

Phe Gly Gln Gly Val His His Ala Ala Ser Gln Val Gly Lys
1               5                   10

<210> SEQ ID NO 688
<211> LENGTH: 14
<212> TYPE: PRT
<213> ORGANISM: Homo sapiens

<400> SEQUENCE: 688

Val Val Gln Gly Leu His His Gly Val Ser Gln Ala Gly Arg
1               5                   10

<210> SEQ ID NO 689
<211> LENGTH: 18
<212> TYPE: PRT
<213> ORGANISM: Homo sapiens

<400> SEQUENCE: 689

Glu Ala Gly Gln Phe Gly His Asp Ile His His Thr Ala Gly Gln Ala
1               5                   10                  15

Gly Lys

<210> SEQ ID NO 690
<211> LENGTH: 18
<212> TYPE: PRT
<213> ORGANISM: Homo sapiens

<400> SEQUENCE: 690

Glu Gly Asp Ile Ala Val His Gly Val Gln Pro Gly Val His Glu Ala
1               5                   10                  15

Gly Lys

<210> SEQ ID NO 691
<211> LENGTH: 18
<212> TYPE: PRT
<213> ORGANISM: Homo sapiens

<400> SEQUENCE: 691
```

-continued

```
Glu Ala Gly Gln Phe Gly Gln Gly Val His His Thr Leu Glu Gln Ala
1               5                   10                  15

Gly Lys

<210> SEQ ID NO 692
<211> LENGTH: 10
<212> TYPE: PRT
<213> ORGANISM: Homo sapiens

<400> SEQUENCE: 692

Ile Asn Ala Ala Asn Tyr Ala Ser Val Lys
1               5                   10

<210> SEQ ID NO 693
<211> LENGTH: 6
<212> TYPE: PRT
<213> ORGANISM: Homo sapiens

<400> SEQUENCE: 693

Gln Leu Pro Asn His Arg
1               5

<210> SEQ ID NO 694
<211> LENGTH: 14
<212> TYPE: PRT
<213> ORGANISM: Homo sapiens

<400> SEQUENCE: 694

Glu Gly Thr Ile Gln Val Gln Gly Gln Ala Leu Phe Phe Arg
1               5                   10

<210> SEQ ID NO 695
<211> LENGTH: 10
<212> TYPE: PRT
<213> ORGANISM: Homo sapiens

<400> SEQUENCE: 695

Glu Ala Leu Pro Gly Ser Gly Gln Ala Arg
1               5                   10

<210> SEQ ID NO 696
<211> LENGTH: 10
<212> TYPE: PRT
<213> ORGANISM: Homo sapiens

<400> SEQUENCE: 696

Phe Ser Val Leu Leu Leu His Gly Ile Arg
1               5                   10

<210> SEQ ID NO 697
<211> LENGTH: 14
<212> TYPE: PRT
<213> ORGANISM: Homo sapiens

<400> SEQUENCE: 697

Phe Ser Ser Glu Thr Trp Gln Asn Leu Gly Thr Leu His Arg
1               5                   10

<210> SEQ ID NO 698
<211> LENGTH: 13
<212> TYPE: PRT
<213> ORGANISM: Homo sapiens

<400> SEQUENCE: 698
```

```
Ala Val Ala Ile Asp Leu Pro Gly Leu Gly His Ser Lys
1               5                   10
```

<210> SEQ ID NO 699
<211> LENGTH: 6
<212> TYPE: PRT
<213> ORGANISM: Homo sapiens

<400> SEQUENCE: 699

```
Gln Ala Pro Gly Gln Arg
1               5
```

<210> SEQ ID NO 700
<211> LENGTH: 8
<212> TYPE: PRT
<213> ORGANISM: Homo sapiens

<400> SEQUENCE: 700

```
Trp Pro Glu Pro Val Phe Gly Arg
1               5
```

<210> SEQ ID NO 701
<211> LENGTH: 16
<212> TYPE: PRT
<213> ORGANISM: Homo sapiens

<400> SEQUENCE: 701

```
Leu Ala Ser Pro Gly Phe Pro Gly Glu Tyr Ala Asn Asp Gln Glu Arg
1               5                   10                  15
```

<210> SEQ ID NO 702
<211> LENGTH: 10
<212> TYPE: PRT
<213> ORGANISM: Homo sapiens

<400> SEQUENCE: 702

```
Trp Thr Leu Thr Ala Pro Pro Gly Tyr Arg
1               5                   10
```

<210> SEQ ID NO 703
<211> LENGTH: 15
<212> TYPE: PRT
<213> ORGANISM: Homo sapiens

<400> SEQUENCE: 703

```
Asp Thr Phe Tyr Ser Leu Gly Ser Ser Leu Asp Ile Thr Phe Arg
1               5                   10                  15
```

<210> SEQ ID NO 704
<211> LENGTH: 7
<212> TYPE: PRT
<213> ORGANISM: Homo sapiens

<400> SEQUENCE: 704

```
Ala Gly Tyr Val Leu His Arg
1               5
```

<210> SEQ ID NO 705
<211> LENGTH: 15
<212> TYPE: PRT
<213> ORGANISM: Homo sapiens

<400> SEQUENCE: 705

```
Ser Gly Glu Leu Ser Ser Pro Glu Tyr Pro Arg Pro Tyr Pro Lys
1               5                   10                  15
```

```
<210> SEQ ID NO 706
<211> LENGTH: 20
<212> TYPE: PRT
<213> ORGANISM: Homo sapiens

<400> SEQUENCE: 706

Ser Asn Thr Val Thr Ile Thr Phe Val Thr Asp Glu Ser Gly Asp His
1               5                   10                  15

Thr Gly Trp Lys
            20

<210> SEQ ID NO 707
<211> LENGTH: 13
<212> TYPE: PRT
<213> ORGANISM: Homo sapiens

<400> SEQUENCE: 707

Val Glu Tyr Ile Thr Gly Pro Gly Val Thr Thr Tyr Lys
1               5                   10

<210> SEQ ID NO 708
<211> LENGTH: 6
<212> TYPE: PRT
<213> ORGANISM: Homo sapiens

<400> SEQUENCE: 708

Ile Tyr Gly Gly Gln Lys
1               5

<210> SEQ ID NO 709
<211> LENGTH: 9
<212> TYPE: PRT
<213> ORGANISM: Homo sapiens

<400> SEQUENCE: 709

His Asp Ala Ser Ala Leu Asp Ile Arg
1               5

<210> SEQ ID NO 710
<211> LENGTH: 15
<212> TYPE: PRT
<213> ORGANISM: Homo sapiens

<400> SEQUENCE: 710

Thr Asp Asp Ile Gly Thr Ala Ser Gly Trp Gly Leu Thr Gln Arg
1               5                   10                  15

<210> SEQ ID NO 711
<211> LENGTH: 16
<212> TYPE: PRT
<213> ORGANISM: Homo sapiens

<400> SEQUENCE: 711

Gly Asp Ser Gly Gly Ala Leu Val Phe Leu Asp Ser Glu Thr Glu Arg
1               5                   10                  15

<210> SEQ ID NO 712
<211> LENGTH: 15
<212> TYPE: PRT
<213> ORGANISM: Homo sapiens

<400> SEQUENCE: 712

Val Ile Asn Tyr Ile Pro Trp Ile Glu Asn Ile Ile Ser Asp Phe
```

```
1               5                  10                  15
```

<210> SEQ ID NO 713
<211> LENGTH: 14
<212> TYPE: PRT
<213> ORGANISM: Homo sapiens

<400> SEQUENCE: 713

```
Ser Pro Asp Glu Leu Pro Ser Ala Gly Gly Asp Gly Gly Lys
1               5                  10
```

<210> SEQ ID NO 714
<211> LENGTH: 8
<212> TYPE: PRT
<213> ORGANISM: Homo sapiens

<400> SEQUENCE: 714

```
Glu Lys Pro Asn Ser Ala His Arg
1               5
```

<210> SEQ ID NO 715
<211> LENGTH: 10
<212> TYPE: PRT
<213> ORGANISM: Homo sapiens

<400> SEQUENCE: 715

```
Glu Glu Thr Ala Gly Ser Tyr Asp Ser Arg
1               5                  10
```

<210> SEQ ID NO 716
<211> LENGTH: 9
<212> TYPE: PRT
<213> ORGANISM: Homo sapiens

<400> SEQUENCE: 716

```
Phe Gln Pro Leu Leu Asp Gly Leu Lys
1               5
```

<210> SEQ ID NO 717
<211> LENGTH: 8
<212> TYPE: PRT
<213> ORGANISM: Homo sapiens

<400> SEQUENCE: 717

```
Ser Gly Thr Thr Ile Ala Leu Lys
1               5
```

<210> SEQ ID NO 718
<211> LENGTH: 11
<212> TYPE: PRT
<213> ORGANISM: Homo sapiens

<400> SEQUENCE: 718

```
Leu Gly Leu His Gln Val Leu Gln Asp Leu Arg
1               5                  10
```

<210> SEQ ID NO 719
<211> LENGTH: 18
<212> TYPE: PRT
<213> ORGANISM: Homo sapiens

<400> SEQUENCE: 719

```
Val Gln Leu Asn Val Phe Asp Glu Gln Gly Glu Glu Asp Ser Tyr Asp
1               5                  10                  15
```

Leu Lys

<210> SEQ ID NO 720
<211> LENGTH: 16
<212> TYPE: PRT
<213> ORGANISM: Homo sapiens

<400> SEQUENCE: 720

Ala Glu Pro His Phe Leu Ser Ile Leu Gln His Leu Leu Val Arg
1               5                   10                  15

<210> SEQ ID NO 721
<211> LENGTH: 11
<212> TYPE: PRT
<213> ORGANISM: Homo sapiens

<400> SEQUENCE: 721

Asn Asp Tyr Glu Ala Arg Pro Gln Tyr Tyr Lys
1               5                   10

<210> SEQ ID NO 722
<211> LENGTH: 8
<212> TYPE: PRT
<213> ORGANISM: Homo sapiens

<400> SEQUENCE: 722

Asn Gly Ala Asp Pro Asp Phe Lys
1               5

<210> SEQ ID NO 723
<211> LENGTH: 8
<212> TYPE: PRT
<213> ORGANISM: Homo sapiens

<400> SEQUENCE: 723

Leu Gln Asp Leu Gln Gly Glu Lys
1               5

<210> SEQ ID NO 724
<211> LENGTH: 7
<212> TYPE: PRT
<213> ORGANISM: Homo sapiens

<400> SEQUENCE: 724

Asp Ala Leu His Ser Glu Lys
1               5

<210> SEQ ID NO 725
<211> LENGTH: 7
<212> TYPE: PRT
<213> ORGANISM: Homo sapiens

<400> SEQUENCE: 725

Gln Gln Ile Ala Thr Glu Lys
1               5

<210> SEQ ID NO 726
<211> LENGTH: 16
<212> TYPE: PRT
<213> ORGANISM: Homo sapiens

<400> SEQUENCE: 726

Gln Asp Leu Glu Ala Glu Val Ser Gln Leu Thr Gly Glu Val Ala Lys
1               5                   10                  15

<210> SEQ ID NO 727
<211> LENGTH: 9
<212> TYPE: PRT
<213> ORGANISM: Homo sapiens

<400> SEQUENCE: 727

Leu Tyr Lys Pro Glu Val Gln Leu Arg
1               5

<210> SEQ ID NO 728
<211> LENGTH: 6
<212> TYPE: PRT
<213> ORGANISM: Homo sapiens

<400> SEQUENCE: 728

Arg Pro Asn Trp Ser Lys
1               5

<210> SEQ ID NO 729
<211> LENGTH: 9
<212> TYPE: PRT
<213> ORGANISM: Homo sapiens

<400> SEQUENCE: 729

Phe Glu Asn Asn Glu Leu Phe Ala Lys
1               5

<210> SEQ ID NO 730
<211> LENGTH: 10
<212> TYPE: PRT
<213> ORGANISM: Homo sapiens

<400> SEQUENCE: 730

Leu Thr Leu Thr Phe Ser Ala Gln Thr Lys
1               5                   10

<210> SEQ ID NO 731
<211> LENGTH: 8
<212> TYPE: PRT
<213> ORGANISM: Homo sapiens

<400> SEQUENCE: 731

Asp Gln Glu Gly Gly Glu Glu Lys
1               5

<210> SEQ ID NO 732
<211> LENGTH: 13
<212> TYPE: PRT
<213> ORGANISM: Homo sapiens

<400> SEQUENCE: 732

Thr Ala Gln Asn Leu Ser Ile Phe Leu Gly Ser Phe Arg
1               5                   10

<210> SEQ ID NO 733
<211> LENGTH: 7
<212> TYPE: PRT
<213> ORGANISM: Homo sapiens

<400> SEQUENCE: 733

Leu Asn Ala Ile Leu Phe Lys
1               5

<210> SEQ ID NO 734

<211> LENGTH: 10
<212> TYPE: PRT
<213> ORGANISM: Homo sapiens

<400> SEQUENCE: 734

Phe Pro Asp Glu Leu Ala His Val Glu Lys
1               5                   10

<210> SEQ ID NO 735
<211> LENGTH: 8
<212> TYPE: PRT
<213> ORGANISM: Homo sapiens

<400> SEQUENCE: 735

Val Ser Ala Glu Asn Leu Gln Lys
1               5

<210> SEQ ID NO 736
<211> LENGTH: 7
<212> TYPE: PRT
<213> ORGANISM: Homo sapiens

<400> SEQUENCE: 736

Gln Ile Ser Asp Val Glu Arg
1               5

<210> SEQ ID NO 737
<211> LENGTH: 12
<212> TYPE: PRT
<213> ORGANISM: Homo sapiens

<400> SEQUENCE: 737

Asp Val Gln Asn Phe Pro Ala Ala Thr Asp Glu Lys
1               5                   10

<210> SEQ ID NO 738
<211> LENGTH: 8
<212> TYPE: PRT
<213> ORGANISM: Homo sapiens

<400> SEQUENCE: 738

Asp Ala Gln Glu Gln Tyr Asn Lys
1               5

<210> SEQ ID NO 739
<211> LENGTH: 11
<212> TYPE: PRT
<213> ORGANISM: Homo sapiens

<400> SEQUENCE: 739

Glu Leu Gly Glu Tyr Phe Leu Phe Asp Pro Lys
1               5                   10

<210> SEQ ID NO 740
<211> LENGTH: 13
<212> TYPE: PRT
<213> ORGANISM: Homo sapiens

<400> SEQUENCE: 740

Asn Ser Glu Thr Phe Pro Thr Ile Leu Glu Glu Ala Lys
1               5                   10

<210> SEQ ID NO 741
<211> LENGTH: 17
<212> TYPE: PRT

<213> ORGANISM: Homo sapiens

<400> SEQUENCE: 741

Val Pro Ala Gln Leu Leu Gly Leu Leu Leu Trp Leu Pro Gly Ala
1               5                   10                  15
Lys

<210> SEQ ID NO 742
<211> LENGTH: 18
<212> TYPE: PRT
<213> ORGANISM: Homo sapiens

<400> SEQUENCE: 742

Ala Ser Gln Ser Ile Ser Ser Trp Leu Ala Trp Tyr Gln Gln Lys Pro
1               5                   10                  15
Gly Lys

<210> SEQ ID NO 743
<211> LENGTH: 17
<212> TYPE: PRT
<213> ORGANISM: Homo sapiens

<400> SEQUENCE: 743

Glu Val Asn Thr Ser Gly Phe Ala Pro Ala Arg Pro Pro Gln Pro
1               5                   10                  15
Arg

<210> SEQ ID NO 744
<211> LENGTH: 11
<212> TYPE: PRT
<213> ORGANISM: Homo sapiens

<400> SEQUENCE: 744

Asp Asp Val Ser Ile Ser Val Glu Glu Gly Lys
1               5                   10

<210> SEQ ID NO 745
<211> LENGTH: 20
<212> TYPE: PRT
<213> ORGANISM: Homo sapiens

<400> SEQUENCE: 745

Glu Asn Ile Leu His Val Ser Glu Asn Val Ile Phe Thr Asp Val Asn
1               5                   10                  15
Ser Ile Leu Arg
            20

<210> SEQ ID NO 746
<211> LENGTH: 10
<212> TYPE: PRT
<213> ORGANISM: Homo sapiens

<400> SEQUENCE: 746

Gly Asn Ala Ala Trp Gln Glu Gln Leu Lys
1               5                   10

<210> SEQ ID NO 747
<211> LENGTH: 6
<212> TYPE: PRT
<213> ORGANISM: Homo sapiens

<400> SEQUENCE: 747

```
Ala Pro Val His Val Lys
1               5

<210> SEQ ID NO 748
<211> LENGTH: 17
<212> TYPE: PRT
<213> ORGANISM: Homo sapiens

<400> SEQUENCE: 748

Trp Phe Gly Phe Leu Glu Ala Gln Gln Ala Phe Gln Ser Val Gly Thr
1               5                   10                  15

Lys

<210> SEQ ID NO 749
<211> LENGTH: 7
<212> TYPE: PRT
<213> ORGANISM: Homo sapiens

<400> SEQUENCE: 749

Trp Asp Val Ser Thr Thr Lys
1               5

<210> SEQ ID NO 750
<211> LENGTH: 15
<212> TYPE: PRT
<213> ORGANISM: Homo sapiens

<400> SEQUENCE: 750

Phe Pro Pro Glu Ala Ser Gly Tyr Leu His Ile Gly His Ala Lys
1               5                   10                  15

<210> SEQ ID NO 751
<211> LENGTH: 13
<212> TYPE: PRT
<213> ORGANISM: Homo sapiens

<400> SEQUENCE: 751

Ala Ala Leu Leu Asn Gln His Tyr Gln Val Asn Phe Lys
1               5                   10

<210> SEQ ID NO 752
<211> LENGTH: 6
<212> TYPE: PRT
<213> ORGANISM: Homo sapiens

<400> SEQUENCE: 752

Ile Gln Pro His Pro Arg
1               5

<210> SEQ ID NO 753
<211> LENGTH: 7
<212> TYPE: PRT
<213> ORGANISM: Homo sapiens

<400> SEQUENCE: 753

Thr Thr Glu Tyr His Asp Arg
1               5

<210> SEQ ID NO 754
<211> LENGTH: 14
<212> TYPE: PRT
<213> ORGANISM: Homo sapiens

<400> SEQUENCE: 754
```

```
Asp Glu Gln Phe Tyr Trp Ile Ile Glu Ala Leu Gly Ile Arg
1               5                   10
```

<210> SEQ ID NO 755
<211> LENGTH: 9
<212> TYPE: PRT
<213> ORGANISM: Homo sapiens

<400> SEQUENCE: 755

```
Lys Pro Tyr Ile Trp Glu Tyr Ser Arg
1               5
```

<210> SEQ ID NO 756
<211> LENGTH: 10
<212> TYPE: PRT
<213> ORGANISM: Homo sapiens

<400> SEQUENCE: 756

```
Leu Asn Leu Asn Asn Thr Val Leu Ser Lys
1               5                   10
```

<210> SEQ ID NO 757
<211> LENGTH: 17
<212> TYPE: PRT
<213> ORGANISM: Homo sapiens

<400> SEQUENCE: 757

```
Leu Thr Trp Phe Val Asn Glu Gly Leu Val Asp Gly Trp Asp Asp Pro
1               5                   10                  15
Arg
```

<210> SEQ ID NO 758
<211> LENGTH: 10
<212> TYPE: PRT
<213> ORGANISM: Homo sapiens

<400> SEQUENCE: 758

```
Gln Phe Ile Ala Ala Gln Gly Ser Ser Arg
1               5                   10
```

<210> SEQ ID NO 759
<211> LENGTH: 6
<212> TYPE: PRT
<213> ORGANISM: Homo sapiens

<400> SEQUENCE: 759

```
Ile Trp Ala Phe Asn Lys
1               5
```

<210> SEQ ID NO 760
<211> LENGTH: 8
<212> TYPE: PRT
<213> ORGANISM: Homo sapiens

<400> SEQUENCE: 760

```
Val Ile Asp Pro Val Ala Pro Arg
1               5
```

<210> SEQ ID NO 761
<211> LENGTH: 6
<212> TYPE: PRT
<213> ORGANISM: Homo sapiens

<400> SEQUENCE: 761

Tyr Val Ala Leu Leu Lys
1               5

<210> SEQ ID NO 762
<211> LENGTH: 14
<212> TYPE: PRT
<213> ORGANISM: Homo sapiens

<400> SEQUENCE: 762

Asn Pro Glu Val Gly Leu Lys Pro Val Trp Tyr Ser Pro Lys
1               5                   10

<210> SEQ ID NO 763
<211> LENGTH: 7
<212> TYPE: PRT
<213> ORGANISM: Homo sapiens

<400> SEQUENCE: 763

Ile Ile Ser Leu Asp Ala Lys
1               5

<210> SEQ ID NO 764
<211> LENGTH: 6
<212> TYPE: PRT
<213> ORGANISM: Homo sapiens

<400> SEQUENCE: 764

Leu Asn Leu Glu Asn Lys
1               5

<210> SEQ ID NO 765
<211> LENGTH: 8
<212> TYPE: PRT
<213> ORGANISM: Homo sapiens

<400> SEQUENCE: 765

Gly Asp Ile Ile Gln Leu Gln Arg
1               5

<210> SEQ ID NO 766
<211> LENGTH: 8
<212> TYPE: PRT
<213> ORGANISM: Homo sapiens

<400> SEQUENCE: 766

Asn Glu Thr Ser Ala Pro Phe Lys
1               5

<210> SEQ ID NO 767
<211> LENGTH: 9
<212> TYPE: PRT
<213> ORGANISM: Homo sapiens

<400> SEQUENCE: 767

Val Ala Val Gln Gly Asp Val Val Arg
1               5

<210> SEQ ID NO 768
<211> LENGTH: 8
<212> TYPE: PRT
<213> ORGANISM: Homo sapiens

<400> SEQUENCE: 768

Glu Asp Val Asp Ala Ala Val Lys
1               5

```
<210> SEQ ID NO 769
<211> LENGTH: 6
<212> TYPE: PRT
<213> ORGANISM: Homo sapiens

<400> SEQUENCE: 769

Gln Leu Leu Ser Leu Lys
1               5

<210> SEQ ID NO 770
<211> LENGTH: 14
<212> TYPE: PRT
<213> ORGANISM: Homo sapiens

<400> SEQUENCE: 770

Ser Leu Tyr Asp Glu Val Ala Ala Gln Gly Glu Val Val Arg
1               5                   10

<210> SEQ ID NO 771
<211> LENGTH: 19
<212> TYPE: PRT
<213> ORGANISM: Homo sapiens

<400> SEQUENCE: 771

Glu Tyr Ile Pro Gly Gln Pro Pro Leu Ser Gln Ser Ser Asp Ser Ser
1               5                   10                  15

Pro Thr Arg

<210> SEQ ID NO 772
<211> LENGTH: 13
<212> TYPE: PRT
<213> ORGANISM: Homo sapiens

<400> SEQUENCE: 772

Asn Ser Glu Pro Ala Gly Leu Glu Thr Pro Glu Ala Lys
1               5                   10

<210> SEQ ID NO 773
<211> LENGTH: 9
<212> TYPE: PRT
<213> ORGANISM: Homo sapiens

<400> SEQUENCE: 773

Val Ala Ser Gln Gly Glu Val Val Arg
1               5

<210> SEQ ID NO 774
<211> LENGTH: 14
<212> TYPE: PRT
<213> ORGANISM: Homo sapiens

<400> SEQUENCE: 774

Asp Gln Val Asp Ile Ala Val Gln Glu Leu Leu Gln Leu Lys
1               5                   10

<210> SEQ ID NO 775
<211> LENGTH: 18
<212> TYPE: PRT
<213> ORGANISM: Homo sapiens

<400> SEQUENCE: 775

Ser Leu Ile Gly Val Glu Tyr Lys Pro Val Ser Ala Thr Gly Ala Glu
1               5                   10                  15
```

-continued

Asp Lys

<210> SEQ ID NO 776
<211> LENGTH: 6
<212> TYPE: PRT
<213> ORGANISM: Homo sapiens

<400> SEQUENCE: 776

Gln Asn Lys Pro Gln Lys
1               5

<210> SEQ ID NO 777
<211> LENGTH: 6
<212> TYPE: PRT
<213> ORGANISM: Homo sapiens

<400> SEQUENCE: 777

Gln Asn Asp Gly Gln Arg
1               5

<210> SEQ ID NO 778
<211> LENGTH: 18
<212> TYPE: PRT
<213> ORGANISM: Homo sapiens

<400> SEQUENCE: 778

Asn Gln Gly Gly Gly Leu Ser Ser Ser Gly Ala Gly Glu Gly Gln Gly
1               5                   10                  15

Pro Lys

<210> SEQ ID NO 779
<211> LENGTH: 14
<212> TYPE: PRT
<213> ORGANISM: Homo sapiens

<400> SEQUENCE: 779

Glu Glu Asn Leu Ala Asp Trp Tyr Ser Gln Val Ile Thr Lys
1               5                   10

<210> SEQ ID NO 780
<211> LENGTH: 8
<212> TYPE: PRT
<213> ORGANISM: Homo sapiens

<400> SEQUENCE: 780

Asp Phe Phe Asp Ala Glu Ile Lys
1               5

<210> SEQ ID NO 781
<211> LENGTH: 15
<212> TYPE: PRT
<213> ORGANISM: Homo sapiens

<400> SEQUENCE: 781

Thr His Val Ala Asp Phe Ala Pro Glu Val Ala Trp Val Thr Arg
1               5                   10                  15

<210> SEQ ID NO 782
<211> LENGTH: 6
<212> TYPE: PRT
<213> ORGANISM: Homo sapiens

<400> SEQUENCE: 782

```
Trp Val Gln Ser His Arg
1               5

<210> SEQ ID NO 783
<211> LENGTH: 7
<212> TYPE: PRT
<213> ORGANISM: Homo sapiens

<400> SEQUENCE: 783

His Pro Gln Pro Phe Leu Arg
1               5

<210> SEQ ID NO 784
<211> LENGTH: 19
<212> TYPE: PRT
<213> ORGANISM: Homo sapiens

<400> SEQUENCE: 784

Phe Ala Gly Gly Asp Tyr Thr Thr Thr Ile Glu Ala Phe Ile Ser Ala
1               5                   10                  15

Ser Gly Arg

<210> SEQ ID NO 785
<211> LENGTH: 16
<212> TYPE: PRT
<213> ORGANISM: Homo sapiens

<400> SEQUENCE: 785

Ala Ile Gln Gly Gly Thr Ser His His Leu Gly Gln Asn Phe Ser Lys
1               5                   10                  15

<210> SEQ ID NO 786
<211> LENGTH: 13
<212> TYPE: PRT
<213> ORGANISM: Homo sapiens

<400> SEQUENCE: 786

Gln Phe Ala Tyr Gln Asn Ser Trp Gly Leu Thr Thr Arg
1               5                   10

<210> SEQ ID NO 787
<211> LENGTH: 6
<212> TYPE: PRT
<213> ORGANISM: Homo sapiens

<400> SEQUENCE: 787

Glu Ala Leu Ile Ala Lys
1               5

<210> SEQ ID NO 788
<211> LENGTH: 7
<212> TYPE: PRT
<213> ORGANISM: Homo sapiens

<400> SEQUENCE: 788

Leu Leu Ser Val Asn Ile Arg
1               5

<210> SEQ ID NO 789
<211> LENGTH: 8
<212> TYPE: PRT
<213> ORGANISM: Homo sapiens

<400> SEQUENCE: 789
```

```
Asp Asn Tyr Ser Pro Gly Trp Lys
1               5
```

<210> SEQ ID NO 790
<211> LENGTH: 7
<212> TYPE: PRT
<213> ORGANISM: Homo sapiens

<400> SEQUENCE: 790

```
Phe Asn His Trp Glu Leu Lys
1               5
```

<210> SEQ ID NO 791
<211> LENGTH: 11
<212> TYPE: PRT
<213> ORGANISM: Homo sapiens

<400> SEQUENCE: 791

```
Leu Thr Val Ala Glu Asn Glu Ala Glu Thr Lys
1               5                   10
```

<210> SEQ ID NO 792
<211> LENGTH: 15
<212> TYPE: PRT
<213> ORGANISM: Homo sapiens

<400> SEQUENCE: 792

```
Leu Gln Ala Ile Leu Glu Asp Ile Gln Val Thr Leu Phe Thr Arg
1               5                   10                  15
```

<210> SEQ ID NO 793
<211> LENGTH: 7
<212> TYPE: PRT
<213> ORGANISM: Homo sapiens

<400> SEQUENCE: 793

```
Tyr Tyr Thr Leu Phe Gly Arg
1               5
```

<210> SEQ ID NO 794
<211> LENGTH: 8
<212> TYPE: PRT
<213> ORGANISM: Homo sapiens

<400> SEQUENCE: 794

```
Gly Val Phe Val Val Ala Ala Lys
1               5
```

<210> SEQ ID NO 795
<211> LENGTH: 11
<212> TYPE: PRT
<213> ORGANISM: Homo sapiens

<400> SEQUENCE: 795

```
Thr Pro Phe Gly Ala Tyr Gly Gly Leu Leu Lys
1               5                   10
```

<210> SEQ ID NO 796
<211> LENGTH: 13
<212> TYPE: PRT
<213> ORGANISM: Homo sapiens

<400> SEQUENCE: 796

```
Asp Phe Thr Ala Thr Asp Leu Ser Glu Phe Ala Ala Lys
1               5                   10
```

<210> SEQ ID NO 797
<211> LENGTH: 9
<212> TYPE: PRT
<213> ORGANISM: Homo sapiens

<400> SEQUENCE: 797

Glu Thr Pro Ala Leu Thr Ile Asn Arg
1               5

<210> SEQ ID NO 798
<211> LENGTH: 8
<212> TYPE: PRT
<213> ORGANISM: Homo sapiens

<400> SEQUENCE: 798

Tyr Ala Leu Gln Ser Gln Gln Arg
1               5

<210> SEQ ID NO 799
<211> LENGTH: 8
<212> TYPE: PRT
<213> ORGANISM: Homo sapiens

<400> SEQUENCE: 799

His Asn Phe Thr Pro Leu Ala Arg
1               5

<210> SEQ ID NO 800
<211> LENGTH: 8
<212> TYPE: PRT
<213> ORGANISM: Homo sapiens

<400> SEQUENCE: 800

Ser Leu Asp Leu Asp Ile Ser Lys
1               5

<210> SEQ ID NO 801
<211> LENGTH: 20
<212> TYPE: PRT
<213> ORGANISM: Homo sapiens

<400> SEQUENCE: 801

Thr Asn Val Asn Gly Gly Ala Ile Ala Leu Gly His Pro Leu Gly Gly
1               5                   10                  15

Ser Gly Ser Arg
            20

<210> SEQ ID NO 802
<211> LENGTH: 10
<212> TYPE: PRT
<213> ORGANISM: Homo sapiens

<400> SEQUENCE: 802

Ile Thr Ala His Leu Val His Glu Leu Arg
1               5                   10

<210> SEQ ID NO 803
<211> LENGTH: 7
<212> TYPE: PRT
<213> ORGANISM: Homo sapiens

<400> SEQUENCE: 803

Leu Glu Thr Ala Asp Leu Lys

```
1               5
```

<210> SEQ ID NO 804
<211> LENGTH: 25
<212> TYPE: PRT
<213> ORGANISM: Homo sapiens

<400> SEQUENCE: 804

```
Trp Val Thr Phe Pro Gln Val Asp Gly Gln Trp Glu Leu Ser Gly
1               5                   10                  15

Leu Asp Glu Glu Gln His Ser Val Arg
            20                  25
```

<210> SEQ ID NO 805
<211> LENGTH: 9
<212> TYPE: PRT
<213> ORGANISM: Homo sapiens

<400> SEQUENCE: 805

```
Ala Pro Gly Gln Ala His Trp Leu Arg
1               5
```

<210> SEQ ID NO 806
<211> LENGTH: 6
<212> TYPE: PRT
<213> ORGANISM: Homo sapiens

<400> SEQUENCE: 806

```
Thr Gly Trp Val Pro Arg
1               5
```

<210> SEQ ID NO 807
<211> LENGTH: 10
<212> TYPE: PRT
<213> ORGANISM: Homo sapiens

<400> SEQUENCE: 807

```
Gly Ala Val His Val Tyr Ala Thr Leu Arg
1               5                   10
```

<210> SEQ ID NO 808
<211> LENGTH: 11
<212> TYPE: PRT
<213> ORGANISM: Homo sapiens

<400> SEQUENCE: 808

```
Val Asp Thr Val Ala Ala Glu His Leu Thr Arg
1               5                   10
```

<210> SEQ ID NO 809
<211> LENGTH: 9
<212> TYPE: PRT
<213> ORGANISM: Homo sapiens

<400> SEQUENCE: 809

```
Arg Pro Gly Ala Glu Ala Thr Gly Lys
1               5
```

<210> SEQ ID NO 810
<211> LENGTH: 6
<212> TYPE: PRT
<213> ORGANISM: Homo sapiens

<400> SEQUENCE: 810

```
Leu Gly Pro Leu Ser Lys
1               5

<210> SEQ ID NO 811
<211> LENGTH: 7
<212> TYPE: PRT
<213> ORGANISM: Homo sapiens

<400> SEQUENCE: 811

Phe Pro Glu Thr Val Pro Arg
1               5

<210> SEQ ID NO 812
<211> LENGTH: 19
<212> TYPE: PRT
<213> ORGANISM: Homo sapiens

<400> SEQUENCE: 812

Leu Asn Gly Ser Ser Leu His Leu Glu Trp Ser Ala Pro Leu Glu Ser
1               5                   10                  15

Gly Gly Arg

<210> SEQ ID NO 813
<211> LENGTH: 8
<212> TYPE: PRT
<213> ORGANISM: Homo sapiens

<400> SEQUENCE: 813

Glu Asp Leu Thr Tyr Ala Leu Arg
1               5

<210> SEQ ID NO 814
<211> LENGTH: 10
<212> TYPE: PRT
<213> ORGANISM: Homo sapiens

<400> SEQUENCE: 814

Asp Leu Val Glu Pro Trp Val Val Val Arg
1               5                   10

<210> SEQ ID NO 815
<211> LENGTH: 10
<212> TYPE: PRT
<213> ORGANISM: Homo sapiens

<400> SEQUENCE: 815

Glu Val Pro Pro Ala Val Ser Asp Ile Arg
1               5                   10

<210> SEQ ID NO 816
<211> LENGTH: 14
<212> TYPE: PRT
<213> ORGANISM: Homo sapiens

<400> SEQUENCE: 816

Ser Ser Pro Ser Ser Leu Ser Leu Ala Trp Ala Val Pro Arg
1               5                   10

<210> SEQ ID NO 817
<211> LENGTH: 12
<212> TYPE: PRT
<213> ORGANISM: Homo sapiens

<400> SEQUENCE: 817
```

```
Ala Pro Ser Gly Ala Val Leu Asp Tyr Glu Val Lys
 1               5                  10
```

<210> SEQ ID NO 818
<211> LENGTH: 9
<212> TYPE: PRT
<213> ORGANISM: Homo sapiens

<400> SEQUENCE: 818

```
Gly Ala Glu Gly Pro Ser Ser Val Arg
 1               5
```

<210> SEQ ID NO 819
<211> LENGTH: 9
<212> TYPE: PRT
<213> ORGANISM: Homo sapiens

<400> SEQUENCE: 819

```
Gly Ala Ser Tyr Leu Val Gln Val Arg
 1               5
```

<210> SEQ ID NO 820
<211> LENGTH: 25
<212> TYPE: PRT
<213> ORGANISM: Homo sapiens

<400> SEQUENCE: 820

```
Ser Glu Ala Gly Tyr Gly Pro Phe Gly Gln Glu His His Ser Gln Thr
 1               5                  10                  15

Gln Leu Asp Glu Ser Glu Gly Trp Arg
             20                  25
```

<210> SEQ ID NO 821
<211> LENGTH: 7
<212> TYPE: PRT
<213> ORGANISM: Homo sapiens

<400> SEQUENCE: 821

```
Glu Ala Glu Tyr Ser Asp Lys
 1               5
```

<210> SEQ ID NO 822
<211> LENGTH: 11
<212> TYPE: PRT
<213> ORGANISM: Homo sapiens

<400> SEQUENCE: 822

```
His Gly Gln Tyr Leu Ile Gly His Gly Thr Lys
 1               5                  10
```

<210> SEQ ID NO 823
<211> LENGTH: 8
<212> TYPE: PRT
<213> ORGANISM: Homo sapiens

<400> SEQUENCE: 823

```
Glu Ile Asp Val Ser Tyr Val Lys
 1               5
```

<210> SEQ ID NO 824
<211> LENGTH: 6
<212> TYPE: PRT
<213> ORGANISM: Homo sapiens

<400> SEQUENCE: 824

Gly Gly Tyr Thr Glu Arg
1               5

<210> SEQ ID NO 825
<211> LENGTH: 18
<212> TYPE: PRT
<213> ORGANISM: Homo sapiens

<400> SEQUENCE: 825

Phe Leu Glu Glu Asn Ser Ser Asp Pro Thr Tyr Thr Ser Ser Leu Gly
1               5                   10                  15

Gly Lys

<210> SEQ ID NO 826
<211> LENGTH: 10
<212> TYPE: PRT
<213> ORGANISM: Homo sapiens

<400> SEQUENCE: 826

Phe Pro Gln Val Val Ser Ala Leu Asp Lys
1               5                   10

<210> SEQ ID NO 827
<211> LENGTH: 13
<212> TYPE: PRT
<213> ORGANISM: Homo sapiens

<400> SEQUENCE: 827

Glu Asn Gly Gly Ala Ser His Pro Leu Leu Asp Gln Arg
1               5                   10

<210> SEQ ID NO 828
<211> LENGTH: 15
<212> TYPE: PRT
<213> ORGANISM: Homo sapiens

<400> SEQUENCE: 828

Gln Pro His Tyr Ser Ala Phe Gly Ser Val Gly Glu Trp Leu Arg
1               5                   10                  15

<210> SEQ ID NO 829
<211> LENGTH: 18
<212> TYPE: PRT
<213> ORGANISM: Homo sapiens

<400> SEQUENCE: 829

Ser Gln Ala Lys Pro Gly Thr Pro Gly Gly Thr Gly Gly Pro Ala Pro
1               5                   10                  15

Gln Tyr

<210> SEQ ID NO 830
<211> LENGTH: 9
<212> TYPE: PRT
<213> ORGANISM: Homo sapiens

<400> SEQUENCE: 830

Asn Val Lys Pro Asp Gln Trp Val Lys
1               5

<210> SEQ ID NO 831
<211> LENGTH: 10
<212> TYPE: PRT
<213> ORGANISM: Homo sapiens

```
<400> SEQUENCE: 831

Leu Asn Leu Gly Thr Val Gly Phe Tyr Arg
1               5                   10

<210> SEQ ID NO 832
<211> LENGTH: 9
<212> TYPE: PRT
<213> ORGANISM: Homo sapiens

<400> SEQUENCE: 832

Asp Leu Ser Leu Pro Pro Val Asp Arg
1               5

<210> SEQ ID NO 833
<211> LENGTH: 12
<212> TYPE: PRT
<213> ORGANISM: Homo sapiens

<400> SEQUENCE: 833

Leu Gly Leu Gln Asn Asp Leu Phe Ser Leu Ala Arg
1               5                   10

<210> SEQ ID NO 834
<211> LENGTH: 11
<212> TYPE: PRT
<213> ORGANISM: Homo sapiens

<400> SEQUENCE: 834

Ala Gly Ile Ile Ser Thr Val Glu Val Leu Lys
1               5                   10

<210> SEQ ID NO 835
<211> LENGTH: 9
<212> TYPE: PRT
<213> ORGANISM: Homo sapiens

<400> SEQUENCE: 835

Asp Val Phe Ser Pro Ile Gly Glu Arg
1               5

<210> SEQ ID NO 836
<211> LENGTH: 17
<212> TYPE: PRT
<213> ORGANISM: Homo sapiens

<400> SEQUENCE: 836

Leu Gly Trp Asp Pro Lys Pro Gly Glu Gly His Leu Asp Ala Leu Leu
1               5                   10                  15

Arg

<210> SEQ ID NO 837
<211> LENGTH: 6
<212> TYPE: PRT
<213> ORGANISM: Homo sapiens

<400> SEQUENCE: 837

Gly Leu Val Leu Gly Lys
1               5

<210> SEQ ID NO 838
<211> LENGTH: 7
<212> TYPE: PRT
<213> ORGANISM: Homo sapiens
```

<400> SEQUENCE: 838

Ala Thr Leu Glu Glu Ala Arg
1               5

<210> SEQ ID NO 839
<211> LENGTH: 6
<212> TYPE: PRT
<213> ORGANISM: Homo sapiens

<400> SEQUENCE: 839

Asp His Val Glu Gly Lys
1               5

<210> SEQ ID NO 840
<211> LENGTH: 8
<212> TYPE: PRT
<213> ORGANISM: Homo sapiens

<400> SEQUENCE: 840

Gln Ile Leu Ser Ala Asp Leu Arg
1               5

<210> SEQ ID NO 841
<211> LENGTH: 9
<212> TYPE: PRT
<213> ORGANISM: Homo sapiens

<400> SEQUENCE: 841

Ser Pro Val Tyr Leu Thr Val Leu Lys
1               5

<210> SEQ ID NO 842
<211> LENGTH: 13
<212> TYPE: PRT
<213> ORGANISM: Homo sapiens

<400> SEQUENCE: 842

Val Leu Gly Ala Thr Leu Leu Pro Asp Leu Ile Gln Lys
1               5                   10

<210> SEQ ID NO 843
<211> LENGTH: 9
<212> TYPE: PRT
<213> ORGANISM: Homo sapiens

<400> SEQUENCE: 843

Asp Asn Trp Glu Glu Leu Tyr Asn Arg
1               5

<210> SEQ ID NO 844
<211> LENGTH: 9
<212> TYPE: PRT
<213> ORGANISM: Homo sapiens

<400> SEQUENCE: 844

Tyr Gln Gly Gly Phe Leu Ile Ser Arg
1               5

<210> SEQ ID NO 845
<211> LENGTH: 10
<212> TYPE: PRT
<213> ORGANISM: Homo sapiens

<400> SEQUENCE: 845

```
Leu Ser Val Glu Gly Phe Ala Val Asp Lys
1               5                   10

<210> SEQ ID NO 846
<211> LENGTH: 13
<212> TYPE: PRT
<213> ORGANISM: Homo sapiens

<400> SEQUENCE: 846

Ala Phe Phe Glu Ser His Pro Ala Pro Ser Ala Glu Arg
1               5                   10

<210> SEQ ID NO 847
<211> LENGTH: 12
<212> TYPE: PRT
<213> ORGANISM: Homo sapiens

<400> SEQUENCE: 847

Asp Ala Glu Ser Ile His Gln Tyr Leu Leu Gln Arg
1               5                   10

<210> SEQ ID NO 848
<211> LENGTH: 7
<212> TYPE: PRT
<213> ORGANISM: Homo sapiens

<400> SEQUENCE: 848

Asp Ile Ala Ala His Ile Lys
1               5

<210> SEQ ID NO 849
<211> LENGTH: 6
<212> TYPE: PRT
<213> ORGANISM: Homo sapiens

<400> SEQUENCE: 849

Glu Thr Glu Gly Phe Arg
1               5

<210> SEQ ID NO 850
<211> LENGTH: 8
<212> TYPE: PRT
<213> ORGANISM: Homo sapiens

<400> SEQUENCE: 850

Ser Ala Gln Phe Phe Asn Tyr Lys
1               5

<210> SEQ ID NO 851
<211> LENGTH: 14
<212> TYPE: PRT
<213> ORGANISM: Homo sapiens

<400> SEQUENCE: 851

Ile Gln Ala Leu Gly Leu Gly Glu Asp Trp Asn Val Glu Lys
1               5                   10

<210> SEQ ID NO 852
<211> LENGTH: 9
<212> TYPE: PRT
<213> ORGANISM: Homo sapiens

<400> SEQUENCE: 852

Gly Thr Ser Ala Gly Gly Gly Gln Lys
```

```
1               5

<210> SEQ ID NO 853
<211> LENGTH: 20
<212> TYPE: PRT
<213> ORGANISM: Homo sapiens

<400> SEQUENCE: 853

Glu Asp Leu Val Ile Leu Phe Ala Asp Ser Tyr Asp Val Leu Phe Ala
1               5                   10                  15

Ser Gly Pro Arg
            20

<210> SEQ ID NO 854
<211> LENGTH: 15
<212> TYPE: PRT
<213> ORGANISM: Homo sapiens

<400> SEQUENCE: 854

Ser Gln Val Val Phe Ser Ala Glu Glu Leu Ile Tyr Pro Asp Arg
1               5                   10                  15

<210> SEQ ID NO 855
<211> LENGTH: 8
<212> TYPE: PRT
<213> ORGANISM: Homo sapiens

<400> SEQUENCE: 855

Tyr Pro Val Val Ser Asp Gly Lys
1               5

<210> SEQ ID NO 856
<211> LENGTH: 16
<212> TYPE: PRT
<213> ORGANISM: Homo sapiens

<400> SEQUENCE: 856

Phe Leu Gly Ser Gly Gly Phe Ile Gly Tyr Ala Pro Asn Leu Ser Lys
1               5                   10                  15

<210> SEQ ID NO 857
<211> LENGTH: 19
<212> TYPE: PRT
<213> ORGANISM: Homo sapiens

<400> SEQUENCE: 857

Leu Val Ala Glu Trp Glu Gly Gln Asp Ser Asp Ser Asp Gln Leu Phe
1               5                   10                  15

Tyr Thr Lys

<210> SEQ ID NO 858
<211> LENGTH: 7
<212> TYPE: PRT
<213> ORGANISM: Homo sapiens

<400> SEQUENCE: 858

Ile Phe Leu Asp Pro Glu Lys
1               5

<210> SEQ ID NO 859
<211> LENGTH: 10
<212> TYPE: PRT
<213> ORGANISM: Homo sapiens
```

<400> SEQUENCE: 859

Glu Gln Ile Asn Ile Thr Leu Asp His Arg
1               5                   10

<210> SEQ ID NO 860
<211> LENGTH: 15
<212> TYPE: PRT
<213> ORGANISM: Homo sapiens

<400> SEQUENCE: 860

Ile Phe Gln Asn Leu Asp Gly Ala Leu Asp Glu Val Val Leu Lys
1               5                   10                  15

<210> SEQ ID NO 861
<211> LENGTH: 18
<212> TYPE: PRT
<213> ORGANISM: Homo sapiens

<400> SEQUENCE: 861

Asn Leu Ala Tyr Asp Thr Leu Pro Val Leu Ile His Gly Asn Gly Pro
1               5                   10                  15

Thr Lys

<210> SEQ ID NO 862
<211> LENGTH: 12
<212> TYPE: PRT
<213> ORGANISM: Homo sapiens

<400> SEQUENCE: 862

Leu Gln Leu Asn Tyr Leu Gly Asn Tyr Ile Pro Arg
1               5                   10

<210> SEQ ID NO 863
<211> LENGTH: 6
<212> TYPE: PRT
<213> ORGANISM: Homo sapiens

<400> SEQUENCE: 863

Leu His Tyr Pro Gln Lys
1               5

<210> SEQ ID NO 864
<211> LENGTH: 11
<212> TYPE: PRT
<213> ORGANISM: Homo sapiens

<400> SEQUENCE: 864

Leu Phe Ile His Asn His Glu Gln His Lys
1               5                   10

<210> SEQ ID NO 865
<211> LENGTH: 18
<212> TYPE: PRT
<213> ORGANISM: Homo sapiens

<400> SEQUENCE: 865

Ala Gln Val Glu Glu Phe Leu Ala Gln His Gly Ser Glu Tyr Gln Ser
1               5                   10                  15

Val Lys

<210> SEQ ID NO 866
<211> LENGTH: 7
<212> TYPE: PRT

```
<213> ORGANISM: Homo sapiens

<400> SEQUENCE: 866

Leu Leu Ile Gln Gln Asn Lys
1               5

<210> SEQ ID NO 867
<211> LENGTH: 17
<212> TYPE: PRT
<213> ORGANISM: Homo sapiens

<400> SEQUENCE: 867

Leu Trp Ser Asn Phe Trp Gly Ala Leu Ser Ala Asp Gly Tyr Tyr Ala
1               5                   10                  15

Arg

<210> SEQ ID NO 868
<211> LENGTH: 11
<212> TYPE: PRT
<213> ORGANISM: Homo sapiens

<400> SEQUENCE: 868

Ser Glu Asp Tyr Val Asp Ile Val Gln Gly Arg
1               5                   10

<210> SEQ ID NO 869
<211> LENGTH: 16
<212> TYPE: PRT
<213> ORGANISM: Homo sapiens

<400> SEQUENCE: 869

Val Gly Val Trp Asn Val Pro Tyr Ile Ser Asn Ile Tyr Leu Ile Lys
1               5                   10                  15

<210> SEQ ID NO 870
<211> LENGTH: 13
<212> TYPE: PRT
<213> ORGANISM: Homo sapiens

<400> SEQUENCE: 870

Gly Glu Leu Gln Ser Ser Asp Leu Phe His His Ser Lys
1               5                   10

<210> SEQ ID NO 871
<211> LENGTH: 13
<212> TYPE: PRT
<213> ORGANISM: Homo sapiens

<400> SEQUENCE: 871

His Thr Leu Gly His Leu Leu Ser Leu Asp Ser Tyr Arg
1               5                   10

<210> SEQ ID NO 872
<211> LENGTH: 19
<212> TYPE: PRT
<213> ORGANISM: Homo sapiens

<400> SEQUENCE: 872

Thr Thr His Leu His Asn Asp Leu Trp Glu Val Phe Ser Asn Pro Glu
1               5                   10                  15

Asp Trp Lys

<210> SEQ ID NO 873
```

-continued

```
<211> LENGTH: 8
<212> TYPE: PRT
<213> ORGANISM: Homo sapiens

<400> SEQUENCE: 873

Tyr Ile His Gln Asn Tyr Thr Lys
1               5

<210> SEQ ID NO 874
<211> LENGTH: 8
<212> TYPE: PRT
<213> ORGANISM: Homo sapiens

<400> SEQUENCE: 874

Leu Tyr Pro Gly Tyr Tyr Thr Arg
1               5

<210> SEQ ID NO 875
<211> LENGTH: 10
<212> TYPE: PRT
<213> ORGANISM: Homo sapiens

<400> SEQUENCE: 875

Ala Gln Phe Asp Leu Ala Phe Val Val Arg
1               5                   10

<210> SEQ ID NO 876
<211> LENGTH: 12
<212> TYPE: PRT
<213> ORGANISM: Homo sapiens

<400> SEQUENCE: 876

Leu Thr His Tyr His Glu Gly Leu Pro Thr Thr Arg
1               5                   10

<210> SEQ ID NO 877
<211> LENGTH: 9
<212> TYPE: PRT
<213> ORGANISM: Homo sapiens

<400> SEQUENCE: 877

Tyr Ile Ala Val Ser Phe Val Asp Pro
1               5

<210> SEQ ID NO 878
<211> LENGTH: 17
<212> TYPE: PRT
<213> ORGANISM: Homo sapiens

<400> SEQUENCE: 878

Gly Asp Ala Lys Pro Glu Asp Asn Leu Leu Val Leu Thr Val Ala Thr
1               5                   10                  15

Lys

<210> SEQ ID NO 879
<211> LENGTH: 6
<212> TYPE: PRT
<213> ORGANISM: Homo sapiens

<400> SEQUENCE: 879

Asn Asn Phe Val Ile Arg
1               5

<210> SEQ ID NO 880
```

```
<211> LENGTH: 7
<212> TYPE: PRT
<213> ORGANISM: Homo sapiens

<400> SEQUENCE: 880

Asn Pro Ala Asp Pro Gln Arg
1               5

<210> SEQ ID NO 881
<211> LENGTH: 8
<212> TYPE: PRT
<213> ORGANISM: Homo sapiens

<400> SEQUENCE: 881

Ile Pro Ser Asn Pro Ser His Arg
1               5

<210> SEQ ID NO 882
<211> LENGTH: 9
<212> TYPE: PRT
<213> ORGANISM: Homo sapiens

<400> SEQUENCE: 882

Glu Leu Pro Gln Ser Ile Val Tyr Lys
1               5

<210> SEQ ID NO 883
<211> LENGTH: 23
<212> TYPE: PRT
<213> ORGANISM: Homo sapiens

<400> SEQUENCE: 883

Ser Val Pro Ser Asp Ile Phe Gln Ile Gln Ala Thr Thr Ile Tyr Ala
1               5                   10                  15

Asn Thr Ile Asn Thr Phe Arg
            20

<210> SEQ ID NO 884
<211> LENGTH: 11
<212> TYPE: PRT
<213> ORGANISM: Homo sapiens

<400> SEQUENCE: 884

Ser Gly Asn Glu Asn Gly Glu Phe Tyr Leu Arg
1               5                   10

<210> SEQ ID NO 885
<211> LENGTH: 10
<212> TYPE: PRT
<213> ORGANISM: Homo sapiens

<400> SEQUENCE: 885

Leu Thr Ile Ile Val Gly Pro Phe Ser Phe
1               5                   10

<210> SEQ ID NO 886
<211> LENGTH: 12
<212> TYPE: PRT
<213> ORGANISM: Homo sapiens

<400> SEQUENCE: 886

Glu Ala Ala Ile Val Asp Pro Val Gln Pro Gln Lys
1               5                   10
```

```
<210> SEQ ID NO 887
<211> LENGTH: 19
<212> TYPE: PRT
<213> ORGANISM: Homo sapiens

<400> SEQUENCE: 887

Leu Thr Thr Val Leu Thr Thr His His His Trp Asp His Ala Gly Gly
1               5                   10                  15

Asn Glu Lys

<210> SEQ ID NO 888
<211> LENGTH: 6
<212> TYPE: PRT
<213> ORGANISM: Homo sapiens

<400> SEQUENCE: 888

Leu Glu Ser Gly Leu Lys
1               5

<210> SEQ ID NO 889
<211> LENGTH: 7
<212> TYPE: PRT
<213> ORGANISM: Homo sapiens

<400> SEQUENCE: 889

Val Tyr Gly Gly Asp Asp Arg
1               5

<210> SEQ ID NO 890
<211> LENGTH: 7
<212> TYPE: PRT
<213> ORGANISM: Homo sapiens

<400> SEQUENCE: 890

Ile Gly Ala Leu Thr His Lys
1               5

<210> SEQ ID NO 891
<211> LENGTH: 15
<212> TYPE: PRT
<213> ORGANISM: Homo sapiens

<400> SEQUENCE: 891

Ile Thr His Leu Ser Thr Leu Gln Val Gly Ser Leu Asn Val Lys
1               5                   10                  15

<210> SEQ ID NO 892
<211> LENGTH: 8
<212> TYPE: PRT
<213> ORGANISM: Homo sapiens

<400> SEQUENCE: 892

Ala Leu Leu Glu Val Leu Gly Arg
1               5

<210> SEQ ID NO 893
<211> LENGTH: 10
<212> TYPE: PRT
<213> ORGANISM: Homo sapiens

<400> SEQUENCE: 893

His Val Glu Pro Gly Asn Ala Ala Ile Arg
1               5                   10
```

```
<210> SEQ ID NO 894
<211> LENGTH: 7
<212> TYPE: PRT
<213> ORGANISM: Homo sapiens

<400> SEQUENCE: 894

Leu Asp Asp Asp Ser Glu Arg
1               5

<210> SEQ ID NO 895
<211> LENGTH: 8
<212> TYPE: PRT
<213> ORGANISM: Homo sapiens

<400> SEQUENCE: 895

Asp Ile Ser Ser Ile Gly Leu Lys
1               5

<210> SEQ ID NO 896
<211> LENGTH: 7
<212> TYPE: PRT
<213> ORGANISM: Homo sapiens

<400> SEQUENCE: 896

Leu Thr Ser Ala Ile Ala Lys
1               5

<210> SEQ ID NO 897
<211> LENGTH: 7
<212> TYPE: PRT
<213> ORGANISM: Homo sapiens

<400> SEQUENCE: 897

Ile Gly Glu Tyr Leu Glu Lys
1               5

<210> SEQ ID NO 898
<211> LENGTH: 9
<212> TYPE: PRT
<213> ORGANISM: Homo sapiens

<400> SEQUENCE: 898

Thr Val Ser Pro Ala Leu Ile Ser Arg
1               5

<210> SEQ ID NO 899
<211> LENGTH: 12
<212> TYPE: PRT
<213> ORGANISM: Homo sapiens

<400> SEQUENCE: 899

Ala Asp Val Phe His Ala Tyr Leu Ser Leu Leu Lys
1               5                   10

<210> SEQ ID NO 900
<211> LENGTH: 14
<212> TYPE: PRT
<213> ORGANISM: Homo sapiens

<400> SEQUENCE: 900

Ile Thr Ser Glu Ala Leu Leu Val Thr Gln Gln Leu Val Lys
1               5                   10

<210> SEQ ID NO 901
<211> LENGTH: 11
```

<212> TYPE: PRT
<213> ORGANISM: Homo sapiens

<400> SEQUENCE: 901

Ala Leu Thr Leu Ile Ala Gly Ser Pro Leu Lys
1               5                   10

<210> SEQ ID NO 902
<211> LENGTH: 19
<212> TYPE: PRT
<213> ORGANISM: Homo sapiens

<400> SEQUENCE: 902

Ile Asp Leu Arg Pro Val Leu Gly Glu Gly Val Pro Ile Leu Ala Ser
1               5                   10                  15

Phe Leu Arg

<210> SEQ ID NO 903
<211> LENGTH: 12
<212> TYPE: PRT
<213> ORGANISM: Homo sapiens

<400> SEQUENCE: 903

Leu Gly Thr Leu Ser Ala Leu Asp Ile Leu Ile Lys
1               5                   10

<210> SEQ ID NO 904
<211> LENGTH: 8
<212> TYPE: PRT
<213> ORGANISM: Homo sapiens

<400> SEQUENCE: 904

Val Tyr Pro Ser Ser Leu Ser Lys
1               5

<210> SEQ ID NO 905
<211> LENGTH: 14
<212> TYPE: PRT
<213> ORGANISM: Homo sapiens

<400> SEQUENCE: 905

Ile Ser Gly Ser Ile Leu Asn Glu Leu Ile Gly Leu Val Arg
1               5                   10

<210> SEQ ID NO 906
<211> LENGTH: 8
<212> TYPE: PRT
<213> ORGANISM: Homo sapiens

<400> SEQUENCE: 906

Gln Ser Tyr Tyr Ser Ile Ala Lys
1               5

<210> SEQ ID NO 907
<211> LENGTH: 14
<212> TYPE: PRT
<213> ORGANISM: Homo sapiens

<400> SEQUENCE: 907

Glu Gly Pro Ala Val Val Gly Gln Phe Ile Gln Asp Val Lys
1               5                   10

<210> SEQ ID NO 908
<211> LENGTH: 6

```
<212> TYPE: PRT
<213> ORGANISM: Homo sapiens

<400> SEQUENCE: 908

Ser Thr Asp Ser Ile Arg
1               5

<210> SEQ ID NO 909
<211> LENGTH: 23
<212> TYPE: PRT
<213> ORGANISM: Homo sapiens

<400> SEQUENCE: 909

Leu Leu Ala Leu Leu Ser Leu Gly Glu Val Gly His His Ile Asp Leu
1               5                   10                  15

Ser Gly Gln Leu Glu Leu Lys
            20

<210> SEQ ID NO 910
<211> LENGTH: 15
<212> TYPE: PRT
<213> ORGANISM: Homo sapiens

<400> SEQUENCE: 910

Ser Val Ile Leu Glu Ala Phe Ser Ser Pro Ser Glu Glu Val Lys
1               5                   10                  15

<210> SEQ ID NO 911
<211> LENGTH: 9
<212> TYPE: PRT
<213> ORGANISM: Homo sapiens

<400> SEQUENCE: 911

Gln Tyr Leu Leu Leu His Ser Leu Lys
1               5

<210> SEQ ID NO 912
<211> LENGTH: 24
<212> TYPE: PRT
<213> ORGANISM: Homo sapiens

<400> SEQUENCE: 912

Glu Ile Ile Ser Ser Ala Ser Val Val Gly Leu Lys Pro Tyr Val Glu
1               5                   10                  15

Asn Ile Trp Ala Leu Leu Leu Lys
            20

<210> SEQ ID NO 913
<211> LENGTH: 12
<212> TYPE: PRT
<213> ORGANISM: Homo sapiens

<400> SEQUENCE: 913

Leu Thr Leu Ile Asp Pro Glu Thr Leu Leu Pro Arg
1               5                   10

<210> SEQ ID NO 914
<211> LENGTH: 11
<212> TYPE: PRT
<213> ORGANISM: Homo sapiens

<400> SEQUENCE: 914

Gly Tyr Leu Ile Ser Gly Ser Ser Tyr Ala Arg
1               5                   10
```

```
<210> SEQ ID NO 915
<211> LENGTH: 8
<212> TYPE: PRT
<213> ORGANISM: Homo sapiens

<400> SEQUENCE: 915

Ser Ser Val Val Thr Ala Val Lys
1               5

<210> SEQ ID NO 916
<211> LENGTH: 15
<212> TYPE: PRT
<213> ORGANISM: Homo sapiens

<400> SEQUENCE: 916

Phe Thr Ile Ser Asp His Pro Gln Pro Ile Asp Pro Leu Leu Lys
1               5                   10                  15

<210> SEQ ID NO 917
<211> LENGTH: 10
<212> TYPE: PRT
<213> ORGANISM: Homo sapiens

<400> SEQUENCE: 917

Thr Leu Glu Asp Pro Asp Leu Asn Val Arg
1               5                   10

<210> SEQ ID NO 918
<211> LENGTH: 18
<212> TYPE: PRT
<213> ORGANISM: Homo sapiens

<400> SEQUENCE: 918

Val Ala Leu Val Thr Phe Asn Ser Ala Ala His Asn Lys Pro Ser Leu
1               5                   10                  15

Ile Arg

<210> SEQ ID NO 919
<211> LENGTH: 15
<212> TYPE: PRT
<213> ORGANISM: Homo sapiens

<400> SEQUENCE: 919

Asp Leu Leu Asp Thr Val Leu Pro His Leu Tyr Asn Glu Thr Lys
1               5                   10                  15

<210> SEQ ID NO 920
<211> LENGTH: 10
<212> TYPE: PRT
<213> ORGANISM: Homo sapiens

<400> SEQUENCE: 920

His Thr Val Asp Asp Gly Leu Asp Ile Arg
1               5                   10

<210> SEQ ID NO 921
<211> LENGTH: 15
<212> TYPE: PRT
<213> ORGANISM: Homo sapiens

<400> SEQUENCE: 921

Leu Asp Ile Phe Glu Phe Leu Asn His Val Glu Asp Gly Leu Lys
1               5                   10                  15
```

<210> SEQ ID NO 922
<211> LENGTH: 6
<212> TYPE: PRT
<213> ORGANISM: Homo sapiens

<400> SEQUENCE: 922

Asp His Tyr Asp Ile Lys
1               5

<210> SEQ ID NO 923
<211> LENGTH: 6
<212> TYPE: PRT
<213> ORGANISM: Homo sapiens

<400> SEQUENCE: 923

Leu Val Glu Pro Leu Arg
1               5

<210> SEQ ID NO 924
<211> LENGTH: 13
<212> TYPE: PRT
<213> ORGANISM: Homo sapiens

<400> SEQUENCE: 924

Ala Val Ala Ala Leu Leu Thr Ile Pro Glu Ala Glu Lys
1               5                   10

<210> SEQ ID NO 925
<211> LENGTH: 18
<212> TYPE: PRT
<213> ORGANISM: Homo sapiens

<400> SEQUENCE: 925

Val Ile Arg Pro Leu Asp Gln Pro Ser Ser Phe Asp Ala Thr Pro Tyr
1               5                   10                  15

Ile Lys

<210> SEQ ID NO 926
<211> LENGTH: 9
<212> TYPE: PRT
<213> ORGANISM: Homo sapiens

<400> SEQUENCE: 926

Ala Ala Asp Ile Asp Gln Glu Val Lys
1               5

<210> SEQ ID NO 927
<211> LENGTH: 15
<212> TYPE: PRT
<213> ORGANISM: Homo sapiens

<400> SEQUENCE: 927

Ser Gln Gly Val Asn Asp Asn Glu Glu Gly Phe Phe Ser Ala Arg
1               5                   10                  15

<210> SEQ ID NO 928
<211> LENGTH: 7
<212> TYPE: PRT
<213> ORGANISM: Homo sapiens

<400> SEQUENCE: 928

Gly His Arg Pro Leu Asp Lys
1               5

<210> SEQ ID NO 929
<211> LENGTH: 19
<212> TYPE: PRT
<213> ORGANISM: Homo sapiens

<400> SEQUENCE: 929

Glu Glu Ala Pro Ser Leu Arg Pro Ala Pro Pro Ile Ser Gly Gly
1               5                   10                  15

Gly Tyr Arg

<210> SEQ ID NO 930
<211> LENGTH: 15
<212> TYPE: PRT
<213> ORGANISM: Homo sapiens

<400> SEQUENCE: 930

Asp Asn Glu Asn Val Val Asn Glu Tyr Ser Ser Glu Leu Glu Lys
1               5                   10                  15

<210> SEQ ID NO 931
<211> LENGTH: 18
<212> TYPE: PRT
<213> ORGANISM: Homo sapiens

<400> SEQUENCE: 931

His Gln Leu Tyr Ile Asp Glu Thr Val Asn Ser Asn Ile Pro Thr Asn
1               5                   10                  15

Leu Arg

<210> SEQ ID NO 932
<211> LENGTH: 7
<212> TYPE: PRT
<213> ORGANISM: Homo sapiens

<400> SEQUENCE: 932

Ser Ile Leu Glu Asn Leu Arg
1               5

<210> SEQ ID NO 933
<211> LENGTH: 9
<212> TYPE: PRT
<213> ORGANISM: Homo sapiens

<400> SEQUENCE: 933

Gln Asp Gly Ser Val Asp Phe Gly Arg
1               5

<210> SEQ ID NO 934
<211> LENGTH: 13
<212> TYPE: PRT
<213> ORGANISM: Homo sapiens

<400> SEQUENCE: 934

Gln Gly Phe Gly Asn Val Ala Thr Asn Thr Asp Gly Lys
1               5                   10

<210> SEQ ID NO 935
<211> LENGTH: 14
<212> TYPE: PRT
<213> ORGANISM: Homo sapiens

<400> SEQUENCE: 935

```
Ala His Tyr Gly Gly Phe Thr Val Gln Asn Glu Ala Asn Lys
1               5                   10
```

<210> SEQ ID NO 936
<211> LENGTH: 7
<212> TYPE: PRT
<213> ORGANISM: Homo sapiens

<400> SEQUENCE: 936

```
Tyr Gln Ile Ser Val Asn Lys
1               5
```

<210> SEQ ID NO 937
<211> LENGTH: 11
<212> TYPE: PRT
<213> ORGANISM: Homo sapiens

<400> SEQUENCE: 937

```
Asp Asn Asp Gly Trp Leu Thr Ser Asp Pro Arg
1               5                   10
```

<210> SEQ ID NO 938
<211> LENGTH: 10
<212> TYPE: PRT
<213> ORGANISM: Homo sapiens

<400> SEQUENCE: 938

```
Glu Asp Gly Gly Gly Trp Trp Tyr Asn Arg
1               5                   10
```

<210> SEQ ID NO 939
<211> LENGTH: 8
<212> TYPE: PRT
<213> ORGANISM: Homo sapiens

<400> SEQUENCE: 939

```
Ile Arg Pro Phe Phe Pro Gln Gln
1               5
```

<210> SEQ ID NO 940
<211> LENGTH: 6
<212> TYPE: PRT
<213> ORGANISM: Homo sapiens

<400> SEQUENCE: 940

```
Val Phe Val Phe Pro Arg
1               5
```

<210> SEQ ID NO 941
<211> LENGTH: 7
<212> TYPE: PRT
<213> ORGANISM: Homo sapiens

<400> SEQUENCE: 941

```
Ala Tyr Ser Asp Leu Ser Arg
1               5
```

<210> SEQ ID NO 942
<211> LENGTH: 12
<212> TYPE: PRT
<213> ORGANISM: Homo sapiens

<400> SEQUENCE: 942

```
Ala Tyr Ser Leu Phe Ser Tyr Asn Thr Gln Gly Arg
1               5                   10
```

```
<210> SEQ ID NO 943
<211> LENGTH: 8
<212> TYPE: PRT
<213> ORGANISM: Homo sapiens

<400> SEQUENCE: 943

Asp Asn Glu Leu Leu Val Tyr Lys
1               5

<210> SEQ ID NO 944
<211> LENGTH: 10
<212> TYPE: PRT
<213> ORGANISM: Homo sapiens

<400> SEQUENCE: 944

Val Gly Glu Tyr Ser Leu Tyr Ile Gly Arg
1               5                   10

<210> SEQ ID NO 945
<211> LENGTH: 10
<212> TYPE: PRT
<213> ORGANISM: Homo sapiens

<400> SEQUENCE: 945

Gln Gly Tyr Phe Val Glu Ala Gln Pro Lys
1               5                   10

<210> SEQ ID NO 946
<211> LENGTH: 13
<212> TYPE: PRT
<213> ORGANISM: Homo sapiens

<400> SEQUENCE: 946

Ile Val Leu Gly Gln Glu Gln Asp Ser Tyr Gly Gly Lys
1               5                   10

<210> SEQ ID NO 947
<211> LENGTH: 11
<212> TYPE: PRT
<213> ORGANISM: Homo sapiens

<400> SEQUENCE: 947

Gly Tyr Val Ile Ile Lys Pro Leu Val Trp Val
1               5                   10

<210> SEQ ID NO 948
<211> LENGTH: 14
<212> TYPE: PRT
<213> ORGANISM: Homo sapiens

<400> SEQUENCE: 948

Glu Asp Pro Gln Thr Phe Tyr Tyr Ala Val Ala Val Val Lys
1               5                   10

<210> SEQ ID NO 949
<211> LENGTH: 10
<212> TYPE: PRT
<213> ORGANISM: Homo sapiens

<400> SEQUENCE: 949

Asp Gly Ala Gly Asp Val Ala Phe Val Lys
1               5                   10
```

<210> SEQ ID NO 950
<211> LENGTH: 11
<212> TYPE: PRT
<213> ORGANISM: Homo sapiens

<400> SEQUENCE: 950

His Ser Thr Ile Phe Glu Asn Leu Ala Asn Lys
1               5                   10

<210> SEQ ID NO 951
<211> LENGTH: 7
<212> TYPE: PRT
<213> ORGANISM: Homo sapiens

<400> SEQUENCE: 951

Lys Pro Val Asp Glu Tyr Lys
1               5

<210> SEQ ID NO 952
<211> LENGTH: 17
<212> TYPE: PRT
<213> ORGANISM: Homo sapiens

<400> SEQUENCE: 952

Glu Asp Leu Ile Trp Glu Leu Leu Asn Gln Ala Gln Glu His Phe Gly
1               5                   10                  15

Lys

<210> SEQ ID NO 953
<211> LENGTH: 11
<212> TYPE: PRT
<213> ORGANISM: Homo sapiens

<400> SEQUENCE: 953

Glu Phe Gln Leu Phe Ser Ser Pro His Gly Lys
1               5                   10

<210> SEQ ID NO 954
<211> LENGTH: 8
<212> TYPE: PRT
<213> ORGANISM: Homo sapiens

<400> SEQUENCE: 954

Asp Ser Ala His Gly Phe Leu Lys
1               5

<210> SEQ ID NO 955
<211> LENGTH: 11
<212> TYPE: PRT
<213> ORGANISM: Homo sapiens

<400> SEQUENCE: 955

Ser Ala Ser Asp Leu Thr Trp Asp Asn Leu Lys
1               5                   10

<210> SEQ ID NO 956
<211> LENGTH: 11
<212> TYPE: PRT
<213> ORGANISM: Homo sapiens

<400> SEQUENCE: 956

Glu Gly Tyr Tyr Gly Tyr Thr Gly Ala Phe Arg
1               5                   10

-continued

<210> SEQ ID NO 957
<211> LENGTH: 11
<212> TYPE: PRT
<213> ORGANISM: Homo sapiens

<400> SEQUENCE: 957

His Gln Thr Val Pro Gln Asn Thr Gly Gly Lys
1               5                   10

<210> SEQ ID NO 958
<211> LENGTH: 7
<212> TYPE: PRT
<213> ORGANISM: Homo sapiens

<400> SEQUENCE: 958

Asn Pro Asp Pro Trp Ala Lys
1               5

<210> SEQ ID NO 959
<211> LENGTH: 9
<212> TYPE: PRT
<213> ORGANISM: Homo sapiens

<400> SEQUENCE: 959

Ala Pro Asn His Ala Val Val Thr Arg
1               5

<210> SEQ ID NO 960
<211> LENGTH: 8
<212> TYPE: PRT
<213> ORGANISM: Homo sapiens

<400> SEQUENCE: 960

Tyr Leu Gly Glu Glu Tyr Val Lys
1               5

<210> SEQ ID NO 961
<211> LENGTH: 6
<212> TYPE: PRT
<213> ORGANISM: Homo sapiens

<400> SEQUENCE: 961

Ala Val Gly Asn Leu Arg
1               5

<210> SEQ ID NO 962
<211> LENGTH: 14
<212> TYPE: PRT
<213> ORGANISM: Homo sapiens

<400> SEQUENCE: 962

Ala Val Thr Glu Gln Gly His Glu Leu Ser Asn Glu Glu Arg
1               5                   10

<210> SEQ ID NO 963
<211> LENGTH: 12
<212> TYPE: PRT
<213> ORGANISM: Homo sapiens

<400> SEQUENCE: 963

Tyr Leu Ile Pro Asn Ala Thr Gln Pro Glu Ser Lys
1               5                   10

<210> SEQ ID NO 964
<211> LENGTH: 11

```
<212> TYPE: PRT
<213> ORGANISM: Homo sapiens

<400> SEQUENCE: 964

Tyr Leu Ser Glu Val Ala Ser Gly Asp Asn Lys
1               5                   10

<210> SEQ ID NO 965
<211> LENGTH: 19
<212> TYPE: PRT
<213> ORGANISM: Homo sapiens

<400> SEQUENCE: 965

Gln Thr Thr Val Ser Asn Ser Gln Gln Ala Tyr Gln Glu Ala Phe Glu
1               5                   10                  15

Ile Ser Lys

<210> SEQ ID NO 966
<211> LENGTH: 19
<212> TYPE: PRT
<213> ORGANISM: Homo sapiens

<400> SEQUENCE: 966

Thr Ala Phe Asp Glu Ala Ile Ala Glu Leu Asp Thr Leu Asn Glu Glu
1               5                   10                  15

Ser Tyr Lys

<210> SEQ ID NO 967
<211> LENGTH: 22
<212> TYPE: PRT
<213> ORGANISM: Homo sapiens

<400> SEQUENCE: 967

Asp Asn Leu Thr Leu Trp Thr Ser Glu Asn Gln Gly Asp Glu Gly Asp
1               5                   10                  15

Ala Gly Glu Gly Glu Asn
            20

<210> SEQ ID NO 968
<211> LENGTH: 12
<212> TYPE: PRT
<213> ORGANISM: Homo sapiens

<400> SEQUENCE: 968

Glu Gly Asp Val Leu Thr Leu Leu Glu Ser Glu Arg
1               5                   10

<210> SEQ ID NO 969
<211> LENGTH: 6
<212> TYPE: PRT
<213> ORGANISM: Homo sapiens

<400> SEQUENCE: 969

Gln Ala Pro Gly Gln Arg
1               5

<210> SEQ ID NO 970
<211> LENGTH: 17
<212> TYPE: PRT
<213> ORGANISM: Homo sapiens

<400> SEQUENCE: 970

Glu Val Asn Thr Ser Gly Phe Ala Pro Ala Arg Pro Pro Pro Gln Pro
```

```
1               5                   10                  15

Arg

<210> SEQ ID NO 971
<211> LENGTH: 9
<212> TYPE: PRT
<213> ORGANISM: Homo sapiens

<400> SEQUENCE: 971

Asn Val Lys Pro Asp Gln Trp Val Lys
1               5

<210> SEQ ID NO 972
<211> LENGTH: 10
<212> TYPE: PRT
<213> ORGANISM: Homo sapiens

<400> SEQUENCE: 972

Leu Asn Leu Gly Thr Val Gly Phe Tyr Arg
1               5                   10

<210> SEQ ID NO 973
<211> LENGTH: 9
<212> TYPE: PRT
<213> ORGANISM: Homo sapiens

<400> SEQUENCE: 973

Asp Leu Ser Leu Pro Pro Val Asp Arg
1               5

<210> SEQ ID NO 974
<211> LENGTH: 12
<212> TYPE: PRT
<213> ORGANISM: Homo sapiens

<400> SEQUENCE: 974

Leu Gly Leu Gln Asn Asp Leu Phe Ser Leu Ala Arg
1               5                   10

<210> SEQ ID NO 975
<211> LENGTH: 11
<212> TYPE: PRT
<213> ORGANISM: Homo sapiens

<400> SEQUENCE: 975

Ala Gly Ile Ile Ser Thr Val Glu Val Leu Lys
1               5                   10

<210> SEQ ID NO 976
<211> LENGTH: 9
<212> TYPE: PRT
<213> ORGANISM: Homo sapiens

<400> SEQUENCE: 976

Asp Val Phe Ser Pro Ile Gly Glu Arg
1               5

<210> SEQ ID NO 977
<211> LENGTH: 17
<212> TYPE: PRT
<213> ORGANISM: Homo sapiens

<400> SEQUENCE: 977

Leu Gly Trp Asp Pro Lys Pro Gly Glu Gly His Leu Asp Ala Leu Leu
1               5                   10                  15
```

-continued

```
1               5                   10                  15

Arg

<210> SEQ ID NO 978
<211> LENGTH: 6
<212> TYPE: PRT
<213> ORGANISM: Homo sapiens

<400> SEQUENCE: 978

Gly Leu Val Leu Gly Lys
1               5

<210> SEQ ID NO 979
<211> LENGTH: 7
<212> TYPE: PRT
<213> ORGANISM: Homo sapiens

<400> SEQUENCE: 979

Ala Thr Leu Glu Glu Ala Arg
1               5

<210> SEQ ID NO 980
<211> LENGTH: 6
<212> TYPE: PRT
<213> ORGANISM: Homo sapiens

<400> SEQUENCE: 980

Asp His Val Glu Gly Lys
1               5

<210> SEQ ID NO 981
<211> LENGTH: 8
<212> TYPE: PRT
<213> ORGANISM: Homo sapiens

<400> SEQUENCE: 981

Gln Ile Leu Ser Ala Asp Leu Arg
1               5

<210> SEQ ID NO 982
<211> LENGTH: 9
<212> TYPE: PRT
<213> ORGANISM: Homo sapiens

<400> SEQUENCE: 982

Ser Pro Val Tyr Leu Thr Val Leu Lys
1               5

<210> SEQ ID NO 983
<211> LENGTH: 13
<212> TYPE: PRT
<213> ORGANISM: Homo sapiens

<400> SEQUENCE: 983

Val Leu Gly Ala Thr Leu Leu Pro Asp Leu Ile Gln Lys
1               5                   10

<210> SEQ ID NO 984
<211> LENGTH: 9
<212> TYPE: PRT
<213> ORGANISM: Homo sapiens

<400> SEQUENCE: 984

Asp Asn Trp Glu Glu Leu Tyr Asn Arg
```

```
1               5

<210> SEQ ID NO 985
<211> LENGTH: 9
<212> TYPE: PRT
<213> ORGANISM: Homo sapiens

<400> SEQUENCE: 985

Tyr Gln Gly Gly Phe Leu Ile Ser Arg
1               5

<210> SEQ ID NO 986
<211> LENGTH: 10
<212> TYPE: PRT
<213> ORGANISM: Homo sapiens

<400> SEQUENCE: 986

Leu Ser Val Glu Gly Phe Ala Val Asp Lys
1               5                   10

<210> SEQ ID NO 987
<211> LENGTH: 13
<212> TYPE: PRT
<213> ORGANISM: Homo sapiens

<400> SEQUENCE: 987

Ala Phe Phe Glu Ser His Pro Ala Pro Ser Ala Glu Arg
1               5                   10

<210> SEQ ID NO 988
<211> LENGTH: 12
<212> TYPE: PRT
<213> ORGANISM: Homo sapiens

<400> SEQUENCE: 988

Asp Ala Glu Ser Ile His Gln Tyr Leu Leu Gln Arg
1               5                   10

<210> SEQ ID NO 989
<211> LENGTH: 7
<212> TYPE: PRT
<213> ORGANISM: Homo sapiens

<400> SEQUENCE: 989

Asp Ile Ala Ala His Ile Lys
1               5

<210> SEQ ID NO 990
<211> LENGTH: 6
<212> TYPE: PRT
<213> ORGANISM: Homo sapiens

<400> SEQUENCE: 990

Asn Asn Phe Val Ile Arg
1               5

<210> SEQ ID NO 991
<211> LENGTH: 7
<212> TYPE: PRT
<213> ORGANISM: Homo sapiens

<400> SEQUENCE: 991

Asn Pro Ala Asp Pro Gln Arg
1               5
```

<210> SEQ ID NO 992
<211> LENGTH: 8
<212> TYPE: PRT
<213> ORGANISM: Homo sapiens

<400> SEQUENCE: 992

Ile Pro Ser Asn Pro Ser His Arg
1               5

<210> SEQ ID NO 993
<211> LENGTH: 9
<212> TYPE: PRT
<213> ORGANISM: Homo sapiens

<400> SEQUENCE: 993

Glu Leu Pro Gln Ser Ile Val Tyr Lys
1               5

<210> SEQ ID NO 994
<211> LENGTH: 23
<212> TYPE: PRT
<213> ORGANISM: Homo sapiens

<400> SEQUENCE: 994

Ser Val Pro Ser Asp Ile Phe Gln Ile Gln Ala Thr Thr Ile Tyr Ala
1               5                   10                  15

Asn Thr Ile Asn Thr Phe Arg
            20

<210> SEQ ID NO 995
<211> LENGTH: 11
<212> TYPE: PRT
<213> ORGANISM: Homo sapiens

<400> SEQUENCE: 995

Ser Gly Asn Glu Asn Gly Glu Phe Tyr Leu Arg
1               5                   10

<210> SEQ ID NO 996
<211> LENGTH: 10
<212> TYPE: PRT
<213> ORGANISM: Homo sapiens

<400> SEQUENCE: 996

Leu Thr Ile Ile Val Gly Pro Phe Ser Phe
1               5                   10

<210> SEQ ID NO 997
<211> LENGTH: 15
<212> TYPE: PRT
<213> ORGANISM: Homo sapiens

<400> SEQUENCE: 997

Val Gly Ala His Ala Gly Glu Tyr Gly Ala Glu Ala Leu Glu Arg
1               5                   10                  15

<210> SEQ ID NO 998
<211> LENGTH: 16
<212> TYPE: PRT
<213> ORGANISM: Homo sapiens

<400> SEQUENCE: 998

Thr Tyr Phe Pro His Phe Asp Leu Ser His Gly Ser Ala Gln Val Lys
1               5                   10                  15

<210> SEQ ID NO 999
<211> LENGTH: 12
<212> TYPE: PRT
<213> ORGANISM: Homo sapiens

<400> SEQUENCE: 999

Phe Leu Ala Ser Val Ser Thr Val Leu Thr Ser Lys
1               5                   10

<210> SEQ ID NO 1000
<211> LENGTH: 20
<212> TYPE: PRT
<213> ORGANISM: Homo sapiens

<400> SEQUENCE: 1000

Glu Leu Leu Leu Pro Asn Trp Gln Gly Ser Gly Ser His Gly Leu Thr
1               5                   10                  15

Ile Ala Gln Arg
            20

<210> SEQ ID NO 1001
<211> LENGTH: 17
<212> TYPE: PRT
<213> ORGANISM: Homo sapiens

<400> SEQUENCE: 1001

Asp Asp Gly Val Phe Val Gln Glu Val Thr Gln Asn Ser Pro Ala Ala
1               5                   10                  15

Arg

<210> SEQ ID NO 1002
<211> LENGTH: 10
<212> TYPE: PRT
<213> ORGANISM: Homo sapiens

<400> SEQUENCE: 1002

Ser Pro Glu Pro Gly Gln Thr Trp Thr Arg
1               5                   10

<210> SEQ ID NO 1003
<211> LENGTH: 15
<212> TYPE: PRT
<213> ORGANISM: Homo sapiens

<400> SEQUENCE: 1003

Ser Glu Asp Gly Val Glu Gly Asp Leu Gly Glu Thr Gln Ser Arg
1               5                   10                  15

<210> SEQ ID NO 1004
<211> LENGTH: 6
<212> TYPE: PRT
<213> ORGANISM: Homo sapiens

<400> SEQUENCE: 1004

Thr Ile Thr Val Thr Arg
1               5

<210> SEQ ID NO 1005
<211> LENGTH: 11
<212> TYPE: PRT
<213> ORGANISM: Homo sapiens

<400> SEQUENCE: 1005

Val Thr Ala Tyr Thr Val Asp Val Thr Gly Arg
1               5                   10

<210> SEQ ID NO 1006
<211> LENGTH: 10
<212> TYPE: PRT
<213> ORGANISM: Homo sapiens

<400> SEQUENCE: 1006

Asp Ile Asp Ile Ser Ser Pro Glu Phe Lys
1               5                   10

<210> SEQ ID NO 1007
<211> LENGTH: 17
<212> TYPE: PRT
<213> ORGANISM: Homo sapiens

<400> SEQUENCE: 1007

His Glu Leu Thr Glu Ile Ser Asn Val Asp Val Glu Thr Gln Ser Gly
1               5                   10                  15

Lys

<210> SEQ ID NO 1008
<211> LENGTH: 18
<212> TYPE: PRT
<213> ORGANISM: Homo sapiens

<400> SEQUENCE: 1008

Leu Pro Ser Gly Ser Gly Ala Ala Ser Pro Thr Gly Ser Ala Val Asp
1               5                   10                  15

Ile Arg

<210> SEQ ID NO 1009
<211> LENGTH: 18
<212> TYPE: PRT
<213> ORGANISM: Homo sapiens

<400> SEQUENCE: 1009

Ala Gly Ala Ile Ser Ala Ser Gly Pro Glu Leu Gln Gly Ala Gly His
1               5                   10                  15

Ser Lys

<210> SEQ ID NO 1010
<211> LENGTH: 11
<212> TYPE: PRT
<213> ORGANISM: Homo sapiens

<400> SEQUENCE: 1010

Val Gly Gly Ser Gly Val Asn Val Asn Ala Lys
1               5                   10

<210> SEQ ID NO 1011
<211> LENGTH: 7
<212> TYPE: PRT
<213> ORGANISM: Homo sapiens

<400> SEQUENCE: 1011

Gly Leu Asp Leu Gly Gly Arg
1               5

<210> SEQ ID NO 1012
<211> LENGTH: 17

```
<212> TYPE: PRT
<213> ORGANISM: Homo sapiens

<400> SEQUENCE: 1012

Gly Gly Val Gln Val Pro Ala Val Asp Ile Ser Ser Ser Leu Gly Gly
1               5                   10                  15

Arg

<210> SEQ ID NO 1013
<211> LENGTH: 16
<212> TYPE: PRT
<213> ORGANISM: Homo sapiens

<400> SEQUENCE: 1013

Ala Val Glu Val Gln Gly Pro Ser Leu Glu Ser Gly Asp His Gly Lys
1               5                   10                  15

<210> SEQ ID NO 1014
<211> LENGTH: 7
<212> TYPE: PRT
<213> ORGANISM: Homo sapiens

<400> SEQUENCE: 1014

Phe Gly Val Ser Thr Gly Arg
1               5

<210> SEQ ID NO 1015
<211> LENGTH: 6
<212> TYPE: PRT
<213> ORGANISM: Homo sapiens

<400> SEQUENCE: 1015

Glu Gly Gln Thr Pro Lys
1               5

<210> SEQ ID NO 1016
<211> LENGTH: 11
<212> TYPE: PRT
<213> ORGANISM: Homo sapiens

<400> SEQUENCE: 1016

Val Ser Ala Pro Glu Val Ser Val Gly His Lys
1               5                   10

<210> SEQ ID NO 1017
<211> LENGTH: 16
<212> TYPE: PRT
<213> ORGANISM: Homo sapiens

<400> SEQUENCE: 1017

Gly Pro Gln Ile Thr Gly Pro Ser Leu Glu Gly Asp Leu Gly Leu Lys
1               5                   10                  15

<210> SEQ ID NO 1018
<211> LENGTH: 7
<212> TYPE: PRT
<213> ORGANISM: Homo sapiens

<400> SEQUENCE: 1018

Phe Ser Val Ser Gly Ala Lys
1               5

<210> SEQ ID NO 1019
<211> LENGTH: 11
```

```
<212> TYPE: PRT
<213> ORGANISM: Homo sapiens

<400> SEQUENCE: 1019

Val Ser Ala Pro Gly Val Gln Gly Asp Val Lys
1               5                   10

<210> SEQ ID NO 1020
<211> LENGTH: 7
<212> TYPE: PRT
<213> ORGANISM: Homo sapiens

<400> SEQUENCE: 1020

Gly Pro Gln Val Ala Leu Lys
1               5

<210> SEQ ID NO 1021
<211> LENGTH: 16
<212> TYPE: PRT
<213> ORGANISM: Homo sapiens

<400> SEQUENCE: 1021

Val Asp Ile Glu Thr Pro Asn Leu Glu Gly Thr Leu Thr Gly Pro Arg
1               5                   10                  15

<210> SEQ ID NO 1022
<211> LENGTH: 7
<212> TYPE: PRT
<213> ORGANISM: Homo sapiens

<400> SEQUENCE: 1022

Leu Gly Ser Pro Ser Gly Lys
1               5

<210> SEQ ID NO 1023
<211> LENGTH: 9
<212> TYPE: PRT
<213> ORGANISM: Homo sapiens

<400> SEQUENCE: 1023

Gly Gly Val Asp Val Thr Leu Pro Arg
1               5

<210> SEQ ID NO 1024
<211> LENGTH: 7
<212> TYPE: PRT
<213> ORGANISM: Homo sapiens

<400> SEQUENCE: 1024

Val Pro Glu Val Asp Val Arg
1               5

<210> SEQ ID NO 1025
<211> LENGTH: 18
<212> TYPE: PRT
<213> ORGANISM: Homo sapiens

<400> SEQUENCE: 1025

Val Asp Val Ser Ala Pro Asp Val Glu Ala His Gly Pro Glu Trp Asn
1               5                   10                  15

Leu Lys

<210> SEQ ID NO 1026
<211> LENGTH: 9
```

```
<212> TYPE: PRT
<213> ORGANISM: Homo sapiens

<400> SEQUENCE: 1026

Gly Asp Ile Ser Ile Ser Gly Pro Lys
1               5

<210> SEQ ID NO 1027
<211> LENGTH: 16
<212> TYPE: PRT
<213> ORGANISM: Homo sapiens

<400> SEQUENCE: 1027

Val Asn Val Glu Ala Pro Asp Val Asn Leu Glu Gly Leu Gly Gly Lys
1               5                   10                  15

<210> SEQ ID NO 1028
<211> LENGTH: 9
<212> TYPE: PRT
<213> ORGANISM: Homo sapiens

<400> SEQUENCE: 1028

Gly Glu Tyr Asp Val Thr Val Pro Lys
1               5

<210> SEQ ID NO 1029
<211> LENGTH: 18
<212> TYPE: PRT
<213> ORGANISM: Homo sapiens

<400> SEQUENCE: 1029

Val Asp Ile Asp Ala Pro Asp Val Asp Val His Gly Pro Asp Trp His
1               5                   10                  15

Leu Lys

<210> SEQ ID NO 1030
<211> LENGTH: 7
<212> TYPE: PRT
<213> ORGANISM: Homo sapiens

<400> SEQUENCE: 1030

Phe Ser Val Pro Gly Phe Lys
1               5

<210> SEQ ID NO 1031
<211> LENGTH: 12
<212> TYPE: PRT
<213> ORGANISM: Homo sapiens

<400> SEQUENCE: 1031

Ala Glu Gly Pro Glu Val Asp Val Asn Leu Pro Lys
1               5                   10

<210> SEQ ID NO 1032
<211> LENGTH: 9
<212> TYPE: PRT
<213> ORGANISM: Homo sapiens

<400> SEQUENCE: 1032

Ala Asp Val Asp Ile Ser Gly Pro Lys
1               5

<210> SEQ ID NO 1033
<211> LENGTH: 16
```

```
<212> TYPE: PRT
<213> ORGANISM: Homo sapiens

<400> SEQUENCE: 1033

Ile Asp Val Thr Ala Pro Asp Val Ser Ile Glu Glu Pro Glu Gly Lys
1               5                   10                  15

<210> SEQ ID NO 1034
<211> LENGTH: 7
<212> TYPE: PRT
<213> ORGANISM: Homo sapiens

<400> SEQUENCE: 1034

Val Pro Asp Val Glu Leu Lys
1               5

<210> SEQ ID NO 1035
<211> LENGTH: 16
<212> TYPE: PRT
<213> ORGANISM: Homo sapiens

<400> SEQUENCE: 1035

Val Gly Val Glu Val Pro Asp Val Asn Ile Glu Gly Pro Glu Gly Lys
1               5                   10                  15

<210> SEQ ID NO 1036
<211> LENGTH: 12
<212> TYPE: PRT
<213> ORGANISM: Homo sapiens

<400> SEQUENCE: 1036

Gly Glu Gly Pro Glu Phe Asp Val Asn Leu Ser Lys
1               5                   10

<210> SEQ ID NO 1037
<211> LENGTH: 9
<212> TYPE: PRT
<213> ORGANISM: Homo sapiens

<400> SEQUENCE: 1037

Ala Asn Val Asp Ile Ser Ala Pro Lys
1               5

<210> SEQ ID NO 1038
<211> LENGTH: 16
<212> TYPE: PRT
<213> ORGANISM: Homo sapiens

<400> SEQUENCE: 1038

Val Asp Thr Asn Ala Pro Asp Leu Ser Leu Glu Gly Pro Glu Gly Lys
1               5                   10                  15

<210> SEQ ID NO 1039
<211> LENGTH: 9
<212> TYPE: PRT
<213> ORGANISM: Homo sapiens

<400> SEQUENCE: 1039

Gly Asn Val Asp Ile Ser Ala Pro Lys
1               5

<210> SEQ ID NO 1040
<211> LENGTH: 14
<212> TYPE: PRT
<213> ORGANISM: Homo sapiens
```

<400> SEQUENCE: 1040

Ala Pro Asp Val Glu Gly Gln Gly Leu Asp Trp Ser Leu Lys
1               5                   10

<210> SEQ ID NO 1041
<211> LENGTH: 12
<212> TYPE: PRT
<213> ORGANISM: Homo sapiens

<400> SEQUENCE: 1041

Gly Glu Gly Pro Glu Val Asp Val Asn Leu Pro Lys
1               5                   10

<210> SEQ ID NO 1042
<211> LENGTH: 9
<212> TYPE: PRT
<213> ORGANISM: Homo sapiens

<400> SEQUENCE: 1042

Ala Asp Val Val Val Ser Gly Pro Lys
1               5

<210> SEQ ID NO 1043
<211> LENGTH: 16
<212> TYPE: PRT
<213> ORGANISM: Homo sapiens

<400> SEQUENCE: 1043

Val Asp Ile Glu Ala Pro Asp Val Ser Leu Glu Gly Pro Glu Gly Lys
1               5                   10                  15

<210> SEQ ID NO 1044
<211> LENGTH: 9
<212> TYPE: PRT
<213> ORGANISM: Homo sapiens

<400> SEQUENCE: 1044

Gly Asp Val Asp Val Ser Val Pro Lys
1               5

<210> SEQ ID NO 1045
<211> LENGTH: 7
<212> TYPE: PRT
<213> ORGANISM: Homo sapiens

<400> SEQUENCE: 1045

Val Pro Asp Val Glu Ile Lys
1               5

<210> SEQ ID NO 1046
<211> LENGTH: 8
<212> TYPE: PRT
<213> ORGANISM: Homo sapiens

<400> SEQUENCE: 1046

Glu Val Asp Val Asn Leu Pro Lys
1               5

<210> SEQ ID NO 1047
<211> LENGTH: 9
<212> TYPE: PRT
<213> ORGANISM: Homo sapiens

<400> SEQUENCE: 1047

Ala Asp Ile Asp Val Ser Gly Pro Lys
1               5

<210> SEQ ID NO 1048
<211> LENGTH: 16
<212> TYPE: PRT
<213> ORGANISM: Homo sapiens

<400> SEQUENCE: 1048

Val Asp Val Glu Val Pro Asp Val Ser Leu Glu Gly Pro Glu Gly Lys
1               5                   10                  15

<210> SEQ ID NO 1049
<211> LENGTH: 18
<212> TYPE: PRT
<213> ORGANISM: Homo sapiens

<400> SEQUENCE: 1049

Val Asp Ile Ser Ala Pro Asp Val Asp Val His Gly Pro Asp Trp His
1               5                   10                  15

Leu Lys

<210> SEQ ID NO 1050
<211> LENGTH: 9
<212> TYPE: PRT
<213> ORGANISM: Homo sapiens

<400> SEQUENCE: 1050

Gly Glu Gly Pro Glu Val Asp Val Lys
1               5

<210> SEQ ID NO 1051
<211> LENGTH: 9
<212> TYPE: PRT
<213> ORGANISM: Homo sapiens

<400> SEQUENCE: 1051

Ala Asp Val Asp Val Ser Gly Pro Lys
1               5

<210> SEQ ID NO 1052
<211> LENGTH: 11
<212> TYPE: PRT
<213> ORGANISM: Homo sapiens

<400> SEQUENCE: 1052

Ile Ser Ile Pro Asp Val Gly Leu His Leu Lys
1               5                   10

<210> SEQ ID NO 1053
<211> LENGTH: 9
<212> TYPE: PRT
<213> ORGANISM: Homo sapiens

<400> SEQUENCE: 1053

Gly Asp Tyr Asp Val Thr Val Pro Lys
1               5

<210> SEQ ID NO 1054
<211> LENGTH: 6
<212> TYPE: PRT
<213> ORGANISM: Homo sapiens

<400> SEQUENCE: 1054

```
Val Glu Gly Glu Ile Lys
1               5

<210> SEQ ID NO 1055
<211> LENGTH: 7
<212> TYPE: PRT
<213> ORGANISM: Homo sapiens

<400> SEQUENCE: 1055

Ala Pro Asp Val Asp Ile Lys
1               5

<210> SEQ ID NO 1056
<211> LENGTH: 18
<212> TYPE: PRT
<213> ORGANISM: Homo sapiens

<400> SEQUENCE: 1056

Val Asp Ile Asn Ala Pro Asp Val Glu Val His Gly Pro Asp Trp His
1               5                   10                  15

Leu Lys

<210> SEQ ID NO 1057
<211> LENGTH: 9
<212> TYPE: PRT
<213> ORGANISM: Homo sapiens

<400> SEQUENCE: 1057

Ala Asp Leu Gly Val Ser Gly Pro Lys
1               5

<210> SEQ ID NO 1058
<211> LENGTH: 16
<212> TYPE: PRT
<213> ORGANISM: Homo sapiens

<400> SEQUENCE: 1058

Val Asp Ile Asp Val Pro Asp Val Asn Leu Glu Ala Pro Glu Gly Lys
1               5                   10                  15

<210> SEQ ID NO 1059
<211> LENGTH: 9
<212> TYPE: PRT
<213> ORGANISM: Homo sapiens

<400> SEQUENCE: 1059

Thr Asp Val Asp Val Ser Leu Pro Lys
1               5

<210> SEQ ID NO 1060
<211> LENGTH: 6
<212> TYPE: PRT
<213> ORGANISM: Homo sapiens

<400> SEQUENCE: 1060

Val Glu Gly Asp Leu Lys
1               5

<210> SEQ ID NO 1061
<211> LENGTH: 7
<212> TYPE: PRT
<213> ORGANISM: Homo sapiens

<400> SEQUENCE: 1061
```

```
Gly Pro Glu Ile Asp Val Lys
1               5

<210> SEQ ID NO 1062
<211> LENGTH: 18
<212> TYPE: PRT
<213> ORGANISM: Homo sapiens

<400> SEQUENCE: 1062

Val Asp Ile Asp Ala Pro Asp Val Glu Val His Asp Pro Asp Trp His
1               5                   10                  15

Leu Lys

<210> SEQ ID NO 1063
<211> LENGTH: 25
<212> TYPE: PRT
<213> ORGANISM: Homo sapiens

<400> SEQUENCE: 1063

Ala Asp Ile Asp Val Ser Gly Pro Ser Val Asp Thr Asp Ala Pro Asp
1               5                   10                  15

Leu Asp Ile Glu Gly Pro Glu Gly Lys
            20                  25

<210> SEQ ID NO 1064
<211> LENGTH: 15
<212> TYPE: PRT
<213> ORGANISM: Homo sapiens

<400> SEQUENCE: 1064

Gly Glu Ile Asp Ala Ser Val Pro Glu Leu Glu Gly Asp Leu Arg
1               5                   10                  15

<210> SEQ ID NO 1065
<211> LENGTH: 9
<212> TYPE: PRT
<213> ORGANISM: Homo sapiens

<400> SEQUENCE: 1065

Gly Asp Ala Asp Val Ser Val Pro Lys
1               5

<210> SEQ ID NO 1066
<211> LENGTH: 9
<212> TYPE: PRT
<213> ORGANISM: Homo sapiens

<400> SEQUENCE: 1066

Gly Asp Val Asp Val Ser Leu Pro Lys
1               5

<210> SEQ ID NO 1067
<211> LENGTH: 7
<212> TYPE: PRT
<213> ORGANISM: Homo sapiens

<400> SEQUENCE: 1067

Val Pro Asp Val Asp Ile Arg
1               5

<210> SEQ ID NO 1068
<211> LENGTH: 9
<212> TYPE: PRT
```

```
<213> ORGANISM: Homo sapiens

<400> SEQUENCE: 1068

Gly Asp Val Asp Val Ser Ala Pro Lys
1               5

<210> SEQ ID NO 1069
<211> LENGTH: 7
<212> TYPE: PRT
<213> ORGANISM: Homo sapiens

<400> SEQUENCE: 1069

Gly Pro Glu Leu Asp Val Lys
1               5

<210> SEQ ID NO 1070
<211> LENGTH: 9
<212> TYPE: PRT
<213> ORGANISM: Homo sapiens

<400> SEQUENCE: 1070

Gly Glu Val Asp Val Asp Val Pro Lys
1               5

<210> SEQ ID NO 1071
<211> LENGTH: 19
<212> TYPE: PRT
<213> ORGANISM: Homo sapiens

<400> SEQUENCE: 1071

Gly Pro His Val Asp Val Ser Gly Pro Asp Ile Asp Ile Glu Gly Pro
1               5                   10                  15

Glu Gly Lys

<210> SEQ ID NO 1072
<211> LENGTH: 13
<212> TYPE: PRT
<213> ORGANISM: Homo sapiens

<400> SEQUENCE: 1072

Gly Asp Val Asp Val Ser Val Pro Glu Val Glu Gly Lys
1               5                   10

<210> SEQ ID NO 1073
<211> LENGTH: 16
<212> TYPE: PRT
<213> ORGANISM: Homo sapiens

<400> SEQUENCE: 1073

Val Asp Val Asn Ala Pro Asp Val Gln Ala Pro Asp Trp His Leu Lys
1               5                   10                  15

<210> SEQ ID NO 1074
<211> LENGTH: 16
<212> TYPE: PRT
<213> ORGANISM: Homo sapiens

<400> SEQUENCE: 1074

Val Asp Ile Glu Gly Pro Asp Val Asn Ile Glu Gly Pro Glu Gly Lys
1               5                   10                  15

<210> SEQ ID NO 1075
<211> LENGTH: 7
<212> TYPE: PRT
```

<213> ORGANISM: Homo sapiens

<400> SEQUENCE: 1075

Gly Pro Glu Val Asp Ile Lys
1               5

<210> SEQ ID NO 1076
<211> LENGTH: 18
<212> TYPE: PRT
<213> ORGANISM: Homo sapiens

<400> SEQUENCE: 1076

Val Asp Ile Asn Ala Pro Asp Val Gly Val Gln Gly Pro Asp Trp His
1               5                   10                  15

Leu Lys

<210> SEQ ID NO 1077
<211> LENGTH: 9
<212> TYPE: PRT
<213> ORGANISM: Homo sapiens

<400> SEQUENCE: 1077

Gly Glu Gly Pro Asp Gly Asp Val Lys
1               5

<210> SEQ ID NO 1078
<211> LENGTH: 12
<212> TYPE: PRT
<213> ORGANISM: Homo sapiens

<400> SEQUENCE: 1078

Gly Glu Gly Pro Asp Val Asp Val Asn Leu Pro Lys
1               5                   10

<210> SEQ ID NO 1079
<211> LENGTH: 9
<212> TYPE: PRT
<213> ORGANISM: Homo sapiens

<400> SEQUENCE: 1079

Gly Asp Val Asp Val Thr Gly Pro Lys
1               5

<210> SEQ ID NO 1080
<211> LENGTH: 7
<212> TYPE: PRT
<213> ORGANISM: Homo sapiens

<400> SEQUENCE: 1080

Gly Pro Glu Val Asp Leu Lys
1               5

<210> SEQ ID NO 1081
<211> LENGTH: 18
<212> TYPE: PRT
<213> ORGANISM: Homo sapiens

<400> SEQUENCE: 1081

Val Asp Ile Asp Val Pro Asp Val Asn Val Gln Gly Pro Asp Trp His
1               5                   10                  15

Leu Lys

<210> SEQ ID NO 1082

```
<211> LENGTH: 16
<212> TYPE: PRT
<213> ORGANISM: Homo sapiens

<400> SEQUENCE: 1082

Val Asp Val Glu Gly Pro Asp Val Asn Ile Glu Gly Pro Glu Gly Lys
1               5                   10                  15

<210> SEQ ID NO 1083
<211> LENGTH: 9
<212> TYPE: PRT
<213> ORGANISM: Homo sapiens

<400> SEQUENCE: 1083

Gly Asp Val Asp Ile Ser Leu Pro Lys
1               5

<210> SEQ ID NO 1084
<211> LENGTH: 7
<212> TYPE: PRT
<213> ORGANISM: Homo sapiens

<400> SEQUENCE: 1084

Gly Pro Glu Val Asp Ile Arg
1               5

<210> SEQ ID NO 1085
<211> LENGTH: 21
<212> TYPE: PRT
<213> ORGANISM: Homo sapiens

<400> SEQUENCE: 1085

Gly Pro Gln Val Asp Ile Asp Val Pro Asp Val Gly Val Gln Gly Pro
1               5                   10                  15

Asp Trp His Leu Lys
            20

<210> SEQ ID NO 1086
<211> LENGTH: 9
<212> TYPE: PRT
<213> ORGANISM: Homo sapiens

<400> SEQUENCE: 1086

Ala Asp Leu Asp Val Ser Gly Pro Lys
1               5

<210> SEQ ID NO 1087
<211> LENGTH: 16
<212> TYPE: PRT
<213> ORGANISM: Homo sapiens

<400> SEQUENCE: 1087

Val Asp Ile Asp Val Pro Asp Val Asn Ile Glu Gly Pro Glu Gly Lys
1               5                   10                  15

<210> SEQ ID NO 1088
<211> LENGTH: 18
<212> TYPE: PRT
<213> ORGANISM: Homo sapiens

<400> SEQUENCE: 1088

Val Asp Ile Asn Ala Pro Asp Val Asp Val Gln Gly Pro Asp Trp His
1               5                   10                  15

Leu Lys
```

```
<210> SEQ ID NO 1089
<211> LENGTH: 16
<212> TYPE: PRT
<213> ORGANISM: Homo sapiens

<400> SEQUENCE: 1089

Val Asp Val Asp Val Pro Asp Val Asn Ile Glu Gly Pro Asp Ala Lys
1               5                   10                  15

<210> SEQ ID NO 1090
<211> LENGTH: 15
<212> TYPE: PRT
<213> ORGANISM: Homo sapiens

<400> SEQUENCE: 1090

Gly Glu Val Asp Val Ser Leu Ala Asn Val Glu Gly Asp Leu Lys
1               5                   10                  15

<210> SEQ ID NO 1091
<211> LENGTH: 7
<212> TYPE: PRT
<213> ORGANISM: Homo sapiens

<400> SEQUENCE: 1091

Gly Pro Ala Leu Asp Ile Lys
1               5

<210> SEQ ID NO 1092
<211> LENGTH: 16
<212> TYPE: PRT
<213> ORGANISM: Homo sapiens

<400> SEQUENCE: 1092

Ile Asp Val Asp Ala Pro Asp Ile Asp Ile His Gly Pro Asp Ala Lys
1               5                   10                  15

<210> SEQ ID NO 1093
<211> LENGTH: 9
<212> TYPE: PRT
<213> ORGANISM: Homo sapiens

<400> SEQUENCE: 1093

Gly Asp Val Asp Val Ser Gly Pro Lys
1               5

<210> SEQ ID NO 1094
<211> LENGTH: 7
<212> TYPE: PRT
<213> ORGANISM: Homo sapiens

<400> SEQUENCE: 1094

Ala Pro Ser Leu Asp Ile Lys
1               5

<210> SEQ ID NO 1095
<211> LENGTH: 10
<212> TYPE: PRT
<213> ORGANISM: Homo sapiens

<400> SEQUENCE: 1095

Gly Pro Glu Val Asp Val Ser Gly Pro Lys
1               5                   10
```

```
<210> SEQ ID NO 1096
<211> LENGTH: 6
<212> TYPE: PRT
<213> ORGANISM: Homo sapiens

<400> SEQUENCE: 1096

Leu Asn Ile Glu Gly Lys
1               5

<210> SEQ ID NO 1097
<211> LENGTH: 7
<212> TYPE: PRT
<213> ORGANISM: Homo sapiens

<400> SEQUENCE: 1097

Phe Asn Phe Ser Gly Ser Lys
1               5

<210> SEQ ID NO 1098
<211> LENGTH: 9
<212> TYPE: PRT
<213> ORGANISM: Homo sapiens

<400> SEQUENCE: 1098

Val Gln Thr Pro Glu Val Asp Val Lys
1               5

<210> SEQ ID NO 1099
<211> LENGTH: 10
<212> TYPE: PRT
<213> ORGANISM: Homo sapiens

<400> SEQUENCE: 1099

Lys Pro Asp Ile Asp Ile Thr Gly Pro Lys
1               5                   10

<210> SEQ ID NO 1100
<211> LENGTH: 13
<212> TYPE: PRT
<213> ORGANISM: Homo sapiens

<400> SEQUENCE: 1100

Val Asp Ile Asn Ala Pro Asp Val Glu Val Gln Gly Lys
1               5                   10

<210> SEQ ID NO 1101
<211> LENGTH: 15
<212> TYPE: PRT
<213> ORGANISM: Homo sapiens

<400> SEQUENCE: 1101

Gly Asp Leu Asp Ile Ala Gly Pro Asn Leu Glu Gly Asp Phe Lys
1               5                   10                  15

<210> SEQ ID NO 1102
<211> LENGTH: 21
<212> TYPE: PRT
<213> ORGANISM: Homo sapiens

<400> SEQUENCE: 1102

Ala Pro Glu Val Asn Leu Asn Ala Pro Asp Val Asp Val His Gly Pro
1               5                   10                  15

Asp Trp Asn Leu Lys
            20
```

```
<210> SEQ ID NO 1103
<211> LENGTH: 12
<212> TYPE: PRT
<213> ORGANISM: Homo sapiens

<400> SEQUENCE: 1103

Ala Glu Gly Pro Asp Val Ala Val Asp Leu Pro Lys
1               5                   10

<210> SEQ ID NO 1104
<211> LENGTH: 18
<212> TYPE: PRT
<213> ORGANISM: Homo sapiens

<400> SEQUENCE: 1104

Val Asp Ile Asn Ala Pro Asp Val Asp Val His Gly Pro Asp Trp His
1               5                   10                  15

Leu Lys

<210> SEQ ID NO 1105
<211> LENGTH: 12
<212> TYPE: PRT
<213> ORGANISM: Homo sapiens

<400> SEQUENCE: 1105

Gly Glu Gly Pro Glu Val Asp Val Thr Leu Pro Lys
1               5                   10

<210> SEQ ID NO 1106
<211> LENGTH: 25
<212> TYPE: PRT
<213> ORGANISM: Homo sapiens

<400> SEQUENCE: 1106

Ala Asp Ile Asp Ile Ser Gly Pro Asn Val Asp Val Asp Val Pro Asp
1               5                   10                  15

Val Asn Ile Glu Gly Pro Asp Ala Lys
            20                  25

<210> SEQ ID NO 1107
<211> LENGTH: 9
<212> TYPE: PRT
<213> ORGANISM: Homo sapiens

<400> SEQUENCE: 1107

Gly Asp Val Val Val Ser Leu Pro Lys
1               5

<210> SEQ ID NO 1108
<211> LENGTH: 16
<212> TYPE: PRT
<213> ORGANISM: Homo sapiens

<400> SEQUENCE: 1108

Val Asp Ile Asp Thr Pro Asp Ile Asn Ile Glu Gly Ser Glu Gly Lys
1               5                   10                  15

<210> SEQ ID NO 1109
<211> LENGTH: 11
<212> TYPE: PRT
<213> ORGANISM: Homo sapiens

<400> SEQUENCE: 1109
```

Val Asp Ile Asn Ala Pro Asp Val Asp Val Arg
1               5                   10

<210> SEQ ID NO 1110
<211> LENGTH: 7
<212> TYPE: PRT
<213> ORGANISM: Homo sapiens

<400> SEQUENCE: 1110

Gly Pro Asp Trp His Leu Lys
1               5

<210> SEQ ID NO 1111
<211> LENGTH: 7
<212> TYPE: PRT
<213> ORGANISM: Homo sapiens

<400> SEQUENCE: 1111

Ala Pro Glu Val Asp Ile Lys
1               5

<210> SEQ ID NO 1112
<211> LENGTH: 16
<212> TYPE: PRT
<213> ORGANISM: Homo sapiens

<400> SEQUENCE: 1112

Val Asp Ile Asp Thr Pro Asp Ile Asp Ile His Gly Pro Glu Gly Lys
1               5                   10                  15

<210> SEQ ID NO 1113
<211> LENGTH: 18
<212> TYPE: PRT
<213> ORGANISM: Homo sapiens

<400> SEQUENCE: 1113

Val Asp Ile Asp Val Pro Asp Val Asp Val Gln Gly Pro Asp Trp His
1               5                   10                  15

Leu Lys

<210> SEQ ID NO 1114
<211> LENGTH: 16
<212> TYPE: PRT
<213> ORGANISM: Homo sapiens

<400> SEQUENCE: 1114

Val Asp Ile Asp Val Pro Asp Val Asn Ile Glu Gly Pro Asp Ala Lys
1               5                   10                  15

<210> SEQ ID NO 1115
<211> LENGTH: 12
<212> TYPE: PRT
<213> ORGANISM: Homo sapiens

<400> SEQUENCE: 1115

Gly Glu Gly Pro Asp Val Asp Val Thr Leu Pro Lys
1               5                   10

<210> SEQ ID NO 1116
<211> LENGTH: 9
<212> TYPE: PRT
<213> ORGANISM: Homo sapiens

<400> SEQUENCE: 1116

Ala Asp Ile Glu Ile Ser Gly Pro Lys
1               5

<210> SEQ ID NO 1117
<211> LENGTH: 16
<212> TYPE: PRT
<213> ORGANISM: Homo sapiens

<400> SEQUENCE: 1117

Val Asp Ile Asp Ala Pro Asp Val Ser Ile Glu Gly Pro Asp Ala Lys
1               5                   10                  15

<210> SEQ ID NO 1118
<211> LENGTH: 19
<212> TYPE: PRT
<213> ORGANISM: Homo sapiens

<400> SEQUENCE: 1118

Gly Pro Ser Leu Asp Ile Asp Thr Pro Asp Val Asn Ile Glu Gly Pro
1               5                   10                  15

Glu Gly Lys

<210> SEQ ID NO 1119
<211> LENGTH: 12
<212> TYPE: PRT
<213> ORGANISM: Homo sapiens

<400> SEQUENCE: 1119

Gly Pro Glu Val Asp Ile Glu Gly Pro Glu Gly Lys
1               5                   10

<210> SEQ ID NO 1120
<211> LENGTH: 16
<212> TYPE: PRT
<213> ORGANISM: Homo sapiens

<400> SEQUENCE: 1120

Val Gly Ile Asp Thr Pro Asp Ile Asp Ile His Gly Pro Glu Gly Lys
1               5                   10                  15

<210> SEQ ID NO 1121
<211> LENGTH: 9
<212> TYPE: PRT
<213> ORGANISM: Homo sapiens

<400> SEQUENCE: 1121

Gly Asp Val Asp Val Thr Leu Pro Lys
1               5

<210> SEQ ID NO 1122
<211> LENGTH: 7
<212> TYPE: PRT
<213> ORGANISM: Homo sapiens

<400> SEQUENCE: 1122

Gly Pro Glu Ala Asp Ile Lys
1               5

<210> SEQ ID NO 1123
<211> LENGTH: 18
<212> TYPE: PRT
<213> ORGANISM: Homo sapiens

<400> SEQUENCE: 1123

-continued

```
Val Asp Ile Asn Thr Pro Asp Val Asp Val His Gly Pro Asp Trp His
1               5                   10                  15

Leu Lys

<210> SEQ ID NO 1124
<211> LENGTH: 12
<212> TYPE: PRT
<213> ORGANISM: Homo sapiens

<400> SEQUENCE: 1124

Gly Glu Gly Pro Asp Val Asp Val Ser Leu Pro Lys
1               5                   10

<210> SEQ ID NO 1125
<211> LENGTH: 16
<212> TYPE: PRT
<213> ORGANISM: Homo sapiens

<400> SEQUENCE: 1125

Val Asp Val Asp Ile Pro Asp Val Asn Ile Glu Gly Pro Asp Ala Lys
1               5                   10                  15

<210> SEQ ID NO 1126
<211> LENGTH: 11
<212> TYPE: PRT
<213> ORGANISM: Homo sapiens

<400> SEQUENCE: 1126

Ile Ser Ile Pro Asp Val Asp Leu Asp Leu Lys
1               5                   10

<210> SEQ ID NO 1127
<211> LENGTH: 9
<212> TYPE: PRT
<213> ORGANISM: Homo sapiens

<400> SEQUENCE: 1127

Gly Asp Phe Asp Val Ser Val Pro Lys
1               5

<210> SEQ ID NO 1128
<211> LENGTH: 6
<212> TYPE: PRT
<213> ORGANISM: Homo sapiens

<400> SEQUENCE: 1128

Val Glu Gly Thr Leu Lys
1               5

<210> SEQ ID NO 1129
<211> LENGTH: 9
<212> TYPE: PRT
<213> ORGANISM: Homo sapiens

<400> SEQUENCE: 1129

Leu Asp Phe Glu Gly Pro Asp Ala Lys
1               5

<210> SEQ ID NO 1130
<211> LENGTH: 7
<212> TYPE: PRT
<213> ORGANISM: Homo sapiens

<400> SEQUENCE: 1130
```

Leu Ser Gly Pro Ser Leu Lys
1               5

<210> SEQ ID NO 1131
<211> LENGTH: 11
<212> TYPE: PRT
<213> ORGANISM: Homo sapiens

<400> SEQUENCE: 1131

Val Thr Ala Pro Asp Val Asp Leu His Leu Lys
1               5                   10

<210> SEQ ID NO 1132
<211> LENGTH: 7
<212> TYPE: PRT
<213> ORGANISM: Homo sapiens

<400> SEQUENCE: 1132

Ile Gly Phe Ser Gly Pro Lys
1               5

<210> SEQ ID NO 1133
<211> LENGTH: 9
<212> TYPE: PRT
<213> ORGANISM: Homo sapiens

<400> SEQUENCE: 1133

Leu Glu Gly Gly Glu Val Asp Leu Lys
1               5

<210> SEQ ID NO 1134
<211> LENGTH: 6
<212> TYPE: PRT
<213> ORGANISM: Homo sapiens

<400> SEQUENCE: 1134

Phe Gly Phe Gly Ala Lys
1               5

<210> SEQ ID NO 1135
<211> LENGTH: 25
<212> TYPE: PRT
<213> ORGANISM: Homo sapiens

<400> SEQUENCE: 1135

Ser Pro Ser Leu Asp Val Thr Val Pro Glu Ala Glu Leu Asn Leu Glu
1               5                   10                  15

Thr Pro Glu Ile Ser Val Gly Gly Lys
            20                  25

<210> SEQ ID NO 1136
<211> LENGTH: 17
<212> TYPE: PRT
<213> ORGANISM: Homo sapiens

<400> SEQUENCE: 1136

Gln Gly Phe Asp Leu Asn Val Pro Gly Gly Glu Ile Asp Ala Ser Leu
1               5                   10                  15

Lys

<210> SEQ ID NO 1137
<211> LENGTH: 16
<212> TYPE: PRT

<400> SEQUENCE: 1137

Ala Pro Asp Val Asp Val Asn Ile Ala Gly Pro Asp Ala Ala Leu Lys
1               5                   10                  15

<210> SEQ ID NO 1138
<211> LENGTH: 9
<212> TYPE: PRT
<213> ORGANISM: Homo sapiens

<400> SEQUENCE: 1138

Ala Glu Ala Pro Leu Pro Ser Pro Lys
1               5

<210> SEQ ID NO 1139
<211> LENGTH: 25
<212> TYPE: PRT
<213> ORGANISM: Homo sapiens

<400> SEQUENCE: 1139

Leu Glu Gly Glu Leu Gln Ala Pro Asp Leu Glu Leu Ser Leu Pro Ala
1               5                   10                  15

Ile His Val Glu Gly Leu Asp Ile Lys
            20                  25

<210> SEQ ID NO 1140
<211> LENGTH: 6
<212> TYPE: PRT
<213> ORGANISM: Homo sapiens

<400> SEQUENCE: 1140

Ile Glu Gly Asp Leu Lys
1               5

<210> SEQ ID NO 1141
<211> LENGTH: 18
<212> TYPE: PRT
<213> ORGANISM: Homo sapiens

<400> SEQUENCE: 1141

Val Gln Ala Asn Leu Gly Ala Pro Asp Ile Asn Ile Glu Gly Leu Asp
1               5                   10                  15

Ala Lys

<210> SEQ ID NO 1142
<211> LENGTH: 21
<212> TYPE: PRT
<213> ORGANISM: Homo sapiens

<400> SEQUENCE: 1142

Thr Pro Ser Phe Gly Ile Ser Ala Pro Gln Val Ser Ile Pro Asp Val
1               5                   10                  15

Asn Val Asn Leu Lys
            20

<210> SEQ ID NO 1143
<211> LENGTH: 21
<212> TYPE: PRT
<213> ORGANISM: Homo sapiens

<400> SEQUENCE: 1143

Gly Asp Val Pro Ser Val Gly Leu Glu Gly Pro Asp Val Asp Leu Gln
1               5                   10                  15

Gly Pro Glu Ala Lys
            20

<210> SEQ ID NO 1144
<211> LENGTH: 7
<212> TYPE: PRT
<213> ORGANISM: Homo sapiens

<400> SEQUENCE: 1144

Ile Gly Ile Pro Gly Val Lys
1               5

<210> SEQ ID NO 1145
<211> LENGTH: 9
<212> TYPE: PRT
<213> ORGANISM: Homo sapiens

<400> SEQUENCE: 1145

Leu Glu Gly Pro Asp Val Ser Leu Lys
1               5

<210> SEQ ID NO 1146
<211> LENGTH: 11
<212> TYPE: PRT
<213> ORGANISM: Homo sapiens

<400> SEQUENCE: 1146

Val Ser Gly Pro Asp Leu Asp Leu Asn Leu Lys
1               5                   10

<210> SEQ ID NO 1147
<211> LENGTH: 14
<212> TYPE: PRT
<213> ORGANISM: Homo sapiens

<400> SEQUENCE: 1147

Val His Ala Pro Gly Leu Asn Leu Ser Gly Val Gly Gly Lys
1               5                   10

<210> SEQ ID NO 1148
<211> LENGTH: 9
<212> TYPE: PRT
<213> ORGANISM: Homo sapiens

<400> SEQUENCE: 1148

Val Pro Gly Ile Asp Ala Thr Thr Lys
1               5

<210> SEQ ID NO 1149
<211> LENGTH: 11
<212> TYPE: PRT
<213> ORGANISM: Homo sapiens

<400> SEQUENCE: 1149

Leu Asn Val Gly Ala Pro Asp Val Thr Leu Arg
1               5                   10

<210> SEQ ID NO 1150
<211> LENGTH: 15
<212> TYPE: PRT
<213> ORGANISM: Homo sapiens

<400> SEQUENCE: 1150

Gly Pro Ser Leu Gln Gly Asp Leu Ala Val Ser Gly Asp Ile Lys

<210> SEQ ID NO 1151
<211> LENGTH: 18
<212> TYPE: PRT
<213> ORGANISM: Homo sapiens

<400> SEQUENCE: 1151

Val Ser Val Gly Ala Pro Asp Leu Ser Leu Glu Ala Ser Glu Gly Ser
1               5                   10                  15

Ile Lys

<210> SEQ ID NO 1152
<211> LENGTH: 18
<212> TYPE: PRT
<213> ORGANISM: Homo sapiens

<400> SEQUENCE: 1152

Leu Pro Gln Phe Gly Ile Ser Thr Pro Gly Ser Asp Leu His Val Asn
1               5                   10                  15

Ala Lys

<210> SEQ ID NO 1153
<211> LENGTH: 9
<212> TYPE: PRT
<213> ORGANISM: Homo sapiens

<400> SEQUENCE: 1153

Gly Pro Gln Val Ser Gly Glu Leu Lys
1               5

<210> SEQ ID NO 1154
<211> LENGTH: 9
<212> TYPE: PRT
<213> ORGANISM: Homo sapiens

<400> SEQUENCE: 1154

Gly Pro Gly Val Asp Val Asn Leu Lys
1               5

<210> SEQ ID NO 1155
<211> LENGTH: 14
<212> TYPE: PRT
<213> ORGANISM: Homo sapiens

<400> SEQUENCE: 1155

Ile Ser Ala Pro Asn Val Asp Phe Asn Leu Glu Gly Pro Lys
1               5                   10

<210> SEQ ID NO 1156
<211> LENGTH: 10
<212> TYPE: PRT
<213> ORGANISM: Homo sapiens

<400> SEQUENCE: 1156

Gly Ser Leu Gly Ala Thr Gly Glu Ile Lys
1               5                   10

<210> SEQ ID NO 1157
<211> LENGTH: 12
<212> TYPE: PRT
<213> ORGANISM: Homo sapiens

<400> SEQUENCE: 1157

Leu Pro Thr Gly Gln Ile Ser Gly Pro Glu Ile Lys
1               5                   10

<210> SEQ ID NO 1158
<211> LENGTH: 16
<212> TYPE: PRT
<213> ORGANISM: Homo sapiens

<400> SEQUENCE: 1158

Gly Ser Glu Val Gly Phe His Gly Ala Ala Pro Asp Ile Ser Val Lys
1               5                   10                  15

<210> SEQ ID NO 1159
<211> LENGTH: 24
<212> TYPE: PRT
<213> ORGANISM: Homo sapiens

<400> SEQUENCE: 1159

Gly Gly Ala Asp Val Ser Gly Val Ser Ala Pro Asp Ile Ser Leu
1               5                   10                  15

Gly Glu Gly His Leu Ser Val Lys
            20

<210> SEQ ID NO 1160
<211> LENGTH: 7
<212> TYPE: PRT
<213> ORGANISM: Homo sapiens

<400> SEQUENCE: 1160

Gly Ser Gly Gly Glu Trp Lys
1               5

<210> SEQ ID NO 1161
<211> LENGTH: 14
<212> TYPE: PRT
<213> ORGANISM: Homo sapiens

<400> SEQUENCE: 1161

Gly Pro Gln Val Ser Ser Ala Leu Asn Leu Asp Thr Ser Lys
1               5                   10

<210> SEQ ID NO 1162
<211> LENGTH: 11
<212> TYPE: PRT
<213> ORGANISM: Homo sapiens

<400> SEQUENCE: 1162

Phe Ala Gly Gly Leu His Phe Ser Gly Pro Lys
1               5                   10

<210> SEQ ID NO 1163
<211> LENGTH: 6
<212> TYPE: PRT
<213> ORGANISM: Homo sapiens

<400> SEQUENCE: 1163

Val Glu Gly Gly Val Lys
1               5

<210> SEQ ID NO 1164
<211> LENGTH: 6
<212> TYPE: PRT
<213> ORGANISM: Homo sapiens

```
<400> SEQUENCE: 1164

Phe Thr Phe Ser Gly Arg
1               5

<210> SEQ ID NO 1165
<211> LENGTH: 20
<212> TYPE: PRT
<213> ORGANISM: Homo sapiens

<400> SEQUENCE: 1165

Ala Glu Ala Ser Ile Gln Ala Gly Ala Gly Asp Gly Glu Trp Glu Glu
1               5                   10                  15

Ser Glu Val Lys
            20

<210> SEQ ID NO 1166
<211> LENGTH: 7
<212> TYPE: PRT
<213> ORGANISM: Homo sapiens

<400> SEQUENCE: 1166

Phe Asn Phe Ser Lys Pro Lys
1               5

<210> SEQ ID NO 1167
<211> LENGTH: 15
<212> TYPE: PRT
<213> ORGANISM: Homo sapiens

<400> SEQUENCE: 1167

Gly Gly Val Thr Gly Ser Pro Glu Ala Ser Ile Ser Gly Ser Lys
1               5                   10                  15

<210> SEQ ID NO 1168
<211> LENGTH: 18
<212> TYPE: PRT
<213> ORGANISM: Homo sapiens

<400> SEQUENCE: 1168

Ala Ser Leu Gly Ser Leu Glu Gly Glu Ala Glu Ala Glu Ala Ser Ser
1               5                   10                  15

Pro Lys

<210> SEQ ID NO 1169
<211> LENGTH: 8
<212> TYPE: PRT
<213> ORGANISM: Homo sapiens

<400> SEQUENCE: 1169

Ser Asn Ser Phe Ser Asp Glu Arg
1               5

<210> SEQ ID NO 1170
<211> LENGTH: 25
<212> TYPE: PRT
<213> ORGANISM: Homo sapiens

<400> SEQUENCE: 1170

Glu Phe Ser Gly Pro Ser Thr Pro Thr Gly Thr Leu Glu Phe Glu Gly
1               5                   10                  15

Gly Glu Val Ser Leu Glu Gly Gly Lys
            20                  25
```

<210> SEQ ID NO 1171
<211> LENGTH: 10
<212> TYPE: PRT
<213> ORGANISM: Homo sapiens

<400> SEQUENCE: 1171

Phe Gly Thr Phe Gly Gly Leu Gly Ser Lys
1               5                   10

<210> SEQ ID NO 1172
<211> LENGTH: 14
<212> TYPE: PRT
<213> ORGANISM: Homo sapiens

<400> SEQUENCE: 1172

Gly His Tyr Glu Val Thr Gly Ser Asp Asp Glu Thr Gly Lys
1               5                   10

<210> SEQ ID NO 1173
<211> LENGTH: 11
<212> TYPE: PRT
<213> ORGANISM: Homo sapiens

<400> SEQUENCE: 1173

Leu Gln Gly Ser Gly Val Ser Leu Ala Ser Lys
1               5                   10

<210> SEQ ID NO 1174
<211> LENGTH: 12
<212> TYPE: PRT
<213> ORGANISM: Homo sapiens

<400> SEQUENCE: 1174

Leu Ser Ser Ser Ser Ser Asn Asp Ser Gly Asn Lys
1               5                   10

<210> SEQ ID NO 1175
<211> LENGTH: 15
<212> TYPE: PRT
<213> ORGANISM: Homo sapiens

<400> SEQUENCE: 1175

Val Gly Ile Gln Leu Pro Glu Val Glu Leu Ser Val Ser Thr Lys
1               5                   10                  15

<210> SEQ ID NO 1176
<211> LENGTH: 9
<212> TYPE: PRT
<213> ORGANISM: Homo sapiens

<400> SEQUENCE: 1176

Val Asp Gly Ser Val Asp Phe Tyr Arg
1               5

<210> SEQ ID NO 1177
<211> LENGTH: 6
<212> TYPE: PRT
<213> ORGANISM: Homo sapiens

<400> SEQUENCE: 1177

Asp Trp Ala Thr Tyr Lys
1               5

<210> SEQ ID NO 1178

```
<211> LENGTH: 23
<212> TYPE: PRT
<213> ORGANISM: Homo sapiens

<400> SEQUENCE: 1178

Leu Gly Glu Phe Trp Leu Gly Asn Asp Asn Ile His Ala Leu Thr Ala
1               5                   10                  15

Gln Gly Thr Ser Glu Leu Arg
            20

<210> SEQ ID NO 1179
<211> LENGTH: 14
<212> TYPE: PRT
<213> ORGANISM: Homo sapiens

<400> SEQUENCE: 1179

Val Asp Leu Val Asp Phe Glu Asp Asn Tyr Gln Phe Ala Lys
1               5                   10

<210> SEQ ID NO 1180
<211> LENGTH: 13
<212> TYPE: PRT
<213> ORGANISM: Homo sapiens

<400> SEQUENCE: 1180

Gly Thr His Gly Ser Phe Ala Asn Gly Ile Asn Trp Lys
1               5                   10

<210> SEQ ID NO 1181
<211> LENGTH: 7
<212> TYPE: PRT
<213> ORGANISM: Homo sapiens

<400> SEQUENCE: 1181

Gly Tyr Asn Tyr Ser Tyr Lys
1               5

<210> SEQ ID NO 1182
<211> LENGTH: 8
<212> TYPE: PRT
<213> ORGANISM: Homo sapiens

<400> SEQUENCE: 1182

Gly Glu Ala Gly Thr Asn Gly Lys
1               5

<210> SEQ ID NO 1183
<211> LENGTH: 6
<212> TYPE: PRT
<213> ORGANISM: Homo sapiens

<400> SEQUENCE: 1183

Gln Ala Pro Gly Gln Arg
1               5

<210> SEQ ID NO 1184
<211> LENGTH: 8
<212> TYPE: PRT
<213> ORGANISM: Homo sapiens

<400> SEQUENCE: 1184

Trp Pro Glu Pro Val Phe Gly Arg
1               5
```

```
<210> SEQ ID NO 1185
<211> LENGTH: 16
<212> TYPE: PRT
<213> ORGANISM: Homo sapiens

<400> SEQUENCE: 1185

Leu Ala Ser Pro Gly Phe Pro Gly Glu Tyr Ala Asn Asp Gln Glu Arg
1               5                   10                  15

<210> SEQ ID NO 1186
<211> LENGTH: 10
<212> TYPE: PRT
<213> ORGANISM: Homo sapiens

<400> SEQUENCE: 1186

Trp Thr Leu Thr Ala Pro Pro Gly Tyr Arg
1               5                   10

<210> SEQ ID NO 1187
<211> LENGTH: 15
<212> TYPE: PRT
<213> ORGANISM: Homo sapiens

<400> SEQUENCE: 1187

Asp Thr Phe Tyr Ser Leu Gly Ser Ser Leu Asp Ile Thr Phe Arg
1               5                   10                  15

<210> SEQ ID NO 1188
<211> LENGTH: 7
<212> TYPE: PRT
<213> ORGANISM: Homo sapiens

<400> SEQUENCE: 1188

Ala Gly Tyr Val Leu His Arg
1               5

<210> SEQ ID NO 1189
<211> LENGTH: 15
<212> TYPE: PRT
<213> ORGANISM: Homo sapiens

<400> SEQUENCE: 1189

Ser Gly Glu Leu Ser Ser Pro Glu Tyr Pro Arg Pro Tyr Pro Lys
1               5                   10                  15

<210> SEQ ID NO 1190
<211> LENGTH: 20
<212> TYPE: PRT
<213> ORGANISM: Homo sapiens

<400> SEQUENCE: 1190

Ser Asn Thr Val Thr Ile Thr Phe Val Thr Asp Glu Ser Gly Asp His
1               5                   10                  15

Thr Gly Trp Lys
            20

<210> SEQ ID NO 1191
<211> LENGTH: 13
<212> TYPE: PRT
<213> ORGANISM: Homo sapiens

<400> SEQUENCE: 1191

Val Glu Tyr Ile Thr Gly Pro Gly Val Thr Thr Tyr Lys
1               5                   10
```

<210> SEQ ID NO 1192
<211> LENGTH: 6
<212> TYPE: PRT
<213> ORGANISM: Homo sapiens

<400> SEQUENCE: 1192

Ile Tyr Gly Gly Gln Lys
1               5

<210> SEQ ID NO 1193
<211> LENGTH: 9
<212> TYPE: PRT
<213> ORGANISM: Homo sapiens

<400> SEQUENCE: 1193

His Asp Ala Ser Ala Leu Asp Ile Arg
1               5

<210> SEQ ID NO 1194
<211> LENGTH: 15
<212> TYPE: PRT
<213> ORGANISM: Homo sapiens

<400> SEQUENCE: 1194

Thr Asp Asp Ile Gly Thr Ala Ser Gly Trp Gly Leu Thr Gln Arg
1               5                   10                  15

<210> SEQ ID NO 1195
<211> LENGTH: 16
<212> TYPE: PRT
<213> ORGANISM: Homo sapiens

<400> SEQUENCE: 1195

Gly Asp Ser Gly Gly Ala Leu Val Phe Leu Asp Ser Glu Thr Glu Arg
1               5                   10                  15

<210> SEQ ID NO 1196
<211> LENGTH: 15
<212> TYPE: PRT
<213> ORGANISM: Homo sapiens

<400> SEQUENCE: 1196

Val Ile Asn Tyr Ile Pro Trp Ile Glu Asn Ile Ile Ser Asp Phe
1               5                   10                  15

<210> SEQ ID NO 1197
<211> LENGTH: 14
<212> TYPE: PRT
<213> ORGANISM: Homo sapiens

<400> SEQUENCE: 1197

Ser Pro Asp Glu Leu Pro Ser Ala Gly Gly Asp Gly Gly Lys
1               5                   10

<210> SEQ ID NO 1198
<211> LENGTH: 8
<212> TYPE: PRT
<213> ORGANISM: Homo sapiens

<400> SEQUENCE: 1198

Glu Lys Pro Asn Ser Ala His Arg
1               5

<210> SEQ ID NO 1199

```
<211> LENGTH: 10
<212> TYPE: PRT
<213> ORGANISM: Homo sapiens

<400> SEQUENCE: 1199

Glu Glu Thr Ala Gly Ser Tyr Asp Ser Arg
1               5                   10

<210> SEQ ID NO 1200
<211> LENGTH: 9
<212> TYPE: PRT
<213> ORGANISM: Homo sapiens

<400> SEQUENCE: 1200

Phe Gln Pro Leu Leu Asp Gly Leu Lys
1               5

<210> SEQ ID NO 1201
<211> LENGTH: 8
<212> TYPE: PRT
<213> ORGANISM: Homo sapiens

<400> SEQUENCE: 1201

Ser Gly Thr Thr Ile Ala Leu Lys
1               5

<210> SEQ ID NO 1202
<211> LENGTH: 11
<212> TYPE: PRT
<213> ORGANISM: Homo sapiens

<400> SEQUENCE: 1202

Leu Gly Leu His Gln Val Leu Gln Asp Leu Arg
1               5                   10

<210> SEQ ID NO 1203
<211> LENGTH: 18
<212> TYPE: PRT
<213> ORGANISM: Homo sapiens

<400> SEQUENCE: 1203

Val Gln Leu Asn Val Phe Asp Glu Gln Gly Glu Asp Ser Tyr Asp
1               5                   10                  15

Leu Lys

<210> SEQ ID NO 1204
<211> LENGTH: 16
<212> TYPE: PRT
<213> ORGANISM: Homo sapiens

<400> SEQUENCE: 1204

Ala Glu Pro His Phe Leu Ser Ile Leu Gln His Leu Leu Val Arg
1               5                   10                  15

<210> SEQ ID NO 1205
<211> LENGTH: 11
<212> TYPE: PRT
<213> ORGANISM: Homo sapiens

<400> SEQUENCE: 1205

Asn Asp Tyr Glu Ala Arg Pro Gln Tyr Tyr Lys
1               5                   10

<210> SEQ ID NO 1206
```

```
<211> LENGTH: 8
<212> TYPE: PRT
<213> ORGANISM: Homo sapiens

<400> SEQUENCE: 1206

Asn Gly Ala Asp Pro Asp Phe Lys
1               5

<210> SEQ ID NO 1207
<211> LENGTH: 8
<212> TYPE: PRT
<213> ORGANISM: Homo sapiens

<400> SEQUENCE: 1207

Leu Gln Asp Leu Gln Gly Glu Lys
1               5

<210> SEQ ID NO 1208
<211> LENGTH: 7
<212> TYPE: PRT
<213> ORGANISM: Homo sapiens

<400> SEQUENCE: 1208

Asp Ala Leu His Ser Glu Lys
1               5

<210> SEQ ID NO 1209
<211> LENGTH: 7
<212> TYPE: PRT
<213> ORGANISM: Homo sapiens

<400> SEQUENCE: 1209

Gln Gln Ile Ala Thr Glu Lys
1               5

<210> SEQ ID NO 1210
<211> LENGTH: 16
<212> TYPE: PRT
<213> ORGANISM: Homo sapiens

<400> SEQUENCE: 1210

Gln Asp Leu Glu Ala Glu Val Ser Gln Leu Thr Gly Glu Val Ala Lys
1               5                   10                  15

<210> SEQ ID NO 1211
<211> LENGTH: 9
<212> TYPE: PRT
<213> ORGANISM: Homo sapiens

<400> SEQUENCE: 1211

Leu Tyr Lys Pro Glu Val Gln Leu Arg
1               5

<210> SEQ ID NO 1212
<211> LENGTH: 6
<212> TYPE: PRT
<213> ORGANISM: Homo sapiens

<400> SEQUENCE: 1212

Arg Pro Asn Trp Ser Lys
1               5

<210> SEQ ID NO 1213
<211> LENGTH: 9
<212> TYPE: PRT
```

-continued

<213> ORGANISM: Homo sapiens

<400> SEQUENCE: 1213

Phe Glu Asn Asn Glu Leu Phe Ala Lys
1               5

<210> SEQ ID NO 1214
<211> LENGTH: 10
<212> TYPE: PRT
<213> ORGANISM: Homo sapiens

<400> SEQUENCE: 1214

Leu Thr Leu Thr Phe Ser Ala Gln Thr Lys
1               5                   10

<210> SEQ ID NO 1215
<211> LENGTH: 8
<212> TYPE: PRT
<213> ORGANISM: Homo sapiens

<400> SEQUENCE: 1215

Asp Gln Glu Gly Gly Glu Glu Lys
1               5

<210> SEQ ID NO 1216
<211> LENGTH: 13
<212> TYPE: PRT
<213> ORGANISM: Homo sapiens

<400> SEQUENCE: 1216

Thr Ala Gln Asn Leu Ser Ile Phe Leu Gly Ser Phe Arg
1               5                   10

<210> SEQ ID NO 1217
<211> LENGTH: 7
<212> TYPE: PRT
<213> ORGANISM: Homo sapiens

<400> SEQUENCE: 1217

Leu Asn Ala Ile Leu Phe Lys
1               5

<210> SEQ ID NO 1218
<211> LENGTH: 10
<212> TYPE: PRT
<213> ORGANISM: Homo sapiens

<400> SEQUENCE: 1218

Phe Pro Asp Glu Leu Ala His Val Glu Lys
1               5                   10

<210> SEQ ID NO 1219
<211> LENGTH: 8
<212> TYPE: PRT
<213> ORGANISM: Homo sapiens

<400> SEQUENCE: 1219

Val Ser Ala Glu Asn Leu Gln Lys
1               5

<210> SEQ ID NO 1220
<211> LENGTH: 7
<212> TYPE: PRT
<213> ORGANISM: Homo sapiens

```
<400> SEQUENCE: 1220

Gln Ile Ser Asp Val Glu Arg
1               5

<210> SEQ ID NO 1221
<211> LENGTH: 12
<212> TYPE: PRT
<213> ORGANISM: Homo sapiens

<400> SEQUENCE: 1221

Asp Val Gln Asn Phe Pro Ala Ala Thr Asp Glu Lys
1               5                   10

<210> SEQ ID NO 1222
<211> LENGTH: 8
<212> TYPE: PRT
<213> ORGANISM: Homo sapiens

<400> SEQUENCE: 1222

Asp Ala Gln Glu Gln Tyr Asn Lys
1               5

<210> SEQ ID NO 1223
<211> LENGTH: 11
<212> TYPE: PRT
<213> ORGANISM: Homo sapiens

<400> SEQUENCE: 1223

Glu Leu Gly Glu Tyr Phe Leu Phe Asp Pro Lys
1               5                   10

<210> SEQ ID NO 1224
<211> LENGTH: 13
<212> TYPE: PRT
<213> ORGANISM: Homo sapiens

<400> SEQUENCE: 1224

Asn Ser Glu Thr Phe Pro Thr Ile Leu Glu Glu Ala Lys
1               5                   10

<210> SEQ ID NO 1225
<211> LENGTH: 17
<212> TYPE: PRT
<213> ORGANISM: Homo sapiens

<400> SEQUENCE: 1225

Val Pro Ala Gln Leu Leu Gly Leu Leu Leu Trp Leu Pro Gly Ala
1               5                   10                  15

Lys

<210> SEQ ID NO 1226
<211> LENGTH: 18
<212> TYPE: PRT
<213> ORGANISM: Homo sapiens

<400> SEQUENCE: 1226

Ala Ser Gln Ser Ile Ser Ser Trp Leu Ala Trp Tyr Gln Gln Lys Pro
1               5                   10                  15

Gly Lys

<210> SEQ ID NO 1227
<211> LENGTH: 17
<212> TYPE: PRT
```

<213> ORGANISM: Homo sapiens

<400> SEQUENCE: 1227

Glu Val Asn Thr Ser Gly Phe Ala Pro Ala Arg Pro Pro Pro Gln Pro
1               5                   10                  15
Arg

<210> SEQ ID NO 1228
<211> LENGTH: 8
<212> TYPE: PRT
<213> ORGANISM: Homo sapiens

<400> SEQUENCE: 1228

Gly Val Phe Val Val Ala Ala Lys
1               5

<210> SEQ ID NO 1229
<211> LENGTH: 11
<212> TYPE: PRT
<213> ORGANISM: Homo sapiens

<400> SEQUENCE: 1229

Thr Pro Phe Gly Ala Tyr Gly Gly Leu Leu Lys
1               5                   10

<210> SEQ ID NO 1230
<211> LENGTH: 13
<212> TYPE: PRT
<213> ORGANISM: Homo sapiens

<400> SEQUENCE: 1230

Asp Phe Thr Ala Thr Asp Leu Ser Glu Phe Ala Ala Lys
1               5                   10

<210> SEQ ID NO 1231
<211> LENGTH: 9
<212> TYPE: PRT
<213> ORGANISM: Homo sapiens

<400> SEQUENCE: 1231

Glu Thr Pro Ala Leu Thr Ile Asn Arg
1               5

<210> SEQ ID NO 1232
<211> LENGTH: 8
<212> TYPE: PRT
<213> ORGANISM: Homo sapiens

<400> SEQUENCE: 1232

Tyr Ala Leu Gln Ser Gln Gln Arg
1               5

<210> SEQ ID NO 1233
<211> LENGTH: 8
<212> TYPE: PRT
<213> ORGANISM: Homo sapiens

<400> SEQUENCE: 1233

His Asn Phe Thr Pro Leu Ala Arg
1               5

<210> SEQ ID NO 1234
<211> LENGTH: 8
<212> TYPE: PRT

-continued

<213> ORGANISM: Homo sapiens

<400> SEQUENCE: 1234

Ser Leu Asp Leu Asp Ile Ser Lys
1               5

<210> SEQ ID NO 1235
<211> LENGTH: 20
<212> TYPE: PRT
<213> ORGANISM: Homo sapiens

<400> SEQUENCE: 1235

Thr Asn Val Asn Gly Gly Ala Ile Ala Leu Gly His Pro Leu Gly Gly
1               5                   10                  15

Ser Gly Ser Arg
            20

<210> SEQ ID NO 1236
<211> LENGTH: 10
<212> TYPE: PRT
<213> ORGANISM: Homo sapiens

<400> SEQUENCE: 1236

Ile Thr Ala His Leu Val His Glu Leu Arg
1               5                   10

<210> SEQ ID NO 1237
<211> LENGTH: 7
<212> TYPE: PRT
<213> ORGANISM: Homo sapiens

<400> SEQUENCE: 1237

Leu Glu Thr Ala Asp Leu Lys
1               5

<210> SEQ ID NO 1238
<211> LENGTH: 25
<212> TYPE: PRT
<213> ORGANISM: Homo sapiens

<400> SEQUENCE: 1238

Trp Val Thr Phe Pro Gln Val Asp Gly Gln Trp Glu Leu Ser Gly
1               5                   10                  15

Leu Asp Glu Glu Gln His Ser Val Arg
            20                  25

<210> SEQ ID NO 1239
<211> LENGTH: 9
<212> TYPE: PRT
<213> ORGANISM: Homo sapiens

<400> SEQUENCE: 1239

Ala Pro Gly Gln Ala His Trp Leu Arg
1               5

<210> SEQ ID NO 1240
<211> LENGTH: 6
<212> TYPE: PRT
<213> ORGANISM: Homo sapiens

<400> SEQUENCE: 1240

Thr Gly Trp Val Pro Arg
1               5

<210> SEQ ID NO 1241
<211> LENGTH: 10
<212> TYPE: PRT
<213> ORGANISM: Homo sapiens

<400> SEQUENCE: 1241

Gly Ala Val His Val Tyr Ala Thr Leu Arg
1               5                   10

<210> SEQ ID NO 1242
<211> LENGTH: 11
<212> TYPE: PRT
<213> ORGANISM: Homo sapiens

<400> SEQUENCE: 1242

Val Asp Thr Val Ala Ala Glu His Leu Thr Arg
1               5                   10

<210> SEQ ID NO 1243
<211> LENGTH: 9
<212> TYPE: PRT
<213> ORGANISM: Homo sapiens

<400> SEQUENCE: 1243

Arg Pro Gly Ala Glu Ala Thr Gly Lys
1               5

<210> SEQ ID NO 1244
<211> LENGTH: 6
<212> TYPE: PRT
<213> ORGANISM: Homo sapiens

<400> SEQUENCE: 1244

Leu Gly Pro Leu Ser Lys
1               5

<210> SEQ ID NO 1245
<211> LENGTH: 7
<212> TYPE: PRT
<213> ORGANISM: Homo sapiens

<400> SEQUENCE: 1245

Phe Pro Glu Thr Val Pro Arg
1               5

<210> SEQ ID NO 1246
<211> LENGTH: 19
<212> TYPE: PRT
<213> ORGANISM: Homo sapiens

<400> SEQUENCE: 1246

Leu Asn Gly Ser Ser Leu His Leu Glu Trp Ser Ala Pro Leu Glu Ser
1               5                   10                  15

Gly Gly Arg

<210> SEQ ID NO 1247
<211> LENGTH: 8
<212> TYPE: PRT
<213> ORGANISM: Homo sapiens

<400> SEQUENCE: 1247

Glu Asp Leu Thr Tyr Ala Leu Arg
1               5

```
<210> SEQ ID NO 1248
<211> LENGTH: 10
<212> TYPE: PRT
<213> ORGANISM: Homo sapiens

<400> SEQUENCE: 1248

Asp Leu Val Glu Pro Trp Val Val Val Arg
1               5                   10

<210> SEQ ID NO 1249
<211> LENGTH: 10
<212> TYPE: PRT
<213> ORGANISM: Homo sapiens

<400> SEQUENCE: 1249

Glu Val Pro Pro Ala Val Ser Asp Ile Arg
1               5                   10

<210> SEQ ID NO 1250
<211> LENGTH: 14
<212> TYPE: PRT
<213> ORGANISM: Homo sapiens

<400> SEQUENCE: 1250

Ser Ser Pro Ser Ser Leu Ser Leu Ala Trp Ala Val Pro Arg
1               5                   10

<210> SEQ ID NO 1251
<211> LENGTH: 12
<212> TYPE: PRT
<213> ORGANISM: Homo sapiens

<400> SEQUENCE: 1251

Ala Pro Ser Gly Ala Val Leu Asp Tyr Glu Val Lys
1               5                   10

<210> SEQ ID NO 1252
<211> LENGTH: 9
<212> TYPE: PRT
<213> ORGANISM: Homo sapiens

<400> SEQUENCE: 1252

Gly Ala Glu Gly Pro Ser Ser Val Arg
1               5

<210> SEQ ID NO 1253
<211> LENGTH: 9
<212> TYPE: PRT
<213> ORGANISM: Homo sapiens

<400> SEQUENCE: 1253

Gly Ala Ser Tyr Leu Val Gln Val Arg
1               5

<210> SEQ ID NO 1254
<211> LENGTH: 25
<212> TYPE: PRT
<213> ORGANISM: Homo sapiens

<400> SEQUENCE: 1254

Ser Glu Ala Gly Tyr Gly Pro Phe Gly Gln Glu His His Ser Gln Thr
1               5                   10                  15

Gln Leu Asp Glu Ser Glu Gly Trp Arg
            20                  25
```

<210> SEQ ID NO 1255
<211> LENGTH: 7
<212> TYPE: PRT
<213> ORGANISM: Homo sapiens

<400> SEQUENCE: 1255

Glu Ala Glu Tyr Ser Asp Lys
1               5

<210> SEQ ID NO 1256
<211> LENGTH: 11
<212> TYPE: PRT
<213> ORGANISM: Homo sapiens

<400> SEQUENCE: 1256

His Gly Gln Tyr Leu Ile Gly His Gly Thr Lys
1               5                   10

<210> SEQ ID NO 1257
<211> LENGTH: 8
<212> TYPE: PRT
<213> ORGANISM: Homo sapiens

<400> SEQUENCE: 1257

Glu Ile Asp Val Ser Tyr Val Lys
1               5

<210> SEQ ID NO 1258
<211> LENGTH: 6
<212> TYPE: PRT
<213> ORGANISM: Homo sapiens

<400> SEQUENCE: 1258

Gly Gly Tyr Thr Glu Arg
1               5

<210> SEQ ID NO 1259
<211> LENGTH: 18
<212> TYPE: PRT
<213> ORGANISM: Homo sapiens

<400> SEQUENCE: 1259

Phe Leu Glu Glu Asn Ser Ser Asp Pro Thr Tyr Thr Ser Ser Leu Gly
1               5                   10                  15

Gly Lys

<210> SEQ ID NO 1260
<211> LENGTH: 10
<212> TYPE: PRT
<213> ORGANISM: Homo sapiens

<400> SEQUENCE: 1260

Phe Pro Gln Val Val Ser Ala Leu Asp Lys
1               5                   10

<210> SEQ ID NO 1261
<211> LENGTH: 13
<212> TYPE: PRT
<213> ORGANISM: Homo sapiens

<400> SEQUENCE: 1261

Glu Asn Gly Gly Ala Ser His Pro Leu Leu Asp Gln Arg
1               5                   10

<210> SEQ ID NO 1262
<211> LENGTH: 15
<212> TYPE: PRT
<213> ORGANISM: Homo sapiens

<400> SEQUENCE: 1262

Gln Pro His Tyr Ser Ala Phe Gly Ser Val Gly Glu Trp Leu Arg
1               5                   10                  15

<210> SEQ ID NO 1263
<211> LENGTH: 18
<212> TYPE: PRT
<213> ORGANISM: Homo sapiens

<400> SEQUENCE: 1263

Ser Gln Ala Lys Pro Gly Thr Pro Gly Gly Thr Gly Gly Pro Ala Pro
1               5                   10                  15

Gln Tyr

<210> SEQ ID NO 1264
<211> LENGTH: 9
<212> TYPE: PRT
<213> ORGANISM: Homo sapiens

<400> SEQUENCE: 1264

Asn Val Lys Pro Asp Gln Trp Val Lys
1               5

<210> SEQ ID NO 1265
<211> LENGTH: 10
<212> TYPE: PRT
<213> ORGANISM: Homo sapiens

<400> SEQUENCE: 1265

Leu Asn Leu Gly Thr Val Gly Phe Tyr Arg
1               5                   10

<210> SEQ ID NO 1266
<211> LENGTH: 9
<212> TYPE: PRT
<213> ORGANISM: Homo sapiens

<400> SEQUENCE: 1266

Asp Leu Ser Leu Pro Pro Val Asp Arg
1               5

<210> SEQ ID NO 1267
<211> LENGTH: 12
<212> TYPE: PRT
<213> ORGANISM: Homo sapiens

<400> SEQUENCE: 1267

Leu Gly Leu Gln Asn Asp Leu Phe Ser Leu Ala Arg
1               5                   10

<210> SEQ ID NO 1268
<211> LENGTH: 11
<212> TYPE: PRT
<213> ORGANISM: Homo sapiens

<400> SEQUENCE: 1268

Ala Gly Ile Ile Ser Thr Val Glu Val Leu Lys
1               5                   10

```
<210> SEQ ID NO 1269
<211> LENGTH: 9
<212> TYPE: PRT
<213> ORGANISM: Homo sapiens

<400> SEQUENCE: 1269

Asp Val Phe Ser Pro Ile Gly Glu Arg
1               5

<210> SEQ ID NO 1270
<211> LENGTH: 17
<212> TYPE: PRT
<213> ORGANISM: Homo sapiens

<400> SEQUENCE: 1270

Leu Gly Trp Asp Pro Lys Pro Gly Glu Gly His Leu Asp Ala Leu Leu
1               5                   10                  15

Arg

<210> SEQ ID NO 1271
<211> LENGTH: 6
<212> TYPE: PRT
<213> ORGANISM: Homo sapiens

<400> SEQUENCE: 1271

Gly Leu Val Leu Gly Lys
1               5

<210> SEQ ID NO 1272
<211> LENGTH: 7
<212> TYPE: PRT
<213> ORGANISM: Homo sapiens

<400> SEQUENCE: 1272

Ala Thr Leu Glu Glu Ala Arg
1               5

<210> SEQ ID NO 1273
<211> LENGTH: 6
<212> TYPE: PRT
<213> ORGANISM: Homo sapiens

<400> SEQUENCE: 1273

Asp His Val Glu Gly Lys
1               5

<210> SEQ ID NO 1274
<211> LENGTH: 8
<212> TYPE: PRT
<213> ORGANISM: Homo sapiens

<400> SEQUENCE: 1274

Gln Ile Leu Ser Ala Asp Leu Arg
1               5

<210> SEQ ID NO 1275
<211> LENGTH: 9
<212> TYPE: PRT
<213> ORGANISM: Homo sapiens

<400> SEQUENCE: 1275

Ser Pro Val Tyr Leu Thr Val Leu Lys
1               5
```

```
<210> SEQ ID NO 1276
<211> LENGTH: 13
<212> TYPE: PRT
<213> ORGANISM: Homo sapiens

<400> SEQUENCE: 1276

Val Leu Gly Ala Thr Leu Leu Pro Asp Leu Ile Gln Lys
1               5                   10

<210> SEQ ID NO 1277
<211> LENGTH: 9
<212> TYPE: PRT
<213> ORGANISM: Homo sapiens

<400> SEQUENCE: 1277

Asp Asn Trp Glu Glu Leu Tyr Asn Arg
1               5

<210> SEQ ID NO 1278
<211> LENGTH: 9
<212> TYPE: PRT
<213> ORGANISM: Homo sapiens

<400> SEQUENCE: 1278

Tyr Gln Gly Gly Phe Leu Ile Ser Arg
1               5

<210> SEQ ID NO 1279
<211> LENGTH: 10
<212> TYPE: PRT
<213> ORGANISM: Homo sapiens

<400> SEQUENCE: 1279

Leu Ser Val Glu Gly Phe Ala Val Asp Lys
1               5                   10

<210> SEQ ID NO 1280
<211> LENGTH: 13
<212> TYPE: PRT
<213> ORGANISM: Homo sapiens

<400> SEQUENCE: 1280

Ala Phe Phe Glu Ser His Pro Ala Pro Ser Ala Glu Arg
1               5                   10

<210> SEQ ID NO 1281
<211> LENGTH: 12
<212> TYPE: PRT
<213> ORGANISM: Homo sapiens

<400> SEQUENCE: 1281

Asp Ala Glu Ser Ile His Gln Tyr Leu Leu Gln Arg
1               5                   10

<210> SEQ ID NO 1282
<211> LENGTH: 7
<212> TYPE: PRT
<213> ORGANISM: Homo sapiens

<400> SEQUENCE: 1282

Asp Ile Ala Ala His Ile Lys
1               5
```

-continued

```
<210> SEQ ID NO 1283
<211> LENGTH: 6
<212> TYPE: PRT
<213> ORGANISM: Homo sapiens

<400> SEQUENCE: 1283

Glu Thr Glu Gly Phe Arg
1               5

<210> SEQ ID NO 1284
<211> LENGTH: 8
<212> TYPE: PRT
<213> ORGANISM: Homo sapiens

<400> SEQUENCE: 1284

Ser Ala Gln Phe Phe Asn Tyr Lys
1               5

<210> SEQ ID NO 1285
<211> LENGTH: 14
<212> TYPE: PRT
<213> ORGANISM: Homo sapiens

<400> SEQUENCE: 1285

Ile Gln Ala Leu Gly Leu Gly Glu Asp Trp Asn Val Glu Lys
1               5                   10

<210> SEQ ID NO 1286
<211> LENGTH: 9
<212> TYPE: PRT
<213> ORGANISM: Homo sapiens

<400> SEQUENCE: 1286

Gly Thr Ser Ala Gly Gly Gly Gln Lys
1               5

<210> SEQ ID NO 1287
<211> LENGTH: 20
<212> TYPE: PRT
<213> ORGANISM: Homo sapiens

<400> SEQUENCE: 1287

Glu Asp Leu Val Ile Leu Phe Ala Asp Ser Tyr Asp Val Leu Phe Ala
1               5                   10                  15

Ser Gly Pro Arg
            20

<210> SEQ ID NO 1288
<211> LENGTH: 15
<212> TYPE: PRT
<213> ORGANISM: Homo sapiens

<400> SEQUENCE: 1288

Ser Gln Val Val Phe Ser Ala Glu Glu Leu Ile Tyr Pro Asp Arg
1               5                   10                  15

<210> SEQ ID NO 1289
<211> LENGTH: 8
<212> TYPE: PRT
<213> ORGANISM: Homo sapiens

<400> SEQUENCE: 1289

Tyr Pro Val Val Ser Asp Gly Lys
1               5
```

<210> SEQ ID NO 1290
<211> LENGTH: 16
<212> TYPE: PRT
<213> ORGANISM: Homo sapiens

<400> SEQUENCE: 1290

Phe Leu Gly Ser Gly Gly Phe Ile Gly Tyr Ala Pro Asn Leu Ser Lys
1               5                   10                  15

<210> SEQ ID NO 1291
<211> LENGTH: 19
<212> TYPE: PRT
<213> ORGANISM: Homo sapiens

<400> SEQUENCE: 1291

Leu Val Ala Glu Trp Glu Gly Gln Asp Ser Asp Ser Asp Gln Leu Phe
1               5                   10                  15

Tyr Thr Lys

<210> SEQ ID NO 1292
<211> LENGTH: 7
<212> TYPE: PRT
<213> ORGANISM: Homo sapiens

<400> SEQUENCE: 1292

Ile Phe Leu Asp Pro Glu Lys
1               5

<210> SEQ ID NO 1293
<211> LENGTH: 10
<212> TYPE: PRT
<213> ORGANISM: Homo sapiens

<400> SEQUENCE: 1293

Glu Gln Ile Asn Ile Thr Leu Asp His Arg
1               5                   10

<210> SEQ ID NO 1294
<211> LENGTH: 15
<212> TYPE: PRT
<213> ORGANISM: Homo sapiens

<400> SEQUENCE: 1294

Ile Phe Gln Asn Leu Asp Gly Ala Leu Asp Glu Val Val Leu Lys
1               5                   10                  15

<210> SEQ ID NO 1295
<211> LENGTH: 18
<212> TYPE: PRT
<213> ORGANISM: Homo sapiens

<400> SEQUENCE: 1295

Asn Leu Ala Tyr Asp Thr Leu Pro Val Leu Ile His Gly Asn Gly Pro
1               5                   10                  15

Thr Lys

<210> SEQ ID NO 1296
<211> LENGTH: 12
<212> TYPE: PRT
<213> ORGANISM: Homo sapiens

<400> SEQUENCE: 1296

Leu Gln Leu Asn Tyr Leu Gly Asn Tyr Ile Pro Arg

```
1               5               10
```

<210> SEQ ID NO 1297
<211> LENGTH: 6
<212> TYPE: PRT
<213> ORGANISM: Homo sapiens

<400> SEQUENCE: 1297

```
Leu His Tyr Pro Gln Lys
1               5
```

<210> SEQ ID NO 1298
<211> LENGTH: 11
<212> TYPE: PRT
<213> ORGANISM: Homo sapiens

<400> SEQUENCE: 1298

```
Leu Phe Ile His Asn His Glu Gln His His Lys
1               5               10
```

<210> SEQ ID NO 1299
<211> LENGTH: 18
<212> TYPE: PRT
<213> ORGANISM: Homo sapiens

<400> SEQUENCE: 1299

```
Ala Gln Val Glu Glu Phe Leu Ala Gln His Gly Ser Glu Tyr Gln Ser
1               5                   10                  15

Val Lys
```

<210> SEQ ID NO 1300
<211> LENGTH: 7
<212> TYPE: PRT
<213> ORGANISM: Homo sapiens

<400> SEQUENCE: 1300

```
Leu Leu Ile Gln Gln Asn Lys
1               5
```

<210> SEQ ID NO 1301
<211> LENGTH: 17
<212> TYPE: PRT
<213> ORGANISM: Homo sapiens

<400> SEQUENCE: 1301

```
Leu Trp Ser Asn Phe Trp Gly Ala Leu Ser Ala Asp Gly Tyr Tyr Ala
1               5                   10                  15

Arg
```

<210> SEQ ID NO 1302
<211> LENGTH: 11
<212> TYPE: PRT
<213> ORGANISM: Homo sapiens

<400> SEQUENCE: 1302

```
Ser Glu Asp Tyr Val Asp Ile Val Gln Gly Arg
1               5                   10
```

<210> SEQ ID NO 1303
<211> LENGTH: 16
<212> TYPE: PRT
<213> ORGANISM: Homo sapiens

<400> SEQUENCE: 1303

Val Gly Val Trp Asn Val Pro Tyr Ile Ser Asn Ile Tyr Leu Ile Lys
1               5                   10                  15

<210> SEQ ID NO 1304
<211> LENGTH: 13
<212> TYPE: PRT
<213> ORGANISM: Homo sapiens

<400> SEQUENCE: 1304

Gly Glu Leu Gln Ser Ser Asp Leu Phe His His Ser Lys
1               5                   10

<210> SEQ ID NO 1305
<211> LENGTH: 13
<212> TYPE: PRT
<213> ORGANISM: Homo sapiens

<400> SEQUENCE: 1305

His Thr Leu Gly His Leu Leu Ser Leu Asp Ser Tyr Arg
1               5                   10

<210> SEQ ID NO 1306
<211> LENGTH: 19
<212> TYPE: PRT
<213> ORGANISM: Homo sapiens

<400> SEQUENCE: 1306

Thr Thr His Leu His Asn Asp Leu Trp Glu Val Phe Ser Asn Pro Glu
1               5                   10                  15

Asp Trp Lys

<210> SEQ ID NO 1307
<211> LENGTH: 8
<212> TYPE: PRT
<213> ORGANISM: Homo sapiens

<400> SEQUENCE: 1307

Tyr Ile His Gln Asn Tyr Thr Lys
1               5

<210> SEQ ID NO 1308
<211> LENGTH: 8
<212> TYPE: PRT
<213> ORGANISM: Homo sapiens

<400> SEQUENCE: 1308

Leu Tyr Pro Gly Tyr Tyr Thr Arg
1               5

<210> SEQ ID NO 1309
<211> LENGTH: 10
<212> TYPE: PRT
<213> ORGANISM: Homo sapiens

<400> SEQUENCE: 1309

Ala Gln Phe Asp Leu Ala Phe Val Val Arg
1               5                   10

<210> SEQ ID NO 1310
<211> LENGTH: 12
<212> TYPE: PRT
<213> ORGANISM: Homo sapiens

<400> SEQUENCE: 1310

```
Leu Thr His Tyr His Glu Gly Leu Pro Thr Thr Arg
1               5                   10
```

<210> SEQ ID NO 1311
<211> LENGTH: 9
<212> TYPE: PRT
<213> ORGANISM: Homo sapiens

<400> SEQUENCE: 1311

```
Tyr Ile Ala Val Ser Phe Val Asp Pro
1               5
```

<210> SEQ ID NO 1312
<211> LENGTH: 17
<212> TYPE: PRT
<213> ORGANISM: Homo sapiens

<400> SEQUENCE: 1312

```
Gly Asp Ala Lys Pro Glu Asp Asn Leu Leu Val Leu Thr Val Ala Thr
1               5                   10                  15

Lys
```

<210> SEQ ID NO 1313
<211> LENGTH: 6
<212> TYPE: PRT
<213> ORGANISM: Homo sapiens

<400> SEQUENCE: 1313

```
Asn Asn Phe Val Ile Arg
1               5
```

<210> SEQ ID NO 1314
<211> LENGTH: 7
<212> TYPE: PRT
<213> ORGANISM: Homo sapiens

<400> SEQUENCE: 1314

```
Asn Pro Ala Asp Pro Gln Arg
1               5
```

<210> SEQ ID NO 1315
<211> LENGTH: 8
<212> TYPE: PRT
<213> ORGANISM: Homo sapiens

<400> SEQUENCE: 1315

```
Ile Pro Ser Asn Pro Ser His Arg
1               5
```

<210> SEQ ID NO 1316
<211> LENGTH: 9
<212> TYPE: PRT
<213> ORGANISM: Homo sapiens

<400> SEQUENCE: 1316

```
Glu Leu Pro Gln Ser Ile Val Tyr Lys
1               5
```

<210> SEQ ID NO 1317
<211> LENGTH: 23
<212> TYPE: PRT
<213> ORGANISM: Homo sapiens

<400> SEQUENCE: 1317

```
Ser Val Pro Ser Asp Ile Phe Gln Ile Gln Ala Thr Thr Ile Tyr Ala
1               5                   10                  15

Asn Thr Ile Asn Thr Phe Arg
            20

<210> SEQ ID NO 1318
<211> LENGTH: 11
<212> TYPE: PRT
<213> ORGANISM: Homo sapiens

<400> SEQUENCE: 1318

Ser Gly Asn Glu Asn Gly Glu Phe Tyr Leu Arg
1               5                   10

<210> SEQ ID NO 1319
<211> LENGTH: 10
<212> TYPE: PRT
<213> ORGANISM: Homo sapiens

<400> SEQUENCE: 1319

Leu Thr Ile Ile Val Gly Pro Phe Ser Phe
1               5                   10

<210> SEQ ID NO 1320
<211> LENGTH: 19
<212> TYPE: PRT
<213> ORGANISM: Homo sapiens

<400> SEQUENCE: 1320

Ala Gly Val Ala Gly Leu Ser Ala Trp Thr Leu Gln Pro Gln Trp Ile
1               5                   10                  15

Gln Val Arg

<210> SEQ ID NO 1321
<211> LENGTH: 12
<212> TYPE: PRT
<213> ORGANISM: Homo sapiens

<400> SEQUENCE: 1321

Ile Tyr Gly Leu Gly Ser Leu Ala Leu Tyr Glu Lys
1               5                   10

<210> SEQ ID NO 1322
<211> LENGTH: 10
<212> TYPE: PRT
<213> ORGANISM: Homo sapiens

<400> SEQUENCE: 1322

His Leu Leu Ile Gly Val Ser Ser Asp Arg
1               5                   10

<210> SEQ ID NO 1323
<211> LENGTH: 11
<212> TYPE: PRT
<213> ORGANISM: Homo sapiens

<400> SEQUENCE: 1323

Ser Glu Val Ala Thr Leu Thr Ala Ala Gly Lys
1               5                   10

<210> SEQ ID NO 1324
<211> LENGTH: 11
<212> TYPE: PRT
```

<213> ORGANISM: Homo sapiens

<400> SEQUENCE: 1324

Thr His Ser Asp Gln Phe Leu Val Ala Phe Lys
1               5                   10

<210> SEQ ID NO 1325
<211> LENGTH: 6
<212> TYPE: PRT
<213> ORGANISM: Homo sapiens

<400> SEQUENCE: 1325

Ser Val Ile Ser Tyr Lys
1               5

<210> SEQ ID NO 1326
<211> LENGTH: 10
<212> TYPE: PRT
<213> ORGANISM: Homo sapiens

<400> SEQUENCE: 1326

Glu Ser Thr Thr Ser Glu Gln Ser Ala Arg
1               5                   10

<210> SEQ ID NO 1327
<211> LENGTH: 7
<212> TYPE: PRT
<213> ORGANISM: Homo sapiens

<400> SEQUENCE: 1327

Leu Thr Leu Thr Phe Asn Arg
1               5

<210> SEQ ID NO 1328
<211> LENGTH: 6
<212> TYPE: PRT
<213> ORGANISM: Homo sapiens

<400> SEQUENCE: 1328

Gln Ala Val Ile Thr Lys
1               5

<210> SEQ ID NO 1329
<211> LENGTH: 13
<212> TYPE: PRT
<213> ORGANISM: Homo sapiens

<400> SEQUENCE: 1329

Glu Leu Ile Glu Ile Ile Ser Gly Ala Ala Ala Leu Asp
1               5                   10

<210> SEQ ID NO 1330
<211> LENGTH: 6
<212> TYPE: PRT
<213> ORGANISM: Homo sapiens

<400> SEQUENCE: 1330

Leu His Leu Ile Thr Arg
1               5

<210> SEQ ID NO 1331
<211> LENGTH: 10
<212> TYPE: PRT
<213> ORGANISM: Homo sapiens

```
<400> SEQUENCE: 1331

Asn Leu Gln Glu Val Leu Gly Glu Glu Lys
1               5                   10

<210> SEQ ID NO 1332
<211> LENGTH: 6
<212> TYPE: PRT
<213> ORGANISM: Homo sapiens

<400> SEQUENCE: 1332

Ile Ala Asp Phe Leu Lys
1               5

<210> SEQ ID NO 1333
<211> LENGTH: 9
<212> TYPE: PRT
<213> ORGANISM: Homo sapiens

<400> SEQUENCE: 1333

Ala Pro Trp Glu Leu Leu Glu Leu Arg
1               5

<210> SEQ ID NO 1334
<211> LENGTH: 9
<212> TYPE: PRT
<213> ORGANISM: Homo sapiens

<400> SEQUENCE: 1334

Val Ser Tyr Tyr Glu Asn Val Ile Lys
1               5

<210> SEQ ID NO 1335
<211> LENGTH: 8
<212> TYPE: PRT
<213> ORGANISM: Homo sapiens

<400> SEQUENCE: 1335

Gly Thr Asp Tyr Gln Leu Ser Lys
1               5

<210> SEQ ID NO 1336
<211> LENGTH: 8
<212> TYPE: PRT
<213> ORGANISM: Homo sapiens

<400> SEQUENCE: 1336

Glu Tyr Thr Leu Asp Val Tyr Arg
1               5

<210> SEQ ID NO 1337
<211> LENGTH: 11
<212> TYPE: PRT
<213> ORGANISM: Homo sapiens

<400> SEQUENCE: 1337

Leu Ser Ser Val Val Thr Gln His Asp Ser Lys
1               5                   10

<210> SEQ ID NO 1338
<211> LENGTH: 7
<212> TYPE: PRT
<213> ORGANISM: Homo sapiens

<400> SEQUENCE: 1338
```

```
Ala Gly Ala Glu Val Val Lys
1               5

<210> SEQ ID NO 1339
<211> LENGTH: 24
<212> TYPE: PRT
<213> ORGANISM: Homo sapiens

<400> SEQUENCE: 1339

Gln Val Glu His Pro Leu Leu Ser Gly Leu Leu Tyr Pro Gly Leu Gln
1               5                   10                  15

Ala Leu Asp Glu Glu Tyr Leu Lys
            20

<210> SEQ ID NO 1340
<211> LENGTH: 11
<212> TYPE: PRT
<213> ORGANISM: Homo sapiens

<400> SEQUENCE: 1340

Val Asp Ala Gln Phe Gly Gly Ile Asp Gln Arg
1               5                   10

<210> SEQ ID NO 1341
<211> LENGTH: 7
<212> TYPE: PRT
<213> ORGANISM: Homo sapiens

<400> SEQUENCE: 1341

Ile Phe Thr Phe Ala Glu Lys
1               5

<210> SEQ ID NO 1342
<211> LENGTH: 9
<212> TYPE: PRT
<213> ORGANISM: Homo sapiens

<400> SEQUENCE: 1342

Tyr Leu Pro Ala Leu Gly Tyr Ser Lys
1               5

<210> SEQ ID NO 1343
<211> LENGTH: 7
<212> TYPE: PRT
<213> ORGANISM: Homo sapiens

<400> SEQUENCE: 1343

His Val Leu Phe Pro Leu Lys
1               5

<210> SEQ ID NO 1344
<211> LENGTH: 7
<212> TYPE: PRT
<213> ORGANISM: Homo sapiens

<400> SEQUENCE: 1344

Ser Glu Phe Val Ile Leu Arg
1               5

<210> SEQ ID NO 1345
<211> LENGTH: 10
<212> TYPE: PRT
<213> ORGANISM: Homo sapiens

<400> SEQUENCE: 1345
```

```
Thr Tyr Thr Ala Tyr Val Asp Leu Glu Lys
1               5                   10

<210> SEQ ID NO 1346
<211> LENGTH: 13
<212> TYPE: PRT
<213> ORGANISM: Homo sapiens

<400> SEQUENCE: 1346

Asp Phe Ala Ala Glu Val Val His Pro Gly Asp Leu Lys
1               5                   10

<210> SEQ ID NO 1347
<211> LENGTH: 9
<212> TYPE: PRT
<213> ORGANISM: Homo sapiens

<400> SEQUENCE: 1347

Asn Ser Val Glu Val Ala Leu Asn Lys
1               5

<210> SEQ ID NO 1348
<211> LENGTH: 6
<212> TYPE: PRT
<213> ORGANISM: Homo sapiens

<400> SEQUENCE: 1348

Leu Leu Asp Pro Ile Arg
1               5

<210> SEQ ID NO 1349
<211> LENGTH: 7
<212> TYPE: PRT
<213> ORGANISM: Homo sapiens

<400> SEQUENCE: 1349

Phe Asn Thr Pro Ala Leu Lys
1               5

<210> SEQ ID NO 1350
<211> LENGTH: 11
<212> TYPE: PRT
<213> ORGANISM: Homo sapiens

<400> SEQUENCE: 1350

Leu Ala Ser Ala Ala Tyr Pro Asp Pro Ser Lys
1               5                   10

<210> SEQ ID NO 1351
<211> LENGTH: 11
<212> TYPE: PRT
<213> ORGANISM: Homo sapiens

<400> SEQUENCE: 1351

Asn Ser Glu Pro Glu Glu Val Ile Pro Ser Arg
1               5                   10

<210> SEQ ID NO 1352
<211> LENGTH: 6
<212> TYPE: PRT
<213> ORGANISM: Homo sapiens

<400> SEQUENCE: 1352

Ile Ile Thr Val Glu Lys
```

```
1               5
```

<210> SEQ ID NO 1353
<211> LENGTH: 11
<212> TYPE: PRT
<213> ORGANISM: Homo sapiens

<400> SEQUENCE: 1353

```
His Pro Asp Ala Asp Ser Leu Tyr Val Glu Lys
1               5                   10
```

<210> SEQ ID NO 1354
<211> LENGTH: 9
<212> TYPE: PRT
<213> ORGANISM: Homo sapiens

<400> SEQUENCE: 1354

```
Ile Asp Val Gly Glu Ala Glu Pro Arg
1               5
```

<210> SEQ ID NO 1355
<211> LENGTH: 12
<212> TYPE: PRT
<213> ORGANISM: Homo sapiens

<400> SEQUENCE: 1355

```
Thr Val Val Ser Gly Leu Val Gln Phe Val Pro Lys
1               5                   10
```

<210> SEQ ID NO 1356
<211> LENGTH: 20
<212> TYPE: PRT
<213> ORGANISM: Homo sapiens

<400> SEQUENCE: 1356

```
Gln Val Glu Pro Leu Asp Pro Pro Ala Gly Ser Ala Pro Gly Glu His
1               5                   10                  15

Val Phe Val Lys
            20
```

<210> SEQ ID NO 1357
<211> LENGTH: 10
<212> TYPE: PRT
<213> ORGANISM: Homo sapiens

<400> SEQUENCE: 1357

```
Gly Gln Pro Asp Glu Glu Leu Lys Pro Lys
1               5                   10
```

<210> SEQ ID NO 1358
<211> LENGTH: 6
<212> TYPE: PRT
<213> ORGANISM: Homo sapiens

<400> SEQUENCE: 1358

```
Leu Gln Ala Asp Phe Lys
1               5
```

<210> SEQ ID NO 1359
<211> LENGTH: 12
<212> TYPE: PRT
<213> ORGANISM: Homo sapiens

<400> SEQUENCE: 1359

```
Glu Ala Ala Ile Val Asp Pro Val Gln Pro Gln Lys
1               5                   10
```

<210> SEQ ID NO 1360
<211> LENGTH: 19
<212> TYPE: PRT
<213> ORGANISM: Homo sapiens

<400> SEQUENCE: 1360

```
Leu Thr Thr Val Leu Thr Thr His His His Trp Asp His Ala Gly Gly
1               5                   10                  15

Asn Glu Lys
```

<210> SEQ ID NO 1361
<211> LENGTH: 6
<212> TYPE: PRT
<213> ORGANISM: Homo sapiens

<400> SEQUENCE: 1361

```
Leu Glu Ser Gly Leu Lys
1               5
```

<210> SEQ ID NO 1362
<211> LENGTH: 7
<212> TYPE: PRT
<213> ORGANISM: Homo sapiens

<400> SEQUENCE: 1362

```
Val Tyr Gly Gly Asp Asp Arg
1               5
```

<210> SEQ ID NO 1363
<211> LENGTH: 7
<212> TYPE: PRT
<213> ORGANISM: Homo sapiens

<400> SEQUENCE: 1363

```
Ile Gly Ala Leu Thr His Lys
1               5
```

<210> SEQ ID NO 1364
<211> LENGTH: 15
<212> TYPE: PRT
<213> ORGANISM: Homo sapiens

<400> SEQUENCE: 1364

```
Ile Thr His Leu Ser Thr Leu Gln Val Gly Ser Leu Asn Val Lys
1               5                   10                  15
```

<210> SEQ ID NO 1365
<211> LENGTH: 8
<212> TYPE: PRT
<213> ORGANISM: Homo sapiens

<400> SEQUENCE: 1365

```
Ala Leu Leu Glu Val Leu Gly Arg
1               5
```

<210> SEQ ID NO 1366
<211> LENGTH: 10
<212> TYPE: PRT
<213> ORGANISM: Homo sapiens

<400> SEQUENCE: 1366

```
His Val Glu Pro Gly Asn Ala Ala Ile Arg
1               5                   10

<210> SEQ ID NO 1367
<211> LENGTH: 7
<212> TYPE: PRT
<213> ORGANISM: Homo sapiens

<400> SEQUENCE: 1367

Leu Asp Asp Asp Ser Glu Arg
1               5

<210> SEQ ID NO 1368
<211> LENGTH: 8
<212> TYPE: PRT
<213> ORGANISM: Homo sapiens

<400> SEQUENCE: 1368

Asp Ile Ser Ser Ile Gly Leu Lys
1               5

<210> SEQ ID NO 1369
<211> LENGTH: 7
<212> TYPE: PRT
<213> ORGANISM: Homo sapiens

<400> SEQUENCE: 1369

Leu Thr Ser Ala Ile Ala Lys
1               5

<210> SEQ ID NO 1370
<211> LENGTH: 7
<212> TYPE: PRT
<213> ORGANISM: Homo sapiens

<400> SEQUENCE: 1370

Ile Gly Glu Tyr Leu Glu Lys
1               5

<210> SEQ ID NO 1371
<211> LENGTH: 9
<212> TYPE: PRT
<213> ORGANISM: Homo sapiens

<400> SEQUENCE: 1371

Thr Val Ser Pro Ala Leu Ile Ser Arg
1               5

<210> SEQ ID NO 1372
<211> LENGTH: 12
<212> TYPE: PRT
<213> ORGANISM: Homo sapiens

<400> SEQUENCE: 1372

Ala Asp Val Phe His Ala Tyr Leu Ser Leu Leu Lys
1               5                   10

<210> SEQ ID NO 1373
<211> LENGTH: 14
<212> TYPE: PRT
<213> ORGANISM: Homo sapiens

<400> SEQUENCE: 1373

Ile Thr Ser Glu Ala Leu Leu Val Thr Gln Gln Leu Val Lys
1               5                   10
```

<210> SEQ ID NO 1374
<211> LENGTH: 11
<212> TYPE: PRT
<213> ORGANISM: Homo sapiens

<400> SEQUENCE: 1374

Ala Leu Thr Leu Ile Ala Gly Ser Pro Leu Lys
1               5                   10

<210> SEQ ID NO 1375
<211> LENGTH: 19
<212> TYPE: PRT
<213> ORGANISM: Homo sapiens

<400> SEQUENCE: 1375

Ile Asp Leu Arg Pro Val Leu Gly Glu Gly Val Pro Ile Leu Ala Ser
1               5                   10                  15

Phe Leu Arg

<210> SEQ ID NO 1376
<211> LENGTH: 12
<212> TYPE: PRT
<213> ORGANISM: Homo sapiens

<400> SEQUENCE: 1376

Leu Gly Thr Leu Ser Ala Leu Asp Ile Leu Ile Lys
1               5                   10

<210> SEQ ID NO 1377
<211> LENGTH: 8
<212> TYPE: PRT
<213> ORGANISM: Homo sapiens

<400> SEQUENCE: 1377

Val Tyr Pro Ser Ser Leu Ser Lys
1               5

<210> SEQ ID NO 1378
<211> LENGTH: 14
<212> TYPE: PRT
<213> ORGANISM: Homo sapiens

<400> SEQUENCE: 1378

Ile Ser Gly Ser Ile Leu Asn Glu Leu Ile Gly Leu Val Arg
1               5                   10

<210> SEQ ID NO 1379
<211> LENGTH: 8
<212> TYPE: PRT
<213> ORGANISM: Homo sapiens

<400> SEQUENCE: 1379

Gln Ser Tyr Tyr Ser Ile Ala Lys
1               5

<210> SEQ ID NO 1380
<211> LENGTH: 14
<212> TYPE: PRT
<213> ORGANISM: Homo sapiens

<400> SEQUENCE: 1380

Glu Gly Pro Ala Val Val Gly Gln Phe Ile Gln Asp Val Lys
1               5                   10

<210> SEQ ID NO 1381
<211> LENGTH: 6
<212> TYPE: PRT
<213> ORGANISM: Homo sapiens

<400> SEQUENCE: 1381

Ser Thr Asp Ser Ile Arg
1               5

<210> SEQ ID NO 1382
<211> LENGTH: 23
<212> TYPE: PRT
<213> ORGANISM: Homo sapiens

<400> SEQUENCE: 1382

Leu Leu Ala Leu Leu Ser Leu Gly Glu Val Gly His His Ile Asp Leu
1               5                   10                  15

Ser Gly Gln Leu Glu Leu Lys
            20

<210> SEQ ID NO 1383
<211> LENGTH: 15
<212> TYPE: PRT
<213> ORGANISM: Homo sapiens

<400> SEQUENCE: 1383

Ser Val Ile Leu Glu Ala Phe Ser Ser Pro Ser Glu Glu Val Lys
1               5                   10                  15

<210> SEQ ID NO 1384
<211> LENGTH: 9
<212> TYPE: PRT
<213> ORGANISM: Homo sapiens

<400> SEQUENCE: 1384

Gln Tyr Leu Leu Leu His Ser Leu Lys
1               5

<210> SEQ ID NO 1385
<211> LENGTH: 24
<212> TYPE: PRT
<213> ORGANISM: Homo sapiens

<400> SEQUENCE: 1385

Glu Ile Ile Ser Ser Ala Ser Val Val Gly Leu Lys Pro Tyr Val Glu
1               5                   10                  15

Asn Ile Trp Ala Leu Leu Leu Lys
            20

<210> SEQ ID NO 1386
<211> LENGTH: 12
<212> TYPE: PRT
<213> ORGANISM: Homo sapiens

<400> SEQUENCE: 1386

Leu Thr Leu Ile Asp Pro Glu Thr Leu Leu Pro Arg
1               5                   10

<210> SEQ ID NO 1387
<211> LENGTH: 11
<212> TYPE: PRT
<213> ORGANISM: Homo sapiens

<400> SEQUENCE: 1387

Gly Tyr Leu Ile Ser Gly Ser Ser Tyr Ala Arg
1               5                   10

<210> SEQ ID NO 1388
<211> LENGTH: 8
<212> TYPE: PRT
<213> ORGANISM: Homo sapiens

<400> SEQUENCE: 1388

Ser Ser Val Val Thr Ala Val Lys
1               5

<210> SEQ ID NO 1389
<211> LENGTH: 15
<212> TYPE: PRT
<213> ORGANISM: Homo sapiens

<400> SEQUENCE: 1389

Phe Thr Ile Ser Asp His Pro Gln Pro Ile Asp Pro Leu Leu Lys
1               5                   10                  15

<210> SEQ ID NO 1390
<211> LENGTH: 10
<212> TYPE: PRT
<213> ORGANISM: Homo sapiens

<400> SEQUENCE: 1390

Thr Leu Glu Asp Pro Asp Leu Asn Val Arg
1               5                   10

<210> SEQ ID NO 1391
<211> LENGTH: 18
<212> TYPE: PRT
<213> ORGANISM: Homo sapiens

<400> SEQUENCE: 1391

Val Ala Leu Val Thr Phe Asn Ser Ala Ala His Asn Lys Pro Ser Leu
1               5                   10                  15

Ile Arg

<210> SEQ ID NO 1392
<211> LENGTH: 15
<212> TYPE: PRT
<213> ORGANISM: Homo sapiens

<400> SEQUENCE: 1392

Asp Leu Leu Asp Thr Val Leu Pro His Leu Tyr Asn Glu Thr Lys
1               5                   10                  15

<210> SEQ ID NO 1393
<211> LENGTH: 10
<212> TYPE: PRT
<213> ORGANISM: Homo sapiens

<400> SEQUENCE: 1393

His Thr Val Asp Asp Gly Leu Asp Ile Arg
1               5                   10

<210> SEQ ID NO 1394
<211> LENGTH: 15
<212> TYPE: PRT
<213> ORGANISM: Homo sapiens

```
<400> SEQUENCE: 1394

Leu Asp Ile Phe Glu Phe Leu Asn His Val Glu Asp Gly Leu Lys
1               5                   10                  15

<210> SEQ ID NO 1395
<211> LENGTH: 6
<212> TYPE: PRT
<213> ORGANISM: Homo sapiens

<400> SEQUENCE: 1395

Asp His Tyr Asp Ile Lys
1               5

<210> SEQ ID NO 1396
<211> LENGTH: 6
<212> TYPE: PRT
<213> ORGANISM: Homo sapiens

<400> SEQUENCE: 1396

Leu Val Glu Pro Leu Arg
1               5

<210> SEQ ID NO 1397
<211> LENGTH: 13
<212> TYPE: PRT
<213> ORGANISM: Homo sapiens

<400> SEQUENCE: 1397

Ala Val Ala Ala Leu Leu Thr Ile Pro Glu Ala Glu Lys
1               5                   10

<210> SEQ ID NO 1398
<211> LENGTH: 18
<212> TYPE: PRT
<213> ORGANISM: Homo sapiens

<400> SEQUENCE: 1398

Val Ile Arg Pro Leu Asp Gln Pro Ser Ser Phe Asp Ala Thr Pro Tyr
1               5                   10                  15

Ile Lys

<210> SEQ ID NO 1399
<211> LENGTH: 9
<212> TYPE: PRT
<213> ORGANISM: Homo sapiens

<400> SEQUENCE: 1399

Ala Ala Asp Ile Asp Gln Glu Val Lys
1               5

<210> SEQ ID NO 1400
<211> LENGTH: 10
<212> TYPE: PRT
<213> ORGANISM: Homo sapiens

<400> SEQUENCE: 1400

Ser Asp Gly Thr Pro Phe Pro Trp Asn Lys
1               5                   10

<210> SEQ ID NO 1401
<211> LENGTH: 23
<212> TYPE: PRT
<213> ORGANISM: Homo sapiens
```

-continued

```
<400> SEQUENCE: 1401

Val Glu Ile Thr Ala Ser Gln Pro Thr Ser Thr Ile Ile Leu His Ser
1               5                   10                  15

His His Leu Gln Ile Ser Arg
            20

<210> SEQ ID NO 1402
<211> LENGTH: 13
<212> TYPE: PRT
<213> ORGANISM: Homo sapiens

<400> SEQUENCE: 1402

Leu Ser Glu Glu Pro Leu Gln Val Leu Glu His Pro Arg
1               5                   10

<210> SEQ ID NO 1403
<211> LENGTH: 13
<212> TYPE: PRT
<213> ORGANISM: Homo sapiens

<400> SEQUENCE: 1403

Ile Leu Ala Ser Thr Gln Phe Glu Pro Thr Ala Ala Arg
1               5                   10

<210> SEQ ID NO 1404
<211> LENGTH: 6
<212> TYPE: PRT
<213> ORGANISM: Homo sapiens

<400> SEQUENCE: 1404

Ala Ser Phe Ser Ile Lys
1               5

<210> SEQ ID NO 1405
<211> LENGTH: 18
<212> TYPE: PRT
<213> ORGANISM: Homo sapiens

<400> SEQUENCE: 1405

Ser Val Thr Val Ala Glu Gly Leu Ile Glu Asp His Phe Asp Val Thr
1               5                   10                  15

Val Lys

<210> SEQ ID NO 1406
<211> LENGTH: 9
<212> TYPE: PRT
<213> ORGANISM: Homo sapiens

<400> SEQUENCE: 1406

Val Ser Val Tyr Ala Val Pro Asp Lys
1               5

<210> SEQ ID NO 1407
<211> LENGTH: 10
<212> TYPE: PRT
<213> ORGANISM: Homo sapiens

<400> SEQUENCE: 1407

Glu Ser Ala Leu Leu Phe Asp Ala Glu Lys
1               5                   10

<210> SEQ ID NO 1408
<211> LENGTH: 8
```

```
<212> TYPE: PRT
<213> ORGANISM: Homo sapiens

<400> SEQUENCE: 1408

Val Gly Asp Tyr Phe Phe Gly Lys
1               5

<210> SEQ ID NO 1409
<211> LENGTH: 9
<212> TYPE: PRT
<213> ORGANISM: Homo sapiens

<400> SEQUENCE: 1409

Glu Tyr Leu Ser Ala Asp Ala Phe Lys
1               5

<210> SEQ ID NO 1410
<211> LENGTH: 9
<212> TYPE: PRT
<213> ORGANISM: Homo sapiens

<400> SEQUENCE: 1410

Ser Gly Ile Val Gln Tyr Leu Gln Lys
1               5

<210> SEQ ID NO 1411
<211> LENGTH: 18
<212> TYPE: PRT
<213> ORGANISM: Homo sapiens

<400> SEQUENCE: 1411

Ser Gln His Ser Ser Ser Ser His Trp His Gln Glu Gly Val Asp
1               5                   10                  15

Val Lys

<210> SEQ ID NO 1412
<211> LENGTH: 10
<212> TYPE: PRT
<213> ORGANISM: Homo sapiens

<400> SEQUENCE: 1412

Gly Phe Pro Leu Ile Thr Ile Thr Val Arg
1               5                   10

<210> SEQ ID NO 1413
<211> LENGTH: 22
<212> TYPE: PRT
<213> ORGANISM: Homo sapiens

<400> SEQUENCE: 1413

Gly Ser Asp Gly Ala Pro Asp Thr Gly Tyr Leu Trp His Val Pro Leu
1               5                   10                  15

Thr Phe Ile Thr Ser Lys
                20

<210> SEQ ID NO 1414
<211> LENGTH: 14
<212> TYPE: PRT
<213> ORGANISM: Homo sapiens

<400> SEQUENCE: 1414

Thr Asp Val Leu Ile Leu Pro Glu Glu Val Glu Trp Ile Lys
1               5                   10
```

<210> SEQ ID NO 1415
<211> LENGTH: 11
<212> TYPE: PRT
<213> ORGANISM: Homo sapiens

<400> SEQUENCE: 1415

Gly Thr His Thr Ala Val Ser Ser Asn Asp Arg
1               5                   10

<210> SEQ ID NO 1416
<211> LENGTH: 15
<212> TYPE: PRT
<213> ORGANISM: Homo sapiens

<400> SEQUENCE: 1416

Ala Ser Leu Ile Asn Asn Ala Phe Gln Leu Val Ser Ile Gly Lys
1               5                   10                  15

<210> SEQ ID NO 1417
<211> LENGTH: 9
<212> TYPE: PRT
<213> ORGANISM: Homo sapiens

<400> SEQUENCE: 1417

Ala Leu Asp Leu Ser Leu Tyr Leu Lys
1               5

<210> SEQ ID NO 1418
<211> LENGTH: 12
<212> TYPE: PRT
<213> ORGANISM: Homo sapiens

<400> SEQUENCE: 1418

Gln Thr Trp Thr Asp Glu Gly Ser Val Ser Glu Arg
1               5                   10

<210> SEQ ID NO 1419
<211> LENGTH: 10
<212> TYPE: PRT
<213> ORGANISM: Homo sapiens

<400> SEQUENCE: 1419

Tyr Gln Phe Ser Leu Ser Ser Thr Glu Lys
1               5                   10

<210> SEQ ID NO 1420
<211> LENGTH: 10
<212> TYPE: PRT
<213> ORGANISM: Homo sapiens

<400> SEQUENCE: 1420

Leu Gln Trp Leu Leu Asp Glu Ser Phe Lys
1               5                   10

<210> SEQ ID NO 1421
<211> LENGTH: 13
<212> TYPE: PRT
<213> ORGANISM: Homo sapiens

<400> SEQUENCE: 1421

Thr Gln Glu Phe Pro Gln Ile Leu Thr Leu Ile Gly Arg
1               5                   10

<210> SEQ ID NO 1422

```
<211> LENGTH: 13
<212> TYPE: PRT
<213> ORGANISM: Homo sapiens

<400> SEQUENCE: 1422

Asn Pro Val Gly Tyr Pro Leu Ala Trp Gln Phe Leu Arg
1               5                   10

<210> SEQ ID NO 1423
<211> LENGTH: 7
<212> TYPE: PRT
<213> ORGANISM: Homo sapiens

<400> SEQUENCE: 1423

Gly Phe Phe Ser Ser Leu Lys
1               5

<210> SEQ ID NO 1424
<211> LENGTH: 7
<212> TYPE: PRT
<213> ORGANISM: Homo sapiens

<400> SEQUENCE: 1424

Glu Asn Gly Ser Gln Leu Arg
1               5

<210> SEQ ID NO 1425
<211> LENGTH: 7
<212> TYPE: PRT
<213> ORGANISM: Homo sapiens

<400> SEQUENCE: 1425

Val Trp Leu Gln Ser Glu Lys
1               5

<210> SEQ ID NO 1426
<211> LENGTH: 24
<212> TYPE: PRT
<213> ORGANISM: Homo sapiens

<400> SEQUENCE: 1426

Gly Ser Val Leu Leu Ala Gln Glu Leu Pro Gln Gln Leu Thr Ser Pro
1               5                   10                  15

Gly Tyr Pro Glu Pro Tyr Gly Lys
            20

<210> SEQ ID NO 1427
<211> LENGTH: 9
<212> TYPE: PRT
<213> ORGANISM: Homo sapiens

<400> SEQUENCE: 1427

Gly Gln Glu Ser Ser Thr Asp Ile Lys
1               5

<210> SEQ ID NO 1428
<211> LENGTH: 8
<212> TYPE: PRT
<213> ORGANISM: Homo sapiens

<400> SEQUENCE: 1428

Ala Pro Glu Gly Phe Ala Val Arg
1               5
```

```
<210> SEQ ID NO 1429
<211> LENGTH: 7
<212> TYPE: PRT
<213> ORGANISM: Homo sapiens

<400> SEQUENCE: 1429

Glu Phe Val Ser Ser Gly Arg
1               5

<210> SEQ ID NO 1430
<211> LENGTH: 8
<212> TYPE: PRT
<213> ORGANISM: Homo sapiens

<400> SEQUENCE: 1430

Thr Gln Pro Ser Ser Glu Asn Lys
1               5

<210> SEQ ID NO 1431
<211> LENGTH: 6
<212> TYPE: PRT
<213> ORGANISM: Homo sapiens

<400> SEQUENCE: 1431

Thr Ala His Leu His Lys
1               5

<210> SEQ ID NO 1432
<211> LENGTH: 22
<212> TYPE: PRT
<213> ORGANISM: Homo sapiens

<400> SEQUENCE: 1432

Gly Phe Leu Ala Leu Tyr Gln Thr Val Ala Val Asn Tyr Ser Gln Pro
1               5                   10                  15

Ile Ser Glu Ala Ser Arg
            20

<210> SEQ ID NO 1433
<211> LENGTH: 14
<212> TYPE: PRT
<213> ORGANISM: Homo sapiens

<400> SEQUENCE: 1433

Gly Ser Glu Ala Ile Asn Ala Pro Gly Asp Asn Pro Ala Lys
1               5                   10

<210> SEQ ID NO 1434
<211> LENGTH: 15
<212> TYPE: PRT
<213> ORGANISM: Homo sapiens

<400> SEQUENCE: 1434

Leu Gly Asn Phe Pro Trp Gln Ala Phe Thr Ser Ile His Gly Arg
1               5                   10                  15

<210> SEQ ID NO 1435
<211> LENGTH: 12
<212> TYPE: PRT
<213> ORGANISM: Homo sapiens

<400> SEQUENCE: 1435

Trp Ile Leu Thr Ala Ala His Thr Ile Tyr Pro Lys
1               5                   10
```

```
<210> SEQ ID NO 1436
<211> LENGTH: 8
<212> TYPE: PRT
<213> ORGANISM: Homo sapiens

<400> SEQUENCE: 1436

Leu Gly Asn His Pro Val His Arg
1               5

<210> SEQ ID NO 1437
<211> LENGTH: 8
<212> TYPE: PRT
<213> ORGANISM: Homo sapiens

<400> SEQUENCE: 1437

Val Val Val His Pro Asp Tyr Arg
1               5

<210> SEQ ID NO 1438
<211> LENGTH: 9
<212> TYPE: PRT
<213> ORGANISM: Homo sapiens

<400> SEQUENCE: 1438

Val Leu Ser Tyr Val Asp Trp Ile Lys
1               5

<210> SEQ ID NO 1439
<211> LENGTH: 13
<212> TYPE: PRT
<213> ORGANISM: Homo sapiens

<400> SEQUENCE: 1439

Thr Phe Ile Ile Asp Tyr Tyr Phe Glu Val Val Gln Lys
1               5                   10

<210> SEQ ID NO 1440

<400> SEQUENCE: 1440

000

<210> SEQ ID NO 1441
<211> LENGTH: 9
<212> TYPE: PRT
<213> ORGANISM: Homo sapiens

<400> SEQUENCE: 1441

Phe Gly Val Tyr Asp Ile Asp Asn Lys
1               5

<210> SEQ ID NO 1442
<211> LENGTH: 7
<212> TYPE: PRT
<213> ORGANISM: Homo sapiens

<400> SEQUENCE: 1442

Thr Gly Arg Pro Ala Gly Lys
1               5

<210> SEQ ID NO 1443
<211> LENGTH: 11
<212> TYPE: PRT
<213> ORGANISM: Homo sapiens
```

-continued

<400> SEQUENCE: 1443

Gly Ser Ile Thr Ile Ser Ala Glu Glu Ile Lys
1               5                   10

<210> SEQ ID NO 1444
<211> LENGTH: 9
<212> TYPE: PRT
<213> ORGANISM: Homo sapiens

<400> SEQUENCE: 1444

Ser Asp Pro Tyr Leu Glu Phe His Lys
1               5

<210> SEQ ID NO 1445
<211> LENGTH: 11
<212> TYPE: PRT
<213> ORGANISM: Homo sapiens

<400> SEQUENCE: 1445

Asn Asn Leu Asn Pro Val Trp Arg Pro Phe Lys
1               5                   10

<210> SEQ ID NO 1446
<211> LENGTH: 8
<212> TYPE: PRT
<213> ORGANISM: Homo sapiens

<400> SEQUENCE: 1446

Asn Ser Gly Val Ile Ser Val Lys
1               5

<210> SEQ ID NO 1447
<211> LENGTH: 16
<212> TYPE: PRT
<213> ORGANISM: Homo sapiens

<400> SEQUENCE: 1447

Leu Tyr Gly Pro Thr Asn Phe Ser Pro Ile Ile Asn His Val Ala Arg
1               5                   10                  15

<210> SEQ ID NO 1448
<211> LENGTH: 8
<212> TYPE: PRT
<213> ORGANISM: Homo sapiens

<400> SEQUENCE: 1448

Gln Ala Ile Val Asn Ala Ser Arg
1               5

<210> SEQ ID NO 1449
<211> LENGTH: 9
<212> TYPE: PRT
<213> ORGANISM: Homo sapiens

<400> SEQUENCE: 1449

Ser Pro Leu Gly Glu Val Ala Ile Arg
1               5

<210> SEQ ID NO 1450
<211> LENGTH: 7
<212> TYPE: PRT
<213> ORGANISM: Homo sapiens

<400> SEQUENCE: 1450

Gln Phe Gln Asn Ala Pro Lys
1               5

<210> SEQ ID NO 1451
<211> LENGTH: 11
<212> TYPE: PRT
<213> ORGANISM: Homo sapiens

<400> SEQUENCE: 1451

Asn Thr Ala Glu Trp Leu Leu Ser His Thr Lys
1               5                   10

<210> SEQ ID NO 1452
<211> LENGTH: 17
<212> TYPE: PRT
<213> ORGANISM: Homo sapiens

<400> SEQUENCE: 1452

Leu Thr Gln Ala Gln Ile Phe Asp Tyr Gly Glu Ile Pro Asn Phe Pro
1               5                   10                  15

Arg

<210> SEQ ID NO 1453
<211> LENGTH: 9
<212> TYPE: PRT
<213> ORGANISM: Homo sapiens

<400> SEQUENCE: 1453

Ser Thr Val Pro Gly His Ala Gly Arg
1               5

<210> SEQ ID NO 1454
<211> LENGTH: 9
<212> TYPE: PRT
<213> ORGANISM: Homo sapiens

<400> SEQUENCE: 1454

Leu Val Phe Gly Phe Leu Asn Gly Arg
1               5

<210> SEQ ID NO 1455
<211> LENGTH: 22
<212> TYPE: PRT
<213> ORGANISM: Homo sapiens

<400> SEQUENCE: 1455

Val Phe His Leu Leu Gly Val Asp Thr Leu Val Val Thr Asn Ala Ala
1               5                   10                  15

Gly Gly Leu Asn Pro Lys
            20

<210> SEQ ID NO 1456
<211> LENGTH: 15
<212> TYPE: PRT
<213> ORGANISM: Homo sapiens

<400> SEQUENCE: 1456

Asp His Ile Asn Leu Pro Gly Phe Ser Gly Gln Asn Pro Leu Arg
1               5                   10                  15

<210> SEQ ID NO 1457
<211> LENGTH: 6
<212> TYPE: PRT
<213> ORGANISM: Homo sapiens

```
<400> SEQUENCE: 1457

Gly Pro Asn Asp Glu Arg
1               5

<210> SEQ ID NO 1458
<211> LENGTH: 6
<212> TYPE: PRT
<213> ORGANISM: Homo sapiens

<400> SEQUENCE: 1458

Ala Leu Ser Thr Trp Lys
1               5

<210> SEQ ID NO 1459
<211> LENGTH: 10
<212> TYPE: PRT
<213> ORGANISM: Homo sapiens

<400> SEQUENCE: 1459

Val Phe Gly Phe Ser Leu Ile Thr Asn Lys
1               5                   10

<210> SEQ ID NO 1460
<211> LENGTH: 11
<212> TYPE: PRT
<213> ORGANISM: Homo sapiens

<400> SEQUENCE: 1460

Ala Asn His Glu Glu Val Leu Ala Ala Gly Lys
1               5                   10

<210> SEQ ID NO 1461
<211> LENGTH: 6
<212> TYPE: PRT
<213> ORGANISM: Homo sapiens

<400> SEQUENCE: 1461

Ile Leu Asn Arg Pro Lys
1               5

<210> SEQ ID NO 1462
<211> LENGTH: 11
<212> TYPE: PRT
<213> ORGANISM: Homo sapiens

<400> SEQUENCE: 1462

Leu Glu Glu Phe Val Gln Gly Asn Leu Glu Arg
1               5                   10

<210> SEQ ID NO 1463
<211> LENGTH: 8
<212> TYPE: PRT
<213> ORGANISM: Homo sapiens

<400> SEQUENCE: 1463

Glu Val Phe Glu Asn Thr Glu Arg
1               5

<210> SEQ ID NO 1464
<211> LENGTH: 6
<212> TYPE: PRT
<213> ORGANISM: Homo sapiens

<400> SEQUENCE: 1464
```

```
Thr Thr Glu Phe Trp Lys
1               5

<210> SEQ ID NO 1465
<211> LENGTH: 6
<212> TYPE: PRT
<213> ORGANISM: Homo sapiens

<400> SEQUENCE: 1465

Asn Ser Ala Asp Asn Lys
1               5

<210> SEQ ID NO 1466
<211> LENGTH: 6
<212> TYPE: PRT
<213> ORGANISM: Homo sapiens

<400> SEQUENCE: 1466

Leu Ala Glu Asn Gln Lys
1               5

<210> SEQ ID NO 1467
<211> LENGTH: 8
<212> TYPE: PRT
<213> ORGANISM: Homo sapiens

<400> SEQUENCE: 1467

Val Ser Val Ser Gln Thr Ser Lys
1               5

<210> SEQ ID NO 1468
<211> LENGTH: 21
<212> TYPE: PRT
<213> ORGANISM: Homo sapiens

<400> SEQUENCE: 1468

Val Val Gly Gly Glu Asp Ala Lys Pro Gly Gln Phe Pro Trp Gln Val
1               5                   10                  15

Val Leu Asn Gly Lys
            20

<210> SEQ ID NO 1469
<211> LENGTH: 19
<212> TYPE: PRT
<213> ORGANISM: Homo sapiens

<400> SEQUENCE: 1469

Ile Thr Val Val Ala Gly Glu His Asn Ile Glu Glu Thr Glu His Thr
1               5                   10                  15

Glu Gln Lys

<210> SEQ ID NO 1470
<211> LENGTH: 13
<212> TYPE: PRT
<213> ORGANISM: Homo sapiens

<400> SEQUENCE: 1470

Ile Ile Pro His His Asn Tyr Asn Ala Ala Ile Asn Lys
1               5                   10

<210> SEQ ID NO 1471
<211> LENGTH: 8
<212> TYPE: PRT
```

-continued

```
<213> ORGANISM: Homo sapiens

<400> SEQUENCE: 1471

Glu Tyr Thr Asn Ile Phe Leu Lys
1               5

<210> SEQ ID NO 1472
<211> LENGTH: 11
<212> TYPE: PRT
<213> ORGANISM: Homo sapiens

<400> SEQUENCE: 1472

Phe Gly Ser Gly Tyr Val Ser Gly Trp Gly Arg
1               5                   10

<210> SEQ ID NO 1473
<211> LENGTH: 9
<212> TYPE: PRT
<213> ORGANISM: Homo sapiens

<400> SEQUENCE: 1473

Ser Ala Leu Val Leu Gln Tyr Leu Arg
1               5

<210> SEQ ID NO 1474
<211> LENGTH: 6
<212> TYPE: PRT
<213> ORGANISM: Homo sapiens

<400> SEQUENCE: 1474

Val Pro Leu Val Asp Arg
1               5

<210> SEQ ID NO 1475
<211> LENGTH: 11
<212> TYPE: PRT
<213> ORGANISM: Homo sapiens

<400> SEQUENCE: 1475

Ala Leu Asp Phe Ala Val Gly Glu Tyr Asn Lys
1               5                   10

<210> SEQ ID NO 1476
<211> LENGTH: 16
<212> TYPE: PRT
<213> ORGANISM: Homo sapiens

<400> SEQUENCE: 1476

Gln Ile Val Ala Gly Val Asn Tyr Phe Leu Asp Val Glu Leu Gly Arg
1               5                   10                  15

<210> SEQ ID NO 1477
<211> LENGTH: 17
<212> TYPE: PRT
<213> ORGANISM: Homo sapiens

<400> SEQUENCE: 1477

Val Pro Ala Gln Leu Leu Gly Leu Leu Leu Leu Trp Leu Ser Gly Ala
1               5                   10                  15

Arg

<210> SEQ ID NO 1478
<211> LENGTH: 16
<212> TYPE: PRT
```

```
<213> ORGANISM: Homo sapiens

<400> SEQUENCE: 1478

Leu Leu Ile Tyr Asp Ala Ser Asn Leu Glu Thr Gly Val Pro Ser Arg
1               5                   10                  15

<210> SEQ ID NO 1479
<211> LENGTH: 22
<212> TYPE: PRT
<213> ORGANISM: Homo sapiens

<400> SEQUENCE: 1479

Gly Leu Glu Trp Val Ser Ala Ile Ser Gly Ser Gly Gly Ser Thr Tyr
1               5                   10                  15

Tyr Ala Asp Ser Val Lys
            20

<210> SEQ ID NO 1480
<211> LENGTH: 6
<212> TYPE: PRT
<213> ORGANISM: Homo sapiens

<400> SEQUENCE: 1480

Ala His Gln Val Leu Arg
1               5

<210> SEQ ID NO 1481
<211> LENGTH: 9
<212> TYPE: PRT
<213> ORGANISM: Homo sapiens

<400> SEQUENCE: 1481

Ala Asn Ser Phe Leu Glu Glu Leu Arg
1               5

<210> SEQ ID NO 1482
<211> LENGTH: 15
<212> TYPE: PRT
<213> ORGANISM: Homo sapiens

<400> SEQUENCE: 1482

Glu Ile Phe Gln Asn Val Asp Thr Leu Ala Phe Trp Ser Lys
1               5                   10                  15

<210> SEQ ID NO 1483
<211> LENGTH: 6
<212> TYPE: PRT
<213> ORGANISM: Homo sapiens

<400> SEQUENCE: 1483

Ser Gly Trp Glu Gly Arg
1               5

<210> SEQ ID NO 1484
<211> LENGTH: 12
<212> TYPE: PRT
<213> ORGANISM: Homo sapiens

<400> SEQUENCE: 1484

Asp Thr Glu Asp Gln Glu Asp Gln Val Asp Pro Arg
1               5                   10

<210> SEQ ID NO 1485
<211> LENGTH: 13
```

```
<212> TYPE: PRT
<213> ORGANISM: Homo sapiens

<400> SEQUENCE: 1485

Gly Asp Ser Pro Trp Gln Val Val Leu Leu Asp Ser Lys
1               5                   10

<210> SEQ ID NO 1486
<211> LENGTH: 7
<212> TYPE: PRT
<213> ORGANISM: Homo sapiens

<400> SEQUENCE: 1486

Leu Gly Glu Tyr Asp Leu Arg
1               5

<210> SEQ ID NO 1487
<211> LENGTH: 8
<212> TYPE: PRT
<213> ORGANISM: Homo sapiens

<400> SEQUENCE: 1487

Trp Glu Leu Asp Leu Asp Ile Lys
1               5

<210> SEQ ID NO 1488
<211> LENGTH: 10
<212> TYPE: PRT
<213> ORGANISM: Homo sapiens

<400> SEQUENCE: 1488

Glu Val Phe Val His Pro Asn Tyr Ser Lys
1               5                   10

<210> SEQ ID NO 1489
<211> LENGTH: 20
<212> TYPE: PRT
<213> ORGANISM: Homo sapiens

<400> SEQUENCE: 1489

Glu Leu Asn Gln Ala Gly Gln Glu Thr Leu Val Thr Gly Trp Gly Tyr
1               5                   10                  15

His Ser Ser Arg
            20

<210> SEQ ID NO 1490
<211> LENGTH: 8
<212> TYPE: PRT
<213> ORGANISM: Homo sapiens

<400> SEQUENCE: 1490

Thr Phe Val Leu Asn Phe Ile Lys
1               5

<210> SEQ ID NO 1491
<211> LENGTH: 10
<212> TYPE: PRT
<213> ORGANISM: Homo sapiens

<400> SEQUENCE: 1491

Tyr Leu Asp Trp Ile His Gly His Ile Arg
1               5                   10

<210> SEQ ID NO 1492
```

<211> LENGTH: 13
<212> TYPE: PRT
<213> ORGANISM: Homo sapiens

<400> SEQUENCE: 1492

Thr Ile Pro Ile Asp Gly Asp Phe Phe Ser Tyr Thr Arg
1               5                   10

<210> SEQ ID NO 1493
<211> LENGTH: 17
<212> TYPE: PRT
<213> ORGANISM: Homo sapiens

<400> SEQUENCE: 1493

Val Ala Glu Gln Thr Pro Leu Thr Ala Leu Tyr Val Ala Asn Leu Ile
1               5                   10                  15

Lys

<210> SEQ ID NO 1494
<211> LENGTH: 11
<212> TYPE: PRT
<213> ORGANISM: Homo sapiens

<400> SEQUENCE: 1494

Val Ala Phe Thr Gly Ser Thr Glu Ile Gly Arg
1               5                   10

<210> SEQ ID NO 1495
<211> LENGTH: 12
<212> TYPE: PRT
<213> ORGANISM: Homo sapiens

<400> SEQUENCE: 1495

Val Ile Gln Val Ala Ala Gly Ser Ser Asn Leu Lys
1               5                   10

<210> SEQ ID NO 1496
<211> LENGTH: 14
<212> TYPE: PRT
<213> ORGANISM: Homo sapiens

<400> SEQUENCE: 1496

Thr Phe Val Gln Glu Asp Ile Tyr Asp Glu Phe Val Glu Arg
1               5                   10

<210> SEQ ID NO 1497
<211> LENGTH: 9
<212> TYPE: PRT
<213> ORGANISM: Homo sapiens

<400> SEQUENCE: 1497

Val Val Gly Asn Pro Phe Asp Ser Lys
1               5

<210> SEQ ID NO 1498
<211> LENGTH: 13
<212> TYPE: PRT
<213> ORGANISM: Homo sapiens

<400> SEQUENCE: 1498

Thr Glu Gln Gly Pro Gln Val Asp Glu Thr Gln Phe Lys
1               5                   10

<210> SEQ ID NO 1499

```
<211> LENGTH: 9
<212> TYPE: PRT
<213> ORGANISM: Homo sapiens

<400> SEQUENCE: 1499

Ile Leu Gly Tyr Ile Asn Thr Gly Lys
1               5

<210> SEQ ID NO 1500
<211> LENGTH: 8
<212> TYPE: PRT
<213> ORGANISM: Homo sapiens

<400> SEQUENCE: 1500

Thr Ile Glu Glu Val Val Gly Arg
1               5

<210> SEQ ID NO 1501
<211> LENGTH: 15
<212> TYPE: PRT
<213> ORGANISM: Homo sapiens

<400> SEQUENCE: 1501

Ala Asn Asn Ser Thr Tyr Gly Leu Ala Ala Ala Val Phe Thr Lys
1               5                   10                  15

<210> SEQ ID NO 1502
<211> LENGTH: 14
<212> TYPE: PRT
<213> ORGANISM: Homo sapiens

<400> SEQUENCE: 1502

Glu Leu Gly Glu Tyr Gly Leu Gln Ala Tyr Thr Glu Val Lys
1               5                   10

<210> SEQ ID NO 1503
<211> LENGTH: 10
<212> TYPE: PRT
<213> ORGANISM: Homo sapiens

<400> SEQUENCE: 1503

Ala Ala Phe Gln Leu Gly Ser Pro Trp Arg
1               5                   10

<210> SEQ ID NO 1504
<211> LENGTH: 10
<212> TYPE: PRT
<213> ORGANISM: Homo sapiens

<400> SEQUENCE: 1504

Leu Leu Gly Ile Glu Thr Pro Leu Pro Lys
1               5                   10

<210> SEQ ID NO 1505
<211> LENGTH: 9
<212> TYPE: PRT
<213> ORGANISM: Homo sapiens

<400> SEQUENCE: 1505

Glu Leu Leu Leu Pro Gly Asn Asn Arg
1               5

<210> SEQ ID NO 1506
<211> LENGTH: 11
<212> TYPE: PRT
```

```
<213> ORGANISM: Homo sapiens

<400> SEQUENCE: 1506

Thr Phe Leu Thr Val Tyr Trp Thr Pro Glu Arg
1               5                   10

<210> SEQ ID NO 1507
<211> LENGTH: 14
<212> TYPE: PRT
<213> ORGANISM: Homo sapiens

<400> SEQUENCE: 1507

Val Glu Leu Ala Pro Leu Pro Ser Trp Gln Pro Val Gly Lys
1               5                   10

<210> SEQ ID NO 1508
<211> LENGTH: 9
<212> TYPE: PRT
<213> ORGANISM: Homo sapiens

<400> SEQUENCE: 1508

Ala Asn Leu Thr Val Val Leu Leu Arg
1               5

<210> SEQ ID NO 1509
<211> LENGTH: 17
<212> TYPE: PRT
<213> ORGANISM: Homo sapiens

<400> SEQUENCE: 1509

Glu Pro Ala Val Gly Glu Pro Ala Glu Val Thr Thr Thr Val Leu Val
1               5                   10                  15

Arg

<210> SEQ ID NO 1510
<211> LENGTH: 15
<212> TYPE: PRT
<213> ORGANISM: Homo sapiens

<400> SEQUENCE: 1510

Leu Asn Pro Thr Val Thr Tyr Gly Asn Asp Ser Phe Ser Ala Lys
1               5                   10                  15

<210> SEQ ID NO 1511
<211> LENGTH: 14
<212> TYPE: PRT
<213> ORGANISM: Homo sapiens

<400> SEQUENCE: 1511

Ala Ser Val Ser Val Thr Ala Glu Asp Glu Gly Thr Gln Arg
1               5                   10

<210> SEQ ID NO 1512
<211> LENGTH: 14
<212> TYPE: PRT
<213> ORGANISM: Homo sapiens

<400> SEQUENCE: 1512

Val Thr Leu Asn Gly Val Pro Ala Gln Pro Leu Gly Pro Arg
1               5                   10

<210> SEQ ID NO 1513
<211> LENGTH: 6
<212> TYPE: PRT
```

```
<213> ORGANISM: Homo sapiens

<400> SEQUENCE: 1513

Ala Gln Leu Leu Leu Lys
1               5

<210> SEQ ID NO 1514
<211> LENGTH: 8
<212> TYPE: PRT
<213> ORGANISM: Homo sapiens

<400> SEQUENCE: 1514

Ala Thr Pro Glu Asp Asn Gly Arg
1               5

<210> SEQ ID NO 1515
<211> LENGTH: 6
<212> TYPE: PRT
<213> ORGANISM: Homo sapiens

<400> SEQUENCE: 1515

Val Leu Tyr Gly Pro Arg
1               5

<210> SEQ ID NO 1516
<211> LENGTH: 16
<212> TYPE: PRT
<213> ORGANISM: Homo sapiens

<400> SEQUENCE: 1516

Asp Gly Thr Phe Pro Leu Pro Ile Gly Glu Ser Val Thr Val Thr Arg
1               5                   10                  15

<210> SEQ ID NO 1517
<211> LENGTH: 8
<212> TYPE: PRT
<213> ORGANISM: Homo sapiens

<400> SEQUENCE: 1517

Ser Thr Gln Gly Glu Val Thr Arg
1               5

<210> SEQ ID NO 1518
<211> LENGTH: 9
<212> TYPE: PRT
<213> ORGANISM: Homo sapiens

<400> SEQUENCE: 1518

Val Thr Val Asn Val Leu Ser Pro Arg
1               5

<210> SEQ ID NO 1519
<211> LENGTH: 6
<212> TYPE: PRT
<213> ORGANISM: Homo sapiens

<400> SEQUENCE: 1519

Val Val Val Ile Thr Lys
1               5

<210> SEQ ID NO 1520
<211> LENGTH: 15
<212> TYPE: PRT
<213> ORGANISM: Homo sapiens
```

```
<400> SEQUENCE: 1520

Asn Pro Asp Asp Ile Thr Gln Glu Glu Tyr Gly Glu Phe Tyr Lys
1               5                   10                  15

<210> SEQ ID NO 1521
<211> LENGTH: 7
<212> TYPE: PRT
<213> ORGANISM: Homo sapiens

<400> SEQUENCE: 1521

Ala Leu Leu Phe Ile Pro Arg
1               5

<210> SEQ ID NO 1522
<211> LENGTH: 7
<212> TYPE: PRT
<213> ORGANISM: Homo sapiens

<400> SEQUENCE: 1522

Phe Tyr Glu Ala Phe Ser Lys
1               5

<210> SEQ ID NO 1523
<211> LENGTH: 10
<212> TYPE: PRT
<213> ORGANISM: Homo sapiens

<400> SEQUENCE: 1523

Leu Gly Ile His Glu Asp Ser Thr Asn Arg
1               5                   10

<210> SEQ ID NO 1524
<211> LENGTH: 15
<212> TYPE: PRT
<213> ORGANISM: Homo sapiens

<400> SEQUENCE: 1524

His Leu Glu Ile Asn Pro Asp His Pro Ile Val Glu Thr Leu Arg
1               5                   10                  15

<210> SEQ ID NO 1525
<211> LENGTH: 12
<212> TYPE: PRT
<213> ORGANISM: Homo sapiens

<400> SEQUENCE: 1525

Gly Thr Val Thr Asp Phe Pro Gly Phe Asp Glu Arg
1               5                   10

<210> SEQ ID NO 1526
<211> LENGTH: 7
<212> TYPE: PRT
<213> ORGANISM: Homo sapiens

<400> SEQUENCE: 1526

Ala Asp Ala Glu Thr Leu Arg
1               5

<210> SEQ ID NO 1527
<211> LENGTH: 16
<212> TYPE: PRT
<213> ORGANISM: Homo sapiens

<400> SEQUENCE: 1527
```

```
Gly Leu Gly Thr Asp Glu Glu Ser Ile Leu Thr Leu Leu Thr Ser Arg
1               5                   10                  15
```

<210> SEQ ID NO 1528
<211> LENGTH: 8
<212> TYPE: PRT
<213> ORGANISM: Homo sapiens

<400> SEQUENCE: 1528

```
Gln Glu Ile Ser Ala Ala Phe Lys
1               5
```

<210> SEQ ID NO 1529
<211> LENGTH: 7
<212> TYPE: PRT
<213> ORGANISM: Homo sapiens

<400> SEQUENCE: 1529

```
Asp Leu Leu Asp Asp Leu Lys
1               5
```

<210> SEQ ID NO 1530
<211> LENGTH: 6
<212> TYPE: PRT
<213> ORGANISM: Homo sapiens

<400> SEQUENCE: 1530

```
Ser Glu Leu Thr Gly Lys
1               5
```

<210> SEQ ID NO 1531
<211> LENGTH: 8
<212> TYPE: PRT
<213> ORGANISM: Homo sapiens

<400> SEQUENCE: 1531

```
Leu Tyr Asp Ala Tyr Glu Leu Lys
1               5
```

<210> SEQ ID NO 1532
<211> LENGTH: 7
<212> TYPE: PRT
<213> ORGANISM: Homo sapiens

<400> SEQUENCE: 1532

```
Gly Ala Gly Thr Asn Glu Lys
1               5
```

<210> SEQ ID NO 1533
<211> LENGTH: 9
<212> TYPE: PRT
<213> ORGANISM: Homo sapiens

<400> SEQUENCE: 1533

```
Val Leu Thr Glu Ile Ile Ala Ser Arg
1               5
```

<210> SEQ ID NO 1534
<211> LENGTH: 25
<212> TYPE: PRT
<213> ORGANISM: Homo sapiens

<400> SEQUENCE: 1534

```
Gln Val Tyr Glu Glu Tyr Gly Ser Ser Leu Glu Asp Asp Val Val
1               5                   10                  15
```

Gly Asp Thr Ser Gly Tyr Tyr Gln Arg
            20                  25

<210> SEQ ID NO 1535
<211> LENGTH: 25
<212> TYPE: PRT
<213> ORGANISM: Homo sapiens

<400> SEQUENCE: 1535

Asp Pro Asp Ala Gly Ile Asp Glu Ala Gln Val Glu Gln Asp Ala Gln
1               5                   10                  15

Ala Leu Phe Gln Ala Gly Glu Leu Lys
            20                  25

<210> SEQ ID NO 1536
<211> LENGTH: 7
<212> TYPE: PRT
<213> ORGANISM: Homo sapiens

<400> SEQUENCE: 1536

Trp Gly Thr Asp Glu Glu Lys
1               5

<210> SEQ ID NO 1537
<211> LENGTH: 8
<212> TYPE: PRT
<213> ORGANISM: Homo sapiens

<400> SEQUENCE: 1537

Phe Ile Thr Ile Phe Gly Thr Arg
1               5

<210> SEQ ID NO 1538
<211> LENGTH: 15
<212> TYPE: PRT
<213> ORGANISM: Homo sapiens

<400> SEQUENCE: 1538

Glu Thr Ser Gly Asn Leu Glu Gln Leu Leu Leu Ala Val Val Lys
1               5                   10                  15

<210> SEQ ID NO 1539
<211> LENGTH: 11
<212> TYPE: PRT
<213> ORGANISM: Homo sapiens

<400> SEQUENCE: 1539

Gly Ala Gly Thr Asp Asp His Thr Leu Ile Arg
1               5                   10

<210> SEQ ID NO 1540
<211> LENGTH: 9
<212> TYPE: PRT
<213> ORGANISM: Homo sapiens

<400> SEQUENCE: 1540

Ser Glu Ile Asp Leu Phe Asn Ile Arg
1               5

<210> SEQ ID NO 1541
<211> LENGTH: 8
<212> TYPE: PRT
<213> ORGANISM: Homo sapiens

```
<400> SEQUENCE: 1541

Gly Asp Thr Ser Gly Asp Tyr Lys
1               5

<210> SEQ ID NO 1542
<211> LENGTH: 24
<212> TYPE: PRT
<213> ORGANISM: Homo sapiens

<400> SEQUENCE: 1542

Gln Ser Gly Val Asn Ala Thr Leu Pro Glu Glu Asn Gln Pro Val Val
1               5                   10                  15

Phe Asn His Val Tyr Asn Ile Lys
            20

<210> SEQ ID NO 1543
<211> LENGTH: 12
<212> TYPE: PRT
<213> ORGANISM: Homo sapiens

<400> SEQUENCE: 1543

Leu Glu Glu Leu Glu Asn Leu Val Ser Ser Leu Arg
1               5                   10

<210> SEQ ID NO 1544
<211> LENGTH: 22
<212> TYPE: PRT
<213> ORGANISM: Homo sapiens

<400> SEQUENCE: 1544

Val Pro Gly Asp Gln Thr Ser Thr Ile Ile Gln Glu Leu Glu Pro Gly
1               5                   10                  15

Val Glu Tyr Phe Ile Arg
            20

<210> SEQ ID NO 1545
<211> LENGTH: 8
<212> TYPE: PRT
<213> ORGANISM: Homo sapiens

<400> SEQUENCE: 1545

Val Phe Ala Ile Leu Glu Asn Lys
1               5

<210> SEQ ID NO 1546
<211> LENGTH: 7
<212> TYPE: PRT
<213> ORGANISM: Homo sapiens

<400> SEQUENCE: 1546

Ser Ile Pro Val Ser Ala Arg
1               5

<210> SEQ ID NO 1547
<211> LENGTH: 12
<212> TYPE: PRT
<213> ORGANISM: Homo sapiens

<400> SEQUENCE: 1547

Val Ala Thr Tyr Leu Pro Ala Pro Glu Gly Leu Lys
1               5                   10

<210> SEQ ID NO 1548
```

```
<211> LENGTH: 23
<212> TYPE: PRT
<213> ORGANISM: Homo sapiens

<400> SEQUENCE: 1548

Glu Thr Ser Val Glu Val Glu Trp Asp Pro Leu Asp Ile Ala Phe Glu
1               5                   10                  15

Thr Trp Glu Ile Ile Phe Arg
            20

<210> SEQ ID NO 1549
<211> LENGTH: 8
<212> TYPE: PRT
<213> ORGANISM: Homo sapiens

<400> SEQUENCE: 1549

Glu Asp Glu Gly Glu Ile Thr Lys
1               5

<210> SEQ ID NO 1550
<211> LENGTH: 7
<212> TYPE: PRT
<213> ORGANISM: Homo sapiens

<400> SEQUENCE: 1550

Arg Pro Glu Thr Ser Tyr Arg
1               5

<210> SEQ ID NO 1551
<211> LENGTH: 18
<212> TYPE: PRT
<213> ORGANISM: Homo sapiens

<400> SEQUENCE: 1551

Gln Thr Gly Leu Ala Pro Gly Gln Glu Tyr Glu Ile Ser Leu His Ile
1               5                   10                  15

Val Lys

<210> SEQ ID NO 1552
<211> LENGTH: 10
<212> TYPE: PRT
<213> ORGANISM: Homo sapiens

<400> SEQUENCE: 1552

Leu Asp Ala Pro Ser Gln Ile Glu Val Lys
1               5                   10

<210> SEQ ID NO 1553
<211> LENGTH: 11
<212> TYPE: PRT
<213> ORGANISM: Homo sapiens

<400> SEQUENCE: 1553

Glu Thr Phe Thr Thr Gly Leu Asp Ala Pro Arg
1               5                   10

<210> SEQ ID NO 1554
<211> LENGTH: 13
<212> TYPE: PRT
<213> ORGANISM: Homo sapiens

<400> SEQUENCE: 1554

Val Ser Gln Thr Asp Asn Ser Ile Thr Leu Glu Trp Arg
1               5                   10
```

<210> SEQ ID NO 1555
<211> LENGTH: 7
<212> TYPE: PRT
<213> ORGANISM: Homo sapiens

<400> SEQUENCE: 1555

Ala Ala Ile Asp Ser Tyr Arg
1               5

<210> SEQ ID NO 1556
<211> LENGTH: 16
<212> TYPE: PRT
<213> ORGANISM: Homo sapiens

<400> SEQUENCE: 1556

Tyr Ala Pro Ile Ser Gly Gly Asp His Ala Glu Val Asp Val Pro Lys
1               5                   10                  15

<210> SEQ ID NO 1557
<211> LENGTH: 7
<212> TYPE: PRT
<213> ORGANISM: Homo sapiens

<400> SEQUENCE: 1557

Ser Gln Gln Ala Thr Thr Lys
1               5

<210> SEQ ID NO 1558
<211> LENGTH: 20
<212> TYPE: PRT
<213> ORGANISM: Homo sapiens

<400> SEQUENCE: 1558

Thr Thr Leu Thr Gly Leu Arg Pro Gly Thr Glu Tyr Gly Ile Gly Val
1               5                   10                  15

Ser Ala Val Lys
            20

<210> SEQ ID NO 1559
<211> LENGTH: 17
<212> TYPE: PRT
<213> ORGANISM: Homo sapiens

<400> SEQUENCE: 1559

Glu Ser Asn Pro Ala Thr Ile Asn Ala Ala Thr Glu Leu Asp Thr Pro
1               5                   10                  15

Lys

<210> SEQ ID NO 1560
<211> LENGTH: 17
<212> TYPE: PRT
<213> ORGANISM: Homo sapiens

<400> SEQUENCE: 1560

Asp Leu Gln Val Ser Glu Thr Ala Glu Thr Ser Leu Thr Leu Leu Trp
1               5                   10                  15

Lys

<210> SEQ ID NO 1561
<211> LENGTH: 17
<212> TYPE: PRT
<213> ORGANISM: Homo sapiens

```
<400> SEQUENCE: 1561

Leu Asn Tyr Ser Leu Pro Thr Gly Gln Trp Val Gly Val Gln Leu Pro
1               5                   10                  15

Arg

<210> SEQ ID NO 1562
<211> LENGTH: 8
<212> TYPE: PRT
<213> ORGANISM: Homo sapiens

<400> SEQUENCE: 1562

Asn Thr Thr Ser Tyr Val Leu Arg
1               5

<210> SEQ ID NO 1563
<211> LENGTH: 16
<212> TYPE: PRT
<213> ORGANISM: Homo sapiens

<400> SEQUENCE: 1563

Gly Leu Glu Pro Gly Gln Glu Tyr Asn Val Leu Leu Thr Ala Glu Lys
1               5                   10                  15

<210> SEQ ID NO 1564
<211> LENGTH: 23
<212> TYPE: PRT
<213> ORGANISM: Homo sapiens

<400> SEQUENCE: 1564

Ala Ser Thr Glu Gln Ala Pro Glu Leu Glu Asn Leu Thr Val Thr Glu
1               5                   10                  15

Val Gly Trp Asp Gly Leu Arg
            20

<210> SEQ ID NO 1565
<211> LENGTH: 22
<212> TYPE: PRT
<213> ORGANISM: Homo sapiens

<400> SEQUENCE: 1565

Leu Asn Trp Thr Ala Ala Asp Gln Ala Tyr Glu His Phe Ile Ile Gln
1               5                   10                  15

Val Gln Glu Ala Asn Lys
            20

<210> SEQ ID NO 1566
<211> LENGTH: 9
<212> TYPE: PRT
<213> ORGANISM: Homo sapiens

<400> SEQUENCE: 1566

Asn Leu Thr Val Pro Gly Ser Leu Arg
1               5

<210> SEQ ID NO 1567
<211> LENGTH: 8
<212> TYPE: PRT
<213> ORGANISM: Homo sapiens

<400> SEQUENCE: 1567

Ala Val Asp Ile Pro Gly Leu Lys
1               5
```

```
<210> SEQ ID NO 1568
<211> LENGTH: 17
<212> TYPE: PRT
<213> ORGANISM: Homo sapiens

<400> SEQUENCE: 1568

Ala Ala Thr Pro Tyr Thr Val Ser Ile Tyr Gly Val Ile Gln Gly Tyr
1               5                   10                  15

Arg

<210> SEQ ID NO 1569
<211> LENGTH: 8
<212> TYPE: PRT
<213> ORGANISM: Homo sapiens

<400> SEQUENCE: 1569

Ser Thr Asp Leu Pro Gly Leu Lys
1               5

<210> SEQ ID NO 1570
<211> LENGTH: 10
<212> TYPE: PRT
<213> ORGANISM: Homo sapiens

<400> SEQUENCE: 1570

Ala Ala Thr His Tyr Thr Ile Thr Ile Arg
1               5                   10

<210> SEQ ID NO 1571
<211> LENGTH: 14
<212> TYPE: PRT
<213> ORGANISM: Homo sapiens

<400> SEQUENCE: 1571

Ala Gly Thr Pro Tyr Thr Val Thr Leu His Gly Glu Val Arg
1               5                   10

<210> SEQ ID NO 1572
<211> LENGTH: 22
<212> TYPE: PRT
<213> ORGANISM: Homo sapiens

<400> SEQUENCE: 1572

Leu Asn Trp Thr Ala Ala Asp Asn Ala Tyr Glu His Phe Val Ile Gln
1               5                   10                  15

Val Gln Glu Val Asn Lys
            20

<210> SEQ ID NO 1573
<211> LENGTH: 14
<212> TYPE: PRT
<213> ORGANISM: Homo sapiens

<400> SEQUENCE: 1573

Val Glu Ala Ala Gln Asn Leu Thr Leu Pro Gly Ser Leu Arg
1               5                   10

<210> SEQ ID NO 1574
<211> LENGTH: 14
<212> TYPE: PRT
<213> ORGANISM: Homo sapiens

<400> SEQUENCE: 1574
```

Ala Val Asp Ile Pro Gly Leu Glu Ala Ala Thr Pro Tyr Arg
1               5                   10

<210> SEQ ID NO 1575
<211> LENGTH: 8
<212> TYPE: PRT
<213> ORGANISM: Homo sapiens

<400> SEQUENCE: 1575

Val Ser Ile Tyr Gly Val Ile Arg
1               5

<210> SEQ ID NO 1576
<211> LENGTH: 12
<212> TYPE: PRT
<213> ORGANISM: Homo sapiens

<400> SEQUENCE: 1576

Thr Pro Val Leu Ser Ala Glu Ala Ser Thr Ala Lys
1               5                   10

<210> SEQ ID NO 1577
<211> LENGTH: 14
<212> TYPE: PRT
<213> ORGANISM: Homo sapiens

<400> SEQUENCE: 1577

Leu Leu Glu Thr Val Glu Tyr Asn Ile Ser Gly Ala Glu Arg
1               5                   10

<210> SEQ ID NO 1578
<211> LENGTH: 25
<212> TYPE: PRT
<213> ORGANISM: Homo sapiens

<400> SEQUENCE: 1578

Thr Ala His Ile Ser Gly Leu Pro Pro Ser Thr Asp Phe Ile Val Tyr
1               5                   10                  15

Leu Ser Gly Leu Ala Pro Ser Ile Arg
            20                  25

<210> SEQ ID NO 1579
<211> LENGTH: 14
<212> TYPE: PRT
<213> ORGANISM: Homo sapiens

<400> SEQUENCE: 1579

Leu Leu Asp Pro Gln Glu Phe Thr Leu Ser Gly Thr Gln Arg
1               5                   10

<210> SEQ ID NO 1580
<211> LENGTH: 25
<212> TYPE: PRT
<213> ORGANISM: Homo sapiens

<400> SEQUENCE: 1580

Ala Glu Ile Val Thr Glu Ala Glu Pro Glu Val Asp Asn Leu Leu Val
1               5                   10                  15

Ser Asp Ala Thr Pro Asp Gly Phe Arg
            20                  25

<210> SEQ ID NO 1581
<211> LENGTH: 16

```
<212> TYPE: PRT
<213> ORGANISM: Homo sapiens

<400> SEQUENCE: 1581

Leu Ser Trp Thr Ala Asp Glu Gly Val Phe Asp Asn Phe Val Leu Lys
1               5                   10                  15

<210> SEQ ID NO 1582
<211> LENGTH: 14
<212> TYPE: PRT
<213> ORGANISM: Homo sapiens

<400> SEQUENCE: 1582

Gln Ser Glu Pro Leu Glu Ile Thr Leu Leu Ala Pro Glu Arg
1               5                   10

<210> SEQ ID NO 1583
<211> LENGTH: 14
<212> TYPE: PRT
<213> ORGANISM: Homo sapiens

<400> SEQUENCE: 1583

Glu Ala Thr Glu Tyr Glu Ile Glu Leu Tyr Gly Ile Ser Lys
1               5                   10

<210> SEQ ID NO 1584
<211> LENGTH: 17
<212> TYPE: PRT
<213> ORGANISM: Homo sapiens

<400> SEQUENCE: 1584

Glu Val Ile Phe Ser Asp Ile Thr Glu Asn Ser Ala Thr Val Ser Trp
1               5                   10                  15

Arg

<210> SEQ ID NO 1585
<211> LENGTH: 10
<212> TYPE: PRT
<213> ORGANISM: Homo sapiens

<400> SEQUENCE: 1585

Ala Pro Thr Ala Gln Val Glu Ser Phe Arg
1               5                   10

<210> SEQ ID NO 1586
<211> LENGTH: 19
<212> TYPE: PRT
<213> ORGANISM: Homo sapiens

<400> SEQUENCE: 1586

Trp Gln Pro Ala Ile Ala Thr Val Asp Ser Tyr Val Ile Ser Tyr Thr
1               5                   10                  15

Gly Glu Lys

<210> SEQ ID NO 1587
<211> LENGTH: 6
<212> TYPE: PRT
<213> ORGANISM: Homo sapiens

<400> SEQUENCE: 1587

Val Pro Glu Ile Thr Arg
1               5
```

```
<210> SEQ ID NO 1588
<211> LENGTH: 23
<212> TYPE: PRT
<213> ORGANISM: Homo sapiens

<400> SEQUENCE: 1588

Thr Val Ser Gly Asn Thr Val Glu Tyr Ala Leu Thr Asp Leu Glu Pro
1               5                   10                  15

Ala Thr Glu Tyr Thr Leu Arg
            20

<210> SEQ ID NO 1589
<211> LENGTH: 7
<212> TYPE: PRT
<213> ORGANISM: Homo sapiens

<400> SEQUENCE: 1589

Ser Ser Thr Ile Thr Ala Lys
1               5

<210> SEQ ID NO 1590
<211> LENGTH: 9
<212> TYPE: PRT
<213> ORGANISM: Homo sapiens

<400> SEQUENCE: 1590

Phe Thr Thr Asp Leu Asp Ser Pro Arg
1               5

<210> SEQ ID NO 1591
<211> LENGTH: 20
<212> TYPE: PRT
<213> ORGANISM: Homo sapiens

<400> SEQUENCE: 1591

Asp Leu Thr Ala Thr Glu Val Gln Ser Glu Thr Ala Leu Leu Thr Trp
1               5                   10                  15

Arg Pro Pro Arg
            20

<210> SEQ ID NO 1592
<211> LENGTH: 18
<212> TYPE: PRT
<213> ORGANISM: Homo sapiens

<400> SEQUENCE: 1592

Ala Ser Val Thr Gly Tyr Leu Leu Val Tyr Glu Ser Val Asp Gly Thr
1               5                   10                  15

Val Lys

<210> SEQ ID NO 1593
<211> LENGTH: 25
<212> TYPE: PRT
<213> ORGANISM: Homo sapiens

<400> SEQUENCE: 1593

Glu Val Ile Val Gly Pro Asp Thr Thr Ser Tyr Ser Leu Ala Asp Leu
1               5                   10                  15

Ser Pro Ser Thr His Tyr Thr Ala Lys
            20                  25

<210> SEQ ID NO 1594
<211> LENGTH: 9
```

```
<212> TYPE: PRT
<213> ORGANISM: Homo sapiens

<400> SEQUENCE: 1594

Ile Gln Ala Leu Asn Gly Pro Leu Arg
1               5

<210> SEQ ID NO 1595
<211> LENGTH: 8
<212> TYPE: PRT
<213> ORGANISM: Homo sapiens

<400> SEQUENCE: 1595

Glu Asn Phe Tyr Gln Asn Trp Lys
1               5

<210> SEQ ID NO 1596
<211> LENGTH: 9
<212> TYPE: PRT
<213> ORGANISM: Homo sapiens

<400> SEQUENCE: 1596

Ala Tyr Ala Ala Gly Phe Gly Asp Arg
1               5

<210> SEQ ID NO 1597
<211> LENGTH: 12
<212> TYPE: PRT
<213> ORGANISM: Homo sapiens

<400> SEQUENCE: 1597

Glu Glu Phe Trp Leu Gly Leu Asp Asn Leu Asn Lys
1               5                   10

<210> SEQ ID NO 1598
<211> LENGTH: 10
<212> TYPE: PRT
<213> ORGANISM: Homo sapiens

<400> SEQUENCE: 1598

Ile Thr Ala Gln Gly Gln Tyr Glu Leu Arg
1               5                   10

<210> SEQ ID NO 1599
<211> LENGTH: 12
<212> TYPE: PRT
<213> ORGANISM: Homo sapiens

<400> SEQUENCE: 1599

Asp His Gly Glu Thr Ala Phe Ala Val Tyr Asp Lys
1               5                   10

<210> SEQ ID NO 1600
<211> LENGTH: 7
<212> TYPE: PRT
<213> ORGANISM: Homo sapiens

<400> SEQUENCE: 1600

Phe Ser Val Gly Asp Ala Lys
1               5

<210> SEQ ID NO 1601
<211> LENGTH: 7
<212> TYPE: PRT
<213> ORGANISM: Homo sapiens
```

<400> SEQUENCE: 1601

Ser Phe Ser Thr Phe Asp Lys
1               5

<210> SEQ ID NO 1602
<211> LENGTH: 6
<212> TYPE: PRT
<213> ORGANISM: Homo sapiens

<400> SEQUENCE: 1602

Gly Ala Phe Trp Tyr Arg
1               5

<210> SEQ ID NO 1603
<211> LENGTH: 16
<212> TYPE: PRT
<213> ORGANISM: Homo sapiens

<400> SEQUENCE: 1603

Tyr Gly Asp Asn Asn His Ser Gln Gly Val Asn Trp Phe His Trp Lys
1               5                   10                  15

<210> SEQ ID NO 1604
<211> LENGTH: 9
<212> TYPE: PRT
<213> ORGANISM: Homo sapiens

<400> SEQUENCE: 1604

His Gly Ser Leu Gly Phe Leu Pro Arg
1               5

<210> SEQ ID NO 1605
<211> LENGTH: 16
<212> TYPE: PRT
<213> ORGANISM: Homo sapiens

<400> SEQUENCE: 1605

Asp Asp Pro Ser Lys Pro Val His Leu Thr Ala Phe Leu Gly Tyr Lys
1               5                   10                  15

<210> SEQ ID NO 1606
<211> LENGTH: 8
<212> TYPE: PRT
<213> ORGANISM: Homo sapiens

<400> SEQUENCE: 1606

Glu Val Asp Arg Pro Gly Ser Lys
1               5

<210> SEQ ID NO 1607
<211> LENGTH: 7
<212> TYPE: PRT
<213> ORGANISM: Homo sapiens

<400> SEQUENCE: 1607

Trp Gln Asp Glu Asp Gly Lys
1               5

<210> SEQ ID NO 1608
<211> LENGTH: 7
<212> TYPE: PRT
<213> ORGANISM: Homo sapiens

<400> SEQUENCE: 1608

Val Ala Phe Ser Val Ala Arg
1               5

<210> SEQ ID NO 1609
<211> LENGTH: 8
<212> TYPE: PRT
<213> ORGANISM: Homo sapiens

<400> SEQUENCE: 1609

Ile Gly Gln Gly Tyr Leu Ile Lys
1               5

<210> SEQ ID NO 1610
<211> LENGTH: 12
<212> TYPE: PRT
<213> ORGANISM: Homo sapiens

<400> SEQUENCE: 1610

Asn Asn Ala Ser Thr Asp Tyr Asp Leu Ser Asp Lys
1               5                   10

<210> SEQ ID NO 1611
<211> LENGTH: 7
<212> TYPE: PRT
<213> ORGANISM: Homo sapiens

<400> SEQUENCE: 1611

Ser Leu Leu Val Gln Thr Lys
1               5

<210> SEQ ID NO 1612
<211> LENGTH: 8
<212> TYPE: PRT
<213> ORGANISM: Homo sapiens

<400> SEQUENCE: 1612

Gln Gln Leu Glu Glu Leu Ala Arg
1               5

<210> SEQ ID NO 1613
<211> LENGTH: 9
<212> TYPE: PRT
<213> ORGANISM: Homo sapiens

<400> SEQUENCE: 1613

Ala Leu Ala Glu Gly Val Leu Leu Arg
1               5

<210> SEQ ID NO 1614
<211> LENGTH: 6
<212> TYPE: PRT
<213> ORGANISM: Homo sapiens

<400> SEQUENCE: 1614

Asn Ile Phe Asp Gln Arg
1               5

<210> SEQ ID NO 1615
<211> LENGTH: 9
<212> TYPE: PRT
<213> ORGANISM: Homo sapiens

<400> SEQUENCE: 1615

Ala Ile Glu Asn Glu Leu Leu Ala Arg

```
1               5

<210> SEQ ID NO 1616
<211> LENGTH: 6
<212> TYPE: PRT
<213> ORGANISM: Homo sapiens

<400> SEQUENCE: 1616

Asn Ile His Val Ile Arg
1               5

<210> SEQ ID NO 1617
<211> LENGTH: 8
<212> TYPE: PRT
<213> ORGANISM: Homo sapiens

<400> SEQUENCE: 1617

Thr Phe Glu Asp Ile Ser Glu Lys
1               5

<210> SEQ ID NO 1618
<211> LENGTH: 7
<212> TYPE: PRT
<213> ORGANISM: Homo sapiens

<400> SEQUENCE: 1618

Gly Ser Leu Asp Gln Asp Arg
1               5

<210> SEQ ID NO 1619
<211> LENGTH: 14
<212> TYPE: PRT
<213> ORGANISM: Homo sapiens

<400> SEQUENCE: 1619

Leu Phe Val Asp Gly Gln Glu Ile Ala Val Val Tyr Phe Arg
1               5                   10

<210> SEQ ID NO 1620
<211> LENGTH: 10
<212> TYPE: PRT
<213> ORGANISM: Homo sapiens

<400> SEQUENCE: 1620

Gln Tyr Ser Leu Gln Asn Trp Glu Ala Arg
1               5                   10

<210> SEQ ID NO 1621
<211> LENGTH: 7
<212> TYPE: PRT
<213> ORGANISM: Homo sapiens

<400> SEQUENCE: 1621

Phe Val Leu Lys Pro Gln Arg
1               5

<210> SEQ ID NO 1622
<211> LENGTH: 7
<212> TYPE: PRT
<213> ORGANISM: Homo sapiens

<400> SEQUENCE: 1622

His Val Gly His Leu Leu Arg
1               5
```

```
<210> SEQ ID NO 1623
<211> LENGTH: 22
<212> TYPE: PRT
<213> ORGANISM: Homo sapiens

<400> SEQUENCE: 1623

Ala Ile Glu His Ala Asp Gly Gly Val Ala Ala Gly Val Ala Val Leu
1               5                   10                  15

Asp Asn Pro Tyr Pro Val
            20

<210> SEQ ID NO 1624
<211> LENGTH: 7
<212> TYPE: PRT
<213> ORGANISM: Homo sapiens

<400> SEQUENCE: 1624

Gln Asp Asp Phe Thr Ala Arg
1               5

<210> SEQ ID NO 1625
<211> LENGTH: 13
<212> TYPE: PRT
<213> ORGANISM: Homo sapiens

<400> SEQUENCE: 1625

Glu Gly Ile Ala Gln Thr Val Phe Leu Gly Leu Asn Arg
1               5                   10

<210> SEQ ID NO 1626
<211> LENGTH: 9
<212> TYPE: PRT
<213> ORGANISM: Homo sapiens

<400> SEQUENCE: 1626

Ser Ala Asp Gly Ser Pro Ala Leu Lys
1               5

<210> SEQ ID NO 1627
<211> LENGTH: 17
<212> TYPE: PRT
<213> ORGANISM: Homo sapiens

<400> SEQUENCE: 1627

Gln Ile Glu Ile Asn Thr Ile Ser Ala Ser Phe Gly Gly Leu Ala Ser
1               5                   10                  15

Arg

<210> SEQ ID NO 1628
<211> LENGTH: 6
<212> TYPE: PRT
<213> ORGANISM: Homo sapiens

<400> SEQUENCE: 1628

Thr Pro Ala Val His Arg
1               5

<210> SEQ ID NO 1629
<211> LENGTH: 8
<212> TYPE: PRT
<213> ORGANISM: Homo sapiens

<400> SEQUENCE: 1629
```

His Val Leu Ser Val Leu Ser Lys
1               5

<210> SEQ ID NO 1630
<211> LENGTH: 8
<212> TYPE: PRT
<213> ORGANISM: Homo sapiens

<400> SEQUENCE: 1630

Ile Leu Ser Asn Asn Pro Ser Lys
1               5

<210> SEQ ID NO 1631
<211> LENGTH: 8
<212> TYPE: PRT
<213> ORGANISM: Homo sapiens

<400> SEQUENCE: 1631

Gly Leu Ala Leu Gly Ile Ala Lys
1               5

<210> SEQ ID NO 1632
<211> LENGTH: 19
<212> TYPE: PRT
<213> ORGANISM: Homo sapiens

<400> SEQUENCE: 1632

Ala Trp Glu Leu Tyr Gly Ser Pro Asn Ala Leu Val Leu Leu Ile Ala
1               5                   10                  15

Gln Glu Lys

<210> SEQ ID NO 1633
<211> LENGTH: 7
<212> TYPE: PRT
<213> ORGANISM: Homo sapiens

<400> SEQUENCE: 1633

Asp Gly His Ser Leu Gly Arg
1               5

<210> SEQ ID NO 1634
<211> LENGTH: 8
<212> TYPE: PRT
<213> ORGANISM: Homo sapiens

<400> SEQUENCE: 1634

Ala Ile Asp Gly Ile Asn Gln Arg
1               5

<210> SEQ ID NO 1635
<211> LENGTH: 8
<212> TYPE: PRT
<213> ORGANISM: Homo sapiens

<400> SEQUENCE: 1635

Ser Ser Asp Ala Asn Leu Tyr Arg
1               5

<210> SEQ ID NO 1636
<211> LENGTH: 9
<212> TYPE: PRT
<213> ORGANISM: Homo sapiens

<400> SEQUENCE: 1636

```
Phe Ala Leu Leu Gly Asp Phe Phe Arg
1               5

<210> SEQ ID NO 1637
<211> LENGTH: 7
<212> TYPE: PRT
<213> ORGANISM: Homo sapiens

<400> SEQUENCE: 1637

Ala Leu Leu Leu Trp Gly Arg
1               5

<210> SEQ ID NO 1638
<211> LENGTH: 8
<212> TYPE: PRT
<213> ORGANISM: Homo sapiens

<400> SEQUENCE: 1638

His Glu Phe Gln Ala Glu Thr Lys
1               5

<210> SEQ ID NO 1639
<211> LENGTH: 7
<212> TYPE: PRT
<213> ORGANISM: Homo sapiens

<400> SEQUENCE: 1639

Leu Leu Asp Ile Val Ala Arg
1               5

<210> SEQ ID NO 1640
<211> LENGTH: 6
<212> TYPE: PRT
<213> ORGANISM: Homo sapiens

<400> SEQUENCE: 1640

Ser Leu Tyr Ser Glu Lys
1               5

<210> SEQ ID NO 1641
<211> LENGTH: 12
<212> TYPE: PRT
<213> ORGANISM: Homo sapiens

<400> SEQUENCE: 1641

Glu Leu Ile Ser Asn Ala Ser Asp Ala Leu Glu Lys
1               5                   10

<210> SEQ ID NO 1642
<211> LENGTH: 15
<212> TYPE: PRT
<213> ORGANISM: Homo sapiens

<400> SEQUENCE: 1642

Ala Phe Leu Asp Ala Leu Gln Asn Gln Ala Glu Ala Ser Ser Lys
1               5                   10                  15

<210> SEQ ID NO 1643
<211> LENGTH: 6
<212> TYPE: PRT
<213> ORGANISM: Homo sapiens

<400> SEQUENCE: 1643

Ile Ile Ile His Leu Lys
1               5
```

```
<210> SEQ ID NO 1644
<211> LENGTH: 7
<212> TYPE: PRT
<213> ORGANISM: Homo sapiens

<400> SEQUENCE: 1644

Glu Phe Ser Ser Glu Ala Arg
1               5

<210> SEQ ID NO 1645
<211> LENGTH: 14
<212> TYPE: PRT
<213> ORGANISM: Homo sapiens

<400> SEQUENCE: 1645

Tyr Ser Asn Phe Val Ser Phe Pro Leu Tyr Leu Asn Gly Arg
1               5                   10

<210> SEQ ID NO 1646
<211> LENGTH: 9
<212> TYPE: PRT
<213> ORGANISM: Homo sapiens

<400> SEQUENCE: 1646

Glu Trp Gln His Glu Glu Phe Tyr Arg
1               5

<210> SEQ ID NO 1647
<211> LENGTH: 10
<212> TYPE: PRT
<213> ORGANISM: Homo sapiens

<400> SEQUENCE: 1647

Tyr Val Ala Gln Ala His Asp Lys Pro Arg
1               5                   10

<210> SEQ ID NO 1648
<211> LENGTH: 6
<212> TYPE: PRT
<213> ORGANISM: Homo sapiens

<400> SEQUENCE: 1648

Tyr Thr Leu His Tyr Lys
1               5

<210> SEQ ID NO 1649
<211> LENGTH: 8
<212> TYPE: PRT
<213> ORGANISM: Homo sapiens

<400> SEQUENCE: 1649

Thr Asp Ala Pro Leu Asn Ile Arg
1               5

<210> SEQ ID NO 1650
<211> LENGTH: 11
<212> TYPE: PRT
<213> ORGANISM: Homo sapiens

<400> SEQUENCE: 1650

Glu Leu Gly Ser Ser Val Ala Leu Tyr Ser Arg
1               5                   10
```

-continued

```
<210> SEQ ID NO 1651
<211> LENGTH: 6
<212> TYPE: PRT
<213> ORGANISM: Homo sapiens

<400> SEQUENCE: 1651

Val Leu Ile Gln Thr Lys
1               5

<210> SEQ ID NO 1652
<211> LENGTH: 7
<212> TYPE: PRT
<213> ORGANISM: Homo sapiens

<400> SEQUENCE: 1652

Ala Thr Asp Ile Leu Pro Lys
1               5

<210> SEQ ID NO 1653
<211> LENGTH: 14
<212> TYPE: PRT
<213> ORGANISM: Homo sapiens

<400> SEQUENCE: 1653

Gly Val Val Asp Ser Glu Asp Ile Pro Leu Asn Leu Ser Arg
1               5                   10

<210> SEQ ID NO 1654
<211> LENGTH: 10
<212> TYPE: PRT
<213> ORGANISM: Homo sapiens

<400> SEQUENCE: 1654

Glu Leu Leu Gln Glu Ser Ala Leu Ile Arg
1               5                   10

<210> SEQ ID NO 1655
<211> LENGTH: 7
<212> TYPE: PRT
<213> ORGANISM: Homo sapiens

<400> SEQUENCE: 1655

Phe Phe Ile Asp Gln Ser Lys
1               5

<210> SEQ ID NO 1656
<211> LENGTH: 12
<212> TYPE: PRT
<213> ORGANISM: Homo sapiens

<400> SEQUENCE: 1656

Glu Gly Ile Val Thr Ala Thr Glu Gln Glu Val Lys
1               5                   10

<210> SEQ ID NO 1657
<211> LENGTH: 20
<212> TYPE: PRT
<213> ORGANISM: Homo sapiens

<400> SEQUENCE: 1657

Tyr Glu Ser Ser Ala Leu Pro Ser Gly Gln Leu Thr Ser Leu Ser Glu
1               5                   10                  15

Tyr Ala Ser Arg
            20
```

```
<210> SEQ ID NO 1658
<211> LENGTH: 14
<212> TYPE: PRT
<213> ORGANISM: Homo sapiens

<400> SEQUENCE: 1658

Leu Ile Ser Val Glu Thr Asp Ile Val Val Asp His Tyr Lys
1               5                   10

<210> SEQ ID NO 1659
<211> LENGTH: 6
<212> TYPE: PRT
<213> ORGANISM: Homo sapiens

<400> SEQUENCE: 1659

Asn Val Leu Gly Ser Arg
1               5

<210> SEQ ID NO 1660
<211> LENGTH: 13
<212> TYPE: PRT
<213> ORGANISM: Homo sapiens

<400> SEQUENCE: 1660

Ala Gln Leu Leu Gln Pro Thr Leu Glu Ile Asn Pro Arg
1               5                   10

<210> SEQ ID NO 1661
<211> LENGTH: 7
<212> TYPE: PRT
<213> ORGANISM: Homo sapiens

<400> SEQUENCE: 1661

Leu Asn Glu Leu Leu Val Lys
1               5

<210> SEQ ID NO 1662
<211> LENGTH: 8
<212> TYPE: PRT
<213> ORGANISM: Homo sapiens

<400> SEQUENCE: 1662

Thr Thr Ala Gln Leu Gly Pro Arg
1               5

<210> SEQ ID NO 1663
<211> LENGTH: 10
<212> TYPE: PRT
<213> ORGANISM: Homo sapiens

<400> SEQUENCE: 1663

Asn Pro Ala Trp Ser Leu Gln Ala Gly Arg
1               5                   10

<210> SEQ ID NO 1664
<211> LENGTH: 10
<212> TYPE: PRT
<213> ORGANISM: Homo sapiens

<400> SEQUENCE: 1664

Leu Phe Ser Thr Gln Thr Ala Glu Asp Lys
1               5                   10

<210> SEQ ID NO 1665
```

```
<211> LENGTH: 20
<212> TYPE: PRT
<213> ORGANISM: Homo sapiens

<400> SEQUENCE: 1665

Glu Glu Pro Leu His Ser Ile Ile Ser Ser Thr Glu Ser Val Gln Gly
1               5                   10                  15

Ser Thr Ser Lys
            20

<210> SEQ ID NO 1666
<211> LENGTH: 6
<212> TYPE: PRT
<213> ORGANISM: Homo sapiens

<400> SEQUENCE: 1666

Ser Ile Thr Gln Ile Lys
1               5

<210> SEQ ID NO 1667
<211> LENGTH: 10
<212> TYPE: PRT
<213> ORGANISM: Homo sapiens

<400> SEQUENCE: 1667

Glu Gly Asp Leu Leu Phe Thr Val Ala Lys
1               5                   10

<210> SEQ ID NO 1668
<211> LENGTH: 14
<212> TYPE: PRT
<213> ORGANISM: Homo sapiens

<400> SEQUENCE: 1668

Asp Pro Ile Val Asn Val Trp Tyr Ser Val Asn Gly Glu Arg
1               5                   10

<210> SEQ ID NO 1669
<211> LENGTH: 6
<212> TYPE: PRT
<213> ORGANISM: Homo sapiens

<400> SEQUENCE: 1669

Thr Asn Ser Ala Val Arg
1               5

<210> SEQ ID NO 1670
<211> LENGTH: 9
<212> TYPE: PRT
<213> ORGANISM: Homo sapiens

<400> SEQUENCE: 1670

Ser Gly Glu Val Leu Val Asn Val Lys
1               5

<210> SEQ ID NO 1671
<211> LENGTH: 9
<212> TYPE: PRT
<213> ORGANISM: Homo sapiens

<400> SEQUENCE: 1671

Gln Ile Asn Asp Ile Gln Leu Ser Arg
1               5
```

<210> SEQ ID NO 1672
<211> LENGTH: 11
<212> TYPE: PRT
<213> ORGANISM: Homo sapiens

<400> SEQUENCE: 1672

Leu Phe Asp Ser Thr Thr Leu Glu His Gln Lys
1               5                   10

<210> SEQ ID NO 1673
<211> LENGTH: 12
<212> TYPE: PRT
<213> ORGANISM: Homo sapiens

<400> SEQUENCE: 1673

Phe Phe His Leu Ala Phe Glu Glu Glu Phe Gly Arg
1               5                   10

<210> SEQ ID NO 1674
<211> LENGTH: 16
<212> TYPE: PRT
<213> ORGANISM: Homo sapiens

<400> SEQUENCE: 1674

Gly His Phe Gly Pro Ile Asn Ser Val Ala Phe His Pro Asp Gly Lys
1               5                   10                  15

<210> SEQ ID NO 1675
<211> LENGTH: 12
<212> TYPE: PRT
<213> ORGANISM: Homo sapiens

<400> SEQUENCE: 1675

Ser Tyr Ser Ser Gly Gly Glu Asp Gly Tyr Val Arg
1               5                   10

<210> SEQ ID NO 1676
<211> LENGTH: 15
<212> TYPE: PRT
<213> ORGANISM: Homo sapiens

<400> SEQUENCE: 1676

Ile His Tyr Phe Asp Pro Gln Tyr Phe Glu Phe Glu Phe Glu Ala
1               5                   10                  15

<210> SEQ ID NO 1677
<211> LENGTH: 13
<212> TYPE: PRT
<213> ORGANISM: Homo sapiens

<400> SEQUENCE: 1677

Asn Glu Glu Asp Glu Gly His Ser Asn Ser Ser Pro Arg
1               5                   10

<210> SEQ ID NO 1678
<211> LENGTH: 9
<212> TYPE: PRT
<213> ORGANISM: Homo sapiens

<400> SEQUENCE: 1678

His Ser Glu Ala Ala Thr Ala Gln Arg
1               5

<210> SEQ ID NO 1679
<211> LENGTH: 7

```
<212> TYPE: PRT
<213> ORGANISM: Homo sapiens

<400> SEQUENCE: 1679

Leu Asp Pro Ile Thr Gly Arg
1               5

<210> SEQ ID NO 1680
<211> LENGTH: 7
<212> TYPE: PRT
<213> ORGANISM: Homo sapiens

<400> SEQUENCE: 1680

Glu Ser Glu Ser Val Asp Lys
1               5

<210> SEQ ID NO 1681
<211> LENGTH: 14
<212> TYPE: PRT
<213> ORGANISM: Homo sapiens

<400> SEQUENCE: 1681

Ile Phe Val Gly Gly Leu Ser Pro Asp Thr Pro Glu Glu Lys
1               5                   10

<210> SEQ ID NO 1682
<211> LENGTH: 8
<212> TYPE: PRT
<213> ORGANISM: Homo sapiens

<400> SEQUENCE: 1682

Tyr His Asn Val Gly Leu Ser Lys
1               5

<210> SEQ ID NO 1683
<211> LENGTH: 12
<212> TYPE: PRT
<213> ORGANISM: Homo sapiens

<400> SEQUENCE: 1683

Glu Gln Tyr Gln Gln Gln Gln Trp Gly Ser Arg
1               5                   10

<210> SEQ ID NO 1684
<211> LENGTH: 10
<212> TYPE: PRT
<213> ORGANISM: Homo sapiens

<400> SEQUENCE: 1684

Gly Gly His Gln Asn Ser Tyr Lys Pro Tyr
1               5                   10

<210> SEQ ID NO 1685
<211> LENGTH: 7
<212> TYPE: PRT
<213> ORGANISM: Homo sapiens

<400> SEQUENCE: 1685

Gly His Leu Asp Tyr Pro Arg
1               5

<210> SEQ ID NO 1686
<211> LENGTH: 6
<212> TYPE: PRT
<213> ORGANISM: Homo sapiens
```

<400> SEQUENCE: 1686

Ile Asp His Leu Glu Arg
1               5

<210> SEQ ID NO 1687
<211> LENGTH: 13
<212> TYPE: PRT
<213> ORGANISM: Homo sapiens

<400> SEQUENCE: 1687

Leu Leu Ala Glu Asn Asn Glu Ile Ile Ser Asn Ile Arg
1               5                   10

<210> SEQ ID NO 1688
<211> LENGTH: 15
<212> TYPE: PRT
<213> ORGANISM: Homo sapiens

<400> SEQUENCE: 1688

Asp Ser Val Ile Asn Leu Ser Glu Ser Val Glu Asp Gly Pro Lys
1               5                   10                  15

<210> SEQ ID NO 1689
<211> LENGTH: 7
<212> TYPE: PRT
<213> ORGANISM: Homo sapiens

<400> SEQUENCE: 1689

Thr Phe Asn Asp Tyr Phe Arg
1               5

<210> SEQ ID NO 1690
<211> LENGTH: 11
<212> TYPE: PRT
<213> ORGANISM: Homo sapiens

<400> SEQUENCE: 1690

Phe Ile Trp Ser Glu Ile Ser Tyr Leu Ser Lys
1               5                   10

<210> SEQ ID NO 1691
<211> LENGTH: 9
<212> TYPE: PRT
<213> ORGANISM: Homo sapiens

<400> SEQUENCE: 1691

Trp Trp Asp Ile Ile Asp Ile Gln Lys
1               5

<210> SEQ ID NO 1692
<211> LENGTH: 6
<212> TYPE: PRT
<213> ORGANISM: Homo sapiens

<400> SEQUENCE: 1692

Val His Tyr Ala Val Lys
1               5

<210> SEQ ID NO 1693
<211> LENGTH: 6
<212> TYPE: PRT
<213> ORGANISM: Homo sapiens

<400> SEQUENCE: 1693

His Phe Ala Leu His Lys
1               5

<210> SEQ ID NO 1694
<211> LENGTH: 7
<212> TYPE: PRT
<213> ORGANISM: Homo sapiens

<400> SEQUENCE: 1694

Thr Leu Glu Phe Phe Trp Arg
1               5

<210> SEQ ID NO 1695
<211> LENGTH: 11
<212> TYPE: PRT
<213> ORGANISM: Homo sapiens

<400> SEQUENCE: 1695

Val Leu Leu Ala Pro Leu Gly Asp Asp Phe Arg
1               5                   10

<210> SEQ ID NO 1696
<211> LENGTH: 15
<212> TYPE: PRT
<213> ORGANISM: Homo sapiens

<400> SEQUENCE: 1696

Ile Gln Phe Gly Thr Leu Ser Asp Phe Asp Ala Leu Asp Lys
1               5                   10                  15

<210> SEQ ID NO 1697
<211> LENGTH: 6
<212> TYPE: PRT
<213> ORGANISM: Homo sapiens

<400> SEQUENCE: 1697

Ala Asp Glu Thr Gln Arg
1               5

<210> SEQ ID NO 1698
<211> LENGTH: 16
<212> TYPE: PRT
<213> ORGANISM: Homo sapiens

<400> SEQUENCE: 1698

Asp Asp His Tyr Trp Ser Gly Tyr Phe Thr Ser Arg Pro Phe Tyr Lys
1               5                   10                  15

<210> SEQ ID NO 1699
<211> LENGTH: 11
<212> TYPE: PRT
<213> ORGANISM: Homo sapiens

<400> SEQUENCE: 1699

Ala Ala Glu Ile Leu Tyr Tyr Phe Ala Leu Arg
1               5                   10

<210> SEQ ID NO 1700
<211> LENGTH: 14
<212> TYPE: PRT
<213> ORGANISM: Homo sapiens

<400> SEQUENCE: 1700

Phe Leu Ser Ser Ser Leu Tyr Thr Ala Leu Thr Glu Ala Arg

-continued

```
1               5                   10
```

<210> SEQ ID NO 1701
<211> LENGTH: 16
<212> TYPE: PRT
<213> ORGANISM: Homo sapiens

<400> SEQUENCE: 1701

```
Asn Leu Gly Leu Phe Gln His His Asp Ala Ile Thr Gly Thr Ala Lys
1               5                   10                  15
```

<210> SEQ ID NO 1702
<211> LENGTH: 10
<212> TYPE: PRT
<213> ORGANISM: Homo sapiens

<400> SEQUENCE: 1702

```
Asp Trp Val Val Val Asp Tyr Gly Thr Arg
1               5                   10
```

<210> SEQ ID NO 1703
<211> LENGTH: 12
<212> TYPE: PRT
<213> ORGANISM: Homo sapiens

<400> SEQUENCE: 1703

```
Ile Ile Gly Asn Ser Ala Phe Leu Leu Ile Leu Lys
1               5                   10
```

<210> SEQ ID NO 1704
<211> LENGTH: 8
<212> TYPE: PRT
<213> ORGANISM: Homo sapiens

<400> SEQUENCE: 1704

```
Ser Gln Asp Ser Leu Pro Gln Lys
1               5
```

<210> SEQ ID NO 1705
<211> LENGTH: 12
<212> TYPE: PRT
<213> ORGANISM: Homo sapiens

<400> SEQUENCE: 1705

```
Tyr Leu Val Val Tyr Asn Pro Leu Glu Gln Asp Arg
1               5                   10
```

<210> SEQ ID NO 1706
<211> LENGTH: 9
<212> TYPE: PRT
<213> ORGANISM: Homo sapiens

<400> SEQUENCE: 1706

```
Ala His Ile Pro Pro Leu Gly Leu Lys
1               5
```

<210> SEQ ID NO 1707
<211> LENGTH: 18
<212> TYPE: PRT
<213> ORGANISM: Homo sapiens

<400> SEQUENCE: 1707

```
Ile Leu Glu Ser Ala Ser Ser Asn Ser His Leu Ala Asp Tyr Val Leu
1               5                   10                  15
```

Tyr Lys

<210> SEQ ID NO 1708
<211> LENGTH: 10
<212> TYPE: PRT
<213> ORGANISM: Homo sapiens

<400> SEQUENCE: 1708

Val Glu Asp Ser Gly Ile Phe Thr Ile Lys
1               5                   10

<210> SEQ ID NO 1709
<211> LENGTH: 16
<212> TYPE: PRT
<213> ORGANISM: Homo sapiens

<400> SEQUENCE: 1709

His His Glu Val Asn Val Gln Phe Ser Trp Tyr Gly Thr Thr Ile Lys
1               5                   10                  15

<210> SEQ ID NO 1710
<211> LENGTH: 24
<212> TYPE: PRT
<213> ORGANISM: Homo sapiens

<400> SEQUENCE: 1710

Ser Gly Ala Tyr Leu Phe Leu Pro Asp Gly Asn Ala Lys Pro Tyr Val
1               5                   10                  15

Tyr Thr Thr Pro Pro Phe Val Arg
            20

<210> SEQ ID NO 1711
<211> LENGTH: 21
<212> TYPE: PRT
<213> ORGANISM: Homo sapiens

<400> SEQUENCE: 1711

Leu Tyr His Ile Gln Gly Ile Glu Gly Gln Ser Val Glu Val Ser Asn
1               5                   10                  15

Ile Val Asp Ile Arg
            20

<210> SEQ ID NO 1712
<211> LENGTH: 6
<212> TYPE: PRT
<213> ORGANISM: Homo sapiens

<400> SEQUENCE: 1712

Ile Ser Ser Asp Ile Lys
1               5

<210> SEQ ID NO 1713
<211> LENGTH: 13
<212> TYPE: PRT
<213> ORGANISM: Homo sapiens

<400> SEQUENCE: 1713

Phe Tyr Thr Asp Leu Asn Gly Tyr Gln Ile Gln Pro Arg
1               5                   10

<210> SEQ ID NO 1714
<211> LENGTH: 10
<212> TYPE: PRT
<213> ORGANISM: Homo sapiens

```
<400> SEQUENCE: 1714

Gly Leu Glu Gln Gly Ile Gln Asp Asn Lys
1               5                   10

<210> SEQ ID NO 1715
<211> LENGTH: 7
<212> TYPE: PRT
<213> ORGANISM: Homo sapiens

<400> SEQUENCE: 1715

Ile Thr Ala Asn Leu Phe Arg
1               5

<210> SEQ ID NO 1716
<211> LENGTH: 9
<212> TYPE: PRT
<213> ORGANISM: Homo sapiens

<400> SEQUENCE: 1716

Ser Ala Val Asn Thr Glu Glu Glu Lys
1               5

<210> SEQ ID NO 1717
<211> LENGTH: 15
<212> TYPE: PRT
<213> ORGANISM: Homo sapiens

<400> SEQUENCE: 1717

Val Gly Asn Gly His Ser Asn Glu Ala Ala Leu Ile Leu His Arg
1               5                   10                  15

<210> SEQ ID NO 1718
<211> LENGTH: 10
<212> TYPE: PRT
<213> ORGANISM: Homo sapiens

<400> SEQUENCE: 1718

Ala Gly Phe Gly Gly Asp Asp Ala Pro Arg
1               5                   10

<210> SEQ ID NO 1719
<211> LENGTH: 11
<212> TYPE: PRT
<213> ORGANISM: Homo sapiens

<400> SEQUENCE: 1719

Ile Trp Tyr His Thr Phe Tyr Asn Glu Leu Arg
1               5                   10

<210> SEQ ID NO 1720
<211> LENGTH: 18
<212> TYPE: PRT
<213> ORGANISM: Homo sapiens

<400> SEQUENCE: 1720

Val Ala Pro Asp Glu His Pro Ile Leu Leu Thr Glu Ala Pro Leu Asn
1               5                   10                  15

Pro Lys

<210> SEQ ID NO 1721
<211> LENGTH: 10
<212> TYPE: PRT
<213> ORGANISM: Homo sapiens
```

<400> SEQUENCE: 1721

Gly Tyr Asn Phe Thr Thr Thr Ala Glu Arg
1               5                   10

<210> SEQ ID NO 1722
<211> LENGTH: 9
<212> TYPE: PRT
<213> ORGANISM: Homo sapiens

<400> SEQUENCE: 1722

Ala Ala Ala Ser Ser Ser Pro Glu Arg
1               5

<210> SEQ ID NO 1723
<211> LENGTH: 13
<212> TYPE: PRT
<213> ORGANISM: Homo sapiens

<400> SEQUENCE: 1723

Gln Glu Tyr Asp Glu Ala Gly Pro Pro Ile Val His Arg
1               5                   10

<210> SEQ ID NO 1724
<211> LENGTH: 8
<212> TYPE: PRT
<213> ORGANISM: Homo sapiens

<400> SEQUENCE: 1724

Ser Ser Phe Leu Thr Glu Glu Lys
1               5

<210> SEQ ID NO 1725
<211> LENGTH: 9
<212> TYPE: PRT
<213> ORGANISM: Homo sapiens

<400> SEQUENCE: 1725

Leu Tyr Leu Glu Asn Gly Gln Thr Lys
1               5

<210> SEQ ID NO 1726
<211> LENGTH: 8
<212> TYPE: PRT
<213> ORGANISM: Homo sapiens

<400> SEQUENCE: 1726

Phe Glu Ala Asn Thr Thr Val Lys
1               5

<210> SEQ ID NO 1727
<211> LENGTH: 7
<212> TYPE: PRT
<213> ORGANISM: Homo sapiens

<400> SEQUENCE: 1727

Asp Ile Ile Leu Thr Val Lys
1               5

<210> SEQ ID NO 1728
<211> LENGTH: 17
<212> TYPE: PRT
<213> ORGANISM: Homo sapiens

<400> SEQUENCE: 1728

```
Ser Ile Glu Tyr Phe Ala Leu Ala Leu Glu Glu Gln Tyr Ser Ile Ser
1               5                   10                  15

Arg

<210> SEQ ID NO 1729
<211> LENGTH: 16
<212> TYPE: PRT
<213> ORGANISM: Homo sapiens

<400> SEQUENCE: 1729

Leu His Leu Leu His Glu Glu Glu Leu Ile Gln Gln Val Val Glu Arg
1               5                   10                  15

<210> SEQ ID NO 1730
<211> LENGTH: 7
<212> TYPE: PRT
<213> ORGANISM: Homo sapiens

<400> SEQUENCE: 1730

Glu Glu Ser His Asp Tyr Arg
1               5

<210> SEQ ID NO 1731
<211> LENGTH: 7
<212> TYPE: PRT
<213> ORGANISM: Homo sapiens

<400> SEQUENCE: 1731

Asp Pro Leu Asp Leu Leu Lys
1               5

<210> SEQ ID NO 1732
<211> LENGTH: 9
<212> TYPE: PRT
<213> ORGANISM: Homo sapiens

<400> SEQUENCE: 1732

Leu Ala Ala Leu His Ile Gln Glu Arg
1               5

<210> SEQ ID NO 1733
<211> LENGTH: 14
<212> TYPE: PRT
<213> ORGANISM: Homo sapiens

<400> SEQUENCE: 1733

Asp Trp Gly Ile Glu Asn Phe Ile Ser Pro Thr Leu Leu Arg
1               5                   10

<210> SEQ ID NO 1734
<211> LENGTH: 8
<212> TYPE: PRT
<213> ORGANISM: Homo sapiens

<400> SEQUENCE: 1734

Asn Gln Asn Leu Leu Glu Pro Arg
1               5

<210> SEQ ID NO 1735
<211> LENGTH: 9
<212> TYPE: PRT
<213> ORGANISM: Homo sapiens

<400> SEQUENCE: 1735
```

Gln Leu Ile Ser Ala Ala Gln Leu Arg
1               5

<210> SEQ ID NO 1736
<211> LENGTH: 11
<212> TYPE: PRT
<213> ORGANISM: Homo sapiens

<400> SEQUENCE: 1736

Leu Asn Tyr Leu Gln Ile Leu Gly Glu Leu Lys
1               5                   10

<210> SEQ ID NO 1737
<211> LENGTH: 11
<212> TYPE: PRT
<213> ORGANISM: Homo sapiens

<400> SEQUENCE: 1737

Glu Ser Tyr Ile Ala Leu Leu Val Gly Ala Lys
1               5                   10

<210> SEQ ID NO 1738
<211> LENGTH: 10
<212> TYPE: PRT
<213> ORGANISM: Homo sapiens

<400> SEQUENCE: 1738

Tyr Gly Ile Ser Gln Val Ile Asn Ser Lys
1               5                   10

<210> SEQ ID NO 1739
<211> LENGTH: 9
<212> TYPE: PRT
<213> ORGANISM: Homo sapiens

<400> SEQUENCE: 1739

Val Glu Leu Thr Glu Glu Ser Glu Lys
1               5

<210> SEQ ID NO 1740
<211> LENGTH: 7
<212> TYPE: PRT
<213> ORGANISM: Homo sapiens

<400> SEQUENCE: 1740

Val Tyr Leu Gln Asp Val Lys
1               5

<210> SEQ ID NO 1741
<211> LENGTH: 12
<212> TYPE: PRT
<213> ORGANISM: Homo sapiens

<400> SEQUENCE: 1741

Val Leu Thr Leu Leu Leu Glu Ser Asn Ser Ala Lys
1               5                   10

<210> SEQ ID NO 1742
<211> LENGTH: 16
<212> TYPE: PRT
<213> ORGANISM: Homo sapiens

<400> SEQUENCE: 1742

Leu Leu Val Asp Pro Val Thr Ser Ile Phe Leu Trp Pro Gly Asn Lys

```
                1               5                    10                   15

<210> SEQ ID NO 1743
<211> LENGTH: 10
<212> TYPE: PRT
<213> ORGANISM: Homo sapiens

<400> SEQUENCE: 1743

Val Ser Ala Glu Glu Gly Tyr Glu Ser Arg
1               5                   10

<210> SEQ ID NO 1744
<211> LENGTH: 15
<212> TYPE: PRT
<213> ORGANISM: Homo sapiens

<400> SEQUENCE: 1744

Glu Glu Gln Pro Pro Gly Asn Ser Pro Thr Pro Glu Val Ala Arg
1               5                   10                  15

<210> SEQ ID NO 1745
<211> LENGTH: 23
<212> TYPE: PRT
<213> ORGANISM: Homo sapiens

<400> SEQUENCE: 1745

Ser Thr Phe Phe His Phe Gly Ser Pro Gly Leu Ala Glu Ser Ile Asp
1               5                   10                  15

Ser Asp Ser Gln Glu Glu Arg
            20

<210> SEQ ID NO 1746
<211> LENGTH: 22
<212> TYPE: PRT
<213> ORGANISM: Homo sapiens

<400> SEQUENCE: 1746

Thr Glu Phe Ser Glu Ser Ala Ala Leu Glu Thr Phe Gly Trp Ala Pro
1               5                   10                  15

Glu Leu Ser Thr Val Arg
            20

<210> SEQ ID NO 1747
<211> LENGTH: 9
<212> TYPE: PRT
<213> ORGANISM: Homo sapiens

<400> SEQUENCE: 1747

Val Ala Ala Ala Asp Gly Pro Ala Arg
1               5

<210> SEQ ID NO 1748
<211> LENGTH: 10
<212> TYPE: PRT
<213> ORGANISM: Homo sapiens

<400> SEQUENCE: 1748

Asn Pro Thr Gln Thr Leu Ile Pro Val Arg
1               5                   10

<210> SEQ ID NO 1749
<211> LENGTH: 6
<212> TYPE: PRT
```

```
<400> SEQUENCE: 1749

Ala Val Asp Ile Leu Arg
1               5

<210> SEQ ID NO 1750
<211> LENGTH: 12
<212> TYPE: PRT
<213> ORGANISM: Homo sapiens

<400> SEQUENCE: 1750

Glu Ala Glu Asp Ser Leu Ser Ile Thr Val Val Arg
1               5                   10

<210> SEQ ID NO 1751
<211> LENGTH: 11
<212> TYPE: PRT
<213> ORGANISM: Homo sapiens

<400> SEQUENCE: 1751

Leu Thr Pro Pro Gly Pro Pro Ser Gly Pro Arg
1               5                   10

<210> SEQ ID NO 1752
<211> LENGTH: 15
<212> TYPE: PRT
<213> ORGANISM: Homo sapiens

<400> SEQUENCE: 1752

Asp Val Ser Thr Ala Glu Pro Ser Ala Thr Ser Leu Gln Asn Lys
1               5                   10                  15

<210> SEQ ID NO 1753
<211> LENGTH: 9
<212> TYPE: PRT
<213> ORGANISM: Homo sapiens

<400> SEQUENCE: 1753

Ala Leu Gly Leu Leu Ala Pro Leu Arg
1               5

<210> SEQ ID NO 1754
<211> LENGTH: 7
<212> TYPE: PRT
<213> ORGANISM: Homo sapiens

<400> SEQUENCE: 1754

Ser Thr Asn Pro Ala Ser Arg
1               5

<210> SEQ ID NO 1755
<211> LENGTH: 6
<212> TYPE: PRT
<213> ORGANISM: Homo sapiens

<400> SEQUENCE: 1755

Ser Val Ile Asp Ser Arg
1               5

<210> SEQ ID NO 1756
<211> LENGTH: 8
<212> TYPE: PRT
<213> ORGANISM: Homo sapiens

<400> SEQUENCE: 1756
```

Val Ser Ser Ile Ser Ala Ile Arg
1               5

<210> SEQ ID NO 1757
<211> LENGTH: 6
<212> TYPE: PRT
<213> ORGANISM: Homo sapiens

<400> SEQUENCE: 1757

Ile Asp Pro Asn Asn Lys
1               5

<210> SEQ ID NO 1758
<211> LENGTH: 22
<212> TYPE: PRT
<213> ORGANISM: Homo sapiens

<400> SEQUENCE: 1758

Glu Pro Thr Ile Glu His Gly Asp Ser Ser Phe Ser Leu Ser Ser Gly
1               5                   10                  15

Asp Pro Asn Pro Asp Arg
            20

<210> SEQ ID NO 1759
<211> LENGTH: 9
<212> TYPE: PRT
<213> ORGANISM: Homo sapiens

<400> SEQUENCE: 1759

Tyr Thr Glu Pro Leu Leu Ser Pro Arg
1               5

<210> SEQ ID NO 1760
<211> LENGTH: 7
<212> TYPE: PRT
<213> ORGANISM: Homo sapiens

<400> SEQUENCE: 1760

Ile Ala Ser Ile Pro Thr Lys
1               5

<210> SEQ ID NO 1761
<211> LENGTH: 11
<212> TYPE: PRT
<213> ORGANISM: Homo sapiens

<400> SEQUENCE: 1761

Glu Glu Pro Gln Gly Gln Leu Ser Leu Glu Arg
1               5                   10

<210> SEQ ID NO 1762
<211> LENGTH: 11
<212> TYPE: PRT
<213> ORGANISM: Homo sapiens

<400> SEQUENCE: 1762

Asn Gly Thr Asn Val Phe Gln Glu Glu Ser Arg
1               5                   10

<210> SEQ ID NO 1763
<211> LENGTH: 25
<212> TYPE: PRT
<213> ORGANISM: Homo sapiens

```
<400> SEQUENCE: 1763

Asp Ser Gly Asp Ser Pro Gly Asp Val Ser Asn Asn Val Ser Gln Thr
1               5                   10                  15

Leu Asp Ile Ser Ser Pro Ala Gly Lys
            20                  25

<210> SEQ ID NO 1764
<211> LENGTH: 23
<212> TYPE: PRT
<213> ORGANISM: Homo sapiens

<400> SEQUENCE: 1764

Ile Val Thr Ser Leu Ser Leu Asp Ala Pro Val Thr Gly Thr Glu Gln
1               5                   10                  15

Ile Pro Pro His Pro Pro Arg
            20

<210> SEQ ID NO 1765
<211> LENGTH: 7
<212> TYPE: PRT
<213> ORGANISM: Homo sapiens

<400> SEQUENCE: 1765

Asp Pro Gln Gly Gln Ser Arg
1               5

<210> SEQ ID NO 1766
<211> LENGTH: 15
<212> TYPE: PRT
<213> ORGANISM: Homo sapiens

<400> SEQUENCE: 1766

Leu Phe Val Glu Leu Asp Leu Asp Pro Asp Phe Phe Leu Gly Lys
1               5                   10                  15

<210> SEQ ID NO 1767
<211> LENGTH: 13
<212> TYPE: PRT
<213> ORGANISM: Homo sapiens

<400> SEQUENCE: 1767

Gln Thr Val Ser Pro Ala Val Pro Pro Glu Gly Ile Lys
1               5                   10

<210> SEQ ID NO 1768
<211> LENGTH: 15
<212> TYPE: PRT
<213> ORGANISM: Homo sapiens

<400> SEQUENCE: 1768

Ala Glu Ala Pro Asn His Val Thr Gly Gln Asp Ile Ala Pro Arg
1               5                   10                  15

<210> SEQ ID NO 1769
<211> LENGTH: 11
<212> TYPE: PRT
<213> ORGANISM: Homo sapiens

<400> SEQUENCE: 1769

Gly Pro Gln Pro Glu Thr Glu Glu Glu Asp Arg
1               5                   10

<210> SEQ ID NO 1770
```

```
<211> LENGTH: 7
<212> TYPE: PRT
<213> ORGANISM: Homo sapiens

<400> SEQUENCE: 1770

Glu Ala Ala Gly Asn Leu Arg
1               5

<210> SEQ ID NO 1771
<211> LENGTH: 14
<212> TYPE: PRT
<213> ORGANISM: Homo sapiens

<400> SEQUENCE: 1771

Asp Val Val Tyr Thr Tyr His Gln Phe Ile Glu Ala Ala Lys
1               5                   10

<210> SEQ ID NO 1772
<211> LENGTH: 8
<212> TYPE: PRT
<213> ORGANISM: Homo sapiens

<400> SEQUENCE: 1772

Gly Tyr His Asp Leu Ser Val Lys
1               5

<210> SEQ ID NO 1773
<211> LENGTH: 7
<212> TYPE: PRT
<213> ORGANISM: Homo sapiens

<400> SEQUENCE: 1773

Val Tyr Leu Pro Trp Ser Arg
1               5

<210> SEQ ID NO 1774
<211> LENGTH: 10
<212> TYPE: PRT
<213> ORGANISM: Homo sapiens

<400> SEQUENCE: 1774

Val Tyr Ser Thr Ser Val Thr Gly Ser Arg
1               5                   10

<210> SEQ ID NO 1775
<211> LENGTH: 8
<212> TYPE: PRT
<213> ORGANISM: Homo sapiens

<400> SEQUENCE: 1775

Ser Gln Gln Ser Glu Val Thr Arg
1               5

<210> SEQ ID NO 1776
<211> LENGTH: 15
<212> TYPE: PRT
<213> ORGANISM: Homo sapiens

<400> SEQUENCE: 1776

Ile Gln Tyr Gln Leu Val Asp Ile Ser Gln Asp Asn Ala Leu Arg
1               5                   10                  15

<210> SEQ ID NO 1777
<211> LENGTH: 9
<212> TYPE: PRT
```

-continued

<213> ORGANISM: Homo sapiens

<400> SEQUENCE: 1777

Gly Ala Ser Ala Leu Gln Leu Glu Arg
1               5

<210> SEQ ID NO 1778
<211> LENGTH: 11
<212> TYPE: PRT
<213> ORGANISM: Homo sapiens

<400> SEQUENCE: 1778

Ile Ser Val Tyr Tyr Asn Glu Ala Tyr Gly Arg
1               5                   10

<210> SEQ ID NO 1779
<211> LENGTH: 23
<212> TYPE: PRT
<213> ORGANISM: Homo sapiens

<400> SEQUENCE: 1779

Leu Gly Ala Leu Phe Gln Pro Asp Ser Phe Val His Gly Asn Ser Gly
1               5                   10                  15

Ala Gly Asn Asn Trp Ala Lys
            20

<210> SEQ ID NO 1780
<211> LENGTH: 18
<212> TYPE: PRT
<213> ORGANISM: Homo sapiens

<400> SEQUENCE: 1780

Gly His Tyr Thr Glu Gly Ala Glu Leu Ile Glu Asn Val Leu Glu Val
1               5                   10                  15

Val Arg

<210> SEQ ID NO 1781
<211> LENGTH: 12
<212> TYPE: PRT
<213> ORGANISM: Homo sapiens

<400> SEQUENCE: 1781

Glu Val Asp Gln Gln Leu Leu Ser Val Gln Thr Arg
1               5                   10

<210> SEQ ID NO 1782
<211> LENGTH: 9
<212> TYPE: PRT
<213> ORGANISM: Homo sapiens

<400> SEQUENCE: 1782

Leu Val Asn Ile Ala Val Asp Glu Arg
1               5

<210> SEQ ID NO 1783
<211> LENGTH: 8
<212> TYPE: PRT
<213> ORGANISM: Homo sapiens

<400> SEQUENCE: 1783

Ser Ser Pro Tyr Tyr Ala Leu Arg
1               5

```
<210> SEQ ID NO 1784
<211> LENGTH: 21
<212> TYPE: PRT
<213> ORGANISM: Homo sapiens

<400> SEQUENCE: 1784

Glu Glu Ile Tyr Phe Leu Asn Thr Asn Asn Ala Phe Ser Gly Val Ala
1               5                   10                  15

Thr Tyr Thr Asp Lys
            20

<210> SEQ ID NO 1785
<211> LENGTH: 13
<212> TYPE: PRT
<213> ORGANISM: Homo sapiens

<400> SEQUENCE: 1785

Trp Glu Asp Ile Leu Ser Asp Glu Val Asn Val Ala Arg
1               5                   10

<210> SEQ ID NO 1786
<211> LENGTH: 9
<212> TYPE: PRT
<213> ORGANISM: Homo sapiens

<400> SEQUENCE: 1786

Gly Val Ala Ser Leu Phe Ala Gly Arg
1               5

<210> SEQ ID NO 1787
<211> LENGTH: 6
<212> TYPE: PRT
<213> ORGANISM: Homo sapiens

<400> SEQUENCE: 1787

Gly Ile Leu Ala Leu Arg
1               5

<210> SEQ ID NO 1788
<211> LENGTH: 10
<212> TYPE: PRT
<213> ORGANISM: Homo sapiens

<400> SEQUENCE: 1788

Asp Val Ala Ala Glu Ala Gly Val Ser Lys
1               5                   10

<210> SEQ ID NO 1789
<211> LENGTH: 22
<212> TYPE: PRT
<213> ORGANISM: Homo sapiens

<400> SEQUENCE: 1789

Gly Asp Gly Thr Phe Val Asp Ala Ala Ala Ser Ala Gly Val Asp Asp
1               5                   10                  15

Pro His Gln His Gly Arg
            20

<210> SEQ ID NO 1790
<211> LENGTH: 9
<212> TYPE: PRT
<213> ORGANISM: Homo sapiens

<400> SEQUENCE: 1790
```

```
Gly Val Ala Leu Ala Asp Phe Asn Arg
1               5

<210> SEQ ID NO 1791
<211> LENGTH: 13
<212> TYPE: PRT
<213> ORGANISM: Homo sapiens

<400> SEQUENCE: 1791

Val Asp Ile Val Tyr Gly Asn Trp Asn Gly Pro His Arg
1               5                   10

<210> SEQ ID NO 1792
<211> LENGTH: 6
<212> TYPE: PRT
<213> ORGANISM: Homo sapiens

<400> SEQUENCE: 1792

Asp Ile Ala Ser Pro Lys
1               5

<210> SEQ ID NO 1793
<211> LENGTH: 23
<212> TYPE: PRT
<213> ORGANISM: Homo sapiens

<400> SEQUENCE: 1793

Thr Val Ile Thr Ala Asp Phe Asp Asn Asp Gln Glu Leu Glu Ile Phe
1               5                   10                  15

Phe Asn Asn Ile Ala Tyr Arg
            20

<210> SEQ ID NO 1794
<211> LENGTH: 6
<212> TYPE: PRT
<213> ORGANISM: Homo sapiens

<400> SEQUENCE: 1794

Ser Ser Ser Ala Asn Arg
1               5

<210> SEQ ID NO 1795
<211> LENGTH: 21
<212> TYPE: PRT
<213> ORGANISM: Homo sapiens

<400> SEQUENCE: 1795

Glu His Gly Asp Pro Leu Ile Glu Glu Leu Asn Pro Gly Asp Ala Leu
1               5                   10                  15

Glu Pro Glu Gly Arg
            20

<210> SEQ ID NO 1796
<211> LENGTH: 11
<212> TYPE: PRT
<213> ORGANISM: Homo sapiens

<400> SEQUENCE: 1796

Gly Asn Gln Gly Phe Asn Asn Asn Trp Leu Arg
1               5                   10

<210> SEQ ID NO 1797
<211> LENGTH: 6
<212> TYPE: PRT
```

```
<213> ORGANISM: Homo sapiens

<400> SEQUENCE: 1797

Phe Gly Ala Phe Ala Arg
1               5

<210> SEQ ID NO 1798
<211> LENGTH: 6
<212> TYPE: PRT
<213> ORGANISM: Homo sapiens

<400> SEQUENCE: 1798

Val Val Leu Tyr Thr Lys
1               5

<210> SEQ ID NO 1799
<211> LENGTH: 6
<212> TYPE: PRT
<213> ORGANISM: Homo sapiens

<400> SEQUENCE: 1799

Ser Gly Ala His Leu Arg
1               5

<210> SEQ ID NO 1800
<211> LENGTH: 14
<212> TYPE: PRT
<213> ORGANISM: Homo sapiens

<400> SEQUENCE: 1800

Asp Glu Ala Ser Ser Val Glu Val Thr Trp Pro Asp Gly Lys
1               5                   10

<210> SEQ ID NO 1801
<211> LENGTH: 7
<212> TYPE: PRT
<213> ORGANISM: Homo sapiens

<400> SEQUENCE: 1801

Tyr Gly Phe Gln Ser Leu Arg
1               5

<210> SEQ ID NO 1802
<211> LENGTH: 13
<212> TYPE: PRT
<213> ORGANISM: Homo sapiens

<400> SEQUENCE: 1802

Tyr Gln Ser His Asp Tyr Ala Phe Ser Ser Val Glu Lys
1               5                   10

<210> SEQ ID NO 1803
<211> LENGTH: 8
<212> TYPE: PRT
<213> ORGANISM: Homo sapiens

<400> SEQUENCE: 1803

Thr Leu Leu Glu Thr Leu Gln Lys
1               5

<210> SEQ ID NO 1804
<211> LENGTH: 6
<212> TYPE: PRT
<213> ORGANISM: Homo sapiens
```

-continued

```
<400> SEQUENCE: 1804

Ala Gly Phe Ser Glu Lys
1               5

<210> SEQ ID NO 1805
<211> LENGTH: 7
<212> TYPE: PRT
<213> ORGANISM: Homo sapiens

<400> SEQUENCE: 1805

Tyr Thr Gly Asn Pro Thr Lys
1               5

<210> SEQ ID NO 1806
<211> LENGTH: 15
<212> TYPE: PRT
<213> ORGANISM: Homo sapiens

<400> SEQUENCE: 1806

Ser Asp Phe Tyr Asp Ile Val Leu Val Ala Thr Pro Leu Asn Arg
1               5                   10                  15

<210> SEQ ID NO 1807
<211> LENGTH: 15
<212> TYPE: PRT
<213> ORGANISM: Homo sapiens

<400> SEQUENCE: 1807

Gly Glu Leu Asn Thr Ser Ile Phe Ser Ser Arg Pro Ile Asp Lys
1               5                   10                  15

<210> SEQ ID NO 1808
<211> LENGTH: 14
<212> TYPE: PRT
<213> ORGANISM: Homo sapiens

<400> SEQUENCE: 1808

Glu Asp Pro Glu Pro Ser Thr Asp Gly Thr Tyr Val Trp Lys
1               5                   10

<210> SEQ ID NO 1809
<211> LENGTH: 9
<212> TYPE: PRT
<213> ORGANISM: Homo sapiens

<400> SEQUENCE: 1809

Ile Phe Ser Gln Glu Thr Leu Thr Lys
1               5

<210> SEQ ID NO 1810
<211> LENGTH: 10
<212> TYPE: PRT
<213> ORGANISM: Homo sapiens

<400> SEQUENCE: 1810

Leu Phe Leu Ser Tyr Asp Tyr Ala Val Lys
1               5                   10

<210> SEQ ID NO 1811
<211> LENGTH: 14
<212> TYPE: PRT
<213> ORGANISM: Homo sapiens

<400> SEQUENCE: 1811
```

```
Lys Pro Trp Leu Ala Tyr Pro His Tyr Lys Pro Pro Glu Lys
1               5                   10
```

<210> SEQ ID NO 1812
<211> LENGTH: 18
<212> TYPE: PRT
<213> ORGANISM: Homo sapiens

<400> SEQUENCE: 1812

```
Ile Ala Ile Ile Gly Ala Gly Ile Gly Gly Thr Ser Ala Ala Tyr Tyr
1               5                   10                  15

Leu Arg
```

<210> SEQ ID NO 1813
<211> LENGTH: 6
<212> TYPE: PRT
<213> ORGANISM: Homo sapiens

<400> SEQUENCE: 1813

```
Ile Asp Leu Phe Glu Arg
1               5
```

<210> SEQ ID NO 1814
<211> LENGTH: 6
<212> TYPE: PRT
<213> ORGANISM: Homo sapiens

<400> SEQUENCE: 1814

```
Glu Glu Val Gly Gly Arg
1               5
```

<210> SEQ ID NO 1815
<211> LENGTH: 8
<212> TYPE: PRT
<213> ORGANISM: Homo sapiens

<400> SEQUENCE: 1815

```
Glu Ala Val Gln Thr Ala Ala Lys
1               5
```

<210> SEQ ID NO 1816
<211> LENGTH: 10
<212> TYPE: PRT
<213> ORGANISM: Homo sapiens

<400> SEQUENCE: 1816

```
Leu Leu Gln Ala Gly Phe Ser Glu Leu Lys
1               5                   10
```

<210> SEQ ID NO 1817
<211> LENGTH: 8
<212> TYPE: PRT
<213> ORGANISM: Homo sapiens

<400> SEQUENCE: 1817

```
Trp Asn Ile Lys Pro Glu Ser Lys
1               5
```

<210> SEQ ID NO 1818
<211> LENGTH: 24
<212> TYPE: PRT
<213> ORGANISM: Homo sapiens

<400> SEQUENCE: 1818

Ser Gln Val Gly Phe Gln Gln Val Gly Val Glu Thr Tyr Gly Gly Gly
1               5                   10                  15

Ile Trp Ser Thr Trp Phe Asp Arg
            20

<210> SEQ ID NO 1819
<211> LENGTH: 7
<212> TYPE: PRT
<213> ORGANISM: Homo sapiens

<400> SEQUENCE: 1819

Asp Leu Thr Leu Ala Gly Arg
1               5

<210> SEQ ID NO 1820
<211> LENGTH: 14
<212> TYPE: PRT
<213> ORGANISM: Homo sapiens

<400> SEQUENCE: 1820

Leu Glu Gln Gln Leu Val His Val Glu Arg Pro Ile Leu Arg
1               5                   10

<210> SEQ ID NO 1821
<211> LENGTH: 10
<212> TYPE: PRT
<213> ORGANISM: Homo sapiens

<400> SEQUENCE: 1821

Ile Pro His Leu Ala Ile His Leu Gln Arg
1               5                   10

<210> SEQ ID NO 1822
<211> LENGTH: 14
<212> TYPE: PRT
<213> ORGANISM: Homo sapiens

<400> SEQUENCE: 1822

Gly Thr Pro Glu Pro Gly Pro Leu Asn Ala Val Asp Glu Arg
1               5                   10

<210> SEQ ID NO 1823
<211> LENGTH: 11
<212> TYPE: PRT
<213> ORGANISM: Homo sapiens

<400> SEQUENCE: 1823

His Glu Glu Asn His Arg Pro Leu Phe His Lys
1               5                   10

<210> SEQ ID NO 1824
<211> LENGTH: 12
<212> TYPE: PRT
<213> ORGANISM: Homo sapiens

<400> SEQUENCE: 1824

Tyr Ala Ser Asn Ala Val Ser Glu Ala Leu Ile Arg
1               5                   10

<210> SEQ ID NO 1825
<211> LENGTH: 16
<212> TYPE: PRT
<213> ORGANISM: Homo sapiens

<400> SEQUENCE: 1825

```
Gly Phe Phe Glu Leu Phe Pro Ser Leu Ser His Asn Leu Leu Val Asp
1               5                   10                  15

<210> SEQ ID NO 1826
<211> LENGTH: 10
<212> TYPE: PRT
<213> ORGANISM: Homo sapiens

<400> SEQUENCE: 1826

Gly Ser Gly Thr Asn Gly Tyr Val Gln Arg
1               5                   10

<210> SEQ ID NO 1827
<211> LENGTH: 6
<212> TYPE: PRT
<213> ORGANISM: Homo sapiens

<400> SEQUENCE: 1827

Asn Leu Ser Leu Val Arg
1               5

<210> SEQ ID NO 1828
<211> LENGTH: 7
<212> TYPE: PRT
<213> ORGANISM: Homo sapiens

<400> SEQUENCE: 1828

Gly Glu Arg Pro Asp Tyr Lys
1               5

<210> SEQ ID NO 1829
<211> LENGTH: 7
<212> TYPE: PRT
<213> ORGANISM: Homo sapiens

<400> SEQUENCE: 1829

Leu Glu Ala Ala Leu Val Lys
1               5

<210> SEQ ID NO 1830
<211> LENGTH: 11
<212> TYPE: PRT
<213> ORGANISM: Homo sapiens

<400> SEQUENCE: 1830

Arg Pro Asn Pro Asp Ile Leu Asp His Glu Arg
1               5                   10

<210> SEQ ID NO 1831
<211> LENGTH: 7
<212> TYPE: PRT
<213> ORGANISM: Homo sapiens

<400> SEQUENCE: 1831

Asp Val Asn Pro Gly Gly Lys
1               5

<210> SEQ ID NO 1832
<211> LENGTH: 22
<212> TYPE: PRT
<213> ORGANISM: Homo sapiens

<400> SEQUENCE: 1832

Glu Glu Thr Pro Gly Gln Arg Pro Ala Val Thr Glu Thr His Gln Leu
```

Ala Glu Leu Asn Glu Lys
            20

<210> SEQ ID NO 1833
<211> LENGTH: 19
<212> TYPE: PRT
<213> ORGANISM: Homo sapiens

<400> SEQUENCE: 1833

Ala Ala Phe Gly Ile Ser Asp Ser Tyr Val Asp Gly Ser Ser Phe Asp
1               5                   10                  15

Pro Gln Arg

<210> SEQ ID NO 1834
<211> LENGTH: 14
<212> TYPE: PRT
<213> ORGANISM: Homo sapiens

<400> SEQUENCE: 1834

Gln Pro Ala Pro Glu Pro Pro Lys Pro Tyr Ser Leu Val Arg
1               5                   10

<210> SEQ ID NO 1835
<211> LENGTH: 7
<212> TYPE: PRT
<213> ORGANISM: Homo sapiens

<400> SEQUENCE: 1835

Ser Thr Thr Pro Ala Pro Lys
1               5

<210> SEQ ID NO 1836
<211> LENGTH: 14
<212> TYPE: PRT
<213> ORGANISM: Homo sapiens

<400> SEQUENCE: 1836

Ser Thr Ser Ala Asp Ser Ala Ser Ser Asp Thr Ser Arg
1               5                   10

<210> SEQ ID NO 1837
<211> LENGTH: 9
<212> TYPE: PRT
<213> ORGANISM: Homo sapiens

<400> SEQUENCE: 1837

Thr His Thr Thr Ala Leu Ala Gly Arg
1               5

<210> SEQ ID NO 1838
<211> LENGTH: 8
<212> TYPE: PRT
<213> ORGANISM: Homo sapiens

<400> SEQUENCE: 1838

Ser Pro Ser Pro Ala Ser Gly Arg
1               5

<210> SEQ ID NO 1839
<211> LENGTH: 9
<212> TYPE: PRT
<213> ORGANISM: Homo sapiens

<400> SEQUENCE: 1839

Gln Pro Ser Ser Pro Tyr Glu Asp Lys
1               5

<210> SEQ ID NO 1840
<211> LENGTH: 11
<212> TYPE: PRT
<213> ORGANISM: Homo sapiens

<400> SEQUENCE: 1840

Ser Ala Thr Arg Pro Ser Pro Ser Pro Glu Arg
1               5                   10

<210> SEQ ID NO 1841
<211> LENGTH: 17
<212> TYPE: PRT
<213> ORGANISM: Homo sapiens

<400> SEQUENCE: 1841

Ser Ser Thr Gly Pro Glu Pro Pro Ala Pro Thr Pro Leu Leu Ala Glu
1               5                   10                  15

Arg

<210> SEQ ID NO 1842
<211> LENGTH: 18
<212> TYPE: PRT
<213> ORGANISM: Homo sapiens

<400> SEQUENCE: 1842

Leu Pro Gln Ser Ser Ser Ser Glu Ser Ser Pro Pro Ser Pro Gln Pro
1               5                   10                  15

Thr Lys

<210> SEQ ID NO 1843
<211> LENGTH: 19
<212> TYPE: PRT
<213> ORGANISM: Homo sapiens

<400> SEQUENCE: 1843

His Ala Ser Ser Ser Pro Glu Ser Pro Lys Pro Ala Pro Ala Pro Gly
1               5                   10                  15

Ser His Arg

<210> SEQ ID NO 1844
<211> LENGTH: 9
<212> TYPE: PRT
<213> ORGANISM: Homo sapiens

<400> SEQUENCE: 1844

Glu Ile Ser Ser Ser Pro Thr Ser Lys
1               5

<210> SEQ ID NO 1845
<211> LENGTH: 8
<212> TYPE: PRT
<213> ORGANISM: Homo sapiens

<400> SEQUENCE: 1845

Ser His Ser His Thr Pro Ser Arg
1               5

<210> SEQ ID NO 1846

```
<211> LENGTH: 6
<212> TYPE: PRT
<213> ORGANISM: Homo sapiens

<400> SEQUENCE: 1846

Ser Pro Ala Thr Ala Lys
1               5

<210> SEQ ID NO 1847
<211> LENGTH: 9
<212> TYPE: PRT
<213> ORGANISM: Homo sapiens

<400> SEQUENCE: 1847

Ser Pro Gln Arg Pro Gly Trp Ser Arg
1               5

<210> SEQ ID NO 1848
<211> LENGTH: 7
<212> TYPE: PRT
<213> ORGANISM: Homo sapiens

<400> SEQUENCE: 1848

Ser Gly Ser Ser Gln Pro Lys
1               5

<210> SEQ ID NO 1849
<211> LENGTH: 8
<212> TYPE: PRT
<213> ORGANISM: Homo sapiens

<400> SEQUENCE: 1849

Ser Ser Ser Ser Pro Pro Pro Lys
1               5

<210> SEQ ID NO 1850
<211> LENGTH: 11
<212> TYPE: PRT
<213> ORGANISM: Homo sapiens

<400> SEQUENCE: 1850

Gln Ser His Ser Ser Ser Ser Pro His Pro Lys
1               5                   10

<210> SEQ ID NO 1851
<211> LENGTH: 6
<212> TYPE: PRT
<213> ORGANISM: Homo sapiens

<400> SEQUENCE: 1851

Ser Gly Thr Pro Pro Arg
1               5

<210> SEQ ID NO 1852
<211> LENGTH: 18
<212> TYPE: PRT
<213> ORGANISM: Homo sapiens

<400> SEQUENCE: 1852

Gln Gly Ser Ile Thr Ser Pro Gln Ala Asn Glu Gln Ser Val Thr Pro
1               5                   10                  15

Gln Arg

<210> SEQ ID NO 1853
```

```
<211> LENGTH: 6
<212> TYPE: PRT
<213> ORGANISM: Homo sapiens

<400> SEQUENCE: 1853

Ala Ile Ile Ser Pro Arg
1               5

<210> SEQ ID NO 1854
<211> LENGTH: 12
<212> TYPE: PRT
<213> ORGANISM: Homo sapiens

<400> SEQUENCE: 1854

Ser His Ser Gly Ser Ser Ser Pro Ser Pro Ser Arg
1               5                   10

<210> SEQ ID NO 1855
<211> LENGTH: 12
<212> TYPE: PRT
<213> ORGANISM: Homo sapiens

<400> SEQUENCE: 1855

Tyr Ser His Ser Gly Ser Ser Ser Pro Asp Thr Lys
1               5                   10

<210> SEQ ID NO 1856
<211> LENGTH: 8
<212> TYPE: PRT
<213> ORGANISM: Homo sapiens

<400> SEQUENCE: 1856

Val Lys Pro Glu Thr Pro Pro Arg
1               5

<210> SEQ ID NO 1857
<211> LENGTH: 12
<212> TYPE: PRT
<213> ORGANISM: Homo sapiens

<400> SEQUENCE: 1857

Gln Ser His Ser Gly Ser Ile Ser Pro Tyr Pro Lys
1               5                   10

<210> SEQ ID NO 1858
<211> LENGTH: 13
<212> TYPE: PRT
<213> ORGANISM: Homo sapiens

<400> SEQUENCE: 1858

Ala Gln Thr Pro Pro Gly Pro Ser Leu Ser Gly Ser Lys
1               5                   10

<210> SEQ ID NO 1859
<211> LENGTH: 18
<212> TYPE: PRT
<213> ORGANISM: Homo sapiens

<400> SEQUENCE: 1859

Ser Ser Thr Pro Pro Gly Glu Ser Tyr Phe Gly Val Ser Ser Leu Gln
1               5                   10                  15

Leu Lys

<210> SEQ ID NO 1860
```

```
<211> LENGTH: 10
<212> TYPE: PRT
<213> ORGANISM: Homo sapiens

<400> SEQUENCE: 1860

Gly Gln Ser Gln Thr Ser Pro Asp His Arg
1               5                   10

<210> SEQ ID NO 1861
<211> LENGTH: 9
<212> TYPE: PRT
<213> ORGANISM: Homo sapiens

<400> SEQUENCE: 1861

Ser Asp Thr Ser Ser Pro Glu Val Arg
1               5

<210> SEQ ID NO 1862
<211> LENGTH: 12
<212> TYPE: PRT
<213> ORGANISM: Homo sapiens

<400> SEQUENCE: 1862

Gln Ser His Ser Glu Ser Pro Ser Leu Gln Ser Lys
1               5                   10

<210> SEQ ID NO 1863
<211> LENGTH: 6
<212> TYPE: PRT
<213> ORGANISM: Homo sapiens

<400> SEQUENCE: 1863

Ser Gln Thr Ser Pro Lys
1               5

<210> SEQ ID NO 1864
<211> LENGTH: 11
<212> TYPE: PRT
<213> ORGANISM: Homo sapiens

<400> SEQUENCE: 1864

Ser Ser Ser Pro Val Thr Glu Leu Ala Ser Arg
1               5                   10

<210> SEQ ID NO 1865
<211> LENGTH: 21
<212> TYPE: PRT
<213> ORGANISM: Homo sapiens

<400> SEQUENCE: 1865

Phe Gln Ser Asp Ser Ser Ser Tyr Pro Thr Val Asp Ser Asn Ser Leu
1               5                   10                  15

Leu Gly Gln Ser Arg
            20

<210> SEQ ID NO 1866
<211> LENGTH: 7
<212> TYPE: PRT
<213> ORGANISM: Homo sapiens

<400> SEQUENCE: 1866

Leu Glu Thr Ala Glu Ser Lys
1               5
```

```
<210> SEQ ID NO 1867
<211> LENGTH: 17
<212> TYPE: PRT
<213> ORGANISM: Homo sapiens

<400> SEQUENCE: 1867

Phe Ser Pro Phe Pro Val Gln Asp Arg Pro Glu Ser Ser Leu Val Phe
1               5                   10                  15

Lys

<210> SEQ ID NO 1868
<211> LENGTH: 10
<212> TYPE: PRT
<213> ORGANISM: Homo sapiens

<400> SEQUENCE: 1868

Ser Gly Ala Gly Ser Ser Pro Glu Thr Lys
1               5                   10

<210> SEQ ID NO 1869
<211> LENGTH: 17
<212> TYPE: PRT
<213> ORGANISM: Homo sapiens

<400> SEQUENCE: 1869

Ser Glu Glu Pro Ala Gly Gln Ile Leu Ser His Leu Ser Ser Glu Leu
1               5                   10                  15

Lys

<210> SEQ ID NO 1870
<211> LENGTH: 8
<212> TYPE: PRT
<213> ORGANISM: Homo sapiens

<400> SEQUENCE: 1870

Glu Leu Ser Asn Ser Pro Leu Arg
1               5

<210> SEQ ID NO 1871
<211> LENGTH: 11
<212> TYPE: PRT
<213> ORGANISM: Homo sapiens

<400> SEQUENCE: 1871

Glu Asn Ser Phe Gly Ser Pro Leu Glu Phe Arg
1               5                   10

<210> SEQ ID NO 1872
<211> LENGTH: 16
<212> TYPE: PRT
<213> ORGANISM: Homo sapiens

<400> SEQUENCE: 1872

Ser Ser Gly His Ser Ser Glu Leu Ser Pro Asp Ala Val Glu Lys
1               5                   10                  15

<210> SEQ ID NO 1873
<211> LENGTH: 8
<212> TYPE: PRT
<213> ORGANISM: Homo sapiens

<400> SEQUENCE: 1873

Ser Gly Ser Ser Pro Gly Leu Arg
1               5
```

<210> SEQ ID NO 1874
<211> LENGTH: 8
<212> TYPE: PRT
<213> ORGANISM: Homo sapiens

<400> SEQUENCE: 1874

Asp Gly Ser Gly Thr Pro Ser Arg
1               5

<210> SEQ ID NO 1875
<211> LENGTH: 9
<212> TYPE: PRT
<213> ORGANISM: Homo sapiens

<400> SEQUENCE: 1875

Ala Leu Pro Gln Thr Pro Arg Pro Arg
1               5

<210> SEQ ID NO 1876
<211> LENGTH: 10
<212> TYPE: PRT
<213> ORGANISM: Homo sapiens

<400> SEQUENCE: 1876

Ser Pro Ser Ser Pro Glu Leu Asn Asn Lys
1               5                   10

<210> SEQ ID NO 1877
<211> LENGTH: 10
<212> TYPE: PRT
<213> ORGANISM: Homo sapiens

<400> SEQUENCE: 1877

Ser Gly Ser Glu Ser Ser Val Asp Gln Lys
1               5                   10

<210> SEQ ID NO 1878
<211> LENGTH: 6
<212> TYPE: PRT
<213> ORGANISM: Homo sapiens

<400> SEQUENCE: 1878

Thr Pro Leu Gly Gln Arg
1               5

<210> SEQ ID NO 1879
<211> LENGTH: 18
<212> TYPE: PRT
<213> ORGANISM: Homo sapiens

<400> SEQUENCE: 1879

Ser Gly Ser Ser Gln Glu Leu Asp Val Lys Pro Ser Ala Ser Pro Gln
1               5                   10                  15

Glu Arg

<210> SEQ ID NO 1880
<211> LENGTH: 10
<212> TYPE: PRT
<213> ORGANISM: Homo sapiens

<400> SEQUENCE: 1880

Ser Glu Ser Asp Ser Ser Pro Asp Ser Lys
1               5                   10

<210> SEQ ID NO 1881
<211> LENGTH: 10
<212> TYPE: PRT
<213> ORGANISM: Homo sapiens

<400> SEQUENCE: 1881

Ser Gly Ser Ser Pro Glu Val Asp Ser Lys
1               5                   10

<210> SEQ ID NO 1882
<211> LENGTH: 8
<212> TYPE: PRT
<213> ORGANISM: Homo sapiens

<400> SEQUENCE: 1882

Ser Gly Ser Ser Pro Glu Val Lys
1               5

<210> SEQ ID NO 1883
<211> LENGTH: 12
<212> TYPE: PRT
<213> ORGANISM: Homo sapiens

<400> SEQUENCE: 1883

Ala Gln Ser Gly Ser Asp Ser Ser Pro Glu Pro Lys
1               5                   10

<210> SEQ ID NO 1884
<211> LENGTH: 19
<212> TYPE: PRT
<213> ORGANISM: Homo sapiens

<400> SEQUENCE: 1884

Gly Pro Ser Pro Glu Gly Ser Ser Ser Thr Glu Ser Ser Pro Glu His
1               5                   10                  15

Pro Pro Lys

<210> SEQ ID NO 1885
<211> LENGTH: 7
<212> TYPE: PRT
<213> ORGANISM: Homo sapiens

<400> SEQUENCE: 1885

Ser Ser Pro Glu Leu Thr Arg
1               5

<210> SEQ ID NO 1886
<211> LENGTH: 9
<212> TYPE: PRT
<213> ORGANISM: Homo sapiens

<400> SEQUENCE: 1886

Ser Ala Ser Ser Ser Pro Glu Thr Arg
1               5

<210> SEQ ID NO 1887
<211> LENGTH: 12
<212> TYPE: PRT
<213> ORGANISM: Homo sapiens

<400> SEQUENCE: 1887

Ser Pro Ser Val Ser Ser Pro Glu Pro Ala Glu Lys
1               5                   10

<210> SEQ ID NO 1888
<211> LENGTH: 7
<212> TYPE: PRT
<213> ORGANISM: Homo sapiens

<400> SEQUENCE: 1888

Ser Pro Ser Pro Lys Pro Arg
1               5

<210> SEQ ID NO 1889
<211> LENGTH: 9
<212> TYPE: PRT
<213> ORGANISM: Homo sapiens

<400> SEQUENCE: 1889

Ser Gly Ser Ser Gln Ser Thr Ser Arg
1               5

<210> SEQ ID NO 1890
<211> LENGTH: 8
<212> TYPE: PRT
<213> ORGANISM: Homo sapiens

<400> SEQUENCE: 1890

Gly Gly Ser Gly Tyr His Ser Arg
1               5

<210> SEQ ID NO 1891
<211> LENGTH: 7
<212> TYPE: PRT
<213> ORGANISM: Homo sapiens

<400> SEQUENCE: 1891

Thr Ser Pro Ala Pro Trp Lys
1               5

<210> SEQ ID NO 1892
<211> LENGTH: 7
<212> TYPE: PRT
<213> ORGANISM: Homo sapiens

<400> SEQUENCE: 1892

Ala Ser Pro Ala Thr His Arg
1               5

<210> SEQ ID NO 1893
<211> LENGTH: 6
<212> TYPE: PRT
<213> ORGANISM: Homo sapiens

<400> SEQUENCE: 1893

Thr Pro Leu Ile Ser Arg
1               5

<210> SEQ ID NO 1894
<211> LENGTH: 6
<212> TYPE: PRT
<213> ORGANISM: Homo sapiens

<400> SEQUENCE: 1894

Thr Pro Pro Val Thr Arg
1               5

```
<210> SEQ ID NO 1895
<211> LENGTH: 6
<212> TYPE: PRT
<213> ORGANISM: Homo sapiens

<400> SEQUENCE: 1895

Thr Ser Pro Ile Thr Arg
1               5

<210> SEQ ID NO 1896
<211> LENGTH: 12
<212> TYPE: PRT
<213> ORGANISM: Homo sapiens

<400> SEQUENCE: 1896

Ser Pro Val Pro Ser Ala Phe Ser Asp Gln Ser Arg
1               5                   10

<210> SEQ ID NO 1897
<211> LENGTH: 9
<212> TYPE: PRT
<213> ORGANISM: Homo sapiens

<400> SEQUENCE: 1897

Val Pro Ser Pro Thr Pro Ala Pro Lys
1               5

<210> SEQ ID NO 1898
<211> LENGTH: 11
<212> TYPE: PRT
<213> ORGANISM: Homo sapiens

<400> SEQUENCE: 1898

Glu Gly Arg Pro Pro Glu Pro Thr Pro Ala Lys
1               5                   10

<210> SEQ ID NO 1899
<211> LENGTH: 7
<212> TYPE: PRT
<213> ORGANISM: Homo sapiens

<400> SEQUENCE: 1899

Lys Pro Pro Pro Gly Glu Arg
1               5

<210> SEQ ID NO 1900
<211> LENGTH: 7
<212> TYPE: PRT
<213> ORGANISM: Homo sapiens

<400> SEQUENCE: 1900

Lys Pro Ile Asp Ser Leu Arg
1               5

<210> SEQ ID NO 1901
<211> LENGTH: 9
<212> TYPE: PRT
<213> ORGANISM: Homo sapiens

<400> SEQUENCE: 1901

Ser Leu Ser Tyr Ser Pro Val Glu Arg
1               5

<210> SEQ ID NO 1902
<211> LENGTH: 9
```

```
<212> TYPE: PRT
<213> ORGANISM: Homo sapiens

<400> SEQUENCE: 1902

Arg Pro Ser Pro Gln Pro Ser Pro Arg
1               5

<210> SEQ ID NO 1903
<211> LENGTH: 9
<212> TYPE: PRT
<213> ORGANISM: Homo sapiens

<400> SEQUENCE: 1903

Asp Gln Gln Ser Ser Ser Ser Glu Arg
1               5

<210> SEQ ID NO 1904
<211> LENGTH: 6
<212> TYPE: PRT
<213> ORGANISM: Homo sapiens

<400> SEQUENCE: 1904

Thr Pro Pro Ala Ile Arg
1               5

<210> SEQ ID NO 1905
<211> LENGTH: 6
<212> TYPE: PRT
<213> ORGANISM: Homo sapiens

<400> SEQUENCE: 1905

Ser Pro Leu Ala Ile Arg
1               5

<210> SEQ ID NO 1906
<211> LENGTH: 6
<212> TYPE: PRT
<213> ORGANISM: Homo sapiens

<400> SEQUENCE: 1906

Ser Pro Pro Ala Ile Arg
1               5

<210> SEQ ID NO 1907
<211> LENGTH: 9
<212> TYPE: PRT
<213> ORGANISM: Homo sapiens

<400> SEQUENCE: 1907

Ser Ala Ser Gly Ser Ser Ser Asp Arg
1               5

<210> SEQ ID NO 1908
<211> LENGTH: 8
<212> TYPE: PRT
<213> ORGANISM: Homo sapiens

<400> SEQUENCE: 1908

Ser Ala Thr Pro Pro Ala Thr Arg
1               5

<210> SEQ ID NO 1909
<211> LENGTH: 6
<212> TYPE: PRT
<213> ORGANISM: Homo sapiens
```

<400> SEQUENCE: 1909

Asn His Ser Gly Ser Arg
1               5

<210> SEQ ID NO 1910
<211> LENGTH: 10
<212> TYPE: PRT
<213> ORGANISM: Homo sapiens

<400> SEQUENCE: 1910

Thr Pro Pro Val Ala Leu Asn Ser Ser Arg
1               5                   10

<210> SEQ ID NO 1911
<211> LENGTH: 6
<212> TYPE: PRT
<213> ORGANISM: Homo sapiens

<400> SEQUENCE: 1911

Ile Pro Asp His Gln Arg
1               5

<210> SEQ ID NO 1912
<211> LENGTH: 11
<212> TYPE: PRT
<213> ORGANISM: Homo sapiens

<400> SEQUENCE: 1912

Thr Ser Val Pro Glu Asn His Ala Gln Ser Arg
1               5                   10

<210> SEQ ID NO 1913
<211> LENGTH: 10
<212> TYPE: PRT
<213> ORGANISM: Homo sapiens

<400> SEQUENCE: 1913

Thr Ala Pro Ala Ala Asn Leu Ala Ser Arg
1               5                   10

<210> SEQ ID NO 1914
<211> LENGTH: 14
<212> TYPE: PRT
<213> ORGANISM: Homo sapiens

<400> SEQUENCE: 1914

Thr Pro Ala Ile Pro Thr Ala Val Asn Leu Ala Asp Ser Arg
1               5                   10

<210> SEQ ID NO 1915
<211> LENGTH: 14
<212> TYPE: PRT
<213> ORGANISM: Homo sapiens

<400> SEQUENCE: 1915

Thr Ala Val Ala Pro Ser Ala Val Asn Leu Ala Asp Pro Arg
1               5                   10

<210> SEQ ID NO 1916
<211> LENGTH: 13
<212> TYPE: PRT
<213> ORGANISM: Homo sapiens

<400> SEQUENCE: 1916

Thr Pro Thr Ala Pro Ala Val Asn Leu Ala Gly Ala Arg
1               5                   10

<210> SEQ ID NO 1917
<211> LENGTH: 14
<212> TYPE: PRT
<213> ORGANISM: Homo sapiens

<400> SEQUENCE: 1917

Thr Pro Gln Ala Pro Ala Ser Ala Asn Leu Val Gly Pro Arg
1               5                   10

<210> SEQ ID NO 1918
<211> LENGTH: 14
<212> TYPE: PRT
<213> ORGANISM: Homo sapiens

<400> SEQUENCE: 1918

Ser Ala His Ala Thr Ala Pro Val Asn Ile Ala Gly Ser Arg
1               5                   10

<210> SEQ ID NO 1919
<211> LENGTH: 14
<212> TYPE: PRT
<213> ORGANISM: Homo sapiens

<400> SEQUENCE: 1919

Thr Ala Ala Ala Leu Ala Pro Ala Ser Leu Thr Ser Ala Arg
1               5                   10

<210> SEQ ID NO 1920
<211> LENGTH: 8
<212> TYPE: PRT
<213> ORGANISM: Homo sapiens

<400> SEQUENCE: 1920

Val Pro Leu Ser Ala Tyr Glu Arg
1               5

<210> SEQ ID NO 1921
<211> LENGTH: 8
<212> TYPE: PRT
<213> ORGANISM: Homo sapiens

<400> SEQUENCE: 1921

Thr Ser Pro Pro Leu Leu Asp Arg
1               5

<210> SEQ ID NO 1922
<211> LENGTH: 10
<212> TYPE: PRT
<213> ORGANISM: Homo sapiens

<400> SEQUENCE: 1922

Thr Pro Pro Ser Ala Pro Ser Gln Ser Arg
1               5                   10

```
<210> SEQ ID NO 1923
<211> LENGTH: 7
<212> TYPE: PRT
<213> ORGANISM: Homo sapiens

<400> SEQUENCE: 1923

Ala Pro Ser Pro Ser Ser Arg
1               5
```